(12) United States Patent
Satterfield et al.

(10) Patent No.: US 10,654,804 B2
(45) Date of Patent: May 19, 2020

(54) SUBSTITUTED CYCLIC AMIDES AND THEIR USE AS HERBICIDES

(71) Applicant: FMC Corporation, Philadelphia, PA (US)

(72) Inventors: Andrew Duncan Satterfield, Furlong, PA (US); Matthew James Campbell, Flemington, NJ (US); James Francis Bereznak, Newtown Square, PA (US); William Guy Whittingham, Berkshire (GB); Glynn Mitchell, Berkshire (GB); Christopher John Mathews, Berkshire (GB); James Nicholas Scutt, Berkshire (GB); James Alan Morris, Berkshire (GB); Jonathan Wesley Paul Dallimore, Berkshire (GB); Katharine Mary Ingram, Berkshire (GB); Timothy Robert Desson, Berkshire (GB); Kenneth Ling, Berkshire (GB)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 15/573,598

(22) PCT Filed: Jun. 1, 2016

(86) PCT No.: PCT/US2016/035214
§ 371 (c)(1),
(2) Date: Nov. 13, 2017

(87) PCT Pub. No.: WO2016/196593
PCT Pub. Date: Dec. 8, 2016

(65) Prior Publication Data
US 2018/0099935 A1    Apr. 12, 2018

Related U.S. Application Data

(60) Provisional application No. 62/170,129, filed on Jun. 2, 2015.

(51) Int. Cl.
| | |
|---|---|
| *C07D 211/40* | (2006.01) |
| *C07D 211/94* | (2006.01) |
| *C07D 207/277* | (2006.01) |
| *C07D 207/46* | (2006.01) |
| *C07D 401/04* | (2006.01) |
| *C07D 401/12* | (2006.01) |
| *C07D 407/04* | (2006.01) |
| *C07D 409/12* | (2006.01) |
| *C07D 413/12* | (2006.01) |
| *C07D 417/04* | (2006.01) |
| *C07D 471/04* | (2006.01) |

(Continued)

(52) U.S. Cl.
CPC ............ *C07D 211/40* (2013.01); *A01N 43/36* (2013.01); *A01N 43/40* (2013.01); *C07D 207/277* (2013.01); *C07D 207/46* (2013.01); *C07D 211/94* (2013.01); *C07D 401/04* (2013.01); *C07D 401/12* (2013.01)

(58) Field of Classification Search
CPC ............... C07D 211/04; C07D 211/94; C07D 207/277; C07D 207/46; C07D 401/04; C07D 401/12; C07D 407/04; C07D 409/12; C07D 413/12; C07D 417/04; C07D 471/04; C07D 495/04; A01N 43/36; A01N 43/40
See application file for complete search history.

(56) References Cited

U.S. PATENT DOCUMENTS

| | | |
|---|---|---|
| 3,741,989 A | 6/1973 | Zaugg |
| 3,959,481 A | 5/1976 | Davis et al. |

(Continued)

FOREIGN PATENT DOCUMENTS

| | | |
|---|---|---|
| CN | 102531918 B | 10/2013 |
| DE | 1 262 277 B | 3/1968 |

(Continued)

OTHER PUBLICATIONS

XP002734980; Jan. 20, 2002.
XP002734981; WO0009481; Feb. 24, 2000.
XP002759805; Jan. 20, 2002.
XP002759806; Mar. 23, 2009.
Murata et al.; "Oxidation of N-Acyl-Pyrrolidines and -Piperidines with Iron(II)-Hydrogen Peroxide and an Iron Complex-Molecular Oxygen"; *J. Chem. Soc. Perkin Trans.*; 1987; 1259-1262. (XP055297105).

(Continued)

*Primary Examiner* — Timothy R Rozof
(74) *Attorney, Agent, or Firm* — Reed A Coats

(57) ABSTRACT

Disclosed are compounds of Formula 1, N-oxides of the compounds and salts of the compounds and N-oxides:

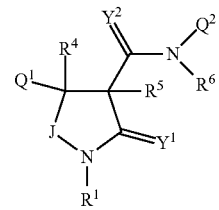

wherein $R^1$, $R^2$, $R^3$, $R^4$, $R^5$, $R^6$, $Q^1$, $Q^2$, J, $Y^1$, and $Y^2$ are as defined in the disclosure.
Also disclosed are compositions containing the compounds, N-oxides and salts, and methods for controlling undesired vegetation comprising contacting the undesired vegetation or its environment with an effective amount of such a compound, N-oxide, salt or composition.

7 Claims, No Drawings

(51) Int. Cl.
*C07D 495/04* (2006.01)
*A01N 43/36* (2006.01)
*A01N 43/40* (2006.01)

(56) References Cited

U.S. PATENT DOCUMENTS

| | | | |
|---|---|---|---|
| 4,594,094 | A | 6/1986 | Kollmeyer |
| 4,874,422 | A | 10/1989 | Woolard |
| 5,856,273 | A | 1/1999 | Kay et al. |
| 7,205,318 | B2 | 4/2007 | Qiao et al. |
| 7,375,232 | B2 | 5/2008 | Clark et al. |
| 8,293,926 | B2 | 10/2012 | Yasuoka et al. |
| 8,461,202 | B2 | 6/2013 | Sancho Sanz et al. |
| 8,575,154 | B2 | 11/2013 | Kori et al. |
| 8,946,216 | B2 | 2/2015 | Deng et al. |
| 9,944,602 | B2 | 4/2018 | Satterfield et al. |
| 2004/0242671 | A1 | 12/2004 | Grimee et al. |
| 2006/0019831 | A1 | 1/2006 | Reinhard et al. |
| 2007/0123508 | A1 | 5/2007 | Olsson et al. |
| 2009/0203694 | A1 | 8/2009 | Hurley et al. |
| 2011/0218199 | A1 | 9/2011 | Georges et al. |
| 2016/0137639 | A1 | 5/2016 | Kotoku et al. |
| 2016/0289228 | A1 | 10/2016 | Defays et al. |
| 2016/0297756 | A1* | 10/2016 | Satterfield ............... A01N 43/78 |
| 2017/0158638 | A1 | 6/2017 | Satterfield et al. |
| 2018/0049437 | A1* | 2/2018 | Satterfield ............ C07D 403/12 |
| 2018/0057442 | A1 | 3/2018 | Satterfield |
| 2018/0077931 | A1 | 3/2018 | Stevenson et al. |
| 2018/0141904 | A1 | 5/2018 | Campbell et al. |
| 2018/0213788 | A1 | 8/2018 | Satterfield et al. |
| 2018/0215760 | A1 | 8/2018 | Campbell et al. |

FOREIGN PATENT DOCUMENTS

| | | |
|---|---|---|
| EP | 2336104 A1 | 6/2011 |
| IN | 1462DEL08 | 6/2008 |
| JP | 53-056288 A | 5/1978 |
| JP | 54-088114 A | 7/1979 |
| JP | 08-269145 A | 10/1996 |
| KR | 20130142477 A | 12/2013 |
| RU | 2555370 C1 | 7/2015 |
| WO | 2000/09481 A1 | 2/2000 |
| WO | 2004/046081 A1 | 6/2004 |
| WO | 2006/081562 A2 | 8/2006 |
| WO | 2009/062371 A1 | 5/2009 |
| WO | 2015/084796 A1 | 6/2015 |
| WO | 2016/003997 A1 | 1/2016 |
| WO | 2016/094117 A1 | 6/2016 |
| WO | 2016/164201 A1 | 10/2016 |
| WO | 2016/176082 A1 | 11/2016 |
| WO | 2016/182780 A1 | 11/2016 |
| WO | 2016/196019 A1 | 12/2016 |
| WO | 2017/023515 A1 | 2/2017 |
| WO | 2018/118384 A1 | 6/2018 |
| WO | 20180175226 | 9/2018 |
| WO | 20180175231 | 9/2018 |

OTHER PUBLICATIONS

Cauliez et al.; "Studies on Pyrrolidinones. On the Carbamoylation of Some Pyroglutamic Derivatives"; *J. Het. Chem.*; 33; 1996; 1233-1237. (XP055297107).

Hwang et al.; "Diastereoselective Synthesis of Oxazolidinone Derivatives and Their Antifungal Activities"; *Korean J. of Med. Chem.*; vol. 4, No. 1; 1994; 52-56. (XP009191451).

Campaigne et el.; Synthesis of Some Ureidodihydrofurans and Related Pyrimidones as Potential Antimalarials; *J. Med. Chem.*; 1969; 339-342. (XP002278920).

IPCOM000241978D; Jun. 11, 2015.

PubChem Entry CID 29937915 (4S)-4-[3-(trifluoromethyl)phenyl]pyrrolidin-2-one: May 28, 2009.

* cited by examiner

US 10,654,804 B2

SUBSTITUTED CYCLIC AMIDES AND THEIR USE AS HERBICIDES

CROSS-REFERENCE TO RELATED PATENT APPLICATION

This disclosure claims priority to U.S. Provisional Patent Application No. 62/170,129 (filed Jun. 2, 2015). The entire text of the above-referenced patent application is incorporated by reference into this patent filing

FIELD OF THE DISCLOSURE

This disclosure relates to certain pyrrolidinones, N-oxides thereof, and salts of the pyrrolidinones and N-oxides; compositions comprising such pyrrolidinones, N-oxides and salts; processes for making such pyrrolidinones, N-oxides, salts and compositions; and methods for using such pyrrolidinones, N-oxides, salts and compositions to control undesirable vegetation.

BACKGROUND

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safer or have different sites of action.

SUMMARY

This disclosure relates, in part, to compounds of Formula 1 (including all stereoisomers), N-oxides of such compounds, and salts of such compounds and N-oxides:

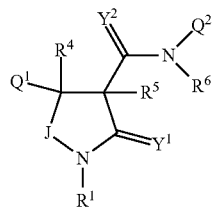

1 wherein
$Q^1$ is a phenyl ring or a naphthalenyl ring system, each ring or ring system optionally substituted with up to 5 substituents independently selected from $R^7$; or a 4- to 7-membered heterocyclic ring; or an 8- to 10-membered bicyclic ring system, each ring or ring system containing ring members selected from carbon atoms and 1 to 5 heteroatoms independently selected from up to 2 O, up to 2 S and up to 5 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^7$ on carbon atom ring members and selected from $R^9$ on nitrogen atom ring members; or $Q^1$ is $C_2$-$C_{10}$ alkenyl, $C_2$-$C_{10}$ alkynyl, $C_2$-$C_{10}$ haloalkenyl, $C_2$-$C_{10}$ haloalkynyl, $C_4$-$C_{10}$ cycloalkenyl, $C_4$-$C_{10}$ halocycloalkenyl, $C_2$-$C_8$ alkylcarbonyl or $C_2$-$C_8$ alkoxyalkyl;

$Q^2$ is a phenyl ring or a naphthalenyl ring system, each ring or ring system optionally substituted with up to 5 substituents independently selected from $R^{10}$; or a 4- to 7-membered heterocyclic ring; or an 8- to 10-membered bicyclic ring system, each ring or ring system containing ring members selected from carbon atoms and 1 to 4 heteroatoms independently selected from up to 2 O, up to 2 S and up to 5 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^{10}$ on carbon atom ring members and selected from $R^{11}$ on nitrogen atom ring members; or $Q^2$ is $C_2$-$C_{10}$ alkenyl, $C_2$-$C_{10}$ alkynyl, $C_2$-$C_{10}$ haloalkenyl, $C_2$-$C_{10}$ haloalkynyl, $C_4$-$C_{10}$ cycloalkenyl, $C_4$-$C_{10}$ halocycloalkenyl, $C_2$-$C_8$ alkylcarbonyl or $C_2$-$C_8$ alkoxyalkyl;

J is —$CR^2R^3$—, —$NR^{2a}$— or —O—;

$Y^1$ and $Y^2$ are each independently O, S or $NR^{12}$;

$R^1$ is H, hydroxy, amino, cyano, formyl, $C_3$-$C_8$ alkylcarbonylalkyl, —$C(C_1$-$C_4$ alkyl)=N—$O(C_1$-$C_4$ alkyl), —$C(O)NH_2$, $C_1$-$C_6$ alkyl, $C_1$-$C_6$ haloalkyl, $C_2$-$C_6$ alkenyl, $C_3$-$C_6$ alkynyl, $C_2$-$C_6$ cyanoalkyl, $C_3$-$C_6$ cycloalkyl, $C_3$-$C_8$ cycloalkenyl, $C_4$-$C_8$ cycloalkylalkyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkenylalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_5$-$C_{10}$ cycloalkylcarbonylalkyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl; or —$CPh$=$N$—$O(C_1$-$C_4$ alkyl), each optionally substituted on ring members with up to 5 substituents independently selected from $R^{13}$; or $G^1$; or $W^1G^1$;

$R^2$ and $R^3$ are each independently H, halogen, hydroxy, $C_1$-$C_4$ alkyl, $C_1$-$C_4$ haloalkyl or $C_1$-$C_4$ alkoxy; or $R^2$ and $R^3$ are taken together with the carbon atom to which they are bonded to form a $C_3$-$C_7$ cycloalkyl ring;

$R^{2a}$ is $C_1$-$C_6$ alkyl, $C_2$-$C_6$ alkenyl, $C_3$-$C_6$ alkynyl or $C_1$-$C_6$ alkoxy; or $R^1$ and $R^{2a}$ are taken together as $C_3$-$C_6$ alkylene or —$CH_2OCH_2$—;

$R^4$ and $R^5$ are each independently H, halogen, hydroxy, $C_1$-$C_4$ alkoxy, $C_1$-$C_4$ haloalkyl or $C_1$-$C_4$ alkyl;

$R^6$ is H, hydroxy, amino, $C_1$-$C_6$ alkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl or $C_3$-$C_{10}$ trialkylsilyl or $G^1$; or $R^6$ and $Q^2$ are taken together with the nitrogen atom to which they are both bonded to form an 8- to 10-membered bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^7$ on carbon atom ring members and selected from $R^9$ on nitrogen atom ring members;

each $R^7$ and $R^{10}$ is independently halogen, hydroxy, cyano, nitro, amino, $C_1$-$C_8$ alkyl, $C_1$-$C_8$ cyanoalkyl, $C_1$-$C_8$ cyanoalkoxy, $C_1$-$C_8$ haloalkyl, $C_1$-$C_8$ hydroxyalkyl, $C_1$-$C_8$ nitroalkyl, $C_2$-$C_8$ alkenyl, $C_2$-$C_8$ haloalkenyl, $C_2$-$C_8$ nitroalkenyl, $C_2$-$C_8$ alkynyl, $C_2$-$C_8$ haloalkynyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkoxyhaloalkoxy, $C_3$-$C_6$ cycloalkyl, cyclopropylmethyl, 1-methylcyclopropyl, 2-methylcyclopropyl, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ haloalkoxyalkoxy, $C_2$-$C_8$ alkoxyalkoxy, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylamino, $C_2$-$C_8$ dialkylamino, $C_2$-$C_8$ halodialkylamino, $C_2$-$C_8$ alkylaminoalkyl, $C_2$-$C_8$ haloalkylaminoalkyl, $C_4$-$C_{10}$ cycloalkylaminoalkyl, $C_3$-$C_{10}$ dialkylaminoalkyl, —CHO, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH$_2$, $C_2$-$C_8$ alkylaminocarbonyl, $C_4$-$C_{10}$ cycloalkylaminocarbonyl, $C_3$-$C_{10}$ dialkylaminocarbonyl, $C_1$-$C_8$ alkoxy, $C_1$-$C_8$ haloalkoxy, $C_2$-$C_8$ alkoxyalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ cycloalkylsulfonyl, formylamino, $C_2$-$C_8$ alkylcarbonylamino, $C_2$-$C_8$ haloalkylcarbonylamino, $C_3$-$C_8$ cycloalkylamino, $C_2$-$C_8$ alkoxycarbonylamino, $C_1$-$C_6$ alkylsulfonylamino, $C_1$-$C_6$ haloalkylsulfonylamino, —SF$_5$, —SCN, SO$_2$NH$_2$, $C_3$-$C_{12}$ trialkylsilyl, $C_4$-$C_{12}$ trialkylsilylalkyl or $C_4$-$C_{12}$ trialkylsilylalkoxy; or $G^2$; or each $R^7$ is independently $R^{26}S(=O)=N$—, $R^{26}S(=O)_2NR^{25}$—C(=O)—, $R^{26}(R^{25}N=)_qS(=O)_p$—, wherein the free bond projecting to the right indicates the connecting point to $Q^1$; or each $R^{10}$ is independently $R^{17}ON=CR^{17a}$—, $(R^{18})_2C=NO$—, $(R^{19})_2NN=CR^{17a}$—, $(R^{18})_2C=NNR^{20a}$—, $R^{20}N=CR^{17a}$—, $(R^{18})_2C=N$—, $R^{17}ON=CR^{17a}C(R^{23b})_2$—, $(R^{18})_2C=NOC(R^{24a})_2$—, $R^{26}S(=O)=N$—, $R^{26}S(=O)_2NR^{25}$—C(=O)— or $R^{26}(R^{25}N=)_qS(=O)_p$—, wherein the free bond projecting to the right indicates the connecting point to $Q^2$;

each $R^8$ is independently H, cyano, $C_2$-$C_3$ alkylcarbonyl or $C_2$-$C_3$ haloalkylcarbonyl;

each $R^9$ and $R^{11}$ is independently cyano, $C_1$-$C_3$ alkyl, $C_1$-$C_8$ hydroxyalkyl, $C_2$-$C_3$ alkenyl, $C_2$-$C_3$ alkynyl, $C_3$-$C_6$ cycloalkyl, $C_2$-$C_3$ alkoxyalkyl, $C_1$-$C_3$ alkoxy, $C_2$-$C_3$ alkylcarbonyl, $C_2$-$C_3$ alkoxycarbonyl, $C_2$-$C_3$ alkylaminoalkyl or $C_3$-$C_4$ dialkylaminoalkyl;

each $R^{12}$ is independently H, cyano, hydroxy, CHO, $C_1$-$C_4$ alkyl, $C_1$-$C_4$ haloalkyl, $C_1$-$C_4$ alkoxy, $C_2$-$C_6$ alkylcarbonyl, $C_2$-$C_6$ haloalkylcarbonyl, —(C=O)CH$_3$ or —(C=O)CF$_3$;

each $G^1$ is independently phenyl; or a 5- or 6-membered heterocyclic ring, each optionally substituted on ring members with up to 5 substituents independently selected from $R^{13}$;

each $G^2$ is independently phenyl, phenylmethyl (i.e. benzyl), pyridinylmethyl, phenylcarbonyl (i.e. benzoyl), phenoxy, phenylethynyl, phenylsulfonyl or a 5- or 6-membered heterocyclic ring, each optionally substituted on ring members with up to 5 substituents independently selected from $R^{14}$;

$W^1$ is $C_1$-$C_3$ alkylene, $C_2$-$C_4$ alkenylene, $C_2$-$C_4$ alkynylene, —(C$_1$-C$_2$ alkylene)C(=O)—, —C(=O)(C$_1$-C$_2$ alkylene)-, —CH$_2$O—, —CH$_2$NH—, —OCH$_2$—, —NCH$_2$—, —N—, —O—, —S—, —SO— or —SO$_2$— wherein the free bond projecting to the left indicates the connecting point of $W^1$ to N and the free bond projecting to the right indicates the connecting point of $W^1$ to $G^1$.

each $R^{13}$ and $R^{14}$ is independently halogen, cyano, hydroxy, amino, nitro, —CHO, —C(=O)OH, —C(=O)NH$_2$, —SO$_2$NH$_2$, $C_1$-$C_6$ alkyl, $C_1$-$C_6$ haloalkyl, $C_2$-$C_6$ alkenyl, $C_2$-$C_6$ alkynyl, $C_2$-$C_8$ alkylcarbonyl, $C_2$-$C_8$ haloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylaminosulfonyl, $C_2$-$C_8$ dialkylaminosulfonyl, $C_3$-$C_{10}$ trialkylsilyl, $C_1$-$C_6$ alkylamino, $C_2$-$C_8$ dialkylamino, $C_2$-$C_8$ alkylcarbonylamino, $C_1$-$C_6$ alkylsulfonylamino, phenyl, pyridinyl or thienyl;

each $R^{17}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{17a}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy, $C_1$-$C_6$ alkylthio, $C_1$-$C_6$ haloalkylthio, $C_3$-$C_8$ cycloalkylthio, $C_3$-$C_{10}$ trialkylsilyl or $G^1$;

each $R^{18}$ is independently H, hydroxy, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{19}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{20}$ is independently H, hydroxy, amino, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{20a}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy, $C_3$-$C_{10}$ trialkylsilyl or $G^1$;

each $R^{23b}$ is independently H, halogen, cyano, hydroxy, $C_1$-$C_4$ alkyl, $C_3$-$C_8$ cycloalkyl, $C_4$-$C_8$ cycloalkylalkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl or $C_3$-$C_6$ cycloalkyl;

each $R^{24a}$ is independently H, $C_1$-$C_4$ alkyl, $C_3$-$C_8$ cycloalkyl, $C_4$-$C_8$ cycloalkylalkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl or $C_3$-$C_6$ cycloalkyl;

each $R^{25}$ is independently H, cyano, $C_2$-$C_3$ alkylcarbonyl or $C_2$-$C_3$ haloalkylcarbonyl;

each $R^{26}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy, $C_3$-$C_{10}$ trialkylsilyl or $G^1$; and each u and v are independently 0, 1 or 2 in each instance of $S(=O)_u(=NR^8)_v$, provided that the sum of u and v is 0, 1 or 2;

each p and q are independently 0, 1 or 2 in each instance of $R^{26}(R^{25}N=)_qS(=O)_p$—, provided that the sum of u and v is 0, 1 or 2 and when p is 0, q is other than 1 or 2;

provided that
(a) the compound of Formula 1 is other than N-1H-benzotriazol-1-yl-2-oxo-4-phenyl-3-pyrrolidinecarboxamide;
(b) when $Q^1$ comprises a 3-furanyl or 3-pyridinyl ring directly bonded to the remainder of Formula 1, then said ring is substituted with at least one substituent selected from $R^7$;
(c) when $Q^1$ is an unsubstituted phenyl ring, and $Q^2$ comprises a phenyl ring directly bonded to the remainder of Formula 1, then said $Q^2$ ring is substituted with $R^{10}$ other than optionally substituted phenoxy or F at a 2-position, cyano or —$CF_3$ at the 4-position and $R^5$ is H or halogen;
(d) when $Q^1$ is unsubstituted phenyl, and $Q^2$ comprises a pyridinyl ring directly bonded to the remainder of Formula 1, then said pyridinyl ring is substituted with at least one substituent selected from $R^{10}$;
(e) when $Q^1$ is a phenyl ring substituted with 4-phenyl or 4-phenoxy, said $Q^1$ ring is further substituted with and $R^7$ substituent;
(f) when $Q^1$ comprises a phenyl ring directly bonded to the remainder of Formula 1 and said ring is substituted with $R^7$ at both ortho positions (relative to the bond to the remainder of Formula 1), then said ring is also independently substituted with $R^7$ on at least one additional position;
(g) when $Q^1$ is other than unsubstituted 1-naphthalenyl, then $Q^2$ is other than 2,3-di-fluorophenyl or 2-$CF_3$-phenyl;
(h) $Q^2$ is other than optionally substituted 1H-pyrazol-5-yl; and
(i) when $Q^2$ comprises a 1H-pyrazol-3-yl ring directly bonded to the remainder of Formula 1, said ring is substituted at the 1-position with $R^9$.

This disclosure also relates, in part, to an agricultural (generally herbicidal) composition comprising such a compound, N-oxide or salt in a herbicidally effective amount and at least one component selected from the group consisting of surfactants, solid diluents and liquid diluents, the composition optionally further comprising at least one additional active ingredient selected from the group consisting of other herbicides and herbicide safeners.

This disclosure also relates, in part, to processes for making the above-identified compounds, N-oxides, salts and compositions.

This disclosure also relates, in part, to methods for controlling the growth of undesired vegetation comprising contacting the vegetation or its environment with a herbicidally effective amount of an above-identified compound, N-oxide, salt or composition.

DETAILED DESCRIPTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process, or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method that includes materials, steps, features, components, or elements, in addition to those literally disclosed, provided that these additional materials, steps, features, components, or elements do not materially affect the basic and novel characteristic(s) of the recited subject matter. The term "consisting essentially of" occupies a middle ground between "comprising" and "consisting of".

Where applicants have defined subject matter with an open-ended term such as "comprising," it should be readily understood that (unless otherwise stated) the description should be interpreted to also describe such subject matter using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed.

As referred to herein, the term "broadleaf" used either alone or in words such as "broadleaf weed" means dicot or dicotyledon, a term used to describe a group of angiosperms characterized by embryos having two cotyledons.

As used herein, the term "alkylating agent" refers to a chemical compound in which a carbon-containing radical is bound through a carbon atom to a leaving group such as halide or sulfonate, which is displaceable by bonding of a nucleophile to said carbon atom. Unless otherwise indicated, the term "alkylating" does not limit the carbon-containing radical to alkyl; the carbon-containing radicals in alkylating agents include the variety of carbon-bound substituent radicals specified for $R^1$.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkylene" denotes a straight-chain or branched alkanediyl. Examples of "alkylene" include $CH_2$, $CH_2CH_2$, $CH(CH_3)$, $CH_2CH_2CH_2$, $CH_2CH(CH_3)$ and the different butylene, pentylene and hexylene isomers. "Alkenylene" denotes a straight-chain or branched alkenediyl. Examples of "alkenylene" include —CH=CH—, —CH$_2$CH=CH—, —CH$_2$CH=C(CH$_3$)— and the different butyl, pentyl and hexyl isomers. "Alkynylene" denotes a straight-chain or branched alkynediyl. Examples of "alkynylene" include $CH_2C\equiv C$—, —$CH_2CH_2C\equiv C$— and the different butyl and pentyl isomers "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxyalkyl" denotes at least alkoxy substitution on the alkoxy moiety of alkoxyalkyl moiety. Examples of "alkoxyalkoxyalkyl" include $CH_3OCH_2OCH_2$—, $CH_3CH_2O(CH_3)CHOCH_2$— and $(CH_3O)_2CHOCH_2$—. "Alkoxyalkoxy" denotes alkoxy substitution on alkoxy. "Alkenyloxy" includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC\equiv CCH_2O$, $CH_3C\equiv CCH_2O$ and $CH_3C\equiv CCH_2CH_2O$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$—, $CH_3CH_2S(O)$—, $CH_3CH_2CH_2S(O)$—, $(CH_3)_2CHS(O)$— and the different butylsulfinyl, pentylsulfinyl and hexylsulfinyl isomers. Examples of "alkylsulfonyl" include $CH_3S(O)_2$—, $CH_3CH_2S(O)_2$—, $CH_3CH_2CH_2S(O)_2$—, $(CH_3)_2CHS(O)_2$—, and the different butylsulfonyl, pentylsulfonyl and hexylsulfonyl isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Alkylsulfinylalkyl" denotes alkylsulfinyl substitution on alkyl. Examples of "alkylsulfinylalkyl" include $CH_3S(=O)CH_2$, $CH_3S(=O)CH_2CH_2$, $CH_3CH_2S(=O)CH_2$ and $CH_3CH_2S(=O)CH_2CH_2$. "Alkylsulfonylalkyl" denotes alkylsulfonyl substitution on alkyl. Examples of "alkylsulfonylalkyl" include $CH_3S(=O)_2CH_2$, $CH_3S(=O)_2CH_2CH_2$, $CH_3CH_2S(=O)_2CH_2$ and $CH_3CH_2S(=O)_2CH_2CH_2$. "Alkylamino", "dialkylamino", and the like, are defined analogously to the above examples. Examples of "alkylaminoalkyl" include $CH_3NHCH_2$—, $(CH_3)_2CHN$-

HCH$_2$— and CH$_3$NHCH(CH$_3$)—. Examples of "dialkylaminoalkyl" include (CH$_3$)$_2$NCH$_2$—, (CH$_3$)$_2$NC(CH$_3$)H— and (CH$_3$)(CH$_3$)NCH$_2$—. Examples of "dialkylaminocarbonyl" include (CH$_3$)$_2$NC(O)—. Examples of "dialkylaminosulfonyl" include (CH$_3$)$_2$NS(O)$_2$—. The term "alkoxycarbonylamino" denotes a straight-chain or branched alkoxy moieties bonded to a C(=O) moiety of carbonylamino group. Examples of "alkoxycarbonylamino" include CH$_3$OC(=O)NH— and CH$_3$CH$_2$OC(=O)NH—.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. The term "cycloalkoxy" denotes cycloalkyl linked through an oxygen atom such as cyclopentyloxy and cyclohexyloxy. "Cycloalkylalkoxy" denotes cycloalkylalkyl linked through an oxygen atom attached to the alkyl chain. Examples of "cycloalkylalkoxy" include cyclopropylmethoxy, cyclopentylethoxy, and other cycloalkyl moieties bonded to straight-chain or branched alkoxy groups. "Cycloalkenyl" includes groups such as cyclopentenyl and cyclohexenyl as well as groups with more than one double bond such as 1,3- and 1,4-cyclohexadienyl.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include F$_3$C, ClCH$_2$, CF$_3$CH$_2$ and CF$_3$CCl$_2$. The terms "halocycloalkyl", "haloalkoxy", "haloalkylthio", "haloalkenyl", "haloalkynyl", "haloalkenyloxy", "haloalkylcarbonylamino", "haloalkylsulfonylamino", "haloalkylsulfonyloxy", "haloalkoxyalkyl", "haloalkylcarbonyloxy", "haloalkylaminoalkyl" and the like, are defined analogously to the term "haloalkyl". Examples of "haloalkoxy" include CF$_3$O—, CCl$_3$CH$_2$O—, HCF$_2$CH$_2$CH$_2$O— and CF$_3$CH$_2$O—. Examples of "haloalkylthio" include CCl$_3$S—, CF$_3$S—, CCl$_3$CH$_2$S— and ClCH$_2$CH$_2$CH$_2$S—. Examples of "haloalkylsulfinyl" include CF$_3$S(O)—, CCl$_3$S(O)—, CF$_3$CH$_2$S(O)— and CF$_3$CF$_2$S(O)—. Examples of "haloalkylsulfonyl" include CF$_3$S(O)$_2$—, CCl$_3$S(O)$_2$—, CF$_3$CH$_2$S(O)$_2$— and CF$_3$CF$_2$S(O)$_2$—. Examples of "haloalkenyl" include (Cl)$_2$C=CHCH$_2$— and CF$_3$CH$_2$CH=CHCH$_2$—. Examples of "haloalkenyloxy" include (Cl)$_2$C=CHCH$_2$O— and CF$_3$CH$_2$CH=CHCH$_2$O—. Examples of "haloalkynyl" include HC≡CCHCl—, CF$_3$C≡C—, CCl$_3$C≡C— and FCH$_2$C≡CCH$_2$—. Examples of "haloalkoxyalkyl" include CF$_3$OCH$_2$—, ClCH$_2$CH$_2$OCH$_2$CH$_2$—, Cl$_3$CCH$_2$OCH$_2$— as well as branched alkyl derivatives. Examples of "haloalkoxycarbonyl" include CF$_3$OC(O)—, ClCH$_2$CH$_2$OCH$_2$CH$_2$—, Cl$_3$CCH$_2$OCH$_2$OC(O)— as well as branched alkyl derivatives.

"Alkylcarbonyl" denotes a straight-chain or branched alkyl moieties bonded to a C(=O) moiety. Examples of "alkylcarbonyl" include CH$_3$C(=O)—, CH$_3$CH$_2$CH$_2$C(=O)— and (CH$_3$)$_2$CHC(=O)—. Examples of "alkoxycarbonyl" include CH$_3$OC(=O)—, CH$_3$CH$_2$OC(=O)—, CH$_3$CH$_2$CH$_2$OC(=O)—, (CH$_3$)$_2$CHOC(=O)— and the different butoxy- or pentoxycarbonyl isomers. "Cycloalkylalkoxycarbonyl" denotes a cycloalkylalkyl moieties bonded to an oxygen atom of alkoxycarbonyl moiety. Examples of "cycloalkylalkoxycarbonyl" include cyclopropyl-CH$_2$OC(=O)—, cyclopropyl-CH(CH$_3$)OC(=O)— and cyclopentyl-CH$_2$OC(=O)—.

The total number of carbon atoms in a substituent group is indicated by the "$C_i$-$C_j$" prefix where i and j are numbers from 1 to 12. For example, $C_1$-$C_4$ alkylsulfonyl designates methylsulfonyl through butylsulfonyl; $C_2$ alkoxyalkyl designates CH$_3$OCH$_2$—; $C_3$ alkoxyalkyl designates, for example, CH$_3$CH(OCH$_3$)—, CH$_3$OCH$_2$CH$_2$— or CH$_3$CH$_2$OCH$_2$—; and $C_4$ alkoxyalkyl designates the various isomers of an alkyl group substituted with an alkoxy group containing a total of four carbon atoms, examples including CH$_3$CH$_2$CH$_2$OCH$_2$— and CH$_3$CH$_2$OCH$_2$CH$_2$—.

When a compound is substituted with a substituent bearing a subscript that indicates the number of said substituents can exceed 1, said substituents (when they exceed 1) are independently selected from the group of defined substituents, e.g., [R$^{7)}_n$], n is 1, 2, 3, 4 or 5). Further, when the subscript indicates a range, e.g. (R)$_{i-j}$, then the number of substituents may be selected from the integers between i and j inclusive. When a group contains a substituent which can be hydrogen, for example R$^1$ or R$^2$, then when this substituent is taken as hydrogen, it is recognized that this is equivalent to said group being unsubstituted. When a variable group is shown to be optionally attached to a position, for example [R$^{(7)}_n$] wherein n may be 0, then hydrogen may be at the position even if not recited in the variable group definition. When one or more positions on a group are said to be "not substituted" or "unsubstituted", then hydrogen atoms are attached to take up any free valency.

The expression "fully saturated" in relatior to a ring of atoms means that the bonds between the atoms of the ring are all single. The expression "fully unsaturated" in relatior to a ring means that the bonds between the atoms in the ring are single or double bonds according to valence bond theory and furthermore the bonds between the atoms in the ring include as many double bonds as possible without double bonds being cumulative (i.e. no C=C=C, N=C=C, etc.). The term "partially unsaturated" in relatior to a ring denotes a ring comprising at least one ring member bonded to an adjacent ring member though a double bond and which conceptually potentially accommodates a number of non-cumulated double bonds through adjacent ring members (i.e. in its fully unsaturated counterpart form) greater than the number of double bonds present (i.e. in its partially unsaturated form). When a fully unsaturated ring satisfies Hückel's rule then it can also be described as aromatic.

Unless otherwise indicated, a "ring" or "ring system" as a component of Formula 1 (e.g., substituent Q$^1$) is carbocyclic or heterocyclic. The term "ring system" denotes two or more fused rings. The terms "bicyclic ring system" and "fused bicyclic ring system" denote a ring system consisting of two fused rings, in which either ring can be saturated, partially unsaturated, or fully unsaturated unless otherwise indicated. The term "fused heterobicyclic ring system" denotes a fused bicyclic ring system in which at least one ring atom is not carbon. The term "ring member" refers to an atom or other moiety (e.g., C(=O), C(=S), S(O) or S(O)$_2$) forming the backbone of a ring or ring system.

The terms "carbocyclic ring", "carbocycle" or "carbocyclic ring system" denote a ring or ring system wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

The terms "heterocyclic ring", "heterocycle" or "heterocyclic ring system" denote a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or "aromatic heterocyclic ring". Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and that $(4n+2)\pi$ electrons, where n is a positive integer, are associated with the ring to comply with Hückel's rule. The term "aromatic ring or ring system" denotes a carbocyclic or heterocyclic ring or ring system in which the ring or at least one ring of the ring system is aromatic. The term "aromatic ring or ring system" is also referred to as "aryl". The term "aryl" can be used alone or in compound words such as "arylcarbonyl". "Arylcarbonyl" denotes an aryl group bonded to a C(=O) moiety. The terms "arylalkenylalkyl" is defined similarly. The term "aromatic carbocyclic ring system" denotes a carbocyclic ring system in which at least one ring of the ring system is aromatic. The term "aromatic heterocyclic ring system" denotes a heterocyclic ring system in which at least one ring of the ring system is aromatic. The term "nonaromatic ring system" denotes a carbocyclic or heterocyclic ring system that may be fully saturated, as well as partially or fully unsaturated, provided that none of the rings in the ring system are aromatic. The term "nonaromatic carbocyclic ring system" in which no ring in the ring system is aromatic. The term "nonaromatic heterocyclic ring system" denotes a heterocyclic ring system in which no ring in the ring system is aromatic.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

When $Q^1$ or $Q^2$ is 5- or 6-membered nitrogen-containing heterocyclic ring, it may be attached to the remainder of Formula 1 though any available carbon or nitrogen ring atom, unless otherwise described. As noted above, $Q^1$ and $Q^2$ can be (among others) phenyl optionally substituted with one or more substituents selected from a group of substituents as defined in the Summary. An example of phenyl optionally substituted with one to five substituents is the ring illustrated as U-1 in Exhibit 1, wherein, for example, $R^v$ is $R^7$ as defined in the Summary for $Q^1$, or $R^v$ is $R^{10}$ as defined in the Summary for $Q^2$, and r is an integer (from 0 to 5).

As noted above, $Q^1$ and $Q^2$ can be (among others) a 5- or 6-membered fully unsaturated heterocyclic ring, optionally substituted with one or more substituents selected from a group of substituents as defined in the Summary. Examples of a 5- or 6-membered unsaturated aromatic heterocyclic ring optionally substituted with from one or more substituents include the rings U-2 through U-61 illustrated in Exhibit 1 wherein $R^v$ is any substituent as defined in the Summary for $Q^1$ and $Q^2$, and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Exhibit 1

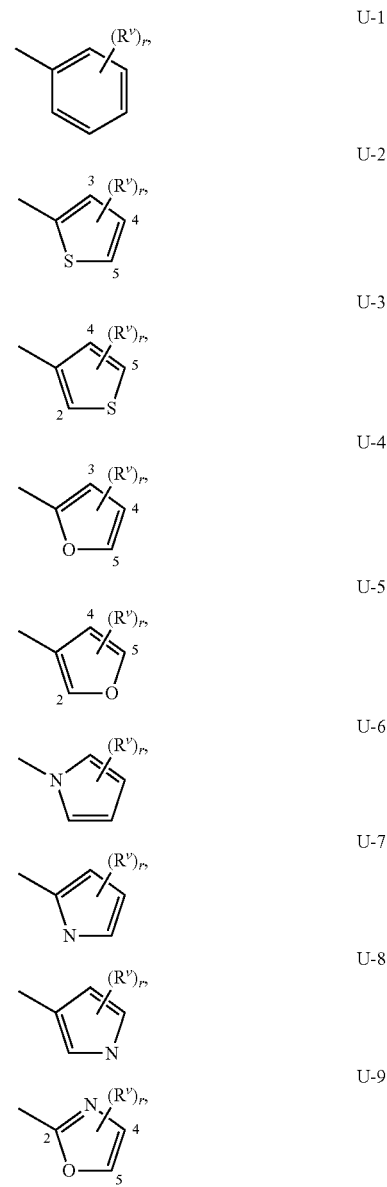

-continued
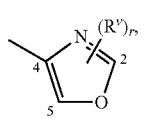 U-10
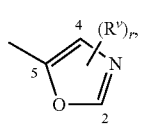 U-11
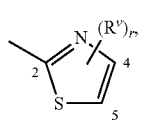 U-12
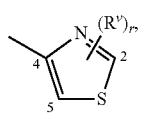 U-13
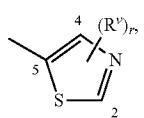 U-14
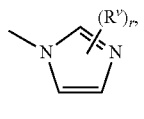 U-15
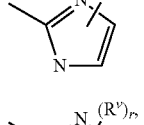 U-16
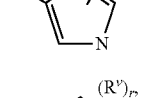 U-17
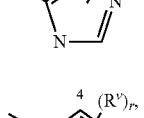 U-18
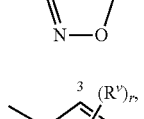 U-19
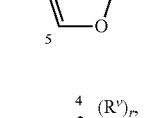 U-20
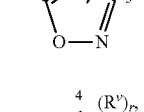 U-21
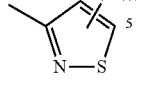 U-22
-continued
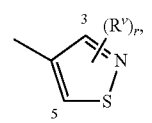 U-23
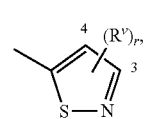 U-24
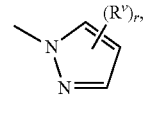 U-25
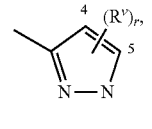 U-26
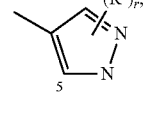 U-27
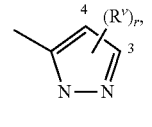 U-28
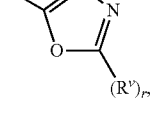 U-29
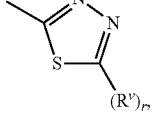 U-30
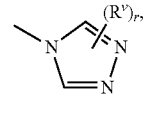 U-31
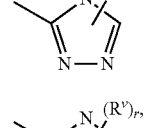 U-32
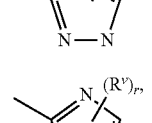 U-33
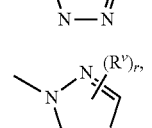 U-34
U-35

| | |
|---|---|
| U-36 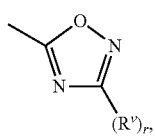 | U-48 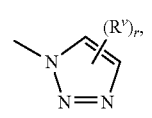 |
| U-37 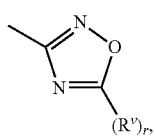 | U-49 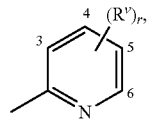 |
| U-38 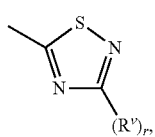 | U-50 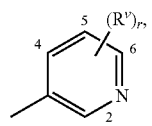 |
| U-39 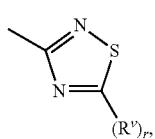 | U-51 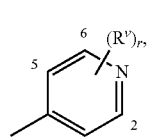 |
| U-40 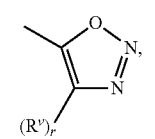 | U-52 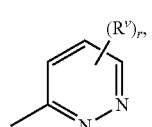 |
| U-41 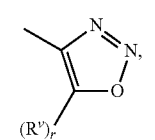 | U-53 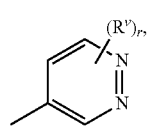 |
| U-42 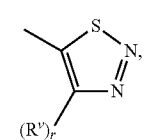 | U-54 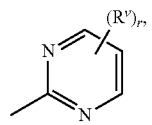 |
| U-43 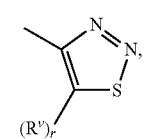 | U-55 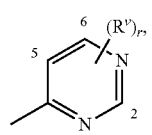 |
| U-44 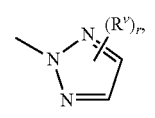 | U-56 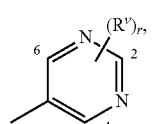 |
| U-45 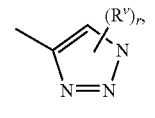 | U-57 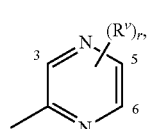 |
| U-46 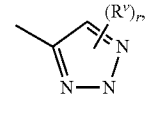 | U-58 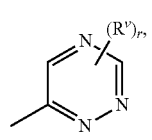 |
| U-47 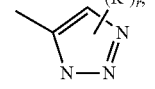 | |

-continued

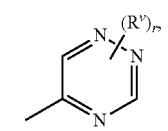 U-59

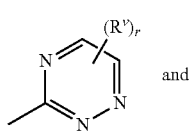 U-60
and

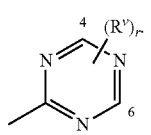 U-61
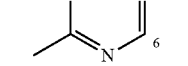

As noted above, $Q^1$ and $Q^2$ can be an 8- to 10-membered heterocyclic ring system optionally substituted with one or more substituents selected from a group of substituents as defined in the Summary for $Q^1$ and $Q^2$. Examples of 8- to 10-membered heterocyclic ring system optionally substituted with from one or more substituents include the rings U-62 through U-102 illustrated in Exhibit 2 wherein $R^v$ is any substituent as defined in the Summary for $Q^1$ or $Q^2$, and r is typically an integer from 0 to 5. The free bond denoted by a straight line can be located on either ring irregardless of where they are drawn. The free bond connected to $(R^v)_r$ can be located on either ring irregardless of where they are drawn.

Exhibit 2

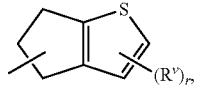 U-62

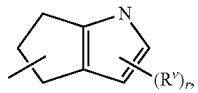 U-63

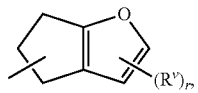 U-64

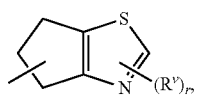 U-65

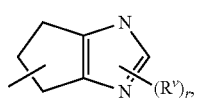 U-66

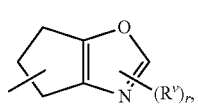 U-67

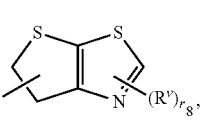 U-68

-continued

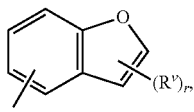 U-69

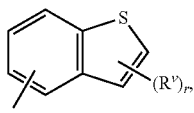 U-70

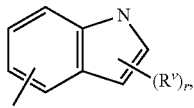 U-71

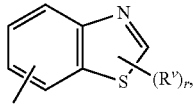 U-72

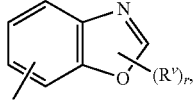 U-73

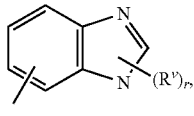 U-74

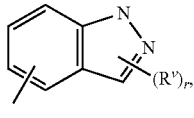 U-75

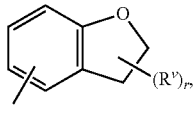 U-76

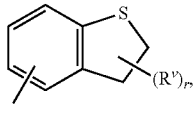 U-77

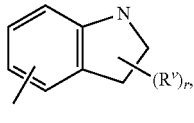 U-78

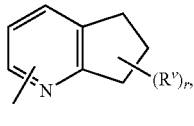 U-79

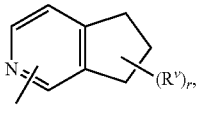 U-80

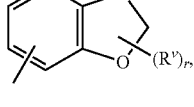 U-81

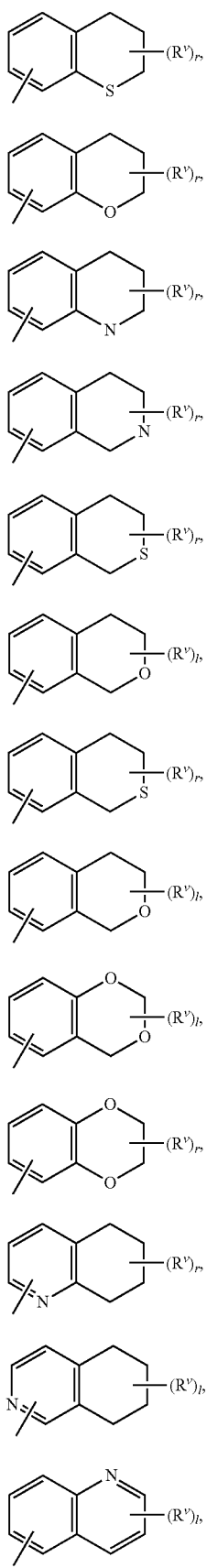
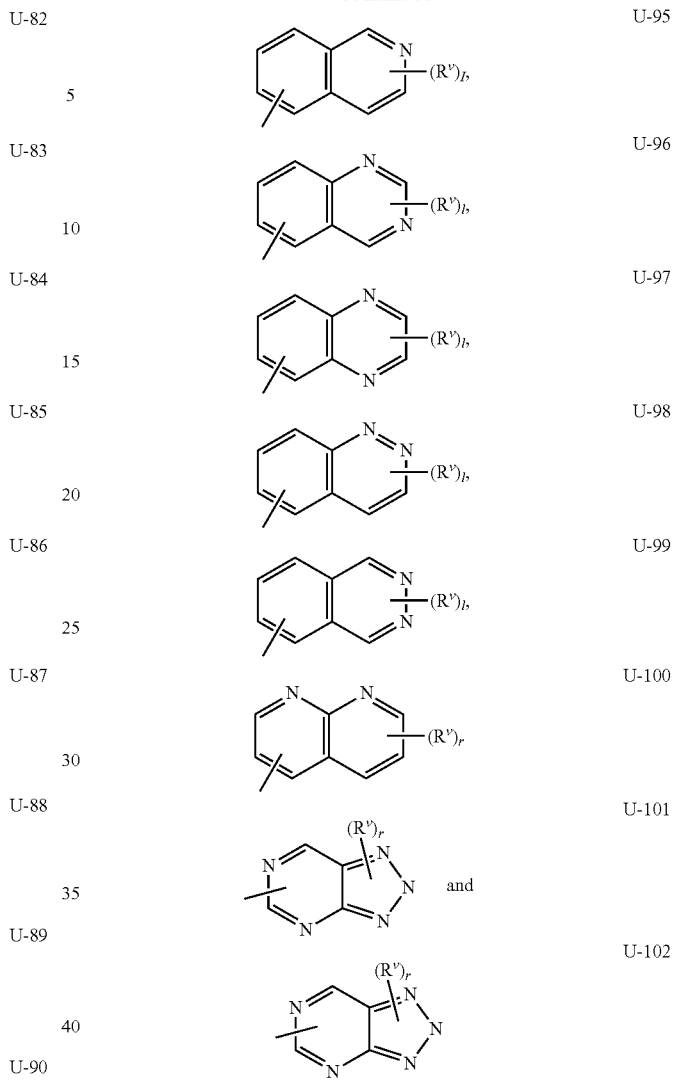

Although $R^v$ groups are shown in the structures U-1 through U-102, it is noted that they do not need to be present since they are optional substituents. Note that when $R^v$ is H when attached to an atom, this is the same as if said atom is unsubstituted. The nitrogen atoms that require substitution to fill their valence are substituted with H or $R^v$. Note that when the attachment point between $(R^v)_r$ and the U group is illustrated as floating, $(R^v)_r$ can be attached to any available carbon atom or nitrogen atom of the U group. Note that when the attachment point on the U group is illustrated as floating, the U group can be attached to the remainder of Formula 1 through any available carbon or nitrogen of the U group by replacement of a hydrogen atom. In some embodiments, for greatest herbicidal activity, the U group is attached to the remainder of Formula 1 through an available carbon or nitrogen on a fully unsaturated ring of the U group. Note that some U groups can only be substituted with less than 4 $R^v$ groups (e.g., U-2 through U-5, U-7 through U-48, and U-52 through U-61).

As noted above, $R^6$ and $Q^2$ can be taken together with the nitrogen atom to which they are both bonded to form an 8- to 10-membered bicyclic ring system. Examples of $R^6$ and $Q^2$ taken together are shown in Exhibit 3.

Exhibit 3

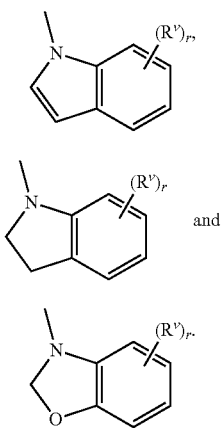

In the present disclosure, the term "pyrrolidinone" and related terms such as "pyrrolidinone ring" refer to 2-oxo-pyrrolidine derivatives according to the Chemical Abstracts system of nomenclature, including derivatives in which the oxygen atom of the 2-oxo moiety is replaced by S or $NR^{12}$ as $Y^1$, unless limited to oxygen by particular context.

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this disclosure can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Compounds of this disclosure may be present as a mixture of stereoisomers, individual stereoisomers or as an optically active form. Particularly when $R^4$ and $R^5$ are each H, the $C(O)N(Q^2)(R^6)$ and $Q^1$ substituents are typically mostly in the thermodynamically preferred trans configuration on the pyrrolidinone ring.

For example, as shown in the following, the $C(O)N(Q^2)(R^6)$ moiety (i.e. in Formula 1 wherein both $Y^1$ and $Y^2$ are O; and J is —$CR^2R^3$— and $R^2$ and $R^3$ are both H) bonded to the carbon at the 3-position of the cyclic amide ring and $Q^1$ bonded to the carbon at the 4-position of the cyclic amide ring are generally found in the trans configuration. These two carbon atoms both possess a chiral center. The most prevalent pair of enantiomers are depicted as Formula 1' and Formula 1". While this disclosure pertains to all stereoisomers, in some embodiments, the enantiomer for biological operability is identified as Formula 1'. For a comprehensive discussion of all aspects of stereoisomerism, see Ernest L. Eliel and Samuel H. Wilen, *Stereochemistry of Organic Compounds*, John Wiley & Sons, 1994.

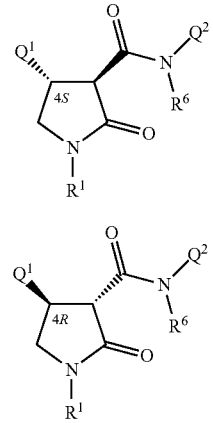

The skilled artisan will also recognize that the carbon atom at the 5-position of the pyrrolidinone ring (i.e. when J is —$CR^2R^3$—, the carbon atom to which both $R^2$ and $R^3$ are bonded) also contains a stereocenter indicated by a (*) as shown in Formula 1'". This disclosure pertains to all stereoisomers, and therefore, when either $R^2$ or $R^3$ are other than the same substituent, then a mixture of diastereomers is possible.

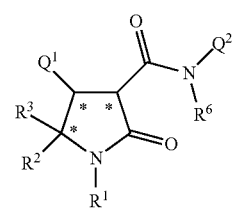

Molecular depictions drawn herein follow standard conventions for depicting stereochemistry. To indicate stereoconfiguration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the narrow end of the wedge is attached to the atom further away from the viewer. Constant width lines indicate bonds with a direction opposite or neutral relative to bonds shown with solid or dashed wedges; constant width lines also depict bonds in molecules or parts of molecules in which no particular stereoconfiguration is intended to be specified.

This disclosure also comprises racemic mixtures, for example, equal amounts of the enantiomers of Formulae 1' and 1" (and optionally 1'"). In addition, this disclosure includes compounds that are enriched compared to the racemic mixture in an enantiomer of Formula 1. Also included are the essentially pure enantiomers of compounds of Formula 1, for example, Formula 1' and Formula 1".

When enantiomerically enriched, one enantiomer is present in greater amounts than the other, and the extent of enrichment can be defined by an expression of enantiomeric ratio (ER) expressed as the relative area % of the two enantiomers determined by chiral high-performance liquid chromatography.

In some embodiments, the compositions of this disclosure have at least a 50% ER. In some embodiments, the compositions of this disclosure have at least a 75% ER. In some embodiments, the compositions of this disclosure have at least a 90% ER. In some embodiments, the compositions of this disclosure have at least a 94% ER of the more active isomer. Of particular note are enantiomerically pure embodiments of the more active isomer.

Compounds of Formula 1 can comprise additional chiral centers. For example, substituents and other molecular constituents such as $R^2$, $R^3$ and $R^6$ may themselves contain chiral centers. This disclosure comprises racemic mixtures as well as enriched and essentially pure stereoconfigurations at these additional chiral centers.

Compounds of this disclosure can exist as one or more conformational isomers due to restricted rotation about the amide bond $C(O)N(Q^2)(R^6)$ in Formula 1. This disclosure comprises mixtures of conformational isomers. In addition, this disclosure includes compounds that are enriched in one conformer relative to others. Compounds of Formula 1 typically exist in more than one form, and Formula 1 thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present disclosure comprises compounds selected from Formula 1, N-oxides and agriculturally suitable salts thereof.

Embodiments of the present disclosure as described in the Summary include (where Formula 1 as used in the following Embodiments includes N-oxides and salts thereof):

Embodiment 1. A compound of Formula 1 wherein $Q^1$ is a 4- or 7-membered heterocyclic ring or an 8- to 10-membered bicyclic ring system, each ring or ring system containing ring members selected from carbon atoms and 1 to 5 heteroatoms independently selected from up to 2 O, up to 2 S and up to 5 N atoms, wherein up to 3 carbon ring members are independently selected from $C(=O)$ and $C(=S)$, and the sulfur atom ring members are independently selected from $S(=O)_u$ $(=NR^8)_v$, each ring or ring system optionally substituted with up to 5 substituents independently selected from $R^7$ on carbon atom ring members and selected from $R^9$ on nitrogen atom ring members.

Embodiment 2. A compound of Embodiment 1 wherein $Q^1$ is $C_2$-$C_{10}$ alkenyl, $C_2$-$C_{10}$ alkynyl, $C_2$-$C_{10}$ haloalkenyl, $C_2$-$C_{10}$ haloalkynyl, $C_4$-$C_{10}$ cycloalkenyl, $C_4$-$C_{10}$ halocycloalkenyl, $C_2$-$C_8$ alkylcarbonyl or $C_2$-$C_8$ alkoxyalkyl.

Embodiment 3. A compound of Embodiment 1 wherein $Q^1$ is an 8- to 10-membered bicyclic ring system, containing ring members selected from carbon atoms and 1 to 5 heteroatoms independently selected from up to 2 O, up to 2 S and up to 5 N atoms, wherein up to 3 carbon ring members are independently selected from $C(=O)$ and $C(=S)$, and the sulfur atom ring members are independently selected from $S(=O)_u(=NR^8)_v$, the said ring system optionally substituted with up to 5 substituents independently selected from $R^7$ on carbon atom ring members and selected from $R^9$ on nitrogen atom ring members.

Embodiment 4. A compound of Embodiment 1 wherein $Q^1$ is a 4- or 7-membered heterocyclic ring, containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^8)_v$, the said ring optionally substituted with up to 5 substituents independently selected from $R^7$ on carbon atom ring members and selected from $R^9$ on nitrogen atom ring members.

Embodiment 5. A compound of Formula 1 wherein $Q^1$ is a phenyl ring optionally substituted with up to 5 substituents independently selected from $R^7$.

Embodiment 6. A compound of Embodiment 5 wherein $Q^1$ is a phenyl ring substituted with 1 to 3 substituents independently selected from $R^7$.

Embodiment 7. A compound of Embodiment 6 wherein $Q^1$ is a phenyl ring substituted with 1 to 2 substituents independently selected from $R^7$.

Embodiment 8. A compound of Formula 1 or any one of Embodiments 5 through 7 wherein $Q^1$ is a phenyl ring having at least one substituent selected from $R^7$ at the para position and optionally other substituents.

Embodiment 9. A compound of Formula 1 or any one of Embodiments 5 through 8 wherein $Q^1$ is a phenyl ring substituted with at least two substituents selected from $R^7$, and one substituent is at the para position and at least one other substituent is at a meta position of the phenyl ring.

Embodiment 10. A compound of Formula 1 wherein $Q^2$ is a 4- or 7-membered heterocyclic ring or an 8- to 10-membered bicyclic ring system, each ring or ring system containing ring members selected from carbon atoms and 1 to 5 heteroatoms independently selected from up to 2 O, up to 2 S and up to 5 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^7$ on carbon atom ring members and selected from $R^9$ on nitrogen atom ring members.

Embodiment 11. A compound of Formula 1 wherein $Q^2$ is $C_2$-$C_{10}$ alkenyl, $C_2$-$C_{10}$ alkynyl, $C_2$-$C_{10}$ haloalkenyl, $C_2$-$C_{10}$ haloalkynyl, $C_4$-$C_{10}$ cycloalkenyl, $C_4$-$C_{10}$ halocycloalkenyl, $C_2$-$C_8$ alkylcarbonyl or $C_2$-$C_8$ alkoxyalkyl.

Embodiment 12. A compound of Embodiment 10 wherein $Q^2$ is an 8- to 10-membered bicyclic ring system, containing ring members selected from carbon atoms and 1 to 5 heteroatoms independently selected from up to 2 O, up to 2 S and up to 5 N atoms, wherein up to 3 carbon ring members are independently selected from C(=O) and C(=S), and the sulfur atom ring members are independently selected from $S(=O)_u(=NR^8)_v$, the said ring system optionally substituted with up to 5 substituents independently selected from $R^{10}$ on carbon atom ring members and selected from $R^{11}$ on nitrogen atom ring members.

Embodiment 13. A compound of Embodiment 10 wherein $Q^2$ is a 4- or 7-membered heterocyclic ring, containing ring members selected from carbon atoms and 1 to 5 heteroatoms independently selected from up to 2 O, up to 2 S and up to 5 N atoms, wherein up to 3 carbon ring members are independently selected from C(=O) and C(=S), and the sulfur atom ring members are independently selected from $S(=O)_u(=NR^8)_v$, the said ring optionally substituted with up to 5 substituents independently selected from $R^{10}$ on carbon atom ring members and selected from $R^{11}$ on nitrogen atom ring members.

Embodiment 14. A compound of Formula 1 wherein $Q^2$ is a phenyl ring substituted with up to 5 substituents independently selected from $R^{10}$.

Embodiment 15. A compound of Embodiment 14 wherein $Q^2$ is a phenyl ring substituted with 1 to 3 substituents independently selected from $R^{10}$.

Embodiment 16. A compound of Embodiment 15 wherein $Q^2$ is a phenyl ring substituted with 1 to 2 substituents independently selected from $R^{10}$.

Embodiment 17. A compound of Formula 1 or any one of Embodiments 1 through 16 wherein $Q^2$ is a phenyl ring having at least one substituent selected from $R^{10}$ at an ortho position and optionally other substituents.

Embodiment 18. A compound of Formula 1 or any one of Embodiments 1 through 17 wherein $Q^2$ is a phenyl ring substituted with at least two substituents selected from $R^{10}$, and at least one substituent is at an ortho position and at least one substituent is at an adjacent meta position of the phenyl ring.

Embodiment 19. A compound of Formula 1 or any one of Embodiments 1 through 17 wherein when $Q^2$ is a phenyl ring substituted with at least two substituents selected from $R^{10}$, then at least one substituent is at an ortho position and at least one substituent is at para position of the phenyl ring.

Embodiment 20. A compound of Formula 1 wherein J is —$CR^2R^3$—, —$NR^{2a}$— or —O—.

Embodiment 21. A compound of Embodiment 20 wherein J is —$CR^2R^3$—.

Embodiment 22. A compound of Embodiment 20 wherein J is —$NR^{2a}$—.

Embodiment 23. A compound of Embodiment 20 wherein J is —O—.

Embodiment 24. A compound of Formula 1 or Embodiment 22 wherein $R^{2a}$ is $C_1$-$C_6$ alkyl, $C_2$-$C_6$ alkenyl, $C_3$-$C_6$ alkynyl or $C_1$-$C_6$ alkoxy.

Embodiment 25. A compound of Formula 1 or any one of Embodiments 1 through 24 wherein, independently, each $R^7$ and $R^{10}$ is independently halogen, hydroxy, cyano, nitro, amino, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_2$-$C_6$ alkoxyalkyl, $C_3$-$C_6$ alkoxyalkoxyalkyl, $C_2$-$C_6$ haloalkoxyalkyl, $C_2$-$C_6$ haloalkoxyhaloalkoxy, $C_3$-$C_6$ cycloalkyl, cyclopropylmethyl, 1-methylcyclopropyl, 2-methylcyclopropyl, $C_1$-$C_4$ nitroalkyl, $C_2$-$C_4$ nitroalkenyl, $C_2$-$C_4$ alkoxyalkyl, $C_2$-$C_4$ haloalkoxyalkyl, $C_3$-$C_4$ cycloalkyl, $C_3$-$C_4$ halocycloalkyl, cyclopropylmethyl, methylcyclopropyl, $C_1$-$C_4$ alkoxy, $C_1$-$C_4$ haloalkoxy, $C_2$-$C_4$ alkenyloxy, $C_2$-$C_4$ haloalkenyloxy, $C_3$-$C_4$ alkynyloxy, $C_3$-$C_4$ haloalkynyloxy, $C_3$-$C_4$ cycloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, hydroxy, formyl, $C_2$-$C_4$ alkylcarbonyl, $C_2$-$C_4$ alkylcarbonyloxy, $C_1$-$C_4$ alkylsulfonyloxy, $C_1$-$C_4$ haloalkylsulfonyloxy, amino, $C_1$-$C_4$ alkylamino, $C_2$-$C_4$ dialkylamino, formylamino, $C_2$-$C_4$ alkylcarbonylamino, —SF$_5$, —SCN, C$_3$-C$_4$ trialkylsilyl, trimethylsilylmethyl or trimethylsilylmethoxy.

Embodiment 26. A compound of Formula 1 wherein each R$^7$ and R$^{10}$ is independently hydroxy, amino, C$_2$-C$_8$ alkoxyalkyl, C$_3$-C$_8$ alkoxyalkoxyalkyl, C$_2$-C$_8$ haloalkoxyalkyl, C$_2$-C$_8$ haloalkoxyhaloalkoxy, C$_3$-C$_6$ cycloalkyl, cyclopropylmethyl, 1-methylcyclopropyl, 2-methylcyclopropyl, C$_2$-C$_8$ alkylamino, C$_2$-C$_8$ dialkylamino, C$_2$-C$_8$ halodialkylamino or C$_3$-C$_8$ cycloalkylamino; or G$^2$; or each R$^7$ is independently R$^{26}$S(=O)=N—, R$^{26}$S(=O)$_2$NR$^{25}$—C(=O)—, R$^{26}$(R$^{25}$N=)$_q$S(=O)$_p$—, wherein the free bond projecting to the right indicates the connecting point to Q$^1$; or each R$^{10}$ is independently R$^{17}$ON=CR$^{17a}$—, (R$^{18}$)$_2$C=NO—, (R$^{19}$)$_2$NN=CR$^{17a}$—, (R$^{18}$)$_2$C=NNR$^{20a}$—, R$^{20}$N=CR$^{17a}$—, (R$^{18}$)$_2$C=N—, R$^{17}$ON=CR$^{17a}$C(R$^{23b}$)$_2$—, (R$^{18}$)$_2$C=NOC(R$^{24a}$)$_2$—, R$^{26}$S(=O)=N—, R$^{26}$S(=O)$_2$NR$^{25}$—C(=O)— or R$^{26}$(R$^{25}$N=)$_q$S(=O)$_p$—, wherein the free bond projecting to the right indicates the connecting point to Q$^2$;

Embodiment 27. A compound of Embodiment 26 wherein each p and q are independently 0, 1 or 2 in each instance of R$^{26}$(R$^{25}$N=)$_q$S(=O)$_p$—, provided that the sum of u and v is 0, 1 or 2 and when p is 0, q is other than 1 or 2;

Embodiment 28. A compound of Embodiment 26 wherein each R$^{17}$ is independently H, C$_1$-C$_6$ alkyl, C$_3$-C$_8$ cycloalkyl, C$_4$-C$_8$ cycloalkylalkyl, C$_1$-C$_6$ haloalkyl, C$_2$-C$_6$ alkenyl, C$_3$-C$_6$ alkynyl, C$_2$-C$_8$ alkoxyalkyl, C$_2$-C$_8$ haloalkoxyalkyl, C$_2$-C$_8$ alkylthioalkyl, C$_2$-C$_8$ alkylsulfinylalkyl, C$_2$-C$_8$ alkylsulfonylalkyl, C$_2$-C$_8$ alkylcarbonyl, C$_2$-C$_8$ haloalkylcarbonyl, C$_4$-C$_{10}$ cycloalkylcarbonyl, C$_2$-C$_8$ alkoxycarbonyl, C$_2$-C$_8$ haloalkoxycarbonyl, C$_4$-C$_{10}$ cycloalkoxycarbonyl, C$_2$-C$_8$ alkylaminocarbonyl, C$_3$-C$_{10}$ dialkylaminocarbonyl, C$_4$-C$_{10}$ cycloalkylaminocarbonyl, C$_1$-C$_6$ alkylsulfinyl, C$_1$-C$_6$ haloalkylsulfinyl, C$_3$-C$_8$ cycloalkylsulfinyl, C$_1$-C$_6$ alkylsulfonyl, C$_1$-C$_6$ haloalkylsulfonyl, C$_3$-C$_8$ cycloalkylsulfonyl, C$_1$-C$_6$ alkylaminosulfonyl, C$_2$-C$_8$ dialkylaminosulfonyl, C$_3$-C$_{10}$ trialkylsilyl or G$^1$;

each R$^{17a}$ is independently H, C$_1$-C$_6$ alkyl, C$_3$-C$_8$ cycloalkyl, C$_4$-C$_8$ cycloalkylalkyl, C$_1$-C$_6$ haloalkyl, C$_2$-C$_6$ alkenyl, C$_3$-C$_6$ alkynyl, C$_2$-C$_8$ alkoxyalkyl, C$_2$-C$_8$ haloalkoxyalkyl, C$_2$-C$_8$ alkylthioalkyl, C$_2$-C$_8$ alkylsulfinylalkyl, C$_2$-C$_8$ alkylsulfonylalkyl, C$_1$-C$_6$ alkoxy, C$_1$-C$_6$ alkylthio, C$_1$-C$_6$ haloalkylthio, C$_3$-C$_8$ cycloalkylthio, C$_3$-C$_{10}$ trialkylsilyl or G$^1$;

each R$^{18}$ is independently H, hydroxy, C$_1$-C$_6$ alkyl, C$_3$-C$_8$ cycloalkyl, C$_4$-C$_8$ cycloalkylalkyl, C$_1$-C$_6$ haloalkyl, C$_2$-C$_6$ alkenyl, C$_3$-C$_6$ alkynyl, C$_2$-C$_8$ alkoxyalkyl, C$_2$-C$_8$ haloalkoxyalkyl, C$_2$-C$_8$ alkylthioalkyl, C$_2$-C$_8$ alkylsulfinylalkyl, C$_2$-C$_8$ alkylsulfonylalkyl, C$_2$-C$_8$ alkylcarbonyl, C$_2$-C$_8$ haloalkylcarbonyl, C$_4$-C$_{10}$ cycloalkylcarbonyl, C$_2$-C$_8$ alkoxycarbonyl, C$_2$-C$_8$ haloalkoxycarbonyl, C$_4$-C$_{10}$ cycloalkoxycarbonyl, C$_2$-C$_8$ alkylaminocarbonyl, C$_3$-C$_{10}$ dialkylaminocarbonyl, C$_4$-C$_{10}$ cycloalkylaminocarbonyl, C$_1$-C$_6$ alkoxy, C$_1$-C$_6$ alkylthio, C$_1$-C$_6$ haloalkylthio, C$_3$-C$_8$ cycloalkylthio, C$_1$-C$_6$ alkylsulfinyl, C$_1$-C$_6$ haloalkylsulfinyl, C$_3$-C$_8$ cycloalkylsulfinyl, C$_1$-C$_6$ alkylsulfonyl, C$_1$-C$_6$ haloalkylsulfonyl, C$_3$-C$_8$ cycloalkylsulfonyl, C$_1$-C$_6$ alkylaminosulfonyl, C$_2$-C$_8$ dialkylaminosulfonyl, C$_3$-C$_{10}$ trialkylsilyl or G$^1$;

each R$^{19}$ is independently H, C$_1$-C$_6$ alkyl, C$_3$-C$_8$ cycloalkyl, C$_4$-C$_8$ cycloalkylalkyl, C$_1$-C$_6$ haloalkyl, C$_2$-C$_6$ alkenyl, C$_3$-C$_6$ alkynyl, C$_2$-C$_8$ alkoxyalkyl, C$_2$-C$_8$ haloalkoxyalkyl, C$_2$-C$_8$ alkylthioalkyl, C$_2$-C$_8$ alkylsulfinylalkyl, C$_2$-C$_8$ alkylsulfonylalkyl, C$_2$-C$_8$ alkylcarbonyl, C$_2$-C$_8$ haloalkylcarbonyl, C$_4$-C$_{10}$ cycloalkylcarbonyl, C$_2$-C$_8$ alkoxycarbonyl, C$_2$-C$_8$ haloalkoxycarbonyl, C$_4$-C$_{10}$ cycloalkoxycarbonyl, C$_2$-C$_8$ alkylaminocarbonyl, C$_3$-C$_{10}$ dialkylaminocarbonyl, C$_4$-C$_{10}$ cycloalkylaminocarbonyl, C$_1$-C$_6$ alkoxy, C$_1$-C$_6$ alkylsulfinyl, C$_1$-C$_6$ haloalkylsulfinyl, C$_3$-C$_8$ cycloalkylsulfinyl, C$_1$-C$_6$ alkylsulfonyl, C$_1$-C$_6$ haloalkylsulfonyl, C$_3$-C$_8$ cycloalkylsulfonyl, C$_1$-C$_6$ alkylaminosulfonyl, C$_2$-C$_8$ dialkylaminosulfonyl, C$_3$-C$_{10}$ trialkylsilyl or G$^1$;

each R$^{20}$ is independently H, hydroxy, amino, C$_1$-C$_6$ alkyl, C$_3$-C$_8$ cycloalkyl, C$_4$-C$_8$ cycloalkylalkyl, C$_1$-C$_6$ haloalkyl, C$_2$-C$_6$ alkenyl, C$_3$-C$_6$ alkynyl, C$_2$-C$_8$ alkoxyalkyl, C$_2$-C$_8$ haloalkoxyalkyl, C$_2$-C$_8$ alkylthioalkyl, C$_2$-C$_8$ alkylsulfinylalkyl, C$_2$-C$_8$ alkylsulfonylalkyl, C$_2$-C$_8$ alkylcarbonyl, C$_2$-C$_8$ haloalkylcarbonyl, C$_4$-C$_{10}$ cycloalkylcarbonyl, C$_2$-C$_8$ alkoxycarbonyl, C$_2$-C$_8$ haloalkoxycarbonyl, C$_4$-C$_{10}$ cycloalkoxycarbonyl, C$_2$-C$_8$ alkylaminocarbonyl, C$_3$-C$_{10}$ dialkylaminocarbonyl, C$_4$-C$_{10}$ cycloalkylaminocarbonyl, C$_1$-C$_6$ alkoxy, C$_1$-C$_6$ alkylsulfinyl, C$_1$-C$_6$ haloalkylsulfinyl, C$_3$-C$_8$ cycloalkylsulfinyl, C$_1$-C$_6$ alkylsulfonyl, C$_1$-C$_6$ haloalkylsulfonyl, C$_3$-C$_8$ cycloalkylsulfonyl, C$_1$-C$_6$ alkylaminosulfonyl, C$_2$-C$_8$ dialkylaminosulfonyl, C$_3$-C$_{10}$ trialkylsilyl or G$^1$;

each R$^{20a}$ is independently H, C$_1$-C$_6$ alkyl, C$_3$-C$_8$ cycloalkyl, C$_4$-C$_8$ cycloalkylalkyl, C$_1$-C$_6$ haloalkyl, C$_2$-C$_6$ alkenyl, C$_3$-C$_6$ alkynyl, C$_2$-C$_8$ alkoxyalkyl, C$_2$-C$_8$ haloalkoxyalkyl, C$_2$-C$_8$ alkylthioalkyl, C$_2$-C$_8$ alkylsulfinylalkyl, C$_2$-C$_8$ alkylsulfonylalkyl, C$_1$-C$_6$ alkoxy, C$_3$-C$_{10}$ trialkylsilyl or G$^1$;

each R$^{23b}$ is independently H, halogen, cyano, hydroxy, C$_1$-C$_4$ alkyl, C$_3$-C$_8$ cycloalkyl, C$_4$-C$_8$ cycloalkylalkyl, C$_1$-C$_4$ haloalkyl, C$_1$-C$_4$ alkoxy, C$_1$-C$_4$ haloalkoxy, C$_2$-C$_4$ alkoxyalkyl, C$_2$-C$_4$ alkylcarbonyl, C$_2$-C$_4$ alkoxycarbonyl or C$_3$-C$_6$ cycloalkyl;

each R$^{24a}$ is independently H, C$_1$-C$_4$ alkyl, C$_3$-C$_8$ cycloalkyl, C$_4$-C$_8$ cycloalkylalkyl, C$_1$-C$_4$ haloalkyl, C$_1$-C$_4$ alkoxy, C$_1$-C$_4$ haloalkoxy, C$_2$-C$_4$ alkoxyalkyl, C$_2$-C$_4$ alkylcarbonyl, C$_2$-C$_4$ alkoxycarbonyl or C$_3$-C$_6$ cycloalkyl; each R$^{25}$ is independently H, cyano, C$_2$-C$_3$ alkylcarbonyl or C$_2$-C$_3$ haloalkylcarbonyl;

each R$^{26}$ is independently H, C$_1$-C$_6$ alkyl, C$_3$-C$_8$ cycloalkyl, C$_4$-C$_8$ cycloalkylalkyl, C$_1$-C$_6$ haloalkyl, C$_2$-C$_6$ alkenyl, C$_3$-C$_6$ alkynyl, C$_2$-C$_8$ alkoxyalkyl, C$_2$-C$_8$ haloalkoxyalkyl, C$_2$-C$_8$ alkylthioalkyl, C$_2$-C$_8$ alkylsulfinylalkyl, C$_2$-C$_8$ alkylsulfonylalkyl, C$_1$-C$_6$ alkoxy, C$_3$-C$_{10}$ trialkylsilyl or G$^1$; and Embodiment 29. A compound of Formula 1 or Embodiment 26 wherein each G$^2$ is a 5- or 6-membered heterocyclic ring, each optionally substituted on ring members with up to 5 substituents independently selected from R$^{14}$;

Embodiment 30. A compound of Embodiment 25 wherein each R$^7$ is independently halogen, cyano, C$_1$-C$_2$ alkyl, C$_1$-C$_3$ haloalkyl or C$_1$-C$_3$ alkylsulfonyl.

Embodiment 31. A compound of Embodiment 30 wherein each R$^7$ is independently halogen or C$_1$-C$_2$ haloalkyl.

Embodiment 32. A compound of Embodiment 31 wherein each R$^7$ is independently halogen or C$_1$ haloalkyl.

Embodiment 33. A compound of Embodiment 32 wherein each $R^7$ is independently halogen or $C_1$ fluoroalkyl.

Embodiment 34. A compound of Embodiment 33 wherein each $R^7$ is independently halogen or $CF_3$.

Embodiment 35. A compound of Embodiment 34 wherein each $R^7$ is independently F, Cl, Br or $CF_3$.

Embodiment 36. A compound of Embodiment 35 wherein each $R^7$ is independently F or $CF_3$.

Embodiment 37. A compound of Embodiment 35 or 36 wherein at most only one $CF_3$ substituent is present and is at the para position of the $Q^1$ phenyl ring.

Embodiment 38. A compound of Embodiment 25 or Embodiment 26 wherein each $R^{10}$ is independently halogen, cyano, nitro, $C_1$-$C_2$ alkyl, $C_1$-$C_3$ haloalkyl or $C_1$-$C_3$ alkylsulfonyl.

Embodiment 39. A compound of Embodiment 38 wherein each $R^{10}$ is independently halogen or $C_1$-$C_2$ haloalkyl.

Embodiment 40. A compound of Embodiment 39 wherein each $R^{10}$ is independently halogen or $C_1$ haloalkyl.

Embodiment 41. A compound of Embodiment 40 wherein each $R^{10}$ is independently halogen or $C_1$ fluoroalkyl.

Embodiment 42. A compound of Embodiment 41 wherein each $R^{10}$ is independently halogen or $CF_3$.

Embodiment 43. A compound of Embodiment 42 wherein each $R^{10}$ is independently F, Cl, Br or $CF_3$.

Embodiment 44. A compound of Embodiment 43 wherein each $R^{10}$ is independently F or $CF_3$.

Embodiment 45. A compound of Embodiment 44 wherein each $R^{10}$ is F.

Embodiment 46. A compound of Formula 1 or any one of Embodiments 1 through 45 wherein each $R^9$ and $R^{11}$ is independently H or $C_1$-$C_2$ alkyl.

Embodiment 47. A compound of Embodiment 46 wherein, independently, each $R^9$ and $R^{11}$ is $CH_3$.

Embodiment 48. A compound of Formula 1 wherein $Y^1$ and $Y^2$ are each independently $NR^{12}$;

Embodiment 49. A compound of Embodiment 48 wherein each $R^{12}$ is independently hydroxy, CHO, $C_2$-$C_6$ alkylcarbonyl or $C_2$-$C_6$ haloalkylcarbonyl.

Embodiment 50. A compound of Formula 1 or any one of Embodiments 1 through 47 wherein $Y^1$ is O.

Embodiment 51. A compound of Formula 1 or any one of Embodiments 1 through 50 wherein $Y^2$ is O.

Embodiment 52. A compound of Formula 1 or any one of Embodiments 1 through 51 wherein $Y^1$ and $Y^2$ are both O.

Embodiment 53. A compound of Formula 1 wherein $R^1$ is cyano, formyl, $C_3$-$C_8$ alkylcarbonylalkyl, —C($C_1$-$C_4$ alkyl)=N—O($C_1$-$C_4$ alkyl), —C(O)$NH_2$, $C_2$-$C_6$ cyanoalkyl, $C_3$-$C_6$ cycloalkyl, $C_4$-$C_8$ cycloalkenyl; or arylcarbonyl, arylalkenylalkyl, arylcarbonylalkyl or —CPh=N—O($C_1$-$C_4$ alkyl), each optionally substituted on ring members with up to 5 substituents independently selected from $R^{13}$; or $G^1$; or $W^1G^1$.

Embodiment 54. A compound of Embodiment 53 wherein $R^1$ is cyano, formyl, $C_3$-$C_8$ alkylcarbonylalkyl, —C($C_1$-$C_4$ alkyl)=N—O($C_1$-$C_4$ alkyl), —C(O)$NH_2$, $C_2$-$C_6$ cyanoalkyl, $C_3$-$C_6$ cycloalkyl, $C_4$-$C_8$ cycloalkenyl; or arylcarbonyl, arylalkenylalkyl, arylcarbonylalkyl or —CPh=N—O($C_1$-$C_4$ alkyl), each optionally substituted on ring members with up to 5 substituents independently selected from $R^{13}$.

Embodiment 55. A compound of Embodiment 53 wherein $R^1$ is $W^1G^1$.

Embodiment 56. A compound of Embodiment 55 wherein each $G^1$ is independently phenyl, or a 5- or 6-membered heterocyclic ring, each optionally substituted on ring members with up to 5 substituents independently selected from $R^{13}$.

Embodiment 57. A compound of Embodiment 56 wherein $W^1$ is $C_1$-$C_3$ alkylene, $C_2$-$C_4$ alkenylene, $C_2$-$C_4$ alkynylene, —($C_1$-$C_2$ alkylene)C(=O)—, —C(=O)($C_1$-$C_2$ alkylene)-, —$CH_2$O—, —$CH_2$NH—, —$OCH_2$—, —$NCH_2$—, —N—, —O—, —S—, —SO— or —$SO_2$— wherein the free bond projecting to the left indicates the connecting point of $W^1$ to N and the free bond projecting to the right indicates the connecting point of $W^1$ to $G^1$.

Embodiment 58. A compound of Formula 1 or any one of Embodiments 1 through 52 wherein $R^1$ is H, $C_1$-$C_6$ alkyl, $C_1$-$C_6$ haloalkyl, $C_2$-$C_8$ alkylcarbonyl or $C_4$-$C_8$ cycloalkylalkyl.

Embodiment 59. A compound of Embodiment 58 wherein $R^1$ is H, $C_1$-$C_6$ alkyl or $C_1$-$C_6$ haloalkyl.

Embodiment 60. A compound of Embodiment 59 wherein $R^1$ is H, Me, Et or $CHF_2$.

Embodiment 61. A compound of Embodiment 60 wherein $R^1$ is H, Me or Et.

Embodiment 62. A compound of Embodiment 61 wherein $R^1$ is H or $CH_3$.

Embodiment 63. A compound of Embodiment 62 wherein $R^1$ is $CH_3$.

Embodiment 64. A compound of Embodiment 62 wherein $R^1$ is H.

Embodiment 65. A compound of Formula 1 wherein $R^1$ and $R^{2a}$ are taken together as $C_3$-$C_6$ alkylene or —$CH_2OCH_2$—.

Embodiment 66. A compound of Formula 1 wherein wherein $R^2$ and $R^3$ are each independently hydroxy, $C_1$-$C_4$ haloalkyl or $C_1$-$C_4$ alkoxy.

Embodiment 67. A compound of Formula 1 or any one of Embodiments 1 through 20 or Embodiments 24 through 66 wherein $R^2$ is H or $CH_3$.

Embodiment 68. A compound of Embodiment 67 wherein $R^2$ is H.

Embodiment 69. A compound of Formula 1 or any one of Embodiments 1 through 20 or Embodiments 24 through 68 wherein $R^3$ is H or $CH_3$.

Embodiment 70. A compound of Embodiment 69 wherein $R^3$ is H.

Embodiment 71. A compound of Formula 1 wherein $R^2$ and $R^3$ are taken together with the carbon atom to which they are bonded to form a $C_3$-$C_7$ cycloalkyl ring.

Embodiment 72. A compound of Formula 1 wherein $R^4$ and $R^5$ are each independently hydroxy, $C_1$-$C_4$ alkoxy or $C_1$-$C_4$ haloalkyl.

Embodiment 73. A compound of Formula 1 or any one of Embodiments 1 through 71 wherein $R^4$ is H or $CH_3$.

Embodiment 74. A compound of Embodiment 73 wherein $R^4$ is H.

Embodiment 75. A compound of Formula 1 or any one of Embodiments 1 through 74 wherein $R^5$ is H or $CH_3$.

Embodiment 76. A compound of Embodiment 75 wherein $R^5$ is H.

Embodiment 77. A compound of Formula 1 or any one of Embodiments 1 through 76 wherein $R^6$ is H or $CH_3$.

Embodiment 78. A compound of Embodiment 77 wherein $R^6$ is H.

Embodiment 79. A compound of Formula 1 wherein $R^6$ and $Q^2$ are taken together with the nitrogen atom to which they are bonded to form an 8- to 10-membered bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^7$ on carbon atom ring members and selected from $R^9$ on nitrogen atom ring members.

Embodiment 80. A compound of Formula 1 or any one of Embodiments 1 through 78 wherein $Q^2$ is other than 1H-indazol-5-yl optionally substituted at the 3-position.

Embodiment 81. A compound of Embodiment 80 wherein $Q^2$ is other than 1H-indazol-5-yl optionally substituted at the 1- and 3-positions.

Embodiment 82. A compound of Embodiment 81 wherein $Q^2$ is other than optionally substituted 1H-indazol-5-yl.

Embodiment 83. A compound of any one of Embodiments 1 through 82 wherein $Q^1$ is other than unsubstituted phenyl.

Embodiment 84. A compound of any one of Embodiments 1 through 83 wherein $Q^2$ is other than unsubstituted pyridinyl.

Embodiment 85. A compound of any one of Embodiments 1 through 84 wherein $Q^1$ is other than optionally substituted naphthalenyl.

Embodiment 86. A compound of any one of Embodiments 1 through 85 wherein $G^2$ is other than optionally substituted phenyl.

Embodiment 87. A compound of any one of Embodiments 1 through 85 wherein $G^2$ is other then optionally substituted phenyl at the 4 position (of $Q^1$).

Embodiment 88. A compound of any one of Embodiments 1 through 85 wherein $G^2$ is other than optionally substituted phenoxy Embodiment 89. A compound of any one of Embodiments 1 through 85 wherein $G^2$ is other than optionally substituted phenoxy at the 4-position (of $Q^1$).

Embodiment 90. A compound of Formula 1 or any one of Embodiments 1 through 89 wherein the stereochemistry at 4-position is S.

Embodiment 91. A compound of Formula 1 wherein when $R^1$ is H, the $C(Y^2)N(Q^2)(R^6)$ moiety bonded to the carbon at the 3-position and the $Q^1$ moiety bonded to the carbon at the 4-position of the cyclic amide ring are in the trans configuration.

Embodiment 92. A compound of Formula 1 wherein $Q^1$ is an 8- to 10-membered carbocyclic bicyclic ring system, wherein the ring system is optionally substituted with up to 5 substituents independently selected from $R^7$.

Embodiment 93. A compound of Formula 1 wherein $Q^1$ is an 8- to 10-membered heterobicyclic ring system, each ring or ring system containing ring members selected from carbon atoms and 1 to 5 heteroatoms independently selected from up to 2 O, up to 2 S and up to 5 N atoms, wherein up to 3 carbon ring members are independently selected from C(=O) and C(=S), and the sulfur atom ring members are independently selected from $S(=O)_u(=NR^8)_v$, and the ring system is optionally substituted with up to 5 substituents independently selected from $R^7$ on carbon atom ring members and selected from $R^9$ on nitrogen atom ring members.

Embodiment 94. A compound of Formula 1 wherein each of $R^7$ and $R^{10}$ is independently halogen, hydroxy, cyano, nitro, amino, $C_1$-$C_8$ alkyl, $C_1$-$C_8$ cyanoalkyl, $C_1$-$C_8$ cyanoalkoxy, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ nitroalkenyl, $C_2$-$C_8$ alkynyl, $C_2$-$C_8$ haloalkynyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkoxyhaloalkoxy, $C_3$-$C_6$ cycloalkyl, cyclopropylmethyl, 1-methylcyclopropyl, 2-methylcyclopropyl, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ haloalkoxyalkoxy, $C_2$-$C_8$ alkoxyalkoxy, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylamino, $C_2$-$C_8$ dialkylamino, $C_2$-$C_8$ halodialkylamino, $C_2$-$C_8$ alkylaminoalkyl, $C_2$-$C_8$ haloalkylaminoalkyl, $C_4$-$C_{10}$ cycloalkylaminoalkyl, $C_3$-$C_{10}$ dialkylaminoalkyl, —CHO, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH$_2$, $C_2$-$C_8$ alkylaminocarbonyl, $C_4$-$C_{10}$ cycloalkylaminocarbonyl, $C_3$-$C_{10}$ dialkylaminocarbonyl, $C_1$-$C_8$ alkoxy, $C_1$-$C_8$ haloalkoxy, $C_2$-$C_8$ alkoxyalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ cycloalkylsulfonyl, formylamino, $C_2$-$C_8$ alkylcarbonylamino, $C_2$-$C_8$ haloalkylcarbonylamino, $C_3$-$C_8$ cycloalkylamino, $C_2$-$C_8$ alkoxycarbonylamino, $C_1$-$C_6$ alkylsulfonylamino, $C_1$-$C_6$ haloalkylsulfonylamino, —SF$_5$, —SCN, SO$_2$NH$_2$, $C_3$-$C_{12}$ trialkylsilyl, $C_4$-$C_{12}$ trialkylsilylalkyl or $C_4$-$C_{12}$ trialkylsilylalkoxy; or $G^2$.

Embodiment 95. A compound of Formula 1 wherein each of $R^9$ and $R^{11}$ is independently cyano, $C_1$-$C_3$ alkyl, $C_2$-$C_3$ alkenyl, $C_2$-$C_3$ alkynyl, $C_3$-$C_6$ cycloalkyl, $C_2$-$C_3$ alkoxyalkyl, $C_1$-$C_3$ alkoxy, $C_2$-$C_3$ alkylcarbonyl, $C_2$-$C_3$ alkoxycarbonyl, $C_2$-$C_3$ alkylaminoalkyl or $C_3$-$C_4$ dialkylaminoalkyl Embodiment 96. A compound of Formula 1 wherein at least one of $R^7$ is $C_1$-$C_8$ hydroxyalkyl.

Embodiment 97. A compound of Formula 1 wherein at least one of $R^9$ is $C_1$-$C_8$ hydroxyalkyl.

Embodiment 98. A compound of Formula 1 wherein at least one of $R^{10}$ is $C_1$-$C_8$ hydroxyalkyl.

Embodiment 99. A compound of Formula 1 wherein at least one of $R^{11}$ is $C_1$-$C_8$ hydroxyalkyl.

Embodiments of this disclosure, including Embodiments 1-99 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this disclosure, including Embodiments 1-91 above as well as any other embodiments described herein, and any combination thereof, pertain to the compositions and methods of the present disclosure.

Embodiment T1. A compound of Formula 1 wherein $Q^1$ is a 4- or 7-membered heterocyclic ring or an 8- to 10-membered bicyclic ring system, each ring or ring system containing ring members selected from carbon atoms and 1 to 5 heteroatoms independently selected from up to 2 O, up to 2 S and up to 5 N atoms, wherein up to 3 carbon ring members are independently selected from C(=O) and C(=S), and the sulfur atom ring members are independently selected from $S(=O)_u$ $(=NR^8)_v$, each ring or ring system optionally substituted with up to 5 substituents independently selected from $R^7$ on carbon atom ring members and selected from $R^9$ on nitrogen atom ring members.

Embodiment T2. A compound of Formula 1 wherein $Q^1$ is $C_2$-$C_{10}$ alkenyl, $C_2$-$C_{10}$ alkynyl, $C_2$-$C_{10}$ haloalkenyl, $C_2$-$C_{10}$ haloalkynyl, $C_4$-$C_{10}$ cycloalkenyl, $C_4$-$C_{10}$ halocycloalkenyl, $C_2$-$C_8$ alkylcarbonyl or $C_2$-$C_8$ alkoxyalkyl.

Embodiment T3. A compound of Formula 1 wherein $Q^2$ is a 4- or 7-membered heterocyclic ring or an 8- to 10-membered bicyclic ring system, each ring or ring system containing ring members selected from carbon atoms and 1 to 5 heteroatoms independently selected from up to 2 O, up to 2 S and up to 5 N atoms, wherein up to 3 carbon ring members are independently selected from C(=O) and C(=S), and the sulfur atom ring members are independently selected from $S(=O)_u$ $(=NR^8)_v$, each ring or ring system optionally substituted with up to 5 substituents independently selected from $R^7$ on carbon atom ring members and selected from $R^9$ on nitrogen atom ring members.

Embodiment T4. A compound of Formula 1 wherein $Q^2$ is $C_2$-$C_{10}$ alkenyl, $C_2$-$C_{10}$ alkynyl, $C_2$-$C_{10}$ haloalkenyl, $C_2$-$C_{10}$ haloalkynyl, $C_4$-$C_{10}$ cycloalkenyl, $C_4$-$C_{10}$ halocycloalkenyl, $C_2$-$C_8$ alkylcarbonyl or $C_2$-$C_8$ alkoxyalkyl.

Embodiment T5. A compound of Formula 1 wherein J is $-CR^2R^3-$, $-NR^{2a}-$ or $-O-$.

Embodiment T6. A compound of Embodiment T5 wherein J is $-CR^2R^3-$.

Embodiment T7. A compound of Embodiment T5 wherein J is $-NR^{2a}-$.

Embodiment T8. A compound of Embodiment T5 wherein J is $-O-$.

Embodiment T9. A compound of Formula 1 wherein $R^1$ is cyano, formyl, $C_3$-$C_8$ alkylcarbonylalkyl, $-C(C_1$-$C_4$ alkyl)=N-O($C_1$-$C_4$ alkyl), $-C(O)NH_2$, $C_2$-$C_6$ cyanoalkyl, $C_3$-$C_6$ cycloalkyl; or arylcarbonyl, arylalkenylalkyl, arylcarbonylalkyl or $-CPh=N-O(C_1$-$C_4$ alkyl), each optionally substituted on ring members with up to 5 substituents independently selected from $R^{13}$; or $G^1$; or $W^1G^1$.

Embodiment T10. A compound of Embodiment T9 wherein each $G^1$ is independently phenyl, or a 5- or 6-membered heterocyclic ring, each optionally substituted on ring members with up to 5 substituents independently selected from $R^{13}$.

Embodiment T11. A compound of Embodiment T9 wherein $W^1$ is $C_1$-$C_3$ alkylene, $C_2$-$C_4$ alkenylene, $C_2$-$C_4$ alkynylene, $-(C_1$-$C_2$ alkylene)C(=O)-, $-C(=O)(C_1$-$C_2$ alkylene)-, $-CH_2O-$, $-CH_2NH-$, $-OCH_2-$, $-NCH_2-$, $-N-$, $-O-$, $-S-$, $-SO-$ or $-SO_2-$ wherein the free bond projecting to the left indicates the connecting point of $W^1$ to N and the free bond projecting to the right indicates the connecting point of $W^1$ to $G^1$.

Embodiment T12. A compound of Formula 1 wherein $R^2$ and $R^3$ are each independently hydroxy, $C_1$-$C_4$ haloalkyl or $C_1$-$C_4$ alkoxy.

Embodiment T13. A compound of Embodiment T7 wherein $R^{2a}$ is $C_1$-$C_6$ alkyl, $C_2$-$C_6$ alkenyl, $C_3$-$C_6$ alkynyl or $C_1$-$C_6$ alkoxy.

Embodiment T14. A compound of Formula 1 wherein $R^1$ and $R^{2a}$ are taken together as $C_3$-$C_6$ alkylene or $-CH_2OCH_2-$.

Embodiment T15. A compound of Formula 1 wherein $R^4$ and $R^5$ are each independently hydroxy, $C_1$-$C_4$ alkoxy or $C_1$-$C_4$ haloalkyl.

Embodiment T16. A compound of Formula 1 wherein $R^6$ and $Q^2$ are taken together with the nitrogen atom to which they are bonded to form an 8- to 10-membered bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^7$ on carbon atom ring members and selected from $R^9$ on nitrogen atom ring members.

Embodiment T17. A compound of Formula 1 wherein each $R^7$ and $R^{10}$ is independently hydroxy, amino, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkoxyhaloalkoxy, $C_3$-$C_6$ cycloalkyl, cyclopropylmethyl, 1-methylcyclopropyl, 2-methylcyclopropyl, $C_2$-$C_8$ alkylamino, $C_2$-$C_8$ dialkylamino, $C_2$-$C_8$ halodialkylamino or $C_3$-$C_8$ cycloalkylamino; or $G^2$; or each $R^7$ is independently $R^{26}S(=O)=N-$, $R^{26}S(=O)_2NR^{25}-C(=O)-$, $R^{26}(R^{25}N=)_qS(=O)_p-$, wherein the free bond projecting to the right indicates the connecting point to $Q^1$; or each $R^{10}$ is independently $R^{17}ON=CR^{17a}-$, $(R^{18})_2C=NO-$, $(R^{19})_2NN=CR^{17a}-$, $(R^{18})_2C=NNR^{20a}-$, $R^{20}N=CR^{17a}-$, $(R^{18})_2C=N-$, $R^{17}ON=CR^{17a}C(R^{23b})_2-$, $(R^{18})_2C=NOC(R^{24a})_2-$, $R^{26}S(=O)=N-$, $R^{26}S(=O)_2NR^{25}-C(=O)-$ or $R^{26}(R^{25}N=)_qS(=O)_p-$, wherein the free bond projecting to the right indicates the connecting point to $Q^2$.

Embodiment T18. A compound of Embodiment T17 wherein each p and q are independently 0, 1 or 2 in each instance of $R^{26}(R^{25}N=)_qS(=O)_p-$, provided that the sum of u and v is 0, 1 or 2 and when p is 0, q is other than 1 or 2.

Embodiment T19. A compound of Formula 1 wherein $Y^1$ and $Y^2$ are each independently $NR^{12}$.

Embodiment T20. A compound of Embodiment T18 wherein each $R^{12}$ is independently hydroxy, CHO, $C_2$-$C_6$ alkylcarbonyl or $C_2$-$C_6$ haloalkylcarbonyl.

Embodiment T21. A compound of Formula 1 wherein each $G^2$ is a 5- or 6-membered heterocyclic ring, each optionally substituted on ring members with up to 5 substituents independently selected from $R^{14}$.

Embodiment T22. A compound of Formula 1 wherein each $R^{17}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{17a}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy, $C_1$-$C_6$ alkylthio, $C_1$-$C_6$ haloalkylthio, $C_3$-$C_8$ cycloalkylthio, $C_3$-$C_{10}$ trialkylsilyl or $G^1$;

each $R^{18}$ is independently H, hydroxy, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{19}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{20}$ is independently H, hydroxy, amino, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylsulfinyl, $C_1$-$C_6$ haloalkylsulfinyl, $C_3$-$C_8$ cycloalkylsulfinyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{20a}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy, $C_3$-$C_{10}$ trialkylsilyl or $G^1$;

each $R^{23b}$ is independently H, halogen, cyano, hydroxy, $C_1$-$C_4$ alkyl, $C_3$-$C_8$ cycloalkyl, $C_4$-$C_8$ cycloalkylalkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl or $C_3$-$C_6$ cycloalkyl;

each $R^{24a}$ is independently H, $C_1$-$C_4$ alkyl, $C_3$-$C_8$ cycloalkyl, $C_4$-$C_8$ cycloalkylalkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl or $C_3$-$C_6$ cycloalkyl; each $R^{25}$ is independently H, cyano, $C_2$-$C_3$ alkylcarbonyl or $C_2$-$C_3$ haloalkylcarbonyl;

each $R^{26}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy, $C_3$-$C_{10}$ trialkylsilyl or $G^1$.

Embodiment U1. A compound of Formula 1 wherein $Q^1$ is other than a phenyl ring or a naphthalenyl ring system, each ring or ring system optionally substituted with up to 5 substituents independently selected from $R^7$; or a 5- to 6-membered fully unsaturated heterocyclic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from S(=O)$_u$(=NR$^8$)$_v$, each ring or ring system optionally substituted with up to 5 substituents independently selected from $R^7$ on carbon atom ring members and selected from $R^9$ on nitrogen atom ring members.

Embodiment U2. A compound of Formula 1 wherein $Q^2$ is other than a phenyl ring or a naphthalenyl ring system, each ring or ring system optionally substituted with up to 5 substituents independently selected from $R^{10}$; or a 5- to 6-membered fully unsaturated heterocyclic ring or an 8- to 10-membered heteroaromatic bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from S(=O)$_u$(=NR$^8$)$_v$, each ring or ring system optionally substituted with up to 5 substituents independently selected from $R^{10}$ on carbon atom ring members and selected from $R^{11}$ on nitrogen atom ring members.

Embodiment U3. A compound of Formula 1 wherein $Y^1$ is other than O, S or NR$^{12}$.

Embodiment U4. A compound of Formula 1 wherein $Y^2$ is other than O, S or NR$^{12}$.

Embodiment U5. A compound of Formula 1 wherein $R^1$ is other than H, hydroxy, amino, $C_1$-$C_6$ alkyl, $C_1$-$C_6$ haloalkyl, $C_2$-$C_6$ alkenyl, $C_3$-$C_6$ alkynyl, $C_4$-$C_8$ cycloalkylalkyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$.

Embodiment U6. A compound of Formula 1 wherein $R^2$ and $R^3$, independently, are other than H, halogen or $C_1$-$C_4$ alkyl.

Embodiment U7. A compound of Formula 1 wherein $R^2$ and $R^3$ are taken together with the carbon atom to which they are bonded to form other than a $C_3$-$C_7$ cycloalkyl ring.

Embodiment U8. A compound of Formula 1 wherein $R^4$ and $R^5$, independently, are each other than H, halogen or $C_1$-$C_4$ alkyl.

Embodiment U9. A compound of Formula 1 wherein $R^6$ is other than H, hydroxy, amino, $C_1$-$C_6$ alkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$.

Embodiment U10. A compound of Formula 1 wherein each $R^7$ and $R^{10}$, independently, is other than halogen, cyano, nitro, $C_1$-$C_8$ alkyl, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ nitroalkenyl, $C_2$-$C_8$ alkynyl, $C_2$-$C_8$ haloalkynyl, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ alkoxyalkyl, $C_2$-$C_8$ haloalkoxyalkyl, $C_3$-$C_8$ haloalkoxyalkoxy, $C_3$-$C_8$ alkoxyalkoxy, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_3$-$C_8$ haloalkylaminoalkyl, $C_4$-$C_{10}$ cycloalkylaminoalkyl, $C_3$-$C_{10}$ dialkylaminoalkyl, —CHO, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH$_2$, $C_2$-$C_8$ alkylaminocarbonyl, $C_4$-$C_{10}$ cycloalkylaminocarbonyl, $C_3$-$C_{10}$ dialkylaminocarbonyl, $C_1$-$C_8$ alkoxy, $C_1$-$C_8$ haloalkoxy, $C_2$-$C_8$ alkoxyalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ cycloalkylsulfonyl, formylamino, $C_2$-$C_8$ alkylcarbonylamino, $C_2$-$C_8$ haloalkylcarbonylamino, $C_2$-$C_8$ alkoxycarbonylamino, $C_1$-$C_6$ alkylsulfonylamino, $C_1$-$C_6$ haloalkylsulfonylamino, —SF$_5$, —SCN, SO$_2$NH$_2$, $C_3$-$C_{12}$ trialkylsilyl, $C_4$-$C_{12}$ trialkylsilylalkyl, $C_4$-$C_{12}$ trialkylsilylalkoxy or $G^2$.

Embodiment U11. A compound of Formula 1 wherein each $R^8$ is other than H, cyano, $C_2$-$C_3$ alkylcarbonyl or $C_2$-$C_3$ haloalkylcarbonyl.

Embodiment U12. A compound of Formula 1 wherein each $R^9$ and $R^{11}$, independently, is other than cyano, $C_1$-$C_3$ alkyl, $C_2$-$C_3$ alkenyl, $C_2$-$C_3$ alkynyl, $C_3$-$C_6$ cycloalkyl, $C_2$-$C_3$ alkoxyalkyl, $C_1$-$C_3$ alkoxy, $C_2$-$C_3$ alkylcarbonyl, $C_2$-$C_3$ alkoxycarbonyl, $C_2$-$C_3$ alkylaminoalkyl or $C_3$-$C_4$ dialkylaminoalkyl.

Embodiment U13. A compound of Formula 1 wherein each $R^{12}$ is other than H, cyano, $C_1$-$C_4$ alkyl, $C_1$-$C_4$ haloalkyl, —(C=O)CH$_3$ or —(C=O)CF$_3$.

Embodiment U14. A compound of Formula 1 wherein each $G^1$, independently, is other than phenyl, phenylmethyl (i.e. benzyl), pyridinylmethyl, phenylcarbonyl (i.e. benzoyl), phenoxy, phenylethynyl, phenylsulfonyl or a 5- or 6-membered heteroaromatic ring, each optionally substituted on ring members with up to 5 substituents independently selected from $R^{13}$.

Embodiment U15. A compound of Formula 1 wherein each $G^2$, independently, is other than phenyl, phenylmethyl (i.e. benzyl), pyridinylmethyl, phenylcarbonyl (i.e. benzoyl), phenoxy, phenylethynyl, phenylsulfonyl or a 5- or 6-membered heteroaromatic ring, each optionally substituted on ring members with up to 5 substituents independently selected from $R^{14}$.

Embodiment U16. A compound of Formula 1 wherein each $R^{13}$ and $R^{14}$, independently, is other than halogen, cyano, hydroxy, amino, nitro, —CHO, —C(=O)OH, —C(=O)NH$_2$, —SO$_2$NH$_2$, $C_1$-$C_6$ alkyl, $C_1$-$C_6$ haloalkyl, $C_2$-$C_6$ alkenyl, $C_2$-$C_6$ alkynyl, $C_2$-$C_8$ alkylcarbonyl, $C_2$-$C_8$ haloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylaminosulfonyl, $C_2$-$C_8$ dialkylaminosulfonyl, $C_3$-$C_{10}$ trialkylsilyl, $C_1$-$C_6$ alkylamino, $C_2$-$C_8$ dialkylamino, $C_2$-$C_8$ alkylcarbonylamino, $C_1$-$C_6$ alkylsulfonylamino, phenyl, pyridinyl or thienyl.

Embodiment U17. A compound of Formula 1 wherein each u and v, independently, is other than 0, 1 or 2 in each instance of S(=O)$_u$(=NR$^8$)$_v$, provided that the sum of u and v is 0, 1 or 2.

Embodiment U18. A compound of Formula 1 other than wherein $Y^1$ is O; $Y^2$ is O; $R^1$ is H; J is —CR$^2$R$^3$—; $R^2$ is H; $R^3$ is H; $R^4$ is H; $R^5$ is H, $Q^1$ is Ph(3,4-di-F); $Q^2$ is 1,3-benzodioxol-4-yl(2,2-di-F); and $R^6$ is H.

Embodiment U19. A compound of Formula 1 other than wherein $Y^1$ is O; $Y^2$ is O; $R^1$ is H; J is —CR$^2$R$^3$—; $R^2$ is H; $R^3$ is H; $R^4$ is H; $R^5$ is H, $Q^1$ is 1,3-benzodioxol-5-yl(2,2-di-F); $Q^2$ is Ph(2,3-di-F); and $R^6$ is H.

Embodiment U20. A compound of Formula 1 other than wherein $Y^1$ is O; $Y^2$ is O; $R^1$ is H; J is —CR$^2$R$^3$—; $R^2$ is H; $R^3$ is H; $R^4$ is H; $R^5$ is H, $Q^1$ is 1,3-benzodioxol-5-yl(2,2-di-F); $Q^2$ is Ph(2-F); and $R^6$ is H.

Embodiment U21. A compound of Formula 1 other than wherein $Y^1$ is O; $Y^2$ is O; $R^1$ is H; J is —CR$^2$R$^3$—; $R^2$ is H; $R^3$ is H; $R^4$ is H; $R^5$ is H, $Q^1$ is 1,3-benzodioxol-5-yl(2,2-di-F); $Q^2$ is Ph(2-CF$_3$); and $R^6$ is H.

Embodiment U22. A compound of Formula 1 other than wherein $Y^1$ is O; $Y^2$ is O; $R^1$ is H; J is —CR$^2$R$^3$—; $R^2$ is H; R³ is H; R⁴ is H; R⁵ is H, Q¹ is 1,3-benzodioxol-5-yl(2,2-di-F); Q² is Ph(2-F); and R⁶ is H.

Embodiment U23. A compound of Formula 1 other than wherein Y¹ is O; Y² is O; R¹ is H; J is —CR²R³—; R² is H; R³ is H; R⁴ is H; R⁵ is H, Q¹ is 1,3-benzodioxol-5-yl(2,2-di-F); Q² is Ph(2,3,4-tri-F); and R⁶ is H.

Embodiment U24. A compound of Formula 1 other than wherein Y¹ is O; Y² is O; R¹ is Me; J is —CR²R³—; R² is H; R³ is H; R⁴ is H; R⁵ is H, Q¹ is Ph(3-CF₃); Q² is Ph(2-F); and R⁶ is H.

Embodiments of this disclosure, including Embodiments T1 through T22, Embodiments U1 through U24 above as well as any other embodiments (including Embodiments 1 through 91) as described herein, can be combined in any manner, and the descriptions of variables in the embodiments pertain not only to the compounds of Formula 1 but also to the starting compounds and intermediate compounds useful for preparing the compounds of Formula 1. In addition, embodiments of this disclosure, including Embodiments 1-91 above and Embodiments T1 through T22 and Embodiments U1 through U24 as well as any other embodiments described herein, and any combination thereof, pertain to the compositions and methods of the present disclosure.

Specific embodiments include compounds of Formula 1 selected from the group consisting of:

(3S,4S)—N-(2,3-difluorophenyl)-1-methyl-2-oxo-4-[4-(trifluoromethyl)phenyl]-3-pyrrolidinecarboxamide (Compound 623);

(3S,4S)-4-(3,4-difluorophenyl)-N-(2-fluorophenyl)-1-methyl-2-oxo-3-pyrrolidinecarboxamide (Compound 596);

(3S,4S)—N-(2,3-difluorophenyl)-4-(3,4-difluorophenyl)-1-methyl-2-oxo-3-pyrrolidinecarboxamide (Compound 639); and (3S,4S)—N-(2-fluorophenyl)-1-methyl-2-oxo-4-[4-(trifluoromethyl)phenyl]-3-pyrrolidinecarboxamide (Compound 622).

Specific Embodiments include a compound of Formula 1 selected from the group consisting of Compound Numbers (where the Compound Number refers to the compound in Index Tables A, B, C, D, E or F): 353, 354, 355, 357, 358, 359, 360, 441, 442, 443, 444, 511, 524, 525, 684, 685, 714, 715 and 716.

This disclosure also relates to a method for controlling undesired vegetation comprising applying to the locus of the vegetation herbicidally effective amounts of the compounds of this disclosure (e.g., as a composition described herein). Of note as embodiments relating to methods of use are those involving the compounds of embodiments described above. Many compounds of this disclosure are particularly useful for selective control of weeds in crops such as wheat, barley, maize, soybean, sunflower, cotton, oilseed rape and rice, and specialty crops such as sugarcane, citrus, fruit and nut crops.

Also noteworthy as embodiments are herbicidal compositions of the present disclosure comprising the compounds of embodiments described above.

This disclosure also includes a herbicidal mixture comprising (a) a compound selected from Formula 1, N-oxides, and salts thereof, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, metam, methyldymron, oleic acid, oxaziclomefone, pelargonic acid and pyributicarb, and (b16) herbicide safeners; and salts of compounds of (b1) through (b16).

"Photosystem II inhibitors" (b1) are chemical compounds that bind to the D-1 protein at the $Q_B$-binding niche and thus block electron transport from $Q_A$ to $Q_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The $Q_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazon, nitriles such as bromoxynil and phenyl-pyridazines such as pyridate. Examples of photosystem II inhibitors include ametryn, amicarbazone, atrazine, bentazon, bromacil, bromofenoxim, bromoxynil, chlorbromuron, chloridazon, chlorotoluron, chloroxuron, cumyluron, cyanazine, daimuron, desmedipham, desmetryn, dimefuron, dimethametryn, diuron, ethidimuron, fenuron, fluometuron, hexazinone, ioxynil, isoproturon, isouron, lenacil, linuron, metamitron, methabenzthiazuron, metobromuron, metoxuron, metribuzin, monolinuron, neburon, pentanochlor, phenmedipham, prometon, prometryn, propanil, propazine, pyridafol, pyridate, siduron, simazine, simetryn, tebuthiuron, terbacil, terbumeton, terbuthylazine, terbutryn and trietazine. Of note is a compound of the disclosure mixed with atrazine, bromoxynil or metribuzin.

"AHAS inhibitors" (b2) are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for protein synthesis and cell growth. Examples of AHAS inhibitors include amidosulfuron, azimsulfuron, bensulfuron-methyl, bispyribac-sodium, cloransulam-methyl, chlorimuron-ethyl, chlorsulfuron, cinosulfuron, cyclosulfamuron, diclosulam, ethametsulfuron-methyl, ethoxysulfuron, flazasulfuron, florasulam, flucarbazone-sodium, flumetsulam, flupyrsulfuron-methyl, flupyrsulfuron-sodium, foramsulfuron, halosulfuron-methyl, imazamethabenzmethyl, imazamox, imazapic, imazapyr, imazaquin, imazethapyr, imazosulfuron, iodosulfuron-methyl (including sodium salt), iofensulfuron (2-iodo-N-[[(4-methoxy-6-methyl-1,3,5-triazin-2-yl)amino]carbonyl]benzenesulfonamide), mesosulfuron-methyl, metazosulfuron (3-chloro-4-(5,6-dihydro-5-methyl-1,4,2-dioxazin-3-yl)-N-[[(4,6-dimethoxy-2-pyrimidinyl)amino]carbonyl]-1-methyl-1H-pyrazole-5-sulfonamide), metosulam, metsulfuron-methyl, nicosulfuron, oxasulfuron, penoxsulam, primisulfuron-methyl, propoxycarbazone-sodium, propyrisulfuron (2-chloro-N-[[(4,6-dimethoxy-2-pyrimidinyl)amino]carbonyl]-6-propylimidazo[1,2-b]pyridazine-3-sulfonamide), prosulfuron, pyrazosulfuron-ethyl, pyribenzoxim, pyriftalid, pyriminobac-methyl, pyrithiobac-sodium, rimsulfuron, sulfometuron-methyl, sulfosulfuron, thiencarbazone, thifensulfuron-methyl, triafamone (N-[2-[(4,6-dimethoxy-1,3,5-triazin-2-yl)carbonyl]-6-fluorophenyl]-1,1-difluoro-N-methylmethanesulfonamide), triasulfuron, tribenuron-methyl, trifloxysulfuron (including sodium salt), triflusulfuron-methyl and tritosulfuron. Of note is a compound of this disclosure mixed with nicosulfuron, flupyrsulfuron or chlorimuron.

"ACCase inhibitors" (b3) are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include alloxydim, butroxydim, clethodim, clodinafop, cycloxydim, cyhalofop, diclofop, fenoxaprop, fluazifop, haloxyfop, pinoxaden, profoxydim, propaquizafop, quizalofop, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl. Of note is a compound of this disclosure mixed with pinoxaden or quizalofop.

Auxin is a plant hormone that regulates growth in many plant tissues. "Auxin mimics" (b4) are chemical compounds mimicking the plant growth hormone auxin, thus causing uncontrolled and disorganized growth leading to plant death in susceptible species. Examples of auxin mimics include aminocyclopyrachlor (6-amino-5-chloro-2-cyclopropyl-4-pyrimidinecarboxylic acid) and its methyl and ethyl esters and its sodium and potassium salts, aminopyralid, benazolin-ethyl, chloramben, clacyfos, clomeprop, clopyralid, dicamba, 2,4-D, 2,4-DB, dichlorprop, fluroxypyr, halauxifen (4-amino-3-chloro-6-(4-chloro-2-fluoro-3-methoxyphenyl)-2-pyridinecarboxylic acid), halauxifen-methyl (methyl 4-amino-3-chloro-6-(4-chloro-2-fluoro-3-methoxyphenyl)-2-pyridinecarboxylate), MCPA, MCPB, mecoprop, picloram, quinclorac, quinmerac, 2,3,6-TBA, triclopyr, and methyl 4-amino-3-chloro-6-(4-chloro-2-fluoro-3-methoxyphenyl)-5-fluoro-2-pyridinecarboxylate. Of note is a compound of this disclosure mixed with dicamba.

"EPSP synthase inhibitors" (b5) are chemical compounds that inhibit the enzyme, 5-enol-pyruvylshikimate-3-phosphate synthase, which is involved in the synthesis of aromatic amino acids such as tyrosine, tryptophan and phenylalanine. EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate).

"Photosystem I electron diverters" (b6) are chemical compounds that accept electrons from Photosystem I, and after several cycles, generate hydroxyl radicals. These radicals are extremely reactive and readily destroy unsaturated lipids, including membrane fatty acids and chlorophyll. This destroys cell membrane integrity, so that cells and organelles "leak", leading to rapid leaf wilting and desiccation, and eventually to plant death. Examples of this second type of photosynthesis inhibitor include diquat and paraquat.

"PPO inhibitors" (b7) are chemical compounds that inhibit the enzyme protoporphyrinogen oxidase, quickly resulting in formation of highly reactive compounds in plants that rupture cell membranes, causing cell fluids to leak out. Examples of PPO inhibitors include acifluorfen-sodium, azafenidin, benzfendizone, bifenox, butafenacil, carfentrazone, carfentrazone-ethyl, chlomethoxyfen, cinidon-ethyl, fluazolate, flufenpyr-ethyl, flumiclorac-pentyl, flumioxazin, fluoroglycofen-ethyl, fluthiacet-methyl, fomesafen, halosafen, lactofen, oxadiargyl, oxadiazon, oxyfluorfen, pentoxazone, profluazol, pyraclonil, pyraflufen-ethyl, saflufenacil, sulfentrazone, thidiazimin, trifludimoxazin (dihydro-1,5-dimehyl-6-thioxo-3-[2,2,7-trifluoro-3,4-dihydro-3-oxo-4-(2-propyn-1-yl)-2H-1,4-benzoxazin-6-yl]-1,3,5-triazine-2,4(1H,3H)-dione) and tiafenacil (methyl N-[2-[[2-chloro-5-[3,6-dihydro-3-methyl-2,6-dioxo-4-(trifluoromethyl)-1(2H)-pyrimidinyl]-4-fluorophenyl]thiol]-1-oxopropyl]-β-alaninate).

"GS inhibitors" (b8) are chemical compounds that inhibit the activity of the glutamine synthetase enzyme, which plants use to convert ammonia into glutamine. Consequently, ammonia accumulates and glutamine levels decrease. Plant damage probably occurs due to the combined effects of ammonia toxicity and deficiency of amino acids required for other metabolic processes. The GS inhibitors include glufosinate and its esters and salts such as glufosinate-ammonium and other phosphinothricin derivatives, glufosinate-P ((2S)-2-amino-4-(hydroxymethylphosphinyl)butanoic acid) and bilanaphos.

"VLCFA elongase inhibitors" (b9) are herbicides having a wide variety of chemical structures, which inhibit the elongase. Elongase is one of the enzymes located in or near chloroplasts which are involved in biosynthesis of VLCFAs. In plants, very-long-chain fatty acids are the main constituents of hydrophobic polymers that prevent desiccation at the leaf surface and provide stability to pollen grains. Such herbicides include acetochlor, alachlor, anilofos, butachlor, cafenstrole, dimethachlor, dimethenamid, diphenamid, fenoxasulfone (3-[[(2,5-dichloro-4-ethoxyphenyl)methyl]sulfonyl]-4,5-dihydro-5,5-dimethylisoxazole), fentrazamide, flufenacet, indanofan, mefenacet, metazachlor, metolachlor, naproanilide, napropamide, napropamide-M ((2R)—N,N-diethyl-2-(1-naphthalenyloxy)propanamide), pethoxamid, piperophos, pretilachlor, propachlor, propisochlor, pyroxasulfone, and thenylchlor, including resolved forms such as S-metolachlor and chloroacetamides and oxyacetamides. Of note is a compound of this disclosure mixed with flufenacet.

"Auxin transport inhibitors" (b10) are chemical substances that inhibit auxin transport in plants, such as by binding with an auxin-carrier protein. Examples of auxin transport inhibitors include diflufenzopyr, naptalam (also known as N-(1-naphthyl)phthalamic acid and 2-[(1-naphthalenylamino)carbonyl]benzoic acid).

"PDS inhibitors" (b11) are chemical compounds that inhibit carotenoid biosynthesis pathway at the phytoene desaturase step. Examples of PDS inhibitors include beflubutamid, diflufenican, fluridone, flurochloridone, flurtamone norflurzon and picolinafen.

"HPPD inhibitors" (b12) are chemical substances that inhibit the biosynthesis of synthesis of 4-hydroxyphenyl-pyruvate dioxygenase. Examples of HPPD inhibitors include benzobicyclon, benzofenap, bicyclopyrone (4-hydroxy-3-[[2-[(2-methoxyethoxy)methyl]-6-(trifluoromethyl)-3-pyridinyl]carbonyl]bicyclo[3.2.1]oct-3-en-2-one), fenquinotrione (2-[[8-chloro-3,4-dihydro-4-(4-methoxyphenyl)-3-oxo-2-quinoxalinyl]carbonyl]-1,3-cyclohexanedione), isoxachlortole, isoxaflutole, mesotrione, pyrasulfotole, pyrazolynate, pyrazoxyfen, sulcotrione, tefuryltrione, tembotrione, tolpyralate (1-[[1-ethyl-4-[3-(2-methoxy-ethoxy)-2-methyl-4-(methylsulfonyl)benzoyl]-1H-pyrazol-5-yl]oxy]ethyl methyl carbonate), topramezone, 5-chloro-3-[(2-hydroxy-6-oxo-1-cyclohexen-1-yl)carbonyl]-1-(4-methoxyphenyl)-2(1H)-quinoxalinone, 4-(2,6-diethyl-4-methylphenyl)-5-hydroxy-2,6-dimethyl-3(2H)-pyridazinone, 4-(4-fluorophenyl)-6-[(2-hydroxy-6-oxo-1-cyclohexen-1-yl)carbonyl]-2-methyl-1,2,4-triazine-3,5(2H,4H)-dione, 5-[(2-hydroxy-6-oxo-1-cyclohexen-1-yl)carbonyl]-2-(3-methoxyphenyl)-3-(3-methoxypropyl)-4(3H)-pyrimidinone, 2-methyl-N-(4-methyl-1,2,5-oxadiazol-3-yl)-3-(methylsulfinyl)-4-(trifluoromethyl)benzamide and 2-methyl-3-(methylsulfonyl)-N-(1-methyl-1H-tetrazol-5-yl)-4-(trifluoromethyl)benzamide. Of note is a compound of this disclosure mixed with mesotrione or pyrasulfatole.

"HST inhibitors" (b13) disrupt a plant's ability to convert homogentisate to 2-methyl-6-solanyl-1,4-benzoquinone, thereby disrupting carotenoid biosynthesis. Examples of HST inhibitors include haloxydine, pyriclor, 3-(2-chloro-3,6-difluorophenyl)-4-hydroxy-1-methyl-1,5-naphthyridin-2(1H)-one, 7-(3,5-dichloro-4-pyridinyl)-5-(2,2-difluoro-ethyl)-8-hydroxypyrido[2,3-b]pyrazin-6(5H)-one and 4-(2,6-diethyl-4-methylphenyl)-5-hydroxy-2,6-dimethyl-3(2H)-pyridazinone.

HST inhibitors also include compounds of Formulae A and B.

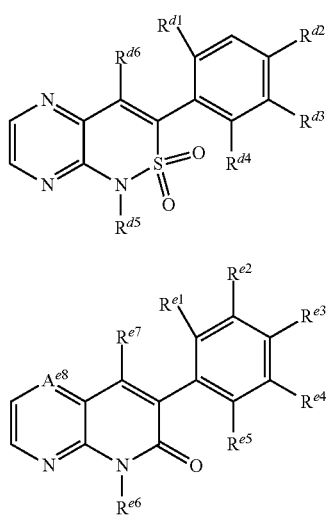

wherein $R^{d1}$ is H, Cl or CF$_3$; $R^{d2}$ is H, Cl or Br; $R^{d3}$ is H or Cl; $R^{d4}$ is H, Cl or CF$_3$; $R^{d5}$ is CH$_3$, CH$_2$CH$_3$ or CH$_2$CHF$_2$; and $R^{d6}$ is OH, or —OC(=O)-i-Pr; and $R^{e1}$ is H, F, Cl, CH$_3$ or CH$_2$CH$_3$; $R^{e2}$ is H or CF$_3$; $R^{e3}$ is H, CH$_3$ or CH$_2$CH$_3$; $R^{e4}$ is H, F or Br; $R^{e5}$ is Cl, CH$_3$, CF$_3$, OCF$_3$ or CH$_2$CH$_3$; $R^{e6}$ is H, CH$_3$, CH$_2$CHF$_2$ or C≡CH; $R^{e7}$ is OH, —OC(=O)Et, —OC(=O)-i-Pr or —OC(=O)-t-Bu; and $A^{e8}$ is N or CH.

"Cellulose biosynthesis inhibitors" (b14) inhibit the biosynthesis of cellulose in certain plants. They are most effective when applied preemergence or early postemergence on young or rapidly growing plants. Examples of cellulose biosynthesis inhibitors include chlorthiamid, dichlobenil, flupoxam, indaziflam (N$^2$-[(1R,2S)-2,3-dihydro-2,6-dimethyl-1H-inden-1-yl]-6-(1-fluoroethyl)-1,3,5-triazine-2,4-diamine), isoxaben and triaziflam.

"Other herbicides" (b15) include herbicides that act through a variety of different modes of action such as mitotic disruptors (e.g., flamprop-M-methyl and flamprop-M-isopropyl), organic arsenicals (e.g., DSMA, and MSMA), 7,8-dihydropteroate synthase inhibitors, chloroplast isoprenoid synthesis inhibitors and cell-wall biosynthesis inhibitors. Other herbicides include those herbicides having unknown modes of action or do not fall into a specific category listed in (b1) through (b14) or act through a combination of modes of action listed above. Examples of other herbicides include aclonifen, asulam, amitrole, bromobutide, cinmethylin, clomazone, cumyluron, cyclopyrimorate (6-chloro-3-(2-cyclopropyl-6-methylphenoxy)-4-pyridazinyl 4-morpholinecarboxylate), daimuron, difenzoquat, etobenzanid, fluometuron, flurenol, fosamine, fosamine-ammonium, dazomet, dymron, ipfencarbazone (1-(2,4-dichlorophenyl)-N-(2,4-difluorophenyl)-1,5-dihydro-N-(1-methylethyl)-5-oxo-4H-1,2,4-triazole-4-carboxamide), metam, methyldymron, oleic acid, oxaziclomefone, pelargonic acid, pyributicarb and 5-[[(2,6-difluorophenyl)methoxy]methyl]-4,5-dihydro-5-methyl-3-(3-methyl-2-thienyl)isoxazole.

"Herbicide safeners" (b16) are substances added to a herbicide formulation to eliminate or reduce phytotoxic effects of the herbicide to certain crops. These compounds protect crops from injury by herbicides but typically do not prevent the herbicide from controlling undesired vegetation. Examples of herbicide safeners include but are not limited to benoxacor, cloquintocet-mexyl, cumyluron, cyometrinil, cyprosulfamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride, oxabetrinil, N-(aminocarbonyl)-2-methylbenzenesulfonamide and N-(aminocarbonyl)-2-fluorobenzenesulfonamide, 1-bromo-4-[(chloromethyl)sulfonyl]]benzene, 2-(dichloromethyl)-2-methyl-1,3-dioxolane (MG 191), 4-(dichloroacetyl)-1-oxa-4-azospiro-[4.5]decane (MON 4660), 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide. Of note is dietholate, 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide (alternatively named N-(2-methoxybenzoyl)-4-[(methylaminocarbonyl)amino] benzenesulfonamide; CAS #129531-12-0). Of particular note is 2-methoxy-N-[[4-[[(methylamino)carbonyl]amino]phenyl]sulfonyl]-benzamide (alternatively named N-(2-methoxybenzoyl)-4-[(methylaminocarbonyl)amino] benzenesulfonamide; CAS #129531-12-0) mixed with any one of the compounds listed in Index Tables A, B, C, D, E or F.

The compounds of Formula 1 can be prepared by general methods known in the art of synthetic organic chemistry. Of note are the following methods described in Schemes 1-22 and variations thereof. The definitions of R$^1$, R$^2$, R$^{2a}$, R$^3$, R$^4$, R$^5$, R$^6$, Q$^1$, Q$^2$, J, Y$^1$, and Y$^2$ in the compounds of Formulae 1 through 20 below are as defined above in the Summary unless otherwise noted. Formulae 1a-1h, 2b, 3a-3b, 4b, 5a, 5a', 5a'' and 10a are various subsets of a compound of Formulae 1, 2, 3, 4, 5 and 10 respectively. Substituents for each subset formula are as defined for its parent formula unless otherwise noted.

As shown in Scheme 1 compounds of Formula 1a (i.e. Formula 1 wherein R$^1$, R$^4$ and R$^5$ are H, Y$^1$ and Y$^2$ are O and J is —CR$^2$R$^3$—) can be prepared by reaction of acids of Formula 2 with amines of Formula 3 in the presence of a dehydrative coupling reagent such as propylphosphonic anhydride, dicyclohexylcarbodiimide, N-(3-dimethylaminopropyl)-N'-ethylcarbodiimide, N,N'-carbonyldiimidazole, 2-chloro-1,3-dimethylimidazolium chloride or 2-chloro-1-methylpyridinium iodide. Polymer-supported reagents, such as polymer-supported cyclohexylcarbodiimide, are also suitable. These reactions are typically run at temperatures ranging from 0-60° C. in a solvent such as dichloromethane, acetonitrile, N,N-dimethylformamide or ethyl acetate in the presence of a base such as triethylamine, N,N-diisopropylamine, or 1,8-diazabicyclo[5.4.0]undec-7-ene. See *Organic Process Research & Development* 2009, 13, 900-906 for coupling conditions employing propylphosphonic anhydride. The method of Scheme 1 utilizing propylphosphonic anhydride is illustrated by Step E of Synthesis Example 1. Substituents in the 3- and 4-positions of the pyrrolidinone ring of compounds of Formula 1a, i.e. C(O)N($Q^2$)($R^6$) and $Q^1$, respectively, are predominantly in the trans configuration. In some instances, the presence of minor amounts of the cis isomer can be detected by NMR.

Scheme 1

2

1a

As shown in Scheme 2 compounds of Formula 2 can be prepared by hydrolysis of esters of Formula 4 by methods well known to those skilled in the art. Hydrolysis is carried out with aqueous base or aqueous acid, typically in the presence of a co-solvent. Suitable bases for the reaction include, but are not limited to, hydroxides such as sodium and potassium hydroxide and carbonates such as sodium and potassium carbonate. Suitable acids for the reaction include, but are not limited to, inorganic acids such as hydrochloric acid, hydrobromic acid and sulfuric acid, and organic acids such as acetic acid and trifluoroacetic acid. A wide variety of co-solvents are suitable for the reaction including, but not limited to, methanol, ethanol and tetrahydrofuran. The reaction is conducted at temperatures ranging from −20° C. to the boiling point of the solvent, and typically from 0 to 100° C. The method of Scheme 2 is illustrated by Step D of Synthesis Example 1.

Scheme 2

4

R' is lower alkyl

2

As shown in Scheme 3, compounds of Formula 4 can be obtained by reduction of compounds of Formula 5 and subsequent in situ cyclization of the resulting intermediate amine. A wide variety of methods for reduction of the aliphatic nitro group in compounds of Formula 5 are known in the literature. Methods well known to those skilled in the art include catalytic hydrogenation in the presence of palladium on carbon or Raney nickel, iron or zinc metal in acidic medium (see, for example, *Berichte der Deutschen Chemischen Gesellschaft* 1904, 37, 3520-3525), and lithium aluminum hydride. Reduction can also be achieved with samarium(II) iodide in the presence of a proton source such as methanol (see for example, *Tetrahedron Letters* 1991, 32 (14), 1699-1702). Alternatively sodium borohydride in the presence of a nickel catalyst such as nickel(II) acetate or nickel(II) chloride can be used (see for example, *Tetrahedron Letters* 1985, 26 (52), 6413-6416). The method of Scheme 3 utilizing sodium borohydride in the presence of nickel(II) acetate is illustrated by Step C of Synthesis Example 1. Specific examples of a compound of Formula 4 that is useful in the preparation of a compound of Formula 1 can be found in Tables I through IV.

Scheme 3

R' is lower alkyl

5

-continued

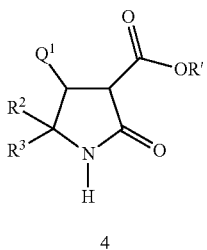

4

As shown in Scheme 4, compounds of Formula 5 can be prepared by reacting diesters of Formula 6 with nitroalkanes of Formula 7, typically in the presence of a base. Suitable bases for the reaction include alkali metal lower alkoxides such as sodium methoxide in methanol or sodium ethoxide in ethanol. The method of Scheme 4 is illustrated by Step B of Synthesis Example 1. Compounds of Formula 6 can readily be prepared by methods known to those skilled in the art, e.g., by Knoevenagel condensation of aldehydes and malonates (see for example G. Jones, *Organic Reactions* Volume 15, John Wiley and Sons, 1967).

Scheme 4

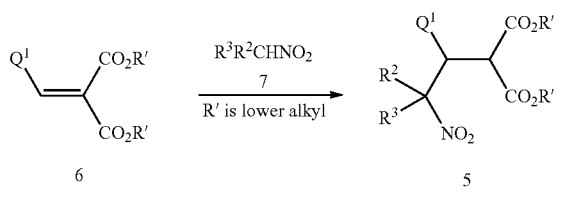

Compounds of Formula 5a (i.e. Formula 5 wherein $R^2$ and $R^3$ are H) can be prepared by reacting nitroalkenes of Formula 8 with malonates of Formula 9 in the presence of a base as shown in Scheme 5. Suitable bases for this reaction include, but are not limited to, alkali metal lower alkoxides such as sodium methoxide in methanol or sodium ethoxide in ethanol, or bases such as lithium bis(trimethylsilyl)amide, sodium bis(trimethylsilyl)amide and lithium diisopropylamide in solvents such as tetrahydrofuran. Typically, the reaction is carried out in the range of from −78° C. to 23° C. See *Synthesis* 2005, 2239-2245 for conditions for effecting this transformation. Conditions for effecting this transformation in refluxing water in the absence of a catalyst have been reported in *Synthetic Communications* 2013, 43, 744-748. Nitroalkenes of Formula 8 can readily be prepared from aldehydes and nitromethane by methods known to those skilled in the art.

Scheme 5

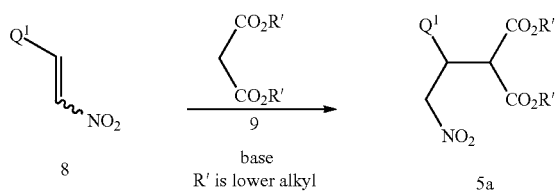

Compounds of Formula 5a' and 5a" can be prepared stereoselectively by reacting nitroalkenes of Formula 8 with malonates of Formula 9 in the presence of a chiral catalyst and optionally in the presence of a suitable base as shown in Scheme 5A. Suitable catalysts include, but are not limited to Ni(II) with vicinal diamine ligands such as Ni(II) Bis[(R,R)—N,N'-dibenzylcyclohexane-1,2-diamine]dibromide, Ni(II) Bi[(S,S)—N,N'-dibenzylcyclohexane-1,2-diamine] dibromide or nickel(II) bromide with chiral 1,1'-bi(tetrahydroisoquinoline) type diamines. Suitable organic bases for this reaction include, but are not limited to, piperidine, morpholine, triethylamine, 4-methylmorpholine or N,N-diisopropylethylamine. This transformation can be accomplished neat or in solvents such as tetrahydrofuran, toluene or dichloromethane. Typically, the reaction is carried out in the range of from −78° C. to 80° C. using 0 to 1 equivalent of catalyst and optionally 0 to 1 equivalent of a base. Conditions for effecting this transformation have been reported in *J. Am. Chem. Soc.* 2005, 9958-9959 or *Eur. J. Org. Chem.* 2011, 5441-5446 for conditions. Nitroalkenes of Formula 8 can readily be prepared from aldehydes and nitromethane by methods known to those skilled in the art.

Scheme 5A

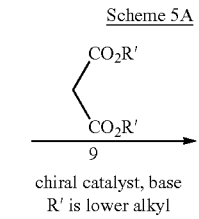

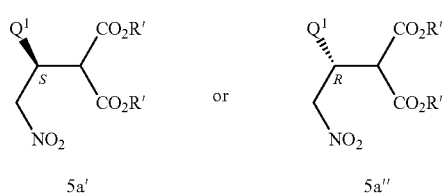

As shown in Scheme 6, compounds of Formula 1a can also be prepared by reductive cyclization of compounds of Formula 10 analogous to the method of Scheme 3. As also shown in Scheme 6, compounds of Formula 1b (i.e. Formula 1 wherein $R^1$ is OH, $R^4$ and $R^5$ are H, and $Y^1$ and $Y^2$ are O) can be prepared from compounds of Formula 10 by catalytic transfer hydrogenation with ammonium formate in the presence of palladium on carbon, and subsequent in situ cyclization of the intermediate hydroxylamine. See *J. Med. Chem.* 1993, 36, 1041-1047 for catalytic transfer hydrogenation/cyclization conditions to produce N-hydroxypyrrolidinones. The method of Scheme 6 for preparing N-hydroxypyrrolidinones is illustrated by Step D of Synthesis Example 3.

Scheme 6

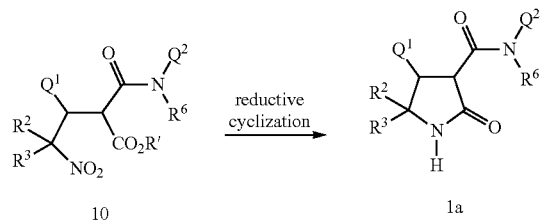

Scheme 8

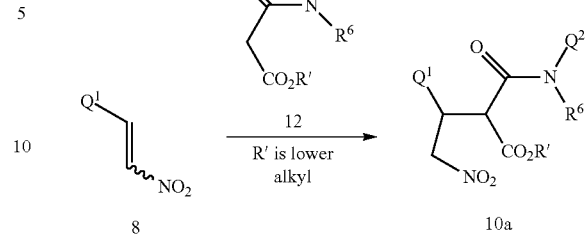

As shown in Scheme 9, compounds of Formula 11 can be prepared by reaction of malonic amide Formula 12 with aldehydes of Formula 14 by methods known to those skilled in the art. As also shown in Scheme 9, malonates of Formula 12 can readily be prepared from lower alkyl malonyl chlorides of Formula 13 such as methyl malonyl chloride and amines of Formula 3 by methods known to those skilled in the art. The method of Scheme 9 is illustrated by Steps A and B of Synthesis Example 3.

Scheme 9

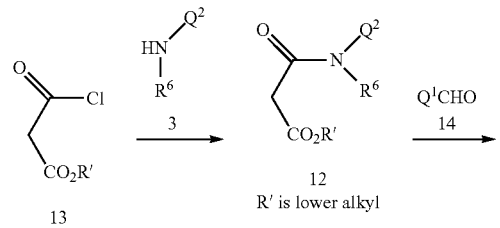

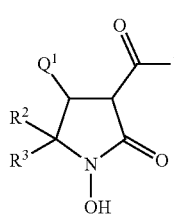

As shown in Scheme 7, compounds of Formula 10 can be prepared by reacting compounds of Formula 11 with nitroalkanes of Formula 7 in a solvent, in the presence of a base analogous to the method described in Scheme 4. The method of Scheme 7 is illustrated by Step C of Synthesis Example 3.

Scheme 7

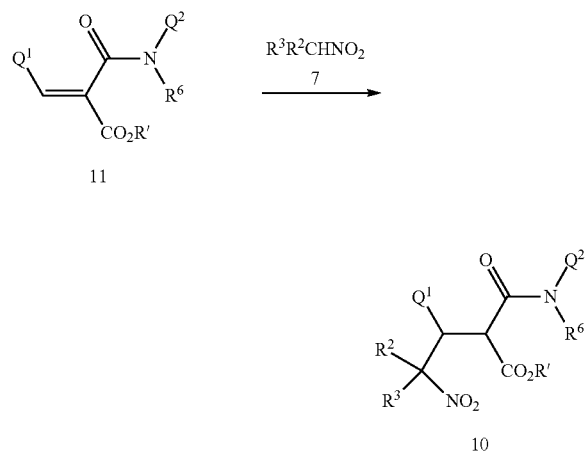

As shown in Scheme 8, compounds of Formula 10a (i.e. Formula 10 wherein $R^2$ and $R^3$ are H) can be prepared, analogous to the method of Scheme 5, by reacting nitroalkenes of Formula 8 with malonates of Formula 12.

As shown in Scheme 10, mixtures of compounds of Formula 1c (i.e. Formula 1 wherein $R^1$ and $R^5$ are H, $R^4$ is halogen and $Y^1$ and $Y^2$ are O) and Formula 1d (i.e. Formula 1 wherein $R^1$ and $R^4$ are H, $R^5$ is halogen and $Y^1$ and $Y^2$ are O) can be prepared by reacting compounds of Formula 1a with a halogen source in a solvent, in the presence or absence of an initiator. Separation of the regioisomers produced in this reaction can be achieved by standard methods such as chromatography or fractional crystallization. Suitable halogen sources for this reaction include bromine, chlorine, N-chlorosuccinimide, N-bromosuccinimide and N-iodosuccinimide. Suitable initiators for this reaction include 2,2'-azobisisobutyronitrile (AIBN) and benzoyl peroxide. Typically, the reaction is carried out in solvents such as dichloromethane in the range of from 0° C. to the boiling point of the solvent. The method of Scheme 10 is illustrated by Synthesis Example 2.

Scheme 10

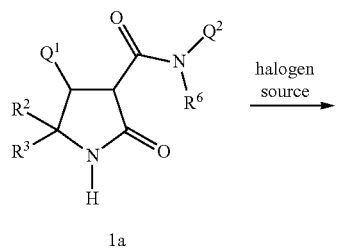

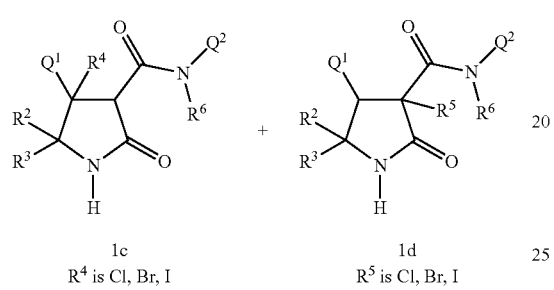

As shown in Scheme 11, compounds of Formula 1e (i.e. Formula 1 wherein $R^1$ is $NH_2$, $R^4$ and $R^5$ are H and $Y^1$ and $Y^2$ are O) can be prepared by reacting compounds of Formula 1a with an aminating reagent such as O-(diphenylphosphinyl)hydroxylamine and hydroxylamino-O-sulphonic acid. For procedures, conditions and reagents see *Bioorganic & Medicinal Chemistry Letters* 2009, 19, 5924-5926 and *Journal of Organic Chemistry* 2002, 67, 6236-6239.

Scheme 11

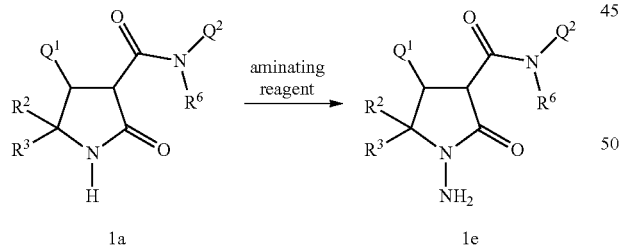

As shown in Scheme 12, compounds of Formula 1f (i.e. Formula 1 wherein $R^4$, $R^5$ and $R^6$ are H and $Y^1$ is O) can be produced by reaction of compounds of Formula 15 with isocyanates (i.e. Formula 16 wherein $Y^2$ is O) or isothiocyanates (i.e. Formula 16 wherein $Y^2$ is S) in the presence of base. Examples of the base which can be used for the present process include those listed for the method of Scheme 4. The reaction temperature can be selected from the range of from −78° C. to the boiling point of an inert solvent used. Typically, the reaction is carried out at temperatures ranging from −78° C. to 100° C. in solvents such as toluene.

Scheme 12

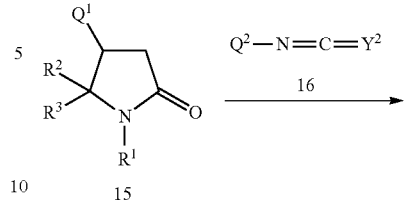

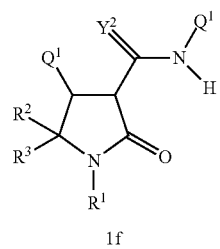

As shown in Scheme 13, compounds of Formula 15 can be prepared by reaction of compounds of Formula 17 with corresponding electrophiles of Formula 18 in the presence of base. In Formula 18, G denotes a leaving group, i.e. a nucleofuge. Depending upon selection of $R^1$, suitable electrophiles for the reaction can include alkyl halides such as chlorides, bromides and iodides, alkylsulfonates, acid anhydrides such as tert-butoxycarbonyl anhydride and acetic anhydride, and haloalkylsilanes such as chlorotrimethylsilane. Suitable bases for the reaction include inorganic bases such as alkali or alkaline earth metal (e.g., lithium, sodium, potassium and cesium) hydroxides, alkoxides, carbonates, and phosphates, and organic bases such as triethylamine, N,N-diisopropylethylamine and 1,8-diazabicyclo[5.4.0]undec-7-ene. A wide variety of solvents are suitable for the reaction including, for example but not limited to, tetrahydrofuran, dichloromethane, N,N-dimethylformamide, N,N-dimethylacetamide, N-methylpyrrolidinone, acetonitrile, $C_2$-$C_6$ alcohols and acetone as well as mixtures of these solvents. This reaction is conducted at temperatures ranging from −20 to 200° C., and typically between 0 and 50° C.

Scheme 13

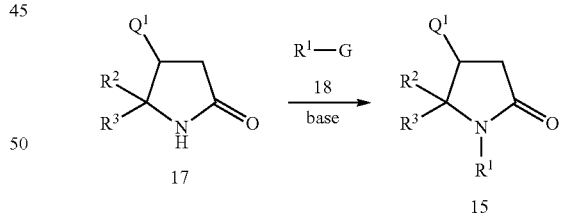

As shown in Scheme 14, compounds of Formula 17 can be prepared by decarboxylation of acids of Formula 2 by methods well known to those skilled in the art. Decarboxylation is carried by heating compounds of Formula 2 in a solvent, typically in the presence of an acid. Suitable acids for the reaction include, but are not limited to, p-toluenesulfonic acid. A wide variety of co-solvents are suitable for the reaction including, but not limited to, toluene, isopropanol acetate and isobutyl methylketone. The reaction is conducted at temperatures ranging from −20° C. and to the boiling point of the solvent, and typically from 0 to 150° C. The method of Scheme 14 is illustrated by Step A of Synthesis Example 6.

Scheme 14

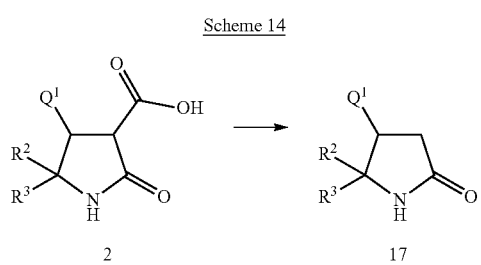

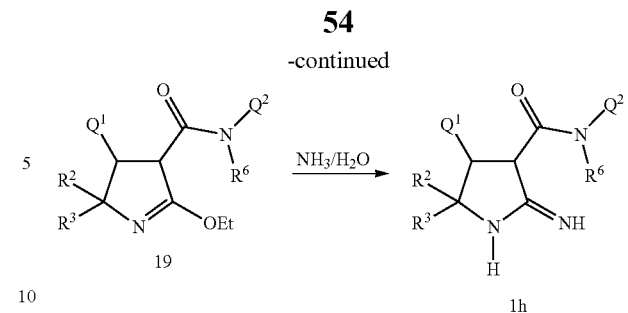

As shown in Scheme 15, compounds of Formula 1g (i.e. Formula 1 wherein $R^1$ is H, $R^4$ and $R^5$ are H, and $Y^1$ and $Y^2$ are S) can be prepared by reacting compounds of Formula 1a with at least two equivalents of a thionation reagent such as Lawesson's reagent, tetraphosphorus decasulfide or diphosphorus pentasulfide in a solvent such as tetrahydrofuran or toluene. Typically, the reaction is carried out at temperatures ranging from 0 to 115° C. One skilled in the art recognizes that using less than two equivalents of the thionating reagent can provide mixtures comprising Formula 1 products wherein $Y^1$ is O and $Y^2$ is S, or $Y^1$ is S and $Y^2$ is O, which can be separated by conventional methods such as chromatography and crystallization.

As shown in Scheme 17, compounds of Formula 1b (i.e. Formula 1 wherein J is $-NR^{2a}-$ or $-O-$; $R^{2a}$ is H; $R^1$, $R^4$, $R^5$ are H; and $Y^1$ and $Y^2$ are both O) can be prepared from acids of Formula 2b using the method as described in Scheme 1.

Scheme 15

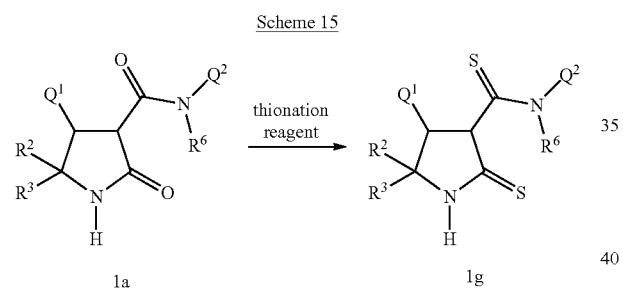

Scheme 17

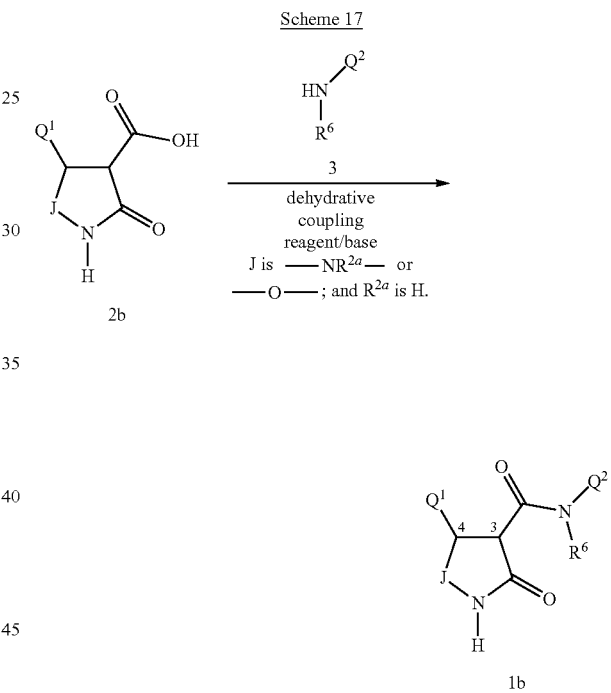

As shown in Scheme 16, compounds of Formula 1h (i.e. Formula 1 wherein $R^1$, $R^4$, $R^5$ are H, $Y^2$ is O and $Y^1$ is NH) can be prepared by alkylation of compounds of Formula 1a triethyloxonium tetrafluoroborate (Meerwein's reagent) followed by treatment of the resulting imino ether of Formula 19 with aqueous ammonia. The method of Scheme 16 is illustrated by Steps A and B of Synthesis Example 4.

As shown in Scheme 18, a compound of Formula 2b can be prepared by hydrolysis of esters of Formula 4b by the method described in Scheme 2.

Scheme 16

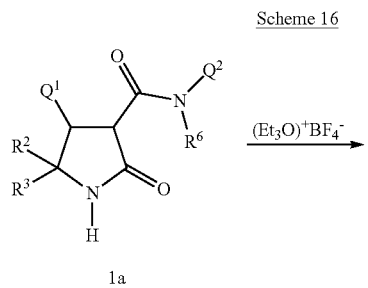

Scheme 18

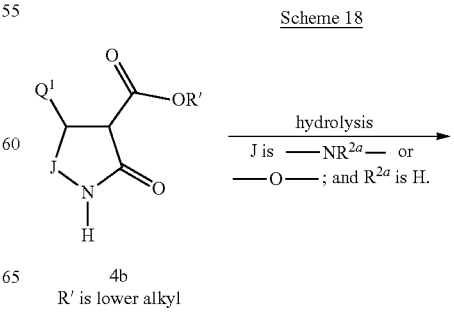

-continued

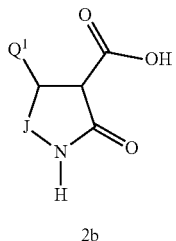
2b

As shown in Scheme 19, esters of Formula 4b can be prepared from diesters of Formula 6 and compounds of Formula 3a using a one step addition-cyclization procedure. The compounds of Formula 3a can be hydroxylamine, hydrazine or hydrazide derivatives. The reaction is carried out optionally in the presence of an acid or base and typically in the presence of a co-solvent. Suitable acids for the reaction include, but are not limited to, inorganic acids such as hydrochloric acid, hydrobromic acid and sulfuric acid, and organic acids such as acetic acid and trifluoroacetic acid. Suitable bases for the reaction include, but are not limited to, hydroxides such as sodium and potassium hydroxide, alkoxides such as sodium and potassium ethoxide, carbonates such as sodium and potassium carbonate, sodium hydride, metal amides such as lithium diisopropylamide and sodium hexamethyldisilazide and neutral nitrogen-containing bases such as triethylamine, N,N-diisopropylamine and 1,8-diazabicyclo[5.4.0]undec-7-ene. A wide variety of co-solvents are suitable for the reaction including, but not limited to, water, methanol, ethanol and tetrahydrofuran. The reaction is conducted at temperatures ranging from −20° C. to the boiling point of the solvent, and typically from 0 to 150° C. Diesters of Formula 6 can readily be prepared by Knoevenagel condensation of aldehydes and malonates (see for example G. Jones, *Organic Reactions* Volume 15, John Wiley and Sons, 1967).

Scheme 19

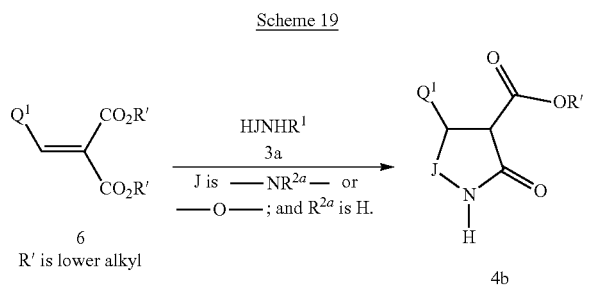

As shown in Scheme 20, the synthesis of a compound of Formula 4b can also be achieved by a two-step procedure proceeding through the formation and subsequent deprotetion/cyclization of an intermediate compound of Formula 20. A compound of Formula 20 can be obtained by carrying out the addition reaction of a compound of Formula 6 with an appropriate protected hydroxylamine, hydrazine or hydrazide derivative, optionally in the presence of an acid or base and typically in the presence of a co-solvent. Suitable protecting groups denoted as PG include, but are not limited to, tert-butyloxycarbonyl or carboxybenzyl. Suitable acids for the reaction include, but are not limited to, inorganic acids such as hydrochloric acid, hydrobromic acid and sulfuric acid, and organic acids such as acetic acid and trifluoroacetic acid. Suitable bases for the reaction include, but are not limited to, hydroxides such as sodium and potassium hydroxide, alkoxides such as sodium and potassium ethoxide, carbonates such as sodium and potassium carbonate, sodium hydride, metal amides such as lithium diisopropylamide and sodium hexamethyldisilazide and neutral nitrogen-containing bases such as triethylamine, N,N-diisopropylamine and 1,8-diazabicyclo[5.4.0]undec-7-ene. A wide variety of co-solvents are suitable for the reaction including, but not limited to, water, methanol, ethanol and tetrahydrofuran. The reaction is conducted at temperatures ranging from −20° C. to the boiling point of the solvent, and typically from 0 to 150° C. Deprotection of a compound of Formula 20 can be carried out by a method obvious to one skilled in the art. If the subsequent cyclization does not occur spontaneously upon deprotection, it can be carried out under the conditions listed above for the one step addition-cyclization.

Scheme 20

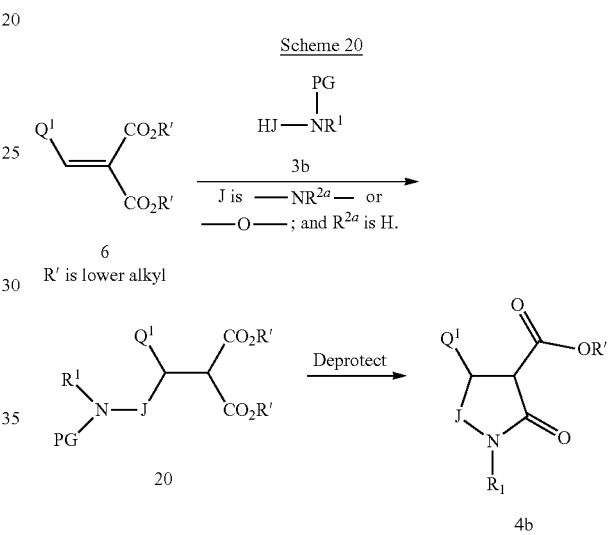

Alternatively, as shown in Schemes 21 and 22, a compound of Formula 1b can be prepared from amides of Formula 11 using the same methods as described in Schemes 19 and 20.

Scheme 21

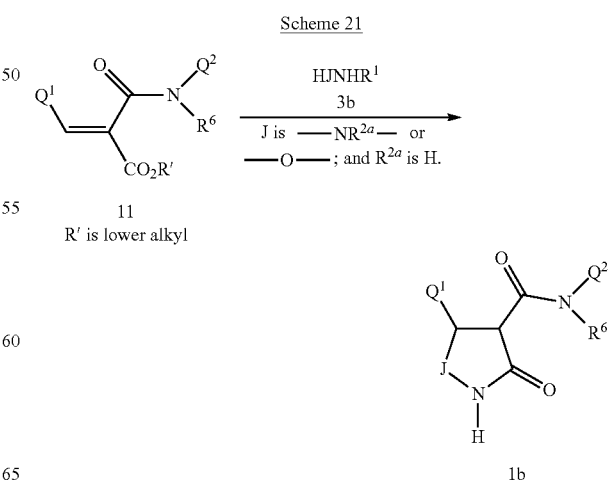

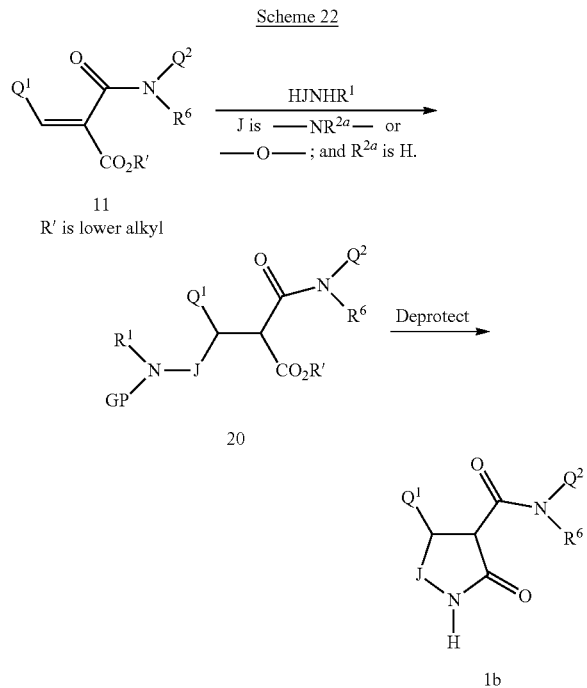

Scheme 22

11
R' is lower alkyl

20

1b

It is recognized by one skilled in the art that various functional groups can be converted into others to provide different compounds of Formula 1. For a valuable resource that illustrates the interconversion of functional groups in a simple and straightforward fashion, see Larock, R. C., *Comprehensive Organic Transformations: A Guide to Functional Group Preparations*, 2nd Ed., Wiley-VCH, New York, 1999. For example, intermediates for the preparation of compounds of Formula 1 may contain aromatic nitro groups, which can be reduced to amino groups, and then be converted via reactions well known in the art such as the Sandmeyer reaction, to various halides, providing compounds of Formula 1. The above reactions can also in many cases be performed in alternate order It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present disclosure to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane in $CDCl_3$ solution unless indicated otherwise; "s" means singlet, "d" means doublet, "t" means triplet, "q" means quartet, "m" means multiplet and "br s" means broad singlet. $^{19}$F NMR spectra are reported in ppm downfield from $CFCl_3$ in $CDCl_3$ unleuss indicated otherwise. The enantiomeric ratio (ER) was determined by chiral high performance liquid chromatography analysis using a Chiralpak AD-RH column and eluting with a 50:50 isopropanol/water mixture at 40° C. at 0.3 mL/min.

SYNTHESIS EXAMPLE 1

Preparation of 4-(3-chloro-4-fluorophenyl)-2-oxo-N-[2-(trifluoromethyl)phenyl]-3-pyrrolidinecarboxamide (e.g. a compound of Formula 1 wherein $Y^1$ and $Y^2$ are both O; J is —$CR^2R^3$—; $R^2$ and $R^3$ are both H; $Q^1$ is Ph(3-Cl, 4-F); $Q^2$ is Ph(2-$CF_3$); $R^4$ and $R^5$ are both H; $R^6$ is H; and $R^1$ is H.)

Step A: Preparation of 1,3-diethyl 2-(3-chloro-4-fluorophenyl)methylenepropanedioate A mixture of 3-chloro-4-fluorobenzaldehyde (3 g, 18.9 mmol), diethyl malonate (3.16 mL, 20.8 mmol), piperidine (0.37 mL, 3.8 mmol) and toluene (40 mL) was refluxed for 18 h with continuous removal of water (Dean-Stark trap). The cooled reaction mixture was concentrated under reduced pressure, and the residue was chromatographed on silica gel, eluted with 0% to 10% ethyl acetate in hexanes, to afford the title compound as a yellow oil (5 g).

$^1$H NMR δ 7.61 (m, 1H), 7.61 (m, 1H), 7.53 (m, 1H), 7.35 (m, 1H), 7.15 (m, 1H), 4.33 (m, 4H), 1.33 (m, 6H).

Step B: Preparation 1,3-diethyl 2-[1-(3-chloro-4-fluorophenyl)-2-nitroethyl]-propanedioate A mixture of 1,3-diethyl 2-(3-chloro-4-fluorophenyl)methylenepropanedioate (i.e. the product of Step A, 5 g, 16.7 mmol), nitromethane (8.9 mL, 166 mmol) and a methanol solution of sodium methoxide (25 wt %, 0.36 g, 1.67 mmol) in ethanol (60 mL) was stirred at 23° C. for 18 h. The reaction mixture was then concentrated under reduced pressure to afford a thick oil, which was diluted with 25% ethyl acetate in hexanes and filtered through a pad of Celite® diatomaceous filter aid to remove insoluble particulates. The filtrate was concentrated under reduced pressure to afford the title compound as a yellow oil (5.3 g).

¹H NMR δ 7.32 (m, 1H), 7.15 (m, 1H), 7.10 (m, 1H), 4.87 (m, 2H), 4.22 (m, 3H), 4.07 (m, 2H), 3.76 (d, 1H), 1.27 (m, 3H), 1.12 (m, 3H).

Step C: Preparation of ethyl 4-(3-chloro-4-fluorophenyl)-2-oxo-3-pyrrolidinecarboxylate A stirred mixture of 1,3-diethyl 2-[1-(3-chloro-4-fluorophenyl)-2-nitroethyl]-propanedioate (i.e. the product of Step B, 5.3 g, 14.7 mmol), nickel(II) acetate tetrahydrate (18.3 g, 73.4 mmol) and ethanol (120 mL) was cooled in an ice bath and treated with sodium borohydride (2.8 g, 73.4 mmol) in 0.5 g portions added over 5 minutes. The resulting mixture was stirred at 26° C. for 18 h. Saturated ammonium chloride solution (120 mL) and ethyl acetate (120 mL) were then added, the mixture was stirred for 1 h and then filtered through a pad of Celite® diatomaceous filter aid to remove insoluble particulates. The layers of the filtrate were separated, and the aqueous layer was extracted with ethyl acetate (2×100 mL). The combined organic extracts were washed with saturated ammonium chloride solution (100 mL), brine (100 mL), dried ($MgSO_4$) and concentrated under reduced pressure to afford the title compound as a yellow-orange solid (4.73 g) which was used without purification. ¹H NMR δ 7.31 (m, 1H), 7.12 (m, 2H), 6.93 (br s, 1H), 4.24 (m, 2H), 4.06 (m, 1H), 3.82 (m, 1H), 3.49 (d, 1H), 3.39 (m, 1H), 1.29 (m, 3H).

Step D: Preparation of 4-(3-chloro-4-fluorophenyl)-2-oxo-3-pyrrolidinecarboxylic acid A mixture of ethyl 4-(3-chloro-4-fluorophenyl)-2-oxo-3-pyrrolidinecarboxylate (i.e. the product of Step C, 4.73 g, 16.5 mmol) and aqueous sodium hydroxide (50 wt %, 1.98 g, 49.5 mmol) in ethanol (50 mL) was stirred at 26° C. for 18 h. The reaction mixture was then diluted with water (50 mL) and extracted with diethyl ether (2×50 mL). The aqueous phase was acidified with concentrated hydrochloric acid to pH 2 and extracted with dichloromethane (3×50 mL). The combined dichloromethane extracts were washed with brine, dried ($MgSO_4$), and concentrated under reduced pressure to afford the title compound as a white solid (2.37 g).
¹H NMR (acetone-$d_6$) δ 7.63 (m, 1H), 7.46 (m, 1H), 7.31 (m, 1H), 4.05 (m, 1H), 3.82 (m, 1H), 3.70 (d, 1H), 3.45 (m, 1H).

Step E: Preparation of 4-(3-chloro-4-fluorophenyl)-2-oxo-N-[2-(trifluoromethyl)-phenyl]-3-pyrrolidinecarboxamide A mixture of 4-(3-chloro-4-fluorophenyl)-2-oxo-3-pyrrolidinecarboxylic acid (i.e. the product of Step D, 0.3 g, 1.17 mmol), triethylamine (0.49 mL, 3.5 mmol) and 2-(trifluoromethyl)aniline (0.16 mL, 1.28 mmol) in dichloromethane (8 mL) was stirred at ambient temperature for 30 minutes, and then treated with propylphosphonic anhydride in ethyl acetate (50%, 1.26 g, 1.98 mmol). The resulting mixture was stirred at ambient temperature for 18 h. The reaction mixture was then concentrated under reduced pressure, and the residue was chromatographed on silica gel, eluted with 0-30% ethyl acetate in hexanes, to afford a solid residue which on trituration with 1-chlorobutane afforded the title product, a compound of the present disclosure, as a light pink solid (0.2 g).
¹H NMR δ 9.85 (s, 1H), 8.15 (m, 1H), 7.62 (m, 1H), 7.52 (m, 1H), 7.43 (m, 1H), 7.27 (m, 1H), 7.22 (m, 1H), 7.14 (m, 1H), 6.93 (s, 1H), 4.15 (m, 1H), 3.82 (m, 1H), 3.55 (d, 1H), 3.44 (m, 1H).

SYNTHESIS EXAMPLE 2

Preparation of 4-bromo-N-(2-fluorophenyl)-2-oxo-4-phenyl-3-pyrrolidinecarboxamide and 3-bromo-N-(2-fluorophenyl)-2-oxo-4-phenyl-3-pyrrolidinecarboxamide (e.g. a compound of Formula 1 wherein $Y^1$ and $Y^2$ are both O; J is —$CR^2R^3$—; $R^2$ and $R^3$ are both H; $Q^1$ is Ph; $Q^2$ is Ph(2-F); $R^4$ is Br; $R^5$ is H; $R^6$ is H; and $R^1$ is H.)

A mixture of 4-phenyl-2-oxo-N-(2-fluorophenyl)-3-pyrrolidinecarboxamide (prepared by the method of Example 1, 0.75 g, 2.5 mmol) in dichloromethane (25 mL) at room temperature was treated with bromine (0.16 mL, 3.0 mmol), and the resulting mixture was stirred for 18 h. The reaction mixture was then concentrated under reduced pressure, and the residue was chromatographed on silica gel, eluted with 0-2% methanol in dichloromethane, to give as the faster eluting product, 4-bromo-N-(2-fluorophenyl)-2-oxo-4-phenyl-3-pyrrolidinecarboxamide, a compound of the present disclosure, as a white solid (90 mg):
¹H NMR δ 10.2 (br s, 1H), 8.00 (m, 1H), 7.28 (m, 5H), 7.02 (m, 3H), 6.45 (br s, 1H), 4.15 (d, 1H), 4.05 (m, 1H), 3.55 (d, 1H);
and the slower eluting product, 3-bromo-N-(2-fluorophenyl)-2-oxo-4-phenyl-3-pyrrolidinecarboxamide, a compound of the present disclosure, as a clear yellow oil (0.31 g):
¹H NMR δ 9.55 (br s, 1H), 8.25 (t, 1H), 7.48 (d, 2H), 7.38 (m, 3H), 7.11 (m, 3H), 6.85 (br s, 1H), 4.45 (m, 1H), 3.77 (m, 1H), 3.65 (m, 1H).

SYNTHESIS EXAMPLE 3

Preparation of 4-(3,4-difluorophenyl)-N-(2-fluorophenyl)-1-hydroxy-2-oxo-3-pyrrolidinecarboxamide (e.g. a compound of Formula 1 wherein $Y^1$ and $Y^2$ are both O; J is —$CR^2R^3$—; $R^2$ and $R^3$ are both H; $Q^1$ is Ph(3,4-di-F); $Q^2$ is Ph(2-F); $R^4$ and $R^5$ are both H; $R^6$ is H; and $R^1$ is OH.)

Step A: Preparation of ethyl 3-[(2-fluorophenyl)amino]-3-oxopropanote

To a stirred solution of 2-fluoroaniline (10 g, 90.0 mmol) and triethylamine (9.1 g, 90.0 mmol) in dichloromethane (50 mL) at 0° C. was added dropwise over 10 minutes a solution of ethyl malonyl chloride (15.5 g, 90.0 mmol) in dichloromethane (30 mL). The resulting mixture was stirred at room temperature for 24 h. The reaction mixture was then poured into water (100 mL), and the organic layer was separated, washed with water (50 mL) and brine (50 mL), dried ($MgSO_4$) and concentrated under reduced pressure to provide the title compound as an amber oil (19.0 g).
¹H NMR δ 9.46 (br s, 1H), 8.28 (m, 1H), 7.1 (m, 2H), 4.26 (m, 2H), 3.51 (s, 2H), 1.32 (t, 3H).

Step B: Preparation of ethyl 3-(3,4-difluorophenyl)-2-[[(2-fluorophenyl)amino]-carbonyl]-2-propenoate A solution of ethyl 3-[(2-fluorophenyl)amino]-3-oxopropanote (i.e. the product of Step A, 20.27 g, 90.0 mmol), 3,4-difluorobenzaldehyde (16.62 g, 117 mmol), acetic acid (2.6 mL, 45 mmol) and piperidine (0.89 mL, 9.0 mmol) in toluene (150 mL) was refluxed for 10 h with continuous removal of water (Dean-Stark trap). The reaction mixture was then cooled to room temperature and poured into water (100 mL). The organic layer was separated, and the water layer was extracted with ethyl acetate (3×50 mL). The combined organic extracts were washed with aqueous hydrochloric acid (1 N, 100 mL), dried (MgSO$_4$) and concentrated under reduced pressure to give a solid residue. Recrystallization of the solid from diethyl ether (100 mL) afforded the title compound as a white solid (10.5 g).

$^1$H NMR δ 8.26-8.48 (m, 1H), 8.15 (m, 1H), 7.74 (s, 1H), 7.51 (m, 1H), 7.35 (m, 1H), 7.11 (m, 4H), 4.35 (m, 2H), 1.36 (t, 3H).

Step C: Preparation of ethyl 3,4-difluoro-α-[[(2-fluorophenyl)amino]carbonyl]-β-(nitromethyl)benzenepropanoate To a stirred suspension of ethyl 3-(3,4-difluorophenyl)-2-[[(2-fluorophenyl)amino]-carbonyl]-2-propenoate (i.e. the product of Step B, 4.42 g, 12.7 mmol) and nitromethane (17 mL, 317.5 mmol) at −20° C. was added 1,1,3,3-tetramethylguanidine (0.288 mL, 2.3 mmol). The mixture was stirred at −20° C. for 30 minutes, and then allowed to come to room temperature and stirred for an additional 2 h. The reaction mixture was diluted with dichloromethane (50 mL) and extracted with water (3×25 mL). The organic layer was dried (MgSO$_4$) and concentrated under reduced pressure to provide a solid residue. The solid was chromatographed on silica gel, eluted with 0-100% ethyl acetate in hexane, to provide the title compound as a white solid (4.42 g).

$^1$H NMR δ 8.6 (br s, 1H), 8.00-8.30 (m, 3H), 7.23 (m, 4H), 5.41 (m, 1H), 4.6 (m, 1H), 4.35 (m, 2H), 3.77-4.00 (m, 2H), 1.45 (m, 3H).

Step D: Preparation of 4-(3,4-difluorophenyl)-N-(2-fluorophenyl)-1-hydroxy-2-oxo-3-pyrrolidinecarboxamide A mixture of ethyl 3,4-difluoro-α-[[(2-fluorophenyl) amino]carbonyl]-β-(nitromethyl)-benzenepropanoate (i.e. the product of Step C, 0.50 g, 1.22 mmol), 5% palladium on carbon (0.25 g) and methanol-ethyl acetate (1:1 by volume, 10 mL) was stirred at room temperature for 30 minutes, then cooled to at 0° C. and treated with ammonium formate (0.5 g). The resulting mixture was stirred for 1 h at room temperature. Additional 5% palladium on carbon (0.25 g) and ammonium formate (0.5 g) were added, and stirring at room temperature was continued for an additional 4 h. The reaction mixture was then filtered, and the filtrate was concentrated under reduced pressure to provide a residue, which was suspended in water (10 mL) and extracted with ethyl acetate (3×20 mL). The combined organic extracts were dried (MgSO$_4$) and concentrated under reduced pressure to provide an oil, which on recrystallization from dichloromethane afforded the title product, a compound of the present disclosure, as a white solid (0.1 g).

$^1$H NMR (DMSO-d$_6$) δ 10.11 (br s, 2H), 8.00 (m, 1H), 7.71 (m, 1H), 7.42 (m, 1H), 7.33 (m, 3H), 7.1 (m, 1H), 4.25-3.61 (m, 4H).

SYNTHESIS EXAMPLE 4

Preparation of 2-amino-4-(3,4-difluorophenyl)-N-(2-fluorophenyl)dihydro-3H-pyrrole-3-carboxamide (e.g. a compound of Formula 1 wherein Y$^1$ is NH; Y$^2$ is O; J is —CR$^2$R$^3$—; R$^2$ and R$^3$ are both H; Q$^1$ is Ph(3,4-di-F); Q$^2$ is Ph(2-F); R$^4$ and R$^5$ are both H; R$^6$ is H; and R$^1$ is H.)

Step A: Preparation of 4-(3,4-difluorophenyl)-N-(2-fluorophenyl)-2-oxo-3-pyrrolidinecarboxamide To a stirred mixture of ethyl 3,4-difluoro-α-[[(2-fluorophenyl)amino]carbonyl]-β-(nitromethyl)benzenepropanoate (i.e. the product of Example 3 Step C, 3.346 g, 8.16 mmol) and nickel(II) acetate tetrahydrate (10.15 g, 40.8 mmol) in ethanol (50 mL) at 0° C., was added portionwise sodium borohydride (1.54 g, 40.8 mmol), and the resulting mixture was stirred at room temperature for 24 h. The reaction mixture was concentrated under reduced pressure, dissolved in ethyl acetate (100 mL) and washed successively with saturated ammonium chloride solution (50 mL), water (2×25 mL) and saturated sodium chloride (20 mL). The organic layer was dried (MgSO$_4$) and concentrated under reduced pressure to provide a solid residue. The residue was chromatographed on silica gel, eluted with 0-100% ethyl acetate in hexane, to provide the title compound as a white solid (0.746 g).

$^1$H NMR δ 9.67 (br s, 1H), 8.21 (m, 1H), 7.09 (m, 6H), 4.75 (br s, 1H), 4.21 (m, 1H), 3.82 (m, 1H), 3.52 (m, 1H), 3.43 (m, 1H).

Step B: Preparation of 4-(3,4-difluorophenyl)-N-(2-fluorophenyl)dihydro-2-methoxy-3H-pyrrole-3-carboxamide A mixture of 4-(3,4-difluorophenyl)-N-(2-fluorophenyl)-2-oxo-3-pyrrolidinecarboxamide (i.e. the product of Step A, 0.187 g, 0.56 mmol) and trimethyloxonium tetrafluoroborate (0.083 g, 0.56 mmol) in dichloromethane (5 mL) was stirred under an atmosphere of nitrogen for 2 d. The reaction mixture was then treated with 1 N aqueous sodium hydroxide until basic (pH 10) and extracted with dichloromethane (3×5 mL). The organic layer was dried (MgSO$_4$) and concentrated under reduced pressure to provide title compound as light yellow oil (0.138 g).

$^1$H NMR δ 9.7 (br s, 1H), 8.62 (m, 1H), 8.25 (s, 1H), 7.26 (m, 4H), 7.00 (m, 1H), 4.26 (m, 2H), 4.00 (s, 3H), 3.42 (m, 2H).

Step C: Preparation of 2-amino-4-(3,4-difluorophenyl)-N-(2-fluorophenyl)dihydro-3H-pyrrole-3-carboxamide A mixture of 4-(3,4-difluorophenyl)-N-(2-fluorophenyl) dihydro-2-methoxy-3H-pyrrole-3-carboxamide (i.e. the product Step B, 0.10 g, 0.287 mmol) and aqueous ammonium hydroxide (50%, 0.5 mL) in ethanol (2 mL) was heated in microwave apparatus for 10 minutes. The reaction mixture was concentrated under reduced pressure and the residue chromatographed on silica gel, eluted with 0-100% ethyl acetate/hexane, to afford the title product, a compound of the present disclosure, as a solid (0.016 g).

$^1$H NMR δ 9.67 (br s, 1H), 8.21 (m, 1H), 7.27-7.01 (m, 6H), 6.50 (br s, 1H), 5.00 (br s, 1H), 4.26 (m, 1H), 3.82 (m, 1H), 3.55 (m, 1H), 3.43 (m, 1H).

SYNTHESIS EXAMPLE 5

Preparation of (3R,4S)—N-(2-fluorophenyl)-2-oxo-4-[3-(trifluoromethyl)phenyl]-3-pyrrolidinecarboxamide (e.g. a compound of Formula 1 wherein Y$^1$ and Y$^2$ are both O; J is —CR$^2$R$^3$—; R$^2$ and R$^3$ are both H; Q$^1$ is Ph(3-CF$_3$); Q$^2$ is Ph(2-F); R$^4$ and R$^5$ are both H; R$^6$ is H; and R$^1$ is H.)

Step A: Preparation of 1-[(E)-2-nitroethenyl]-3-(trifluoromethyl)benzene

To a stirred solution of 3-(trifluoromethyl)benzaldehyde (12.2 g, 70.1 mmol) in methanol (50 mL) was added nitromethane (4.34 g, 71.1 mmol). The mixture was cooled to 2° C. and sodium hydroxide (5.65 g, 70.6 mmol) was added as a 50% solution in 24.3 mL of water dropwise over 15 min. An exotherm was noted and additional ice was added to maintain the temperature below 10° C. while stirring for an additional 1 h. The reaction mixture was poured into 75 mL (75 mmol) of 1 N hydrochloric acid, rinsing the flask with 10 mL of methanol/water. The quenched reaction mixture was transferred to a separatory funnel and extracted with 150 mL of toluene. The aqueous layer was separated and concentrated under vacuum to yield 15.84 g of a yellow oil.

The intermediate thus obtained (15.84 g, 67.3 mmol) was taken up in 160 mL dichloromethane. The solution was cooled to 3° C. and methanesulfonyl chloride (8.03 g, 71.1 mmol) was added via pipette as a solution in 50 mL of dichloromethane. A solution of triethylamine (14.2 g, 140 mmol) in 50 mL of dichloromethane was then added dropwise over 50 min, and the resulting solution was stirred for 2 h. The reaction mixture was poured into 150 mL (150 mmol) of 1 N hydrochloric acid and transferred to a separatory funnel. The layers were separated and the organic layer was washed with 150 mL water and then filtered. The organic layer was concentrated under reduced pressure and the crude solid was tritrated with hexanes to yield 12.09 g of product as a yellow solid.

$^1$H NMR (500 MHz) δ 7.54-7.66 (m, 2H) 7.69-7.84 (m, 3H) 7.96-8.08 (m, 1H).

Step B: Preparation of 1,3-diethyl 2-[(1S)-2-nitro-1-[3-(trifluoromethyl)phenyl]ethyl]propanedioate To a stirred mixture of 1-[(E)-2-nitroethenyl]-3-(trifluoromethyl)benzene (i.e. the product of Step A, 3 g, 13.8 mmol) and diethyl malonate (3.319 g, 20.7 mmol) in toluene (1.5 mL) was added Ni(II) bis[(R,R)—N,N'-dibenzylcyclohexane-1,2-diamine]bromide (prepared as described in *J. Am. Chem. Soc.* 2005, 127, 9958-9959; 0.111 g, 0.1 mmol). The resulting solution was stirred at 55° C. for 16 h. The solution was diluted with dichloromethane (20 mL) and concentrated under reduced pressure onto silica gel and purified by chromatography eluting with a gradient of ethyl acetate in hexanes (0 to 50%) to give 3.6 g of a light yellow oil. ER 94:6 (major eluting at 26.5 min, minor eluting at 20.3 min).

$^1$H NMR (500 MHz) δ 7.54-7.60 (m, 1H), 7.43-7.48 (m, 2H), 7.51 (s, 1H), 4.83-5.00 (m, 2H), 4.17-4.35 (m, 3H), 3.98-4.06 (m, 2H), 3.77-3.85 (m, 1H), 1.20-1.29 (m, 3H), 0.99-1.10 (m, 3H). $^{19}$F NMR (471 MHz) δ−62.78 (s, 3F). ESI [M−1] 376.3.

Step C: Preparation of ethyl (3R,4S)-2-oxo-4-[3-(trifluoromethyl)phenyl]-3-pyrrolidinecarboxylate A stirred mixture of 1,3-diethyl 2-[(1S)-2-nitro-1-[3-(trifluoromethyl)phenyl]ethyl]propanedioate (i.e. the product of Step B, 3.24 g, 8.48 mmol), nickel(II) chloride hexahydrate (2.01 g, 8.48 mmol) and ethanol (60 mL) was cooled in an ice bath and treated with sodium borohydride (0.97 g, 25.8 mmol) in 0.5 g portions added over 5 min. The resulting mixture was stirred at 26° C. for 18 h. Saturated ammonium chloride solution (120 mL) and ethyl acetate (120 mL) were then added, the mixture was stirred for 1 h and then filtered through a pad of Celite® diatomaceous filter aid to remove insoluble particulates. The layers of the filtrate were separated, and the aqueous layer was extracted with ethyl acetate (2×100 mL). The combined organic extracts were washed with saturated ammonium chloride solution (100 mL), brine (100 mL), dried (MgSO$_4$) and concentrated under reduced pressure to afford the title compound as a thick yellow oil (2.66 g) which was used without purification.

$^1$H NMR (500 MHz) δ 7.38-7.62 (m, 4H), 6.50 (br s, 1H), 4.21-4.31 (m, 2H), 4.15-4.21 (m, 1H), 3.82-3.92 (m, 1H), 3.51-3.58 (m, 1H), 3.37-3.50 (m, 1H), 1.27-1.34 (m, 3H). $^{19}$F NMR (471 MHz) δ−62.70 (s, 3F). ESI; [M+1]=302.0.

Step D: Preparation of (3R,4S)-2-oxo-4-[3-(trifluoromethyl)phenyl]-3-pyrrolidinecarboxylic acid A mixture of ethyl (3R,4S)-2-oxo-4-[3-(trifluoromethyl)phenyl]-3-pyrrolidinecarboxylate (i.e. the product of Step C, 2.66 g, 8.8 mmol) and aqueous sodium hydroxide (50 wt %, 2.12 g, 26.5 mmol) in ethanol (30 mL) was stirred at 26° C. for 18 h. The reaction mixture was then diluted with water (50 mL) and extracted with diethyl ether (2×50 mL). The aqueous phase was acidified with concentrated hydrochloric acid to pH 2 and extracted with dichloromethane (3×50 mL). The combined dichloromethane extracts were washed with brine, dried (MgSO$_4$), and concentrated under reduced pressure to afford the title compound as a white solid (2.05 g).

$^1$H NMR (500 MHz, acetone-d$_6$) δ 11.50 (br s, 1H), 7.70-7.89 (m, 2H), 7.56-7.68 (m, 2H), 7.45 (br s, 1H), 4.09-4.21 (m, 1H), 3.83-3.92 (m, 1H), 3.73-3.81 (m, 1H), 3.42-3.55 (m, 1H). $^{19}$F NMR (471 MHz, acetone-d$_6$) δ−63.03 (s, 3F). ESI [M+1] 274.0.

Step E: Preparation of (3R,4S)—N-(2-fluorophenyl)-2-oxo-4-[3-(trifluoromethyl)phenyl]-3-pyrrolidinecarboxamide A mixture of (3R,4S)-2-oxo-4-[3-(trifluoromethyl)phenyl]-3-pyrrolidinecarboxylic acid (i.e. the product of Step D, 2.0 g, 7.32 mmol), triethylamine (3.06 mL, 21.96 mmol) and 2-fluoroaniline (0.85 mL, 8.78 mmol) in dichloromethane (50 mL) was stirred at ambient temperature for 30 min, and then treated with propylphosphonic anhydride in ethyl acetate (50%, 7.92 g, 12.44 mmol). The resulting mixture was stirred at ambient temperature for 18 h. The reaction mixture was then concentrated under reduced pressure, and the residue was chromatographed on silica gel, eluted with 0-100% ethyl acetate in hexanes, to afford a solid residue which on trituration with 1-chlorobutane afforded the title product, a compound of the present disclosure, as a white solid (1.9 g). ER 88:12 (major eluting at 25.86 min, minor eluting at 17.66 min). Specific Rotation +74.71 at 23.4° C. at 589 nm, as a 1% solution (1 g/100 mL) in CHCl$_3$.

$^1$H NMR (500 MHz, acetone-d$_6$) δ 10.05 (br s, 1H), 8.21-8.35 (m, 1H), 7.77-7.91 (m, 2H), 7.58-7.66 (m, 2H), 7.51 (br s, 1H), 7.02-7.22 (m, 3H), 4.18-4.30 (m, 1H), 3.94-4.04 (m, 1H), 3.84-3.93 (m, 1H), 3.42-3.53 (m, 1H).

SYNTHESIS EXAMPLE 6

Preparation of (3S,4S)—N-(2-fluorophenyl)-1-methyl-2-oxo-4-[3-(trifluoromethyl)phenyl]-3-pyrrolidinecarboxamide (e.g. a compound of Formula 1 wherein $Y^1$ and $Y^2$ are both O; J is —$CR^2R^3$—; $R^2$ and $R^3$ are both H; $Q^1$ is Ph(3-CF$_3$); $Q^2$ is Ph(2-F); $R^4$ and $R^5$ are both H; $R^6$ is H; and $R^1$ is Me.)

Step A Preparation of (4S)-4-[3-(trifluoromethyl) phenyl]-2-pyrrolidinone

A mixture of (3R,4S)-2-oxo-4-[3-(trifluoromethyl)phenyl]-3-pyrrolidinecarboxylic acid acid (i.e. the product of Example 5, Step D, 1.5 g, 5.5 mmol) and toluene-4-sulfonic acid (0.010 g, 0.055 mmol) in toluene (12 mL) was stirred at 90° C. overnight. The reaction mixture was then concentrated under reduced pressure to afford a clear oil (1.29 g). The crude product was used without further purification.

$^1$H NMR (500 MHz) δ 7.36-7.59 (m, 4H), 6.84 (br s, 1H), 3.70-3.88 (m, 2H), 3.35-3.50 (m, 1H), 2.72-2.87 (m, 1H), 2.44-2.58 (m, 1H). $^{19}$F NMR (471 MHz) δ−62.66 (s, 3F).

Step B: Preparation of (4S)-1-methyl-4-[3-(trifluoromethyl)phenyl]-2-pyrrolidinone To a solution of (4S)-4-[3-(trifluoromethyl)phenyl]-2-pyrrolidinone (i.e. the product of Step A, 1.29 g, 5.6 mmol) in N,N-dimethylformamide (7 mL) was added sodium hydride (60% dispersion in mineral oil, 0.25 g, 6.2 mmol) in portions. The mixture was stirred for 10 min and then iodomethane (0.88 mL, 14.1 mmol) was added. The solution was stirred overnight at ambient temperature. The reaction mixture was diluted with water and extracted with diethyl ether (2×50 mL). The organic layer was washed with water, brine and then dried (MgSO$_4$), filtered and concentrated under reduced pressure. The crude residue was chromatographed on silica gel, eluted with 0-20% ethyl acetate in dichloromethane, to afford a light brown oil (0.775 g).

$^1$H NMR (500 MHz) δ 7.38-7.57 (m, 4H), 3.75-3.83 (m, 1H), 3.59-3.70 (m, 1H), 3.38-3.45 (m, 1H), 2.90-2.94 (m, 3H), 2.80-2.89 (m, 1H), 2.48-2.58 (m, 1H). $^{19}$F NMR (471 MHz) δ−62.67 (s, 3F).

Step C Preparation of (3R,4S)—N-(2-fluorophenyl)-1-methyl-2-oxo-4-[3-(trifluoromethyl)phenyl]-3-pyrrolidinecarboxamide A solution of (4S)-1-methyl-4-[3-(trifluoromethyl)phenyl]-2-pyrrolidinone (i.e. the product of Step B, 0.350 g, 1.44 mmol) in tetrahydrofuran (5 mL) was cooled to −78° C. To this mixture lithium bis(trimethylsilyl)amide (1.6 mL, 1.6 mmol as a 1 M solution in tetrahydrofuran) was added dropwise and the resulting solution was stirred for 30 min. Then 1-fluoro-2-isocyanatobenzene (0.17 mL, 1.44 mmol) was added dropwise and the solution was stirred for 2 h at −78° C. The reaction mixture was quenched with saturated aqueous ammonium chloride (10 mL), warmed to ambient temperature and the aqueous layer was extracted with ethyl acetate (3×25 mL). The organic layers were combined, washed with brine and then dried (MgSO$_4$), filtered and concentrated under reduced pressure onto silica gel. The crude residue was chromatographed on silica gel, eluting with 0 to 40% ethyl acetate in hexanes, to afford a light pink solid (0.223 g).

$^1$H NMR (500 MHz) δ 9.93 (br s, 1H), 8.15-8.27 (m, 1H), 7.38-7.65 (m, 4H), 6.93-7.15 (m, 3H), 4.10-4.23 (m, 1H), 3.72-3.88 (m, 1H), 3.56-3.68 (m, 1H), 3.39-3.53 (m, 1H), 2.90-3.06 (m, 3H). ESI [M+1] 381.0.

SYNTHESIS EXAMPLE 7

Preparation of 1,3-diethyl 2-[(1S)-1-(3,4-difluorophenyl)-2-nitro-ethyl]propanedioate (e.g. an intermediate to prepare a compound of Formula 1 wherein Y$^1$ and Y$^2$ are both O; J is —CR$^2$R$^3$—; R$^2$ and R$^3$ are H; Q$^1$ is Ph(3,4-di-F); Q$^2$ is Ph(2-F); R$^4$ and R$^5$ are both H; R$^6$ is H; and R$^1$ is H.)

Step A: Preparation of 1,3-diethyl 2-[(1S)-1-(3,4-difluorophenyl)-2-nitro-ethyl]propanedioate To a stirred mixture of 1-[(E)-2-nitroethenyl]-3,4-difluorobenzene (prepared as described generally in WO2008/39882 A1, 1.67 g, 9.0 mmol) and diethyl malonate (1.73 g, 10.8 mmol) in toluene (10 mL) was added Ni(II) bis[(R,R)—N,N'-dibenzylcyclohexane-1,2-diamine]bromide (prepared as described in *J. Am. Chem. Soc.* 2005, 127, 9958-9959; 0.072 g, 0.1 mmol). The resulting solution was stirred at ambient temperature for 72 h. The solution was diluted with dichloromethane (20 mL) and concentrated under reduced pressure onto silica gel and purified by silica gel chromatography eluting with a gradient of ethyl acetate in hexanes (0 to 50%) to provide 2.18 g of a light yellow waxy solid. ER 96:4 (major eluting at 37.05 min, minor eluting at 27.09 min).

$^1$H NMR (500 MHz) δ 7.06-7.16 (m, 2H), 6.95-7.03 (m, 1H), 4.73-4.94 (m, 2H), 4.16-4.29 (m, 3H), 4.01-4.10 (m, 2H), 3.71-3.79 (m, 1H), 1.22-1.30 (m, 3H), 1.07-1.15 (m, 3H). ESI [M+1]; 346.4

SYNTHESIS EXAMPLE 8

Preparation of (3RS,4RS)—N-(2,3-difluorophenyl)-1-methoxy-4-(4-methylphenyl)-2-oxo-pyrrolidine-3-carboxamide (e.g. a compound of Formula 1 wherein Y$^1$ and Y$^2$ are both O; J is —CR$^2$R$^3$—; R$^2$ and R$^3$ are both H; Q$^1$ is Ph(4-Me); Q$^2$ is Ph(2,3-diF); R$^4$ and R$^5$ are both H; R$^6$ is H; and R$^1$ is OMe.)

Step A: Preparation of ethyl (3RS,4SR)-1-hydroxy-4-(4-methylphenyl)-2-oxo-pyrrolidine-3-carboxylate Ammonium formate (9.7 g, 150 mmol), followed by palladium (5% on carbon, 60% water; 6.7 g, 1.9 mmol), was added to a solution of diethyl 2-[1-(4-methylphenyl)-2-nitro-ethyl]-propanedioate (prepared using the method described in SYNTHESIS EXAMPLE 1, Step B; 6.1 g, 19 mmol) in tetrahydrofuran (57 ml) and methanol (13 ml) under nitrogen at ambient temperature. The reaction mixture was heated at 50° C. for 3.5 hours, then allowed to cool and filtered through Celite®. The filtrate was evaporated under reduced pressure and the residue purified by column chromatography to provide ethyl (3RS,4SR)-1-hydroxy-4-(4-methylphenyl)-2-oxo-pyrrolidine-3-carboxylate (2.69 g, 54%).

$^1$H NMR δ=7.15 (m, 4H), 4.23 (m, 2H), 4.05 (m, 1H), 3.94 (q, 1H), 3.70 (dd, 1H), 3.57 (d, 1H), 2.34 (s, 3H), 1.27 (m, 3H)(N—OH not observed).

Step B: Preparation of ethyl (3RS,4SR)-1-methoxy-4-(4-methylphenyl)-2-oxo-pyrrolidine-3-carboxylate A solution of trimethylsilyldiazomethane in hexanes (2.0 mol/l; 3.8 ml, 7.60 mmol) was added dropwise to a solution of ethyl (3RS,4SR)-1-hydroxy-4-(4-methylphenyl)-2-oxo-pyrrolidine-3-carboxylate (1.00 g, 3.80 mmol) in methanol (3.8 ml) and toluene (4.5 ml). The solution was stirred for 1 hour, acetic acid added dropwise until effervescence ceased, then the mixture was evaporated under reduced pressure and the residue purified by column chromatography to provide ethyl (3RS,4SR)-1-methoxy-4-(4-methylphenyl)-2-oxo-pyrrolidine-3-carboxylate (0.74 g, 70%).

$^1$H NMR δ=7.15 (m, 4H), 4.23 (m, 2H), 4.00 (m, 1H), 3.90 (m, 1H), 3.85 (s, 3H), 3.53 (m, 1H), 3.47 (d, 1H), 2.33 (m, 3H), 1.27 (m, 3H).

Step C: Preparation of (3RS,4SR)-1-methoxy-4-(4-methylphenyl)-2-oxo-pyrrolidine-3-carboxylic acid A solution of sodium hydroxide (0.32 g, 8.0 mmol) in water (2.7 ml) was added to a solution of ethyl (3RS,4SR)-1-methoxy-4-(4-methylphenyl)-2-oxo-pyrrolidine-3-carboxylate (0.74 g, 2.7 mmol) in ethanol (8.0 ml). The resulting mixture was stirred at ambient temperature for 1 hour, then water and ethyl acetate were added and the phases separated. The organic phase was extracted with water. The combined aqueous phases were washed with ethyl acetate, then acidified by the addition of hydrochloric acid and extracted with ethyl acetate. The organic extract was dried over magnesium sulphate, filtered and evaporated under reduced pressure to provide (3RS,4SR)-1-methoxy-4-(4-methylphenyl)-2-oxo-pyrrolidine-3-carboxylic acid (0.25 g, 38%), which was used without further purification.

Step D: Preparation of (3RS,4RS)—N-(2,3-difluorophenyl)-1-methoxy-4-(4-methylphenyl)-2-oxo-pyrrolidine-3-carboxamide A solution of 1-propanephosphonic acid cyclic anhydride in ethyl acetate (50 mass %; 0.26 ml, 0.43 mmol) was added to a solution of (3RS,4SR)-1-methoxy-4-(4-methylphenyl)-2-oxo-pyrrolidine-3-carboxylic acid (0.063 g, 0.25 mmol) and 2,3-difluoroaniline (0.039 g, 0.30 mmol) in dichloromethane (1.8 ml), followed by the slow addition of diisopropylethylamine (0.13 ml, 0.76 mmol). The resulting mixture was stirred at ambient temperature for 17 hours, then water and aqueous sodium hydroxide added. The phases were separated and the organic was washed with hydrochloric acid, dried over magnesium sulphate, filtered and evaporated under reduced pressure. The residue was purified by column chromatography to provide (3RS,4RS)—N-(2,3-difluorophenyl)-1-methoxy-4-(4-methylphenyl)-2-oxo-pyrrolidine-3-carboxamide (0.063 g, 69%).

$^1$H NMR δ=9.54 (br s, 1H), 8.00 (m, 1H), 7.26 (m, 2H), 7.18 (m, 2H), 7.00 (m, 1H), 6.89 (m, 1H), 4.01 (m, 2H), 3.88 (s, 3H), 3.59 (m, 2H), 2.34 (s, 3H).

SYNTHESIS EXAMPLE 9

Preparation of (3RS,4RS)-1-allyloxy-N-(2,3-difluorophenyl)-4-(4-methylphenyl)-2-oxo-pyrrolidine-3-carboxamide (e.g. a compound of Formula 1 wherein $Y^1$ and $Y^2$ are both O; J is —$CR^2R^3$—; $R^2$ and $R^3$ are both H; $Q^1$ is Ph(4-Me); $Q^2$ is Ph(2,3-diF); $R^4$ and $R^5$ are both H; $R^6$ is H; and $R^1$ is O-allyl.)

Step A: Preparation of (3RS,4SR)-1-hydroxy-4-(4-methylphenyl)-2-oxo-pyrrolidine-3-carboxylic acid A solution of sodium hydroxide (0.046 g, 1.1 mmol) in water (0.38 ml) was added to a solution of ethyl (3RS,4SR)-1-hydroxy-4-(4-methylphenyl)-2-oxo-pyrrolidine-3-carboxylate (prepared as described in SYNTHESIS EXAMPLE 8, step A; 0.10 g, 0.38 mmol) in ethanol (1.1 ml). The resulting mixture was stirred at ambient temperature for 2 hours, then water and ethyl acetate were added. The phases were separated and the organic extracted with water. The combined aqueous layers were washed with ethyl acetate, acidified by the addition of hydrochloric acid and extracted with ethyl acetate. The organic extract was dried over magnesium sulphate, filtered and evaporated under reduced pressure to provide (3RS,4SR)-1-hydroxy-4-(4-methylphenyl)-2-oxo-pyrrolidine-3-carboxylic acid (0.063 g, 71%).

$^1$H NMR δ=7.14 (s, 4H), 4.04 (m, 1H), 3.91 (m, 1H), 3.71 (m, 1H), 3.60 (m, 1H), 2.32 (s, 3H)(N—OH and $CO_2H$ not observed).

Step B: Preparation of (3RS,4SR)-1-allyloxy-4-(4-methylphenyl)-2-oxo-pyrrolidine-3-carboxylic acid Sodium hydride (60 mass % in oil; 0.023 g, 0.59 mmol) and 3-iodoprop-1-ene (0.029 ml, 0.32 mmol) were added to a solution of (3RS,4SR)-1-hydroxy-4-(4-methylphenyl)-2-oxo-pyrrolidine-3-carboxylic acid (0.063 g, 0.27 mmol) in tetrahydrofuran (1.6 ml) under nitrogen. The resulting mixture was stirred at ambient temperature for 4 days, water added and the mixture extracted with ethyl acetate. The combined organic extracts were dried over magnesium sulphate, filtered and evaporated under reduced pressure to provide a residue that was purified by column chromatograph to provide (3RS,4SR)-1-allyloxy-4-(4-methylphenyl)-2-oxo-pyrrolidine-3-carboxylic acid (0.017 g, 23%).

$^1$H NMR δ=7.16 (m, 4H), 6.02 (tdd, 1H), 5.40 (m, 2H), 4.52 (m, 2H), 3.90 (m, 2H), 3.57 (m, 1H), 3.51 (d, 1H), 2.32 (m, 3H)($CO_2H$ not observed).

Step C: Preparation of (3RS,4RS)-1-allyloxy-N-(2,3-difluorophenyl)-4-(4-methylphenyl)-2-oxo-pyrrolidine-3-carboxamide A solution of 1-propanephosphonic acid cyclic anhydride in ethyl acetate (50 mass %; 0.062 ml, 0.10 mmol) was added to a solution of (3RS,4SR)-1-allyloxy-4-(4-methylphenyl)-2-oxo-pyrrolidine-3-carboxylic acid (0.017 g, 0.062 mmol) and 2,3-difluoroaniline (0.0096 g, 0.074 mmol) in dichloromethane (0.4 ml), followed by the slow addition of diisopropylethylamine (0.032 ml, 0.19 mmol). The resulting mixture was stirred at ambient temperature for 17 hours, then water and aqueous sodium hydroxide added. The phases were separated and the organic was washed with hydrochloric acid, dried over magnesium sulphate, filtered and evaporated under reduced pressure. The residue was purified by column chromatography to provide (3RS,4RS)-1-allyloxy-N-(2,3-difluorophenyl)-4-(4-methylphenyl)-2-oxo-pyrrolidine-3-carboxamide (0.022 g, 92%).

$^1$H NMR δ=9.56 (br s, 1H), 8.00 (m, 1H), 7.22 (m, 4H), 7.00 (ddt, 1H), 6.88 (m, 1H), 6.05 (tdd, 1H), 5.40 (m, 2H), 4.55 (m, 2H), 4.03 (m, 1H), 3.95 (m, 1H), 3.60 (m, 1H), 3.54 (d, 1H), 2.34 (s, 3H).

SYNTHESIS EXAMPLE 10

Preparation of (3RS,4RS)—N-(2,3-difluorophenyl)-4-(4-methylphenyl)-2-oxo-1-prop-2-ynoxy-pyrrolidine-3-carboxamide (e.g. a compound of Formula 1 wherein $Y^1$ and $Y^2$ are both O; J is —$CR^2R^3$—; $R^2$ and $R^3$ are both H; $Q^1$ is Ph(4-Me); $Q^2$ is Ph(2,3-diF); $R^4$ and $R^5$ are both H; $R^6$ is H; and $R^1$ is O-propargyl.)

Step A: Preparation of ethyl (3RS,4SR)-4-(4-methylphenyl)-2-oxo-1-prop-2-ynoxy-pyrrolidine-3-carboxylate Prop-2-yn-1-ol (0.027 ml, 0.46 mmol) and triphenylphosphine (0.14 g, 0.53 mmol) were added to a solution of ethyl (3RS,4SR)-1-hydroxy-4-(4-methylphenyl)-2-oxo-pyrrolidine-3-carboxylate (prepared as described in SYNTHESIS EXAMPLE 8, step A; 0.10 g, 0.38 mmol) in tetrahydrofuran (2.3 ml), then diisopropyl azodicarboxylate (0.097 ml, 0.49 mmol) was added dropwise. The resulting mixture was stirred at ambient temperature for 17 hours, then purified by column chromatography to provide ethyl (3RS,4SR)-4-(4-methylphenyl)-2-oxo-1-prop-2-ynoxy-pyrrolidine-3-carboxylate (0.069 g, 30%), which was used without further characterisation.

Step B: Preparation of (3RS,4RS)—N-(2,3-difluorophenyl)-4-(4-methylphenyl)-2-oxo-1-prop-2-ynoxy-pyrrolidine-3-carboxamide 2,3-Difluoroaniline (0.084 ml, 0.83 mmol) was added to a solution of ethyl (3RS,4SR)-4-(4-methylphenyl)-2-oxo-1-prop-2-ynoxy-pyrrolidine-3-carboxylate (0.050 g, 0.17 mmol) in dry dimethyl sulfoxide (0.50 ml) and the resulting solution was heated in a microwave oven at 160° C. for 10 minutes. The resulting mixture was allowed to cool and purified by column chromatography to provide (3RS,4RS)—N-(2,3-difluorophenyl)-4-(4-methylphenyl)-2-oxo-1-prop-2-ynoxy-pyrrolidine-3-carboxamide (0.006 g, 9%).

$^1$H NMR δ=9.49 (br s, 1H), 8.00 (m, 1H), 7.27 (m, 2H), 7.19 (m, 2H), 7.01 (ddt, 1H), 6.88 (m, 1H), 4.72 (m, 2H), 4.11 (m, 2H), 3.74 (m, 1H), 3.56 (d, 1H), 2.60 (t, 1H), 2.34 (s, 3H).

Formulation/Utility

Compounds of this disclosure are generally useful as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide*, 2nd Ed., Interscience, New York, 1950.

The solid and liquid compositions of the present disclosure often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this disclosure may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Tables A-F. Without further elaboration, it is believed that one skilled in the art using the preceding description can utilize the present disclosure to its fullest extent. The following Examples are, therefore, to be construed as merely illustrative, and not limiting of the disclosure in any way whatsoever. Percentages are by weight except where otherwise indicated.

Example A

| High Strength Concentrate | |
|---|---|
| Compound 352 | 98.5% |
| silica aerogel | 0.5% |
| synthetic amorphous fine silica | 1.0% |

Example B

| Wettable Powder | |
|---|---|
| Compound 352 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
|---|---|
| Compound 352 | 10.0% |
| attapulgite granules (low volatile matter, 0.71/0.30 mm; U.S.S. No. 25-50 sieves) | 90.0% |

Example D

| Extruded Pellet | |
|---|---|
| Compound 352 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
|---|---|
| Compound 352 | 10.0% |
| polyoxyethylene sorbitol hexoleate | 20.0% |
| $C_6$-$C_{10}$ fatty acid methyl ester | 70.0% |

Example F

| Microemulsion | |
|---|---|
| Compound 352 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

| Suspension Concentrate | |
|---|---|
| Compound 352 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |

-continued

| Suspension Concentrate | |
|---|---|
| propylene glycol | 5.0% |
| silicone based defoamer | 0.1% |
| 1,2-benzisothiazolin-3-one | 0.1% |
| water | 53.7% |

Example H

| Emulsion in Water | |
|---|---|
| Compound 352 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example I

| Oil Dispersion | |
|---|---|
| Compound 352 | 25% |
| polyoxyethylene sorbitol hexaoleate | 15% |
| organically modified bentonite clay | 2.5% |
| fatty acid methyl ester | 57.5% |

Example J

| Suspoemulsion | |
|---|---|
| Compound 352 | 10.0% |
| imidacloprid | 5.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0% |
| water | 53.7% |

The present disclosure also includes Examples A through J above except "Compound 352" is replaced with "Compound 353", "Compound 354", "Compound 355", "Compound 356", "Compound 357", "Compound 358", "Compound 359", "Compound 360", "Compound 361", "Compound 362", "Compound 363", "Compound 364", "Compound 365", "Compound 366", "Compound 367", "Compound 368", "Compound 369", "Compound 370", "Compound 371", "Compound 372", "Compound 373", "Compound 374", "Compound 375", "Compound 376", "Compound 377", "Compound 378", "Compound 379", "Compound 380", "Compound 381", "Compound 382", "Compound 383", "Compound 384", "Compound 386", "Compound 387", "Compound 388", "Compound 389", "Compound 390", "Compound 391", "Compound 392", "Compound 393", "Compound 394", "Compound 395", "Compound 396", "Compound 397", "Compound 398", "Compound 399", "Compound 400", "Compound 401", "Compound 402", "Compound 403", "Compound 404", "Compound 405", "Compound 406", "Compound 407", "Compound 408", "Compound 409", "Compound 410", "Compound 411", "Compound 412", "Compound 413", "Compound 414", "Compound 415", "Compound 416", "Compound 417", "Compound 418", "Compound 419", "Compound 420", "Compound 421", "Compound 422", "Compound 423", "Compound 424", "Compound 425", "Compound 426", "Compound 427", "Compound 428", "Compound 429", "Compound 430", "Compound 431", "Compound 432", "Compound 433", "Compound 434", "Compound 435", "Compound 436", "Compound 437", "Compound 438", "Compound 439", "Compound 440", "Compound 441", "Compound 442", "Compound 443", "Compound 444", "Compound 445", "Compound 446", "Compound 447", "Compound 448", "Compound 449", "Compound 450", "Compound 451", "Compound 452", "Compound 453", "Compound 454", "Compound 455", "Compound 456", "Compound 457", "Compound 460", "Compound 461", "Compound 462", "Compound 463", "Compound 464", "Compound 465", "Compound 466", "Compound 467", "Compound 468", "Compound 469", "Compound 470", "Compound 471", "Compound 472", "Compound 473", "Compound 474", "Compound 475", "Compound 476", "Compound 477", "Compound 478", "Compound 479", "Compound 480", "Compound 481", "Compound 482", "Compound 483", "Compound 484", "Compound 485", "Compound 486", "Compound 487", "Compound 488", "Compound 489", "Compound 490", "Compound 491", "Compound 492", "Compound 493", "Compound 494", "Compound 495", "Compound 496", "Compound 497", "Compound 498", "Compound 499", "Compound 500", "Compound 501", "Compound 502", "Compound 503", "Compound 504", "Compound 505", "Compound 506", "Compound 507", "Compound 508", "Compound 509", "Compound 510", "Compound 511", "Compound 512", "Compound 513", "Compound 514", "Compound 515", "Compound 516", "Compound 517", "Compound 518", "Compound 519", "Compound 520", "Compound 521", "Compound 522", "Compound 523", "Compound 524", "Compound 525", "Compound 526", "Compound 527", "Compound 528", "Compound 529", "Compound 530", "Compound 531", "Compound 532", "Compound 533", "Compound 534", "Compound 535", "Compound 536", "Compound 537", "Compound 538", "Compound 539", "Compound 540", "Compound 541", "Compound 544", "Compound 545", "Compound 546", "Compound 547", "Compound 549", "Compound 550", "Compound 551", "Compound 552", "Compound 553", "Compound 554", "Compound 555", "Compound 556", "Compound 557", "Compound 558", "Compound 559", "Compound 560", "Compound 561", "Compound 562", "Compound 563", "Compound 564", "Compound 565", "Compound 566", "Compound 567", "Compound 568", "Compound 569", "Compound 570", "Compound 571", "Compound 572", "Compound 573", "Compound 574", "Compound 575", "Compound 576", "Compound 577", "Compound 578", "Compound 579", "Compound 580", "Compound 581", "Compound 582", "Compound 583", "Compound 584", "Compound 585", "Compound 586", "Compound 587", "Compound 588", "Compound 589", "Compound 590", "Compound 591", "Compound 592", "Compound 593", "Compound 594", "Compound 595", "Compound 596", "Compound 597", "Compound 598", "Compound 599", "Compound 600", "Compound 601", "Compound 602", "Compound 605", "Compound 606", "Compound 607", "Compound 608", "Compound 609", "Compound 610", "Compound 611", "Compound 612", "Compound 613", "Compound 614", "Compound 616", "Compound 617", "Compound 618", "Compound 619", "Compound 620", "Compound 621", "Compound 622", "Compound 623", "Compound 624", "Compound 625", "Compound 630", "Compound 631", "Compound 632", "Compound 633", "Compound 634", "Compound 635", "Compound 636", "Compound 637", "Compound 638", "Compound 639", "Compound 640", "Compound 641", "Compound 642", "Compound 643", "Compound 644", "Compound 645", "Compound 646", "Compound 647", "Compound 648", "Compound 649", "Compound 650", "Compound 651", "Compound 652", "Compound 653", "Compound 654", "Compound 655", "Compound 656", "Compound 657", "Compound 658", "Compound 659", "Compound 660", "Compound 661", "Compound 662", "Compound 663", "Compound 664", "Compound 665", "Compound 666", "Compound 667", "Compound 668", "Compound 674", "Compound 675", "Compound 676", "Compound 677", "Compound 678", "Compound 679", "Compound 680", "Compound 681", "Compound 682", "Compound 683", "Compound 684", "Compound 685", "Compound 686", "Compound 687", "Compound 688", "Compound 689", "Compound 690", "Compound 691", "Compound 692", "Compound 693", "Compound 694", "Compound 695", "Compound 696", "Compound 697", "Compound 698", "Compound 699", "Compound 700", "Compound 701", "Compound 702", "Compound 703", "Compound 704", "Compound 705", "Compound 706", "Compound 711", "Compound 712", "Compound 713", "Compound 714", "Compound 715", "Compound 716", "Compound 717", "Compound 718", "Compound 719", "Compound 720", "Compound 721", "Compound 722", "Compound 723", "Compound 724", "Compound 725", "Compound 726", "Compound 727", "Compound 728", "Compound 729", "Compound 730", "Compound 731", "Compound 732", "Compound 733", "Compound 734", "Compound 735", "Compound 736", "Compound 737", "Compound 738", "Compound 739", "Compound 740", "Compound 741", "Compound 742", "Compound 743", "Compound 744", "Compound 745", "Compound 746", "Compound 747", "Compound 748", "Compound 749", "Compound 750", "Compound 751", "Compound 752", "Compound 753", "Compound 754", "Compound 755", "Compound 756", "Compound 757", "Compound 758", "Compound 759", "Compound 760", "Compound 761", "Compound 762", "Compound 763", "Compound 764", "Compound 765", "Compound 766", "Compound 767", "Compound 768", "Compound 769", "Compound 770", "Compound 771", "Compound 772", "Compound 773", "Compound 774", "Compound 775", "Compound 776", "Compound 777", "Compound 778", "Compound 779", "Compound 780", "Compound 781", "Compound 782", "Compound 783", "Compound 784", "Compound 785", "Compound 786", "Compound 787", "Compound 788", "Compound 789", "Compound 790", "Compound 791", "Compound 792", "Compound 793", "Compound 794", "Compound 795", "Compound 796", "Compound 797", "Compound 798", "Compound 799", "Compound 800", "Compound 801", "Compound 802", "Compound 803", "Compound 804", "Compound 805", "Compound 806", "Compound 807", "Compound 808", "Compound 809", "Compound 810", "Compound 811", "Compound 812", "Compound 813", "Compound 814", "Compound 815", "Compound 816", "Compound 817", "Compound 818", "Compound 819", "Compound 820", "Compound 821", "Compound 822", "Compound 823", "Compound 824", "Compound 825", "Compound 826", "Compound 827", "Compound 828", "Compound 829", "Compound 830", "Compound 831", "Compound 832", "Compound 833", "Compound 834", "Compound 835", "Compound 836", "Compound 837", "Compound 838", "Compound 839", "Compound 840", "Compound 841", "Compound 842", "Compound 843", "Compound 844", "Compound 845", "Compound 846", "Compound 847", "Compound 848", "Compound 849", "Compound 850", "Compound 851", "Compound 852", "Compound 853", "Compound 854", "Compound 855", "Compound 856", "Compound 857", "Compound 858", "Compound 859", "Compound 860", "Compound 861", "Compound 862", "Compound 863", "Compound 864", "Compound 865", "Compound 866", "Compound 867", "Compound 868", "Compound 869", "Compound 870", "Compound 871", "Compound 872", "Compound 873", "Compound 874", "Compound 875", "Compound 876", "Compound 877", "Compound 878", "Compound 879", "Compound 880", "Compound 881", "Compound 882", "Compound 883", "Compound 884", "Compound 885", "Compound 886", "Compound 887", "Compound 888", "Compound 889", "Compound 890", "Compound 891", "Compound 892", "Compound 893", "Compound 894", "Compound 895", "Compound 896", "Compound 897", "Compound 898", "Compound 899", "Compound 900", "Compound 901", "Compound 902", "Compound 903", "Compound 904", "Compound 905", "Compound 906", "Compound 907", "Compound 908", "Compound 909", "Compound 910", "Compound 911", "Compound 912", "Compound 913", "Compound 914", "Compound 915", "Compound 916", "Compound 917", "Compound 918", "Compound 919", "Compound 920", "Compound 921", "Compound 922", "Compound 923", "Compound 924", "Compound 925", "Compound 926", "Compound 927", "Compound 928", "Compound 929", "Compound 930", "Compound 931", "Compound 932", "Compound 933", "Compound 934", "Compound 935", "Compound 936", "Compound 937", "Compound 938", "Compound 939", "Compound 940", "Compound 941", "Compound 942", "Compound 943", "Compound 944", "Compound 945", "Compound 946", "Compound 947", "Compound 948", "Compound 949", "Compound 950", "Compound 951", "Compound 952", "Compound 953", "Compound 954", "Compound 955", "Compound 956", "Compound 957", "Compound 958", "Compound 959", "Compound 960", "Compound 961", "Compound 962", "Compound 963", "Compound 964", "Compound 965", "Compound 966", "Compound 967", "Compound 968", "Compound 969", "Compound 970", "Compound 971", "Compound 972", "Compound 973", "Compound 974", "Compound 975", "Compound 976", "Compound 977", "Compound 978", "Compound 979", "Compound 980", "Compound 981", "Compound 982", "Compound 983", "Compound 984", "Compound 985", "Compound 986", "Compound 987", "Compound 988", "Compound 989", "Compound 990", "Compound 991", "Compound 992", "Compound 993", "Compound 994", "Compound 995", "Compound 996", "Compound 997", "Compound 998", "Compound 999", "Compound 1000", "Compound 1001", "Compound 1002", "Compound 1003", "Compound 1004", "Compound 1005", "Compound 1006", "Compound 1007", "Compound 1008", "Compound 1009", "Compound 1010", "Compound 1011", "Compound 1012", "Compound 1013", "Compound 1014", "Compound 1015", "Compound 1016", "Compound 1017", "Compound 1018", "Compound 1019", "Compound 1020", "Compound 1021", "Compound 1022", "Compound 1023", "Compound 1024", "Compound 1025", "Compound 1026", "Compound 1027", "Compound 1028", "Compound 1029", "Compound 1030", "Compound 1031", "Compound 1032", "Compound 1033", "Compound 1034", "Compound 1035", "Compound 1036", "Compound 1037", "Compound 1038", "Compound 1039", "Compound 1040", "Compound 1041", "Compound 1042", "Compound 1043", "Compound 1044", "Compound 1045", "Compound 1046", "Compound 1047", "Compound 1048", "Compound 1049", "Compound 1050", "Compound 1051", "Compound 1052", "Compound 1053", "Compound 1054", "Compound 1055", "Compound 1056", "Compound 1057", "Compound 1058", "Compound 1059", "Compound 1060", "Compound 1061", "Compound 1062", "Compound 1063", "Compound 1064", "Compound 1065", "Compound 1066", "Compound 1067", "Compound 1068", "Compound 1069", "Compound 1070", "Compound 1071", "Compound 1072", "Compound 1073", "Compound 1074", "Compound 1075", "Compound 1076", "Compound 1077", "Compound 1078", "Compound 1079", "Compound 1080", "Compound 1081", "Compound 1082", "Compound 1083", "Compound 1084", "Compound 1085", "Compound 1086", "Compound 1087", "Compound 1088", "Compound 1089", "Compound 1090", "Compound 1091", "Compound 1092", "Compound 1093", "Compound 1094", "Compound 1095", "Compound 1096", "Compound 1097", "Compound 1098", "Compound 1099", "Compound 1100", "Compound 1101", "Compound 1102", "Compound 1103", "Compound 1104", "Compound 1105", "Compound 1106", "Compound 1107", "Compound 1108", "Compound 1109", "Compound 1110", "Compound 1111", "Compound 1112", "Compound 1113", "Compound 1114", "Compound 1115", "Compound 1116", "Compound 1117", "Compound 1118", "Compound 1119", "Compound 1120", "Compound 1121", "Compound 1122", "Compound 1123", "Compound 1124", "Compound 1125", "Compound 1126", "Compound 1127", "Compound 1128", "Compound 1129", "Compound 1130", "Compound 1131", "Compound 1132", "Compound 1133", "Compound 1134", "Compound 1135", "Compound 1136", "Compound 1137", "Compound 1138", "Compound 1139", "Compound 1140", "Compound 1141", "Compound 1142", "Compound 1143", "Compound 1144", "Compound 1145", "Compound 1146", "Compound 1147", "Compound 1148", "Compound 1149", "Compound 1150", "Compound 1151", "Compound 1152", "Compound 1153", "Compound 1154", "Compound 1155", "Compound 1156", "Compound 1157", "Compound 1158", "Compound 1159", "Compound 1160", "Compound 1161", "Compound 1162", "Compound 1163", "Compound 1164", "Compound 1165", "Compound 1166", "Compound 1167", "Compound 1168", "Compound 1169", "Compound 1170", "Compound 1171", "Compound 1172", "Compound 1173", "Compound 1174", "Compound 1175", "Compound 1176", "Compound 1177", "Compound 1178", "Compound 1179", "Compound 1180", "Compound 1181", "Compound 1182", "Compound 1183", "Compound 1184", "Compound 1185", "Compound 1186", "Compound 1187", "Compound 1188", "Compound 1189", "Compound 1190", "Compound 1191", "Compound 1192", "Compound 1193", "Compound 1194", "Compound 1195", "Compound 1196", "Compound 1197", "Compound 1198", "Compound 1199", "Compound 1200", "Compound 1201", "Compound 1202", "Compound 1203", "Compound 1204", "Compound 1205", "Compound 1206", "Compound 1207", "Compound 1208", "Compound 1209", "Compound 1210", "Compound 1211", "Compound 1212", "Compound 1213", "Compound 1214", "Compound 1215", "Compound 1216", "Compound 1217", "Compound 1218", "Compound 1219", "Compound 1220", "Compound 1221", "Compound 1222", "Compound 1223", "Compound 1224", "Compound 1225", "Compound 1226", "Compound 1227", "Compound 1228", "Compound 1229", "Compound 1230", "Compound 1231", "Compound 1232", "Compound 1233", "Compound 1234", "Compound 1235", "Compound 1236", "Compound 1237", "Compound 1238", "Compound 1239", "Compound 1240", "Compound 1241", "Compound 1242", "Compound 1243", "Compound 1244", "Compound 1245", "Compound 1246", "Compound 1247", "Compound 1248", "Compound 1249", "Compound 1250", "Compound 1251", "Compound 1252", "Compound 1253", "Compound 1254", "Compound 1255", "Compound 1256", "Compound 1257", "Compound 1258", "Compound 1259", "Compound 1260", "Compound 1261", "Compound 1262", "Compound 1263", "Compound 1264", "Compound 1265", "Compound 1266", "Compound 1267", "Compound 1268", "Compound 1269", "Compound 1270", "Compound 1271", "Compound 1272", "Compound 1273", "Compound 1274", "Compound 1275", "Compound 1276", "Compound 1277", "Compound 1278", "Compound 1279", "Compound 1280", "Compound 1281", "Compound 1282", "Compound 1283", "Compound 1284", "Compound 1285", "Compound 1286", "Compound 1287", "Compound 1288", "Compound 1289", "Compound 1290", "Compound 1291", "Compound 1292", "Compound 1293", "Compound 1294", "Compound 1295", "Compound 1296", "Compound 1297", "Compound 1298", "Compound 1299", "Compound 1300", "Compound 1301", "Compound 1302", "Compound 1303", "Compound 1304", "Compound 1305", "Compound 1306", "Compound 1307", "Compound 1308", "Compound 1309", "Compound 1310", "Compound 1311", "Compound 1312", "Compound 1313", "Compound 1314", "Compound 1315", "Compound 1316", "Compound 1317", "Compound 1318", "Compound 1319", "Compound 1320", "Compound 1321", "Compound 1322", "Compound 1323", "Compound 1324", "Compound 1325", "Compound 1326", "Compound 1327", "Compound 1328", "Compound 1329", "Compound 1330", "Compound 1331", "Compound 1332", "Compound 1333", "Compound 1334", "Compound 1335", "Compound 1336", "Compound 1337", "Compound 1338", "Compound 1339", "Compound 1340", "Compound 1341", "Compound 1342", "Compound 1343", "Compound 1344", "Compound 1345", "Compound 1346", "Compound 1347", "Compound 1348", "Compound 1349", "Compound 1350", "Compound 1351", "Compound 1352", "Compound 1353", "Compound 1354", "Compound 1355", "Compound 1356", "Compound 1357", "Compound 1358", "Compound 1359", "Compound 1360", "Compound 1361", "Compound 1362", "Compound 1363", "Compound 1364", "Compound 1365", "Compound 1366", "Compound 1367", "Compound 1368", "Compound 1369", "Compound 1370", "Compound 1371", "Compound 1372", "Compound 1373", "Compound 1374", "Compound 1375", "Compound 1376", "Compound 1377", "Compound 1378", "Compound 1379", "Compound 1380", "Compound 1381", "Compound 1382", "Compound 1383", "Compound 1384", "Compound 1385", "Compound 1386", "Compound 1387", "Compound 1388", "Compound 1389", "Compound 1390", "Compound 1391", "Compound 1392", "Compound 1393", "Compound 1394", "Compound 1395", "Compound 1396", "Compound 1397", "Compound 1398", "Compound 1399", "Compound 1400", "Compound", "Compound", "Compound 1401", "Compound", "Compound", "Compound", "Compound 1402", "Compound", "Compound", "Compound", "Compound 1403", "Compound 1404", "Compound 1405", "Compound 1406", "Compound 1407", "Compound 1408", "Compound 1409", "Compound 1410", "Compound 1411", "Compound 1412", "Compound 1413", "Compound 1414", "Compound 1415", "Compound 1416", "Compound 1417", "Compound 1418", "Compound 1419", "Compound 1420", "Compound 1421", "Compound 1422", "Compound 1423", "Compound 1424", "Compound 1425", "Compound 1426", "Compound 1427", "Compound 1428", "Compound 1429", "Compound 1430", "Compound 1431", "Compound 1432", "Compound 1433", "Compound 1434", "Compound 1435", "Compound 1436", "Compound 1437", "Compound 1438", "Compound 1439", "Compound 1440", "Compound 1441", "Compound 1442", "Compound 1443", "Compound 1444", "Compound 145", "Compound 1446", "Compound 1447", "Compound 1448", "Compound 1449", "Compound 1450", "Compound 1451", "Compound 1452", "Compound 1453", "Compound 1454", "Compound 1455", "Compound 1456", "Compound 1457", "Compound 1458", "Compound 1459", "Compound 1460", "Compound 1461", "Compound 1462", "Compound 1463", "Compound 1464", "Compound 1465", "Compound 1466", "Compound 1467", "Compound 1468", "Compound 1469", "Compound 1470", "Compound 1471", "Compound 1472", "Compound 1473", "Compound 1474", "Compound 1475", "Compound 1476", "Compound 1477", "Compound 1478", "Compound 1479", "Compound 1480", "Compound 1481", "Compound 1482", "Compound 1483", "Compound 1484", "Compound 1485", "Compound 1486", "Compound 1487", "Compound 1488", "Compound 1489", "Compound 1490", "Compound 1491", "Compound 1492", "Compound 1493", "Compound 1494", "Compound 1495", "Compound 1496", "Compound 1497", "Compound 1498", "Compound 1499", "Compound 1500", "Compound 1501", "Compound 1502", "Compound 1503", "Compound 1504", "Compound 1505", "Compound 1506", "Compound 1507", "Compound 1508", "Compound 1509", "Compound 1510", "Compound 1511", "Compound 1512", "Compound 1513", "Compound 1514", "Compound 1515", "Compound 1516", "Compound 1517", "Compound 1518", "Compound 1519", "Compound 1520", "Compound 1521", "Compound 1522", "Compound 1523", "Compound 1524", "Compound 1525", "Compound 1526", "Compound 1527", "Compound 1528", "Compound 1529", "Compound 1530", "Compound 1531", "Compound 1532", "Compound 1533", "Compound 1534", "Compound 1535", "Compound 1536", "Compound 1537", "Compound 1538", "Compound 1539", "Compound 1540", "Compound 1541", "Compound 1542", "Compound 1543", "Compound 1544", "Compound 1545", "Compound 1546", "Compound 1547", "Compound 1548", "Compound 1549", "Compound 1550", "Compound 1551", "Compound 1552", "Compound 1553", "Compound 1554", "Compound 1555", "Compound 1556", "Compound 1557", "Compound 1558", "Compound 1559", "Compound 1560", "Compound 1561", "Compound 1562", "Compound 1563", "Compound 1564", "Compound 1565", "Compound 1566", "Compound 1567", "Compound 1568", "Compound 1569", "Compound 1570", "Compound 1571", "Compound 1572", "Compound 1573", "Compound 1574", "Compound 1575", "Compound 1576", "Compound 1577", "Compound 1578", "Compound 1579", "Compound 1580", "Compound 1581", "Compound 1582", "Compound 1583", "Compound 1584", "Compound 1585", "Compound 1586", "Compound 1587", "Compound 1588", "Compound 1589", "Compound 1590", "Compound 1591", "Compound 1592", "Compound 1593", "Compound 1594", "Compound 1595", "Compound 1596", "Compound 1597", "Compound 1598", "Compound 1599", "Compound 1600", "Compound 1601", "Compound 1602", "Compound 1603", "Compound 1604", "Compound 1605", "Compound 1606", "Compound 1607", "Compound 1608", "Compound 1609", "Compound 1610", "Compound 1611", "Compound 1612", "Compound 1613", "Compound 1614", "Compound 1615", "Compound 1616", "Compound 1617", "Compound 1618", "Compound 1619", "Compound 1620", "Compound 1621", "Compound 1622", "Compound 1623", "Compound 1624", "Compound 1625", "Compound 1626", "Compound 1627", "Compound 1628", "Compound 1629", "Compound 1630", "Compound 1631", "Compound 1632", "Compound 1633", "Compound 1634", "Compound 1635", "Compound 1636", "Compound 1637", "Compound 1638", "Compound 1639", "Compound 1640", "Compound 1641", "Compound 1642", "Compound 1643", "Compound 1644", "Compound 1645", "Compound 1646", "Compound 1647", "Compound 1648", "Compound 1649", "Compound 1650", "Compound 1651", "Compound 1652", "Compound 1653", "Compound 1654", "Compound 1655", "Compound 1656", "Compound 1657", "Compound 1658", "Compound 1659", "Compound 1660", "Compound 1661", "Compound 1662", "Compound 1663", "Compound 1664", "Compound 1665", "Compound 1666", "Compound 1667", "Compound 1668", "Compound 1669", "Compound 1670", "Compound 1671", "Compound 1672", "Compound 1673", "Compound 1674", "Compound 1675", "Compound 1676", "Compound 1677", "Compound 1678", "Compound 1679", "Compound 1680", "Compound 1681", "Compound 1682", "Compound 1683", "Compound 1684", "Compound 1685", "Compound 1686", "Compound 1687", "Compound 1688", "Compound 1689", "Compound 1690", "Compound 1691", "Compound 1692", "Compound 1693", "Compound 1694", "Compound 1695", "Compound 1696", "Compound 1697", "Compound 1698", "Compound 1699", "Compound 1700", "Compound 1701", "Compound 1702", "Compound 1703", "Compound 1704", "Compound 1705", "Compound 1706", "Compound 1707", "Compound 1708", "Compound 1709", "Compound 1710", "Compound 1711", "Compound 1712", "Compound 1713", "Compound 1714", "Compound 1715", "Compound 1716", "Compound 1717", "Compound 1718", "Compound 1719", "Compound 1720", "Compound 1721", "Compound 1722", "Compound 1723", "Compound 1724", "Compound 1725", "Compound 1726", "Compound 1727", "Compound 1728", "Compound 1729", "Compound 1730", "Compound 1731", "Compound 1732", "Compound 1733", "Compound 1734", "Compound 1735", "Compound 1736", "Compound 1737", "Compound 1738", "Compound 1739", "Compound 1740", "Compound 1741", "Compound 1742", "Compound 1743", "Compound 1744", "Compound 1745", "Compound 1746", "Compound 1747", "Compound 1748", "Compound 1749", "Compound 1750", "Compound 1751", "Compound 1752", "Compound 1753", "Compound 1754", "Compound 1755", "Compound 1756", "Compound 1757", "Compound 1758", "Compound 1759", "Compound 1760", "Compound 1761", "Compound 1762", "Compound 1763", "Compound 1764", "Compound 1765", "Compound 1766", "Compound 1767", "Compound 1768", "Compound 1769", "Compound 1770", "Compound 1771", "Compound 1772", "Compound 1773", "Compound 1774", "Compound 1775", "Compound 1776", "Compound 1777", "Compound 1778", "Compound 1779", "Compound 1780", "Compound 1781", "Compound 1782", "Compound 1783", "Compound 1784", "Compound 1785", "Compound 1786", "Compound 1787", "Compound 1788", "Compound 1789", "Compound 1790", "Compound 1791", "Compound 1792", "Compound 1793", "Compound 1794", "Compound 1795", "Compound 1796", "Compound 1797", "Compound 1798", "Compound 1799", "Compound 1800", "Compound 1801", "Compound 1802", "Compound 1803", "Compound 1804", "Compound 1805", "Compound 1806", "Compound 1807", "Compound 1808", "Compound 1809", "Compound 1810", "Compound 1811", "Compound 1812", "Compound 1813", "Compound 1814", "Compound 1815", "Compound 1816", "Compound 1817", "Compound 1818", "Compound 1819", "Compound 1820", "Compound 1821", "Compound 1822", "Compound 1823", "Compound 1824", "Compound 1825", "Compound 1826", "Compound 1827", "Compound 1828", "Compound 1829", "Compound 1830", "Compound 1831", "Compound 1832", "Compound 1833", "Compound 1834", "Compound 1835", "Compound 1836", "Compound 1837", "Compound 1838", "Compound 1839", "Compound 1840", "Compound 1841", "Compound 1842", "Compound 1843", "Compound 1844", "Compound 1845", "Compound 1846", "Compound 1847", "Compound 1848", "Compound 1849", "Compound 1850", "Compound 1851", "Compound 1852", "Compound 1853", "Compound 1854", "Compound 1855", "Compound 1856", "Compound 1857", "Compound 1858", "Compound 1859", "Compound 1860", "Compound 1861", "Compound 1862", "Compound 1863", "Compound 1864", "Compound 1865", "Compound 1866", "Compound 1867", "Compound 1868", "Compound 1869", "Compound 1870", "Compound 1871", "Compound 1872", "Compound 1873" or "Compound 1874" above.

Test results indicate that many compounds of the present disclosure are highly active preemergent and/or postemergent herbicides and/or plant growth regulants. Many compounds of this disclosure generally show highest activity for early postemergence weed control (i.e. applied soon after weed seedlings emerge from the soil) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this disclosure, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that a desired combination of these selectivity factors within a compound or group of compounds can readily be determined by performing routine biological and/or biochemical assays. Compounds of this disclosure may show tolerance to important agronomic crops including, but is not limited to, alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as eucalyptus and conifers (e.g., loblolly pine), and turf species (e.g., Kentucky bluegrass, St. Augustine grass, Kentucky fescue and Bermuda grass). Many compounds of this disclosure can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

As many compounds of this disclosure have (both preemergent and postemergent herbicidal) activity, to control undesired vegetation by killing or injuring the vegetation or reducing its growth, the compounds can be usefully applied by a variety of methods involving contacting a herbicidally effective amount of a compound of this disclosure, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation.

A herbicidally effective amount of the compounds of this disclosure is determined by a number of factors. These factors include: formulation selected, method of application, amount and type of vegetation present, growing conditions, etc. In general, a herbicidally effective amount of compounds of this disclosure is from about 0.005 to about 20 kg/ha. In some embodiments, the range is from about 0.01 to about 1 kg/ha. One skilled in the art can easily determine the herbicidally effective amount necessary for the desired level of weed control.

Compounds of the disclosure are useful in treating all plants and plant parts. Plant varieties and cultivars can be obtained by conventional propagation and breeding methods or by genetic engineering methods. Genetically modified plants (transgenic plants) are those in which a heterologous gene (transgene) has been stably integrated into the plant's genome. A transgene that is defined by its particular location in the plant genome is called a transformation or transgenic event.

Genetically modified plant cultivars which can be treated according to this disclosure include those that are resistant against one or more biotic stresses (pests such as nematodes, insects, mites, fungi, etc.) or abiotic stresses (drought, cold temperature, soil salinity, etc.), or that contain other desirable characteristics. Plants can be genetically modified to exhibit traits of, for example, herbicide tolerance, insect-resistance, modified oil profiles or drought tolerance. Useful genetically modified plants containing single gene transformation events or combinations of transformation events are listed in Table 3. Additional information for the genetic modifications listed in Table 3 can be obtained from publicly available databases maintained, for example, by the U.S. Department of Agriculture.

The following abbreviations, T1 through T37, are used in Table 3 for traits. A "-" means the entry is not available.

| Trait | Description |
| --- | --- |
| T1 | Glyphosate tolerance |
| T2 | High lauric acid oil |
| T3 | Glufosinate tolerance |
| T4 | Phytate breakdown |
| T5 | Oxynil tolerance |
| T6 | Disease resistance |
| T7 | Insect resistance |
| T9 | Modified flower color |
| T11 | ALS Herbicide Tol. |
| T12 | Dicamba Tolerance |
| T13 | Anti-allergy |
| T14 | Salt tolerance |
| T15 | Cold tolerance |
| T16 | Imidazolinone herb. tol. |
| T17 | Modified alpha-amylase |
| T18 | Pollination control |
| T19 | 2,4-D tolerance |
| T20 | Increased lysine |
| T21 | Drought tolerance |
| T22 | Delayed ripening/senescence |
| T23 | Modified product quality |
| T24 | High cellulose |
| T25 | Modified starch/carbohydrate |
| T26 | Insect & disease resist. |
| T27 | High tryptophan |
| T28 | Erect leaves semidwarf |

| Trait | Description |
|---|---|
| T29 | Semidwarf |
| T30 | Low iron tolerance |
| T31 | Modified oil/fatty acid |
| T32 | HPPD tolerance |
| T33 | High oil |
| T34 | Aryloxyalkanoate tol. |
| T35 | Mesotrione tolerance |
| T36 | Reduced nicotine |
| T37 | Modified product |

TABLE 3

| Crop | Event Name | Event Code | Trait(s) | Gene(s) |
|---|---|---|---|---|
| Alfalfa | J101 | MON-00101-8 | T1 | cp4 epsps (aroA:CP4) |
| Alfalfa | J163 | MON-ØØ163-7 | T1 | cp4 epsps (aroA:CP4) |
| Canola* | 23-18-17 (Event 18) | CGN-89465-2 | T2 | te |
| Canola* | 23-198 (Event 23) | CGN-89465-2 | T2 | te |
| Canola* | 61061 | DP-Ø61Ø61-7 | T1 | gat4621 |
| Canola* | 73496 | DP-Ø73496-4 | T1 | gat4621 |
| Canola* | GT200 (RT200) | MON-89249-2 | T1 | cp4 epsps (aroA:CP4); goxv247 |
| Canola* | GT73 (RT73) | MON-ØØØ73-7 | T1 | cp4 epsps (aroA:CP4); goxv247 |
| Canola* | HCN10 (Topas 19/2) | — | T3 | bar |
| Canola* | HCN28 (T45) | ACS-BNØØ8-2 | T3 | pat (syn) |
| Canola* | HCN92 (Topas 19/2) | ACS-BNØØ7-1 | T3 | bar |
| Canola* | MON88302 | MON-883Ø2-9 | T1 | cp4 epsps (aroA:CP4) |
| Canola* | MPS961 | — | T4 | phyA |
| Canola* | MPS962 | — | T4 | phyA |
| Canola* | MPS963 | — | T4 | phyA |
| Canola* | MPS964 | — | T4 | phyA |
| Canola* | MPS965 | — | T4 | phyA |
| Canola* | MS1 (B91-4) | ACS-BNØØ4-7 | T3 | bar |
| Canola* | MS8 | ACS-BNØØ5-8 | T3 | bar |
| Canola* | OXY-235 | ACS-BNØ11-5 | T5 | bxn |
| Canola* | PHY14 | — | T3 | bar |
| Canola* | PHY23 | — | T3 | bar |
| Canola* | PHY35 | — | T3 | bar |
| Canola* | PHY36 | — | T3 | bar |
| Canola* | RF1 (B93-101) | ACS-BNØØ1-4 | T3 | bar |
| Canola* | RF2 (B94-2) | ACS-BNØØ2-5 | T3 | bar |
| Canola* | RF3 | ACS-BNØØ3-6 | T3 | bar |
| Bean | EMBRAPA 5.1 | EMB-PV051-1 | T6 | ac1 (sense and antisense) |
| Brinjal # | EE-1 | — | T7 | cry1Ac |
| Cotton | 19-51a | DD-Ø1951A-7 | T11 | S4-HrA |
| Cotton | 281-24-236 | DAS-24236-5 | T3, T7 | pat (syn); cry1F |
| Cotton | 3006-210-23 | DAS-21Ø23-5 | T3, T7 | pat (syn); cry1Ac |
| Cotton | 31707 | — | T5, T7 | bxn; cry1Ac |
| Cotton | 31803 | — | T5, T7 | bxn; cry1Ac |
| Cotton | 31807 | — | T5, T7 | bxn; cry1Ac |
| Cotton | 31808 | — | T5, T7 | bxn; cry1Ac |
| Cotton | 42317 | — | T5, T7 | bxn; cry1Ac |
| Cotton | BNLA-601 | — | T7 | cry1Ac |
| Cotton | BXN10211 | BXN10211-9 | T5 | bxn; cry1Ac |
| Cotton | BXN10215 | BXN10215-4 | T5 | bxn; cry1Ac |
| Cotton | BXN10222 | BXN10222-2 | T5 | bxn; cry1Ac |
| Cotton | BXN10224 | BXN10224-4 | T5 | bxn; cry1Ac |
| Cotton | COT102 | SYN-IRB102-7 | T7 | vip3A(a) |
| Cotton | COT67B | SYN-IR67B-1 | T7 | cry1Ab |
| Cotton | COT202 | — | T7 | vip3A |
| Cotton | Event 1 | — | T7 | cry1Ac |
| Cotton | GMF Cry1A | GTL-GMF311-7 | T7 | cry1Ab-Ac |
| Cotton | GHB119 | BCS-GH005-8 | T7 | cry2Ae |
| Cotton | GHB614 | BCS-GH002-5 | T1 | 2mepsps |
| Cotton | GK12 | — | T7 | cry1Ab-Ac |
| Cotton | LLCotton25 | ACS-GH001-3 | T3 | bar |
| Cotton | MLS 9124 | — | T7 | cry1C |
| Cotton | MON1076 | MON-89924-2 | T7 | cry1Ac |
| Cotton | MON1445 | MON-01445-2 | T1 | cp4 epsps (aroA:CP4) |
| Cotton | MON15985 | MON-15985-7 | T7 | cry1Ac; cry2Ab2 |
| Cotton | MON1698 | MON-89383-1 | T7 | cp4 epsps (aroA:CP4) |
| Cotton | MON531 | MON-00531-6 | T7 | cry1Ac |
| Cotton | MON757 | MON-00757-7 | T7 | cry1Ac |
| Cotton | MON88913 | MON-88913-8 | T1 | cp4 epsps (aroA:CP4) |
| Cotton | Nqwe Chi 6 Bt | — | T7 | — |
| Cotton | SKG321 | — | T7 | cry1A; CpTI |
| Cotton | T303-3 | BCS-GH003-6 | T3, T7 | cry1Ab; bar |
| Cotton | T304-40 | BCS-GH004-7 | T3, T7 | cry1Ab; bar |
| Cotton | CE43-67B | — | T7 | cry1Ab |
| Cotton | CE46-02A | — | T7 | cry1Ab |
| Cotton | CE44-69D | — | T7 | cry1Ab |

TABLE 3-continued

| Crop | Event Name | Event Code | Trait(s) | Gene(s) |
|---|---|---|---|---|
| Cotton | 1143-14A | — | T7 | cry1Ab |
| Cotton | 1143-51B | — | T7 | cry1Ab |
| Cotton | T342-142 | — | T7 | cry1Ab |
| Cotton | PV-GHGT07 (1445) | — | T1 | cp4 epsps (aroA:CP4) |
| Cotton | EE-GH3 | — | T1 | mepsps |
| Cotton | EE-GH5 | — | T7 | cry1Ab |
| Cotton | MON88701 | MON-88701-3 | T3, T12 | Modified dmo; bar |
| Cotton | OsCr11 | — | T13 | Modified Cry j |
| Flax | FP967 | CDC-FL001-2 | T11 | als |
| Lentil | RH44 | — | T16 | als |
| Maize | 3272 | SYN-E3272-5 | T17 | amy797E |
| Maize | 5307 | SYN-05307-1 | T7 | ecry3.1Ab |
| Maize | 59122 | DAS-59122-7 | T3, T7 | cry34Ab1; cry35Ab1; pat |
| Maize | 676 | PH-000676-7 | T3, T18 | pat; dam |
| Maize | 678 | PH-000678-9 | T3, T18 | pat; dam |
| Maize | 680 | PH-000680-2 | T3, T18 | pat; dam |
| Maize | 98140 | DP-098140-6 | T1, T11 | gat4621; zm-hra |
| Maize | Bt10 | — | T3, T7 | cry1Ab; pat |
| Maize | Bt176 (176) | SYN-EV176-9 | T3, T7 | cry1Ab; bar |
| Maize | BVLA430101 | — | T4 | phyA2 |
| Maize | CBH-351 | ACS-ZM004-3 | T3, T7 | cry9C; bar |
| Maize | DAS40278-9 | DAS40278-9 | T19 | aad-1 |
| Maize | DBT418 | DKB-89614-9 | T3, T7 | cry1Ac; pinII; bar |
| Maize | DLL25 (B16) | DKB-89790-5 | T3 | bar |
| Maize | GA21 | MON-00021-9 | T1 | mepsps |
| Maize | GG25 | — | T1 | mepsps |
| Maize | GJ11 | — | T1 | mepsps |
| Maize | Fl117 | — | T1 | mepsps |
| Maize | GAT-ZM1 | — | T3 | pat |
| Maize | LY038 | REN-00038-3 | T20 | cordapA |
| Maize | MIR 162 | SYN-IR162-4 | T7 | vip3Aa20 |
| Maize | MIR604 | SYN-IR604-5 | T7 | mcry3A |
| Maize | MON801 (MON80100) | MON801 | T1, T7 | cry1Ab; cp4 epsps (aroA:CP4); goxv247 |
| Maize | MON802 | MON-80200-7 | T1, T7 | cry1Ab; cp4 epsps (aroA:CP4); goxv247 |
| Maize | MON809 | PH-MON-809-2 | T1, T7 | cry1Ab; cp4 epsps (aroA:CP4); goxv247 |
| Maize | MON810 | MON-00810-6 | T1, T7 | cry1Ab; cp4 epsps (aroA:CP4); goxv247 |
| Maize | MON832 | — | T1 | cp4 epsps (aroA:CP4); goxv247 |
| Maize | MON863 | MON-00863-5 | T7 | cry3Bb1 |
| Maize | MON87427 | MON-87427-7 | T1 | cp4 epsps (aroA:CP4) |
| Maize | MON87460 | MON-87460-4 | T21 | cspB |
| Maize | MON88017 | MON-88017-3 | T1, T7 | cry3Bb1; cp4 epsps (aroA:CP4) |
| Maize | MON89034 | MON-89034-3 | T7 | cry2Ab2; cry1A.105 |
| Maize | MS3 | ACS-ZM001-9 | T3, T18 | bar; barnase |
| Maize | MS6 | ACS-ZM005-4 | T3, T18 | bar; barnase |
| Maize | NK603 | MON-00603-6 | T1 | cp4 epsps (aroA:CP4) |
| Maize | T14 | ACS-ZM002-1 | T3 | pat (syn) |
| Maize | T25 | ACS-ZM003-2 | T3 | pat (syn) |
| Maize | TC1507 | DAS-01507-1 | T3, T7 | cry1Fa2; pat |
| Maize | TC6275 | DAS-06275-8 | T3, T7 | mocry1F; bar |
| Maize | VIP1034 | — | T3, T7 | vip3A; pat |
| Maize | 43A47 | DP-043A47-3 | T3, T7 | cry1F; cry34Ab1; cry35Ab1; pat |
| Maize | 40416 | DP-040416-8 | T3, T7 | cry1F; cry34Ab1; cry35Ab1; pat |
| Maize | 32316 | DP-032316-8 | T3, T7 | cry1F; cry34Ab1; cry35Ab1; pat |
| Maize | 4114 | DP-004114-3 | T3, T7 | cry1F; cry34Ab1; cry35Ab1; pat |
| Melon | Melon A | — | T22 | sam-k |
| Melon | Melon B | — | T22 | sam-k |
| Papaya | 55-1 | CUH-CP551-8 | T6 | prsv cp |
| Papaya | 63-1 | CUH-CP631-7 | T6 | prsv cp |
| Papaya | Huanong No. 1 | — | T6 | prsv rep |
| Papaya | X17-2 | UFL-X17CP-6 | T6 | prsv cp |
| Plum | C-5 | ARS-PLMC5-6 | T6 | ppv cp |
| Canola** | ZSR500 | — | T1 | cp4 epsps (aroA:CP4); goxv247 |
| Canola** | ZSR502 | — | T1 | cp4 epsps (aroA:CP4); goxv247 |
| Canola** | ZSR503 | — | T1 | cp4 epsps (aroA:CP4); goxv247 |
| Rice | 7Crp#242-95-7 | — | T13 | 7crp |
| Rice | 7Crp#10 | — | T13 | 7crp |
| Rice | GM Shanyou 63 | — | T7 | cry1Ab; cry1Ac |
| Rice | Huahui-1/TT51-1 | — | T7 | cry1Ab; cry1Ac |
| Rice | LLRICE06 | ACS-OS001-4 | T3 | bar |
| Rice | LLRICE601 | BCS-OS003-7 | T3 | bar |
| Rice | LLRICE62 | ACS-OS002-5 | T3 | bar |
| Rice | Tarom molaii + cry1Ab | — | T7 | cry1Ab (truncated) |
| Rice | GAT-OS2 | — | T3 | bar |
| Rice | GAT-OS3 | — | T3 | bar |

TABLE 3-continued

| Crop | Event Name | Event Code | Trait(s) | Gene(s) |
|---|---|---|---|---|
| Rice | PE-7 | — | T7 | Cry1Ac |
| Rice | 7Crp#10 | — | T13 | 7crp |
| Rice | KPD627-8 | — | T27 | OASA1D |
| Rice | KPD722-4 | — | T27 | OASA1D |
| Rice | KA317 | — | T27 | OASA1D |
| Rice | HW5 | — | T27 | OASA1D |
| Rice | HW1 | — | T27 | OASA1D |
| Rice | B-4-1-18 | — | T28 | Δ OsBRI1 |
| Rice | G-3-3-22 | — | T29 | OSGA2ox1 |
| Rice | AD77 | — | T6 | DEF |
| Rice | AD51 | — | T6 | DEF |
| Rice | AD48 | — | T6 | DEF |
| Rice | AD41 | — | T6 | DEF |
| Rice | 13pNasNa800725atAprt1 | — | T30 | HvNAS1; HvNAAT-A; APRT |
| Rice | 13pAprt1 | — | T30 | APRT |
| Rice | gHvNAS1-gHvNAAT-1 | — | T30 | HvNAS1; HvNAAT-A; HvNAAT-B |
| Rice | gHvIDS3-1 | — | T30 | HvIDSS |
| Rice | gHvNAAT1 | — | T30 | HvNAAT-A; HvNAAT-B |
| Rice | gHvNAS1-1 | — | T30 | HvNAS1 |
| Rice | NIA-OS006-4 | — | T6 | WRKY45 |
| Rice | NIA-OS005-3 | — | T6 | WRKY45 |
| Rice | NIA-OS004-2 | — | T6 | WRKY45 |
| Rice | NIA-OS003-1 | — | T6 | WRKY45 |
| Rice | NIA-OS002-9 | — | T6 | WRKY45 |
| Rice | NIA-OS001-8 | — | T6 | WRKY45 |
| Rice | OsCr11 | — | T13 | Modified Cry j |
| Rice | 17053 | — | T1 | cp4 epsps (aroA:CP4) |
| Rice | 17314 | — | T1 | cp4 epsps (aroA:CP4) |
| Rose | WKS82/130-4-1 | IFD-52401-4 | T9 | 5AT; bp40 (f3'5'h) |
| Rose | WKS92/130-9-1 | IFD-52901-9 | T9 | 5AT; bp40 (f3'5'h) |
| Soybean | 260-05 (G94-1, G94-19, G168) | — | T9 | gm-fad2-1 (silencing locus) |
| Soybean | A2704-12 | ACS-GM005-3 | T3 | pat |
| Soybean | A2704-21 | ACS-GM004-2 | T3 | pat |
| Soybean | A5547-127 | ACS-GM006-4 | T3 | pat |
| Soybean | A5547-35 | ACS-GM008-6 | T3 | pat |
| Soybean | CV127 | BPS-CV127-9 | T16 | csr1-2 |
| Soybean | DAS68416-4 | DAS68416-4 | T3 | pat |
| Soybean | DP305423 | DP-305423-1 | T11, T31 | gm-fad2-1 (silencing locus); gm-hra |
| Soybean | DP356043 | DP-356043-5 | T1, T31 | gm-fad2-1 (silencing locus); gat4601 |
| Soybean | FG72 | MST-FG072-3 | T32, T1 | 2mepsps; hppdPF W336 |
| Soybean | GTS 40-3-2 (40-3-2) | MON-04032-6 | T1 | cp4 epsps (aroA:CP4) |
| Soybean | GU262 | ACS-GM003-1 | T3 | pat |
| Soybean | MON87701 | MON-87701-2 | T7 | cry1Ac |
| Soybean | MON87705 | MON-87705-6 | T1, T31 | fatb1-A (sense & antisense); fad2-1A (sense & antisense); cp4 epsps (aroA:CP4) |
| Soybean | MON87708 | MON-87708-9 | T1, T12 | dmo; cp4 epsps (aroA:CP4) |
| Soybean | MON87769 | MON-87769-7 | T1, T31 | Pj.D6D; Nc.Fad3; cp4 epsps (aroA:CP4) |
| Soybean | MON89788 | MON-89788-1 | T1 | cp4 epsps (aroA:CP4) |
| Soybean | W62 | ACS-GM002-9 | T3 | bar |
| Soybean | W98 | ACS-GM001-8 | T3 | bar |
| Soybean | MON87754 | MON-87754-1 | T33 | dgat2A |
| Soybean | DAS21606 | DAS-21606 | T34, T3 | Modified aad-12; pat |
| Soybean | DAS44406 | DAS-44406-6 | T1, T3, T34 | Modified aad-12; 2mepsps; pat |
| Soybean | SYHT04R | SYN-0004R-8 | T35 | Modified avhppd |
| Soybean | 9582.814.19.1 | — | T3, T7 | cry1Ac, cry1F, PAT |
| Squash | CZW3 | SEM-ØCZW3-2 | T6 | cmv cp, zymv cp, wmv cp |
| Squash | ZW20 | SEM-0ZW20-7 | T6 | zymv cp, wmv cp |
| Sugar Beet | GTSB77 (T9100152) | SY-GTSB77-8 | T1 | cp4 epsps (aroA:CP4); goxv247 |
| Sugar Beet | H7-1 | KM-000H71-4 | T1 | cp4 epsps (aroA:CP4) |
| Sugar Beet | T120-7 | ACS-BV001-3 | T3 | pat |
| Sugar Beet | T227-1 | — | T1 | cp4 epsps (aroA:CP4) |
| Sugarcane | NXI-1T | — | T21 | EcbetA |
| Sunflower | X81359 | — | T16 | als |
| Pepper | PK-SP01 | — | T6 | cmv cp |
| Tobacco | C/F/93/08-02 | — | T5 | bxn |
| Tobacco | Vector 21-41 | — | T36 | NtQPT1 (antisense) |
| Sunflower | X81359 | — | T16 | als |
| Wheat | MON71800 | MON-718ØØ-3 | T1 | cp4 epsps (aroA:CP4) |

*Argentine (*Brassica napus*),
**Polish (*B. rapa*),
Eggplant

Treatment of genetically modified plants with compounds of this disclosure may result in super-additive or synergistic effects. For example, reduction in application rates, broadening of the activity spectrum, increased tolerance to biotic/abiotic stresses or enhanced storage stability may be greater than expected from just simple additive effects of the application of compounds of this disclosure on genetically modified plants.

Compounds of this disclosure can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of compounds of this disclosure with other herbicides can broaden the spectrum of activity against additional weed species, and suppress the proliferation of any resistant biotypes. Thus the present disclosure also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present disclosure, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this disclosure may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, cyclopyrimorate, clodinafop-propargyl, clomazone, clomeprop, clopyralid, clopyralid-olamine, cloransulam-methyl, cumyluron, cyanazine, cycloate, cyclopyrimorate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fenquinotrione, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metamsodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiafenacil, tiocarbazil, topramezone, tralkoxydim, tri-allate, triafamone, triasulfuron, triaziflam, tribenuron-methyl, triclopyr, triclopyr-butotyl, triclopyr-triethylammonium, tridiphane, trietazine, trifloxysulfuron, trifluralin, triflusulfuron-methyl, tritosulfuron, vernolate, 3-(2-chloro-3,6-difluorophenyl)-4-hydroxy-1-methyl-1,5-naphthyridin-2(1H)-one, 5-chloro-3-[(2-hydroxy-6-oxo-1-cyclohexen-1-yl)carbonyl]-1-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxypyrido[2,3-b]pyrazin-6(5H)-one), 4-(2,6-diethyl-4-methylphenyl)-5-hydroxy-2,6-dimethyl-3 (2H)-pyridazinone), 5-[[(2,6-difluorophenyl)methoxy] methyl]-4,5-dihydro-5-methyl-3-(3-methyl-2-thienyl)isoxazole (previously methioxolin), 3-[7-fluoro-3,4-dihydro-3-oxo-4-(2-propyn-1-yl)-2H-1,4-benzoxazin-6-yl]dihydro-1, 5-dimethyl-6-thioxo-1,3,5-triazine-2,4(1H,3H)-dione, 4-(4-fluorophenyl)-6-[(2-hydroxy-6-oxo-1-cyclohexen-1-yl) carbonyl]-2-methyl-1,2,4-triazine-3,5(2H,4H)-dione, methyl 4-amino-3-chloro-6-(4-chloro-2-fluoro-3-methoxyphenyl)-5-fluoro-2-pyridinecarboxylate, 2-methyl-3-(methylsulfonyl)-N-(1-methyl-1H-tetrazol-5-yl)-4-(trifluoromethyl)benzamide, and 2-methyl-N-(4-methyl-1,2,5-oxadiazol-3-yl)-3-(methylsulfinyl)-4-(trifluoromethyl) benzamide. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Compounds of this disclosure can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual*, 13*th Edition*, C. D. S. Tomlin, Ed., British Crop Protection Council, Farnham, Surrey, U.K., 2003 and *The BioPesticide Manual, 2nd Edition*, L. G. Copping, Ed., British Crop Protection Council, Farnham, Surrey, U.K., 2001.

For embodiments where one or more of these various mixing partners are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this disclosure with other biologically active (particularly herbicidal) compounds or agents (i.e. active ingredients) can result in a greater-than-additive (i.e. synergistic) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When synergism of herbicidal active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of this disclosure with at least one other herbicidal active ingredient. Of particular note is such a combination where the other herbicidal active ingredient has different site of action from the compound of this disclosure. In certain instances, a combination with at least one other herbicidal active ingredient having a similar spectrum of control but a different site of action will be particularly advantageous for resistance management. Thus, a composition of the present disclosure can further comprise (in a herbicidally effective amount) at least one additional herbicidal active ingredient having a similar spectrum of control but a different site of action.

Compounds of this disclosure can also be used in combination with herbicide safeners such as allidochlor, benoxacor, cloquintocet-mexyl, cumyluron, cyometrinil, cyprosulfonamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride (1,8-naphthalic anhydride), oxabetrinil, N-(aminocarbonyl)-2-methylbenzenesulfonamide, N-(aminocarbonyl)-2-fluorobenzenesulfonamide, 1-bromo-4-[(chloromethyl) sulfonyl]benzene (BCS), 4-(dichloroacetyl)-1-oxa-4-azospiro[4.5]decane (MON 4660), 2-(dichloromethyl)-2-methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, 3-oxo-1-cyclohexen-1-yl 1-(3,4-dimethylphenyl)-1,6-dihydro-6-oxo-2-phenyl-5-pyrimidinecarboxylate, 2,2-dichloro-1-(2,2,5-trimethyl-3-oxazolidinyl)-ethanone and 2-methoxy-N-[[4-[[(methylamino)carbonyl]amino]phenyl]sulfonyl]-benzamide (alternatively named N-(2-methoxybenzoyl)-4-[(methylaminocarbonyl)amino] benzenesulfonamide, CAS #129531-12-0) to increase safety to certain crops. Antidotally effective amounts of the herbicide safeners can be applied at the same time as a compound of this disclosure, or applied as seed treatments. Therefore an aspect of the present disclosure relates to a herbicidal mixture comprising a compound of this disclosure and an antidotally effective amount of a herbicide safener. Seed treatment is particularly useful for selective weed control, because it physically restricts antidoting to the crop plants. Therefore a particularly useful embodiment of the present disclosure is a method for selectively controlling the growth of undesired vegetation in a crop comprising contacting the locus of the crop with a herbicidally effective amount of a compound of this disclosure wherein seed from which the crop is grown is treated with an antidotally effective amount of safener. Antidotally effective amounts of safeners can be easily determined by one skilled in the art through simple experimentation.

Of note is a composition comprising a compound of this disclosure (in a herbicidally effective amount), at least one additional active ingredient selected from the group consisting of other herbicides and herbicide safeners (in an effective amount), and at least one component selected from the group consisting of surfactants, solid diluents and liquid diluents.

In some embodiments, a mixture of a compound of this disclosure is used in combination with another herbicide for better control of undesired vegetation (e.g., lower use rate such as from synergism, broader spectrum of weeds controlled, or enhanced crop safety) or for preventing the development of resistant weeds. Table A1 lists particular combinations of Component (a) (i.e. a specific compound of the present disclosure) with another herbicide as Component (b) illustrative of the mixtures, compositions and methods of the present disclosure. Compound 17 in the Component (a) column is identified in Index Table A. The second column of Table A1 lists the specific Component (b) compound (e.g., "2,4-D" in the first line). The third, fourth and fifth columns of Table A1 lists ranges of weight ratios for rates at which the Component (a) compound is typically applied to a field-grown crop relative to Component (b) (i.e. (a):(b)). Thus, for example, the first line of Table A1 specifically discloses the combination of Component (a) (i.e. Compound 17 in Index Table A) with 2,4-D is typically applied in a weight ratio between 1:192-6:1. The remaining lines of Table A1 are to be construed similarly.

TABLE A1

| Component (a) (Compound #) | Component (b) | Typical Weight Ratio | More Typical Weight Ratio | Most Typical Weight Ratio |
|---|---|---|---|---|
| 352 | 2,4-D | 1:192-6:1 | 1:64-2:1 | 1:24-1:3 |
| 352 | Acetochlor | 1:768-2:1 | 1:256-1:2 | 1:96-1:11 |
| 352 | Acifluorfen | 1:96-12:1 | 1:32-4:1 | 1:12-1:2 |
| 352 | Aclonifen | 1:857-2:1 | 1:285-1:3 | 1:107-1:12 |
| 352 | Alachlor | 1:768-2:1 | 1:256-1:2 | 1:96-1:11 |
| 352 | Ametryn | 1:384-3:1 | 1:128-1:1 | 1:48-1:6 |
| 352 | Amicarbazone | 1:192-6:1 | 1:64-2:1 | 1:24-1:3 |
| 352 | Amidosulfuron | 1:6-168:1 | 1:2-56:1 | 1:1-11:1 |
| 352 | Aminocyclopyrachlor | 1:48-24:1 | 1:16-8:1 | 1:6-2:1 |
| 352 | Aminopyralid | 1:20-56:1 | 1:6-19:1 | 1:2-4:1 |
| 352 | Amitrole | 1:768-2:1 | 1:256-1:2 | 1:96-1:11 |
| 352 | Anilofos | 1:96-12:1 | 1:32-4:1 | 1:12-1:2 |
| 352 | Asulam | 1:960-2:1 | 1:320-1:3 | 1:120-1:14 |
| 352 | Atrazine | 1:192-6:1 | 1:64-2:1 | 1:24-1:3 |
| 352 | Azimsulfuron | 1:6-168:1 | 1:2-56:1 | 1:1-11:1 |
| 352 | Beflubutamid | 1:342-4:1 | 1:114-2:1 | 1:42-1:5 |
| 352 | Benfuresate | 1:617-2:1 | 1:205-1:2 | 1:77-1:9 |
| 352 | Bensulfuron-methyl | 1:25-45:1 | 1:8-15:1 | 1:3-3:1 |
| 352 | Bentazone | 1:192-6:1 | 1:64-2:1 | 1:24-1:3 |
| 352 | Benzobicyclon | 1:85-14:1 | 1:28-5:1 | 1:10-1:2 |
| 352 | Benzofenap | 1:257-5:1 | 1:85-2:1 | 1:32-1:4 |
| 352 | Bicyclopyrone | 1:42-27:1 | 1:14-9:1 | 1:5-2:1 |
| 352 | Bifenox | 1:257-5:1 | 1:85-2:1 | 1:32-1:4 |
| 352 | Bispyribac-sodium | 1:10-112:1 | 1:3-38:1 | 1:1-7:1 |
| 352 | Bromacil | 1:384-3:1 | 1:128-1:1 | 1:48-1:6 |
| 352 | Bromobutide | 1:384-3:1 | 1:128-1:1 | 1:48-1:6 |
| 352 | Bromoxynil | 1:96-12:1 | 1:32-4:1 | 1:12-1:2 |
| 352 | Butachlor | 1:768-2:1 | 1:256-1:2 | 1:96-1:11 |
| 352 | Butafenacil | 1:42-27:1 | 1:14-9:1 | 1:5-2:1 |
| 352 | Butylate | 1:1542-1:2 | 1:514-1:5 | 1:192-1:22 |
| 352 | Cafenstrole | 1:192-6:1 | 1:64-2:1 | 1:24-1:3 |
| 352 | Carfentrazone-ethyl | 1:128-9:1 | 1:42-3:1 | 1:16-1:2 |
| 352 | Chlorimuron-ethyl | 1:8-135:1 | 1:2-45:1 | 1:1-9:1 |
| 352 | Chlorotoluron | 1:768-2:1 | 1:256-1:2 | 1:96-1:11 |
| 352 | Chlorsulfuron | 1:6-168:1 | 1:2-56:1 | 1:1-11:1 |
| 352 | Cinosulfuron | 1:17-68:1 | 1:5-23:1 | 1:2-5:1 |
| 352 | Cinidon-ethyl | 1:384-3:1 | 1:128-1:1 | 1:48-1:6 |
| 352 | Cinmethylin | 1:34-34:1 | 1:11-12:1 | 1:4-3:1 |
| 352 | Clacyfos | 1:34-34:1 | 1:11-12:1 | 1:4-3:1 |
| 352 | Clethodim | 1:48-24:1 | 1:16-8:1 | 1:6-2:1 |
| 352 | Clodinafop-propargyl | 1:20-56:1 | 1:6-19:1 | 1:2-4:1 |
| 352 | Clomazone | 1:384-3:1 | 1:128-1:1 | 1:48-1:6 |
| 352 | Clomeprop | 1:171-7:1 | 1:57-3:1 | 1:21-1:3 |
| 352 | Clopyralid | 1:192-6:1 | 1:64-2:1 | 1:24-1:3 |
| 352 | Cloransulam-methyl | 1:12-96:1 | 1:4-32:1 | 1:1-6:1 |
| 352 | Cumyluron | 1:384-3:1 | 1:128-1:1 | 1:48-1:6 |
| 352 | Cyanazine | 1:384-3:1 | 1:128-1:1 | 1:48-1:6 |
| 352 | Cyclopyrimorate | 1:17-68:1 | 1:5-23:1 | 1:2-5:1 |
| 352 | Cyclosulfamuron | 1:17-68:1 | 1:5-23:1 | 1:2-5:1 |
| 352 | Cycloxydim | 1:96-12:1 | 1:32-4:1 | 1:12-1:2 |
| 352 | Cyhalofop | 1:25-45:1 | 1:8-15:1 | 1:3-3:1 |
| 352 | Daimuron | 1:192-6:1 | 1:64-2:1 | 1:24-1:3 |
| 352 | Desmedipham | 1:322-4:1 | 1:107-2:1 | 1:40-1:5 |
| 352 | Dicamba | 1:192-6:1 | 1:64-2:1 | 1:24-1:3 |
| 352 | Dichlobenil | 1:1371-1:2 | 1:457-1:4 | 1:171-1:20 |
| 352 | Dichlorprop | 1:925-2:1 | 1:308-1:3 | 1:115-1:13 |
| 352 | Diclofop-methyl | 1:384-3:1 | 1:128-1:1 | 1:48-1:6 |
| 352 | Diclosulam | 1:10-112:1 | 1:3-38:1 | 1:1-7:1 |
| 352 | Difenzoquat | 1:288-4:1 | 1:96-2:1 | 1:36-1:4 |
| 352 | Diflufenican | 1:857-2:1 | 1:285-1:3 | 1:107-1:12 |
| 352 | Diflufenzopyr | 1:12-96:1 | 1:4-32:1 | 1:1-6:1 |
| 352 | Dimethachlor | 1:768-2:1 | 1:256-1:2 | 1:96-1:11 |
| 352 | Dimethametryn | 1:192-6:1 | 1:64-2:1 | 1:24-1:3 |
| 352 | Dimethenamid-P | 1:384-3:1 | 1:128-1:1 | 1:48-1:6 |
| 352 | Dithiopyr | 1:192-6:1 | 1:64-2:1 | 1:24-1:3 |

TABLE A1-continued

| Component (a) (Compound #) | Component (b) | Typical Weight Ratio | More Typical Weight Ratio | Most Typical Weight Ratio |
|---|---|---|---|---|
| 352 | Diuron | 1:384-3:1 | 1:128-1:1 | 1:48-1:6 |
| 352 | EPTC | 1:768-2:1 | 1:256-1:2 | 1:96-1:11 |
| 352 | Esprocarb | 1:1371-1:2 | 1:457-1:4 | 1:171-1:20 |
| 352 | Ethalfluralin | 1:384-3:1 | 1:128-1:1 | 1:48-1:6 |
| 352 | Ethametsulfuron-methyl | 1:17-68:1 | 1:5-23:1 | 1:2-5:1 |
| 352 | Ethoxyfen | 1:8-135:1 | 1:2-45:1 | 1:1-9:1 |
| 352 | Ethoxysulfuron | 1:20-56:1 | 1:6-19:1 | 1:2-4:1 |
| 352 | Etobenzanid | 1:257-5:1 | 1:85-2:1 | 1:32-1:4 |
| 352 | Fenoxaprop-ethyl | 1:120-10:1 | 1:40-4:1 | 1:15-1:2 |
| 352 | Fenoxasulfone | 1:85-14:1 | 1:28-5:1 | 1:10-1:2 |
| 352 | Fenquinotrione | 1:17-68:1 | 1:5-23:1 | 1:2-5:1 |
| 352 | Fentrazamide | 1:17-68:1 | 1:5-23:1 | 1:2-5:1 |
| 352 | Flazasulfuron | 1:17-68:1 | 1:5-23:1 | 1:2-5:1 |
| 352 | Florasulam | 1:2-420:1 | 1:1-140:1 | 2:1-27:1 |
| 352 | Fluazifop-butyl | 1:192-6:1 | 1:64-2:1 | 1:24-1:3 |
| 352 | Flucarbazone | 1:8-135:1 | 1:2-45:1 | 1:1-9:1 |
| 352 | Flucetosulfuron | 1:8-135:1 | 1:2-45:1 | 1:1-9:1 |
| 352 | Flufenacet | 1:257-5:1 | 1:85-2:1 | 1:32-1:4 |
| 352 | Flumetsulam | 1:24-48:1 | 1:8-16:1 | 1:3-3:1 |
| 352 | Flumiclorac-pentyl | 1:10-112:1 | 1:3-38:1 | 1:1-7:1 |
| 352 | Flumioxazin | 1:25-45:1 | 1:8-15:1 | 1:3-3:1 |
| 352 | Fluometuron | 1:384-3:1 | 1:128-1:1 | 1:48-1:6 |
| 352 | Flupyrsulfuron-methyl | 1:3-336:1 | 1:1-112:1 | 2:1-21:1 |
| 352 | Fluridone | 1:384-3:1 | 1:128-1:1 | 1:48-1:6 |
| 352 | Fluroxypyr | 1:96-12:1 | 1:32-4:1 | 1:12-1:2 |
| 352 | Flurtamone | 1:857-2:1 | 1:285-1:3 | 1:107-1:12 |
| 352 | Fluthiacet-methyl | 1:48-42:1 | 1:16-14:1 | 1:3-3:1 |
| 352 | Fomesafen | 1:96-12:1 | 1:32-4:1 | 1:12-1:2 |
| 352 | Foramsulfuron | 1:13-84:1 | 1:4-28:1 | 1:1-6:1 |
| 352 | Glufosinate | 1:288-4:1 | 1:96-2:1 | 1:36-1:4 |
| 352 | Glyphosate | 1:288-4:1 | 1:96-2:1 | 1:36-1:4 |
| 352 | Halauxifen | 1:20-56:1 | 1:6-19:1 | 1:2-4:1 |
| 352 | Halauxifen-methyl | 1:20-56:1 | 1:6-19:1 | 1:2-4:1 |
| 352 | Halosulfuron-methyl | 1:17-68:1 | 1:5-23:1 | 1:2-5:1 |
| 352 | Haloxyfop-methyl | 1:34-34:1 | 1:11-12:1 | 1:4-3:1 |
| 352 | Hexazinone | 1:192-6:1 | 1:64-2:1 | 1:24-1:3 |
| 352 | Imazamox | 1:13-84:1 | 1:4-28:1 | 1:1-6:1 |
| 352 | Imazapic | 1:20-56:1 | 1:6-19:1 | 1:2-4:1 |
| 352 | Imazapyr | 1:85-14:1 | 1:28-5:1 | 1:10-1:2 |
| 352 | Imazaquin | 1:34-34:1 | 1:11-12:1 | 1:4-3:1 |
| 352 | Imazethabenz-methyl | 1:171-7:1 | 1:57-3:1 | 1:21-1:3 |
| 352 | Imazethapyr | 1:24-48:1 | 1:8-16:1 | 1:3-3:1 |
| 352 | Imazosulfuron | 1:27-42:1 | 1:9-14:1 | 1:3-3:1 |
| 352 | Indanofan | 1:342-4:1 | 1:114-2:1 | 1:42-1:5 |
| 352 | Indaziflam | 1:25-45:1 | 1:8-15:1 | 1:3-3:1 |
| 352 | Iodosulfuron-methyl | 1:3-336:1 | 1:1-112:1 | 2:1-21:1 |
| 352 | Ioxynil | 1:192-6:1 | 1:64-2:1 | 1:24-1:3 |
| 352 | Ipfencarbazone | 1:85-14:1 | 1:28-5:1 | 1:10-1:2 |
| 352 | Isoproturon | 1:384-3:1 | 1:128-1:1 | 1:48-1:6 |
| 352 | Isoxaben | 1:288-4:1 | 1:96-2:1 | 1:36-1:4 |
| 352 | Isoxaflutole | 1:60-20:1 | 1:20-7:1 | 1:7-2:1 |
| 352 | Lactofen | 1:42-27:1 | 1:14-9:1 | 1:5-2:1 |
| 352 | Lenacil | 1:384-3:1 | 1:128-1:1 | 1:48-1:6 |
| 352 | Linuron | 1:384-3:1 | 1:128-1:1 | 1:48-1:6 |
| 352 | MCPA | 1:192-6:1 | 1:64-2:1 | 1:24-1:3 |
| 352 | MCPB | 1:288-4:1 | 1:96-2:1 | 1:36-1:4 |
| 352 | Mecoprop | 1:768-2:1 | 1:256-1:2 | 1:96-1:11 |
| 352 | Mefenacet | 1:384-3:1 | 1:128-1:1 | 1:48-1:6 |
| 352 | Mefluidide | 1:192-6:1 | 1:64-2:1 | 1:24-1:3 |
| 352 | Mesosulfuron-methyl | 1:5-224:1 | 1:1-75:1 | 1:1-14:1 |
| 352 | Mesotrione | 1:42-27:1 | 1:14-9:1 | 1:5-2:1 |
| 352 | Metamifop | 1:42-27:1 | 1:14-9:1 | 1:5-2:1 |
| 352 | Metazachlor | 1:384-3:1 | 1:128-1:1 | 1:48-1:6 |
| 352 | Metazosulfuron | 1:25-45:1 | 1:8-15:1 | 1:3-3:1 |
| 352 | Methabenzthiazuron | 1:768-2:1 | 1:256-1:2 | 1:96-1:11 |
| 352 | Metolachlor | 1:768-2:1 | 1:256-1:2 | 1:96-1:11 |
| 352 | Metosulam | 1:8-135:1 | 1:2-45:1 | 1:1-9:1 |
| 352 | Metribuzin | 1:192-6:1 | 1:64-2:1 | 1:24-1:3 |
| 352 | Metsulfuron-methyl | 1:2-560:1 | 1:1-187:1 | 3:1-35:1 |
| 352 | Molinate | 1:1028-2:1 | 1:342-1:3 | 1:128-1:15 |
| 352 | Napropamide | 1:384-3:1 | 1:128-1:1 | 1:48-1:6 |
| 352 | Napropamide-M | 1:192-6:1 | 1:64-2:1 | 1:24-1:3 |
| 352 | Naptalam | 1:192-6:1 | 1:64-2:1 | 1:24-1:3 |
| 352 | Nicosulfuron | 1:12-96:1 | 1:4-32:1 | 1:1-6:1 |
| 352 | Norflurazon | 1:1152-1:1 | 1:384-1:3 | 1:144-1:16 |
| 352 | Orbencarb | 1:1371-1:2 | 1:457-1:4 | 1:171-1:20 |
| 352 | Orthosulfamuron | 1:20-56:1 | 1:6-19:1 | 1:2-4:1 |

TABLE A1-continued

| Component (a) (Compound #) | Component (b) | Typical Weight Ratio | More Typical Weight Ratio | Most Typical Weight Ratio |
|---|---|---|---|---|
| 352 | Oryzalin | 1:514-3:1 | 1:171-1:2 | 1:64-1:8 |
| 352 | Oxadiargyl | 1:384-3:1 | 1:128-1:1 | 1:48-1:6 |
| 352 | Oxadiazon | 1:548-3:1 | 1:182-1:2 | 1:68-1:8 |
| 352 | Oxasulfuron | 1:27-42:1 | 1:9-14:1 | 1:3-3:1 |
| 352 | Oxaziclomefone | 1:42-27:1 | 1:14-9:1 | 1:5-2:1 |
| 352 | Oxyfluorfen | 1:384-3:1 | 1:128-1:1 | 1:48-1:6 |
| 352 | Paraquat | 1:192-6:1 | 1:64-2:1 | 1:24-1:3 |
| 352 | Pendimethalin | 1:384-3:1 | 1:128-1:1 | 1:48-1:6 |
| 352 | Penoxsulam | 1:10-112:1 | 1:3-38:1 | 1:1-7:1 |
| 352 | Penthoxamid | 1:384-3:1 | 1:128-1:1 | 1:48-1:6 |
| 352 | Pentoxazone | 1:102-12:1 | 1:34-4:1 | 1:12-1:2 |
| 352 | Phenmedipham | 1:102-12:1 | 1:34-4:1 | 1:12-1:2 |
| 352 | Picloram | 1:96-12:1 | 1:32-4:1 | 1:12-1:2 |
| 352 | Picolinafen | 1:34-34:1 | 1:11-12:1 | 1:4-3:1 |
| 352 | Pinoxaden | 1:25-45:1 | 1:8-15:1 | 1:3-3:1 |
| 352 | Pretilachlor | 1:192-6:1 | 1:64-2:1 | 1:24-1:3 |
| 352 | Primisulfuron-methyl | 1:8-135:1 | 1:2-45:1 | 1:1-9:1 |
| 352 | Prodiamine | 1:384-3:1 | 1:128-1:1 | 1:48-1:6 |
| 352 | Profoxydim | 1:42-27:1 | 1:14-9:1 | 1:5-2:1 |
| 352 | Prometryn | 1:384-3:1 | 1:128-1:1 | 1:48-1:6 |
| 352 | Propachlor | 1:1152-1:1 | 1:384-1:3 | 1:144-1:16 |
| 352 | Propanil | 1:384-3:1 | 1:128-1:1 | 1:48-1:6 |
| 352 | Propaquizafop | 1:48-24:1 | 1:16-8:1 | 1:6-2:1 |
| 352 | Propoxycarbazone | 1:17-68:1 | 1:5-23:1 | 1:2-5:1 |
| 352 | Propyrisulfuron | 1:17-68:1 | 1:5-23:1 | 1:2-5:1 |
| 352 | Propyzamide | 1:384-3:1 | 1:128-1:1 | 1:48-1:6 |
| 352 | Prosulfocarb | 1:1200-1:2 | 1:400-1:4 | 1:150-1:17 |
| 352 | Prosulfuron | 1:6-168:1 | 1:2-56:1 | 1:1-11:1 |
| 352 | Pyraclonil | 1:42-27:1 | 1:14-9:1 | 1:5-2:1 |
| 352 | Pyraflufen-ethyl | 1:5-224:1 | 1:1-75:1 | 1:1-14:1 |
| 352 | Pyrasulfotole | 1:13-84:1 | 1:4-28:1 | 1:1-6:1 |
| 352 | Pyrazolynate | 1:857-2:1 | 1:285-1:3 | 1:107-1:12 |
| 352 | Pyrazosulfuron-ethyl | 1:10-112:1 | 1:3-38:1 | 1:1-7:1 |
| 352 | Pyrazoxyfen | 1:5-224:1 | 1:1-75:1 | 1:1-14:1 |
| 352 | Pyribenzoxim | 1:10-112:1 | 1:3-38:1 | 1:1-7:1 |
| 352 | Pyributicarb | 1:384-3:1 | 1:128-1:1 | 1:48-1:6 |
| 352 | Pyridate | 1:288-4:1 | 1:96-2:1 | 1:36-1:4 |
| 352 | Pyriftalid | 1:10-112:1 | 1:3-38:1 | 1:1-7:1 |
| 352 | Pyriminobac-methyl | 1:20-56:1 | 1:6-19:1 | 1:2-4:1 |
| 352 | Pyrimisulfan | 1:17-68:1 | 1:5-23:1 | 1:2-5:1 |
| 352 | Pyrithiobac | 1:24-48:1 | 1:8-16:1 | 1:3-3:1 |
| 352 | Pyroxasulfone | 1:85-14:1 | 1:28-5:1 | 1:10-1:2 |
| 352 | Pyroxsulam | 1:5-224:1 | 1:1-75:1 | 1:1-14:1 |
| 352 | Quinclorac | 1:192-6:1 | 1:64-2:1 | 1:24-1:3 |
| 352 | Quizalofop-ethyl | 1:42-27:1 | 1:14-9:1 | 1:5-2:1 |
| 352 | Rimsulfuron | 1:13-84:1 | 1:4-28:1 | 1:1-6:1 |
| 352 | Saflufenacil | 1:25-45:1 | 1:8-15:1 | 1:3-3:1 |
| 352 | Sethoxydim | 1:96-12:1 | 1:32-4:1 | 1:12-1:2 |
| 352 | Simazine | 1:384-3:1 | 1:128-1:1 | 1:48-1:6 |
| 352 | Sulcotrione | 1:120-10:1 | 1:40-4:1 | 1:15-1:2 |
| 352 | Sulfentrazone | 1:147-8:1 | 1:49-3:1 | 1:18-1:3 |
| 352 | Sulfometuron-methyl | 1:34-34:1 | 1:11-12:1 | 1:4-3:1 |
| 352 | Sulfosulfuron | 1:8-135:1 | 1:2-45:1 | 1:1-9:1 |
| 352 | Tebuthiuron | 1:384-3:1 | 1:128-1:1 | 1:48-1:6 |
| 352 | Tefuryltrione | 1:42-27:1 | 1:14-9:1 | 1:5-2:1 |
| 352 | Tembotrione | 1:31-37:1 | 1:10-13:1 | 1:3-3:1 |
| 352 | Tepraloxydim | 1:25-45:1 | 1:8-15:1 | 1:3-3:1 |
| 352 | Terbacil | 1:288-4:1 | 1:96-2:1 | 1:36-1:4 |
| 352 | Terbuthylazine | 1:857-2:1 | 1:285-1:3 | 1:107-1:12 |
| 352 | Terbutryn | 1:192-6:1 | 1:64-2:1 | 1:24-1:3 |
| 352 | Thenylchlor | 1:85-14:1 | 1:28-5:1 | 1:10-1:2 |
| 352 | Thiazopyr | 1:384-3:1 | 1:128-1:1 | 1:48-1:6 |
| 352 | Thiencarbazone | 1:3-336:1 | 1:1-112:1 | 2:1-21:1 |
| 352 | Thifensulfuron-methyl | 1:5-224:1 | 1:1-75:1 | 1:1-14:1 |
| 352 | Tiafenacil | 1:17-68:1 | 1:5-23:1 | 1:2-5:1 |
| 352 | Thiobencarb | 1:768-2:1 | 1:256-1:2 | 1:96-1:11 |
| 352 | Topramezone | 1:6-168:1 | 1:2-56:1 | 1:1-11:1 |
| 352 | Tralkoxydim | 1:68-17:1 | 1:22-6:1 | 1:8-2:1 |
| 352 | Triallate | 1:768-2:1 | 1:256-1:2 | 1:96-1:11 |
| 352 | Triasulfuron | 1:5-224:1 | 1:1-75:1 | 1:1-14:1 |
| 352 | Triaziflam | 1:171-7:1 | 1:57-3:1 | 1:21-1:3 |
| 352 | Tribenuron-methyl | 1:3-336:1 | 1:1-112:1 | 2:1-21:1 |
| 352 | Triclopyr | 1:192-6:1 | 1:64-2:1 | 1:24-1:3 |
| 352 | Trifloxysulfuron | 1:2-420:1 | 1:1-140:1 | 2:1-27:1 |
| 352 | Trifluralin | 1:288-4:1 | 1:96-2:1 | 1:36-1:4 |
| 352 | Triflusulfuron-methyl | 1:17-68:1 | 1:5-23:1 | 1:2-5:1 |
| 352 | Tritosulfuron | 1:13-84:1 | 1:4-28:1 | 1:1-6:1 |

TABLE A1-continued

| Component (a) (Compound #) | Component (b) | Typical Weight Ratio | More Typical Weight Ratio | Most Typical Weight Ratio |
|---|---|---|---|---|
| 352 | N-(2-methoxybenzoyl)-4-[(methylaminocarbonyl)amino]benzenesulfonamide | 1:100-100:1 | 1:50-50:1 | 1:2-2:1 |

Table A2 is constructed the same as Table A1 above except that entries below the "Component (a)" column heading are replaced with the respective "Component (a) Column Entry" shown below. Compound 353 in the Component (a) column is identified in Index Table A. Thus, for example, in Table A2 the entries below the "Component (a)" column heading all recite "Compound 353" (i.e. Compound 353 identified in Index Table A), and the first line below the column headings in Table A2 specifically discloses a mixture of Compound 353 with 2,4-D. Tables A3 et seq. are constructed similarly.

| Table No. | Component (a) Column Entry |
|---|---|
| A2 | Compound 353 |
| A3 | Compound 354 |
| A4 | Compound 355 |
| A5 | Compound 356 |
| A6 | Compound 357 |
| A7 | Compound 358 |
| A8 | Compound 359 |
| A9 | Compound 360 |
| A10 | Compound 361 |
| A11 | Compound 362 |
| A12 | Compound 363 |
| A13 | Compound 364 |
| A14 | Compound 365 |
| A15 | Compound 366 |
| A16 | Compound 367 |
| A17 | Compound 368 |
| A18 | Compound 369 |
| A19 | Compound 370 |
| A20 | Compound 371 |
| A21 | Compound 372 |
| A22 | Compound 373 |
| A23 | Compound 374 |
| A24 | Compound 375 |
| A25 | Compound 376 |
| A26 | Compound 377 |
| A27 | Compound 378 |
| A28 | Compound 379 |
| A29 | Compound 380 |
| A30 | Compound 381 |
| A31 | Compound 382 |
| A32 | Compound 383 |
| A33 | Compound 384 |
| A35 | Compound 386 |
| A36 | Compound 387 |
| A37 | Compound 388 |
| A38 | Compound 389 |
| A39 | Compound 390 |
| A40 | Compound 391 |
| A41 | Compound 392 |
| A42 | Compound 393 |
| A43 | Compound 394 |
| A44 | Compound 395 |
| A45 | Compound 396 |
| A46 | Compound 397 |
| A47 | Compound 398 |
| A48 | Compound 399 |
| A49 | Compound 400 |
| A50 | Compound 401 |
| A51 | Compound 402 |
| A52 | Compound 403 |
| A53 | Compound 404 |
| A54 | Compound 405 |
| A55 | Compound 406 |
| A56 | Compound 407 |
| A57 | Compound 408 |
| A58 | Compound 409 |
| A59 | Compound 410 |
| A60 | Compound 411 |
| A61 | Compound 412 |
| A62 | Compound 413 |
| A63 | Compound 414 |
| A64 | Compound 415 |
| A65 | Compound 416 |
| A66 | Compound 417 |
| A67 | Compound 418 |
| A68 | Compound 419 |
| A69 | Compound 420 |
| A70 | Compound 421 |
| A71 | Compound 422 |
| A72 | Compound 423 |
| A73 | Compound 424 |
| A74 | Compound 425 |
| A75 | Compound 426 |
| A76 | Compound 427 |
| A77 | Compound 428 |
| A78 | Compound 429 |
| A79 | Compound 430 |
| A80 | Compound 431 |
| A81 | Compound 432 |
| A82 | Compound 433 |
| A83 | Compound 434 |
| A84 | Compound 435 |
| A85 | Compound 436 |
| A86 | Compound 437 |
| A87 | Compound 438 |
| A88 | Compound 439 |
| A89 | Compound 440 |
| A90 | Compound 441 |
| A91 | Compound 442 |
| A92 | Compound 443 |
| A93 | Compound 444 |
| A94 | Compound 445 |
| A95 | Compound 446 |
| A96 | Compound 447 |
| A97 | Compound 448 |
| A98 | Compound 449 |
| A99 | Compound 450 |
| A100 | Compound 451 |
| A101 | Compound 452 |
| A102 | Compound 453 |
| A103 | Compound 454 |
| A104 | Compound 455 |
| A105 | Compound 456 |
| A106 | Compound 457 |
| A107 | Compound 460 |
| A108 | Compound 461 |
| A109 | Compound 462 |
| A110 | Compound 463 |
| A111 | Compound 464 |
| A112 | Compound 465 |
| A113 | Compound 466 |
| A114 | Compound 467 |
| A115 | Compound 468 |
| A116 | Compound 469 |
| A117 | Compound 470 |
| A118 | Compound 471 |
| A119 | Compound 472 |

| Table No. | Component (a) Column Entry |
|---|---|
| A120 | Compound 473 |
| A121 | Compound 474 |
| A122 | Compound 475 |
| A123 | Compound 476 |
| A124 | Compound 477 |
| A125 | Compound 478 |
| A126 | Compound 479 |
| A127 | Compound 480 |
| A128 | Compound 481 |
| A129 | Compound 482 |
| A130 | Compound 483 |
| A131 | Compound 484 |
| A132 | Compound 485 |
| A133 | Compound 486 |
| A134 | Compound 487 |
| A135 | Compound 488 |
| A136 | Compound 489 |
| A137 | Compound 490 |
| A138 | Compound 491 |
| A139 | Compound 492 |
| A140 | Compound 493 |
| A141 | Compound 494 |
| A142 | Compound 495 |
| A143 | Compound 496 |
| A144 | Compound 497 |
| A145 | Compound 498 |
| A146 | Compound 499 |
| A147 | Compound 500 |
| A148 | Compound 501 |
| A149 | Compound 502 |
| A150 | Compound 503 |
| A151 | Compound 504 |
| A152 | Compound 505 |
| A153 | Compound 506 |
| A154 | Compound 507 |
| A155 | Compound 508 |
| A156 | Compound 509 |
| A157 | Compound 510 |
| A158 | Compound 511 |
| A159 | Compound 512 |
| A160 | Compound 513 |
| A161 | Compound 514 |
| A162 | Compound 515 |
| A163 | Compound 516 |
| A164 | Compound 517 |
| A165 | Compound 518 |
| A166 | Compound 519 |
| A167 | Compound 520 |
| A168 | Compound 521 |
| A169 | Compound 522 |
| A170 | Compound 523 |
| A171 | Compound 524 |
| A172 | Compound 525 |
| A173 | Compound 526 |
| A174 | Compound 527 |
| A175 | Compound 528 |
| A176 | Compound 529 |
| A177 | Compound 530 |
| A178 | Compound 531 |
| A179 | Compound 532 |
| A180 | Compound 533 |
| A181 | Compound 534 |
| A182 | Compound 535 |
| A183 | Compound 536 |
| A184 | Compound 537 |
| A185 | Compound 538 |
| A186 | Compound 539 |
| A187 | Compound 540 |
| A188 | Compound 541 |
| A192 | Compound 545 |
| A193 | Compound 546 |
| A194 | Compound 547 |
| A196 | Compound 549 |
| A197 | Compound 550 |
| A198 | Compound 551 |
| A199 | Compound 552 |
| A200 | Compound 553 |
| A201 | Compound 554 |
| A202 | Compound 555 |
| A203 | Compound 556 |
| A204 | Compound 557 |
| A205 | Compound 558 |
| A206 | Compound 559 |
| A207 | Compound 560 |
| A208 | Compound 561 |
| A209 | Compound 562 |
| A210 | Compound 563 |
| A211 | Compound 564 |
| A212 | Compound 565 |
| A213 | Compound 566 |
| A214 | Compound 567 |
| A215 | Compound 568 |
| A216 | Compound 569 |
| A217 | Compound 570 |
| A218 | Compound 571 |
| A219 | Compound 572 |
| A220 | Compound 573 |
| A221 | Compound 574 |
| A222 | Compound 575 |
| A223 | Compound 576 |
| A224 | Compound 577 |
| A225 | Compound 578 |
| A226 | Compound 579 |
| A227 | Compound 580 |
| A228 | Compound 581 |
| A229 | Compound 582 |
| A230 | Compound 583 |
| A231 | Compound 584 |
| A232 | Compound 585 |
| A233 | Compound 586 |
| A234 | Compound 587 |
| A235 | Compound 588 |
| A236 | Compound 589 |
| A237 | Compound 590 |
| A238 | Compound 591 |
| A239 | Compound 592 |
| A240 | Compound 593 |
| A241 | Compound 594 |
| A242 | Compound 595 |
| A243 | Compound 596 |
| A244 | Compound 597 |
| A245 | Compound 598 |
| A246 | Compound 599 |
| A247 | Compound 600 |
| A248 | Compound 601 |
| A249 | Compound 602 |
| A250 | Compound 605 |
| A251 | Compound 606 |
| A252 | Compound 607 |
| A253 | Compound 608 |
| A254 | Compound 609 |
| A255 | Compound 610 |
| A256 | Compound 611 |
| A257 | Compound 612 |
| A258 | Compound 613 |
| A259 | Compound 614 |
| A260 | Compound 616 |
| A261 | Compound 617 |
| A262 | Compound 618 |
| A263 | Compound 619 |
| A264 | Compound 620 |
| A265 | Compound 621 |
| A266 | Compound 622 |
| A267 | Compound 623 |
| A268 | Compound 624 |
| A269 | Compound 625 |
| A274 | Compound 630 |
| A275 | Compound 631 |
| A276 | Compound 632 |
| A277 | Compound 633 |
| A278 | Compound 634 |
| A279 | Compound 635 |

-continued

| Table No. | Component (a) Column Entry |
|---|---|
| A280 | Compound 636 |
| A281 | Compound 637 |
| A282 | Compound 638 |
| A283 | Compound 639 |
| A284 | Compound 640 |
| A285 | Compound 641 |
| A286 | Compound 642 |
| A287 | Compound 643 |
| A288 | Compound 644 |
| A289 | Compound 645 |
| A290 | Compound 646 |
| A291 | Compound 647 |
| A292 | Compound 648 |
| A293 | Compound 649 |
| A294 | Compound 650 |
| A295 | Compound 651 |
| A296 | Compound 652 |
| A297 | Compound 653 |
| A298 | Compound 654 |
| A299 | Compound 655 |
| A300 | Compound 656 |
| A301 | Compound 657 |
| A302 | Compound 658 |
| A303 | Compound 659 |
| A304 | Compound 660 |
| A305 | Compound 661 |
| A306 | Compound 662 |
| A307 | Compound 663 |
| A308 | Compound 664 |
| A309 | Compound 665 |
| A310 | Compound 666 |
| A311 | Compound 667 |
| A312 | Compound 668 |
| A313 | Compound 674 |
| A314 | Compound 675 |
| A315 | Compound 676 |
| A316 | Compound 677 |
| A317 | Compound 678 |
| A318 | Compound 679 |
| A319 | Compound 680 |
| A320 | Compound 681 |
| A321 | Compound 682 |
| A322 | Compound 683 |
| A323 | Compound 684 |
| A324 | Compound 685 |
| A325 | Compound 686 |
| A326 | Compound 687 |
| A327 | Compound 688 |
| A328 | Compound 689 |
| A329 | Compound 690 |
| A330 | Compound 691 |
| A331 | Compound 692 |
| A332 | Compound 693 |
| A333 | Compound 694 |
| A334 | Compound 695 |
| A335 | Compound 696 |
| A336 | Compound 697 |
| A337 | Compound 698 |
| A338 | Compound 699 |
| A339 | Compound 700 |
| A340 | Compound 701 |
| A341 | Compound 702 |
| A342 | Compound 703 |
| A343 | Compound 704 |
| A344 | Compound 705 |
| A345 | Compound 706 |
| A350 | Compound 711 |
| A351 | Compound 712 |
| A352 | Compound 713 |
| A353 | Compound 714 |
| A354 | Compound 715 |
| A355 | Compound 716 |
| A 356 | Compound 717 |
| A 357 | Compound 718 |
| A 358 | Compound 719 |
| A 359 | Compound 720 |

-continued

| Table No. | Component (a) Column Entry |
|---|---|
| A 360 | Compound 721 |
| A 361 | Compound 722 |
| A 362 | Compound 723 |
| A 363 | Compound 724 |
| A 364 | Compound 725 |
| A 365 | Compound 726 |
| A 366 | Compound 727 |
| A 367 | Compound 728 |
| A 368 | Compound 729 |
| A 369 | Compound 730 |
| A 370 | Compound 731 |
| A 371 | Compound 732 |
| A 372 | Compound 733 |
| A 373 | Compound 734 |
| A 374 | Compound 735 |
| A 375 | Compound 736 |
| A 376 | Compound 737 |
| A 377 | Compound 738 |
| A 378 | Compound 739 |
| A 379 | Compound 740 |
| A 380 | Compound 741 |
| A 381 | Compound 742 |
| A 382 | Compound 743 |
| A 383 | Compound 744 |
| A 384 | Compound 745 |
| A 385 | Compound 746 |
| A 386 | Compound 747 |
| A 387 | Compound 748 |
| A 388 | Compound 749 |
| A 389 | Compound 750 |
| A 390 | Compound 751 |
| A 391 | Compound 752 |
| A 392 | Compound 753 |
| A 393 | Compound 754 |
| A 394 | Compound 755 |
| A 395 | Compound 756 |
| A 396 | Compound 757 |
| A 397 | Compound 758 |
| A 398 | Compound 759 |
| A 399 | Compound 760 |
| A 400 | Compound 761 |
| A 401 | Compound 762 |
| A 402 | Compound 763 |
| A 403 | Compound 764 |
| A 404 | Compound 765 |
| A 405 | Compound 766 |
| A 406 | Compound 767 |
| A 407 | Compound 768 |
| A 408 | Compound 769 |
| A 409 | Compound 770 |
| A 410 | Compound 771 |
| A 411 | Compound 772 |
| A 412 | Compound 773 |
| A 413 | Compound 774 |
| A 414 | Compound 775 |
| A 415 | Compound 776 |
| A 416 | Compound 777 |
| A 417 | Compound 778 |
| A 418 | Compound 779 |
| A 419 | Compound 780 |
| A 420 | Compound 781 |
| A 421 | Compound 782 |
| A 422 | Compound 783 |
| A 423 | Compound 784 |
| A 424 | Compound 785 |
| A 425 | Compound 786 |
| A 426 | Compound 787 |
| A 427 | Compound 788 |
| A 428 | Compound 789 |
| A 429 | Compound 790 |
| A 430 | Compound 791 |
| A 431 | Compound 792 |
| A 432 | Compound 793 |
| A 433 | Compound 794 |
| A 434 | Compound 795 |
| A 435 | Compound 796 |

-continued

| Table No. | Component (a) Column Entry |
|---|---|
| A 436 | Compound 797 |
| A 437 | Compound 798 |
| A 438 | Compound 799 |
| A 439 | Compound 800 |
| A 440 | Compound 801 |
| A 441 | Compound 802 |
| A 442 | Compound 803 |
| A 443 | Compound 804 |
| A 444 | Compound 805 |
| A 445 | Compound 806 |
| A 446 | Compound 807 |
| A 447 | Compound 808 |
| A 448 | Compound 809 |
| A 449 | Compound 810 |
| A 450 | Compound 811 |
| A 451 | Compound 812 |
| A 452 | Compound 813 |
| A 453 | Compound 814 |
| A 454 | Compound 815 |
| A 455 | Compound 816 |
| A 456 | Compound 817 |
| A 457 | Compound 818 |
| A 458 | Compound 819 |
| A 459 | Compound 820 |
| A 460 | Compound 821 |
| A 461 | Compound 822 |
| A 462 | Compound 823 |
| A 463 | Compound 824 |
| A 464 | Compound 825 |
| A 465 | Compound 826 |
| A 466 | Compound 827 |
| A 467 | Compound 828 |
| A 468 | Compound 829 |
| A 469 | Compound 830 |
| A 470 | Compound 831 |
| A 471 | Compound 832 |
| A 472 | Compound 833 |
| A 473 | Compound 834 |
| A 474 | Compound 835 |
| A 475 | Compound 836 |
| A 476 | Compound 837 |
| A 477 | Compound 838 |
| A 478 | Compound 839 |
| A 479 | Compound 840 |
| A 480 | Compound 841 |
| A 481 | Compound 842 |
| A 482 | Compound 843 |
| A 483 | Compound 844 |
| A 484 | Compound 845 |
| A 485 | Compound 846 |
| A 486 | Compound 847 |
| A 487 | Compound 848 |
| A 488 | Compound 849 |
| A 489 | Compound 850 |
| A 490 | Compound 851 |
| A 491 | Compound 852 |
| A 492 | Compound 853 |
| A 493 | Compound 854 |
| A 494 | Compound 855 |
| A 495 | Compound 856 |
| A 496 | Compound 857 |
| A 497 | Compound 858 |
| A 498 | Compound 859 |
| A 499 | Compound 860 |
| A 500 | Compound 861 |
| A 501 | Compound 862 |
| A 502 | Compound 863 |
| A 503 | Compound 864 |
| A 504 | Compound 865 |
| A 505 | Compound 866 |
| A 506 | Compound 867 |
| A 507 | Compound 868 |
| A 508 | Compound 869 |
| A 509 | Compound 870 |
| A 510 | Compound 871 |
| A 511 | Compound 872 |

-continued

| Table No. | Component (a) Column Entry |
|---|---|
| A 512 | Compound 873 |
| A 513 | Compound 874 |
| A 514 | Compound 875 |
| A 515 | Compound 876 |
| A 516 | Compound 877 |
| A 517 | Compound 878 |
| A 518 | Compound 879 |
| A 519 | Compound 880 |
| A 520 | Compound 881 |
| A 521 | Compound 882 |
| A 522 | Compound 883 |
| A 523 | Compound 884 |
| A 524 | Compound 885 |
| A 525 | Compound 886 |
| A 526 | Compound 887 |
| A 527 | Compound 888 |
| A 528 | Compound 889 |
| A 529 | Compound 890 |
| A 530 | Compound 891 |
| A 531 | Compound 892 |
| A 532 | Compound 893 |
| A 533 | Compound 894 |
| A 534 | Compound 895 |
| A 535 | Compound 896 |
| A 536 | Compound 897 |
| A 537 | Compound 898 |
| A 538 | Compound 899 |
| A 539 | Compound 900 |
| A 540 | Compound 901 |
| A 541 | Compound 902 |
| A 542 | Compound 903 |
| A 543 | Compound 904 |
| A 544 | Compound 905 |
| A 545 | Compound 906 |
| A 546 | Compound 907 |
| A 547 | Compound 908 |
| A 548 | Compound 909 |
| A 549 | Compound 910 |
| A 550 | Compound 911 |
| A 551 | Compound 912 |
| A 552 | Compound 913 |
| A 553 | Compound 914 |
| A 554 | Compound 915 |
| A 555 | Compound 916 |
| A 556 | Compound 917 |
| A 557 | Compound 918 |
| A 558 | Compound 919 |
| A 559 | Compound 920 |
| A 560 | Compound 921 |
| A 561 | Compound 922 |
| A 562 | Compound 923 |
| A 563 | Compound 924 |
| A 564 | Compound 925 |
| A 565 | Compound 926 |
| A 566 | Compound 927 |
| A 567 | Compound 928 |
| A 568 | Compound 929 |
| A 569 | Compound 930 |
| A 570 | Compound 931 |
| A 571 | Compound 932 |
| A 572 | Compound 933 |
| A 573 | Compound 934 |
| A 574 | Compound 935 |
| A 575 | Compound 936 |
| A 576 | Compound 937 |
| A 577 | Compound 938 |
| A 578 | Compound 939 |
| A 579 | Compound 940 |
| A 580 | Compound 941 |
| A 581 | Compound 942 |
| A 582 | Compound 943 |
| A 583 | Compound 944 |
| A 584 | Compound 945 |
| A 585 | Compound 946 |
| A 586 | Compound 947 |
| A 587 | Compound 948 |

| Table No. | Component (a) Column Entry |
|---|---|
| A 588 | Compound 949 |
| A 589 | Compound 950 |
| A 590 | Compound 951 |
| A 591 | Compound 952 |
| A 592 | Compound 953 |
| A 593 | Compound 954 |
| A 594 | Compound 955 |
| A 595 | Compound 956 |
| A 596 | Compound 957 |
| A 597 | Compound 958 |
| A 598 | Compound 959 |
| A 599 | Compound 960 |
| A 600 | Compound 961 |
| A 601 | Compound 962 |
| A 602 | Compound 963 |
| A 603 | Compound 964 |
| A 604 | Compound 965 |
| A 605 | Compound 966 |
| A 606 | Compound 967 |
| A 607 | Compound 968 |
| A 608 | Compound 969 |
| A 609 | Compound 970 |
| A 610 | Compound 971 |
| A 611 | Compound 972 |
| A 612 | Compound 973 |
| A 613 | Compound 974 |
| A 614 | Compound 975 |
| A 615 | Compound 976 |
| A 616 | Compound 977 |
| A 617 | Compound 978 |
| A 618 | Compound 979 |
| A 619 | Compound 980 |
| A 620 | Compound 981 |
| A 621 | Compound 982 |
| A 622 | Compound 983 |
| A 623 | Compound 984 |
| A 624 | Compound 985 |
| A 625 | Compound 986 |
| A 626 | Compound 987 |
| A 627 | Compound 988 |
| A 628 | Compound 989 |
| A 629 | Compound 990 |
| A 630 | Compound 991 |
| A 631 | Compound 992 |
| A 632 | Compound 993 |
| A 633 | Compound 994 |
| A 634 | Compound 995 |
| A 635 | Compound 996 |
| A 636 | Compound 997 |
| A 637 | Compound 998 |
| A 638 | Compound 999 |
| A 639 | Compound 1000 |
| A 640 | Compound 1001 |
| A 641 | Compound 1002 |
| A 642 | Compound 1003 |
| A 643 | Compound 1004 |
| A 644 | Compound 1005 |
| A 645 | Compound 1006 |
| A 646 | Compound 1007 |
| A 647 | Compound 1008 |
| A 648 | Compound 1009 |
| A 649 | Compound 1010 |
| A 650 | Compound 1011 |
| A 651 | Compound 1012 |
| A 652 | Compound 1013 |
| A 653 | Compound 1014 |
| A 654 | Compound 1015 |
| A 655 | Compound 1016 |
| A 656 | Compound 1017 |
| A 657 | Compound 1018 |
| A 658 | Compound 1019 |
| A 659 | Compound 1020 |
| A 660 | Compound 1021 |
| A 661 | Compound 1022 |
| A 662 | Compound 1023 |
| A 663 | Compound 1024 |
| A 664 | Compound 1025 |
| A 665 | Compound 1026 |
| A 666 | Compound 1027 |
| A 667 | Compound 1028 |
| A 668 | Compound 1029 |
| A 669 | Compound 1030 |
| A 670 | Compound 1031 |
| A 671 | Compound 1032 |
| A 672 | Compound 1033 |
| A 673 | Compound 1034 |
| A 674 | Compound 1035 |
| A 675 | Compound 1036 |
| A 676 | Compound 1037 |
| A 677 | Compound 1038 |
| A 678 | Compound 1039 |
| A 679 | Compound 1040 |
| A 680 | Compound 1041 |
| A 681 | Compound 1042 |
| A 682 | Compound 1043 |
| A 683 | Compound 1044 |
| A 684 | Compound 1045 |
| A 685 | Compound 1046 |
| A 686 | Compound 1047 |
| A 687 | Compound 1048 |
| A 688 | Compound 1049 |
| A 689 | Compound 1050 |
| A 690 | Compound 1051 |
| A 691 | Compound 1052 |
| A 692 | Compound 1053 |
| A 693 | Compound 1054 |
| A 694 | Compound 1055 |
| A 695 | Compound 1056 |
| A 696 | Compound 1057 |
| A 697 | Compound 1058 |
| A 698 | Compound 1059 |
| A 699 | Compound 1060 |
| A 700 | Compound 1061 |
| A 701 | Compound 1062 |
| A 702 | Compound 1063 |
| A 703 | Compound 1064 |
| A 704 | Compound 1065 |
| A 705 | Compound 1066 |
| A 706 | Compound 1067 |
| A 707 | Compound 1068 |
| A 708 | Compound 1069 |
| A 709 | Compound 1070 |
| A 710 | Compound 1071 |
| A 711 | Compound 1072 |
| A 712 | Compound 1073 |
| A 713 | Compound 1074 |
| A 714 | Compound 1075 |
| A 715 | Compound 1076 |
| A 716 | Compound 1077 |
| A 717 | Compound 1078 |
| A 718 | Compound 1079 |
| A 719 | Compound 1080 |
| A 720 | Compound 1081 |
| A 721 | Compound 1082 |
| A 722 | Compound 1083 |
| A 723 | Compound 1084 |
| A 724 | Compound 1085 |
| A 725 | Compound 1086 |
| A 726 | Compound 1087 |
| A 727 | Compound 1088 |
| A 728 | Compound 1089 |
| A 729 | Compound 1090 |
| A 730 | Compound 1091 |
| A 731 | Compound 1092 |
| A 732 | Compound 1093 |
| A 733 | Compound 1094 |
| A 734 | Compound 1095 |
| A 735 | Compound 1096 |
| A 736 | Compound 1097 |
| A 737 | Compound 1098 |
| A 738 | Compound 1099 |
| A 739 | Compound 1100 |

| Table No. | Component (a) Column Entry |
|---|---|
| A 740 | Compound 1101 |
| A 741 | Compound 1102 |
| A 742 | Compound 1103 |
| A 743 | Compound 1104 |
| A 744 | Compound 1105 |
| A 745 | Compound 1106 |
| A 746 | Compound 1107 |
| A 747 | Compound 1108 |
| A 748 | Compound 1109 |
| A 749 | Compound 1110 |
| A 750 | Compound 1111 |
| A 751 | Compound 1112 |
| A 752 | Compound 1113 |
| A 753 | Compound 1114 |
| A 754 | Compound 1115 |
| A 755 | Compound 1116 |
| A 756 | Compound 1117 |
| A 757 | Compound 1118 |
| A 758 | Compound 1119 |
| A 759 | Compound 1120 |
| A 760 | Compound 1121 |
| A 761 | Compound 1122 |
| A 762 | Compound 1123 |
| A 763 | Compound 1124 |
| A 764 | Compound 1125 |
| A 765 | Compound 1126 |
| A 766 | Compound 1127 |
| A 767 | Compound 1128 |
| A 768 | Compound 1129 |
| A 769 | Compound 1130 |
| A 770 | Compound 1131 |
| A 771 | Compound 1132 |
| A 772 | Compound 1133 |
| A 773 | Compound 1134 |
| A 774 | Compound 1135 |
| A 775 | Compound 1136 |
| A 776 | Compound 1137 |
| A 777 | Compound 1138 |
| A 778 | Compound 1139 |
| A 779 | Compound 1140 |
| A 780 | Compound 1141 |
| A 781 | Compound 1142 |
| A 782 | Compound 1143 |
| A 783 | Compound 1144 |
| A 784 | Compound 1145 |
| A 785 | Compound 1146 |
| A 786 | Compound 1147 |
| A 787 | Compound 1148 |
| A 788 | Compound 1149 |
| A 789 | Compound 1150 |
| A 790 | Compound 1151 |
| A 791 | Compound 1152 |
| A 792 | Compound 1153 |
| A 793 | Compound 1154 |
| A 794 | Compound 1155 |
| A 795 | Compound 1156 |
| A 796 | Compound 1157 |
| A 797 | Compound 1158 |
| A 798 | Compound 1159 |
| A 799 | Compound 1160 |
| A 800 | Compound 1161 |
| A 801 | Compound 1162 |
| A 802 | Compound 1163 |
| A 803 | Compound 1164 |
| A 804 | Compound 1165 |
| A 805 | Compound 1166 |
| A 806 | Compound 1167 |
| A 807 | Compound 1168 |
| A 808 | Compound 1169 |
| A 809 | Compound 1170 |
| A 810 | Compound 1171 |
| A 811 | Compound 1172 |
| A 812 | Compound 1173 |
| A 813 | Compound 1174 |
| A 814 | Compound 1175 |
| A 815 | Compound 1176 |
| A 816 | Compound 1177 |
| A 817 | Compound 1178 |
| A 818 | Compound 1179 |
| A 819 | Compound 1180 |
| A 820 | Compound 1181 |
| A 821 | Compound 1182 |
| A 822 | Compound 1183 |
| A 823 | Compound 1184 |
| A 824 | Compound 1185 |
| A 825 | Compound 1186 |
| A 826 | Compound 1187 |
| A 827 | Compound 1188 |
| A 828 | Compound 1189 |
| A 829 | Compound 1190 |
| A 830 | Compound 1191 |
| A 831 | Compound 1192 |
| A 832 | Compound 1193 |
| A 833 | Compound 1194 |
| A 834 | Compound 1195 |
| A 835 | Compound 1196 |
| A 836 | Compound 1197 |
| A 837 | Compound 1198 |
| A 838 | Compound 1199 |
| A 839 | Compound 1200 |
| A 840 | Compound 1201 |
| A 841 | Compound 1202 |
| A 842 | Compound 1203 |
| A 843 | Compound 1204 |
| A 844 | Compound 1205 |
| A 845 | Compound 1206 |
| A 846 | Compound 1207 |
| A 847 | Compound 1208 |
| A 848 | Compound 1209 |
| A 849 | Compound 1210 |
| A 850 | Compound 1211 |
| A 851 | Compound 1212 |
| A 852 | Compound 1213 |
| A 853 | Compound 1214 |
| A 854 | Compound 1215 |
| A 855 | Compound 1216 |
| A 856 | Compound 1217 |
| A 857 | Compound 1218 |
| A 858 | Compound 1219 |
| A 859 | Compound 1220 |
| A 860 | Compound 1221 |
| A 861 | Compound 1222 |
| A 862 | Compound 1223 |
| A 863 | Compound 1224 |
| A 864 | Compound 1225 |
| A 865 | Compound 1226 |
| A 866 | Compound 1227 |
| A 867 | Compound 1228 |
| A 868 | Compound 1229 |
| A 869 | Compound 1230 |
| A 870 | Compound 1231 |
| A 871 | Compound 1232 |
| A 872 | Compound 1233 |
| A 873 | Compound 1234 |
| A 874 | Compound 1235 |
| A 875 | Compound 1236 |
| A 876 | Compound 1237 |
| A 877 | Compound 1238 |
| A 878 | Compound 1239 |
| A 879 | Compound 1240 |
| A 880 | Compound 1241 |
| A 881 | Compound 1242 |
| A 882 | Compound 1243 |
| A 883 | Compound 1244 |
| A 884 | Compound 1245 |
| A 885 | Compound 1246 |
| A 886 | Compound 1247 |
| A 887 | Compound 1248 |
| A 888 | Compound 1249 |
| A 889 | Compound 1250 |
| A 890 | Compound 1251 |
| A 891 | Compound 1252 |

| Table No. | Component (a) Column Entry |
|---|---|
| A 892 | Compound 1253 |
| A 893 | Compound 1254 |
| A 894 | Compound 1255 |
| A 895 | Compound 1256 |
| A 896 | Compound 1257 |
| A 897 | Compound 1258 |
| A 898 | Compound 1259 |
| A 899 | Compound 1260 |
| A 900 | Compound 1261 |
| A 901 | Compound 1262 |
| A 902 | Compound 1263 |
| A 903 | Compound 1264 |
| A 904 | Compound 1265 |
| A 905 | Compound 1266 |
| A 906 | Compound 1267 |
| A 907 | Compound 1268 |
| A 908 | Compound 1269 |
| A 909 | Compound 1270 |
| A 910 | Compound 1271 |
| A 911 | Compound 1272 |
| A 912 | Compound 1273 |
| A 913 | Compound 1274 |
| A 914 | Compound 1275 |
| A 915 | Compound 1276 |
| A 916 | Compound 1277 |
| A 917 | Compound 1278 |
| A 918 | Compound 1279 |
| A 919 | Compound 1280 |
| A 920 | Compound 1281 |
| A 921 | Compound 1282 |
| A 922 | Compound 1283 |
| A 923 | Compound 1284 |
| A 924 | Compound 1285 |
| A 925 | Compound 1286 |
| A 926 | Compound 1287 |
| A 927 | Compound 1288 |
| A 928 | Compound 1289 |
| A 929 | Compound 1290 |
| A 930 | Compound 1291 |
| A 931 | Compound 1292 |
| A 932 | Compound 1293 |
| A 933 | Compound 1294 |
| A 934 | Compound 1295 |
| A 935 | Compound 1296 |
| A 936 | Compound 1297 |
| A 937 | Compound 1298 |
| A 938 | Compound 1299 |
| A 939 | Compound 1300 |
| A 940 | Compound 1301 |
| A 941 | Compound 1302 |
| A 942 | Compound 1303 |
| A 943 | Compound 1304 |
| A 944 | Compound 1305 |
| A 945 | Compound 1306 |
| A 946 | Compound 1307 |
| A 947 | Compound 1308 |
| A 948 | Compound 1309 |
| A 949 | Compound 1310 |
| A 950 | Compound 1311 |
| A 951 | Compound 1312 |
| A 952 | Compound 1313 |
| A 953 | Compound 1314 |
| A 954 | Compound 1315 |
| A 955 | Compound 1316 |
| A 956 | Compound 1317 |
| A 957 | Compound 1318 |
| A 958 | Compound 1319 |
| A 959 | Compound 1320 |
| A 960 | Compound 1321 |
| A 961 | Compound 1322 |
| A 962 | Compound 1323 |
| A 963 | Compound 1324 |
| A 964 | Compound 1325 |
| A 965 | Compound 1326 |
| A 966 | Compound 1327 |
| A 967 | Compound 1328 |
| A 968 | Compound 1329 |
| A 969 | Compound 1330 |
| A 970 | Compound 1331 |
| A 971 | Compound 1332 |
| A 972 | Compound 1333 |
| A 973 | Compound 1334 |
| A 974 | Compound 1335 |
| A 975 | Compound 1336 |
| A 976 | Compound 1337 |
| A 977 | Compound 1338 |
| A 978 | Compound 1339 |
| A 979 | Compound 1340 |
| A 980 | Compound 1341 |
| A 981 | Compound 1342 |
| A 982 | Compound 1343 |
| A 983 | Compound 1344 |
| A 984 | Compound 1345 |
| A 985 | Compound 1346 |
| A 986 | Compound 1347 |
| A 987 | Compound 1348 |
| A 988 | Compound 1349 |
| A 989 | Compound 1350 |
| A 990 | Compound 1351 |
| A 991 | Compound 1352 |
| A 992 | Compound 1353 |
| A 993 | Compound 1354 |
| A 994 | Compound 1355 |
| A 995 | Compound 1356 |
| A 996 | Compound 1357 |
| A 997 | Compound 1358 |
| A 998 | Compound 1359 |
| A 999 | Compound 1360 |
| A 1000 | Compound 1361 |
| A 1001 | Compound 1362 |
| A 1002 | Compound 1363 |
| A 1003 | Compound 1364 |
| A 1004 | Compound 1365 |
| A 1005 | Compound 1366 |
| A 1006 | Compound 1367 |
| A 1007 | Compound 1368 |
| A 1008 | Compound 1369 |
| A 1009 | Compound 1370 |
| A 1010 | Compound 1371 |
| A 1011 | Compound 1372 |
| A 1012 | Compound 1373 |
| A 1013 | Compound 1374 |
| A 1014 | Compound 1375 |
| A 1015 | Compound 1376 |
| A 1016 | Compound 1377 |
| A 1017 | Compound 1378 |
| A 1018 | Compound 1379 |
| A 1019 | Compound 1380 |
| A 1020 | Compound 1381 |
| A 1021 | Compound 1382 |
| A 1022 | Compound 1383 |
| A 1023 | Compound 1384 |
| A 1024 | Compound 1385 |
| A 1025 | Compound 1386 |
| A 1026 | Compound 1387 |
| A 1027 | Compound 1388 |
| A 1028 | Compound 1389 |
| A 1029 | Compound 1390 |
| A 1030 | Compound 1391 |
| A 1031 | Compound 1392 |
| A 1032 | Compound 1393 |
| A 1033 | Compound 1394 |
| A 1034 | Compound 1395 |
| A 1035 | Compound 1396 |
| A 1036 | Compound 1397 |
| A 1037 | Compound 1398 |
| A 1038 | Compound 1399 |
| A 1039 | Compound 1400 |
| A 1040 | Compound |
| A 1041 | Compound |
| A 1042 | Compound 1401 |
| A 1043 | Compound |

| Table No. | Component (a) Column Entry |
|---|---|
| A 1044 | Compound |
| A 1045 | Compound 1402 |
| A 1046 | Compound |
| A 1047 | Compound |
| A 1048 | Compound 1403 |
| A 1049 | Compound 1404 |
| A 1050 | Compound 1405 |
| A 1051 | Compound 1406 |
| A 1052 | Compound 1407 |
| A 1053 | Compound 1408 |
| A 1054 | Compound 1409 |
| A 1055 | Compound 1410 |
| A 1056 | Compound 1411 |
| A 1057 | Compound 1412 |
| A 1058 | Compound 1413 |
| A 1059 | Compound 1414 |
| A 1060 | Compound 1415 |
| A 1061 | Compound 1416 |
| A 1062 | Compound 1417 |
| A 1063 | Compound 1418 |
| A 1064 | Compound 1419 |
| A 1065 | Compound 1420 |
| A 1066 | Compound 1421 |
| A 1067 | Compound 1422 |
| A 1068 | Compound 1423 |
| A 1069 | Compound 1424 |
| A 1070 | Compound 1425 |
| A 1071 | Compound 1426 |
| A 1072 | Compound 1427 |
| A 1073 | Compound 1428 |
| A 1074 | Compound 1429 |
| A 1075 | Compound 1430 |
| A 1076 | Compound 1431 |
| A 1077 | Compound 1432 |
| A 1078 | Compound 1433 |
| A 1079 | Compound 1434 |
| A 1080 | Compound 1435 |
| A 1081 | Compound 1436 |
| A 1082 | Compound 1437 |
| A 1083 | Compound 1438 |
| A 1084 | Compound 1439 |
| A 1085 | Compound 1440 |
| A 1086 | Compound 1441 |
| A 1087 | Compound 1442 |
| A 1088 | Compound 1443 |
| A 1089 | Compound 1444 |
| A 1090 | Compound 1445 |
| A 1091 | Compound 1446 |
| A 1092 | Compound 1447 |
| A 1093 | Compound 1448 |
| A 1094 | Compound 1449 |
| A 1095 | Compound 1450 |
| A 1096 | Compound 1451 |
| A 1097 | Compound 1452 |
| A 1098 | Compound 1453 |
| A 1099 | Compound 1454 |
| A 1100 | Compound 1455 |
| A 1101 | Compound 1456 |
| A 1102 | Compound 1457 |
| A 1103 | Compound 1458 |
| A 1104 | Compound 1459 |
| A 1105 | Compound 1460 |
| A 1106 | Compound 1461 |
| A 1107 | Compound 1462 |
| A 1108 | Compound 1463 |
| A 1109 | Compound 1464 |
| A 1110 | Compound 1465 |
| A 1111 | Compound 1466 |
| A 1112 | Compound 1467 |
| A 1113 | Compound 1468 |
| A 1114 | Compound 1469 |
| A 1115 | Compound 1470 |
| A 1116 | Compound 1471 |
| A 1117 | Compound 1472 |
| A 1118 | Compound 1473 |
| A 1119 | Compound 1474 |
| A 1120 | Compound 1475 |
| A 1121 | Compound 1476 |
| A 1122 | Compound 1477 |
| A 1123 | Compound 1478 |
| A 1124 | Compound 1479 |
| A 1125 | Compound 1480 |
| A 1126 | Compound 1481 |
| A 1127 | Compound 1482 |
| A 1128 | Compound 1483 |
| A 1129 | Compound 1484 |
| A 1130 | Compound 1485 |
| A 1131 | Compound 1486 |
| A 1132 | Compound 1487 |
| A 1133 | Compound 1488 |
| A 1134 | Compound 1489 |
| A 1135 | Compound 1490 |
| A 1136 | Compound 1491 |
| A 1137 | Compound 1492 |
| A 1138 | Compound 1493 |
| A 1139 | Compound 1494 |
| A 1140 | Compound 1495 |
| A 1141 | Compound 1496 |
| A 1142 | Compound 1497 |
| A 1143 | Compound 1498 |
| A 1144 | Compound 1499 |
| A 1145 | Compound 1500 |
| A 1146 | Compound 1501 |
| A 1147 | Compound 1502 |
| A 1148 | Compound 1503 |
| A 1149 | Compound 1504 |
| A 1150 | Compound 1505 |
| A 1151 | Compound 1506 |
| A 1152 | Compound 1507 |
| A 1153 | Compound 1508 |
| A 1154 | Compound 1509 |
| A 1155 | Compound 1510 |
| A 1156 | Compound 1511 |
| A 1157 | Compound 1512 |
| A 1158 | Compound 1513 |
| A 1159 | Compound 1514 |
| A 1160 | Compound 1515 |
| A 1161 | Compound 1516 |
| A 1162 | Compound 1517 |
| A 1163 | Compound 1518 |
| A 1164 | Compound 1519 |
| A 1165 | Compound 1520 |
| A 1166 | Compound 1521 |
| A 1167 | Compound 1522 |
| A 1168 | Compound 1523 |
| A 1169 | Compound 1524 |
| A 1170 | Compound 1525 |
| A 1171 | Compound 1526 |
| A 1172 | Compound 1527 |
| A 1173 | Compound 1528 |
| A 1174 | Compound 1529 |
| A 1175 | Compound 1530 |
| A 1176 | Compound 1531 |
| A 1177 | Compound 1532 |
| A 1178 | Compound 1533 |
| A 1179 | Compound 1534 |
| A 1180 | Compound 1535 |
| A 1181 | Compound 1536 |
| A 1182 | Compound 1537 |
| A 1183 | Compound 1538 |
| A 1184 | Compound 1539 |
| A 1185 | Compound 1540 |
| A 1186 | Compound 1541 |
| A 1187 | Compound 1542 |
| A 1188 | Compound 1543 |
| A 1189 | Compound 1544 |
| A 1190 | Compound 1545 |
| A 1191 | Compound 1546 |
| A 1192 | Compound 1547 |
| A 1193 | Compound 1548 |
| A 1194 | Compound 1549 |
| A 1195 | Compound 1550 |

| Table No. | Component (a) Column Entry |
| --- | --- |
| A 1196 | Compound 1551 |
| A 1197 | Compound 1552 |
| A 1198 | Compound 1553 |
| A 1199 | Compound 1554 |
| A 1200 | Compound 1555 |
| A 1201 | Compound 1556 |
| A 1202 | Compound 1557 |
| A 1203 | Compound 1558 |
| A 1204 | Compound 1559 |
| A 1205 | Compound 1560 |
| A 1206 | Compound 1561 |
| A 1207 | Compound 1562 |
| A 1208 | Compound 1563 |
| A 1209 | Compound 1564 |
| A 1210 | Compound 1565 |
| A 1211 | Compound 1566 |
| A 1212 | Compound 1567 |
| A 1213 | Compound 1568 |
| A 1214 | Compound 1569 |
| A 1215 | Compound 1570 |
| A 1216 | Compound 1571 |
| A 1217 | Compound 1572 |
| A 1218 | Compound 1573 |
| A 1219 | Compound 1574 |
| A 1220 | Compound 1575 |
| A 1221 | Compound 1576 |
| A 1222 | Compound 1577 |
| A 1223 | Compound 1578 |
| A 1224 | Compound 1579 |
| A 1225 | Compound 1580 |
| A 1226 | Compound 1581 |
| A 1227 | Compound 1582 |
| A 1228 | Compound 1583 |
| A 1229 | Compound 1584 |
| A 1230 | Compound 1585 |
| A 1231 | Compound 1586 |
| A 1232 | Compound 1587 |
| A 1233 | Compound 1588 |
| A 1234 | Compound 1589 |
| A 1235 | Compound 1590 |
| A 1236 | Compound 1591 |
| A 1237 | Compound 1592 |
| A 1238 | Compound 1593 |
| A 1239 | Compound 1594 |
| A 1240 | Compound 1595 |
| A 1241 | Compound 1596 |
| A 1242 | Compound 1597 |
| A 1243 | Compound 1598 |
| A 1244 | Compound 1599 |
| A 1245 | Compound 1600 |
| A 1246 | Compound 1601 |
| A 1247 | Compound 1602 |
| A 1248 | Compound 1603 |
| A 1249 | Compound 1604 |
| A 1250 | Compound 1605 |
| A 1251 | Compound 1606 |
| A 1252 | Compound 1607 |
| A 1253 | Compound 1608 |
| A 1254 | Compound 1609 |
| A 1255 | Compound 1610 |
| A 1256 | Compound 1611 |
| A 1257 | Compound 1612 |
| A 1258 | Compound 1613 |
| A 1259 | Compound 1614 |
| A 1260 | Compound 1615 |
| A 1261 | Compound 1616 |
| A 1262 | Compound 1617 |
| A 1263 | Compound 1618 |
| A 1264 | Compound 1619 |
| A 1265 | Compound 1620 |
| A 1266 | Compound 1621 |
| A 1267 | Compound 1622 |
| A 1268 | Compound 1623 |
| A 1269 | Compound 1624 |
| A 1270 | Compound 1625 |
| A 1271 | Compound 1626 |
| A 1272 | Compound 1627 |
| A 1273 | Compound 1628 |
| A 1274 | Compound 1629 |
| A 1275 | Compound 1630 |
| A 1276 | Compound 1631 |
| A 1277 | Compound 1632 |
| A 1278 | Compound 1633 |
| A 1279 | Compound 1634 |
| A 1280 | Compound 1635 |
| A 1281 | Compound 1636 |
| A 1282 | Compound 1637 |
| A 1283 | Compound 1638 |
| A 1284 | Compound 1639 |
| A 1285 | Compound 1640 |
| A 1286 | Compound 1641 |
| A 1287 | Compound 1642 |
| A 1288 | Compound 1643 |
| A 1289 | Compound 1644 |
| A 1290 | Compound 1645 |
| A 1291 | Compound 1646 |
| A 1292 | Compound 1647 |
| A 1293 | Compound 1648 |
| A 1294 | Compound 1649 |
| A 1295 | Compound 1650 |
| A 1296 | Compound 1651 |
| A 1297 | Compound 1652 |
| A 1298 | Compound 1653 |
| A 1299 | Compound 1654 |
| A 1300 | Compound 1655 |
| A 1301 | Compound 1656 |
| A 1302 | Compound 1657 |
| A 1303 | Compound 1658 |
| A 1304 | Compound 1659 |
| A 1305 | Compound 1660 |
| A 1306 | Compound 1661 |
| A 1307 | Compound 1662 |
| A 1308 | Compound 1663 |
| A 1309 | Compound 1664 |
| A 1310 | Compound 1665 |
| A 1311 | Compound 1666 |
| A 1312 | Compound 1667 |
| A 1313 | Compound 1668 |
| A 1314 | Compound 1669 |
| A 1315 | Compound 1670 |
| A 1316 | Compound 1671 |
| A 1317 | Compound 1672 |
| A 1318 | Compound 1673 |
| A 1319 | Compound 1674 |
| A 1320 | Compound 1675 |
| A 1321 | Compound 1676 |
| A 1322 | Compound 1677 |
| A 1323 | Compound 1678 |
| A 1324 | Compound 1679 |
| A 1325 | Compound 1680 |
| A 1326 | Compound 1681 |
| A 1327 | Compound 1682 |
| A 1328 | Compound 1683 |
| A 1329 | Compound 1684 |
| A 1330 | Compound 1685 |
| A 1331 | Compound 1686 |
| A 1332 | Compound 1687 |
| A 1333 | Compound 1688 |
| A 1334 | Compound 1689 |
| A 1335 | Compound 1690 |
| A 1336 | Compound 1691 |
| A 1337 | Compound 1692 |
| A 1338 | Compound 1693 |
| A 1339 | Compound 1694 |
| A 1340 | Compound 1695 |
| A 1341 | Compound 1696 |
| A 1342 | Compound 1697 |
| A 1343 | Compound 1698 |
| A 1344 | Compound 1699 |
| A 1345 | Compound 1700 |
| A 1346 | Compound 1701 |
| A 1347 | Compound 1702 |

-continued

| Table No. | Component (a) Column Entry |
|---|---|
| A 1348 | Compound 1703 |
| A 1349 | Compound 1704 |
| A 1350 | Compound 1705 |
| A 1351 | Compound 1706 |
| A 1352 | Compound 1707 |
| A 1353 | Compound 1708 |
| A 1354 | Compound 1709 |
| A 1355 | Compound 1710 |
| A 1356 | Compound 1711 |
| A 1357 | Compound 1712 |
| A 1358 | Compound 1713 |
| A 1359 | Compound 1714 |
| A 1360 | Compound 1715 |
| A 1361 | Compound 1716 |
| A 1362 | Compound 1717 |
| A 1363 | Compound 1718 |
| A 1364 | Compound 1719 |
| A 1365 | Compound 1720 |
| A 1366 | Compound 1721 |
| A 1367 | Compound 1722 |
| A 1368 | Compound 1723 |
| A 1369 | Compound 1724 |
| A 1370 | Compound 1725 |
| A 1371 | Compound 1726 |
| A 1372 | Compound 1727 |
| A 1373 | Compound 1728 |
| A 1374 | Compound 1729 |
| A 1375 | Compound 1730 |
| A 1376 | Compound 1731 |
| A 1377 | Compound 1732 |
| A 1378 | Compound 1733 |
| A 1379 | Compound 1734 |
| A 1380 | Compound 1735 |
| A 1381 | Compound 1736 |
| A 1382 | Compound 1737 |
| A 1383 | Compound 1738 |
| A 1384 | Compound 1739 |
| A 1385 | Compound 1740 |
| A 1386 | Compound 1741 |
| A 1387 | Compound 1742 |
| A 1388 | Compound 1743 |
| A 1389 | Compound 1744 |
| A 1390 | Compound 1745 |
| A 1391 | Compound 1746 |
| A 1392 | Compound 1747 |
| A 1393 | Compound 1748 |
| A 1394 | Compound 1749 |
| A 1395 | Compound 1750 |
| A 1396 | Compound 1751 |
| A 1397 | Compound 1752 |
| A 1398 | Compound 1753 |
| A 1399 | Compound 1754 |
| A 1400 | Compound 1755 |
| A 1401 | Compound 1756 |
| A 1402 | Compound 1757 |
| A 1403 | Compound 1758 |
| A 1404 | Compound 1759 |
| A 1405 | Compound 1760 |
| A 1406 | Compound 1761 |
| A 1407 | Compound 1762 |
| A 1408 | Compound 1763 |
| A 1409 | Compound 1764 |
| A 1410 | Compound 1765 |
| A 1411 | Compound 1766 |
| A 1412 | Compound 1767 |
| A 1413 | Compound 1768 |
| A 1414 | Compound 1769 |
| A 1415 | Compound 1770 |
| A 1416 | Compound 1771 |
| A 1417 | Compound 1772 |
| A 1418 | Compound 1773 |
| A 1419 | Compound 1774 |
| A 1420 | Compound 1775 |
| A 1421 | Compound 1776 |
| A 1422 | Compound 1777 |
| A 1423 | Compound 1778 |
| A 1424 | Compound 1779 |
| A 1425 | Compound 1780 |
| A 1426 | Compound 1781 |
| A 1427 | Compound 1782 |
| A 1428 | Compound 1783 |
| A 1429 | Compound 1784 |
| A 1430 | Compound 1785 |
| A 1431 | Compound 1786 |
| A 1432 | Compound 1787 |
| A 1433 | Compound 1788 |
| A 1434 | Compound 1789 |
| A 1435 | Compound 1790 |
| A 1436 | Compound 1791 |
| A 1437 | Compound 1792 |
| A 1438 | Compound 1793 |
| A 1439 | Compound 1794 |
| A 1440 | Compound 1795 |
| A 1441 | Compound 1796 |
| A 1442 | Compound 1797 |
| A 1443 | Compound 1798 |
| A 1444 | Compound 1799 |
| A 1445 | Compound 1800 |
| A 1446 | Compound 1801 |
| A 1447 | Compound 1802 |
| A 1448 | Compound 1803 |
| A 1449 | Compound 1804 |
| A 1450 | Compound 1805 |
| A 1451 | Compound 1806 |
| A 1452 | Compound 1807 |
| A 1453 | Compound 1808 |
| A 1454 | Compound 1809 |
| A 1455 | Compound 1810 |
| A 1456 | Compound 1811 |
| A 1457 | Compound 1812 |
| A 1458 | Compound 1813 |
| A 1459 | Compound 1814 |
| A 1460 | Compound 1815 |
| A 1461 | Compound 1816 |
| A 1462 | Compound 1817 |
| A 1463 | Compound 1818 |
| A 1464 | Compound 1819 |
| A 1465 | Compound 1820 |
| A 1466 | Compound 1821 |
| A 1467 | Compound 1822 |
| A 1468 | Compound 1823 |
| A 1469 | Compound 1824 |
| A 1470 | Compound 1825 |
| A 1471 | Compound 1826 |
| A 1472 | Compound 1827 |
| A 1473 | Compound 1828 |
| A 1474 | Compound 1829 |
| A 1475 | Compound 1830 |
| A 1476 | Compound 1831 |
| A 1477 | Compound 1832 |
| A 1478 | Compound 1833 |
| A 1479 | Compound 1834 |
| A 1480 | Compound 1835 |
| A 1481 | Compound 1836 |
| A 1482 | Compound 1837 |
| A 1483 | Compound 1838 |
| A 1484 | Compound 1839 |
| A 1485 | Compound 1840 |
| A 1486 | Compound 1841 |
| A 1487 | Compound 1842 |
| A 1488 | Compound 1843 |
| A 1489 | Compound 1844 |
| A 1490 | Compound 1845 |
| A 1491 | Compound 1846 |
| A 1492 | Compound 1847 |
| A 1493 | Compound 1848 |
| A 1494 | Compound 1849 |
| A 1495 | Compound 1850 |
| A 1496 | Compound 1851 |
| A 1497 | Compound 1852 |
| A 1498 | Compound 1853 |
| A 1499 | Compound 1854 |

-continued

| Table No. | Component (a) Column Entry |
|---|---|
| A 1500 | Compound 1855 |
| A 1501 | Compound 1856 |
| A 1502 | Compound 1857 |
| A 1503 | Compound 1858 |
| A 1504 | Compound 1859 |
| A 1505 | Compound 1860 |
| A 1506 | Compound 1861 |
| A 1507 | Compound 1862 |
| A 1508 | Compound 1863 |
| A 1509 | Compound 1864 |
| A 1510 | Compound 1865 |
| A 1511 | Compound 1866 |
| A 1512 | Compound 1867 |
| A 1513 | Compound 1868 |
| A 1514 | Compound 1869 |
| A 1515 | Compound 1870 |
| A 1516 | Compound 1871 |
| A 1517 | Compound 1872 |
| A 1518 | Compound 1873 |
| A 1519 | Compound 1874 |

In some embodiments, a mixture of a compound of this disclosure with a herbicide selected from the group consisting of chlorimuron-ethyl, nicosulfuron, mesotrione, thifensulfuron-methyl, flupyrsulfuron-methyl, tribenuron, pyroxasulfone, pinoxaden, tembotrione, pyroxsulam, metolachlor and S-metolachlorfor is used for better control of undesired vegetation (e.g., lower use rate such as from synergism, broader spectrum of weeds controlled, or enhanced crop safety) or for preventing the development of resistant weeds.

The following Tests demonstrate the control efficacy of compounds of this disclosure on specific pathogens. The pathogen control protection afforded by the compounds is not limited, however, to these species. See Index Tables A-F for compound descriptions. The following abbreviations are used in the Index Tables which follow: Me is methyl, allyl is —$CH_2CH$=$CH_2$, allyl(2-Cl) is —$CH_2CCl$=$CH_2$, allyl(3-Cl) is —$CH_2CH$=$CHCl$, allyl(3-Ph) is —$CH_2CH$=$CHPh$, allyl(3-Br) is —$CH_2CH$=$CHBr$, allyl(2-Me) is —$CH_2CMe$=$CH_2$, allyl(3,3-di-Me) is —$CH_2CH$=$CMe_2$, "acn" means acetonitrile (—$CH_2CN$) 1-c-hexen is 1-cyclohexenyl, Ph is phenyl, OMe is methoxy, —CN is cyano, —$NO_2$ is nitro and TMS is trimethylsilyl, s is secondary, n is normal, i is iso, c is cyclo, Et is ethyl, Pr is propyl, i Pr is isopropyl, Bu is butyl, c-Pr is cyclopropyl, OEt is ethoxy, and $NO_2$ is nitro. Mass spectra are reported as the molecular weight of the highest isotopic abundance parent ion (M+1) formed by addition of $H^+$ (molecular weight of 1) to the molecule, or (M−1) formed by the loss of $H^+$ (molecular weight of 1) from the molecule, observed by using liquid chromatography coupled to a mass spectrometer (LCMS) using either atmospheric pressure chemical ionization ($AP^+$) or electrospray ionization ($ESI^+$).

INDEX TABLE A [(1)]

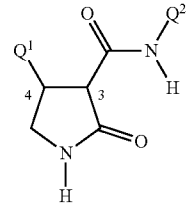

| Cmpd. No. | $Q^1$ | $Q^2$ | m.p. (° C.) | M − 1 | M + 1 |
|---|---|---|---|---|---|
| 352 | pyridin-3-yl | Ph(2-$CF_3$) | 165-168 | | |
| 353 (trans) | Ph(3-$NH_2$) | Ph(2,3-di-F) | | | 332 |
| 354 (cis) | Ph(3-$NH_2$) | Ph(2,3-di-F) | | | 332 |
| 355 | Ph(3,4-di-F) | Ph(2-$NH_2$,3-$CH_3$) | | 344 | |
| 356 | furan-3-yl | Ph(2-F) | 135-138 | | |
| 357 | Ph(3,4-di-F) | Ph(2-$NH_2$,3-$NO_2$) | | 375 | 377 |
| 358 | Ph(3,4-di-F) | Ph(2-$NH_2$,3,4-di-F) | | 366 | 368 |
| 359 (trans) | Ph(3-$NMe_2$) | Ph(2-F) | | | 342 |
| 360 (cis) | Ph(3-$NMe_2$) | Ph(2-F) | | | 342 |
| 361 | Ph(3,4-di-F) | 1H-Pyrazol-3-yl(4-Br) | | 385 | 387 |
| 362 | Ph(3,4-di-F) | 1H-Pyrazol-5-yl(1-Me) | | 319 | 321 |
| 363 | pyridin-3-yl | Ph(2-F) | 179-182 | | |
| 364 | furan-3-yl | Ph(2-$CF_3$) | | | 339 |
| 365 | Ph(4-Ph) | Ph(2-F) | | | 375 |
| 366 | Ph(4-Ph) | Ph(2,3-di-F) | | | 393 |
| 367 | Ph(4-Ph) | Ph(2-$CF_3$) | | | 425 |
| 368 | Ph(3-F,4-Me) | Ph(2-F) | | | 331 |
| 369 | Ph(3-F,4-Me) | Ph(2,3-di-F) | | | 349 |
| 370 | Ph(3-F,4-Me) | Ph(2,4-di-F) | | | 349 |
| 371 | Ph(3-F,4-Me) | Ph(2,3,4-tri-F) | | | 367 |
| 372 | Ph(3-Me) | Ph(2-F) | | 311 | |
| 373 | Ph(3-Me) | Ph(2,3-di-F) | | | 331 |
| 374 | Ph(3-Me) | Ph(2-$CF_3$) | | | 363 |
| 375 | Ph(3-F) | Ph(2,3-di-F) | | 333 | |
| 376 | Ph(3-F) | Ph(2-$CF_3$) | | | 367 |
| 377 | Ph(3-O-i-Pr) | Ph(2,4-di-F) | | 373 | 375 |
| 379 | Ph(2-Ph) | Ph(2,3-di-F) | 129-132 | | |
| 380 | Ph(3-O-n-Pr) | Ph(2,3-di-F) | 138-141 | | |
| 381 | Ph(2-Ph) | Ph(2-F) | 127-130 | | |
| 382 | Ph(2-Ph) | Ph(2,3,4-tri-F) | 161-164 | | |
| 383 | Ph(3-OMe) | Ph(2,3-di-F) | 183-186 | | |
| 384 | Ph(3-OH) | Ph(2,3-di-F) | 176-179 | | |
| 386 | Ph(3-$CF_3$) | Ph(2,4-di-F,3-OMe) | | | 415 |

INDEX TABLE A [(1)]-continued

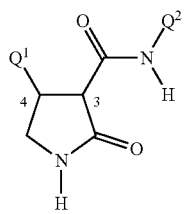

| Cmpd. No. | Q[1] | Q[2] | m.p. (° C.) | M − 1 | M + 1 |
|---|---|---|---|---|---|
| 387 | Ph(3-(2,2-di-F-ethoxy)) | Ph(2-F) | | | 379 |
| 388 | Ph(3-(2,2-di-F-ethoxy)) | Ph(2,4-di-F) | | | 397 |
| 389 | Ph(3-(2,2-di-F-ethoxy)) | Ph(2,3-di-F) | | | 397 |
| 390 | Ph(3-(2,2-di-F-ethoxy)) | Ph(2-Cl) | | | 395 |
| 391 | Ph(3-OCF$_2$CHF$_2$) | Ph(2-CHF$_2$) | | | 447 |
| 394 | CH$_3$C(O)— | Ph(2,3-di-F) | | 357 | |
| 400 | Ph(4-F,3-Me) | Ph(2,3-di-F) | | | 349 |
| 401 | Ph(4-F,3-Me) | Ph(2,3,4-tri-F) | | | 367 |
| 407 | Ph(3-(2,2-di-F-ethoxy)) | Ph(2,3,4-tri-F) | | | 415 |
| 408 | Ph(3,4-di-F) | Ph(2-F-5-Me) | | | 349 |
| 409 | Ph(3,4-di-F) | Ph(2-F,3-Me) | | | 349 |
| 410 | Ph(3,4-di-F) | Ph(2-F,4-Cl) | | | 369 |
| 411 | Ph(3,4-di-F) | Ph(2-Cl,4-F) | | | 369 |
| 412 | Ph(3,4-di-F) | Ph(4-F-3-Me) | | | 349 |
| 413 | Ph(3,4-di-F) | Ph(2-F,4-OMe) | | | 365 |
| 414 | Ph(3,4-di-F) | Ph(4-CF$_3$,3-Me) | | | 399 |
| 415 | Ph(3,4-di-F) | Ph(3-F,4-OMe) | | | 365 |
| 416 | Ph(3,4-di-F) | Ph(2-F,3-OMe) | | | 365 |
| 417 | Ph(3,4-di-F) | Ph(2-CO$_2$Me) | | | 375 |
| 418 | Ph(3,4-di-F) | Ph(2-C(O)Me) | | | 359 |
| 419 | Ph(3,4-di-F) | Ph(2,4-di-F,3-OMe) | | | 383 |
| 420 | Ph(3-OCHF$_2$) | Ph(2-F,3-Me) | | 377 | 379 |
| 421 | Ph(3-OCHF$_2$) | Ph(2,4-di-F) | | | 383 |
| 422 | Ph(3-OCHF$_2$) | Ph(3-OCHF$_2$) | | | 413 |
| 423 | Ph(3-OCHF$_2$) | Ph(2-F,5-Me) | | | 379 |
| 424 | Ph(3-OCHF$_2$) | Ph(4-F,3-Me) | | | 379 |
| 425 | Ph(3-OCHF$_2$) | Ph(2-F,4-OMe) | 95-100 | | |
| 426 | Ph(3-OCHF$_2$) | Ph(2-F,3-OMe) | | | 395 |
| 427 | Ph(3-OCHF$_2$) | Ph(2-OCHF$_2$) | | | 413 |
| 432 | Ph(3-OC(O)CH$_3$) | Ph(2,3-di-F) | 147-150 | | |
| 446 | Ph(4-Br) | Ph(2,3-di-F) | | | 396 |
| 447 | Ph(4-Br) | Ph(2,4-di-F) | | | 396 |
| 448 | Ph(4-Br) | Ph(2-F) | | | 377 |
| 449 | Ph(4-Br) | Ph(3-F) | | 375 | 377 |
| 451 | Ph(3-C≡C—Ph) | Ph(2,3-di-F) | | 415 | 417 |
| 452 | Ph(4-Br) | Ph(2-S(O)$_2$Me) | | | 436 |
| 453 | Ph(4-Br) | Ph(2-Cl) | | | 394 |
| 455 | Ph(2,4-di-F) | Ph(2,3-di-F) | | | 353 |
| 460 | Ph(3-OCF$_2$CHF$_2$) | Ph(2,4-di-F,3-Me) | | | 447 |
| 461 | Ph(3,5-di-F) | Ph(2,4-di-F,3-Me) | | | 367 |
| 462 | Ph(3-F,4-Me) | Ph(2,4-di-F,3-Me) | | | 363 |
| 463 | Ph(3-CF$_3$) | Ph(2,4-di-F,3-Me) | | | 399 |
| 466 | Ph(4-Et) | Ph(2-F) | | | 327 |
| 467 | Ph(4-Et) | Ph(2,3-di-F) | | | 345 |
| 468 | Ph(4-Et) | Ph(2-S(O)$_2$Me) | | | 387 |
| 469 | Ph(4-i-Pr) | Ph(2-F) | | | 341 |
| 470 | Ph(4-i-Pr) | Ph(2,3-di-F) | | | 359 |
| 475 | Ph(2-F,4-CF$_3$) | Ph(2,3-di-F) | | | 402 |
| 487 | Ph(2,3-di-F) | Ph(2,3-di-F) | | | 353 |
| 488 | Ph(3-F,5-CF$_3$) | Ph(2,3-di-F) | 146 | | |
| 489 | Ph(3-F,5-CF$_3$) | Ph(2-F) | 145-149 | | |
| 490 | Ph(3-F,5-CF$_3$) | Ph(2,4-di-F) | 172-178 | | |
| 491 | Ph(3-F,5-Cl) | Ph(2-F) | 179-208 | | |
| 492 | Ph(3-F,5-Cl) | Ph(2,3-di-F) | 122-129 | | |
| 493 | Ph(3-F,5-Cl) | Ph(2,4-di-F) | 139-147 | | |
| 494 | Ph(2,3-di-F) | Ph(2-F) | | | 335 |
| 495 | Ph(2,3-di-F) | Ph(2,4-di-F) | | | 353 |
| 496 | Ph(3-CH$_2$OMe) | Ph(2-F) | | | 343 |
| 497 | Ph(3-CH$_2$OMe) | Ph(2,3-di-F) | | | 361 |
| 498 | Ph(3-CH$_2$OMe) | Ph(2-Cl) | | | 359 |
| 499 | Ph(3-CH$_2$OMe) | Ph(2,4-di-F) | | | 361 |
| 500 | Ph(4-i-Pr) | Ph(2-S(O)$_2$Me) | | | 401 |
| 501 | Ph(4-c-Pr) | Ph(2,3-di-F) | | | 357 |
| 502 | Ph(4-c-Pr) | Ph(2-S(O)$_2$Me) | | | 399 |
| 504 | Ph(3-F,4-CF$_3$) | Ph(2,3-di-F) | | | 403 |
| 507 | Ph(2-F,4-Me) | Ph(2-S(O)$_2$Me) | | | 391 |
| 508 | Ph(2-F,4-Me) | Ph(2,4-di-F) | | | 349 |

INDEX TABLE A [(1)]-continued

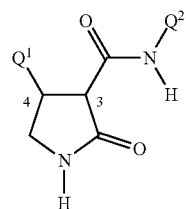

| Cmpd. No. | Q¹ | Q² | m.p. (° C.) | M − 1 | M + 1 |
|---|---|---|---|---|---|
| 509 | Ph(2-F,4-Me) | Ph(2-F) | | | 331 |
| 510 | thiophen-2-yl(4-Br) | Ph(2,3-di-F) | | | 402 |
| 513 | pyridine-4-yl(2-CF₃) | Ph(2-F) | | | 368 |
| 514 | pyridine-4-yl(2-CF₃) | Ph(2,3-di-F) | | | 386 |
| 515 | Ph(2,6-di-F) | Ph(2-F) | | | 335 |
| 516 | Ph(2,6-di-F) | Ph(2,3-di-F) | | | 353 |
| 517 | Ph(2,6-di-F) | Ph(2,4-di-F) | | | 353 |
| 518 | Ph(2,4-di-F) | Ph(2,4-di-F) | | | 353 |
| 519 | Ph(3-Br) | Ph(2-F) | | | 391 |
| 521 | Ph(3-F,4-CF₃) | Ph(2-F) | | | 385 |
| 522 | Ph(3-F,4-CF₃) | Ph(2,4-di-F) | | | 403 |
| 532 | thiophen-3-yl(2,4,5-tri-Br) | Ph(2-F) | | | 542 |
| 533 | thiophen-3-yl(2,4,5-tri-Br) | Ph(2,3-di-F) | | | 561 |
| 534 | Ph(4-OPh) | Ph(2-F) | | | |
| 535 | Ph(4-OPh) | Ph(2,4-di-F) | | | 409 |
| 536 | Ph(4-OPh) | Ph(2,3-di-F) | | | 409 |
| 537 | Ph(4-OPh) | Ph(2,3,4-tri-F) | | | 427 |
| 538 | Ph(4-OPh) | Ph(2-Cl) | | | 407 |
| 540 | Ph(3-OCF₂CHF₂) | Ph(2,4-di-F,3-OMe) | | | 463 |
| 541 | Ph(3,5-di-F) | Ph(2,4-di-F,3-OMe) | | | 383 |
| 544 | Ph(2,5-di-F) | Ph(2-F) | | | 335 |
| 545 | Ph(2,5-di-F) | Ph(2,4-di-F) | | | 353 |
| 546 | Ph(2,5-di-F) | Ph(2,3-di-F) | | | 353 |
| 549 | Ph(2,4,5-tri-F) | Ph(2-F) | | | 353 |
| 550 | Ph(2,4,5-tri-F) | Ph(2,3-di-F) | | | 371 |
| 551 | Ph(2,4,5-tri-F) | Ph(2,4-di-F) | | | 371 |
| 552 | Ph(3-O-i-Pr) | Ph(2-F) | | 355 | 357 |
| 553 | Ph(3-O-i-Pr) | Ph(2,3-di-F) | | 373 | 375 |
| 554 | Ph(3-O-i-Pr) | Ph(2,3,4-tri-F) | | 391 | 393 |
| 555 | Ph(4-CF₃) | Ph(2-OH) | 150-176 | | |
| 556 | Ph(4-CF₃) | Ph(2-F,6-OH) | 197-205 | | |
| 557 | Ph(3-CF₃) | Ph(2-OH) | 55-66 | | |
| 561 | Ph(4-OCHF₂) | Ph(2,3-di-F) | | | 383 |
| 578 | Ph(4-Br,3-Me) | Ph(2-F) | | | 391 |
| 579 | Ph(4-Br,3-Me) | Ph(2,3-di-F) | | | 410 |
| 580 | Ph(3-F,4-OMe) | Ph(2-CF₃) | | | 397 |
| 581 | thiophen-2-yl | Ph(2-F) | | | 305 |
| 582 | thiophen-2-yl | Ph(2,3-di-F) | | | 323 |
| 583 | thiophen-2-yl(5-Br) | Ph(2-F) | | | 384 |
| 584 | thiophen-2-yl(5-Br) | Ph(2,3-di-F) | | | 403 |
| 587 | Ph(3,5-di-CF₃) | Ph(2-F) | 132-150 | | |
| 588 | Ph(3,5-di-CF₃) | Ph(2,3-di-F) | 112-124 | | |
| 589 | Ph(3,5-di-CF₃) | Ph(2,4-di-F) | 163-167 | | |
| 590 | Ph(2-F,3-CF₃) | Ph(2-F) | 111-115 | | |
| 591 | Ph(2-F,3-CF₃) | Ph(2,3-di-F) | 138-141 | | |
| 592 | Ph(2-F-3-CF₃) | Ph(2,4-di-F) | 134-140 | | |
| 593 | Ph(2-F-5-CF₃) | Ph(2-F) | 126-128 | | |
| 594 | Ph(2-F-5-CF₃) | Ph(2,3-di-F) | 119-120 | | |
| 595 | Ph(2-F-5-CF₃) | Ph(2,4-di-F) | 124-126 | | |
| 597 | thiophen-3-yl(2-Br) | Ph(2-F) | | | 384 |
| 598 | thiophen-3-yl(2-Br) | Ph(2,3-di-F) | | | 403 |
| 599 | thiophen-3-yl(2-Cl) | Ph(2-F) | | | 339 |
| 600 | thiophen-3-yl(2-Cl) | Ph(2,3-di-F) | | | 357 |
| 601 | thiophen-3-yl(2,5-di-Cl) | Ph(2,3-di-F) | | | 392 |
| 608 | Ph(4-CF₃) | Ph(2-S(O)₂Me) | | | 423 |
| 609 | Ph(4-CF₃) | Ph(2-F) | | | 363 |
| 610 | Ph(4-CF₃) | Ph(2,3-di-F) | | | 381 |
| 614 | Ph(2,4,5-tri-F) | Ph(2,3,4-tri-F) | | | 389 |
| 620 | Ph(2,4-di-F) | Ph(2-F) | | 333 | 335 |
| 621 | Ph(3-CN) | Ph(2,3-di-F) | | | 342 |
| 630 | thiophen-3-yl(5-Me) | Ph(2-F) | 128-131 | | |
| 634 | Ph(3-CF₃) | Ph(2-S(O)₂NH₂) | | | 428 |
| 635 | 1,3-benzodioxol-5-yl(2,2-di-F) | Ph(2,3-di-F) | | | 397 |
| 642 | Ph(3-CF₃,4-Me) | Ph(2,3-di-F) | | | 399 |
| 648 | thiophen-3-yl(5-Br) | Ph(2-F) | | | 385 |
| 649 | thiophen-3-yl(5-Br) | Ph(2,3-di-F) | | | 403 |
| 654 | Ph(3-CF₃,4-Me) | Ph(2-F) | | 379 | 381 |

INDEX TABLE A [1]-continued

| Cmpd. No. | Q¹ | Q² | m.p. (° C.) | M − 1 | M + 1 |
|---|---|---|---|---|---|
| 655 | Ph(3-CF₃,4-Me) | Ph(2,4-di-F) | | | 399 |
| 656 | thiophen-3-yl(5-Me) | Ph(2,3-di-F) | 144-148 | | |
| 657 | thiophen-3-yl(5-Et) | Ph(2-F) | 96-99 | | |
| 658 | thiophen-3-yl(5-Et) | Ph(2,3-di-F) | 113-117 | | |
| 674 | Ph(3-CF₃) | Ph(2-F,3-OMe) | | | 397 |
| 675 | Ph(3-CF₃) | Ph(2-F,4-Cl) | | | 401 |
| 676 | Ph(3-CF₃) | Ph(2-Cl,4-F) | | | 401 |
| 677 | Ph(3-C≡CH) | Ph(2,3-di-F) | | 339 | |
| 678 | Ph(3-CF₃,4-Me) | Ph(2-F) | | | 381 |
| 679 | Ph(3-CF₃,4-Me) | Ph(2,3-di-F) | | | 399 |
| 680 | Ph(3-CF₃,4-Me) | Ph(2,4-di-F) | | | 399 |
| 681 | Ph(3-CF₃,4-Me) | Ph(2,3,4-tri-F) | | | 417 |
| 686 | Ph(3-Br) | Ph(2-F) | | | 377 |
| 687 | Ph(3-Br) | Ph(2,4-di-F) | | | 395 |
| 688 | Ph(3-Br) | Ph(2,3-di-F) | | | 395 |
| 689 | Ph(3-Br) | Ph(2,3,4-tri-F) | | | 413 |
| 695 | Ph(3-OCF₂CHF₂) | Ph(2-F) | | | 415 |
| 696 | Ph(3-OCF₂CHF₂) | Ph(2,4-di-F) | | | 433 |
| 697 | Ph(3-OCF₂CHF₂) | Ph(2,3-di-F) | | | 433 |
| 698 | Ph(3-OCF₂CHF₂) | Ph(2,3,4-tri-F) | | | 451 |
| 699 | Ph(3-OCF₂CHF₂) | Ph(2-Cl) | | | 431 |
| 700 | Ph(4-I) | Ph(2,3-di-F) | | | 443 |
| 701 | Ph(4-I) | Ph(2,4-di-F) | | | 443 |
| 702 | Ph(4-I) | Ph(2-F) | | | 425 |
| 703 | Ph(4-I) | Ph(3-F) | | | 425 |
| 704 | Ph(4-I) | Ph(2-Cl) | | | 441 |
| 705 | Ph(3-CF₃) | Ph(2-CO₂Me) | | | 407 |
| 706 | Ph(3-CF₃) | Ph(2-C(O)Me) | | | 391 |
| 711 | Naphthalene-1-yl | Ph(2,3-di-F) | | | 367 |
| 712 | Naphthalene-1-yl | Ph(2-CF₃) | | | 399 |
| 714 | Ph(3-OH) | Ph(2-F) | | | 315 |
| 715 | Ph(3-OH) | Ph(2,3-di-F) | | | 333 |
| 716 | Ph(3-OH) | Ph(2-CF₃) | | | 365 |

[1] Substituents in the 3 and 4 positions of the pyrrolidinone ring when, i.e. C(O)N(Q²)(R⁶) (when Y² is O) and Q¹, respectively, are predominately in the trans configuration. In some instances the presence of minor amounts of the cis isomer can be detected by NMR.

INDEX TABLE B

| Cmpd No. | R¹ | Q¹ | R⁵ | R⁶ | Q² | M + 1 |
|---|---|---|---|---|---|---|
| 378 | Me | Ph(3-O-i-Pr) | H | H | Ph(2,4-di-F) | 389 |
| 392 | Me | Ph(3-OCF₂CHF₂) | H | H | Ph(2,3-di-F) | 447 |
| 393 | Me | Ph(3-OCF₂CHF₂) | H | H | Ph(2,4-di-F) | 447 |
| 395 | Me | Ph(3-C≡CH) | OH | H | Ph(2,3-di-F) | 357 |
| 396 | Me | Ph(3-F,4-CF₃) | H | H | Ph(2,3-di-F) | 417 |
| 397 | Me | Ph(3-F,4-CF₃) | H | H | Ph(2-S(O)₂Me) | 459 |
| 398 | Me | Ph(3-F,4-CF₃) | H | H | Ph(2,4-di-F) | 417 |
| 399 | Me | Ph(3-F,4-CF₃) | H | H | Ph(2-F) | 399 |
| 402 | Me | Ph(4-F,3-Me) | H | H | Ph(2-F) | 345 |
| 403 | Me | Ph(4-F,3-Me) | H | H | Ph(2,3-di-F) | 363 |
| 404 | Me | Ph(4-F,3-Me) | H | H | Ph(2,4-di-F) | 363 |
| 405 | Me | Ph(4-F,3-Me) | H | H | Ph(2-S(O)₂Me) | 405 |
| 406 | Me | Ph(4-F,3-Me) | H | H | Ph(2-CF₃) | 395 |
| 428 | Me | Ph(3-CF₃) | Me | H | Ph(2-F) | 395 |

INDEX TABLE B-continued

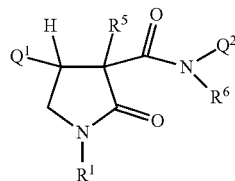

| Cmpd No. | R¹ | Q¹ | R⁵ | R⁶ | Q² | M + 1 |
|---|---|---|---|---|---|---|
| 429 | Me | Ph(3-OCF$_2$CHF$_2$) | H | H | Ph(2,3,4-tri-F) | 465 |
| 430 | Me | Ph(3-OCF$_2$CHF$_2$) | H | H | Ph(2,4-di-F,3-OMe) | 477 |
| 431 | Me | Ph(3-OCF$_2$CHF$_2$) | H | H | Ph(2-CF$_3$) | 479 |
| 433 | Me | Ph(4-Cl) | H | H | Ph(2-F) | 347 |
| 434 | Me | Ph(4-Cl) | H | H | Ph(2,3-di-F) | 365 |
| 435 | Me | Ph(4-Cl) | H | H | Ph(2-S(O)$_2$Me) | 407 |
| 436 | Me | Ph(4-Cl) | H | H | Ph(2,4-di-F) | 365 |
| 437 | Me | Ph(4-F) | H | H | Ph(2-F) | 331 |
| 438 | Me | Ph(4-F) | H | H | Ph(2,3-di-F) | 349 |
| 439 | Me | Ph(4-F) | H | H | Ph(2-S(O)$_2$Me) | 391 |
| 440 | Me | Ph(4-F) | H | H | Ph(2,4-di-F) | 349 |
| 441 | Me | 1,3-benzodioxol-5-yl(2,2-di-F) | H | H | Ph(2-F) | 393 |
| 442 | Me | 1,3-benzodioxol-5-yl(2,2-di-F) | H | H | Ph(2,3-di-F) | 411 |
| 443 | Me | 1,3-benzodioxol-5-yl(2,2-di-F) | H | H | Ph(2-S(O)$_2$Me) | 453 |
| 444 | Me | 1,3-benzodioxol-5-yl(2,2-di-F) | H | H | Ph(2,4-di-F) | 411 |
| 445 | Me | Ph(3-CF$_3$) | H | Ph(2-F) | Ph(2-F) | 518 |
| 456 | Ph | Ph(3-CF$_3$) | H | H | Ph(2-F) | 441* |
| 457 | Ph | Ph(3-CF$_3$) | H | H | Ph(2,3-di-F) | 459* |
| 464 | Me | Ph(3-F,4-Me) | H | H | Ph(2,3-di-F) | 363 |
| 465 | Me | Ph(3-F,4-Me) | H | H | Ph(2-F) | 345 |
| 472 | Me | Ph(2-F,4-CF$_3$) | H | H | Ph(2,3-di-F) | 417 |
| 473 | Me | Ph(2-F,4-CF$_3$) | H | H | Ph(2-S(O)$_2$Me) | 459 |
| 474 | Me | Ph(2-F,4-CF$_3$) | H | H | Ph(2,4-di-F) | 417 |
| 476 | Me | Ph(2-F,4-CF$_3$) | H | H | Ph(2-F) | 399 |
| 477 | allyl(3,3-di-Me) | Ph(3-CF$_3$) | H | H | Ph(2,3-di-F) | 451* |
| 478 | allyl(3,3-di-Me) | Ph(3-CF$_3$) | H | H | Ph(2-F) | 433* |
| 479 | allyl(2-Me) | Ph(3-CF$_3$) | H | H | Ph(2,3-di-F) | 438* |
| 480 | allyl(2-Cl) | Ph(3-CF$_3$) | H | H | Ph(2,3-di-F) | 457* |
| 481 | allyl(2-Me) | Ph(3-CF$_3$) | H | H | Ph(2-F) | 419* |
| 482 | allyl(2-Cl) | Ph(3-CF$_3$) | H | H | Ph(2-F) | 439* |
| 483 | allyl(3-Cl) | Ph(3-CF$_3$) | H | H | Ph(2-F) | 439* |
| 484 | allyl(3-Br) | Ph(3-CF$_3$) | H | H | Ph(2-F) | 485* |
| 485 | allyl(3-Cl) | Ph(3-CF$_3$) | H | H | Ph(2,3-di-F) | 457* |
| 486 | allyl(3-Br) | Ph(3-CF3) | H | H | Ph(2,3-di-F) | 503* |
| 503 | —C(O)Me | Ph(3-CF3) | H | H | Ph(2-F) | |
| 505 | Ph(4-OMe) | Ph(3-CF$_3$) | H | H | Ph(2-F) | 473 |
| 506 | Ph(4-CN) | Ph(3-CF$_3$) | H | H | Ph(2-F) | 406 |
| 511 | allyl(3-Ph) | Ph(3,5-di-F) | H | H | Ph(2,3-di-F) | 469 |
| 512 | allyl(3-Cl) | Ph(3,5-di-F) | H | H | Ph(2,3-di-F) | 427 |
| 520 | Me | Ph(3-Br) | H | H | Ph(2,3-di-F) | 409 |
| 523 | Me | Ph(3-OCHF$_2$) | H | H | Ph(2-S(O)$_2$Me) | 439 |
| 524 | 1-c-hexen-3-yl | Ph(3-CF$_3$) | H | H | Ph(2-F) | 445* |
| 525 | 1-c-hexen-3-yl | Ph(3-CF$_3$) | H | H | Ph(2,3-di-F) | 463* |
| 526 | allyl(3-Br)r | Ph(3-CF$_3$) | H | H | Ph(2-F) | 485* |
| 527 | allyl(3-Br)r | Ph(3-CF$_3$) | H | H | Ph(2,3-di-F) | 503* |
| 528 | Me | Ph(3-F,4-Me) | H | H | Ph(2,4-di-F) | 363 |
| 529 | Me | Ph(3-F,4-Me) | H | H | Ph(2,3,4-tri-F) | 381 |
| 530 | Me | Ph(3-F,4-Me) | H | H | Ph(2-S(O)$_2$Me) | 405 |
| 531 | Me | Ph(3-F,4-Me) | H | H | Ph(2-CF$_3$) | 395 |
| 539 | Me | Ph(3-OCF$_2$CHF$_2$) | H | H | Ph(2-F) | 429 |
| 547 | Me | Ph(2,6-di-F) | H | H | Ph(2,3-di-F) | 367 |
| 558 | Me | Ph(2-F,4-Me) | H | H | Ph(2-S(O)$_2$Me) | 405 |
| 559 | Me | Ph(2-F,4-Me) | H | H | Ph(2,4-di-F) | 363 |
| 560 | Me | Ph(2-F,4-Me) | H | H | Ph(2-F) | 345 |
| 562 | Me | Ph(4-OCHF$_2$) | H | H | Ph(2,3-di-F) | 397 |
| 563 | Me | Ph(4-Br) | H | H | Ph(2-F) | 391 |
| 564 | Me | Ph(4-Br) | H | H | Ph(2,3-di-F) | 409 |
| 565 | Me | Ph(4-Br) | H | H | Ph(2-S(O)$_2$Me) | 451 |
| 566 | Me | Ph(4-Br) | H | H | Ph(2,4-di-F) | 409 |
| 567 | Me | Ph(3-Et) | H | H | Ph(2-F) | 341 |
| 568 | Me | Ph(3-Et) | H | H | Ph(2,3-di-F) | 359 |
| 569 | Me | Ph(3-Et) | H | H | Ph(2-S(O)$_2$Me) | 401 |
| 570 | Me | Ph(3-Et) | H | H | Ph(2,4-di-F) | 359 |
| 571 | Me | Ph(3-CF$_3$) | H | H | Ph(2,4-di-F) | 399 |
| 572 | Me | Ph(3-CF$_3$) | H | H | Ph(2-NO$_2$) | 408 |
| 573 | Me | Ph(3-CF$_3$) | H | H | Ph(3-F,2-Me) | 395 |
| 574 | Me | Ph(3-CF$_3$) | H | H | Ph(2-F,3-Cl) | 415 |

INDEX TABLE B-continued

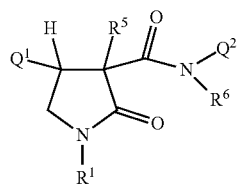

| Cmpd No. | R¹ | Q¹ | R⁵ | R⁶ | Q² | M + 1 |
|---|---|---|---|---|---|---|
| 575 | Me | Ph(3-CF$_3$) | H | H | Ph(4-F,2-Me) | 395 |
| 576 | Me | Ph(3-CF$_3$) | H | H | Ph(2-F,3-CN) | 406 |
| 577 | Me | Ph(3-CF$_3$) | H | H | Ph | 363 |
| 585 | Me | thiophen-2-yl(5-Me) | H | H | Ph(2-F) | 332 |
| 586 | Me | thiophen-2-yl(5-Me) | H | H | Ph(2,3-di-F) | 351 |
| 596 | Me | Ph(3,4-di-F) | H | H | Ph(2-F) | ** |
| 602 | Ph(4-NO$_2$) | Ph(3-CF$_3$) | H | H | Ph(2-F) | 488 |
| 605 | allyl | Ph(3-CF$_3$) | H | H | Ph(2-F) | 407 |
| 606 | allyl | Ph(3-CF$_3$) | H | H | Ph(2,3-di-F) | 425 |
| 607 | —CH$_2$C≡CH | Ph(3-CF$_3$) | H | H | Ph(2-F) | 405 |
| 611 | Me | Ph(4-F,3-CF$_3$) | H | H | Ph(2-F) | 399 |
| 612 | Me | Ph(4-F,3-CF$_3$) | H | H | Ph(2-S(O)$_2$Me) | 459 |
| 613 | Me | Ph(4-F,3-CF$_3$) | H | H | Ph(2,3-di-F) | 417 |
| 616 | Me | Ph(3-OCHF$_2$) | H | H | Ph(2,3-di-F) | 395* |
| 617 | Me | Ph(3-OCHF$_2$) | H | H | Ph(2,4-di-F) | 397 |
| 618 | Me | Ph(3-OCHF$_2$) | H | H | Ph(2-F) | 379 |
| 619 | Me | Ph(3-OCHF$_2$) | Me | H | Ph(2,3-di-F) | 411 |
| 622 | Me | Ph(4-CF$_3$) | H | H | Ph(2-F) | 381 |
| 623 | Me | Ph(4-CF$_3$) | H | H | Ph(2,3-di-F) | 399 |
| 624 | Me | Ph(4-CF$_3$) | H | H | Ph(2-S(O)$_2$Me) | 441 |
| 625 | Me | Ph(4-CF$_3$) | H | H | Ph(2,4-di-F) | 399 |
| 631 | H | Ph(3-O-allyl) | allyl | H | Ph(2,3-di-F) | 411* |
| 632 | Me | Ph(3-F) | H | H | Ph(2,3-di-F) | 349 |
| 633 | Me | Ph(3-F) | H | H | Ph(2,4-di-F) | 349 |
| 636 | Me | Ph(3-CF$_3$) | H | H | Ph(2,3-di-F) | 399 |
| 637 | Me | Ph(3-CF$_3$) | H | H | Ph(2-S(O)$_2$Me) | 441 |
| 638 | Me | Ph(3-CF$_3$) | H | H | Ph(2-CF$_3$) | 431 |
| 639 | Me | Ph(3,4-di-F) | H | H | Ph(2,3-di-F) | 367 |
| 640 | Me | Ph(3,4-di-F) | H | H | Ph(2-S(O)$_2$Me) | 409 |
| 641 | Me | Ph(3,4-di-F) | H | H | Ph(2-CF$_3$) | 399 |
| 643 | Me | Ph(3,5-di-F) | H | H | Ph(2-F) | 349 |
| 644 | Me | Ph(3,5-di-F) | H | H | Ph(2,3-di-F) | 367 |
| 645 | Me | Ph(3,5-di-F) | H | H | Ph(2,4-di-F) | 367 |
| 646 | Me | Ph(3,5-di-F) | H | H | Ph(2,3,4-tri-F) | 385 |
| 647 | Me | Ph(3,5-di-F) | H | H | Ph(2-CF$_3$) | 399 |
| 650 | Me | Ph(3-O-i-Pr) | H | H | Ph(2-F) | 371 |
| 651 | Me | Ph(3-O-i-Pr) | H | H | Ph(2,3-di-F) | 390 |
| 652 | Me | Ph(3-O-i-Pr) | H | H | Ph(2-CF$_3$) | 422 |
| 653 | Me | Ph(3-O-i-Pr) | H | H | Ph(2-S(O)$_2$Me) | 432 |
| 659 | Me | Ph(3,5-di-F) | H | H | Inden(2,3-dihydro)-4-yl | 371 |
| 660 | Me | Ph(3,5-di-F) | H | H | Naph(5,6,7,8-tetrahydro)-1-yl | 385 |
| 661 | Me | Ph(4-Me) | H | H | Ph(2-F) | 327 |
| 662 | Me | Ph(4-Me) | H | H | Ph(2,3-di-F) | 345 |
| 663 | Me | Ph(4-Me) | H | H | Ph(2-S(O)$_2$Me) | 387 |
| 664 | Me | Ph(4-Me) | H | H | Ph(2,4-di-F) | 345 |
| 665 | Me | Ph(4-Me) | H | H | Ph(2-CF$_3$) | 377 |
| 666 | Me | Ph(3-Me) | H | H | Ph(2-F) | 327 |
| 667 | Me | Ph(3-Me) | H | H | Ph(2,3-di-F) | 345 |
| 668 | Me | Ph(3-Me) | H | H | Ph(2-S(O)$_2$Me) | 387 |
| 682 | —CH$_2$-c-Pr | Ph(3-CF$_3$) | H | H | Ph(2-F) | 422 |
| 683 | —CH$_2$-c-Pr | Ph(3-CF$_3$) | H | H | Ph(2,3-di-F) | 440 |
| 684 | c-Pr | Ph(3-CF$_3$) | H | H | Ph(2-F) | 408 |
| 685 | c-Pr | Ph(3-CF$_3$) | H | H | Ph(2,3-di-F) | 426 |
| 690 | Me | Ph(4-CF$_2$CH$_3$) | H | H | Ph(2,3-di-F) | 395 |
| 691 | Me | Ph(4-CF$_2$CH$_3$) | H | H | Ph(2-F) | 377 |
| 692 | Me | Ph(4-CF$_2$CH$_3$) | H | H | Ph(2-S(O)$_2$Me) | 437 |
| 693 | Me | Ph(4-CF$_2$CH$_3$) | H | H | Ph(2,4-di-F) | 395 |
| 694 | Me | Ph(3-CF$_3$) | Et | H | Ph(2,3-di-F) | 427 |
| 713 | H | Ph(3,4-di-F) | H | acn | Ph(2-NO$_2$) | |

*M − 1. M.P. = 116-120° C. *M.P. = 183-186° C.

INDEX TABLE C
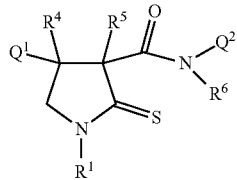
| Cmpd. No. | R[1] | Q[1] | R[4] | R[5] | R[6] | Q[2] | m.p. (° C.) |
|---|---|---|---|---|---|---|---|
| 454 | H | Ph(3-CF$_3$) | H | H | H | Ph(2,3-di-F) | 162-166 |
INDEX TABLE D
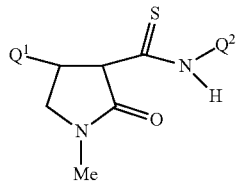
| Cmpd. No. | Q[1] | Q[2] | m.p. (° C.) |
|---|---|---|---|
| 450 | Ph(4-CF$_3$) | Ph(2-F) | 109-112 |
| 471 | Ph | Ph(2-F) | |
INDEX TABLE E
| Ex # | Structure |
|---|---|
| 717 | |
| 718 | |
| 719 | |
| 720 | 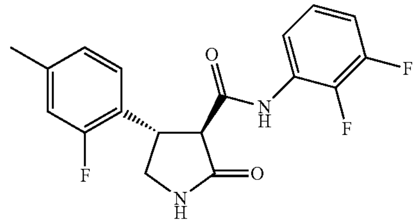 [SMILES: Cc1ccc([C@H]2CNC(=O)[C@@H]2C(=O)Nc2cccc(F)c2F)c(F)c1] |
| 721 | 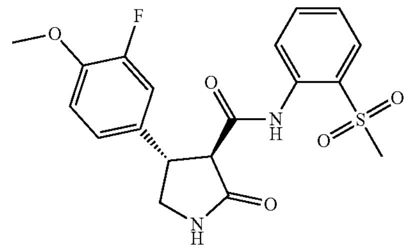 [SMILES: COc1ccc([C@H]2CNC(=O)[C@@H]2C(=O)Nc2ccccc2S(C)(=O)=O)cc1F] |
| 722 | 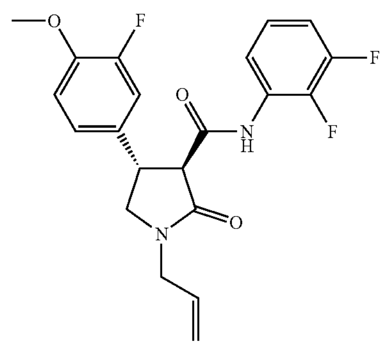 [SMILES: C=CCN1C[C@H](c2ccc(OC)c(F)c2)[C@@H](C(=O)Nc2cccc(F)c2F)C1=O] |
| 723 | 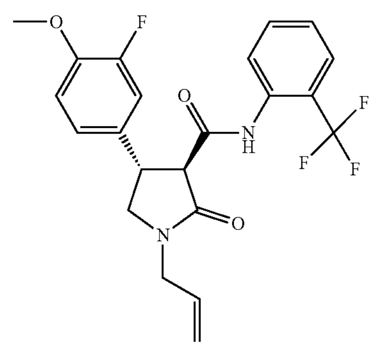 [SMILES: C=CCN1C[C@H](c2ccc(OC)c(F)c2)[C@@H](C(=O)Nc2ccccc2C(F)(F)F)C1=O] |
| 724 | 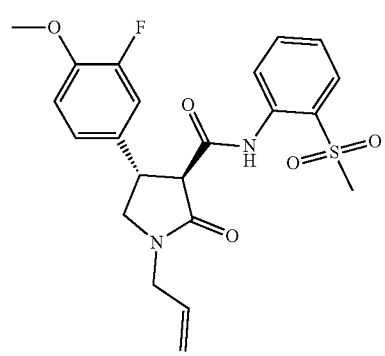 [SMILES: C=CCN1C[C@H](c2ccc(OC)c(F)c2)[C@@H](C(=O)Nc2ccccc2S(C)(=O)=O)C1=O] |

INDEX TABLE E-continued

| Ex # | Structure |
|------|-----------|
| 725 | 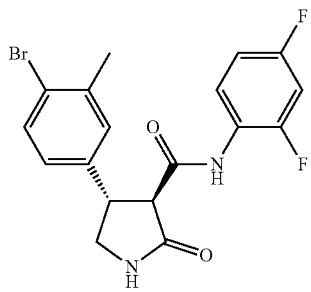 |
| 726 | 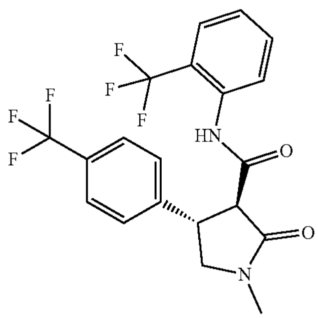 [SMILES: CN1C[C@H](c2ccc(C(F)(F)F)cc2)[C@@H](C(=O)Nc2ccccc2C(F)(F)F)C1=O] |
| 727 | 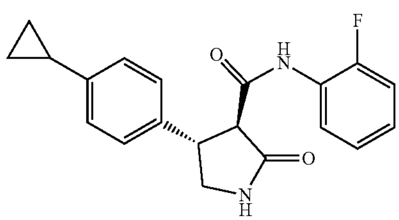 [SMILES: O=C1NC[C@H](c2ccc(C3CC3)cc2)[C@H]1C(=O)Nc1ccccc1F] |
| 728 | 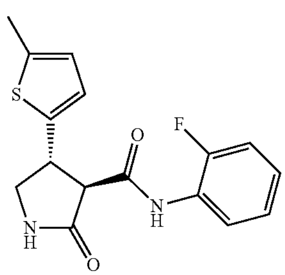 [SMILES: Cc1ccc([C@H]2CNC(=O)[C@@H]2C(=O)Nc2ccccc2F)s1] |
| 729 | 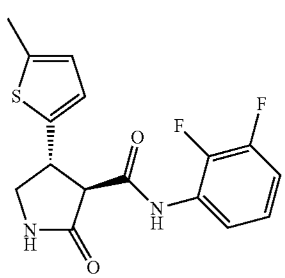 [SMILES: Cc1ccc([C@H]2CNC(=O)[C@@H]2C(=O)Nc2cccc(F)c2F)s1] |

INDEX TABLE E-continued

| Ex # | Structure |
|------|-----------|
| 730 | 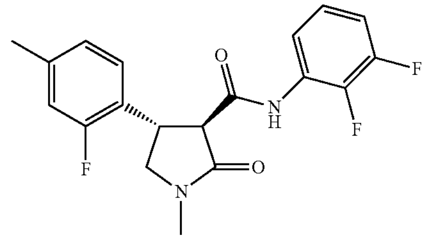 [SMILES: Cc1ccc([C@H]2CN(C)C(=O)[C@@H]2C(=O)Nc2cccc(F)c2F)c(F)c1] |
| 731 | 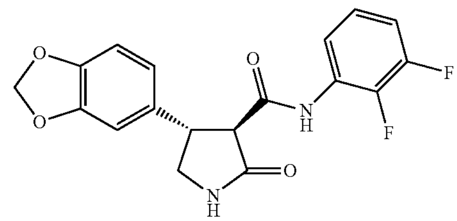 [SMILES: O=C1NC[C@H](c2ccc3c(c2)OCO3)[C@H]1C(=O)Nc1cccc(F)c1F] |
| 732 | 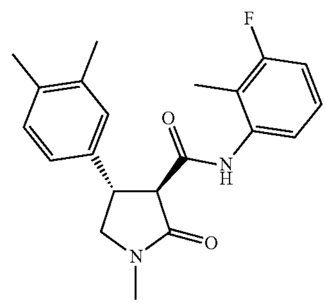 [SMILES: Cc1ccc([C@H]2CN(C)C(=O)[C@@H]2C(=O)Nc2cccc(F)c2C)cc1C] |
| 733 | 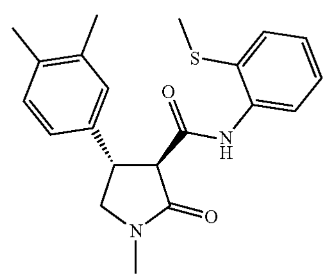 [SMILES: CSc1ccccc1NC(=O)[C@H]1C(=O)N(C)C[C@@H]1c1ccc(C)c(C)c1] |
| 734 | 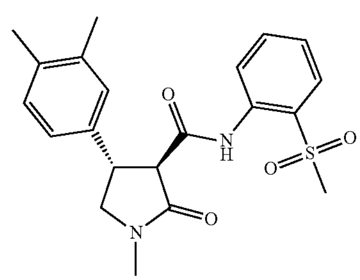 [SMILES: Cc1ccc([C@H]2CN(C)C(=O)[C@@H]2C(=O)Nc2ccccc2S(C)(=O)=O)cc1C] |

INDEX TABLE E-continued

| Ex # | Structure |
|---|---|
| 735 | (3,5-diethylphenyl)-N-(2-fluorophenyl)-1-methyl-2-oxopyrrolidine-3-carboxamide |
| 736 | (3,5-diethylphenyl)-N-(2,3-difluorophenyl)-1-methyl-2-oxopyrrolidine-3-carboxamide |
| 737 | (3,5-diethylphenyl)-1-methyl-2-oxo-N-(2-(trifluoromethyl)phenyl)pyrrolidine-3-carboxamide |
| 738 | (3,5-difluorophenyl)-1-methyl-N-(2-(methylthio)phenyl)-2-oxopyrrolidine-3-carboxamide |
| 739 | (3,5-difluorophenyl)-1-methyl-N-(2-(methylsulfonyl)phenyl)-2-oxopyrrolidine-3-carboxamide |
| 740 | 4-(4-fluoro-3-(1,1,2,2-tetrafluoroethoxy)phenyl)-N-(2-fluorophenyl)-1-methyl-2-oxopyrrolidine-3-carboxamide |
| 741 | N-(2,3-difluorophenyl)-2-oxo-4-(2-(trifluoromethyl)pyrimidin-5-yl)pyrrolidine-3-carboxamide |
| 742 | 4-(2,3-dihydro-1H-inden-5-yl)-N-(2-fluorophenyl)-1-methyl-2-oxopyrrolidine-3-carboxamide |
| 743 | N-(2,3-difluorophenyl)-4-(2,3-dihydro-1H-inden-5-yl)-1-methyl-2-oxopyrrolidine-3-carboxamide |
| 744 | 4-(2,3-dihydro-1H-inden-5-yl)-1-methyl-N-(2-(methylsulfonyl)phenyl)-2-oxopyrrolidine-3-carboxamide |
| 745 | N-(2,3,4-trifluorophenyl)-1-methyl-2-oxo-4-(4-(trifluoromethyl)phenyl)pyrrolidine-3-carboxamide |

INDEX TABLE E-continued

| Ex # | Structure |
|------|-----------|
| 746 | 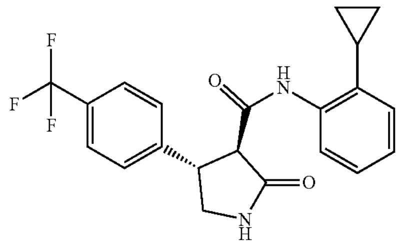 [SMILES: O=C1NC[C@H](c2ccc(C(F)(F)F)cc2)[C@H]1C(=O)Nc1ccccc1C1CC1] |
| 747 | 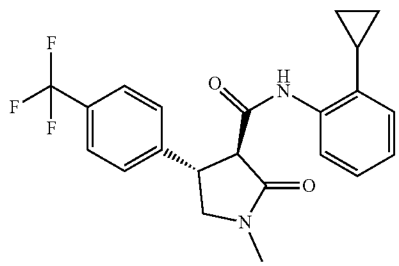 [SMILES: CN1C[C@H](c2ccc(C(F)(F)F)cc2)[C@@H](C(=O)Nc2ccccc2C2CC2)C1=O] |
| 748 | 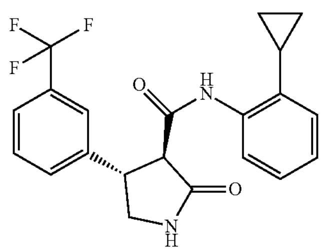 [SMILES: O=C1NC[C@H](c2cccc(C(F)(F)F)c2)[C@H]1C(=O)Nc1ccccc1C1CC1] |
| 749 | 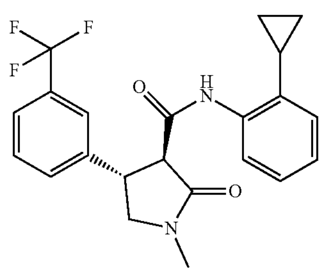 [SMILES: CN1C[C@H](c2cccc(C(F)(F)F)c2)[C@@H](C(=O)Nc2ccccc2C2CC2)C1=O] |
| 750 | 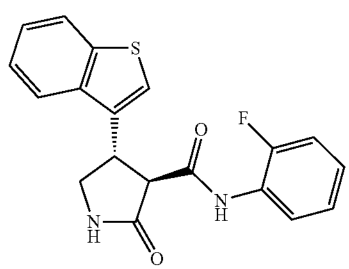 [SMILES: O=C1NC[C@H](c2csc3ccccc23)[C@H]1C(=O)Nc1ccccc1F] |
| 751 | 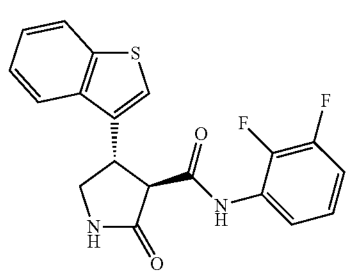 [SMILES: O=C1NC[C@H](c2csc3ccccc23)[C@H]1C(=O)Nc1cccc(F)c1F] |
| 752 | |
| 753 | |
| 754 | |
| 755 | |
| 756 | |
| 757 | |

INDEX TABLE E-continued

| Ex # | Structure |
|---|---|
| 758 | |
| 759 | |
| 760 | |
| 761 | |
| 762 | |
| 763 | 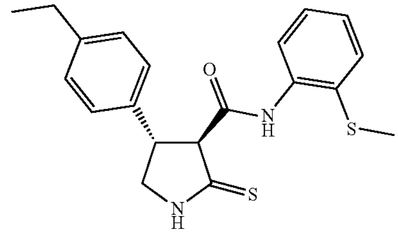 [SMILES: CCc1ccc([C@H]2CNC(=S)[C@@H]2C(=O)Nc2ccccc2SC)cc1] |
| 764 | 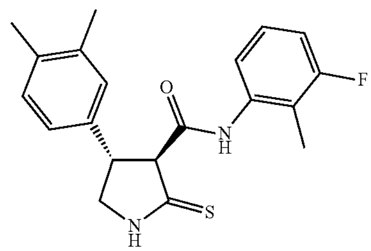 [SMILES: Cc1ccc([C@H]2CNC(=S)[C@@H]2C(=O)Nc2cccc(F)c2F)cc1C] |
| 765 | 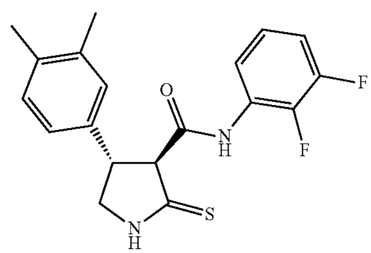 |
| 766 | 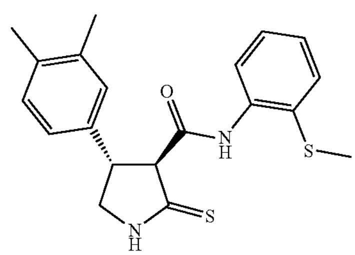 |
| 767 | 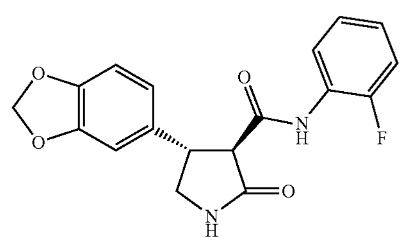 [SMILES: O=C1NC[C@H](c2ccc3c(c2)OCO3)[C@H]1C(=O)Nc1ccccc1F] |
| 768 | 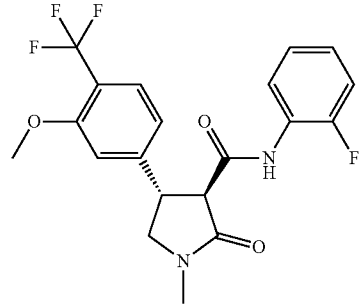 [SMILES: COc1cc([C@H]2CN(C)C(=O)[C@@H]2C(=O)Nc2ccccc2F)ccc1C(F)(F)F] |

INDEX TABLE E-continued

| Ex # | Structure |
|---|---|
| 769 | 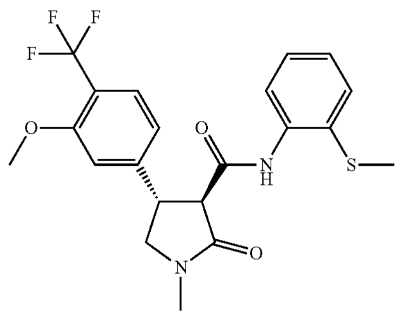 |
| 770 | 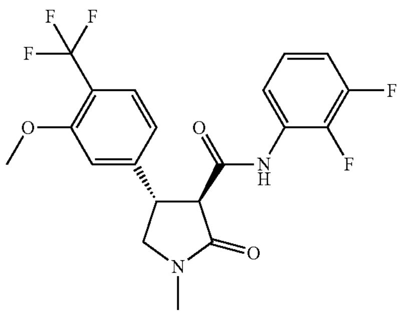 [SMILES: COc1cc([C@H]2CN(C)C(=O)[C@@H]2C(=O)Nc2cccc(F)c2F)ccc1C(F)(F)F] |
| 771 | 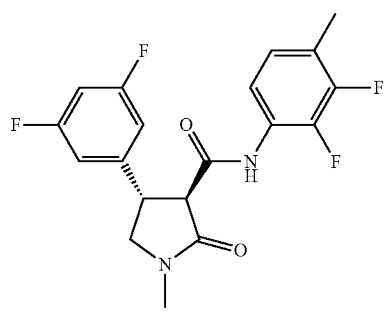 [SMILES: Cc1ccc(NC(=O)[C@H]2C(=O)N(C)C[C@@H]2c2cc(F)cc(F)c2)c(F)c1F] |
| 772 | 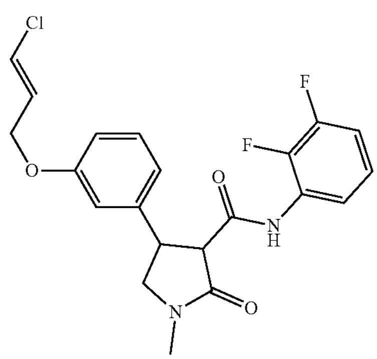 [SMILES: CN1CC(c2cccc(OC/C=C/Cl)c2)C(C(=O)Nc2cccc(F)c2F)C1=O] |
| 773 | 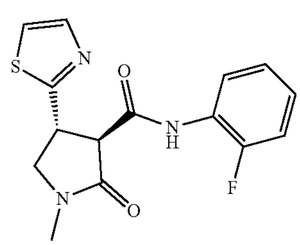 [SMILES: CN1C[C@H](c2nccs2)[C@@H](C(=O)Nc2ccccc2F)C1=O] |
| 774 | |
| 775 | AND Enantiomer |
| 776 | AND Enantiomer |
| 777 | AND Enantiomer |
| 778 | |

INDEX TABLE E-continued

| Ex # | Structure |
|---|---|
| 779 | 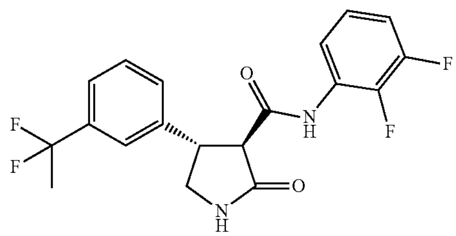 [SMILES: CC(F)(F)c1cccc([C@H]2CNC(=O)[C@@H]2C(=O)Nc2cccc(F)c2F)c1] |
| 780 | 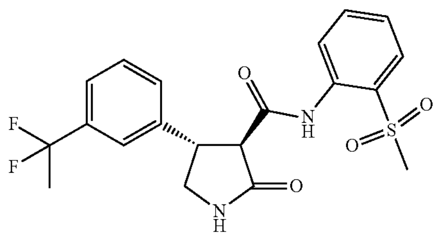 [SMILES: CC(F)(F)c1cccc([C@H]2CNC(=O)[C@@H]2C(=O)Nc2ccccc2S(C)(=O)=O)c1] |
| 781 | 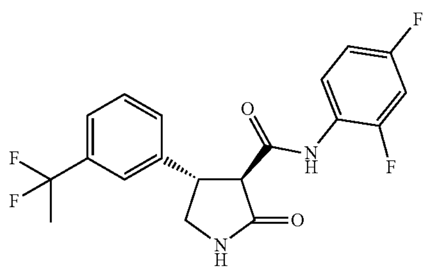 [SMILES: CC(F)(F)c1cccc([C@H]2CNC(=O)[C@@H]2C(=O)Nc2ccc(F)cc2F)c1] |
| 782 | 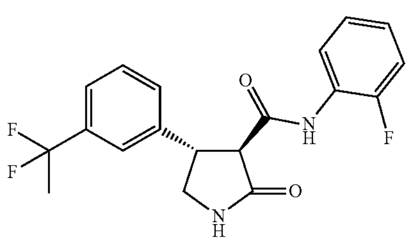 [SMILES: CC(F)(F)c1cccc([C@H]2CNC(=O)[C@@H]2C(=O)Nc2ccccc2F)c1] |
| 783 | 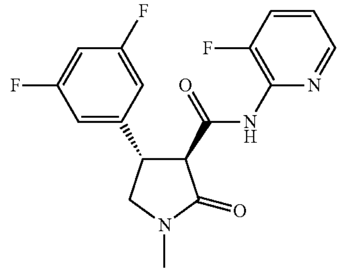 [SMILES: CN1C[C@H](c2cc(F)cc(F)c2)[C@@H](C(=O)Nc2ncccc2F)C1=O] |

INDEX TABLE E-continued

| Ex # | Structure |
|---|---|
| 784 | 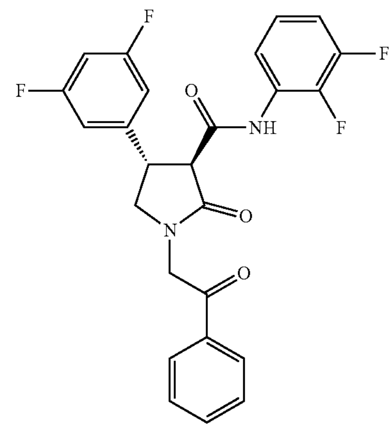 [SMILES: O=C(CN1C[C@H](c2cc(F)cc(F)c2)[C@@H](C(=O)Nc2cccc(F)c2F)C1=O)c1ccccc1] |
| 785 | 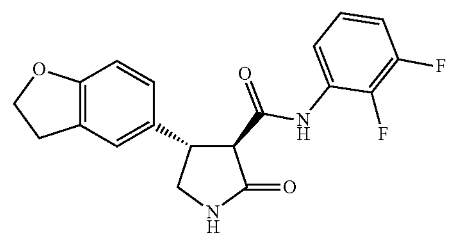 [SMILES: O=C1NC[C@H](c2ccc3c(c2)CCO3)[C@H]1C(=O)Nc1cccc(F)c1F] |
| 786 | 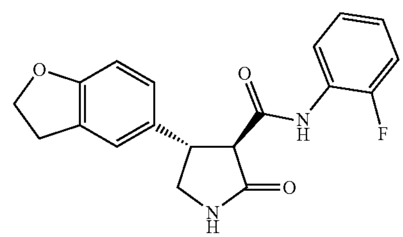 [SMILES: O=C1NC[C@H](c2ccc3c(c2)CCO3)[C@H]1C(=O)Nc1ccccc1F] |
| 787 | 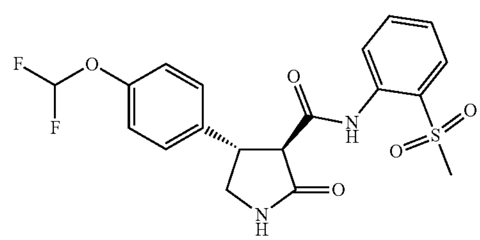 [SMILES: CS(=O)(=O)c1ccccc1NC(=O)[C@H]1C(=O)NC[C@@H]1c1ccc(OC(F)F)cc1] |
| 788 | 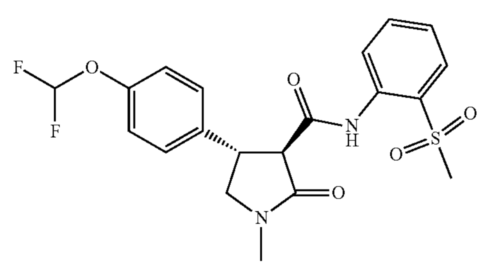 [SMILES: CN1C[C@H](c2ccc(OC(F)F)cc2)[C@@H](C(=O)Nc2ccccc2S(C)(=O)=O)C1=O] |

INDEX TABLE E-continued

| Ex # | Structure |
|------|-----------|
| 789 | 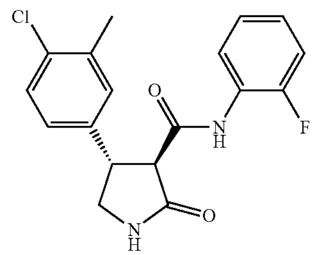 [SMILES: Cc1cc([C@H]2CNC(=O)[C@@H]2C(=O)Nc2ccccc2F)ccc1Cl] |
| 790 | 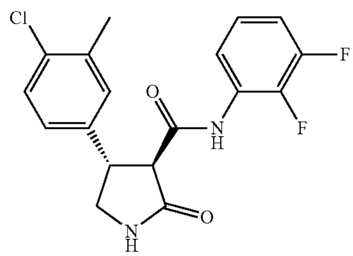 [SMILES: Cc1cc([C@H]2CNC(=O)[C@@H]2C(=O)Nc2cccc(F)c2F)ccc1Cl] |
| 791 | 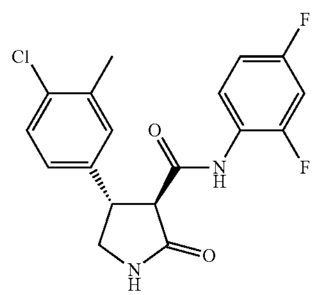 [SMILES: Cc1cc([C@H]2CNC(=O)[C@@H]2C(=O)Nc2ccc(F)cc2F)ccc1Cl] |
| 792 | 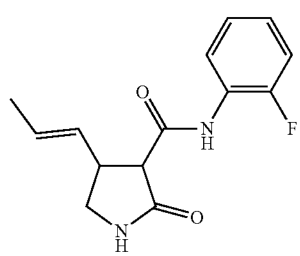 [SMILES: C/C=C/C1CNC(=O)C1C(=O)Nc1ccccc1F] |
| 793 | 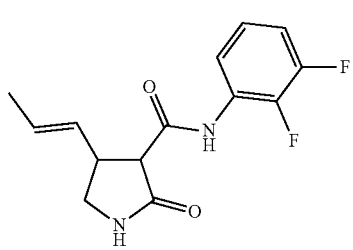 [SMILES: C/C=C/C1CNC(=O)C1C(=O)Nc1cccc(F)c1F] |
| 794 | 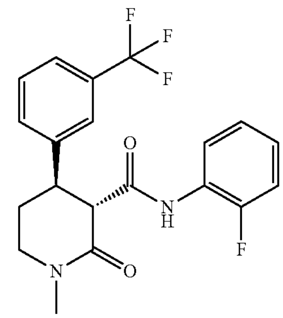 [SMILES: CN1CC[C@@H](c2cccc(C(F)(F)F)c2)[C@H](C(=O)Nc2ccccc2F)C1=O] |
| 795 | 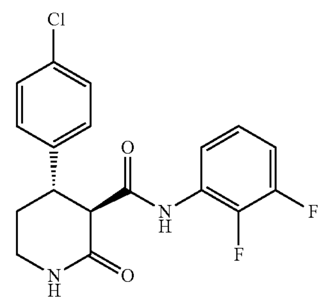 [SMILES: O=C1NCC[C@H](c2ccc(Cl)cc2)[C@H]1C(=O)Nc1cccc(F)c1F] |
| 796 | 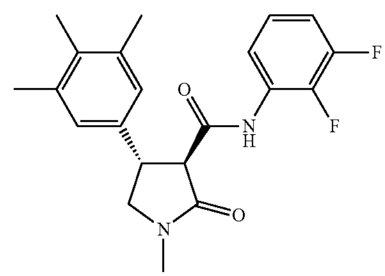 [SMILES: Cc1cc([C@H]2CN(C)C(=O)[C@@H]2C(=O)Nc2cccc(F)c2F)cc(C)c1C] |
| 797 | 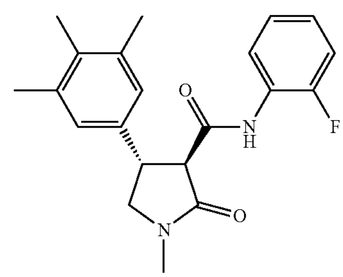 [SMILES: Cc1cc([C@H]2CN(C)C(=O)[C@@H]2C(=O)Nc2ccccc2F)cc(C)c1C] |
| 798 | 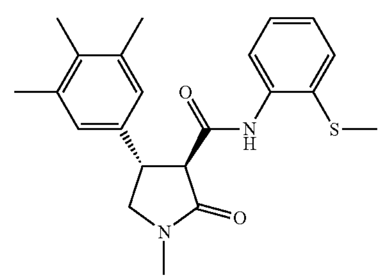 |

INDEX TABLE E-continued

| Ex # | Structure |
|---|---|
| 799 | 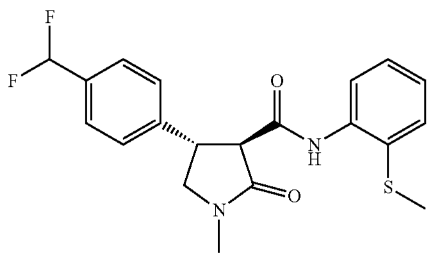 [SMILES: CSc1ccccc1NC(=O)[C@H]1C(=O)N(C)C[C@@H]1c1ccc(C(F)F)cc1] |
| 800 | 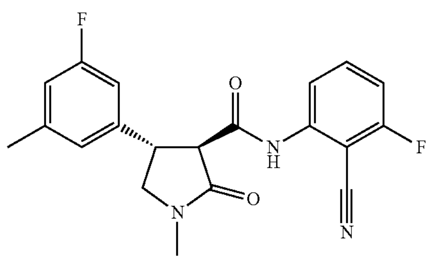 [SMILES: Cc1cc(F)cc([C@H]2CN(C)C(=O)[C@@H]2C(=O)Nc2cccc(F)c2C#N)c1] |
| 801 | 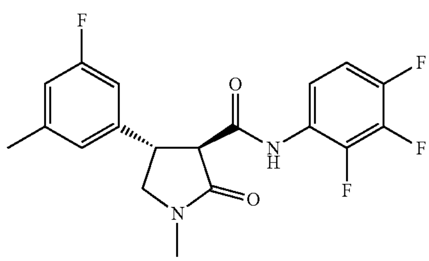 [SMILES: Cc1cc(F)cc([C@H]2CN(C)C(=O)[C@@H]2C(=O)Nc2ccc(F)c(F)c2F)c1] |
| 802 | 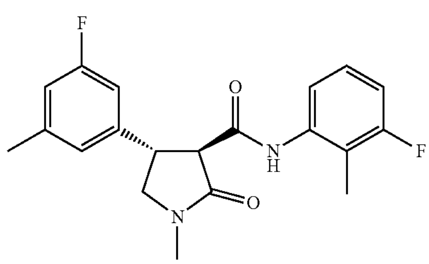 [SMILES: Cc1cc(F)cc([C@H]2CN(C)C(=O)[C@@H]2C(=O)Nc2cccc(F)c2C)c1] |
| 803 | 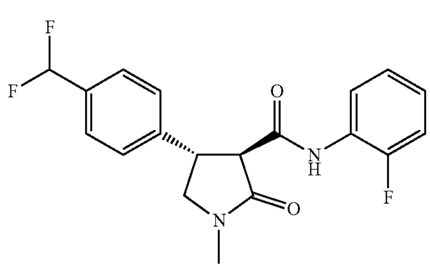 [SMILES: CN1C[C@H](c2ccc(C(F)F)cc2)[C@@H](C(=O)Nc2ccccc2F)C1=O] |
| 804 | 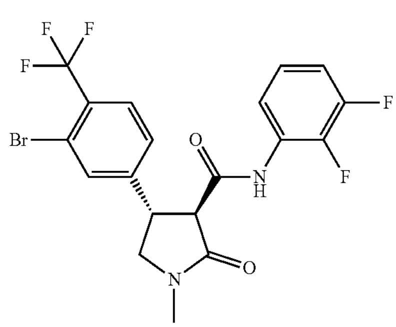 [SMILES: CN1C[C@H](c2ccc(C(F)(F)F)c(Br)c2)[C@@H](C(=O)Nc2cccc(F)c2F)C1=O] |
| 805 | |
| 806 | |
| 807 | |
| 808 | |
| 809 | |

INDEX TABLE E-continued
| Ex # | Structure |
|---|---|
| 810 | 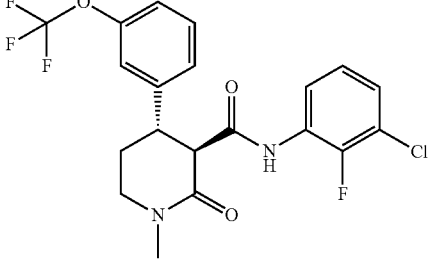 |
| 811 | 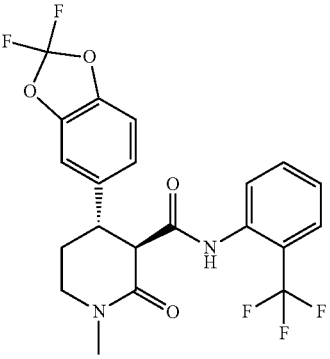 [SMILES: CN1CC[C@H](c2ccc3c(c2)OC(F)(F)O3)[C@@H](C(=O)Nc2ccccc2C(F)(F)F)C1=O] |
| 812 | 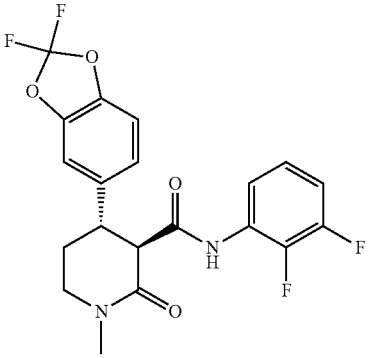 [SMILES: CN1CC[C@H](c2ccc3c(c2)OC(F)(F)O3)[C@@H](C(=O)Nc2cccc(F)c2F)C1=O] |
| 813 | 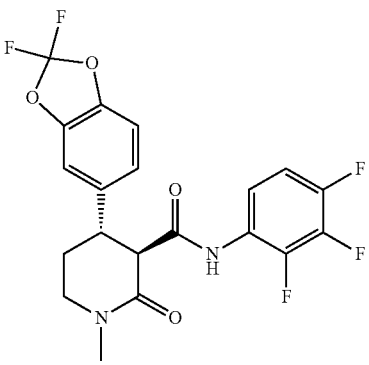 [SMILES: CN1CC[C@H](c2ccc3c(c2)OC(F)(F)O3)[C@@H](C(=O)Nc2ccc(F)c(F)c2F)C1=O] |
INDEX TABLE E-continued
| Ex # | Structure |
|---|---|
| 814 | 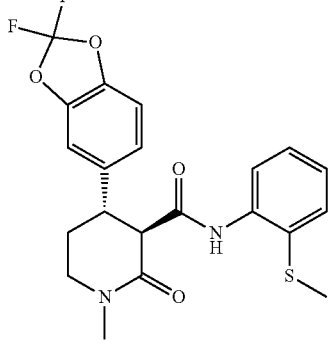 |
| 815 | 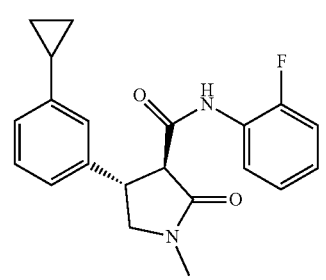 [SMILES: CN1C[C@H](c2cccc(C3CC3)c2)[C@@H](C(=O)Nc2ccccc2F)C1=O] |
| 816 | 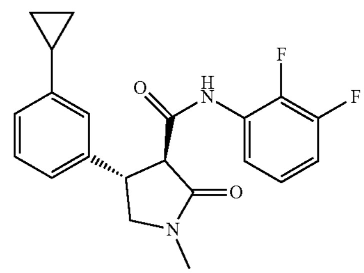 [SMILES: CN1C[C@H](c2cccc(C3CC3)c2)[C@@H](C(=O)Nc2cccc(F)c2F)C1=O] |
| 817 | 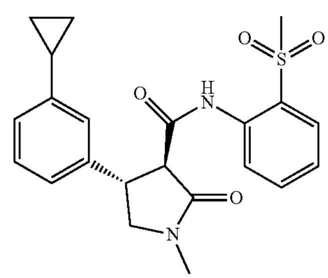 [SMILES: CN1C[C@H](c2cccc(C3CC3)c2)[C@@H](C(=O)Nc2ccccc2S(C)(=O)=O)C1=O] |
| 818 | 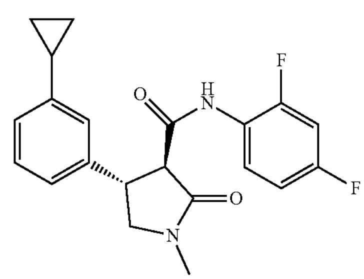 [SMILES: CN1C[C@H](c2cccc(C3CC3)c2)[C@@H](C(=O)Nc2ccc(F)cc2F)C1=O] |

INDEX TABLE E-continued

| Ex # | Structure |
|------|-----------|
| 819  | 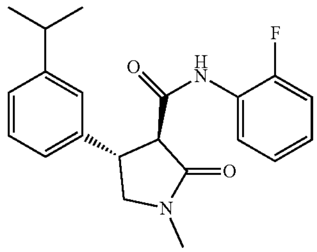 [SMILES: CC(C)c1cccc([C@H]2CN(C)C(=O)[C@@H]2C(=O)Nc2ccccc2F)c1]          |
| 820  | 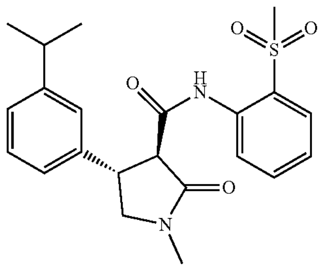 [SMILES: CC(C)c1cccc([C@H]2CN(C)C(=O)[C@@H]2C(=O)Nc2ccccc2S(C)(=O)=O)c1]          |
| 821  | 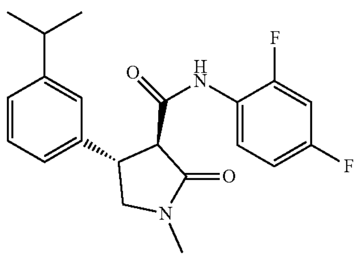 [SMILES: CC(C)c1cccc([C@H]2CN(C)C(=O)[C@@H]2C(=O)Nc2ccc(F)cc2F)c1]          |
| 822  | 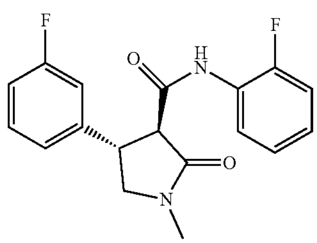 [SMILES: CN1C[C@H](c2cccc(F)c2)[C@@H](C(=O)Nc2ccccc2F)C1=O]          |
| 823  | 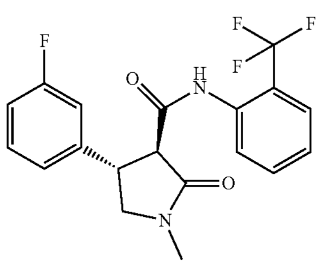 [SMILES: CN1C[C@H](c2cccc(F)c2)[C@@H](C(=O)Nc2ccccc2C(F)(F)F)C1=O]          |
| 824  | 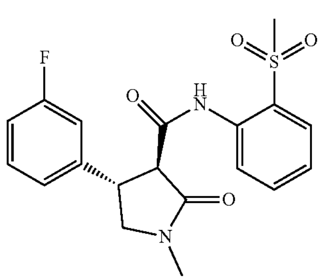 [SMILES: CN1C[C@H](c2cccc(F)c2)[C@@H](C(=O)Nc2ccccc2S(C)(=O)=O)C1=O]          |
| 825  |           |
| 826  |           |
| 827  |           |
| 828  |           |
| 829  |           |

INDEX TABLE E-continued

| Ex # | Structure |
|---|---|
| 830 | (structure) |
| 831 | (structure) |
| 832 | (structure) |
| 833 | (structure) |
| 834 | (structure) |
| 835 | (structure) |
| 836 | (structure) |
| 837 | (structure) |
| 838 | (structure) |
| 839 | (structure) |
| 840 | (structure) |

INDEX TABLE E-continued
| Ex # | Structure |
|---|---|
| 841 | 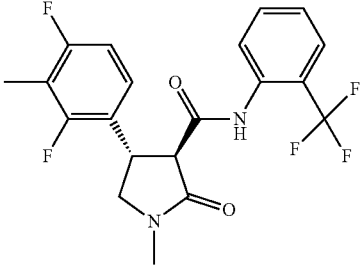 [SMILES: Cc1c(F)ccc([C@H]2CN(C)C(=O)[C@@H]2C(=O)Nc2ccccc2C(F)(F)F)c1F] |
| 842 | 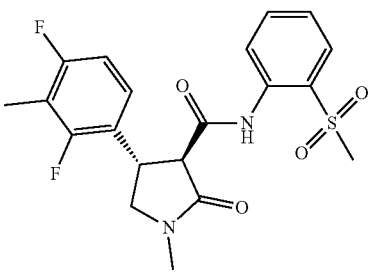 [SMILES: Cc1c(F)ccc([C@H]2CN(C)C(=O)[C@@H]2C(=O)Nc2ccccc2S(C)(=O)=O)c1F] |
| 843 | 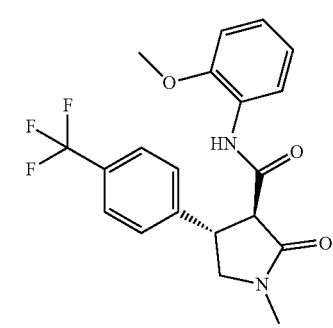 [SMILES: COc1ccccc1NC(=O)[C@H]1C(=O)N(C)C[C@@H]1c1ccc(C(F)(F)F)cc1] |
| 844 | 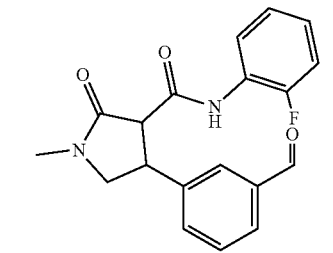 [SMILES: CN1CC(c2cccc(C=O)c2)C(C(=O)Nc2ccccc2F)C1=O] |
| 845 | 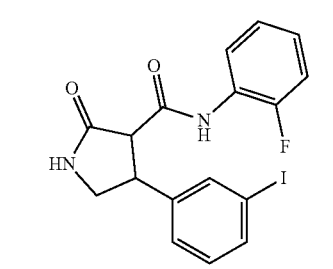 [SMILES: O=C1NCC(c2cccc(I)c2)C1C(=O)Nc1ccccc1F] |
| 846 | 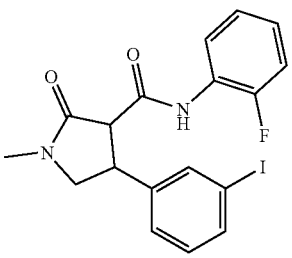 [SMILES: CN1CC(c2cccc(I)c2)C(C(=O)Nc2ccccc2F)C1=O] |
| 847 | 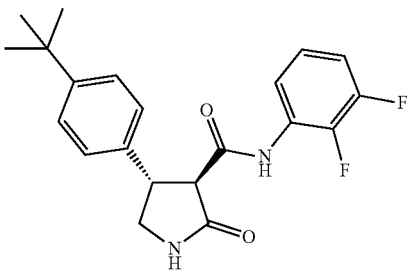 [SMILES: CC(C)(C)c1ccc([C@H]2CNC(=O)[C@@H]2C(=O)Nc2cccc(F)c2F)cc1] |
| 848 | 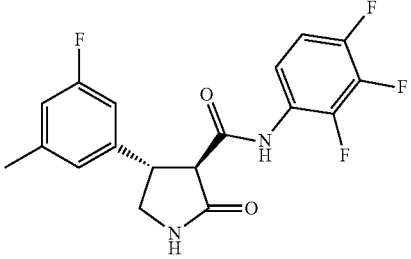 [SMILES: Cc1cc(F)cc([C@H]2CNC(=O)[C@@H]2C(=O)Nc2ccc(F)c(F)c2F)c1] |
| 849 | 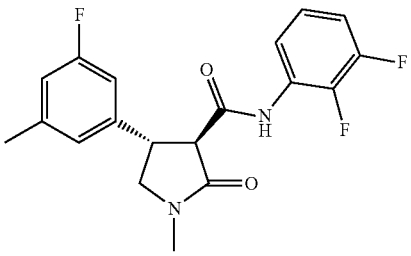 [SMILES: Cc1cc(F)cc([C@H]2CN(C)C(=O)[C@@H]2C(=O)Nc2cccc(F)c2F)c1] |
| 850 | 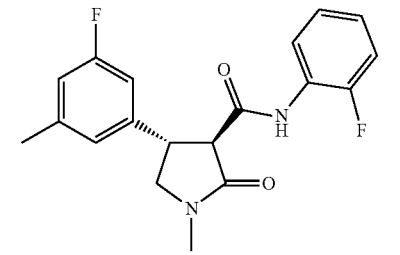 [SMILES: Cc1cc(F)cc([C@H]2CN(C)C(=O)[C@@H]2C(=O)Nc2ccccc2F)c1] |
| 851 | 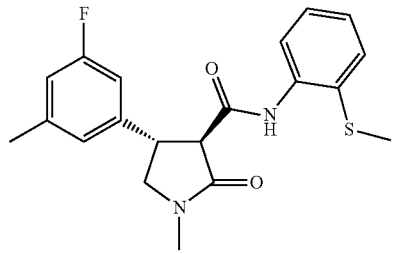 |

INDEX TABLE E-continued

| Ex # | Structure |
|---|---|
| 852 | 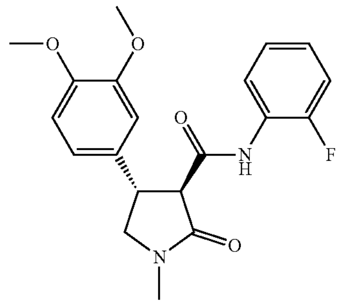 [SMILES: COc1ccc([C@H]2CN(C)C(=O)[C@@H]2C(=O)Nc2ccccc2F)cc1OC] |
| 853 | 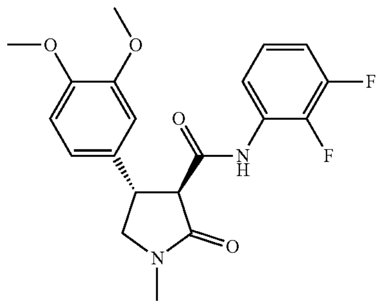 [SMILES: COc1ccc([C@H]2CN(C)C(=O)[C@@H]2C(=O)Nc2cccc(F)c2F)cc1OC] |
| 854 | 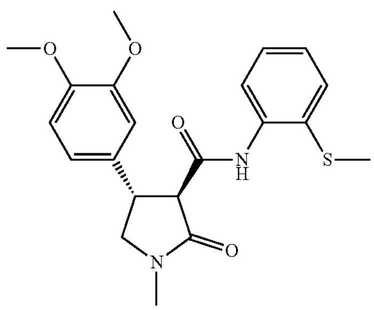 |
| 855 | 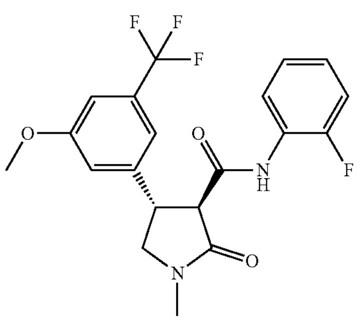 [SMILES: COc1cc([C@H]2CN(C)C(=O)[C@@H]2C(=O)Nc2ccccc2F)cc(C(F)(F)F)c1] |
| 856 | 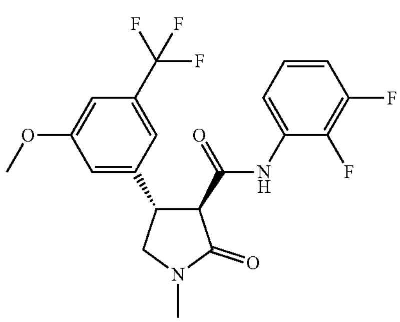 [SMILES: COc1cc([C@H]2CN(C)C(=O)[C@@H]2C(=O)Nc2cccc(F)c2F)cc(C(F)(F)F)c1] |
| 857 | |
| 858 | |
| 859 | |
| 860 | |
| 861 | |

INDEX TABLE E-continued

| Ex # | Structure |
|---|---|
| 862 | 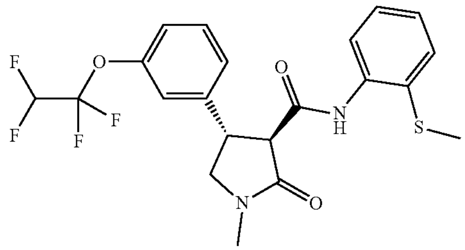 [SMILES: CSc1ccccc1NC(=O)[C@H]1C(=O)N(C)C[C@@H]1c1cccc(OC(F)(F)C(F)F)c1] |
| 863 | 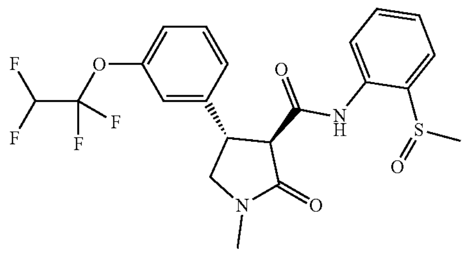 [SMILES: CN1C[C@H](c2cccc(OC(F)(F)C(F)F)c2)[C@@H](C(=O)Nc2ccccc2S(C)=O)C1=O] |
| 864 | 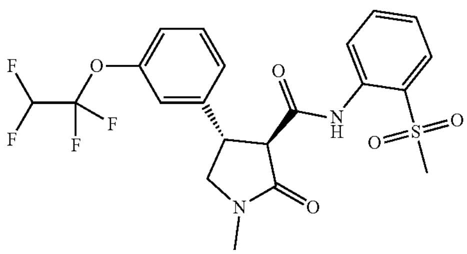 [SMILES: CN1C[C@H](c2cccc(OC(F)(F)C(F)F)c2)[C@@H](C(=O)Nc2ccccc2S(C)(=O)=O)C1=O] |
| 865 | 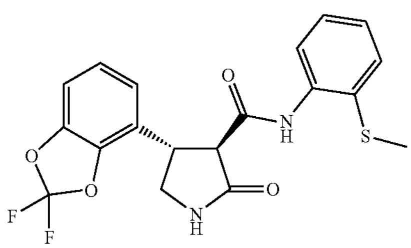 [SMILES: CSc1ccccc1NC(=O)[C@H]1C(=O)NC[C@@H]1c1cccc2c1OC(F)(F)O2] |
| 866 | 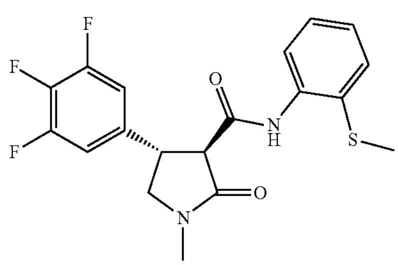 [SMILES: CSc1ccccc1NC(=O)[C@H]1C(=O)N(C)C[C@@H]1c1cc(F)c(F)c(F)c1] |
| 867 | 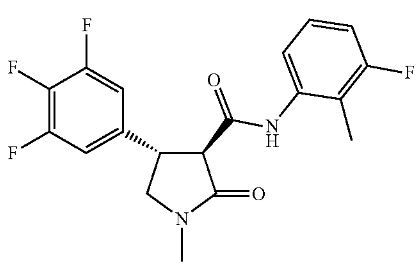 |
| 868 | |
| 869 | |
| 870 | |
| 871 | |
| 872 | |

INDEX TABLE E-continued

| Ex # | Structure |
|---|---|
| 873 | |
| 874 | |
| 875 | |
| 876 | |
| 877 | |
| 878 | 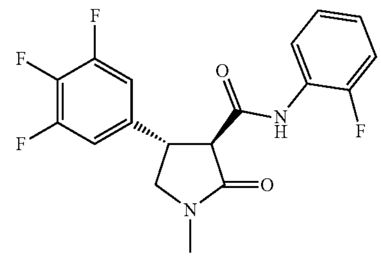 |
| 879 | 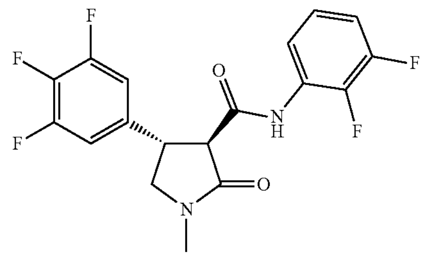 [SMILES: Cc1c(F)cccc1NC(=O)[C@H]1C(=O)N(C)C[C@@H]1c1cc(F)c(F)c(F)c1] |
| 880 | 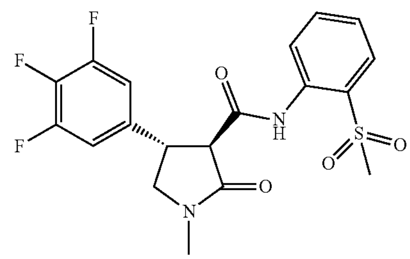 [SMILES: CN1C[C@H](c2cc(F)c(F)c(F)c2)[C@@H](C(=O)Nc2ccccc2S(C)(=O)=O)C1=O] |
| 881 | 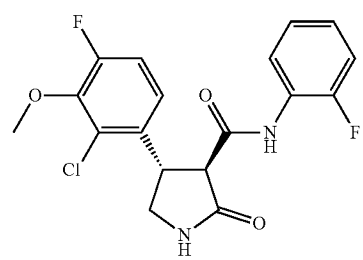 [SMILES: COc1c(F)ccc([C@H]2CNC(=O)[C@@H]2C(=O)Nc2ccccc2F)c1Cl] |
| 882 | 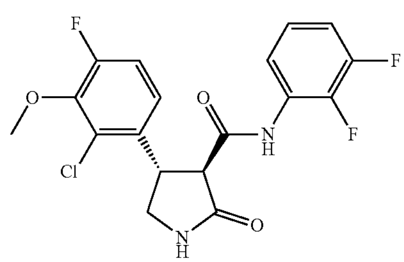 [SMILES: COc1c(F)ccc([C@H]2CNC(=O)[C@@H]2C(=O)Nc2cccc(F)c2F)c1Cl] |
| 883 | 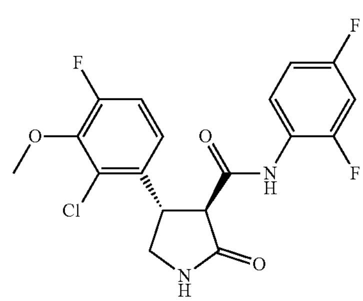 [SMILES: COc1c(F)ccc([C@H]2CNC(=O)[C@@H]2C(=O)Nc2ccc(F)cc2F)c1Cl] |

INDEX TABLE E-continued

| Ex # | Structure |
|------|-----------|
| 884 | 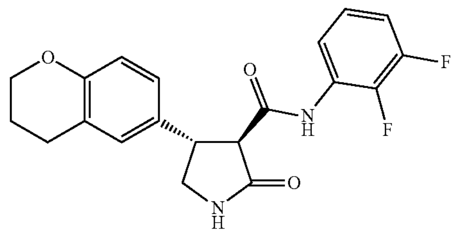 [SMILES: O=C1NC[C@H](c2ccc3c(c2)CCCO3)[C@H]1C(=O)Nc1cccc(F)c1F] |
| 885 | 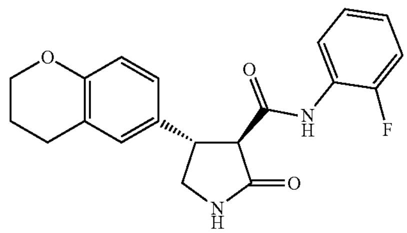 [SMILES: O=C1NC[C@H](c2ccc3c(c2)CCCO3)[C@H]1C(=O)Nc1ccccc1F] |
| 886 | 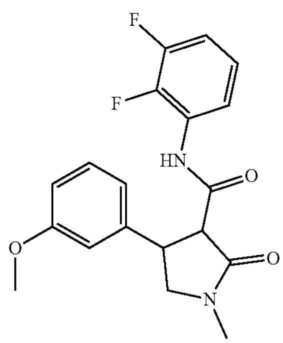 [SMILES: COc1cccc(C2CN(C)C(=O)C2C(=O)Nc2cccc(F)c2F)c1] |
| 887 | 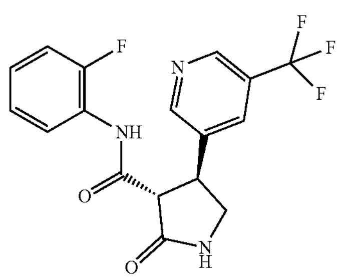 [SMILES: O=C1NC[C@H](c2cncc(C(F)(F)F)c2)[C@H]1C(=O)Nc1ccccc1F] |
| 888 | 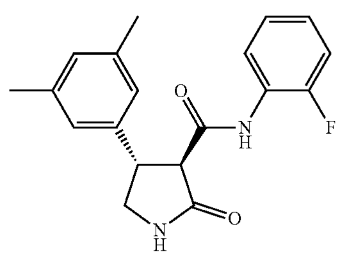 [SMILES: Cc1cc(C)cc([C@H]2CNC(=O)[C@@H]2C(=O)Nc2ccccc2F)c1] |
| 889 | 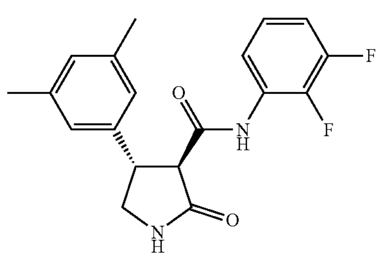 [SMILES: Cc1cc(C)cc([C@H]2CNC(=O)[C@@H]2C(=O)Nc2cccc(F)c2F)c1] |
| 890 | |
| 891 | |
| 892 | |
| 893 | |
| 894 | |

INDEX TABLE E-continued

| Ex # | Structure |
|---|---|
| 895 | 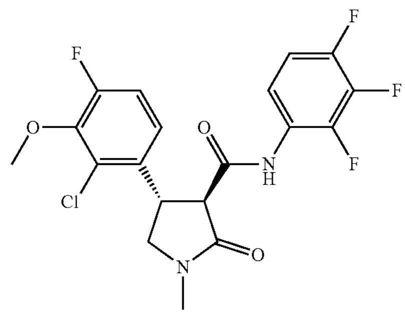 [SMILES: COc1c(F)ccc([C@H]2CN(C)C(=O)[C@@H]2C(=O)Nc2ccc(F)c(F)c2F)c1Cl] |
| 896 | 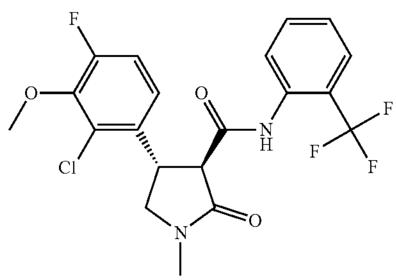 [SMILES: COc1c(F)ccc([C@H]2CN(C)C(=O)[C@@H]2C(=O)Nc2ccccc2C(F)(F)F)c1Cl] |
| 897 | 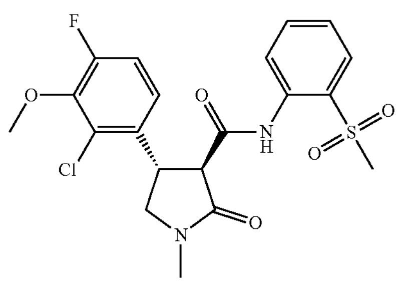 [SMILES: COc1c(F)ccc([C@H]2CN(C)C(=O)[C@@H]2C(=O)Nc2ccccc2S(C)(=O)=O)c1Cl] |
| 898 | 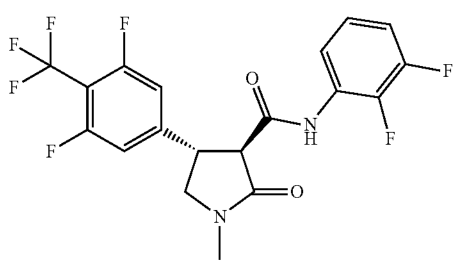 [SMILES: CN1C[C@H](c2cc(F)c(C(F)(F)F)c(F)c2)[C@@H](C(=O)Nc2cccc(F)c2F)C1=O] |
| 899 | 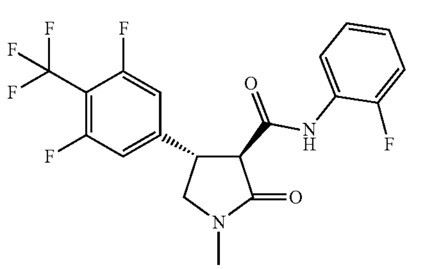 [SMILES: CN1C[C@H](c2cc(F)c(C(F)(F)F)c(F)c2)[C@@H](C(=O)Nc2ccccc2F)C1=O] |
| 900 | 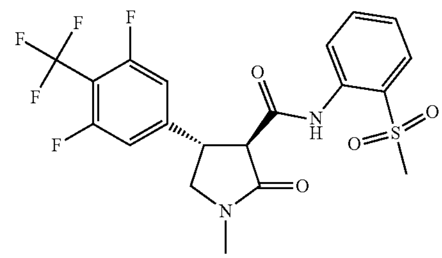 [SMILES: CN1C[C@H](c2cc(F)c(C(F)(F)F)c(F)c2)[C@@H](C(=O)Nc2ccccc2S(C)(=O)=O)C1=O] |
| 901 | 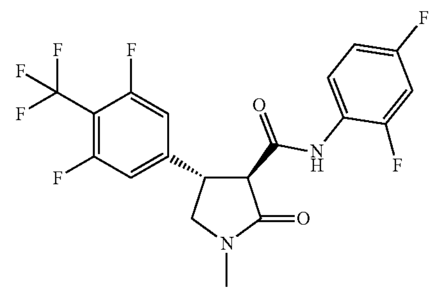 [SMILES: CN1C[C@H](c2cc(F)c(C(F)(F)F)c(F)c2)[C@@H](C(=O)Nc2ccc(F)cc2F)C1=O] |
| 902 | 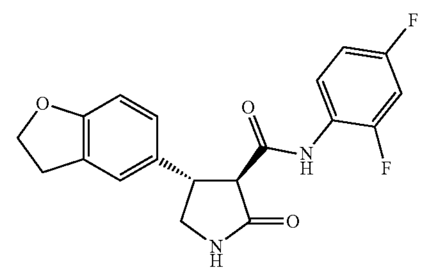 [SMILES: O=C1NC[C@H](c2ccc3c(c2)CCO3)[C@H]1C(=O)Nc1ccc(F)cc1F] |
| 903 | 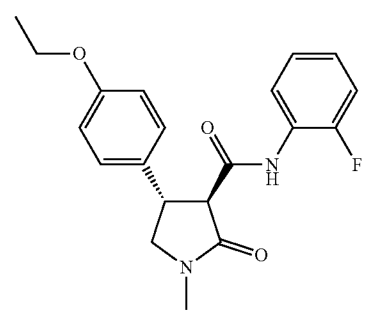 [SMILES: CCOc1ccc([C@H]2CN(C)C(=O)[C@@H]2C(=O)Nc2ccccc2F)cc1] |
| 904 | 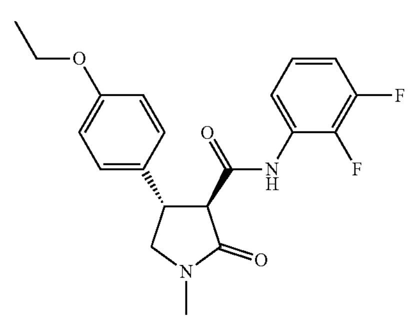 [SMILES: CCOc1ccc([C@H]2CN(C)C(=O)[C@@H]2C(=O)Nc2cccc(F)c2F)cc1] |

INDEX TABLE E-continued

| Ex # | Structure |
|---|---|
| 905 | 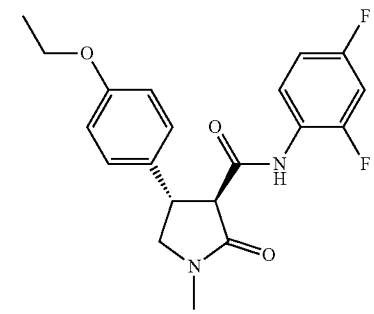 [SMILES: CCOc1ccc([C@H]2CN(C)C(=O)[C@@H]2C(=O)Nc2ccc(F)cc2F)cc1] |
| 906 | 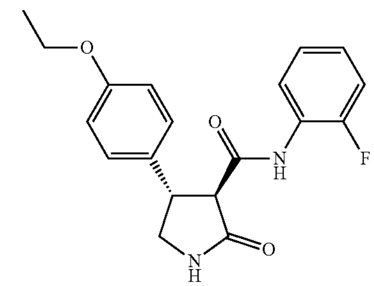 [SMILES: CCOc1ccc([C@H]2CNC(=O)[C@@H]2C(=O)Nc2ccccc2F)cc1] |
| 907 | 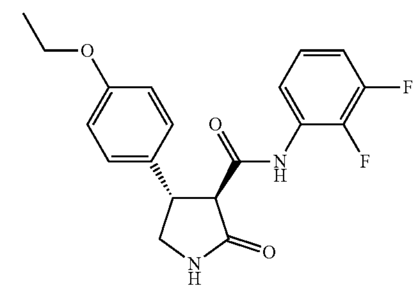 [SMILES: CCOc1ccc([C@H]2CNC(=O)[C@@H]2C(=O)Nc2cccc(F)c2F)cc1] |
| 908 | 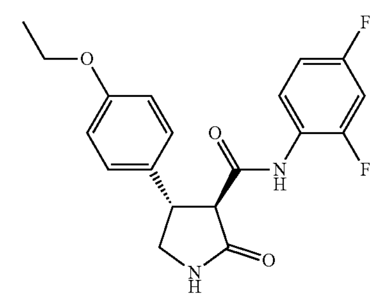 [SMILES: CCOc1ccc([C@H]2CNC(=O)[C@@H]2C(=O)Nc2ccc(F)cc2F)cc1] |
| 909 | 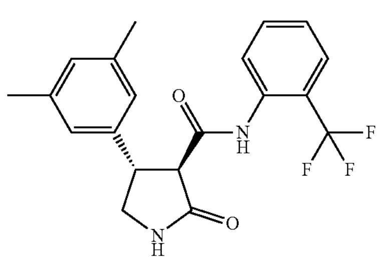 [SMILES: Cc1cc(C)cc([C@H]2CNC(=O)[C@@H]2C(=O)Nc2ccccc2C(F)(F)F)c1] |

INDEX TABLE E-continued

| Ex # | Structure |
|---|---|
| 910 | |
| 911 | |
| 912 | |
| 913 | |
| 914 | AND Enantiomer |

INDEX TABLE E-continued
| Ex # | Structure |
|---|---|
| 915 | 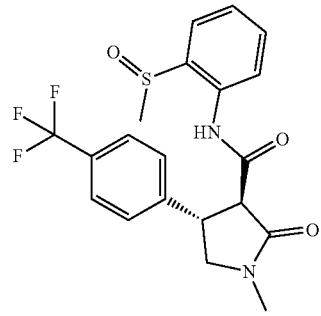 [SMILES: CN1C[C@H](c2ccc(C(F)(F)F)cc2)[C@@H](C(=O)Nc2ccccc2S(C)=O)C1=O] |
| 916 | 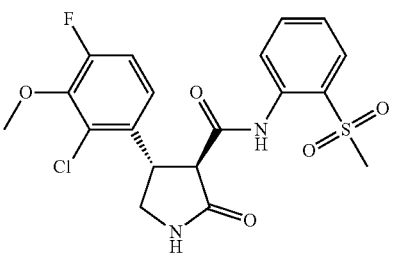 [SMILES: COc1c(F)ccc([C@H]2CNC(=O)[C@@H]2C(=O)Nc2ccccc2S(C)(=O)=O)c1Cl] |
| 917 | 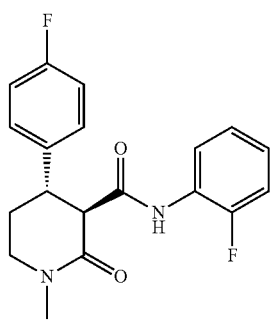 [SMILES: CN1CC[C@H](c2ccc(F)cc2)[C@@H](C(=O)Nc2ccccc2F)C1=O] |
| 918 | 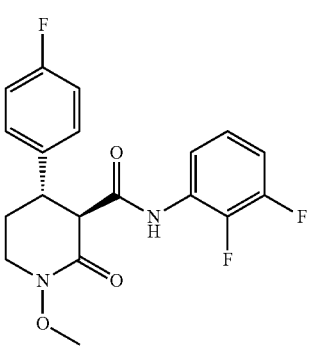 [SMILES: CON1CC[C@H](c2ccc(F)cc2)[C@@H](C(=O)Nc2cccc(F)c2F)C1=O] |
| 919 | 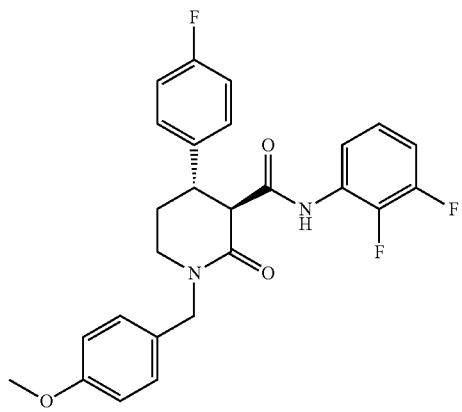 [SMILES: COc1ccc(CN2CC[C@H](c3ccc(F)cc3)[C@@H](C(=O)Nc3cccc(F)c3F)C2=O)cc1] |
| 920 | 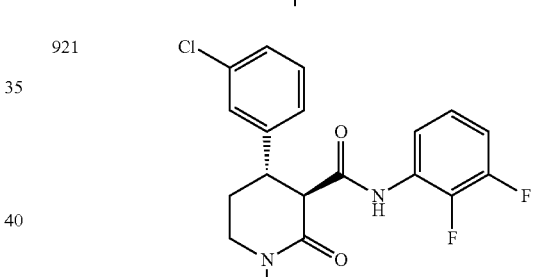 |
| 921 | 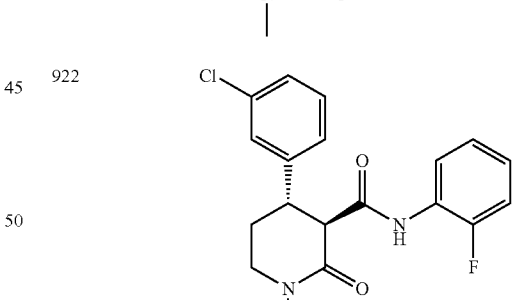 |
| 922 | 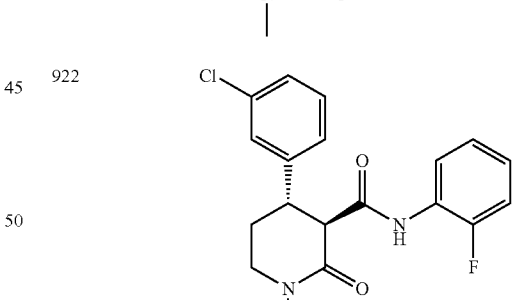 |
| 923 | 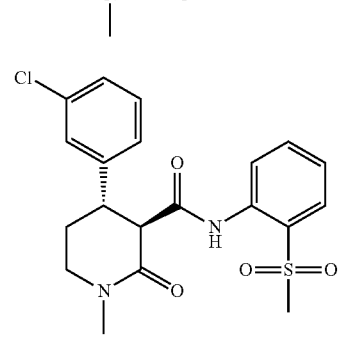 |

INDEX TABLE E-continued

| Ex # | Structure |
|---|---|
| 924 | (3-chlorophenyl piperidinone, N-(3-chloro-2-fluorophenyl) carboxamide, N-methyl) |
| 925 | (3-trifluoromethylphenyl piperidinone, N-(2,3-difluorophenyl) carboxamide, N-cyclopropyl) |
| 926 | (3-trifluoromethylphenyl piperidinone, N-(3-chloro-2-fluorophenyl) carboxamide, N-cyclopropyl) |
| 927 | (3-trifluoromethylphenyl piperidinone, N-(2-methylsulfonylphenyl) carboxamide, N-cyclopropyl) |

INDEX TABLE E-continued

| Ex # | Structure |
|---|---|
| 928 | (4-chloro-3-methylphenyl pyrrolidinone, N-(2-fluorophenyl) carboxamide, N-methyl) |
| 929 | (4-chloro-3-methylphenyl pyrrolidinone, N-(2,3-difluorophenyl) carboxamide, N-methyl) |
| 930 | (4-chloro-3-methylphenyl pyrrolidinone, N-(2,4-difluorophenyl) carboxamide, N-methyl) |
| 931 | (4-chloro-3-methylphenyl pyrrolidinone, N-(2,3,4-trifluorophenyl) carboxamide, N-methyl) |
| 932 | (4-chloro-3-methylphenyl pyrrolidinone, N-(2-trifluoromethylphenyl) carboxamide, N-methyl) |

INDEX TABLE E-continued
| Ex # | Structure |
|---|---|
| 933 | 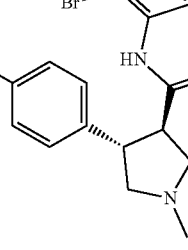 |
| 934 | 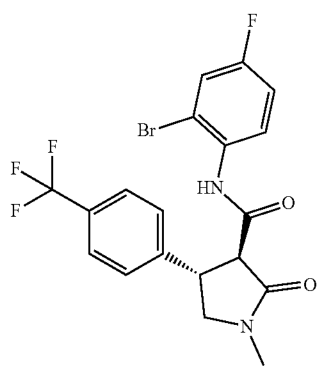 [SMILES: CN1C[C@H](c2ccc(C(F)(F)F)cc2)[C@@H](C(=O)Nc2ccc(F)cc2Br)C1=O] |
| 935 | 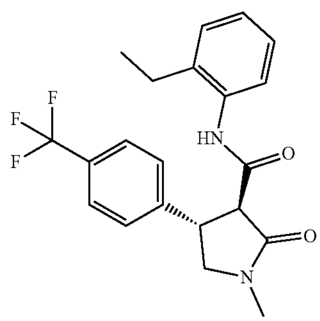 [SMILES: CCc1ccccc1NC(=O)[C@H]1C(=O)N(C)C[C@@H]1c1ccc(C(F)(F)F)cc1] |
| 936 | 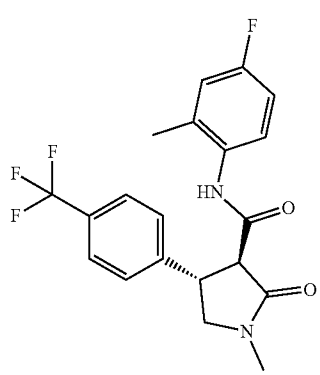 [SMILES: Cc1cc(F)ccc1NC(=O)[C@H]1C(=O)N(C)C[C@@H]1c1ccc(C(F)(F)F)cc1] |
INDEX TABLE E-continued
| Ex # | Structure |
|---|---|
| 937 | 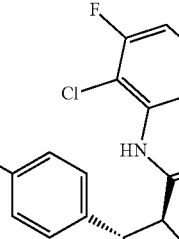 |
| 938 | 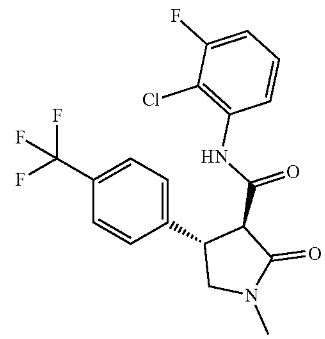 [SMILES: CN1C[C@H](c2ccc(C(F)(F)F)cc2)[C@@H](C(=O)Nc2cccc(F)c2Cl)C1=O] |
| 939 | 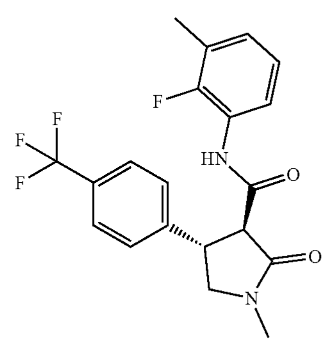 [SMILES: Cc1cccc(NC(=O)[C@H]2C(=O)N(C)C[C@@H]2c2ccc(C(F)(F)F)cc2)c1F] |
| 940 | 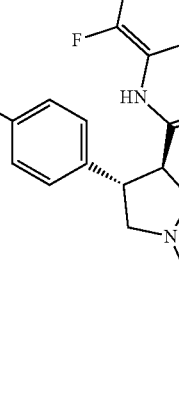 |

INDEX TABLE E-continued

| Ex # | Structure |
|---|---|
| 941 | 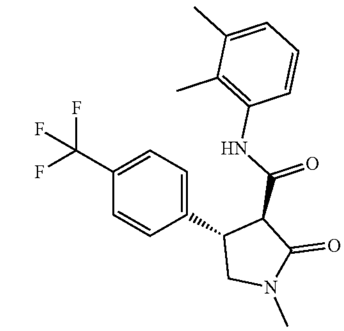 [SMILES: Cc1cccc(NC(=O)[C@H]2C(=O)N(C)C[C@@H]2c2ccc(C(F)(F)F)cc2)c1C] |
| 942 | 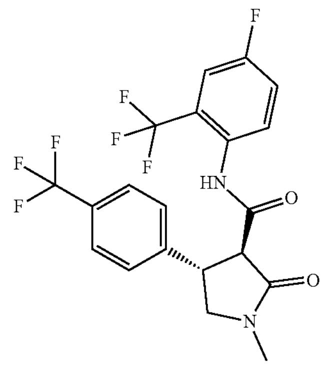 [SMILES: CN1C[C@H](c2ccc(C(F)(F)F)cc2)[C@@H](C(=O)Nc2ccc(F)cc2C(F)(F)F)C1=O] |
| 943 | 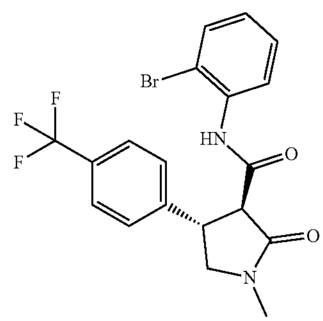 [SMILES: CN1C[C@H](c2ccc(C(F)(F)F)cc2)[C@@H](C(=O)Nc2ccccc2Br)C1=O] |
| 944 | 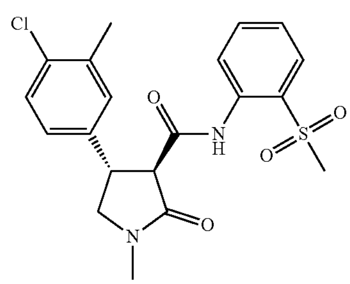 [SMILES: Cc1cc([C@H]2CN(C)C(=O)[C@@H]2C(=O)Nc2ccccc2S(C)(=O)=O)ccc1Cl] |
| 945 | AND Enantiomer |

INDEX TABLE E-continued

| Ex # | Structure |
|---|---|
| 946 | AND Enantiomer |
| 947 | AND Enantiomer |
| 948 | 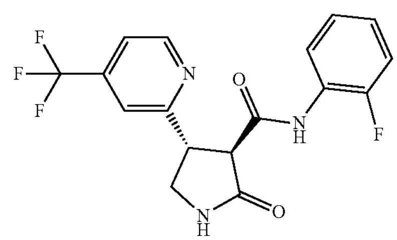 [SMILES: O=C1NC[C@H](c2cc(C(F)(F)F)ccn2)[C@H]1C(=O)Nc1ccccc1F] |
| 949 | 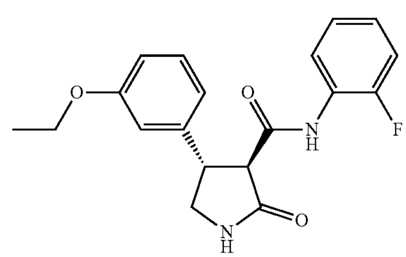 [SMILES: CCOc1cccc([C@H]2CNC(=O)[C@@H]2C(=O)Nc2ccccc2F)c1] |
| 950 | 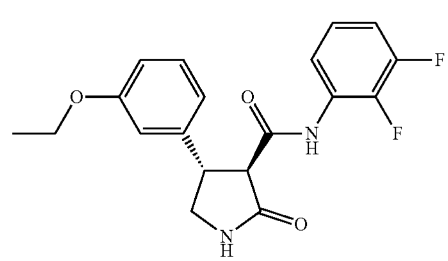 [SMILES: CCOc1cccc([C@H]2CNC(=O)[C@@H]2C(=O)Nc2cccc(F)c2F)c1] |

INDEX TABLE E-continued

| Ex # | Structure |
|---|---|
| 951 | 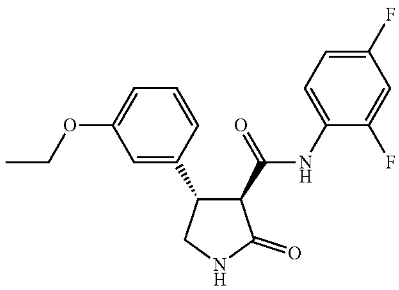 [SMILES: CCOc1cccc([C@H]2CNC(=O)[C@@H]2C(=O)Nc2ccc(F)cc2F)c1] |
| 952 | 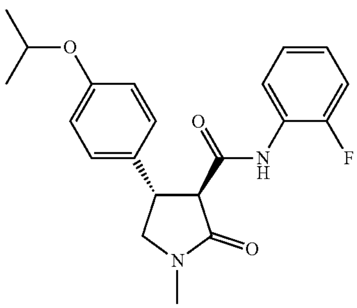 [SMILES: CC(C)Oc1ccc([C@H]2CN(C)C(=O)[C@@H]2C(=O)Nc2ccccc2F)cc1] |
| 953 | 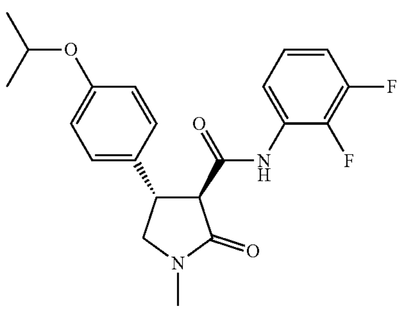 [SMILES: CC(C)Oc1ccc([C@H]2CN(C)C(=O)[C@@H]2C(=O)Nc2cccc(F)c2F)cc1] |
| 954 | 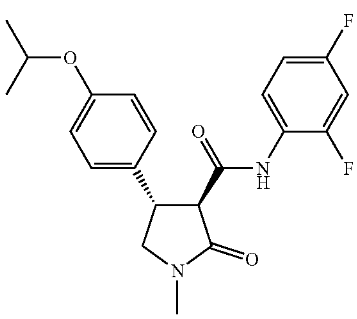 [SMILES: CC(C)Oc1ccc([C@H]2CN(C)C(=O)[C@@H]2C(=O)Nc2ccc(F)cc2F)cc1] |
| 955 | 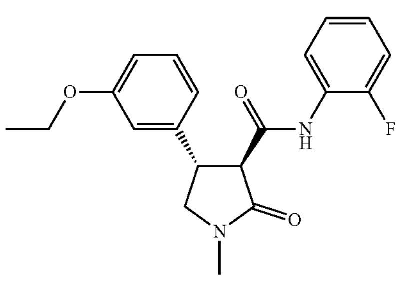 [SMILES: CCOc1cccc([C@H]2CN(C)C(=O)[C@@H]2C(=O)Nc2ccccc2F)c1] |

INDEX TABLE E-continued

| Ex # | Structure |
|---|---|
| 956 | 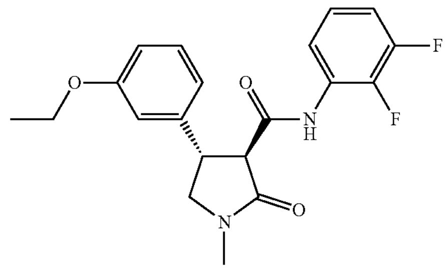 [SMILES: CCOc1cccc([C@H]2CN(C)C(=O)[C@@H]2C(=O)Nc2cccc(F)c2F)c1] |
| 957 | 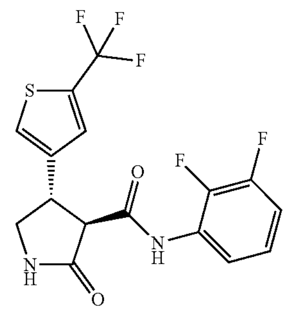 [SMILES: O=C1NC[C@H](c2csc(C(F)(F)F)c2)[C@H]1C(=O)Nc1cccc(F)c1F] |
| 958 | 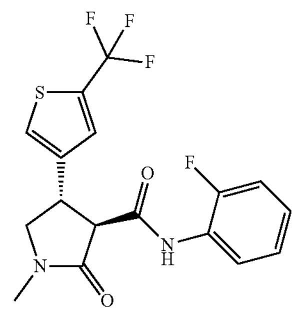 [SMILES: CN1C[C@H](c2csc(C(F)(F)F)c2)[C@@H](C(=O)Nc2ccccc2F)C1=O] |
| 959 | 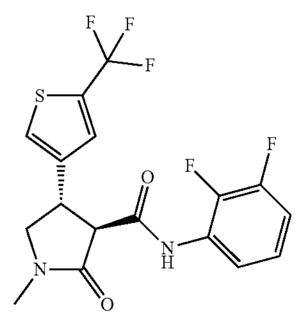 [SMILES: CN1C[C@H](c2csc(C(F)(F)F)c2)[C@@H](C(=O)Nc2cccc(F)c2F)C1=O] |
| 960 | 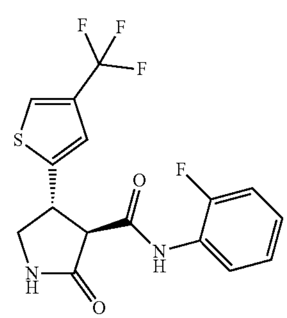 [SMILES: O=C1NC[C@H](c2cc(C(F)(F)F)cs2)[C@H]1C(=O)Nc1ccccc1F] |

INDEX TABLE E-continued

| Ex # | Structure |
|---|---|
| 961 | (structure) |
| 962 | (structure) |
| 963 | (structure) |
| 964 | (structure) |
| 965 | (structure) |
| 966 | (structure) |
| 967 | (structure) |
| 968 | (structure) |
| 969 | (structure) |
| 970 | (structure) |

INDEX TABLE E-continued

| Ex # | Structure |
|---|---|
| 971 | (structure) |
| 972 | (structure) |
| 973 | (structure) |
| 974 | (structure) |
| 975 | (structure) |
| 976 | (structure) |
| 977 | (structure) |
| 978 | (structure) |
| 979 | (structure) |
| 980 | (structure) |

INDEX TABLE E-continued

| Ex # | Structure |
|---|---|
| 981 | 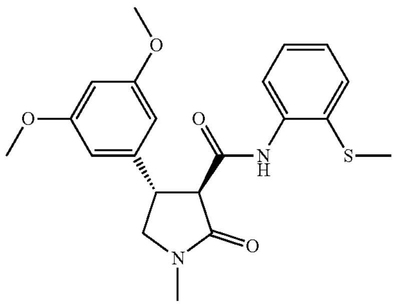 |
| 982 | 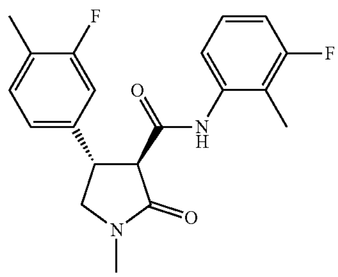 [SMILES: Cc1ccc([C@H]2CN(C)C(=O)[C@@H]2C(=O)Nc2cccc(F)c2C)cc1F] |
| 983 | 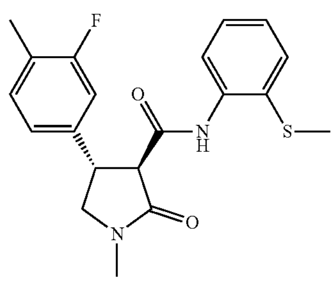 [SMILES: CSc1ccccc1NC(=O)[C@H]1C(=O)N(C)C[C@@H]1c1ccc(C)c(F)c1] |
| 984 | 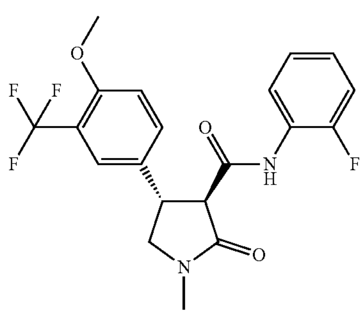 [SMILES: COc1ccc([C@H]2CN(C)C(=O)[C@@H]2C(=O)Nc2ccccc2F)cc1C(F)(F)F] |
| 985 | 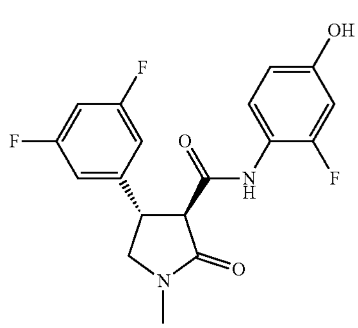 [SMILES: CN1C[C@H](c2cc(F)cc(F)c2)[C@@H](C(=O)Nc2ccc(O)cc2F)C1=O] |
| 986 | |
| 987 | |
| 988 | |
| 989 | |
| 990 | |

INDEX TABLE E-continued
| Ex # | Structure |
|---|---|
| 991 | 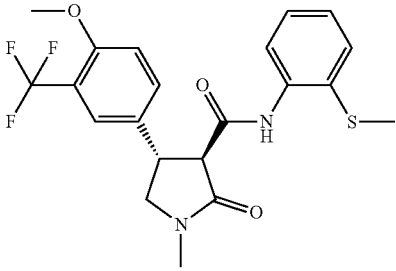 [SMILES: COc1ccc([C@H]2CN(C)C(=O)[C@@H]2C(=O)Nc2ccccc2SC)cc1C(F)(F)F] |
| 992 | 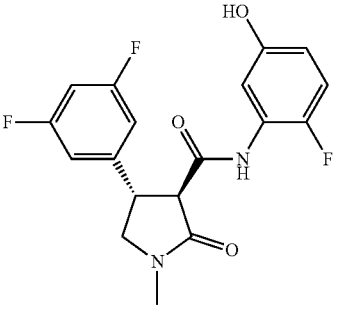 [SMILES: CN1C[C@H](c2cc(F)cc(F)c2)[C@@H](C(=O)Nc2cc(O)ccc2F)C1=O] |
| 993 | 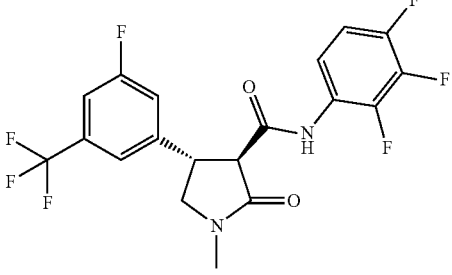 |
| 994 | 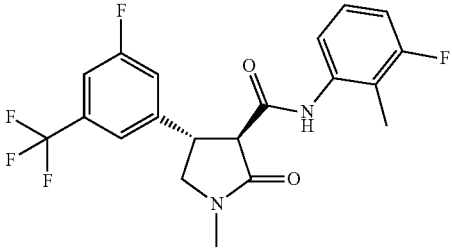 [SMILES: Cc1c(F)cccc1NC(=O)[C@H]1C(=O)N(C)C[C@@H]1c1cc(F)cc(C(F)(F)F)c1] |
| 995 | 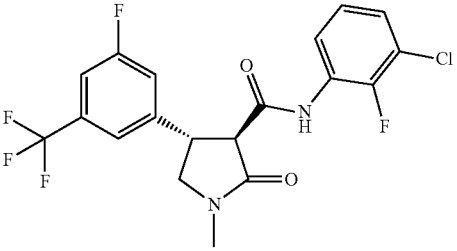 [SMILES: CN1C[C@H](c2cc(F)cc(C(F)(F)F)c2)[C@@H](C(=O)Nc2cccc(Cl)c2F)C1=O] |
INDEX TABLE E-continued
| Ex # | Structure |
|---|---|
| 996 | 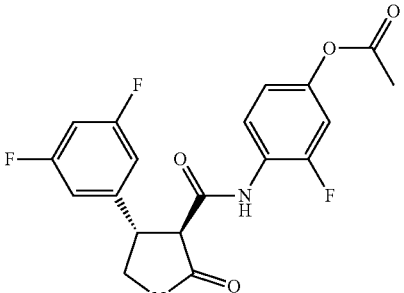 |
| 997 | 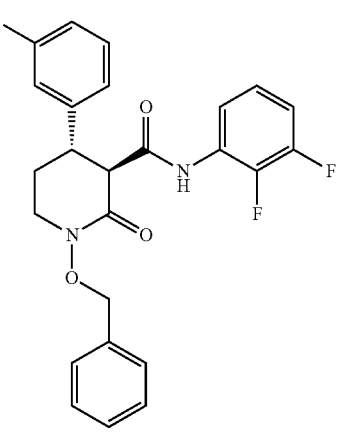 |
| 998 | 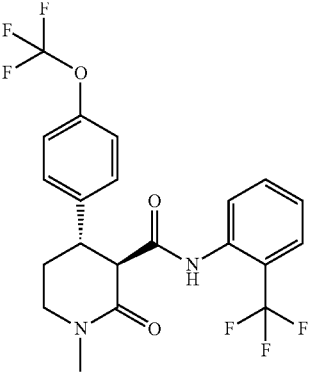 [SMILES: CN1CC[C@H](c2ccc(OC(F)(F)F)cc2)[C@@H](C(=O)Nc2ccccc2C(F)(F)F)C1=O] |
| 999 | 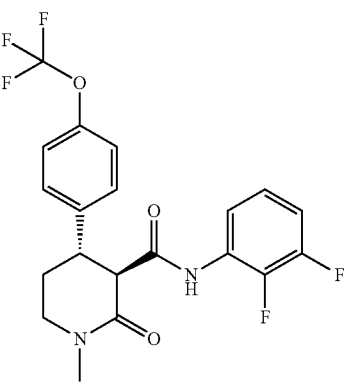 [SMILES: CN1CC[C@H](c2ccc(OC(F)(F)F)cc2)[C@@H](C(=O)Nc2cccc(F)c2F)C1=O] |

INDEX TABLE E-continued

| Ex # | Structure |
|---|---|
| 1000 | 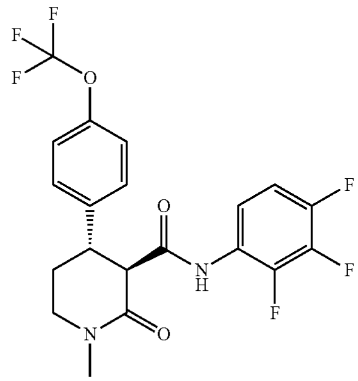 [SMILES: CN1CC[C@H](c2ccc(OC(F)(F)F)cc2)[C@@H](C(=O)Nc2ccc(F)c(F)c2F)C1=O] |
| 1001 | 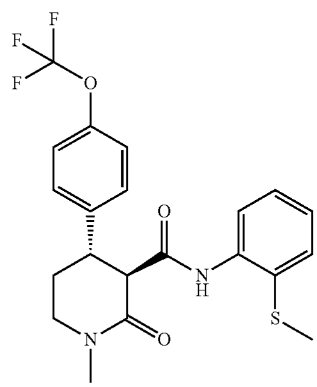 [SMILES: CSc1ccccc1NC(=O)[C@H]1C(=O)N(C)CC[C@@H]1c1ccc(OC(F)(F)F)cc1] |
| 1002 | 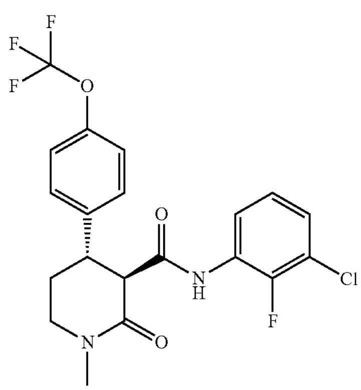 [SMILES: CN1CC[C@H](c2ccc(OC(F)(F)F)cc2)[C@@H](C(=O)Nc2cccc(Cl)c2F)C1=O] |
| 1003 | 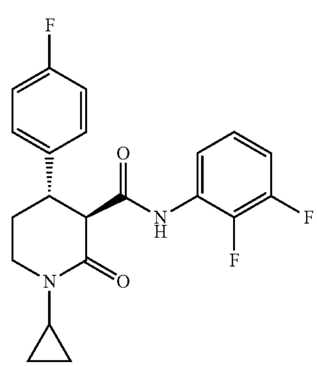 [SMILES: O=C(Nc1cccc(F)c1F)[C@H]1C(=O)N(C2CC2)CC[C@@H]1c1ccc(F)cc1] |
| 1004 | 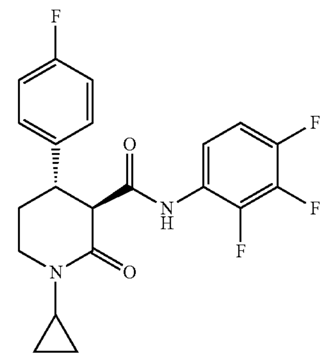 [SMILES: O=C(Nc1ccc(F)c(F)c1F)[C@H]1C(=O)N(C2CC2)CC[C@@H]1c1ccc(F)cc1] |
| 1005 | 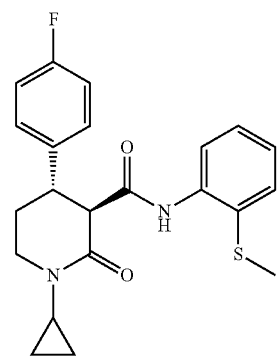 [SMILES: CSc1ccccc1NC(=O)[C@H]1C(=O)N(C2CC2)CC[C@@H]1c1ccc(F)cc1] |
| 1006 | 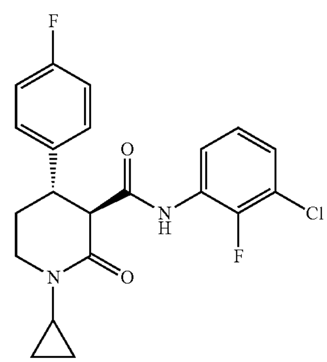 [SMILES: O=C(Nc1cccc(Cl)c1F)[C@H]1C(=O)N(C2CC2)CC[C@@H]1c1ccc(F)cc1] |
| 1007 | 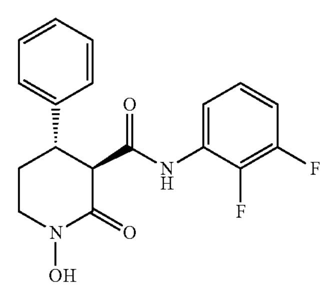 [SMILES: O=C(Nc1cccc(F)c1F)[C@H]1C(=O)N(O)CC[C@@H]1c1ccccc1] |
| 1008 | 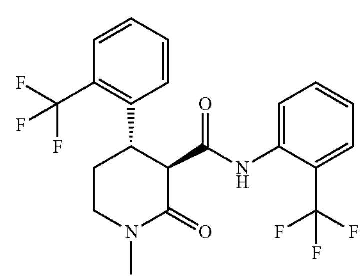 [SMILES: CN1CC[C@H](c2ccccc2C(F)(F)F)[C@@H](C(=O)Nc2ccccc2C(F)(F)F)C1=O] |

INDEX TABLE E-continued

| Ex # | Structure |
|---|---|
| 1009 | 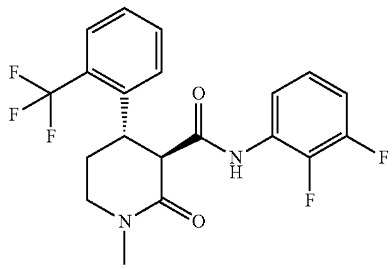 [SMILES: CN1CC[C@H](c2ccccc2C(F)(F)F)[C@@H](C(=O)Nc2cccc(F)c2F)C1=O] |
| 1010 | 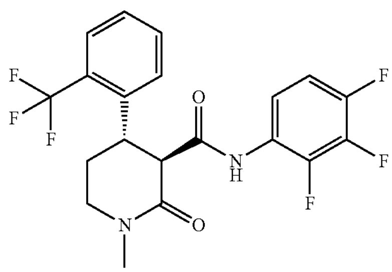 [SMILES: CN1CC[C@H](c2ccccc2C(F)(F)F)[C@@H](C(=O)Nc2ccc(F)c(F)c2F)C1=O] |
| 1011 | 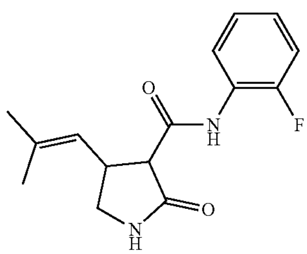 [SMILES: CC(C)=CC1CNC(=O)C1C(=O)Nc1ccccc1F] |
| 1012 | 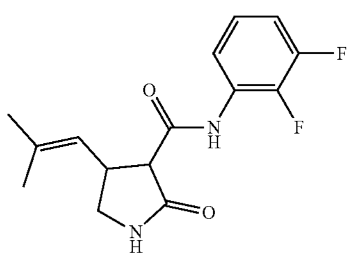 [SMILES: CC(C)=CC1CNC(=O)C1C(=O)Nc1cccc(F)c1F] |
| 1013 | 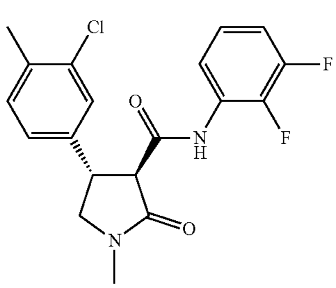 [SMILES: Cc1ccc([C@H]2CN(C)C(=O)[C@@H]2C(=O)Nc2cccc(F)c2F)cc1Cl] |

INDEX TABLE E-continued

| Ex # | Structure |
|---|---|
| 1014 | 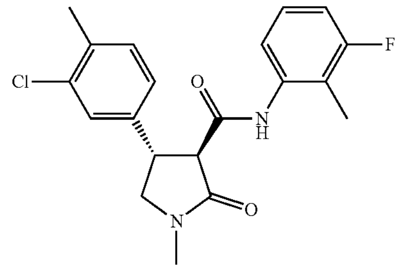 [SMILES: Cc1ccc([C@H]2CN(C)C(=O)[C@@H]2C(=O)Nc2cccc(F)c2C)cc1Cl] |
| 1015 | 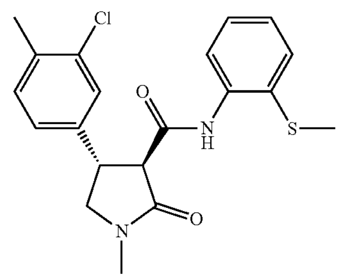 |
| 1016 | 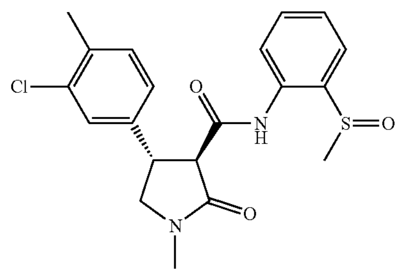 [SMILES: Cc1ccc([C@H]2CN(C)C(=O)[C@@H]2C(=O)Nc2ccccc2S(C)=O)cc1Cl] |
| 1017 | 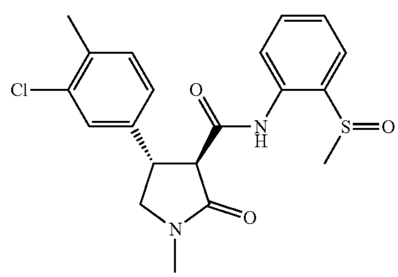 [SMILES: Cc1ccc([C@H]2CN(C)C(=O)[C@@H]2C(=O)Nc2ccccc2S(C)=O)cc1Cl] |
| 1018 | 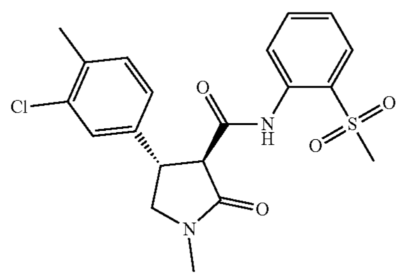 [SMILES: Cc1ccc([C@H]2CN(C)C(=O)[C@@H]2C(=O)Nc2ccccc2S(C)(=O)=O)cc1Cl] |

INDEX TABLE E-continued

| Ex # | Structure |
|---|---|
| 1019 | 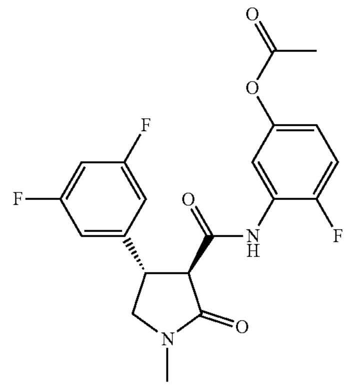 [SMILES: CC(=O)Oc1ccc(F)c(NC(=O)[C@H]2C(=O)N(C)C[C@@H]2c2cc(F)cc(F)c2)c1] |
| 1020 | 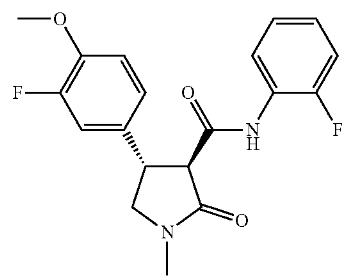 [SMILES: COc1ccc([C@H]2CN(C)C(=O)[C@@H]2C(=O)Nc2ccccc2F)cc1F] |
| 1021 | 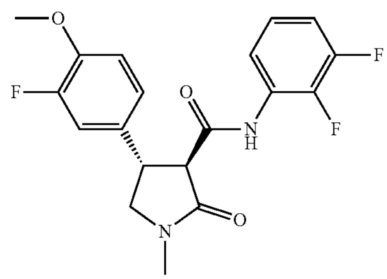 [SMILES: COc1ccc([C@H]2CN(C)C(=O)[C@@H]2C(=O)Nc2cccc(F)c2F)cc1F] |
| 1022 | 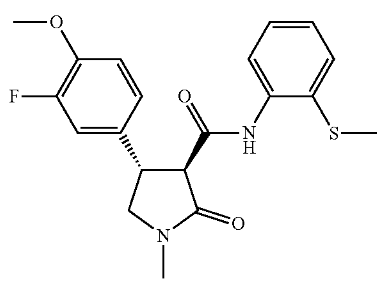 [SMILES: COc1ccc([C@H]2CN(C)C(=O)[C@@H]2C(=O)Nc2ccccc2SC)cc1F] |
| 1023 | 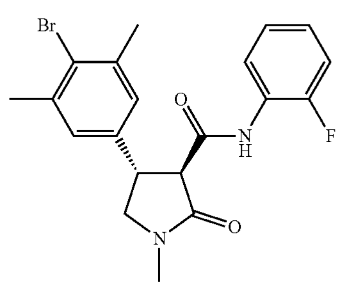 [SMILES: Cc1cc([C@H]2CN(C)C(=O)[C@@H]2C(=O)Nc2ccccc2F)cc(C)c1Br] |

INDEX TABLE E-continued

| Ex # | Structure |
|---|---|
| 1024 | 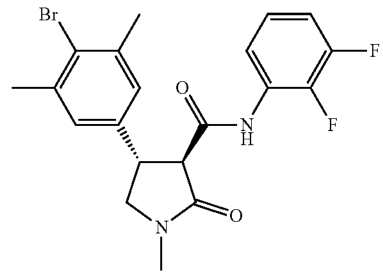 [SMILES: Cc1cc([C@H]2CN(C)C(=O)[C@@H]2C(=O)Nc2cccc(F)c2F)cc(C)c1Br] |
| 1025 | 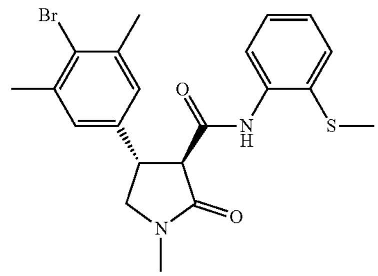 |
| 1026 | 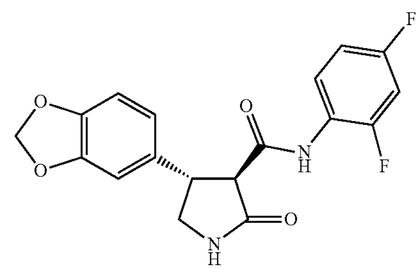 [SMILES: O=C1NC[C@H](c2ccc3c(c2)OCO3)[C@H]1C(=O)Nc1ccc(F)cc1F] |
| 1027 | 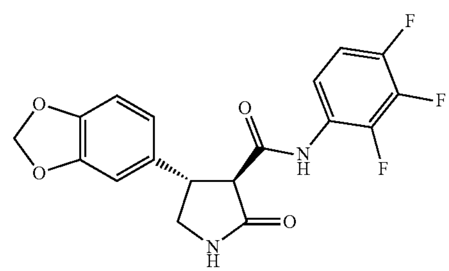 [SMILES: O=C1NC[C@H](c2ccc3c(c2)OCO3)[C@H]1C(=O)Nc1ccc(F)c(F)c1F] |
| 1028 | 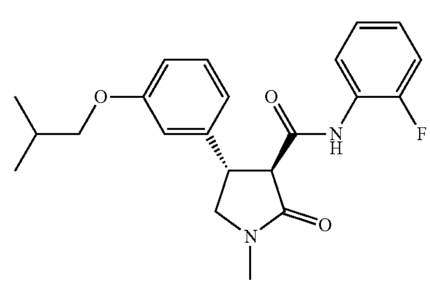 [SMILES: CC(C)COc1cccc([C@H]2CN(C)C(=O)[C@@H]2C(=O)Nc2ccccc2F)c1] |

INDEX TABLE E-continued
| Ex # | Structure |
|---|---|
| 1029 | 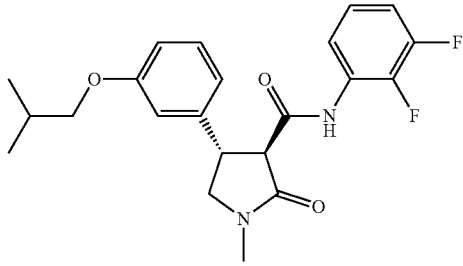 [SMILES: CC(C)COc1cccc([C@H]2CN(C)C(=O)[C@@H]2C(=O)Nc2cccc(F)c2F)c1] |
| 1030 | 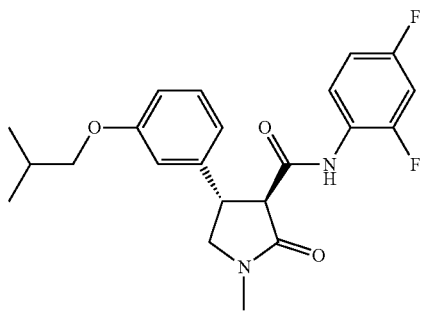 [SMILES: CC(C)COc1cccc([C@H]2CN(C)C(=O)[C@@H]2C(=O)Nc2ccc(F)cc2F)c1] |
| 1031 | 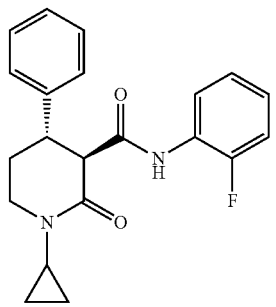 [SMILES: O=C(Nc1ccccc1F)[C@H]1C(=O)N(C2CC2)CC[C@@H]1c1ccccc1] |
| 1032 | 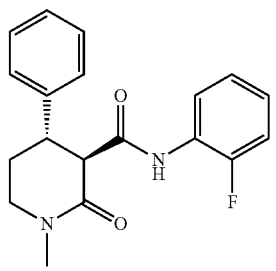 [SMILES: CN1CC[C@H](c2ccccc2)[C@@H](C(=O)Nc2ccccc2F)C1=O] |
| 1033 | 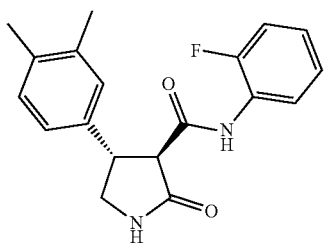 [SMILES: Cc1ccc([C@H]2CNC(=O)[C@@H]2C(=O)Nc2ccccc2F)cc1C] |
INDEX TABLE E-continued
| Ex # | Structure |
|---|---|
| 1034 | 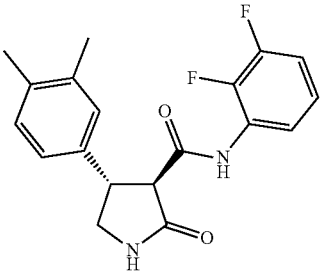 [SMILES: Cc1ccc([C@H]2CNC(=O)[C@@H]2C(=O)Nc2cccc(F)c2F)cc1C] |
| 1035 | 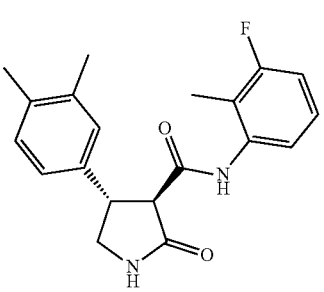 [SMILES: Cc1ccc([C@H]2CNC(=O)[C@@H]2C(=O)Nc2cccc(F)c2C)cc1C] |
| 1036 | 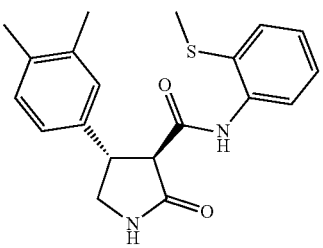 [SMILES: CSc1ccccc1NC(=O)[C@H]1C(=O)NC[C@@H]1c1ccc(C)c(C)c1] |
| 1037 | 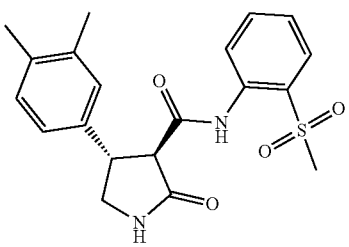 [SMILES: Cc1ccc([C@H]2CNC(=O)[C@@H]2C(=O)Nc2ccccc2S(C)(=O)=O)cc1C] |
| 1038 | 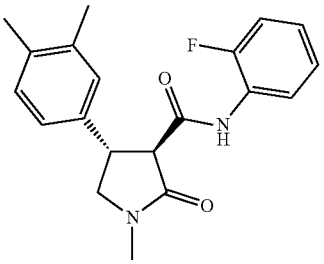 [SMILES: Cc1ccc([C@H]2CN(C)C(=O)[C@@H]2C(=O)Nc2ccccc2F)cc1C] |

INDEX TABLE E-continued

| Ex # | Structure |
|------|-----------|
| 1039 | 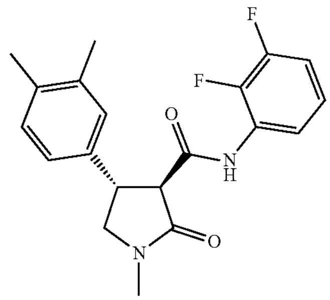 [SMILES: Cc1ccc([C@H]2CN(C)C(=O)[C@@H]2C(=O)Nc2cccc(F)c2F)cc1C] |
| 1040 | 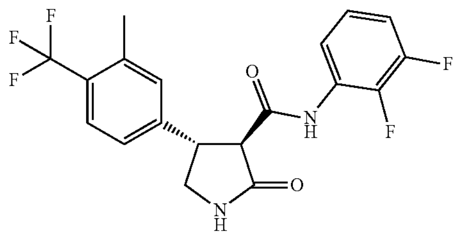 [SMILES: Cc1cc([C@H]2CNC(=O)[C@@H]2C(=O)Nc2cccc(F)c2F)ccc1C(F)(F)F] |
| 1041 | 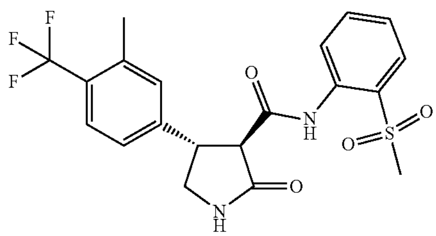 [SMILES: Cc1cc([C@H]2CNC(=O)[C@@H]2C(=O)Nc2ccccc2S(C)(=O)=O)ccc1C(F)(F)F] |
| 1042 | 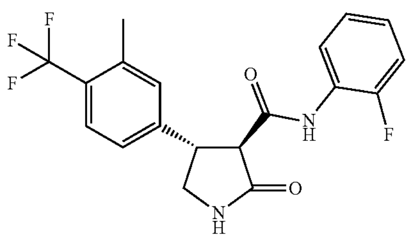 [SMILES: Cc1cc([C@H]2CNC(=O)[C@@H]2C(=O)Nc2ccccc2F)ccc1C(F)(F)F] |
| 1043 | 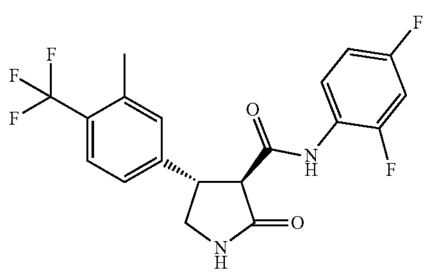 [SMILES: Cc1cc([C@H]2CNC(=O)[C@@H]2C(=O)Nc2ccc(F)cc2F)ccc1C(F)(F)F] |
| 1044 | 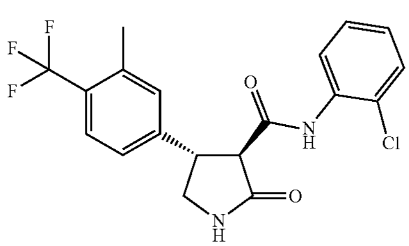 [SMILES: Cc1cc([C@H]2CNC(=O)[C@@H]2C(=O)Nc2ccccc2Cl)ccc1C(F)(F)F] |

INDEX TABLE E-continued

| Ex # | Structure |
|------|-----------|
| 1045 | 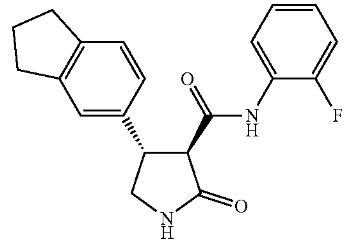 [SMILES: O=C1NC[C@H](c2ccc3c(c2)CCC3)[C@H]1C(=O)Nc1ccccc1F] |
| 1046 | 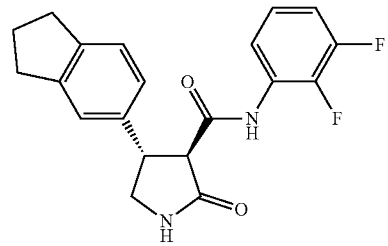 [SMILES: O=C1NC[C@H](c2ccc3c(c2)CCC3)[C@H]1C(=O)Nc1cccc(F)c1F] |
| 1047 | AND Enantiomer |
| 1048 | AND Enantiomer |
| 1049 | AND Enantiomer |

INDEX TABLE E-continued

| Ex # | Structure |
|---|---|
| 1050 | 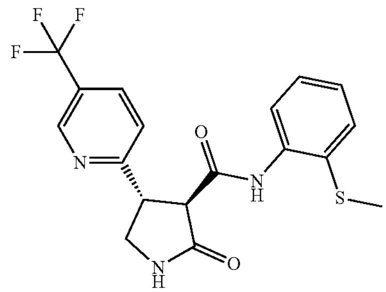 [SMILES: CSc1ccccc1NC(=O)[C@H]1C(=O)NC[C@@H]1c1ccc(C(F)(F)F)cn1] |
| 1051 | 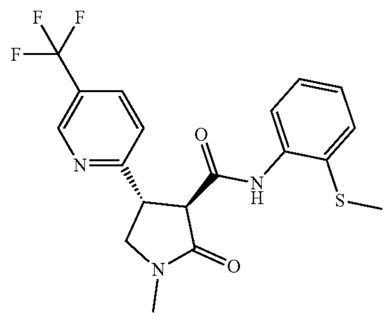 [SMILES: CSc1ccccc1NC(=O)[C@H]1C(=O)N(C)C[C@@H]1c1ccc(C(F)(F)F)cn1] |
| 1052 | 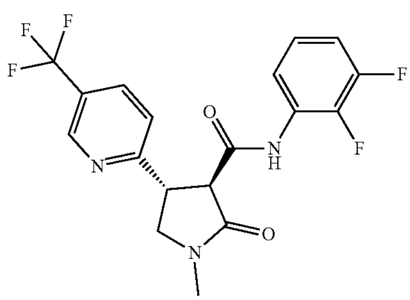 [SMILES: CN1C[C@H](c2ccc(C(F)(F)F)cn2)[C@@H](C(=O)Nc2cccc(F)c2F)C1=O] |
| 1053 | 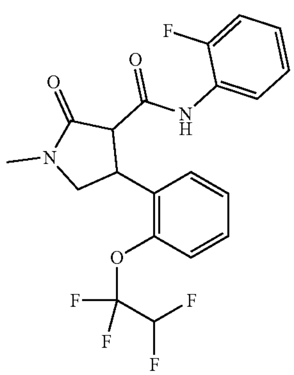 [SMILES: CN1CC(c2ccccc2OC(F)(F)C(F)F)C(C(=O)Nc2ccccc2F)C1=O] |
| 1054 | 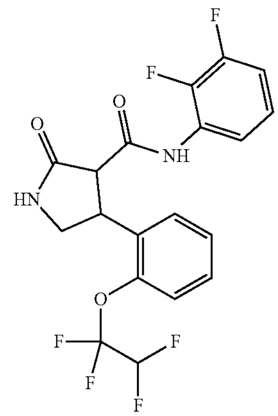 [SMILES: O=C1NCC(c2ccccc2OC(F)(F)C(F)F)C1C(=O)Nc1cccc(F)c1F] |
| 1055 | 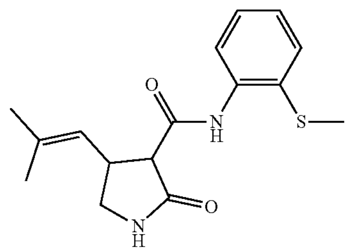 [SMILES: CSc1ccccc1NC(=O)C1C(=O)NCC1C=C(C)C] |
| 1056 | 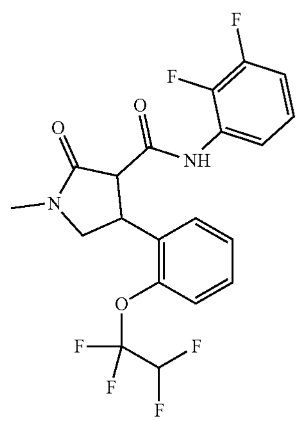 [SMILES: CN1CC(c2ccccc2OC(F)(F)C(F)F)C(C(=O)Nc2cccc(F)c2F)C1=O] |
| 1057 | 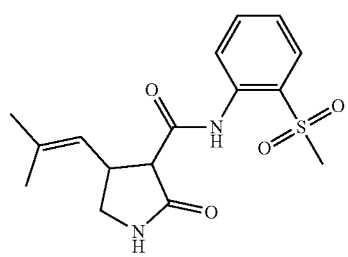 [SMILES: CC(C)=CC1CNC(=O)C1C(=O)Nc1ccccc1S(C)(=O)=O] |
| 1058 | 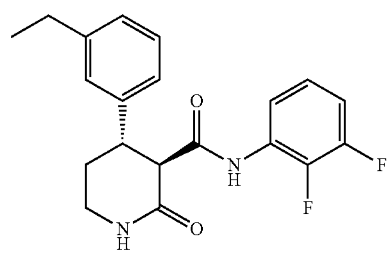 [SMILES: CCc1cccc([C@H]2CCNC(=O)[C@@H]2C(=O)Nc2cccc(F)c2F)c1] |

INDEX TABLE E-continued

| Ex # | Structure |
|------|-----------|
| 1059 | AND Enantiomer |
| 1060 | AND Enantiomer |
| 1061 | 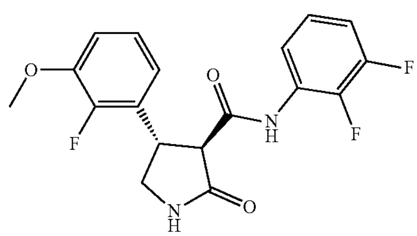 [SMILES: COc1cccc([C@H]2CNC(=O)[C@@H]2C(=O)Nc2cccc(F)c2F)c1F] |
| 1062 | 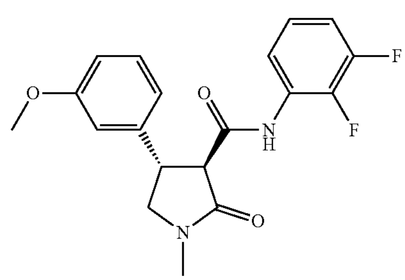 [SMILES: COc1cccc([C@H]2CN(C)C(=O)[C@@H]2C(=O)Nc2cccc(F)c2F)c1] |
| 1063 | 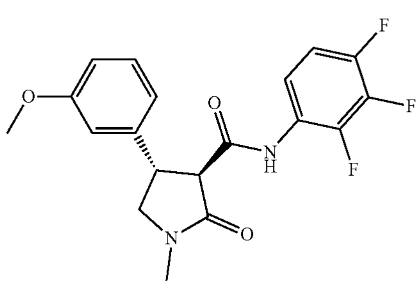 [SMILES: COc1cccc([C@H]2CN(C)C(=O)[C@@H]2C(=O)Nc2ccc(F)c(F)c2F)c1] |
| 1064 | 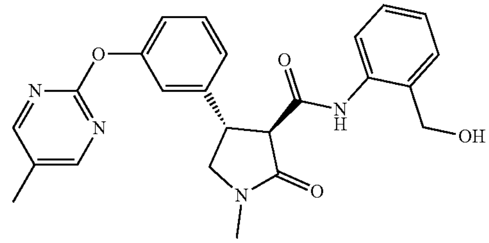 [SMILES: Cc1cnc(Oc2cccc([C@H]3CN(C)C(=O)[C@@H]3C(=O)Nc3ccccc3CO)c2)nc1] |
| 1065 | 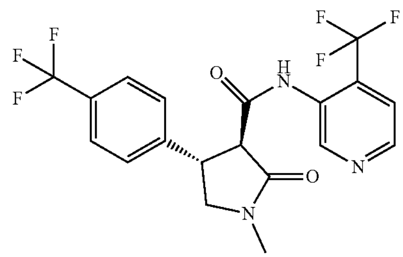 [SMILES: CN1C[C@H](c2ccc(C(F)(F)F)cc2)[C@@H](C(=O)Nc2cnccc2C(F)(F)F)C1=O] |
| 1066 | 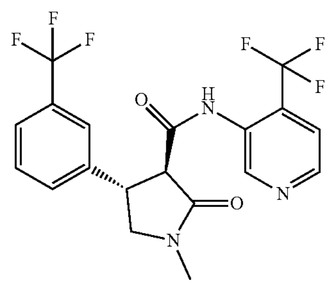 [SMILES: CN1C[C@H](c2cccc(C(F)(F)F)c2)[C@@H](C(=O)Nc2cnccc2C(F)(F)F)C1=O] |
| 1067 | 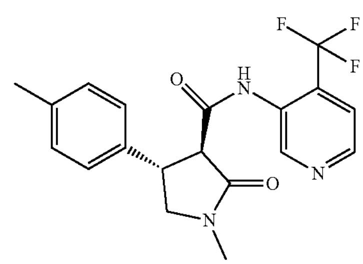 [SMILES: Cc1ccc([C@H]2CN(C)C(=O)[C@@H]2C(=O)Nc2cnccc2C(F)(F)F)cc1] |
| 1068 | 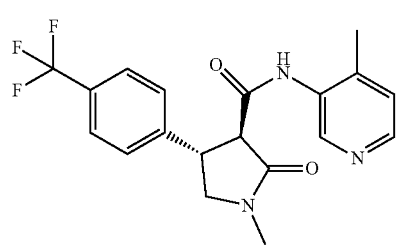 [SMILES: Cc1ccncc1NC(=O)[C@H]1C(=O)N(C)C[C@@H]1c1ccc(C(F)(F)F)cc1] |
| 1069 | 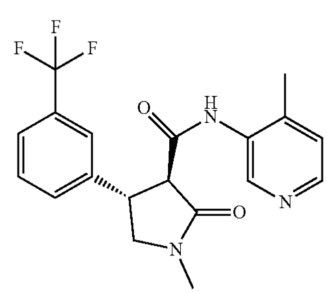 [SMILES: Cc1ccncc1NC(=O)[C@H]1C(=O)N(C)C[C@@H]1c1cccc(C(F)(F)F)c1] |

INDEX TABLE E-continued

| Ex # | Structure |
|------|-----------|
| 1070 | 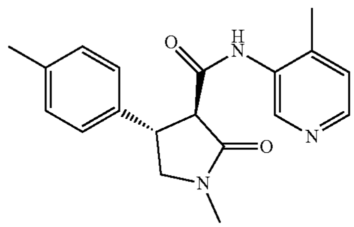 [SMILES: Cc1ccc([C@H]2CN(C)C(=O)[C@@H]2C(=O)Nc2cnccc2C)cc1] |
| 1071 | 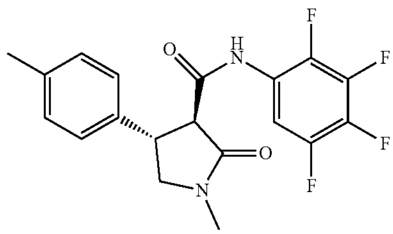 |
| 1072 | 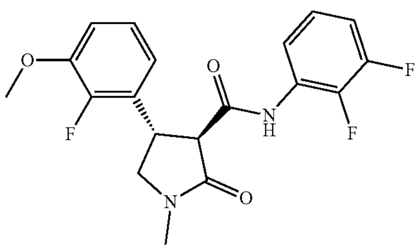 [SMILES: COc1cccc([C@H]2CN(C)C(=O)[C@@H]2C(=O)Nc2cccc(F)c2F)c1F] |
| 1073 | AND Enantiomer |
| 1074 | 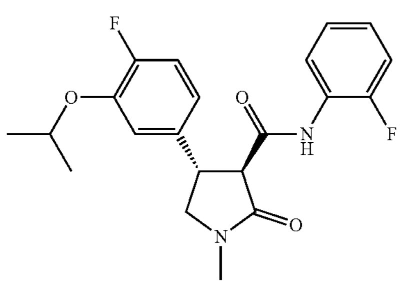 [SMILES: CC(C)Oc1cc([C@H]2CN(C)C(=O)[C@@H]2C(=O)Nc2ccccc2F)ccc1F] |
| 1075 | 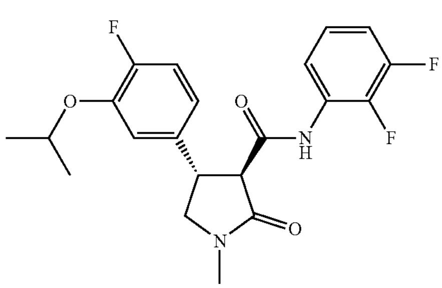 [SMILES: CC(C)Oc1cc([C@H]2CN(C)C(=O)[C@@H]2C(=O)Nc2cccc(F)c2F)ccc1F] |
| 1076 | |
| 1077 | |
| 1078 | |
| 1079 | |
| 1080 | |

INDEX TABLE E-continued
| Ex # | Structure |
|---|---|
| 1081 | 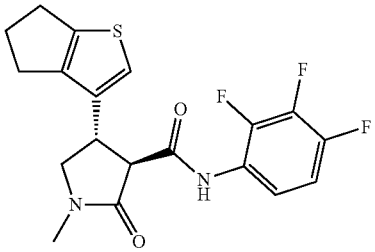 [SMILES: CN1C[C@H](c2csc3c2CCC3)[C@@H](C(=O)Nc2ccc(F)c(F)c2F)C1=O] |
| 1082 | 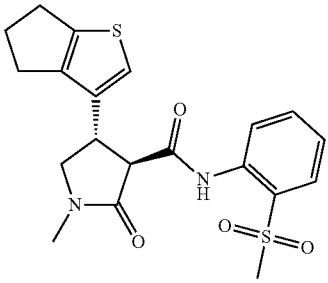 [SMILES: CN1C[C@H](c2csc3c2CCC3)[C@@H](C(=O)Nc2ccccc2S(C)(=O)=O)C1=O] |
| 1083 | 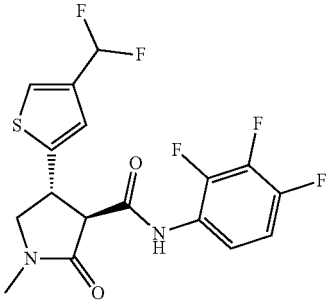 [SMILES: CN1C[C@H](c2cc(C(F)F)cs2)[C@@H](C(=O)Nc2ccc(F)c(F)c2F)C1=O] |
| 1084 | 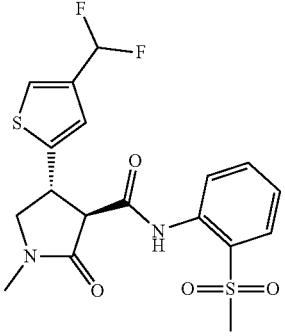 [SMILES: CN1C[C@H](c2cc(C(F)F)cs2)[C@@H](C(=O)Nc2ccccc2S(C)(=O)=O)C1=O] |
| 1085 | 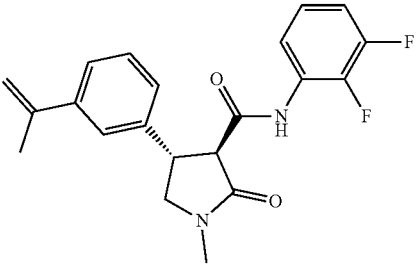 [SMILES: C=C(C)c1cccc([C@H]2CN(C)C(=O)[C@@H]2C(=O)Nc2cccc(F)c2F)c1] |
| 1086 | 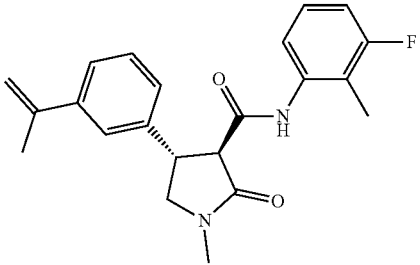 [SMILES: C=C(C)c1cccc([C@H]2CN(C)C(=O)[C@@H]2C(=O)Nc2cccc(F)c2C)c1] |
| 1087 | 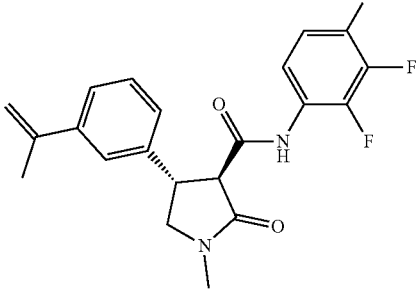 |
| 1088 | 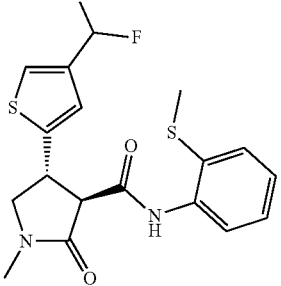 |
| 1089 | 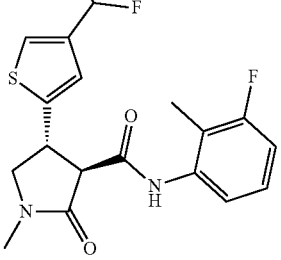 |
| 1090 | 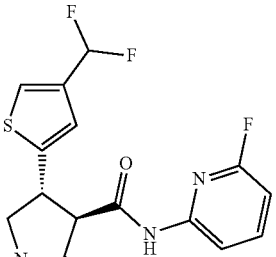 |

INDEX TABLE E-continued

| Ex # | Structure |
|---|---|
| 1091 | |
| 1092 | |
| 1093 | |
| 1094 | AND Enantiomer |

INDEX TABLE E-continued

| Ex # | Structure |
|---|---|
| 1095 | 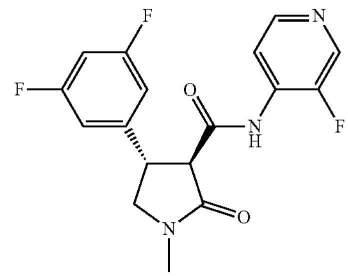 [SMILES: CN1C[C@H](c2cc(F)cc(F)c2)[C@@H](C(=O)Nc2ccncc2F)C1=O] |
| 1096 | 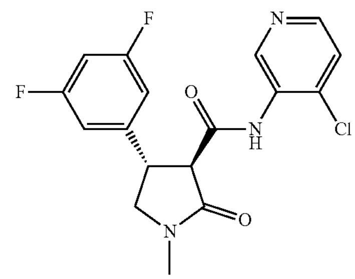 [SMILES: CN1C[C@H](c2cc(F)cc(F)c2)[C@@H](C(=O)Nc2cnccc2Cl)C1=O] |
| 1097 | 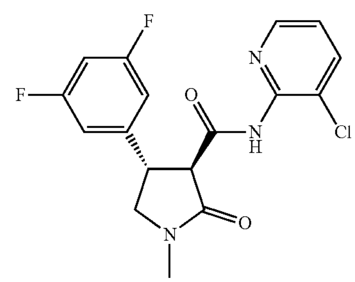 [SMILES: CN1C[C@H](c2cc(F)cc(F)c2)[C@@H](C(=O)Nc2ncccc2Cl)C1=O] |
| 1098 | 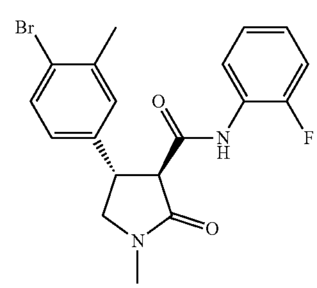 |
| 1099 | 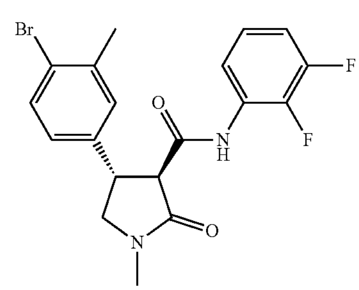 [SMILES: Cc1cc([C@H]2CN(C)C(=O)[C@@H]2C(=O)Nc2cccc(F)c2F)ccc1Br] |

INDEX TABLE E-continued

| Ex # | Structure |
|---|---|
| 1100 | 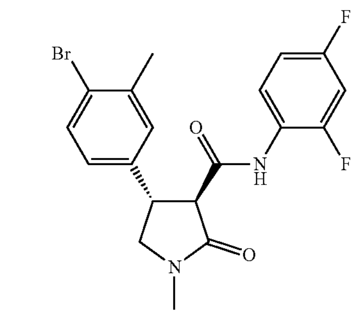 [SMILES: Cc1cc([C@H]2CN(C)C(=O)[C@@H]2C(=O)Nc2ccc(F)cc2F)ccc1Br] |
| 1101 | 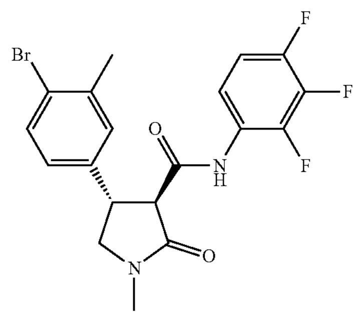 |
| 1102 | 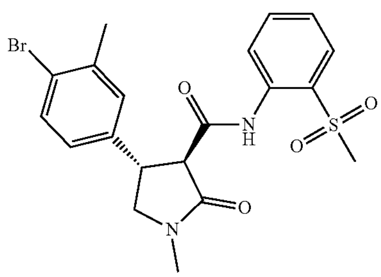 [SMILES: Cc1cc([C@H]2CN(C)C(=O)[C@@H]2C(=O)Nc2ccccc2S(C)(=O)=O)ccc1Br] |
| 1103 | 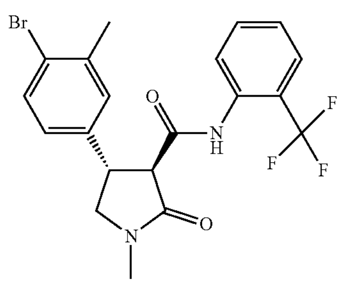 [SMILES: Cc1cc([C@H]2CN(C)C(=O)[C@@H]2C(=O)Nc2ccccc2C(F)(F)F)ccc1Br] |
| 1104 | 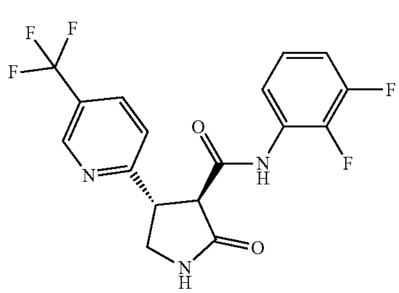 [SMILES: O=C1NC[C@H](c2ccc(C(F)(F)F)cn2)[C@H]1C(=O)Nc1cccc(F)c1F] |

INDEX TABLE E-continued

| Ex # | Structure |
|---|---|
| 1105 | 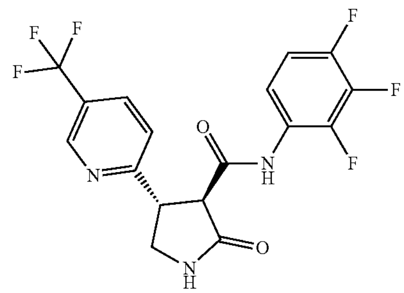 [SMILES: O=C1NC[C@H](c2ccc(C(F)(F)F)cn2)[C@H]1C(=O)Nc1ccc(F)c(F)c1F] |
| 1106 | 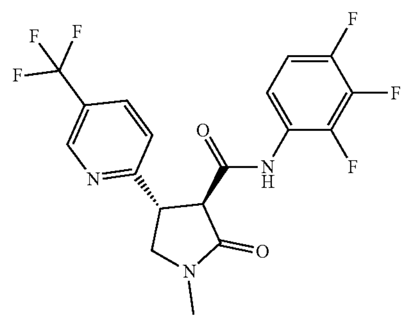 [SMILES: CN1C[C@H](c2ccc(C(F)(F)F)cn2)[C@@H](C(=O)Nc2ccc(F)c(F)c2F)C1=O] |
| 1107 | 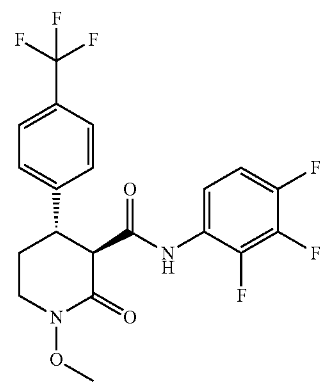 [SMILES: CON1CC[C@H](c2ccc(C(F)(F)F)cc2)[C@@H](C(=O)Nc2ccc(F)c(F)c2F)C1=O] |
| 1108 | 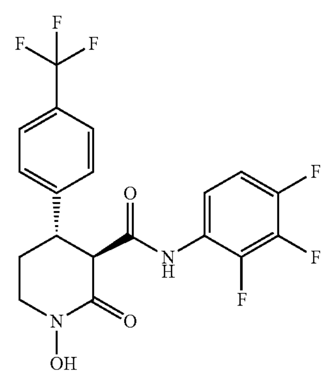 [SMILES: O=C(Nc1ccc(F)c(F)c1F)[C@H]1C(=O)N(O)CC[C@@H]1c1ccc(C(F)(F)F)cc1] |

INDEX TABLE E-continued
| Ex # | Structure |
|---|---|
| 1109 | 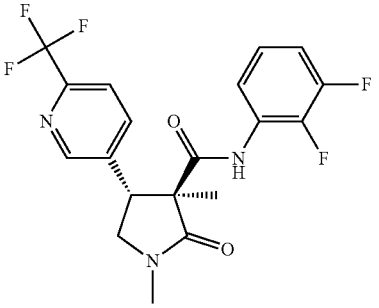 [SMILES: CN1C[C@H](c2ccc(C(F)(F)F)nc2)[C@@](C)(C(=O)Nc2cccc(F)c2F)C1=O] |
| 1110 | 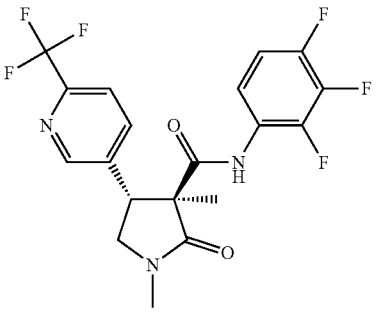 [SMILES: CN1C[C@H](c2ccc(C(F)(F)F)nc2)[C@@](C)(C(=O)Nc2ccc(F)c(F)c2F)C1=O] |
| 1111 | 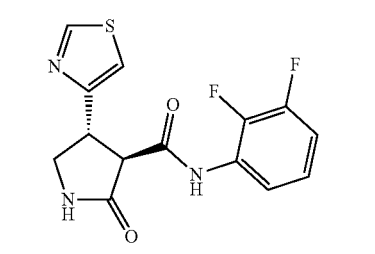 [SMILES: O=C1NC[C@H](c2cscn2)[C@H]1C(=O)Nc1cccc(F)c1F] |
| 1112 | 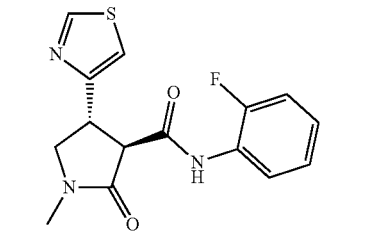 [SMILES: CN1C[C@H](c2cscn2)[C@@H](C(=O)Nc2ccccc2F)C1=O] |
| 1113 | 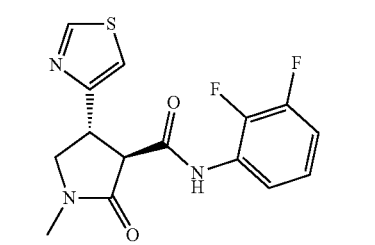 [SMILES: CN1C[C@H](c2cscn2)[C@@H](C(=O)Nc2cccc(F)c2F)C1=O] |
INDEX TABLE E-continued
| Ex # | Structure |
|---|---|
| 1114 | 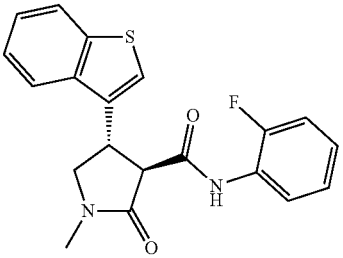 [SMILES: CN1C[C@H](c2csc3ccccc23)[C@@H](C(=O)Nc2ccccc2F)C1=O] |
| 1115 | 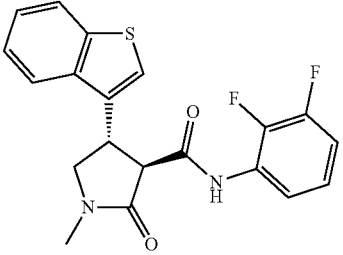 [SMILES: CN1C[C@H](c2csc3ccccc23)[C@@H](C(=O)Nc2cccc(F)c2F)C1=O] |
| 1116 | 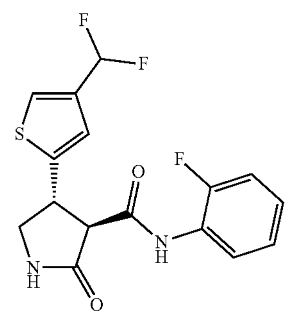 [SMILES: O=C1NC[C@H](c2cc(C(F)F)cs2)[C@H]1C(=O)Nc1ccccc1F] |
| 1117 | 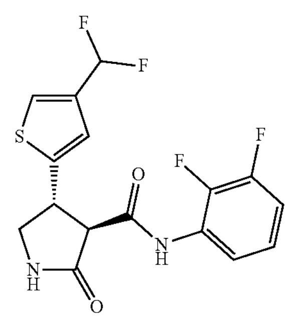 [SMILES: O=C1NC[C@H](c2cc(C(F)F)cs2)[C@H]1C(=O)Nc1cccc(F)c1F] |
| 1118 | 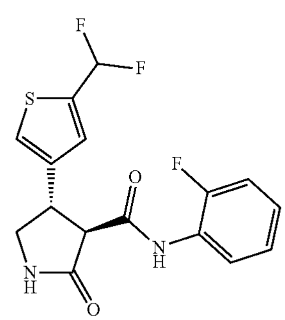 [SMILES: O=C1NC[C@H](c2csc(C(F)F)c2)[C@H]1C(=O)Nc1ccccc1F] |

INDEX TABLE E-continued
| Ex # | Structure |
|---|---|
| 1119 | 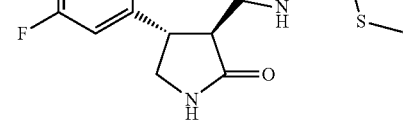 |
| 1120 | |
| 1121 | |
| 1122 | |
| 1123 | |
INDEX TABLE E-continued
| Ex # | Structure |
|---|---|
| 1124 | 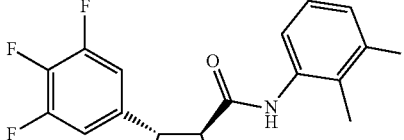 |
| 1125 | 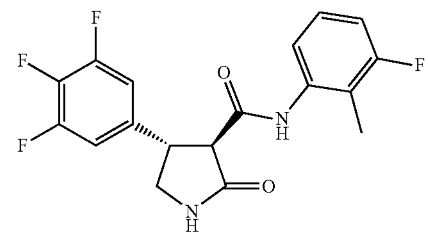 [SMILES: Cc1c(F)cccc1NC(=O)[C@H]1C(=O)NC[C@@H]1c1cc(F)c(F)c(F)c1] |
| 1126 | 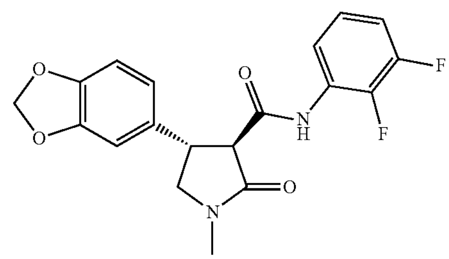 [SMILES: CN1C[C@H](c2ccc3c(c2)OCO3)[C@@H](C(=O)Nc2cccc(F)c2F)C1=O] |
| 1127 | 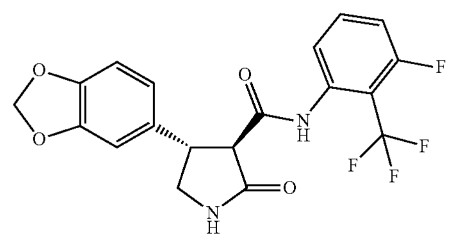 [SMILES: O=C1NC[C@H](c2ccc3c(c2)OCO3)[C@H]1C(=O)Nc1cccc(F)c1C(F)(F)F] |
| 1128 | 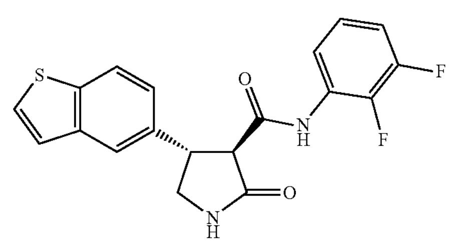 [SMILES: O=C1NC[C@H](c2ccc3sccc3c2)[C@H]1C(=O)Nc1cccc(F)c1F] |
| 1129 | 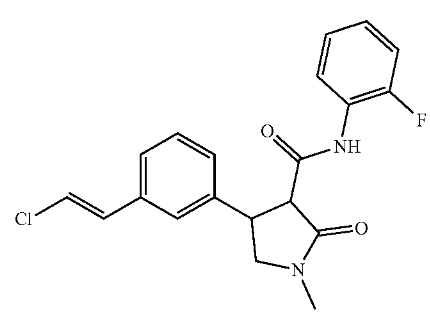 [SMILES: CN1CC(c2cccc(/C=C/Cl)c2)C(C(=O)Nc2ccccc2F)C1=O] |

INDEX TABLE E-continued

| Ex # | Structure |
|---|---|
| 1130 | 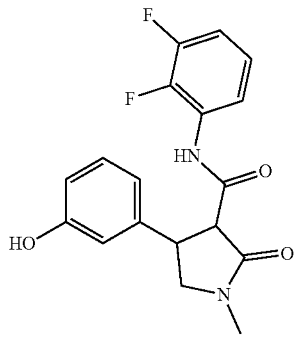 [SMILES: CN1CC(c2cccc(O)c2)C(C(=O)Nc2cccc(F)c2F)C1=O] |
| 1131 | 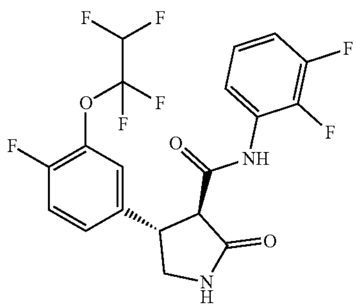 [SMILES: O=C1NC[C@H](c2ccc(F)c(OC(F)(F)C(F)F)c2)[C@H]1C(=O)Nc1cccc(F)c1F] |
| 1132 | 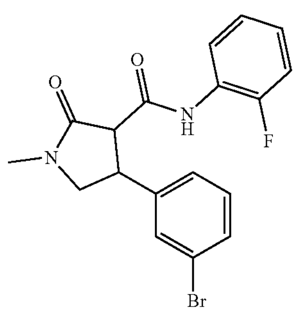 [SMILES: CN1CC(c2cccc(Br)c2)C(C(=O)Nc2ccccc2F)C1=O] |
| 1133 | 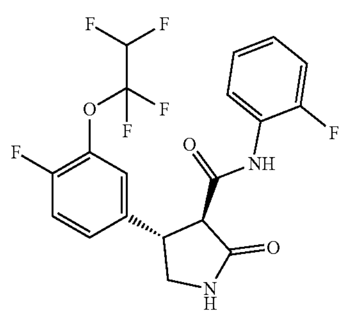 [SMILES: O=C1NC[C@H](c2ccc(F)c(OC(F)(F)C(F)F)c2)[C@H]1C(=O)Nc1ccccc1F] |
| 1134 | 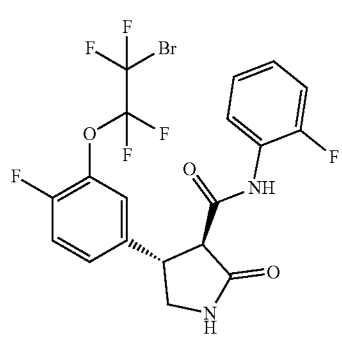 [SMILES: O=C1NC[C@H](c2ccc(F)c(OC(F)(F)C(F)(F)Br)c2)[C@H]1C(=O)Nc1ccccc1F] |
| 1135 | |
| 1136 | |
| 1137 | |
| 1138 | |
| 1139 | |

INDEX TABLE E-continued

| Ex # | Structure |
|---|---|
| 1140 | 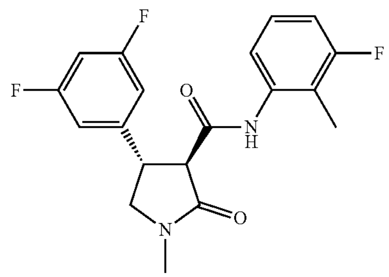 [SMILES: Cc1c(F)cccc1NC(=O)[C@H]1C(=O)N(C)C[C@@H]1c1cc(F)cc(F)c1] |
| 1141 | 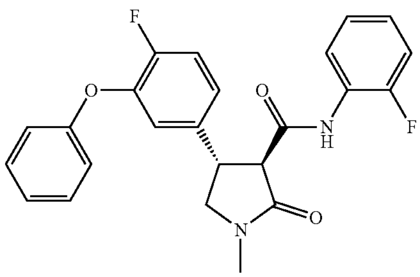 [SMILES: CN1C[C@H](c2ccc(F)c(Oc3ccccc3)c2)[C@@H](C(=O)Nc2ccccc2F)C1=O] |
| 1142 | 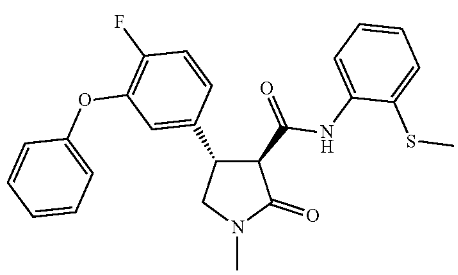 [SMILES: CSc1ccccc1NC(=O)[C@H]1C(=O)N(C)C[C@@H]1c1ccc(F)c(Oc2ccccc2)c1] |
| 1143 | 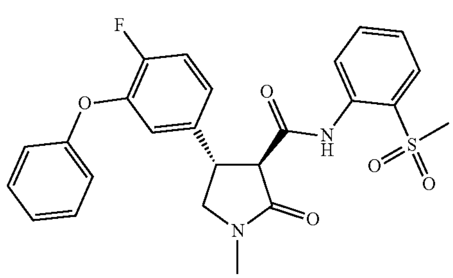 [SMILES: CN1C[C@H](c2ccc(F)c(Oc3ccccc3)c2)[C@@H](C(=O)Nc2ccccc2S(C)(=O)=O)C1=O] |
| 1144 | 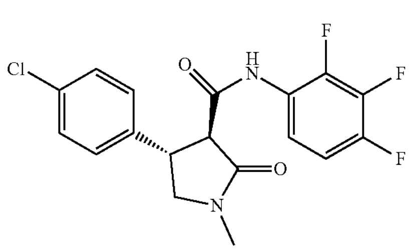 [SMILES: CN1C[C@H](c2ccc(Cl)cc2)[C@@H](C(=O)Nc2ccc(F)c(F)c2F)C1=O] |
| 1145 | |
| 1146 | |
| 1147 | |
| 1148 | |

INDEX TABLE E-continued

| Ex # | Structure |
|---|---|
| 1149 | 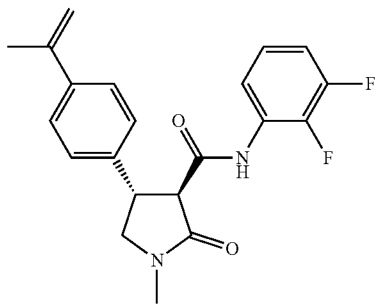 [SMILES: C=C(C)c1ccc([C@H]2CN(C)C(=O)[C@@H]2C(=O)Nc2cccc(F)c2F)cc1] |
| 1150 | 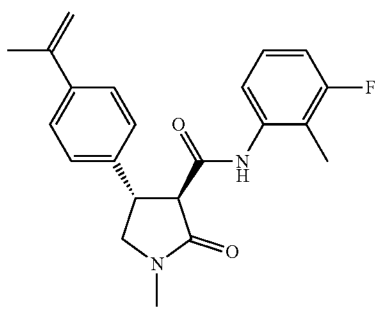 [SMILES: C=C(C)c1ccc([C@H]2CN(C)C(=O)[C@@H]2C(=O)Nc2cccc(F)c2C)cc1] |
| 1151 | AND Enantiomer |
| 1152 | AND Enantiomer |

INDEX TABLE E-continued

| Ex # | Structure |
|---|---|
| 1153 | AND Enantiomer |
| 1154 | AND Enantiomer |
| 1155 | 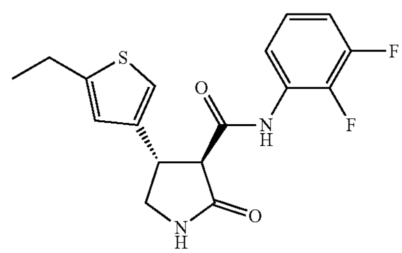 [SMILES: CCc1cc([C@H]2CNC(=O)[C@@H]2C(=O)Nc2cccc(F)c2F)cs1] |
| 1156 | 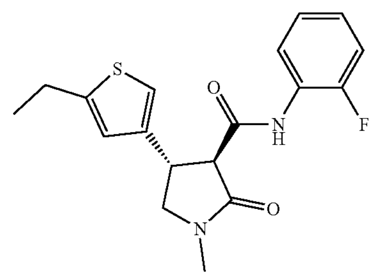 [SMILES: CCc1cc([C@H]2CN(C)C(=O)[C@@H]2C(=O)Nc2ccccc2F)cs1] |
| 1157 | 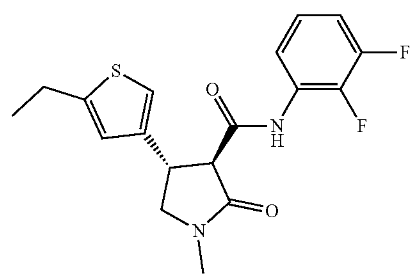 [SMILES: CCc1cc([C@H]2CN(C)C(=O)[C@@H]2C(=O)Nc2cccc(F)c2F)cs1] |

INDEX TABLE E-continued

| Ex # | Structure |
|---|---|
| 1158 | 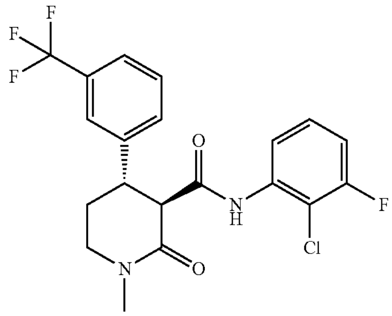 [SMILES: CN1CC[C@H](c2cccc(C(F)(F)F)c2)[C@@H](C(=O)Nc2cccc(F)c2Cl)C1=O] |
| 1159 | 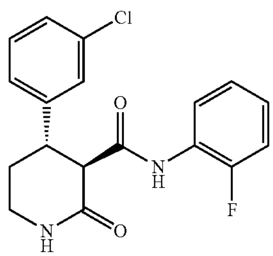 [SMILES: O=C1NCC[C@H](c2cccc(Cl)c2)[C@H]1C(=O)Nc1ccccc1F] |
| 1160 | 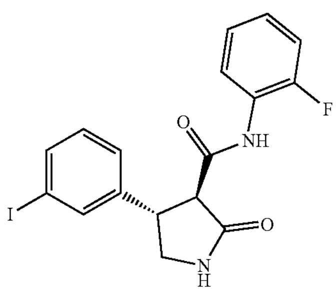 [SMILES: O=C1NC[C@H](c2cccc(I)c2)[C@H]1C(=O)Nc1ccccc1F] |
| 1161 | AND Enantiomer |

INDEX TABLE E-continued

| Ex # | Structure |
|---|---|
| 1162 | AND Enantiomer |
| 1163 | 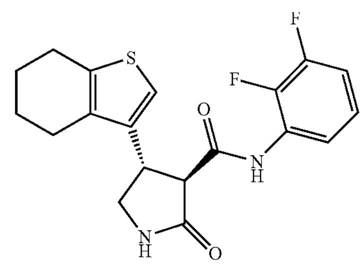 [SMILES: O=C1NC[C@H](c2csc3c2CCCC3)[C@H]1C(=O)Nc1cccc(F)c1F] |
| 1164 | 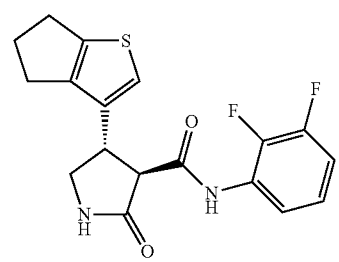 [SMILES: O=C1NC[C@H](c2csc3c2CCC3)[C@H]1C(=O)Nc1cccc(F)c1F] |
| 1165 | 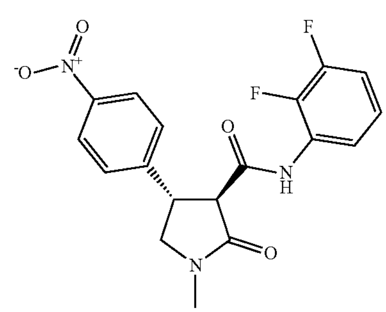 |

INDEX TABLE E-continued

| Ex # | Structure |
|---|---|
| 1166 | 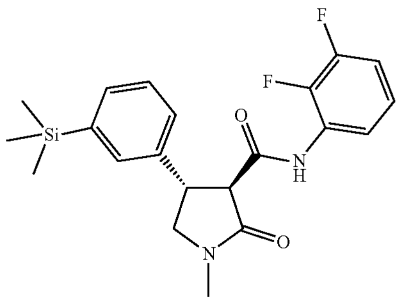 [SMILES: CN1C[C@H](c2cccc([Si](C)(C)C)c2)[C@@H](C(=O)Nc2cccc(F)c2F)C1=O] |
| 1167 | 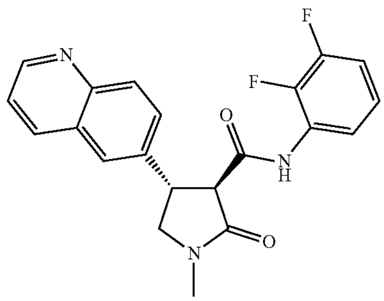 [SMILES: CN1C[C@H](c2ccc3ncccc3c2)[C@@H](C(=O)Nc2cccc(F)c2F)C1=O] |
| 1168 | 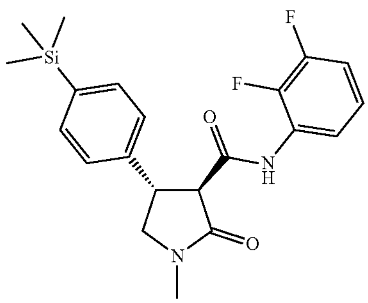 [SMILES: CN1C[C@H](c2ccc([Si](C)(C)C)cc2)[C@@H](C(=O)Nc2cccc(F)c2F)C1=O] |
| 1169 | 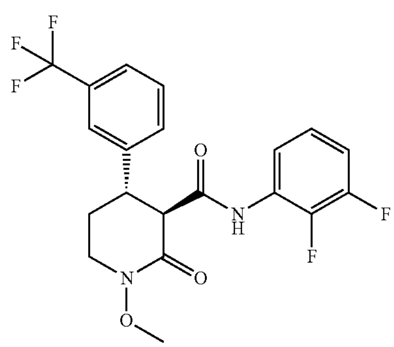 [SMILES: CON1CC[C@H](c2cccc(C(F)(F)F)c2)[C@@H](C(=O)Nc2cccc(F)c2F)C1=O] |
| 1170 | 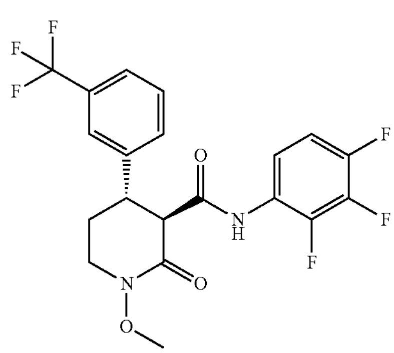 [SMILES: CON1CC[C@H](c2cccc(C(F)(F)F)c2)[C@@H](C(=O)Nc2ccc(F)c(F)c2F)C1=O] |
| 1171 | |
| 1172 | |
| 1173 | |
| 1174 | |

INDEX TABLE E-continued

| Ex # | Structure |
|---|---|
| 1175 | 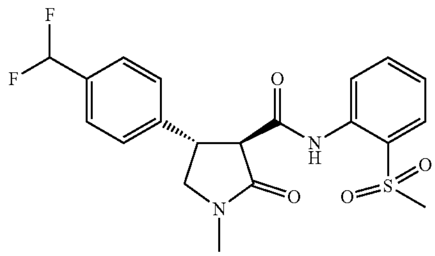 [SMILES: CN1C[C@H](c2ccc(C(F)F)cc2)[C@@H](C(=O)Nc2ccccc2S(C)(=O)=O)C1=O] |
| 1176 | 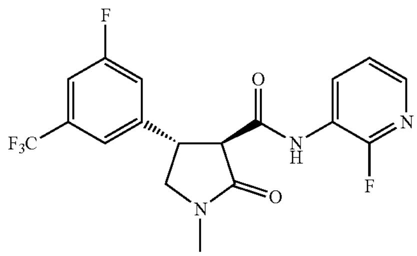 [SMILES: CN1C[C@H](c2cc(F)cc(C(F)(F)F)c2)[C@@H](C(=O)Nc2cccnc2F)C1=O] |
| 1177 | 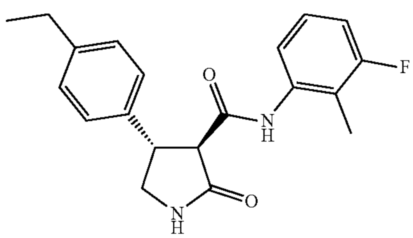 [SMILES: CCc1ccc([C@H]2CNC(=O)[C@@H]2C(=O)Nc2cccc(F)c2C)cc1] |
| 1178 | 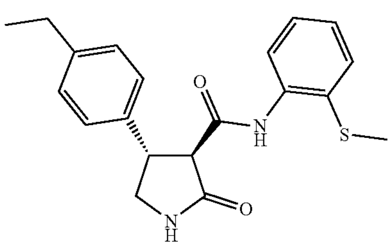 [SMILES: CCc1ccc([C@H]2CNC(=O)[C@@H]2C(=O)Nc2ccccc2SC)cc1] |
| 1179 | 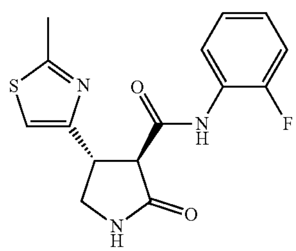 [SMILES: Cc1nc([C@H]2CNC(=O)[C@@H]2C(=O)Nc2ccccc2F)cs1] |
| 1180 | 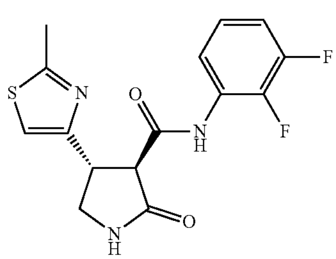 [SMILES: Cc1nc([C@H]2CNC(=O)[C@@H]2C(=O)Nc2cccc(F)c2F)cs1] |
| 1181 | |
| 1182 | |
| 1183 | |
| 1184 | |
| 1185 | |
| 1186 | |

INDEX TABLE E-continued

| Ex # | Structure |
|---|---|
| 1187 | 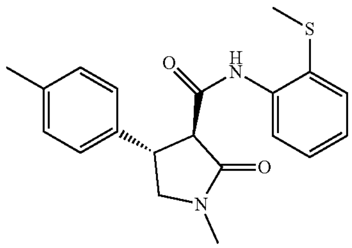 [SMILES: CSc1ccccc1NC(=O)[C@H]1C(=O)N(C)C[C@@H]1c1ccc(C)cc1] |
| 1188 | 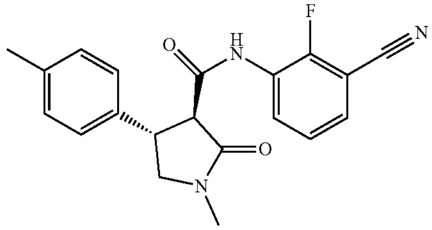 [SMILES: Cc1ccc([C@H]2CN(C)C(=O)[C@@H]2C(=O)Nc2cccc(C#N)c2F)cc1] |
| 1189 | 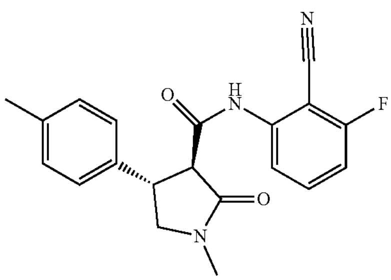 [SMILES: Cc1ccc([C@H]2CN(C)C(=O)[C@@H]2C(=O)Nc2cccc(F)c2C#N)cc1] |
| 1190 | 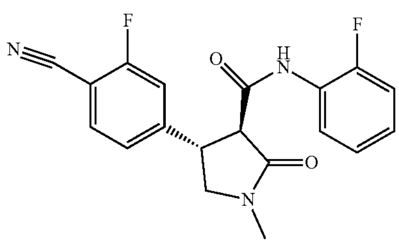 [SMILES: CN1C[C@H](c2ccc(C#N)c(F)c2)[C@@H](C(=O)Nc2ccccc2F)C1=O] |
| 1191 | 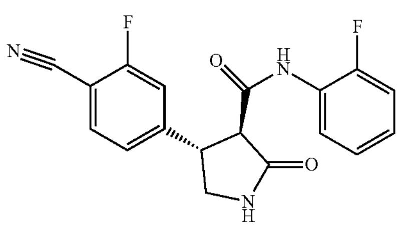 [SMILES: N#Cc1ccc([C@H]2CNC(=O)[C@@H]2C(=O)Nc2ccccc2F)cc1F] |
| 1192 | 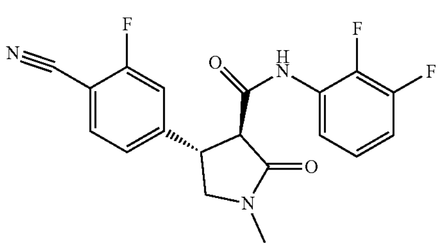 [SMILES: CN1C[C@H](c2ccc(C#N)c(F)c2)[C@@H](C(=O)Nc2cccc(F)c2F)C1=O] |

INDEX TABLE E-continued

| Ex # | Structure |
|---|---|
| 1193 | 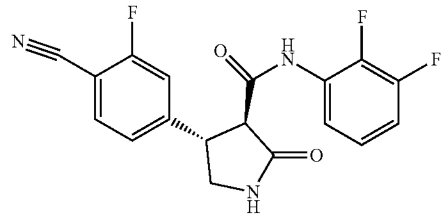 [SMILES: N#Cc1ccc([C@H]2CNC(=O)[C@@H]2C(=O)Nc2cccc(F)c2F)cc1F] |
| 1194 | 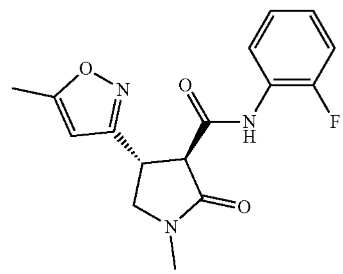 [SMILES: Cc1cc([C@H]2CN(C)C(=O)[C@@H]2C(=O)Nc2ccccc2F)no1] |
| 1195 | 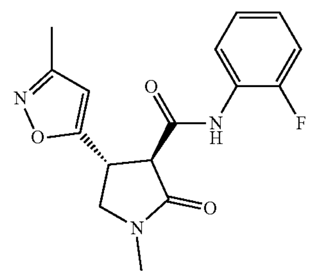 [SMILES: Cc1cc([C@H]2CN(C)C(=O)[C@@H]2C(=O)Nc2ccccc2F)on1] |
| 1196 | 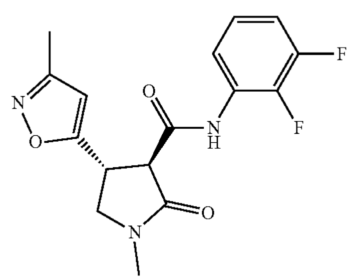 [SMILES: Cc1cc([C@H]2CN(C)C(=O)[C@@H]2C(=O)Nc2cccc(F)c2F)on1] |
| 1197 | 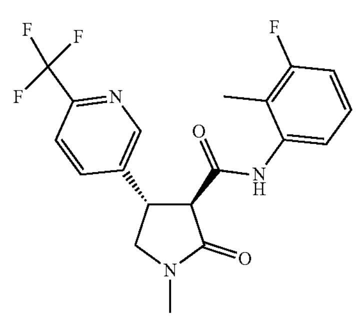 [SMILES: Cc1c(F)cccc1NC(=O)[C@H]1C(=O)N(C)C[C@@H]1c1ccc(C(F)(F)F)nc1] |

INDEX TABLE E-continued

| Ex # | Structure |
|------|-----------|
| 1198 | 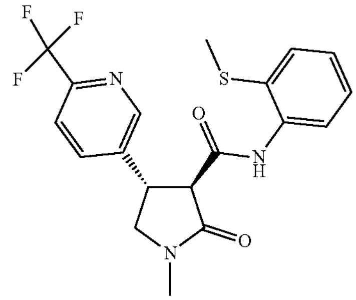 [SMILES: CSc1ccccc1NC(=O)[C@H]1C(=O)N(C)C[C@@H]1c1ccc(C(F)(F)F)nc1] |
| 1199 | 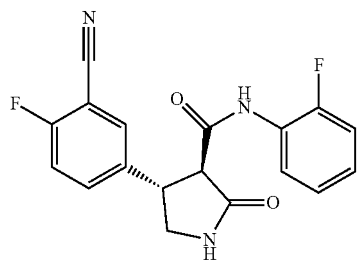 [SMILES: N#Cc1cc([C@H]2CNC(=O)[C@@H]2C(=O)Nc2ccccc2F)ccc1F] |
| 1200 | 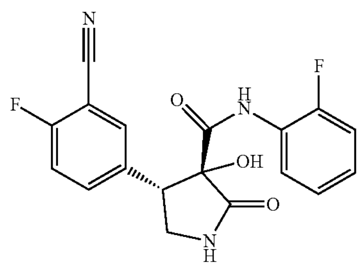 [SMILES: N#Cc1cc([C@H]2CNC(=O)[C@]2(O)C(=O)Nc2ccccc2F)ccc1F] |
| 1201 | 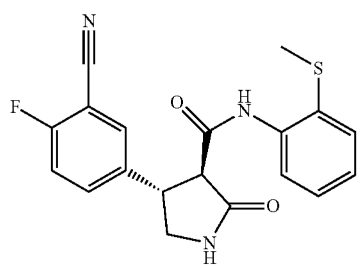 [SMILES: CSc1ccccc1NC(=O)[C@H]1C(=O)NC[C@@H]1c1ccc(F)c(C#N)c1] |
| 1202 | 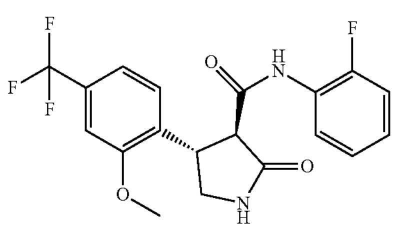 [SMILES: COc1cc(C(F)(F)F)ccc1[C@H]1CNC(=O)[C@@H]1C(=O)Nc1ccccc1F] |
| 1203 | 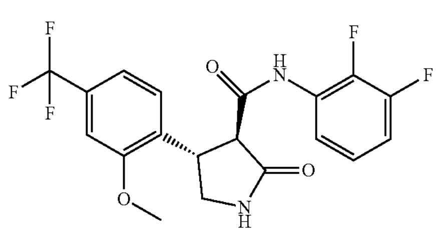 [SMILES: COc1cc(C(F)(F)F)ccc1[C@H]1CNC(=O)[C@@H]1C(=O)Nc1cccc(F)c1F] |
| 1204 | |
| 1205 | |
| 1206 | |
| 1207 | |
| 1208 | |
| 1209 | |

INDEX TABLE E-continued

| Ex # | Structure |
|---|---|
| 1210 | 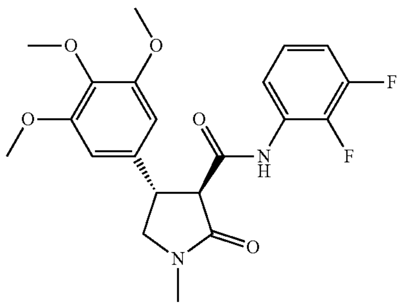 [SMILES: COc1cc([C@H]2CN(C)C(=O)[C@@H]2C(=O)Nc2cccc(F)c2F)cc(OC)c1OC] |
| 1211 | 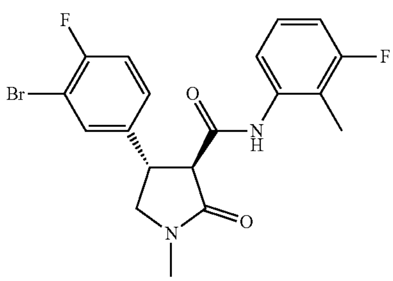 [SMILES: Cc1c(F)cccc1NC(=O)[C@H]1C(=O)N(C)C[C@@H]1c1ccc(F)c(Br)c1] |
| 1212 | 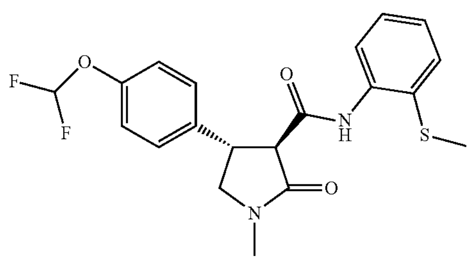 [SMILES: CSc1ccccc1NC(=O)[C@H]1C(=O)N(C)C[C@@H]1c1ccc(OC(F)F)cc1] |
| 1213 | 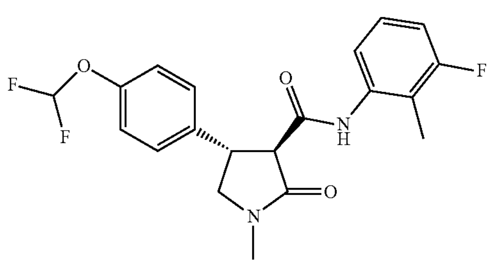 [SMILES: Cc1c(F)cccc1NC(=O)[C@H]1C(=O)N(C)C[C@@H]1c1ccc(OC(F)F)cc1] |
| 1214 | 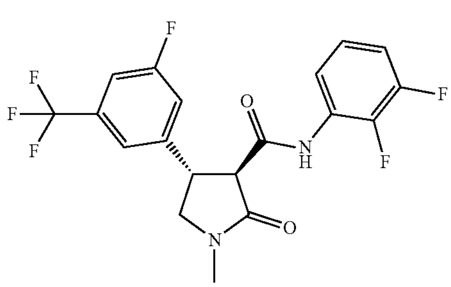 [SMILES: CN1C[C@H](c2cc(F)cc(C(F)(F)F)c2)[C@@H](C(=O)Nc2cccc(F)c2F)C1=O] |

INDEX TABLE E-continued

| Ex # | Structure |
|---|---|
| 1215 | |
| 1216 | |
| 1217 | |
| 1218 | |
| 1219 | |

INDEX TABLE E-continued

| Ex # | Structure |
|---|---|
| 1220 | 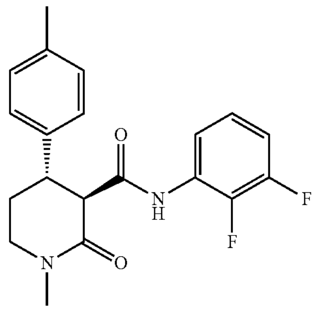 [SMILES: Cc1ccc([C@H]2CCN(C)C(=O)[C@@H]2C(=O)Nc2cccc(F)c2F)cc1] |
| 1221 | 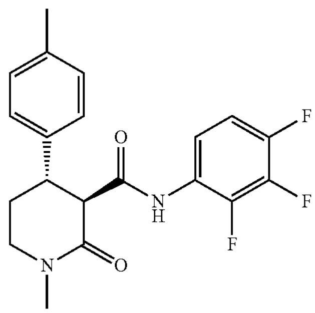 [SMILES: Cc1ccc([C@H]2CCN(C)C(=O)[C@@H]2C(=O)Nc2ccc(F)c(F)c2F)cc1] |
| 1222 | 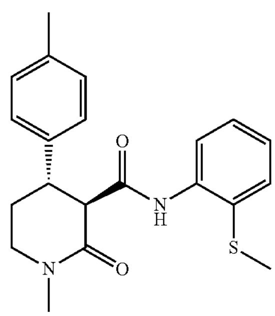 [SMILES: CSc1ccccc1NC(=O)[C@H]1C(=O)N(C)CC[C@@H]1c1ccc(C)cc1] |
| 1223 | 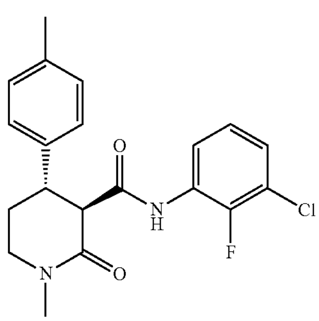 [SMILES: Cc1ccc([C@H]2CCN(C)C(=O)[C@@H]2C(=O)Nc2cccc(Cl)c2F)cc1] |
| 1224 | 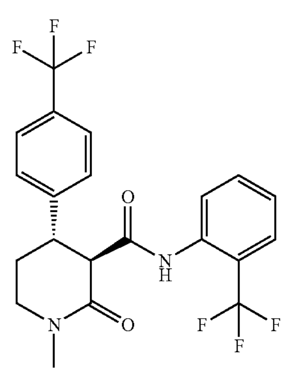 [SMILES: CN1CC[C@H](c2ccc(C(F)(F)F)cc2)[C@@H](C(=O)Nc2ccccc2C(F)(F)F)C1=O] |
| 1225 | |
| 1226 | |
| 1227 | |
| 1228 | |

INDEX TABLE E-continued

| Ex # | Structure |
|------|-----------|
| 1229 | 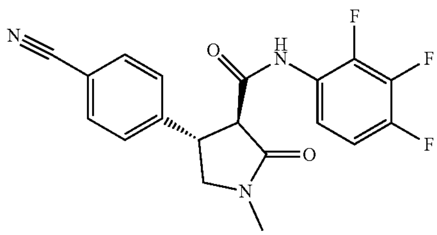 [SMILES: CN1C[C@H](c2ccc(C#N)cc2)[C@@H](C(=O)Nc2ccc(F)c(F)c2F)C1=O] |
| 1230 | 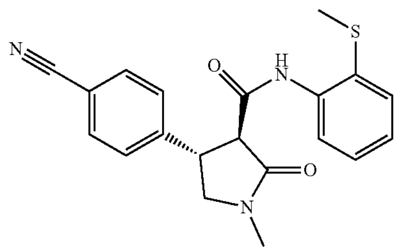 [SMILES: CSc1ccccc1NC(=O)[C@H]1C(=O)N(C)C[C@@H]1c1ccc(C#N)cc1] |
| 1231 | 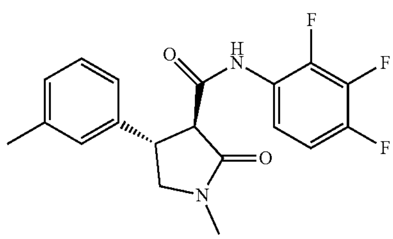 [SMILES: Cc1cccc([C@H]2CN(C)C(=O)[C@@H]2C(=O)Nc2ccc(F)c(F)c2F)c1] |
| 1232 | 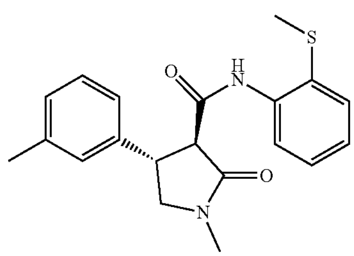 [SMILES: CSc1ccccc1NC(=O)[C@H]1C(=O)N(C)C[C@@H]1c1cccc(C)c1] |
| 1233 | 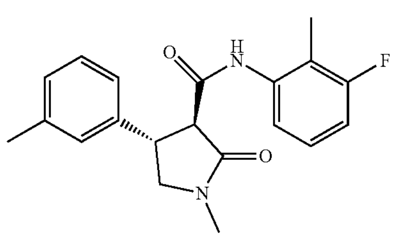 [SMILES: Cc1cccc([C@H]2CN(C)C(=O)[C@@H]2C(=O)Nc2cccc(F)c2C)c1] |
| 1234 | 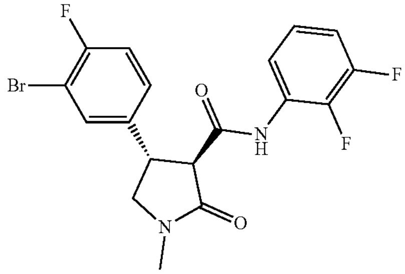 [SMILES: CN1C[C@H](c2ccc(F)c(Br)c2)[C@@H](C(=O)Nc2cccc(F)c2F)C1=O] |
| 1235 | |
| 1236 | |
| 1237 | |
| 1238 | |
| 1239 | |

US 10,654,804 B2
INDEX TABLE E-continued
| Ex # | Structure |
|---|---|
| 1240 | 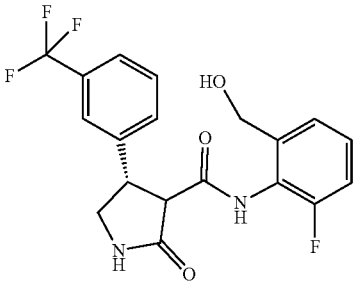 [SMILES: O=C1NC[C@H](c2cccc(C(F)(F)F)c2)C1C(=O)Nc1c(F)cccc1CO] |
| 1241 | 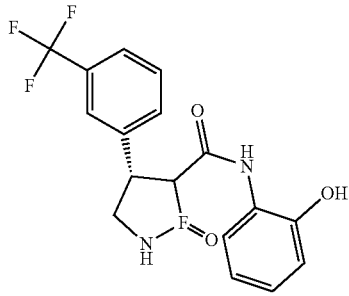 |
| 1242 | 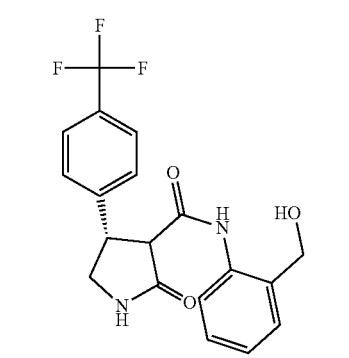 [SMILES: O=C1NC[C@H](c2ccc(C(F)(F)F)cc2)C1C(=O)Nc1ccccc1CO] |
| 1243 | 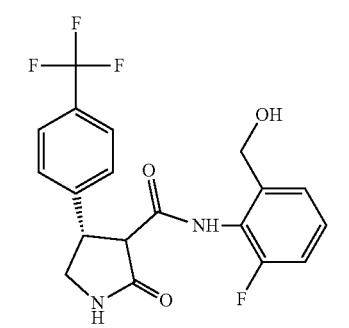 [SMILES: O=C1NC[C@H](c2ccc(C(F)(F)F)cc2)C1C(=O)Nc1c(F)cccc1CO] |
| 1244 | 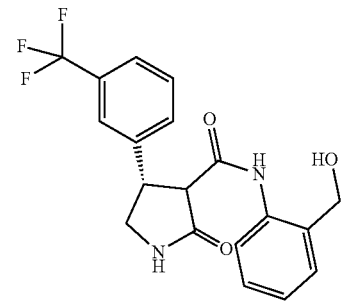 [SMILES: O=C1NC[C@H](c2cccc(C(F)(F)F)c2)C1C(=O)Nc1ccccc1CO] |
| 1245 | 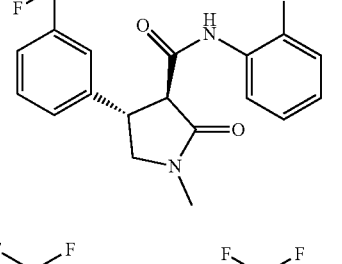 |
| 1246 | 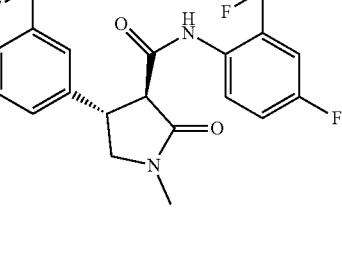 |
| 1247 | 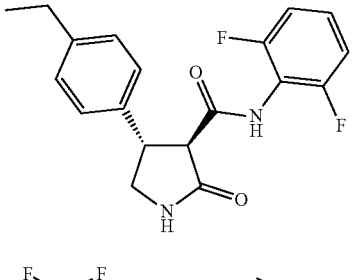 |
| 1248 | 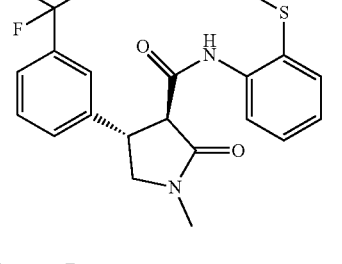 |
| 1249 | 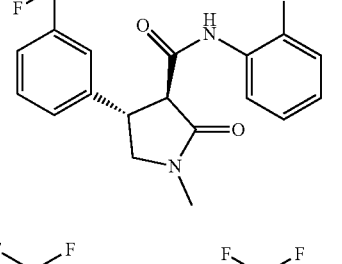 |
| 1250 | 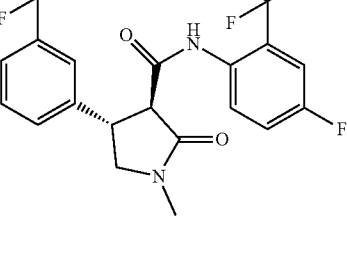 |

INDEX TABLE E-continued

| Ex # | Structure |
|---|---|
| 1251 | 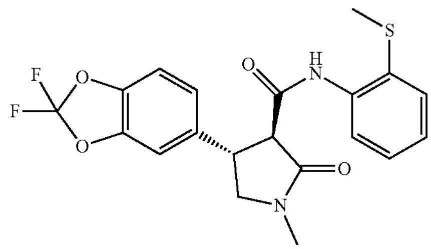 [SMILES: CSc1ccccc1NC(=O)[C@H]1C(=O)N(C)C[C@@H]1c1ccc2c(c1)OC(F)(F)O2] |
| 1252 | 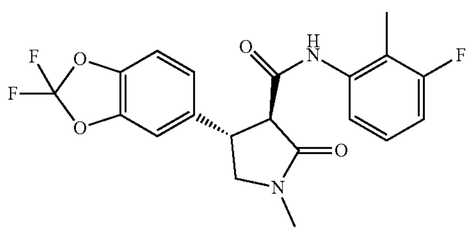 [SMILES: Cc1c(F)cccc1NC(=O)[C@H]1C(=O)N(C)C[C@@H]1c1ccc2c(c1)OC(F)(F)O2] |
| 1253 | 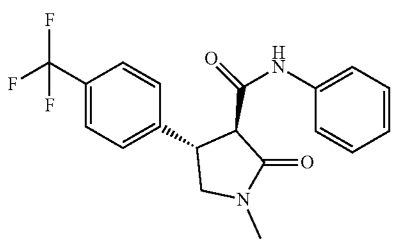 [SMILES: CN1C[C@H](c2ccc(C(F)(F)F)cc2)[C@@H](C(=O)Nc2ccccc2)C1=O] |
| 1254 | 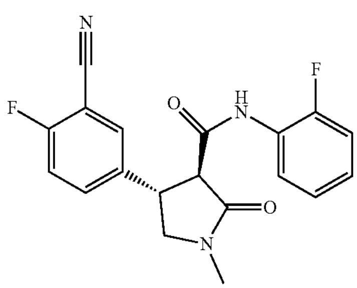 [SMILES: CN1C[C@H](c2ccc(F)c(C#N)c2)[C@@H](C(=O)Nc2ccccc2F)C1=O] |
| 1255 | 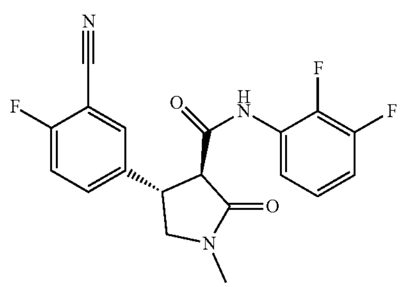 [SMILES: CN1C[C@H](c2ccc(F)c(C#N)c2)[C@@H](C(=O)Nc2cccc(F)c2F)C1=O] |
| 1256 | 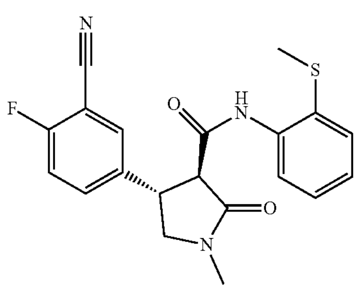 [SMILES: CSc1ccccc1NC(=O)[C@H]1C(=O)N(C)C[C@@H]1c1ccc(F)c(C#N)c1] |
| 1257 | |
| 1258 | |
| 1259 | |
| 1260 | |
| 1261 | |
| 1262 | |

INDEX TABLE E-continued

| Ex # | Structure |
|---|---|
| 1263 | 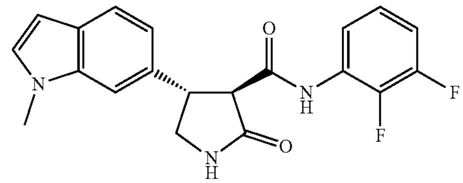 [SMILES: Cn1ccc2ccc([C@H]3CNC(=O)[C@@H]3C(=O)Nc3cccc(F)c3F)cc21] |
| 1264 | 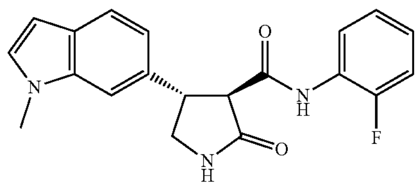 [SMILES: Cn1ccc2ccc([C@H]3CNC(=O)[C@@H]3C(=O)Nc3ccccc3F)cc21] |
| 1265 | 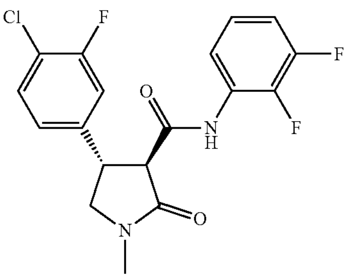 [SMILES: CN1C[C@H](c2ccc(Cl)c(F)c2)[C@@H](C(=O)Nc2cccc(F)c2F)C1=O] |
| 1266 | 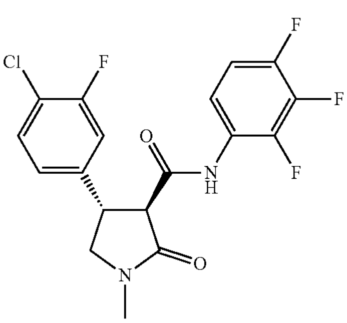 |
| 1267 | 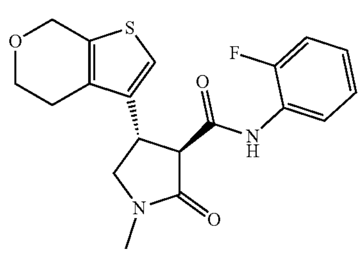 [SMILES: CN1C[C@H](c2csc3c2CCOC3)[C@@H](C(=O)Nc2ccccc2F)C1=O] |
| 1268 | 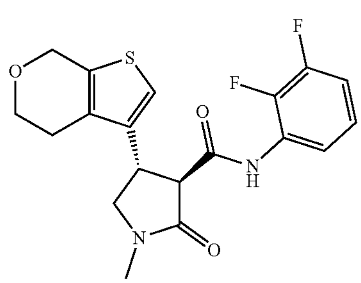 [SMILES: CN1C[C@H](c2csc3c2CCOC3)[C@@H](C(=O)Nc2cccc(F)c2F)C1=O] |
| 1269 | |
| 1270 | |
| 1271 | |
| 1272 | |
| 1273 | |

INDEX TABLE E-continued

| Ex # | Structure |
|------|-----------|
| 1274 | 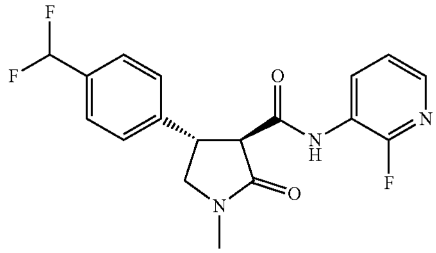 [SMILES: CN1C[C@H](c2ccc(C(F)F)cc2)[C@@H](C(=O)Nc2cccnc2F)C1=O] |
| 1275 | 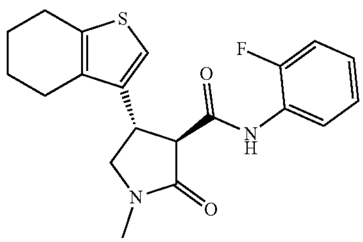 [SMILES: CN1C[C@H](c2csc3c2CCCC3)[C@@H](C(=O)Nc2ccccc2F)C1=O] |
| 1276 | 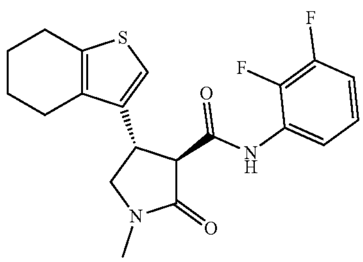 [SMILES: CN1C[C@H](c2csc3c2CCCC3)[C@@H](C(=O)Nc2cccc(F)c2F)C1=O] |
| 1277 | 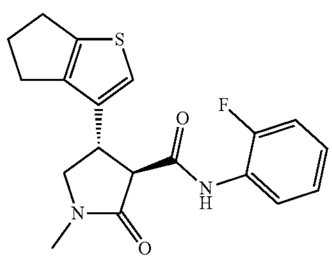 [SMILES: CN1C[C@H](c2csc3c2CCC3)[C@@H](C(=O)Nc2ccccc2F)C1=O] |
| 1278 | 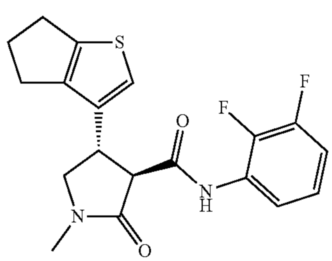 [SMILES: CN1C[C@H](c2csc3c2CCC3)[C@@H](C(=O)Nc2cccc(F)c2F)C1=O] |
| 1279 | 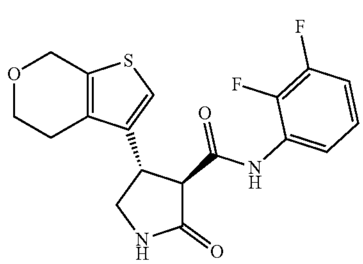 [SMILES: O=C1NC[C@H](c2csc3c2CCOC3)[C@H]1C(=O)Nc1cccc(F)c1F] |
| 1280 | |
| 1281 | |
| 1282 | |
| 1283 | |
| 1284 | |

INDEX TABLE E-continued

| Ex # | Structure |
|---|---|
| 1285 | 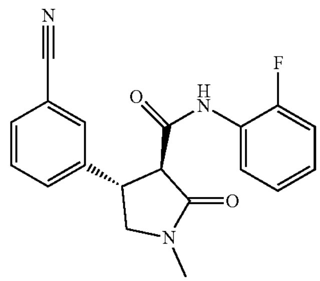 [SMILES: CN1C[C@H](c2cccc(C#N)c2)[C@@H](C(=O)Nc2ccccc2F)C1=O] |
| 1286 | 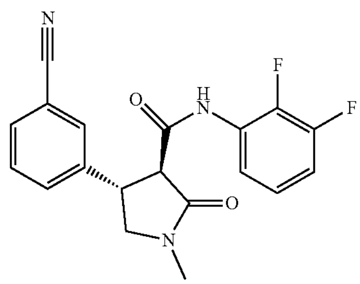 [SMILES: CN1C[C@H](c2cccc(C#N)c2)[C@@H](C(=O)Nc2cccc(F)c2F)C1=O] |
| 1287 | 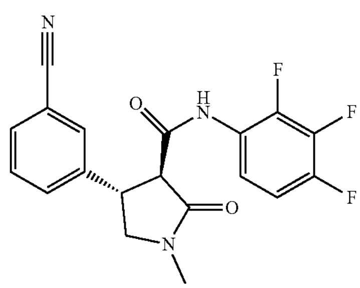 [SMILES: CN1C[C@H](c2cccc(C#N)c2)[C@@H](C(=O)Nc2ccc(F)c(F)c2F)C1=O] |
| 1288 | 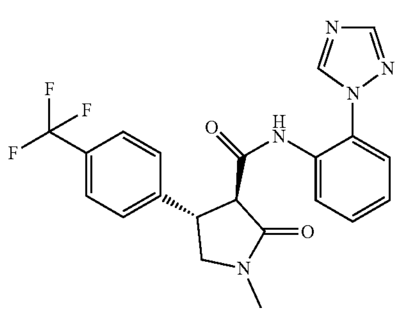 [SMILES: CN1C[C@H](c2ccc(C(F)(F)F)cc2)[C@@H](C(=O)Nc2ccccc2-n2cncn2)C1=O] |
| 1289 | 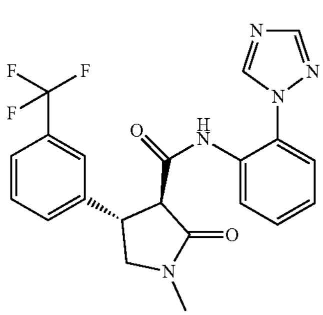 [SMILES: CN1C[C@H](c2cccc(C(F)(F)F)c2)[C@@H](C(=O)Nc2ccccc2-n2cncn2)C1=O] |
| 1290 | |
| 1291 | |
| 1292 | |
| 1293 | |
| 1294 | |

INDEX TABLE E-continued

| Ex # | Structure |
|---|---|
| 1295 | |
| 1296 | |
| 1297 | |
| 1298 | |
| 1299 | 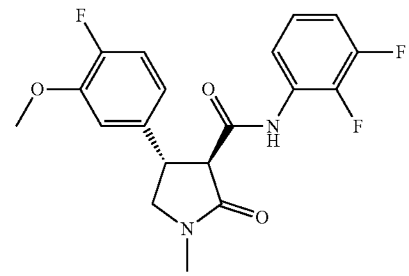 [SMILES: COc1cc([C@H]2CN(C)C(=O)[C@@H]2C(=O)Nc2cccc(F)c2F)ccc1F] |
| 1300 | 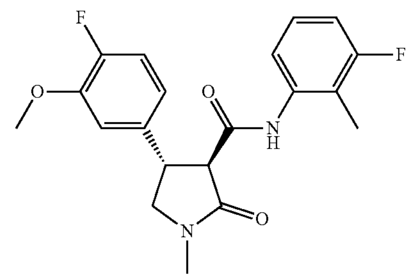 |
| 1301 | 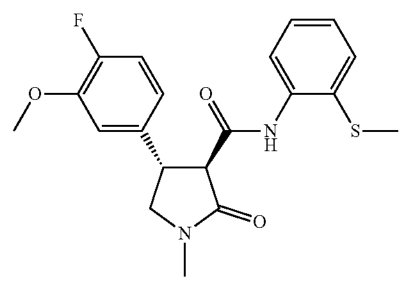 |
| 1302 | 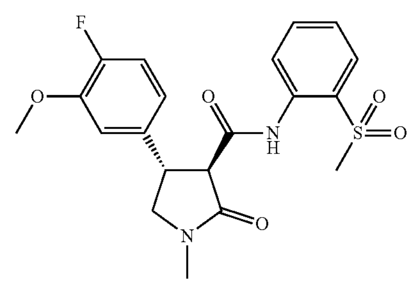 [SMILES: COc1cc([C@H]2CN(C)C(=O)[C@@H]2C(=O)Nc2ccccc2S(C)(=O)=O)ccc1F] |
| 1303 | 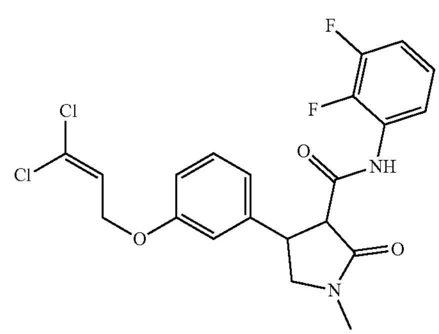 [SMILES: CN1CC(c2cccc(OCC=C(Cl)Cl)c2)C(C(=O)Nc2cccc(F)c2F)C1=O] |

INDEX TABLE E-continued

| Ex # | Structure |
|------|-----------|
| 1304 | 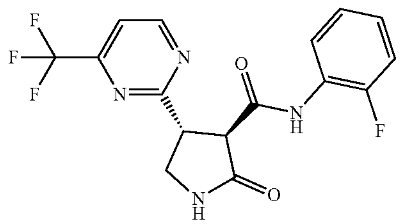 [SMILES: O=C1NC[C@H](c2nccc(C(F)(F)F)n2)[C@H]1C(=O)Nc1ccccc1F] |
| 1305 | 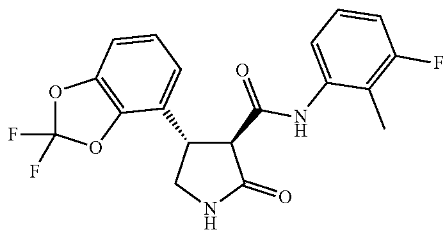 [SMILES: Cc1c(F)cccc1NC(=O)[C@H]1C(=O)NC[C@@H]1c1cccc2c1OC(F)(F)O2] |
| 1306 | 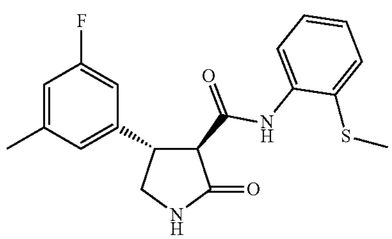 |
| 1307 | 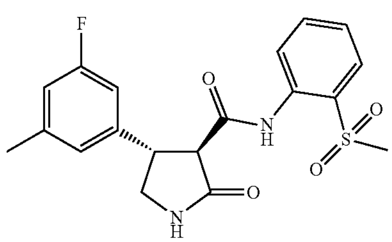 |
| 1308 | 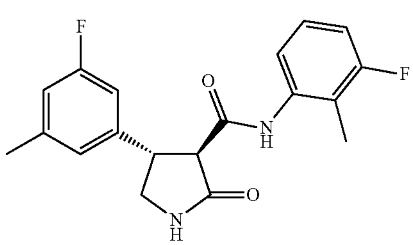 [SMILES: Cc1cc(F)cc([C@H]2CNC(=O)[C@@H]2C(=O)Nc2cccc(F)c2C)c1] |
| 1309 | 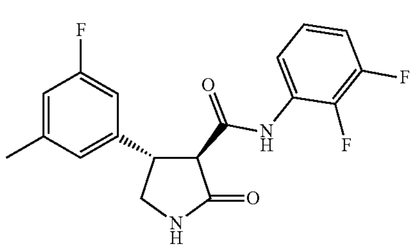 [SMILES: Cc1cc(F)cc([C@H]2CNC(=O)[C@@H]2C(=O)Nc2cccc(F)c2F)c1] |
| 1310 | |
| 1311 | |
| 1312 | |
| 1313 | |
| 1314 | |

INDEX TABLE E-continued

| Ex # | Structure |
|---|---|
| 1315 | 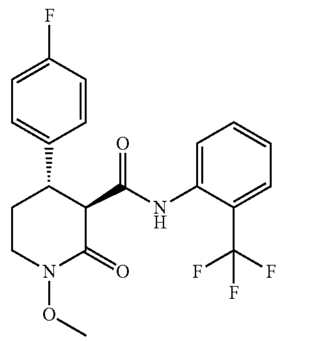 [SMILES: CON1CC[C@H](c2ccc(F)cc2)[C@@H](C(=O)Nc2ccccc2C(F)(F)F)C1=O] |
| 1316 | 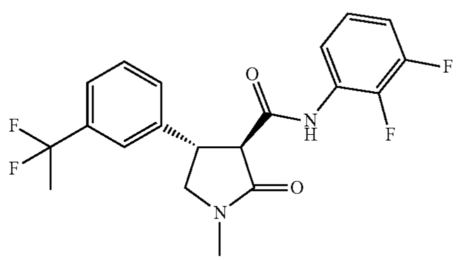 [SMILES: CN1C[C@H](c2cccc(C(C)(F)F)c2)[C@@H](C(=O)Nc2cccc(F)c2F)C1=O] |
| 1317 | 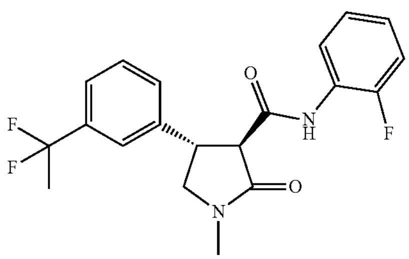 [SMILES: CN1C[C@H](c2cccc(C(C)(F)F)c2)[C@@H](C(=O)Nc2ccccc2F)C1=O] |
| 1318 | 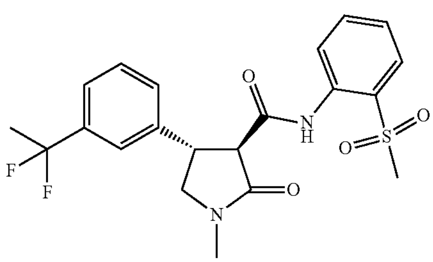 [SMILES: CN1C[C@H](c2cccc(C(C)(F)F)c2)[C@@H](C(=O)Nc2ccccc2S(C)(=O)=O)C1=O] |
| 1319 | 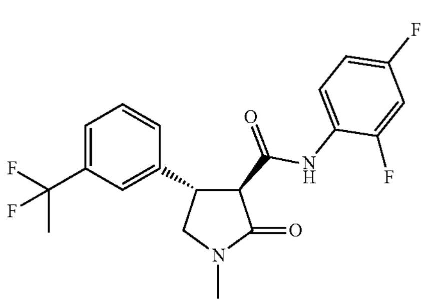 [SMILES: CN1C[C@H](c2cccc(C(C)(F)F)c2)[C@@H](C(=O)Nc2ccc(F)cc2F)C1=O] |
| 1320 | 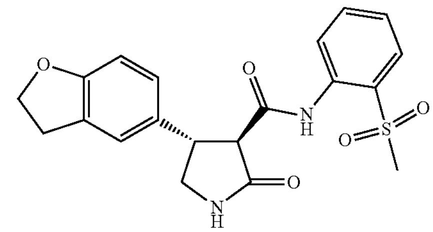 [SMILES: CS(=O)(=O)c1ccccc1NC(=O)[C@H]1C(=O)NC[C@@H]1c1ccc2c(c1)CCO2] |
| 1321 | 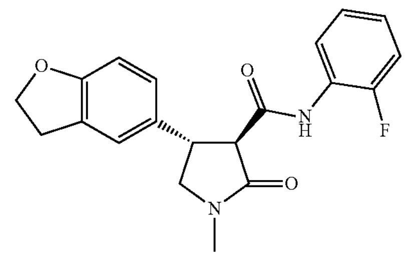 [SMILES: CN1C[C@H](c2ccc3c(c2)CCO3)[C@@H](C(=O)Nc2ccccc2F)C1=O] |
| 1322 | 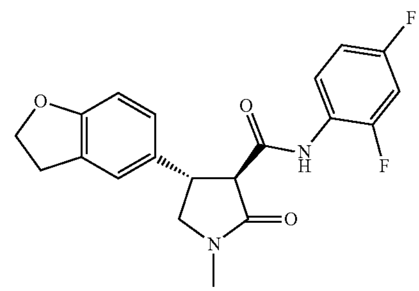 [SMILES: CN1C[C@H](c2ccc3c(c2)CCO3)[C@@H](C(=O)Nc2ccc(F)cc2F)C1=O] |
| 1323 | 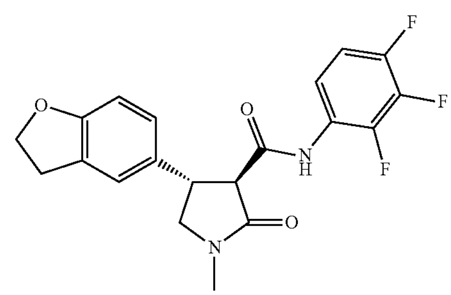 [SMILES: CN1C[C@H](c2ccc3c(c2)CCO3)[C@@H](C(=O)Nc2ccc(F)c(F)c2F)C1=O] |
| 1324 | 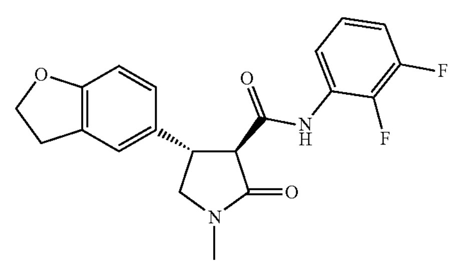 [SMILES: CN1C[C@H](c2ccc3c(c2)CCO3)[C@@H](C(=O)Nc2cccc(F)c2F)C1=O] |
| 1325 | 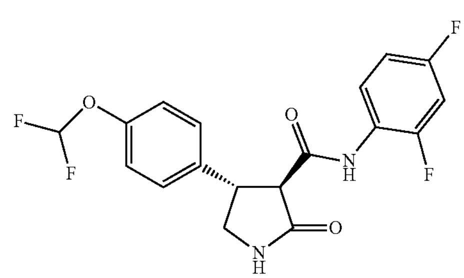 [SMILES: O=C1NC[C@H](c2ccc(OC(F)F)cc2)[C@H]1C(=O)Nc1ccc(F)cc1F] |

INDEX TABLE E-continued
| Ex # | Structure |
|------|-----------|
| 1326 | 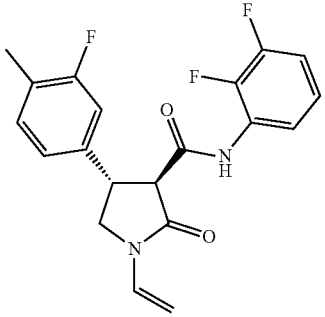 |
| 1327 | 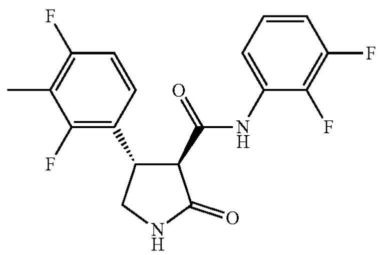 [SMILES: Cc1c(F)ccc([C@H]2CNC(=O)[C@@H]2C(=O)Nc2cccc(F)c2F)c1F] |
| 1328 | 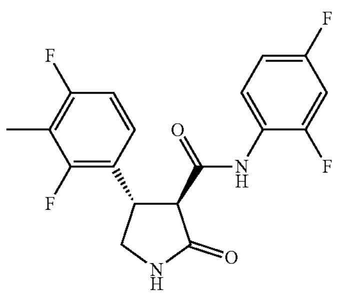 [SMILES: Cc1c(F)ccc([C@H]2CNC(=O)[C@@H]2C(=O)Nc2ccc(F)cc2F)c1F] |
| 1329 | 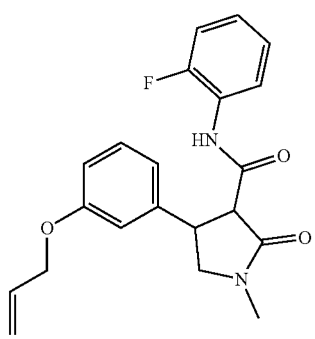 [SMILES: C=CCOc1cccc(C2CN(C)C(=O)C2C(=O)Nc2ccccc2F)c1] |
| 1330 | 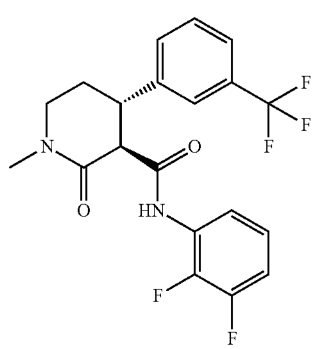 [SMILES: CN1CC[C@H](c2cccc(C(F)(F)F)c2)[C@@H](C(=O)Nc2cccc(F)c2F)C1=O] |
| 1331 | |
| 1332 | AND Enantiomer 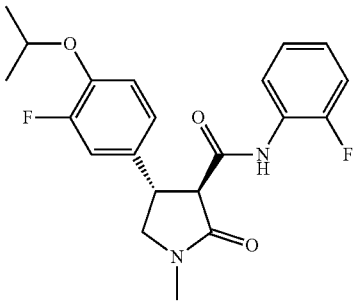 [SMILES: CC(C)Oc1ccc([C@H]2CN(C)C(=O)[C@@H]2C(=O)Nc2ccccc2F)cc1F] |
| 1333 | 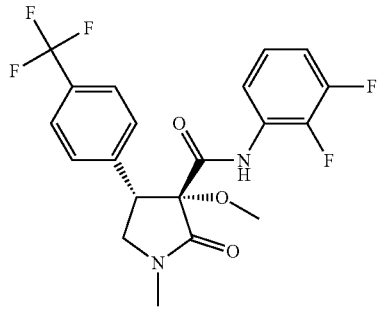 |
| 1334 | AND Enantiomer |
| 1335 | 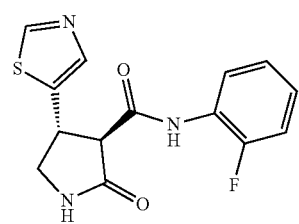 [SMILES: O=C1NC[C@H](c2cncs2)[C@H]1C(=O)Nc1ccccc1F] |

US 10,654,804 B2
INDEX TABLE E-continued
| Ex # | Structure |
|---|---|
| 1336 | 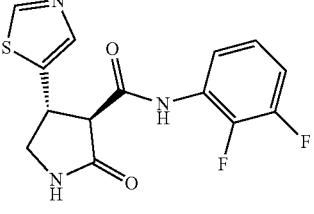 |
| 1337 | 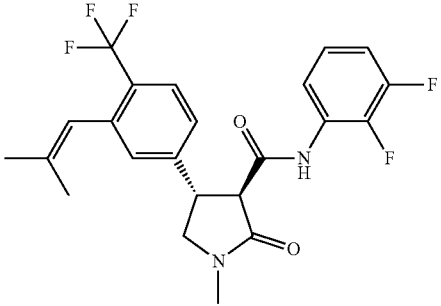 [SMILES: CC(C)=Cc1cc([C@H]2CN(C)C(=O)[C@@H]2C(=O)Nc2cccc(F)c2F)ccc1C(F)(F)F] |
| 1338 | 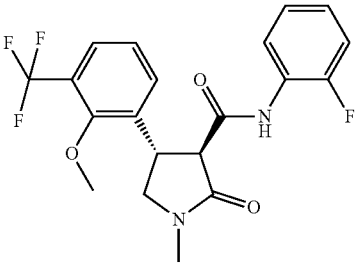 [SMILES: COc1c([C@H]2CN(C)C(=O)[C@@H]2C(=O)Nc2ccccc2F)cccc1C(F)(F)F] |
| 1339 | 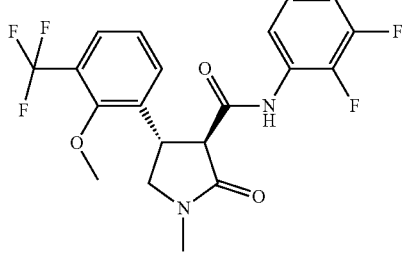 |
| 1340 | 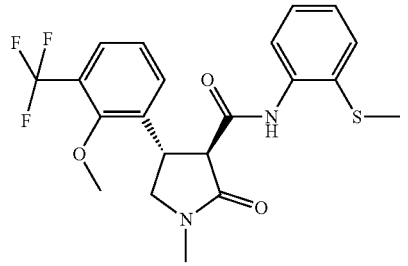 [SMILES: COc1c([C@H]2CN(C)C(=O)[C@@H]2C(=O)Nc2ccccc2SC)cccc1C(F)(F)F] |
INDEX TABLE E-continued
| Ex # | Structure |
|---|---|
| 1341 | 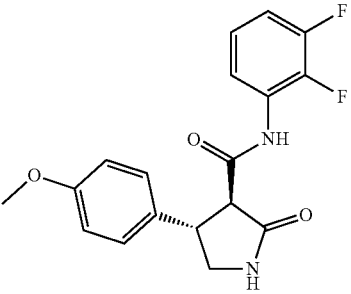 [SMILES: COc1ccc([C@H]2CNC(=O)[C@@H]2C(=O)Nc2cccc(F)c2F)cc1] |
| 1342 | 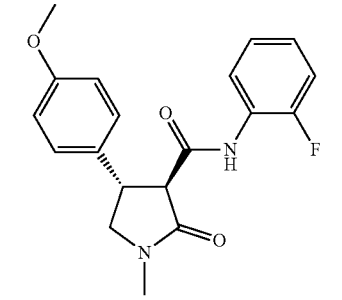 [SMILES: COc1ccc([C@H]2CN(C)C(=O)[C@@H]2C(=O)Nc2ccccc2F)cc1] |
| 1343 | 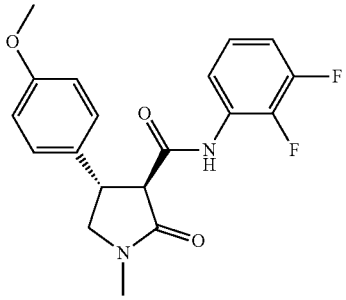 [SMILES: COc1ccc([C@H]2CN(C)C(=O)[C@@H]2C(=O)Nc2cccc(F)c2F)cc1] |
| 1344 | 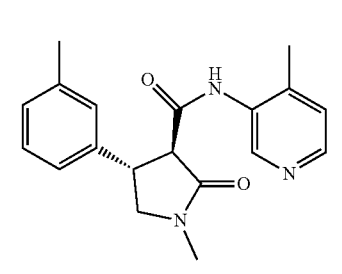 [SMILES: Cc1cccc([C@H]2CN(C)C(=O)[C@@H]2C(=O)Nc2cnccc2C)c1] |
| 1345 | 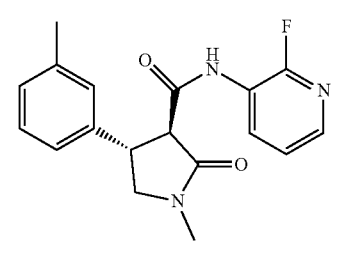 [SMILES: Cc1cccc([C@H]2CN(C)C(=O)[C@@H]2C(=O)Nc2cccnc2F)c1] |

INDEX TABLE E-continued
| Ex # | Structure |
|---|---|
| 1346 | 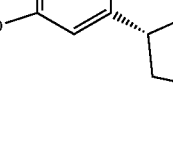 |
| 1347 | 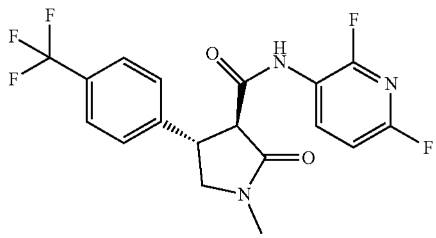 [SMILES: CN1C[C@H](c2ccc(C(F)(F)F)cc2)[C@@H](C(=O)Nc2ccc(F)nc2F)C1=O] |
| 1348 | 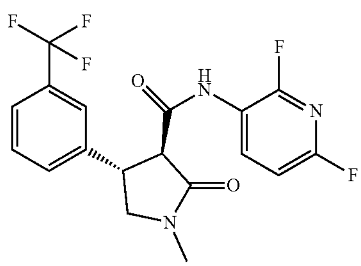 [SMILES: CN1C[C@H](c2cccc(C(F)(F)F)c2)[C@@H](C(=O)Nc2ccc(F)nc2F)C1=O] |
| 1349 | 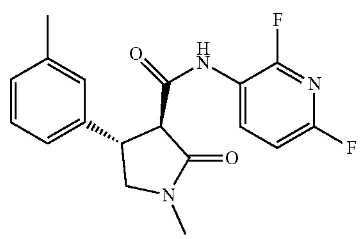 [SMILES: Cc1cccc([C@H]2CN(C)C(=O)[C@@H]2C(=O)Nc2ccc(F)nc2F)c1] |
| 1350 | 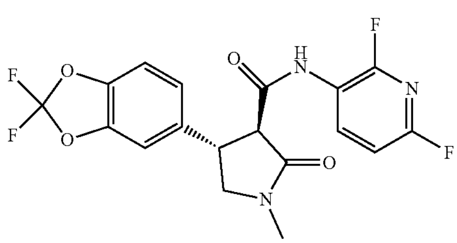 [SMILES: CN1C[C@H](c2ccc3c(c2)OC(F)(F)O3)[C@@H](C(=O)Nc2ccc(F)nc2F)C1=O] |
| 1351 | 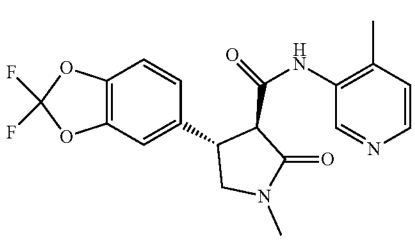 [SMILES: Cc1ccncc1NC(=O)[C@H]1C(=O)N(C)C[C@@H]1c1ccc2c(c1)OC(F)(F)O2] |
INDEX TABLE E-continued
| Ex # | Structure |
|---|---|
| 1352 | 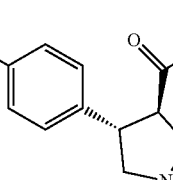 |
| 1353 | 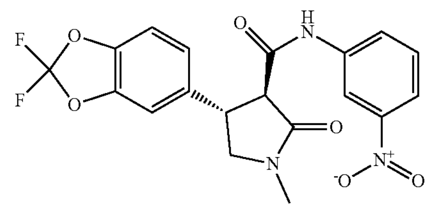 |
| 1354 | 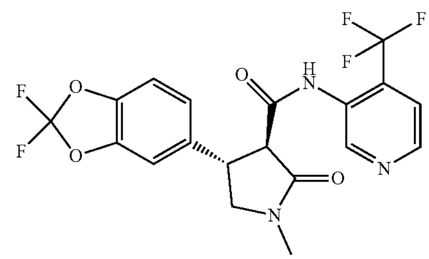 [SMILES: CN1C[C@H](c2ccc3c(c2)OC(F)(F)O3)[C@@H](C(=O)Nc2cnccc2C(F)(F)F)C1=O] |
| 1355 | 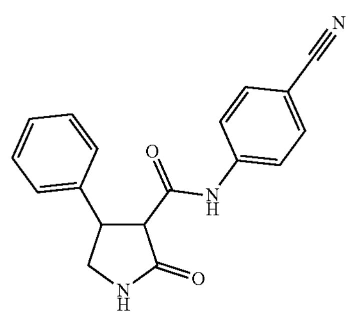 [SMILES: N#Cc1ccc(NC(=O)C2C(=O)NCC2c2ccccc2)cc1] |
| 1356 | 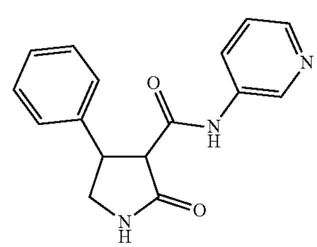 [SMILES: O=C1NCC(c2ccccc2)C1C(=O)Nc1cccnc1] |
| 1357 | 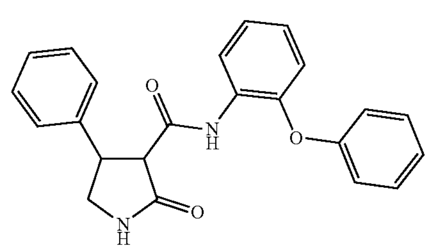 [SMILES: O=C1NCC(c2ccccc2)C1C(=O)Nc1ccccc1Oc1ccccc1] |

INDEX TABLE E-continued

| Ex # | Structure |
|---|---|
| 1358 | 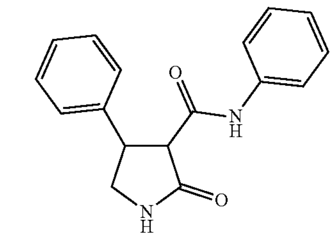 [SMILES: O=C1NCC(c2ccccc2)C1C(=O)Nc1ccccc1] |
| 1359 | 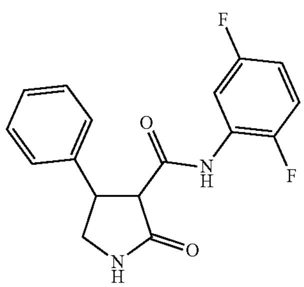 [SMILES: O=C1NCC(c2ccccc2)C1C(=O)Nc1cc(F)ccc1F] |
| 1360 | AND Enantiomer |
| 1361 | 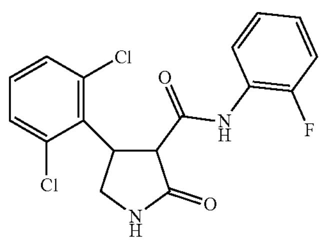 [SMILES: O=C1NCC(c2c(Cl)cccc2Cl)C1C(=O)Nc1ccccc1F] |
| 1362 | 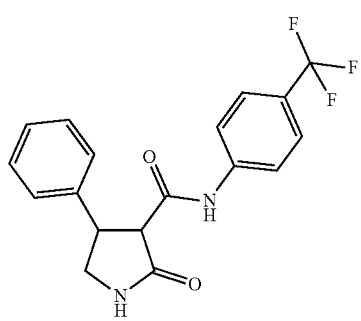 [SMILES: O=C1NCC(c2ccccc2)C1C(=O)Nc1ccc(C(F)(F)F)cc1] |
| 1363 | 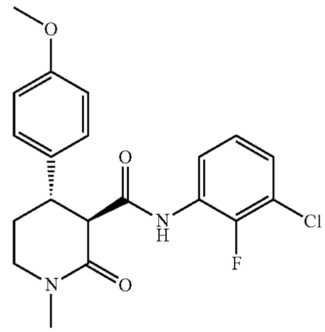 [SMILES: COc1ccc([C@H]2CCN(C)C(=O)[C@@H]2C(=O)Nc2cccc(Cl)c2F)cc1] |
| 1364 | 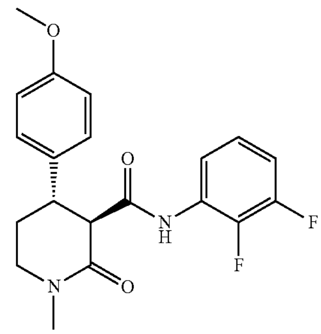 [SMILES: COc1ccc([C@H]2CCN(C)C(=O)[C@@H]2C(=O)Nc2cccc(F)c2F)cc1] |
| 1365 | 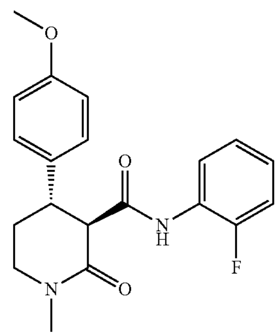 [SMILES: COc1ccc([C@H]2CCN(C)C(=O)[C@@H]2C(=O)Nc2ccccc2F)cc1] |
| 1366 | 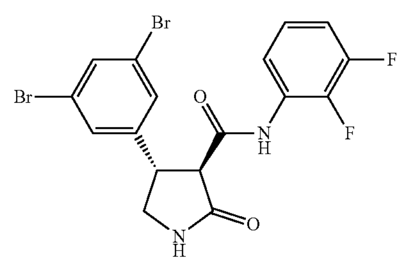 [SMILES: O=C1NC[C@H](c2cc(Br)cc(Br)c2)[C@H]1C(=O)Nc1cccc(F)c1F] |
| 1367 | AND Enantiomer |

INDEX TABLE E-continued

| Ex # | Structure |
|---|---|
| 1368 | AND Enantiomer |
| 1369 | AND Enantiomer |
| 1370 | 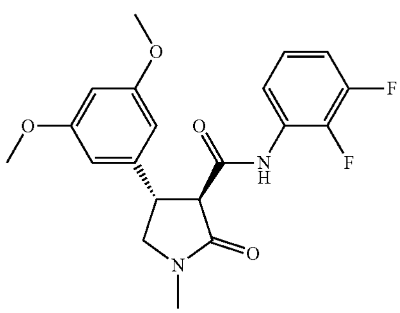 [SMILES: COc1cc(OC)cc([C@H]2CN(C)C(=O)[C@@H]2C(=O)Nc2cccc(F)c2F)c1] |
| 1371 | 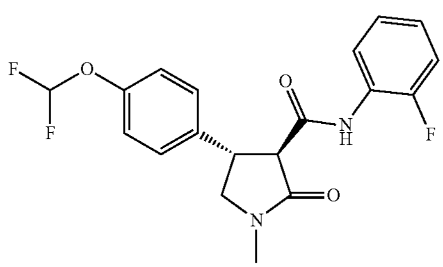 [SMILES: CN1C[C@H](c2ccc(OC(F)F)cc2)[C@@H](C(=O)Nc2ccccc2F)C1=O] |
| 1372 | 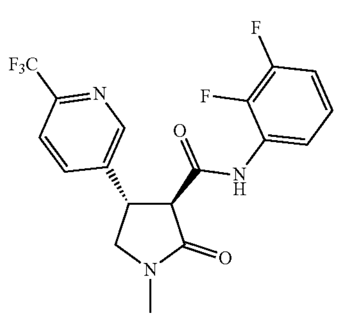 [SMILES: CN1C[C@H](c2ccc(C(F)(F)F)nc2)[C@@H](C(=O)Nc2cccc(F)c2F)C1=O] |
| 1373 | 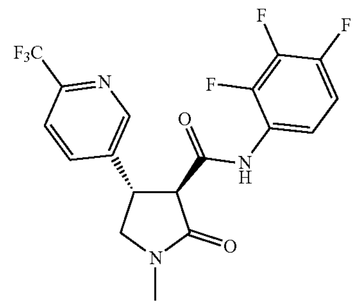 [SMILES: CN1C[C@H](c2ccc(C(F)(F)F)nc2)[C@@H](C(=O)Nc2ccc(F)c(F)c2F)C1=O] |
| 1374 | 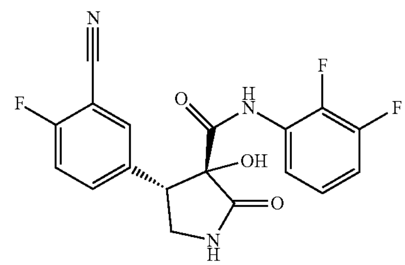 [SMILES: N#Cc1cc([C@H]2CNC(=O)[C@]2(O)C(=O)Nc2cccc(F)c2F)ccc1F] |
| 1375 | 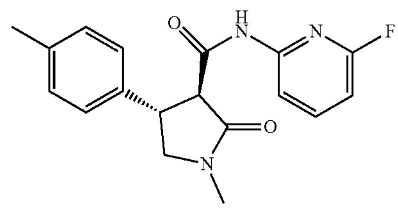 [SMILES: Cc1ccc([C@H]2CN(C)C(=O)[C@@H]2C(=O)Nc2cccc(F)n2)cc1] |
| 1376 | AND Enantiomer |
| 1377 | 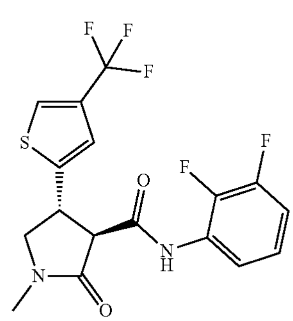 [SMILES: CN1C[C@H](c2cc(C(F)(F)F)cs2)[C@@H](C(=O)Nc2cccc(F)c2F)C1=O] |

INDEX TABLE E-continued

| Ex # | Structure |
|---|---|
| 1378 | 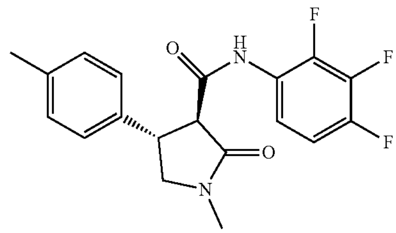 [SMILES: Cc1ccc([C@H]2CN(C)C(=O)[C@@H]2C(=O)Nc2ccc(F)c(F)c2F)cc1] |
| 1379 | 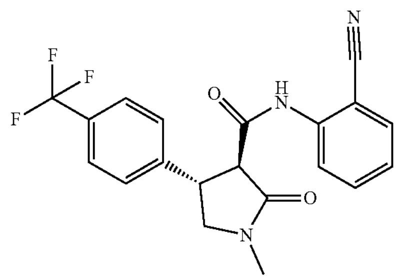 [SMILES: CN1C[C@H](c2ccc(C(F)(F)F)cc2)[C@@H](C(=O)Nc2ccccc2C#N)C1=O] |
| 1380 | 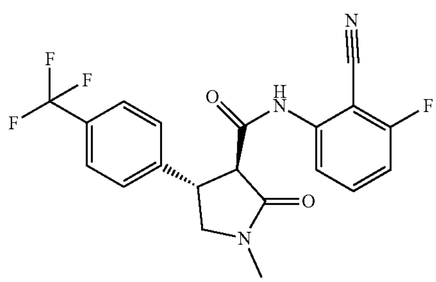 [SMILES: CN1C[C@H](c2ccc(C(F)(F)F)cc2)[C@@H](C(=O)Nc2cccc(F)c2C#N)C1=O] |
| 1381 | 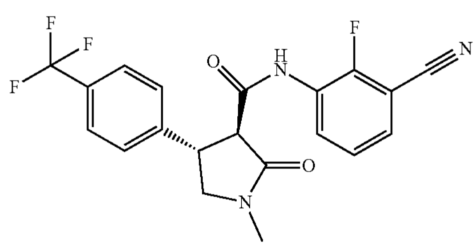 [SMILES: CN1C[C@H](c2ccc(C(F)(F)F)cc2)[C@@H](C(=O)Nc2cccc(C#N)c2F)C1=O] |
| 1382 | 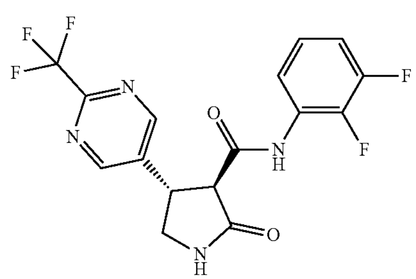 [SMILES: O=C1NC[C@H](c2cnc(C(F)(F)F)nc2)[C@H]1C(=O)Nc1cccc(F)c1F] |

INDEX TABLE E-continued

| Ex # | Structure |
|---|---|
| 1383 | 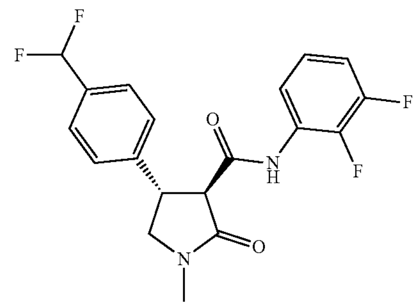 [SMILES: CN1C[C@H](c2ccc(C(F)F)cc2)[C@@H](C(=O)Nc2cccc(F)c2F)C1=O] |
| 1384 | 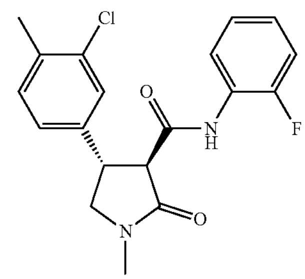 [SMILES: Cc1ccc([C@H]2CN(C)C(=O)[C@@H]2C(=O)Nc2ccccc2F)cc1Cl] |
| 1385 | 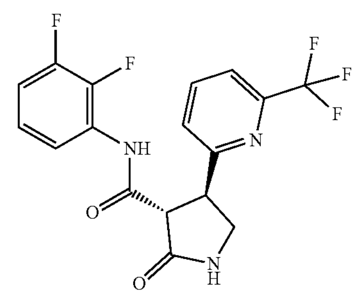 [SMILES: O=C1NC[C@H](c2cccc(C(F)(F)F)n2)[C@H]1C(=O)Nc1cccc(F)c1F] |
| 1386 | 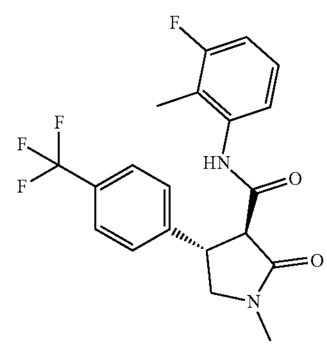 [SMILES: Cc1c(F)cccc1NC(=O)[C@H]1C(=O)N(C)C[C@@H]1c1ccc(C(F)(F)F)cc1] |
| 1387 | AND Enantiomer |

INDEX TABLE E-continued

| Ex # | Structure |
|---|---|
| 1388 | 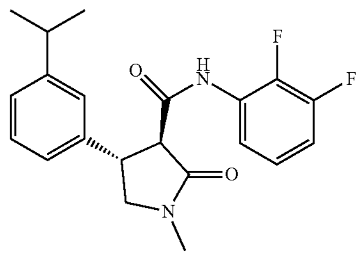 [SMILES: CC(C)c1cccc([C@H]2CN(C)C(=O)[C@@H]2C(=O)Nc2cccc(F)c2F)c1] |
| 1389 | 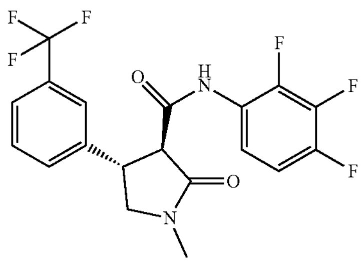 [SMILES: CN1C[C@H](c2cccc(C(F)(F)F)c2)[C@@H](C(=O)Nc2ccc(F)c(F)c2F)C1=O] |
| 1390 | 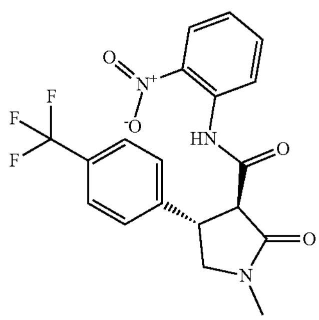 |
| 1391 | 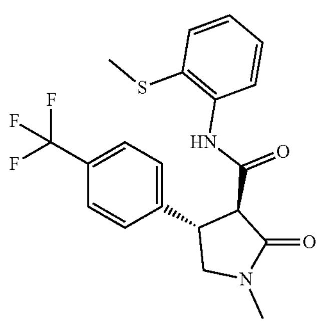 [SMILES: CSc1ccccc1NC(=O)[C@H]1C(=O)N(C)C[C@@H]1c1ccc(C(F)(F)F)cc1] |
| 1392 | 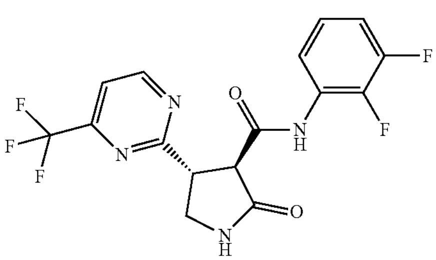 [SMILES: O=C1NC[C@H](c2nccc(C(F)(F)F)n2)[C@H]1C(=O)Nc1cccc(F)c1F] |

INDEX TABLE E-continued

| Ex # | Structure |
|---|---|
| 1393 | 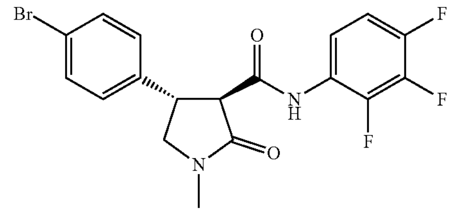 [SMILES: CN1C[C@H](c2ccc(Br)cc2)[C@@H](C(=O)Nc2ccc(F)c(F)c2F)C1=O] |
| 1394 | 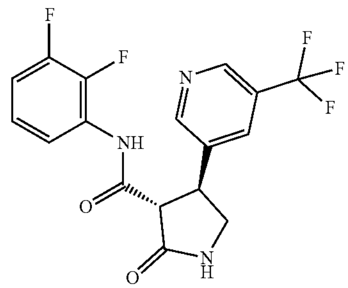 [SMILES: O=C1NC[C@H](c2cncc(C(F)(F)F)c2)[C@H]1C(=O)Nc1cccc(F)c1F] |
| 1395 | 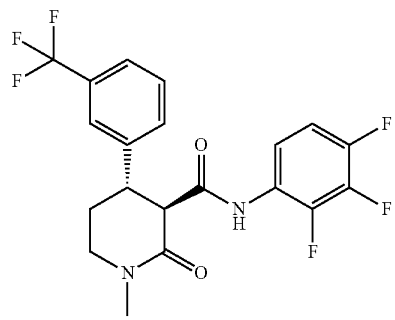 [SMILES: CN1CC[C@H](c2cccc(C(F)(F)F)c2)[C@@H](C(=O)Nc2ccc(F)c(F)c2F)C1=O] |
| 1396 | 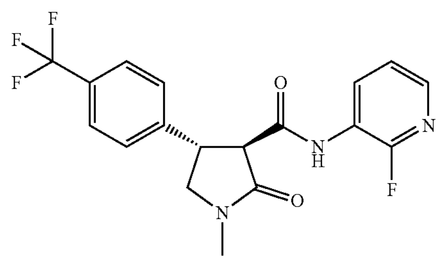 [SMILES: CN1C[C@H](c2ccc(C(F)(F)F)cc2)[C@@H](C(=O)Nc2cccnc2F)C1=O] |
| 1397 | 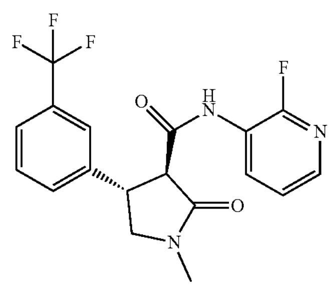 [SMILES: CN1C[C@H](c2cccc(C(F)(F)F)c2)[C@@H](C(=O)Nc2cccnc2F)C1=O] |
| 1398 | 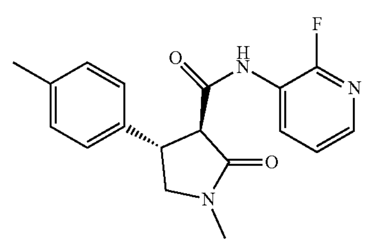 [SMILES: Cc1ccc([C@H]2CN(C)C(=O)[C@@H]2C(=O)Nc2cccnc2F)cc1] |

INDEX TABLE E-continued

| Ex # | Structure |
|---|---|
| 1399 | 4-chlorophenyl, N-methyl pyrrolidinone-3-carboxamide, N-(6-fluoropyridin-2-yl) |
| 1400 | 4-(trifluoromethyl)phenyl, N-methyl pyrrolidinone-3-carboxamide, N-(6-fluoropyridin-2-yl) |
| 1401 | AND Enantiomer; N-methyl pyrrolidinone with 4-(trifluoromethyl)phenyl substituent, carboxamide to 4-(trifluoromethyl)pyridin-3-yl |
| 1402 | 4-methylphenyl, N-methyl pyrrolidinone-3-carboxamide, N-(2,6-difluoropyridin-3-yl) |

Characterization Data for Compounds 717-1402

| Ex # | M + 1 | M − 1 | MP ° C. |
|---|---|---|---|
| 717 | 331 | | |
| 718 | 349 | | |
| 719 | 381 | | |
| 720 | 349 | | |
| 721 | 407 | | |
| 722 | 405 | | |
| 723 | 437 | | |
| 724 | 447 | | |
| 725 | 410 | | |
| 726 | | | 108-111 |
| 727 | 339 | | |
| 728 | 320 | | |
| 729 | 338 | | |

-continued

| Ex # | M + 1 | M − 1 | MP ° C. |
|---|---|---|---|
| 730 | 363 | | |
| 731 | 361 | | |
| 732 | 355.6 | | |
| 733 | 369.5 | | |
| 734 | 401.5 | | |
| 735 | 369.5 | 367.5 | |
| 736 | 385.5 | 387.5 | |
| 737 | 419.5 | 417.5 | |
| 738 | 377.5 | 375.4 | |
| 739 | 409.4 | 407.4 | |
| 741 | | | 227-231 |
| 742 | 353 | | |
| 743 | 371 | | |
| 744 | 202 | | |
| 745 | 417 | | |
| 746 | 389 | | |
| 747 | 403 | | |
| 750 | 355 | | |
| 751 | 373 | | |
| 752 | 306 | | |
| 753 | 439 | | |
| 754 | 379 | | |
| 755 | | | 135-139 |
| 756 | 389 | | |
| 757 | 403 | | |
| 758 | 417.4 | 415.4 | |
| 759 | 367.4 | 365.4 | |
| 760 | 363.4 | 361.4 | |
| 767 | 343 | | |
| 768 | 411.5 | 409.5 | |
| 769 | 439.5 | 437.5 | |
| 770 | 429.4 | 427.5 | |
| 771 | 381.4 | 379.5 | |
| 772 | | | 146-150 |
| 773 | | | 69.5-77 |
| 774 | | | 133.9-140.7 |
| 775 | 356.4 | 354.5 | |
| 776 | 376.3 | | |
| 779 | 381 | | |
| 780 | 423 | | |
| 781 | 381 | | |
| 782 | 363 | | |
| 783 | | 348.3 | |
| 784 | 471.3 | 469.4 | |
| 785 | 359 | | |
| 786 | 341 | | |
| 787 | 425 | | |
| 788 | 439 | | |
| 789 | 347 | | |
| 790 | 365 | | |
| 791 | 365 | | |
| 792 | | | 133-137 |
| 793 | | | 151-155 |
| 795 | | | 86-89 |
| 796 | 373.5 | | |
| 797 | 355.5 | | |
| 798 | 383.5 | | |
| 799 | 391 | | |
| 800 | 370 | | |
| 801 | 381 | | |
| 802 | 359 | | |
| 803 | 363 | | |
| 804 | 477.3 | 477.3 | |
| 805 | | 363.5 | |
| 806 | | 459.4 | |
| 807 | | 427.4 | |
| 808 | | 445.4 | |
| 809 | | 437.4 | |
| 810 | | 443.4 | |
| 811 | | 455.4 | |
| 812 | | 423.4 | |
| 813 | | 441.4 | |
| 814 | | 433.4 | |
| 815 | 353 | | |
| 816 | 371 | | |
| 817 | 413 | | |
| 818 | 371 | | |

| Ex # | M + 1 | M − 1 | MP ° C. |
|---|---|---|---|
| 819 | 355 | | |
| 820 | 415 | | |
| 821 | 373 | | |
| 822 | 331 | | |
| 823 | 381 | | |
| 824 | 391 | | |
| 825 | 394 | | |
| 826 | 381 | | |
| 827 | 429 | | |
| 828 | 381 | | |
| 829 | 392 | | |
| 830 | 385 | | |
| 831 | 399 | | |
| 832 | 409 | | |
| 833 | 363 | | |
| 834 | 381 | | |
| 835 | 381 | | |
| 836 | 399 | | |
| 837 | 403 | | |
| 838 | 421 | | |
| 839 | 463 | | |
| 840 | 421 | | |
| 841 | 413 | | |
| 842 | 423 | | |
| 843 | | | |
| 844 | | | 133-136 |
| 845 | | | 150-153 |
| 846 | | | 132-135 |
| 847 | 373 | | |
| 848 | 367 | | |
| 849 | 363 | | |
| 850 | 345 | | |
| 851 | 373 | | |
| 852 | 373.3 | | |
| 853 | 391.3 | | |
| 854 | 401.3 | | |
| 855 | 411.3 | | |
| 856 | 429.3 | | |
| 857 | 439.3 | | |
| 858 | 411.3 | | |
| 859 | 429.3 | | |
| 860 | 439.3 | | |
| 861 | 457 | | |
| 862 | 457 | | |
| 863 | 473 | | |
| 864 | 489 | | |
| 865 | 407 | | |
| 866 | 395 | | |
| 867 | 381 | | |
| 868 | 418.4 | 416.4 | |
| 869 | 400.5 | 398.5 | |
| 870 | 400.5 | 398.5 | |
| 871 | 393.4 | 391.5 | |
| 872 | 393.4 | 391.5 | |
| 873 | 411 | | |
| 874 | | 405 | |
| 875 | 393 | | |
| 876 | 421 | | |
| 877 | 453 | | |
| 878 | 367 | | |
| 879 | 385 | | |
| 881 | 381 | | |
| 882 | 399 | | |
| 883 | 399 | | |
| 884 | 373 | | |
| 885 | 355 | | |
| 886 | | | 137-140 |
| 887 | | | 192-195 |
| 888 | 327.4 | 325.4 | |
| 889 | 345.4 | 343.4 | |
| 890 | 417 | | |
| 891 | 431 | | |
| 892 | 395 | | |
| 893 | 413 | | |
| 894 | 413 | | |
| 895 | 431 | | |
| 896 | 445 | | |
| 897 | 455 | | |
| 898 | 435 | | |
| 899 | 417 | | |
| 900 | 477 | | |
| 901 | 435 | | |
| 902 | 359 | | |
| 903 | 357.3 | | |
| 904 | 375.2 | | |
| 905 | 375.2 | | |
| 906 | | 341.5 | |
| 907 | | 359.5 | |
| 908 | | 359.5 | |
| 909 | 377.5 | 375.5 | |
| 910 | 377.5 | 339.5 | |
| 911 | 359.5 | 357.5 | |
| 912 | 391.5 | 389.5 | |
| 913 | | | 96-100 |
| 914 | | | |
| 915 | | | 181-184 |
| 916 | 441 | | |
| 917 | | 343.4 | |
| 919 | 469.4 | | |
| 920 | 455.4 | | |
| 921 | | 377.4 | |
| 922 | | 359.4 | |
| 923 | | 419.4 | |
| 924 | | 393.4 | |
| 925 | | 437.5 | |
| 926 | | 453.4 | |
| 927 | | 479.5 | |
| 928 | 361 | | |
| 929 | 379 | | |
| 930 | 379 | | |
| 931 | 397 | | |
| 932 | 411 | | |
| 933 | | | 94-97 |
| 934 | | | 123-126 |
| 935 | | | 116-119 |
| 936 | | | 119-122 |
| 937 | | | 160-163 |
| 938 | | | 169-172 |
| 939 | | | 178-181 |
| 940 | | | 164-167 |
| 941 | | | 166-169 |
| 942 | | | 113-116 |
| 943 | | | 104-107 |
| 944 | 421 | | |
| 945 | | 327.4 | |
| 946 | | 345.4 | |
| 947 | | 347.3 | |
| 948 | | | 115-119 |
| 949 | 343.2 | | |
| 950 | 361.2 | | |
| 951 | 361.2 | | |
| 952 | 371.3 | | |
| 953 | 389.3 | | |
| 954 | 389.3 | | |
| 955 | 357.3 | | |
| 956 | 375.3 | | |
| 957 | 391 | | |
| 958 | 387 | | |
| 959 | 405 | | |
| 960 | 373 | | |
| 961 | 391 | | |
| 962 | 387 | | |
| 963 | 375.3 | | |
| 964 | 371.3 | | |
| 965 | 389.3 | | |
| 966 | 389.3 | | |
| 967 | 345.3 | 343.5 | |
| 968 | 399.4 | 397.5 | |
| 969 | 405.5 | 403.5 | |
| 970 | 336.4 | 334.5 | |
| 971 | 443.5 | | |
| 972 | 457.5 | | |
| 973 | | | 174-176 |
| 974 | 383 | | |

| Ex # | M + 1 | M − 1 | MP ° C. |
|---|---|---|---|
| 975 | 393 | | |
| 976 | 365 | | |
| 977 | 379 | | |
| 978 | 379 | | |
| 979 | 423 | | |
| 980 | 373.3 | | |
| 981 | 401.3 | | |
| 982 | 359 | | |
| 983 | 373 | | |
| 984 | 411.5 | 409.5 | |
| 985 | 365.4 | 363.5 | |
| 986 | 429.5 | 427.5 | |
| 987 | 389 | | |
| 988 | 389 | | |
| 989 | 357 | | |
| 990 | 439 | | |
| 991 | 439.5 | 437.5 | |
| 992 | 365.4 | 363.4 | |
| 993 | 435 | | |
| 994 | 413 | | |
| 995 | 433 | | |
| 996 | 407.5 | 405.5 | |
| 998 | 461.5 | | |
| 999 | 429.5 | | |
| 1000 | 447.5 | | |
| 1001 | 439.5 | | |
| 1002 | 445.4 | | |
| 1003 | 389.5 | | |
| 1004 | 407.5 | | |
| 1005 | 399.5 | | |
| 1006 | 405.5 | | |
| 1007 | | 345.4 | |
| 1008 | 444.5 | | |
| 1009 | 413.4 | | |
| 1010 | 431.4 | | |
| 1011 | | | 136-140 |
| 1012 | | | 162-166 |
| 1013 | 379 | | |
| 1014 | 375 | | |
| 1015 | 389 | | |
| 1016 | 405 | | |
| 1017 | 405 | | |
| 1018 | 421 | | |
| 1019 | 407.5 | 405.5 | |
| 1020 | 361.5 | 359.5 | |
| 1021 | 379.4 | 377.5 | |
| 1022 | 389.5 | 387.5 | |
| 1023 | 421.2 | | |
| 1024 | 439.2 | | |
| 1025 | 449.2 | | |
| 1026 | 361 | | |
| 1027 | 379 | | |
| 1028 | 385.3 | | |
| 1029 | 403.3 | | |
| 1030 | 403.3 | | |
| 1033 | 327.5 | | |
| 1034 | 345.5 | | |
| 1035 | 341.5 | | |
| 1036 | 355.5 | | |
| 1037 | 387.5 | | |
| 1038 | 341.5 | | |
| 1039 | 359.5 | | |
| 1040 | 399 | | |
| 1041 | 441 | | |
| 1042 | 381 | | |
| 1043 | 399 | | |
| 1044 | 398 | | |
| 1045 | 339.3 | 338.4 | |
| 1046 | 357.3 | 355.4 | |
| 1047 | 383.4 | 381.4 | |
| 1048 | 401.3 | 399.4 | |
| 1049 | 433.3 | 431.4 | |
| 1050 | | | 66-70 |
| 1052 | | | 120-124 |
| 1053 | | | 118-121 |
| 1054 | | | 192-196 |
| 1055 | | | 100-104 |

| Ex # | M + 1 | M − 1 | MP ° C. |
|---|---|---|---|
| 1056 | | | 130-134 |
| 1057 | | | 159-163 |
| 1058 | | | 128-132 |
| 1059 | 361.4 | 359.3 | |
| 1061 | | | 161-165 |
| 1062 | 361 | | |
| 1063 | 379 | | |
| 1064 | 433 | | |
| 1065 | 432 | | |
| 1066 | 432 | | |
| 1067 | 378 | | |
| 1068 | 378 | | |
| 1069 | 378 | | |
| 1070 | 324 | | |
| 1071 | 381 | | |
| 1072 | | | 163-167 |
| 1074 | 389.4 | 387.4 | |
| 1075 | 407.4 | 405.4 | |
| 1076 | 417.4 | 415.4 | |
| 1077 | 411 | | |
| 1078 | 435 | | |
| 1079 | 409 | | |
| 1080 | 433 | | |
| 1081 | 395 | | |
| 1082 | 419 | | |
| 1083 | 405 | | |
| 1084 | 429 | | |
| 1085 | | | 113-117 |
| 1086 | | | 89-93 |
| 1087 | | | 98-102 |
| 1088 | 397 | | |
| 1089 | 383 | | |
| 1090 | 370 | | |
| 1091 | 420 | | |
| 1092 | 394 | | |
| 1093 | 394 | | |
| 1095 | 350.7 | 348.4 | |
| 1096 | | 364.3 | |
| 1097 | 366.3 | 364.3 | |
| 1098 | 405 | | |
| 1099 | 423 | | |
| 1100 | 424 | | |
| 1101 | 442 | | |
| 1102 | 467 | | |
| 1103 | 456 | | |
| 1104 | | | 192-196 |
| 1105 | | | 173-176 |
| 1109 | 414.5 | | |
| 1110 | 432.7 | | |
| 1111 | 324 | | |
| 1112 | 320 | | |
| 1113 | 338 | | |
| 1114 | 369 | | |
| 1115 | 387 | | |
| 1116 | 355 | | |
| 1117 | 373 | | |
| 1118 | 355 | | |
| 1119 | 373 | | |
| 1120 | 369 | | |
| 1121 | 387 | | |
| 1122 | 387 | | |
| 1123 | 369 | | |
| 1124 | 381 | | |
| 1125 | 367 | | |
| 1126 | 375 | | |
| 1127 | 411 | | |
| 1129 | | | 97-101 |
| 1130 | | | 216-220 |
| 1132 | | | 142-146 |
| 1133 | | | 119-123 |
| 1134 | | | 133-137 |
| 1135 | 357.3 | | |
| 1136 | 375.3 | | |
| 1137 | 375.3 | | |
| 1138 | 355.5 | 353.5 | |
| 1139 | 373.5 | 371.5 | |
| 1140 | 363.5 | 361.5 | |

| Ex # | M + 1 | M − 1 | MP ° C. |
|---|---|---|---|
| 1143 | | | 141-145 |
| 1144 | 383 | | |
| 1147 | | | 107.5-115.4 |
| 1148 | | | 132-136 |
| 1149 | | | 126-130 |
| 1150 | | | 137-141 |
| 1151 | 417.3 | | |
| 1152 | 417.3 | | |
| 1154 | | | 102-106 |
| 1156 | | | 117-121 |
| 1159 | | | 141-143 |
| 1160 | | | 161-164 |
| 1163 | 377 | | |
| 1164 | 363 | | |
| 1165 | 376.5 | | |
| 1166 | 403.6 | | |
| 1167 | 382.5 | | |
| 1168 | 403.6 | | |
| 1173 | | 413.4 | |
| 1174 | | 439.4 | |
| 1175 | 423 | | |
| 1176 | 400 | | |
| 1177 | 341.5 | | |
| 1178 | 355.5 | | |
| 1181 | | | 123-127.7 |
| 1182 | | | 139.5-153 |
| 1183 | 411.5 | 409.5 | |
| 1184 | 429.5 | 427.6 | |
| 1185 | 439.5 | 437.5 | |
| 1186 | 341 | | |
| 1187 | 355 | | |
| 1188 | 352 | | |
| 1189 | 352 | | |
| 1190 | 356 | | |
| 1191 | 342 | | |
| 1192 | 374 | | |
| 1193 | 360 | | |
| 1196 | | | 144-148 |
| 1197 | 396.5 | | |
| 1198 | 410.5 | | |
| 1199 | 342 | | |
| 1200 | 358 | | |
| 1201 | 370 | | |
| 1202 | 397 | | |
| 1203 | 415 | | |
| 1204 | 429 | | |
| 1206 | 342 | | |
| 1207 | 338 | | |
| 1208 | 356 | | |
| 1209 | 391.3 | | |
| 1210 | 421.3 | | |
| 1211 | 425 | | |
| 1212 | 407 | | |
| 1213 | 393 | | |
| 1214 | 417 | | |
| 1215 | 373.3 | | |
| 1216 | 401.3 | | |
| 1217 | 403.3 | | |
| 1218 | 431.3 | | |
| 1219 | 391.4 | | |
| 1220 | 359.4 | | |
| 1221 | 377.4 | | |
| 1222 | 369.4 | | |
| 1223 | 375.4 | | |
| 1224 | 445.4 | | |
| 1225 | 413.4 | | |
| 1226 | 431.4 | | |
| 1227 | 423.4 | | |
| 1228 | 429.3 | | |
| 1229 | 374 | | |
| 1230 | 366 | | |
| 1231 | 363 | | |
| 1232 | 355 | | |
| 1233 | 341 | | |
| 1234 | 428 | | |
| 1235 | 345 | | |
| 1236 | 359 | | |
| 1237 | | | 97-101 |
| 1238 | | | 138-141 |
| 1239 | | | 123-127 |
| 1240 | | | 52.4-124.1 |
| 1245 | 397 | | |
| 1246 | 407 | | |
| 1247 | 345.5 | 343.6 | |
| 1248 | 345.5 | 343.6 | |
| 1249 | 409 | | |
| 1250 | 449 | | |
| 1251 | 421 | | |
| 1252 | 407 | | |
| 1253 | 363 | | |
| 1254 | 356 | | |
| 1255 | 374 | | |
| 1256 | 386 | | |
| 1257 | 371 | | |
| 1258 | | | 123-127 |
| 1260 | 399 | | |
| 1261 | 377 | | |
| 1262 | 369 | | |
| 1263 | 370 | | |
| 1265 | 383 | | |
| 1266 | 401 | | |
| 1267 | 375 | | |
| 1268 | 393 | | |
| 1270 | | | 88-92 |
| 1273 | | | 136-140 |
| 1274 | 364 | | |
| 1275 | 373 | | |
| 1276 | 391 | | |
| 1277 | 359 | | |
| 1278 | 377 | | |
| 1279 | 379 | | |
| 1282 | 331 | | |
| 1283 | 429 | | |
| 1284 | 429 | | |
| 1285 | 338 | | |
| 1286 | 356 | | |
| 1287 | 374 | | |
| 1288 | 430 | | |
| 1289 | 430 | | |
| 1290 | 416 | | |
| 1291 | 309 | | |
| 1292 | 399 | | |
| 1293 | 431 | | |
| 1294 | 449 | | |
| 1295 | 431 | | |
| 1296 | 449 | | |
| 1297 | 467 | | |
| 1298 | 361.4 | 359.5 | |
| 1299 | 379.4 | 377.5 | |
| 1300 | 375.5 | 373.5 | |
| 1301 | 389.4 | 387.5 | |
| 1302 | 421.5 | 419.5 | |
| 1303 | | | 124-127 |
| 1304 | | | 166-170 |
| 1305 | 393 | | |
| 1306 | 359 | | |
| 1307 | 391 | | |
| 1308 | 345 | | |
| 1309 | 349 | | |
| 1310 | 358 | | |
| 1311 | 359 | | |
| 1312 | 373 | | |
| 1313 | 389 | | |
| 1314 | 389 | | |
| 1315 | 411.4 | | |
| 1316 | 395 | | |
| 1317 | 377 | | |
| 1318 | 437 | | |
| 1319 | 395 | | |
| 1320 | 401 | | |
| 1321 | 355 | | |
| 1322 | 373 | | |
| 1323 | 391 | | |
| 1324 | 373 | | |

| Ex # | M + 1 | M − 1 | MP ° C. |
|---|---|---|---|
| 1325 | 383 | | |
| 1326 | 349 | | |
| 1327 | 367 | | |
| 1328 | 367 | | |
| 1329 | | | 81-84 |
| 1330 | | | 54-57 |
| 1331 | | | 113-116 |
| 1332 | | 373.4 | |
| 1333 | 389.4 | 387.4 | |
| 1334 | 429.4 | | |
| 1336 | | | 111-142 |
| 1337 | 453.5 | 451.5 | |
| 1338 | 411.4 | 409.4 | |
| 1339 | 429.4 | 427.4 | |
| 1340 | 439.4 | 437.4 | |
| 1341 | | | 187-191 |
| 1342 | | | 103-107 |
| 1343 | | | 130-134 |
| 1344 | 324 | | |
| 1345 | 328 | | |
| 1346 | 394 | | |
| 1347 | 400 | | |
| 1348 | 400 | | |
| 1349 | 346 | | |
| 1350 | 412 | | |
| 1351 | 390 | | |
| 1352 | 443 | | |
| 1353 | 420 | | |
| 1354 | 444 | | |
| 1355 | | | 186-188 |
| 1358 | | | 180-181 |
| 1359 | | | 147-149 |
| 1362 | | | 221-223 |
| 1366 | | | 81-85 |
| 1367 | 469 | | |
| 1368 | 445 | | |
| 1369 | 427 | | |
| 1370 | 391.3 | | |
| 1371 | 379 | | |
| 1372 | 400.5 | | 188.1-192.4 |
| 1373 | 418.5 | | |
| 1374 | 376 | | |
| 1375 | 328 | | |
| 1376 | | | 146-150 |
| 1377 | 405 | | |
| 1378 | 363 | | 101.6-102.3 |
| 1379 | 388 | | |
| 1380 | 406 | | |
| 1381 | 406 | | |
| 1382 | | | 170-173 |
| 1383 | 381 | | |
| 1384 | 361 | | |
| 1385 | | | 139-142 |
| 1386 | | | 156-160 |
| 1387 | 365.3 | | |
| 1388 | 373 | | |
| 1389 | 417 | | |
| 1390 | | | 153-156 |
| 1392 | | | 154-158 |
| 1393 | 428 | | |
| 1394 | | | 206-209 |
| 1395 | 431.4 | | |
| 1396 | 382 | | |
| 1397 | | | 382 |
| 1398 | 328 | | |
| 1399 | 348 | | |
| 1400 | 382 | | |
| 1402 | 346 | | |

INDEX TABLE F

| Ex. # | Structure |
|---|---|
| 1403 | AND Enantiomer |
| 1404 | AND Enantiomer |
| 1405 | AND Enantiomer |
| 1406 | AND Enantiomer |

INDEX TABLE F
| Ex. # | Structure |
|---|---|
| 1407 | AND Enantiomer 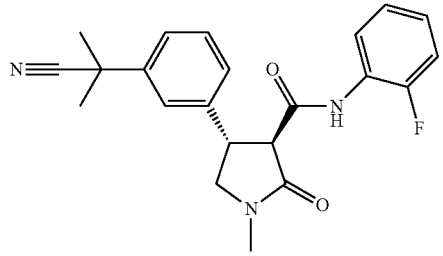 |
| 1408 | AND Enantiomer 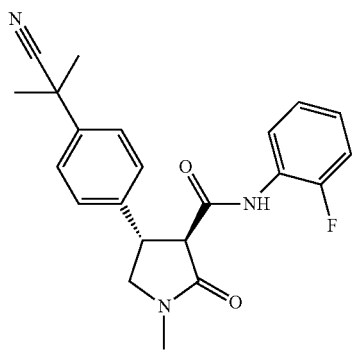 |
| 1409 | AND Enantiomer 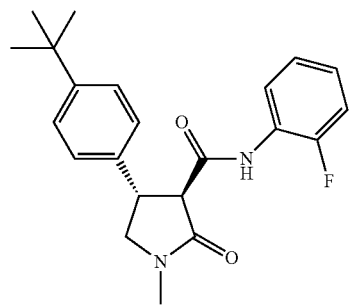 |
| 1410 | AND Enantiomer 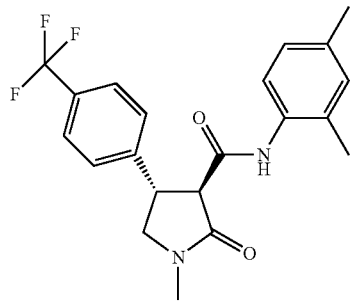 |
INDEX TABLE F
| Ex. # | Structure |
|---|---|
| 1411 | AND Enantiomer 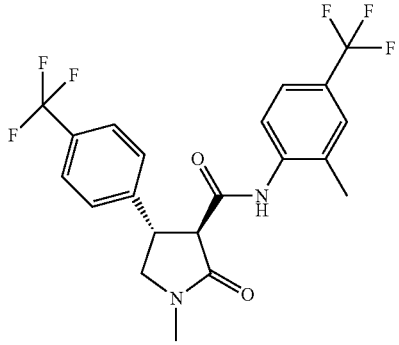 |
| 1412 | AND Enantiomer 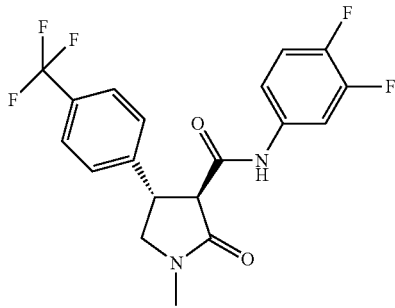 |
| 1413 | AND Enantiomer 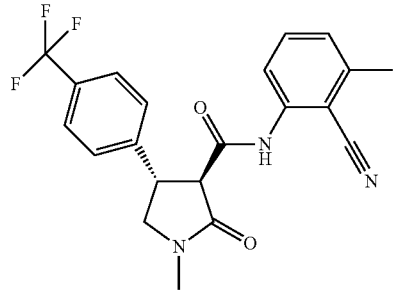 |
| 1414 | AND Enantiomer 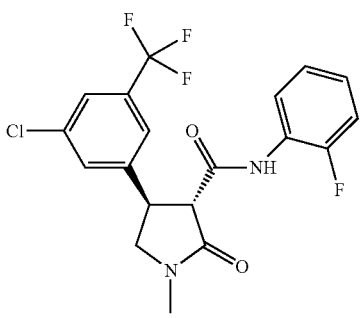 |

INDEX TABLE F
| Ex. # | Structure |
|---|---|
| 1415 | AND Enantiomer 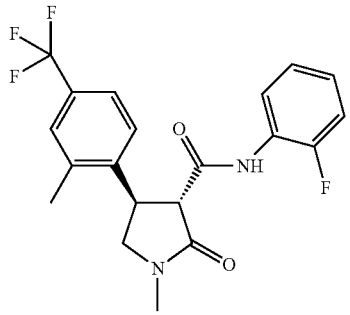 |
| 1416 | AND Enantiomer 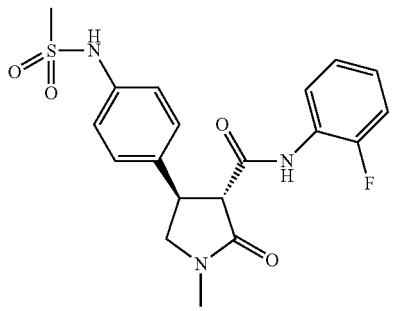 |
| 1417 | AND Enantiomer 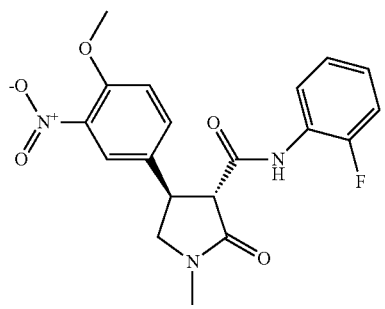 |
| 1418 | AND Enantiomer 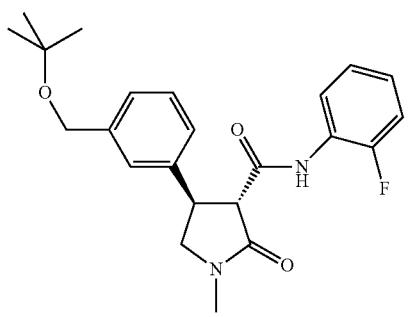 |
INDEX TABLE F
| Ex. # | Structure |
|---|---|
| 1419 | AND Enantiomer 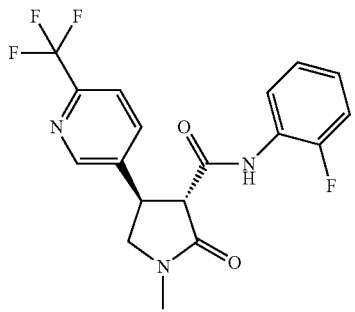 |
| 1420 | AND Enantiomer 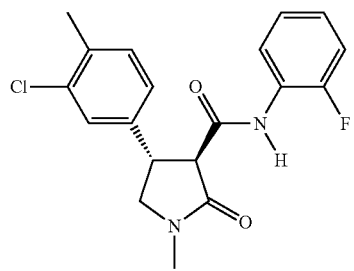 |
| 1421 | AND Enantiomer 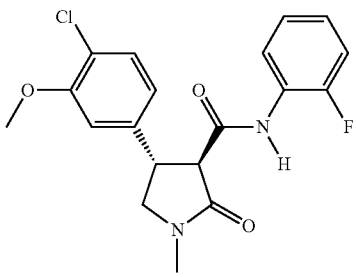 |
| 1422 | AND Enantiomer 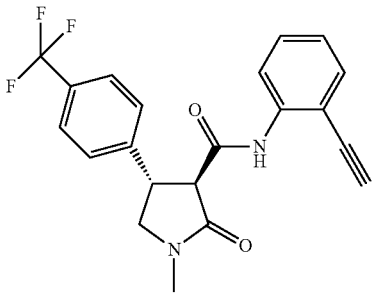 |

281
-continued
INDEX TABLE F
| Ex. # | Structure |
|---|---|
| 1423 | 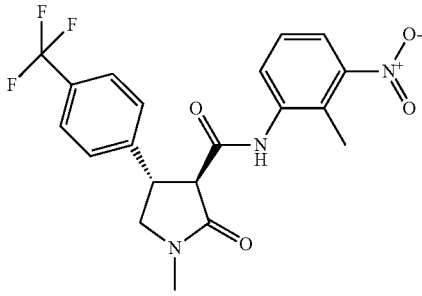 AND Enantiomer |
| 1424 | 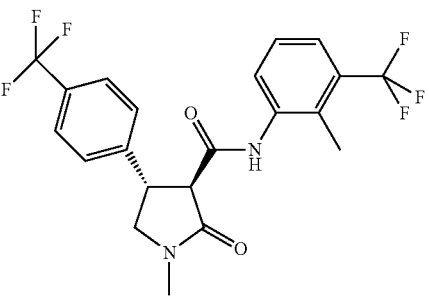 AND Enantiomer |
| 1425 | 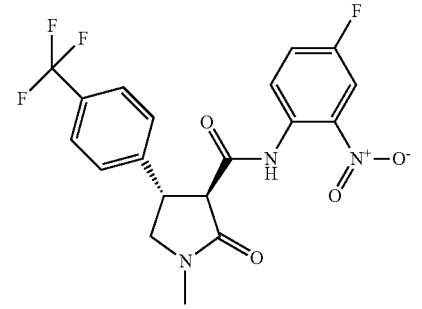 AND Enantiomer |
| 1426 | 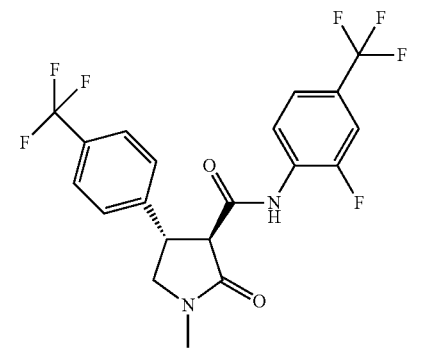 AND Enantiomer |
282
-continued
INDEX TABLE F
| Ex. # | Structure |
|---|---|
| 1427 | 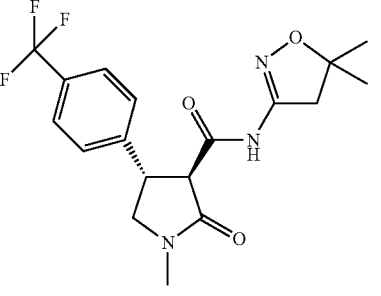 AND Enantiomer |
| 1428 | 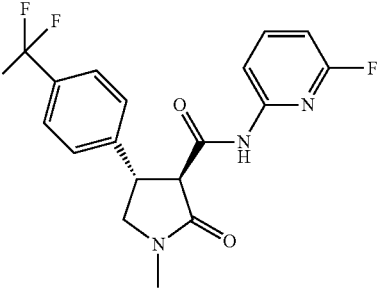 AND Enantiomer |
| 1429 | 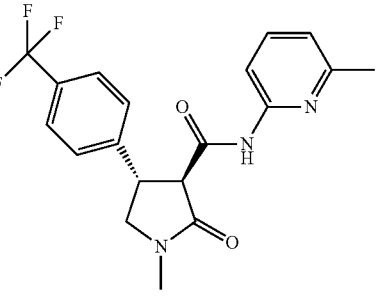 AND Enantiomer |
| 1430 | 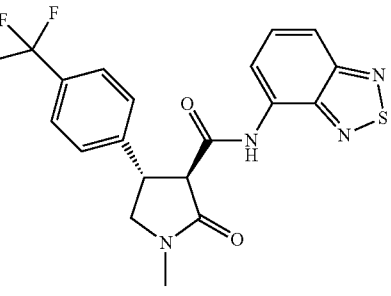 AND Enantiomer |

283
-continued
INDEX TABLE F
| Ex. # | Structure |
|---|---|
| 1431 | AND Enantiomer 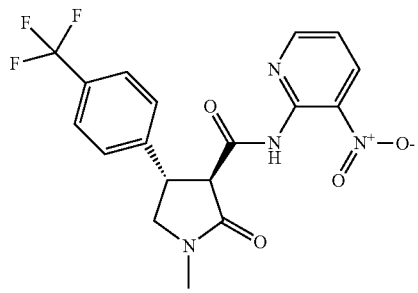 |
| 1432 | AND Enantiomer 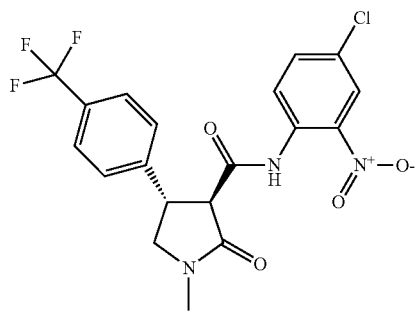 |
| 1433 | AND Enantiomer 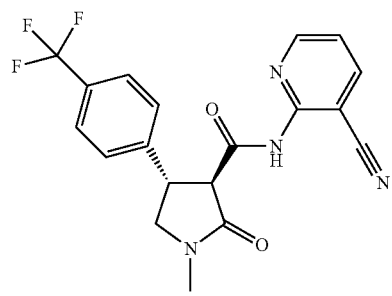 |
| 1434 | AND Enantiomer 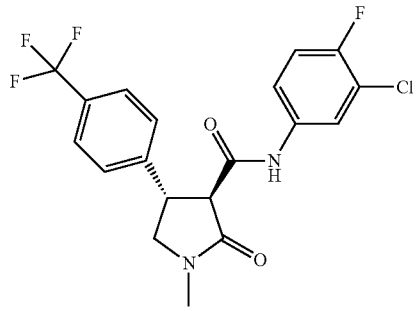 |
284
-continued
INDEX TABLE F
| Ex. # | Structure |
|---|---|
| 1435 | AND Enantiomer 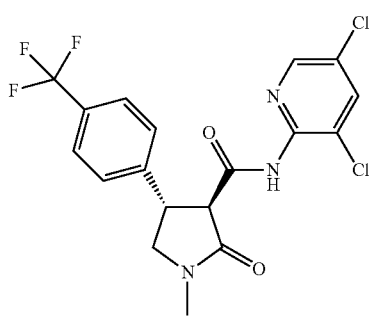 |
| 1436 | AND Enantiomer 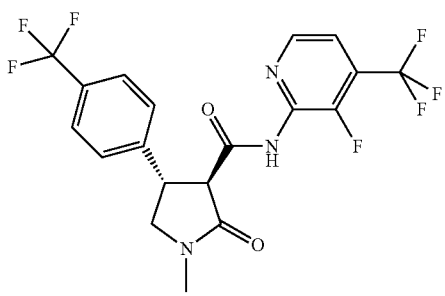 |
| 1437 | 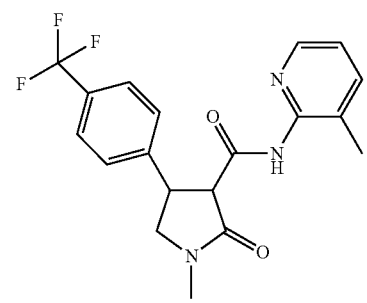 [SMILES: Cc1cccnc1NC(=O)C1C(=O)N(C)CC1c1ccc(C(F)(F)F)cc1] |
| 1438 | AND Enantiomer 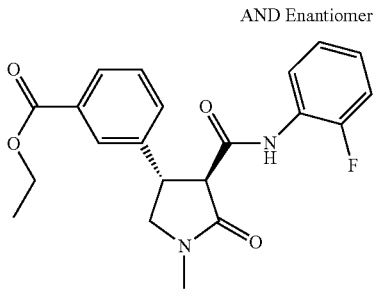 [SMILES: CCOC(=O)c1cccc([C@H]2CN(C)C(=O)[C@@H]2C(=O)Nc2ccccc2F)c1] |

285
-continued

INDEX TABLE F

| Ex. # | Structure |
|---|---|
| 1439 | AND Enantiomer |
| 1440 | AND Enantiomer |
| 1441 | AND Enantiomer |
| 1442 | AND Enantiomer |

286
-continued

INDEX TABLE F

| Ex. # | Structure |
|---|---|
| 1443 | AND Enantiomer |
| 1444 | AND Enantiomer |
| 1445 | AND Enantiomer |
| 1446 | AND Enantiomer |

INDEX TABLE F
| Ex. # | Structure |
|---|---|
| 1447 | AND Enantiomer 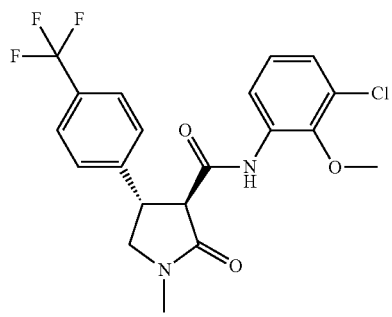 |
| 1448 | AND Enantiomer 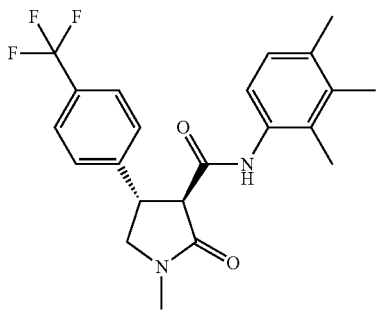 |
| 1449 | AND Enantiomer 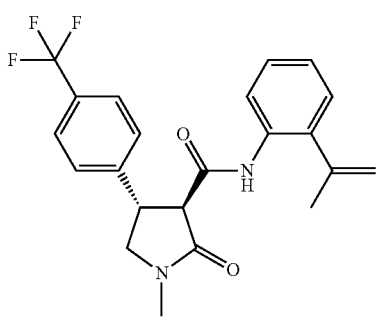 |
| 1450 | AND Enantiomer 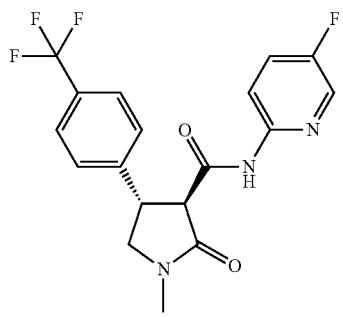 |
INDEX TABLE F
| Ex. # | Structure |
|---|---|
| 1451 | AND Enantiomer 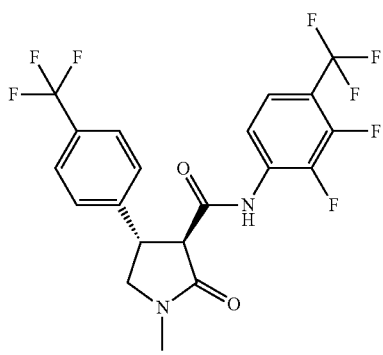 |
| 1452 | AND Enantiomer 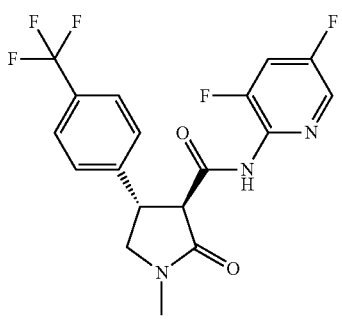 |
| 1453 | AND Enantiomer 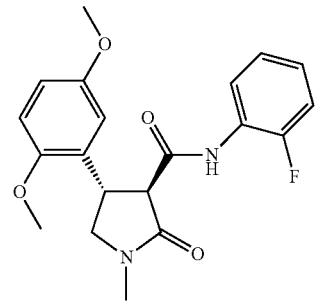 |
| 1454 | AND Enantiomer 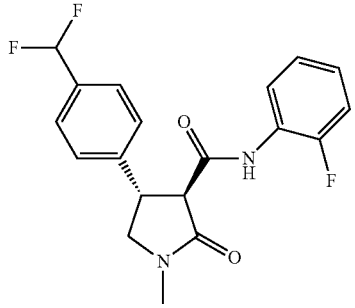 |

INDEX TABLE F
| Ex. # | Structure |
|---|---|
| 1455 | AND Enantiomer 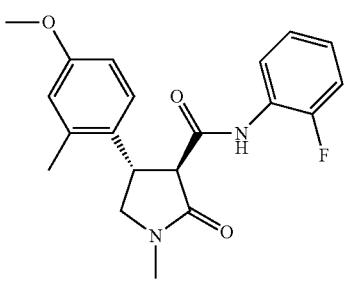 |
| 1456 | AND Enantiomer 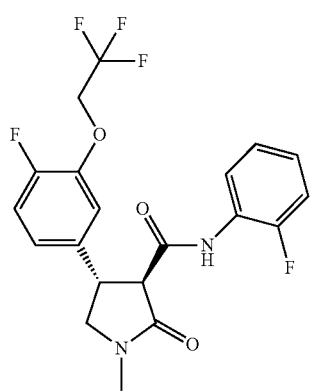 |
| 1457 | AND Enantiomer 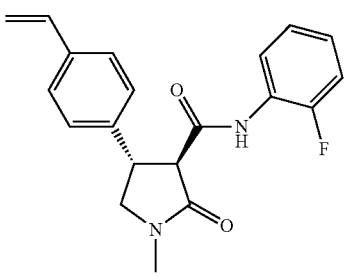 |
| 1458 | AND Enantiomer 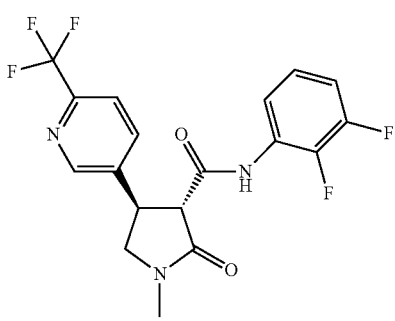 |
| 1459 | AND Enantiomer 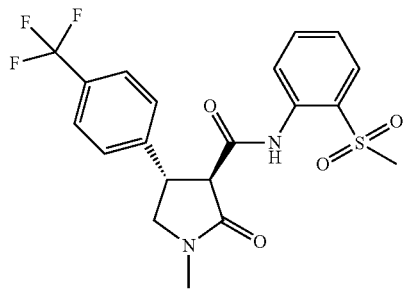 |
| 1460 | AND Enantiomer 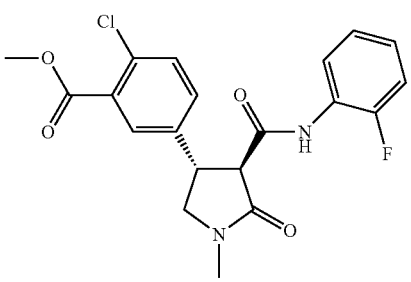 |
| 1461 | AND Enantiomer 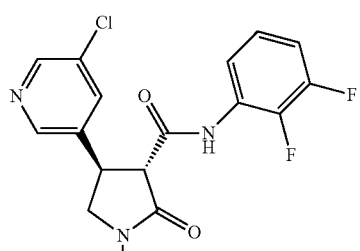 |
| 1462 | AND Enantiomer 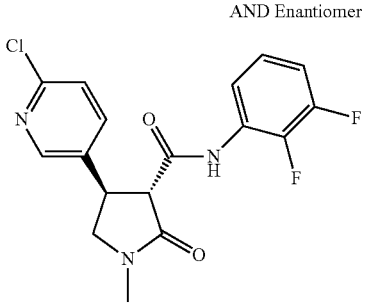 [SMILES: CN1C[C@@H](c2ccc(Cl)nc2)[C@H](C(=O)Nc2cccc(F)c2F)C1=O] |
| 1463 | 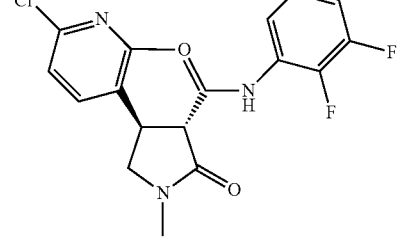 |

INDEX TABLE F

| Ex. # | Structure |
|---|---|
| 1464 | AND Enantiomer |
| 1465 | AND Enantiomer |
| 1466 | AND Enantiomer |
| 1467 | AND Enantiomer |
| 1468 | AND Enantiomer |
| 1469 | AND Enantiomer |
| 1470 | AND Enantiomer |
| 1471 | AND Enantiomer |

INDEX TABLE F
| Ex. # | Structure |
|---|---|
| 1472 | AND Enantiomer 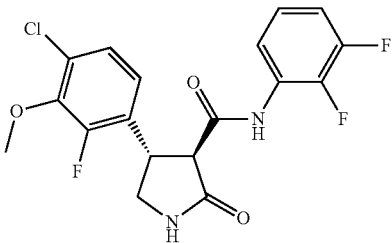 |
| 1473 | AND Enantiomer 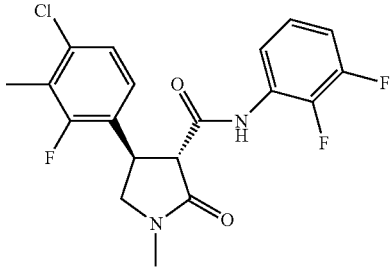 |
| 1474 | AND Enantiomer 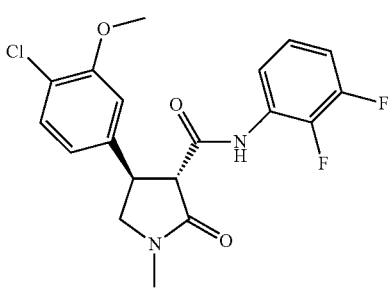 |
| 1475 | AND Enantiomer 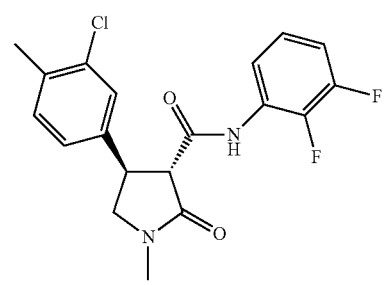 |
| 1476 | AND Enantiomer 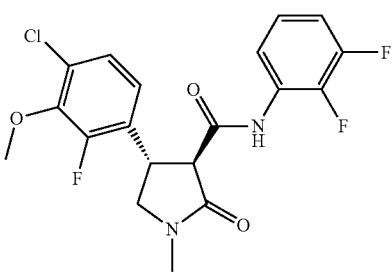 |
| 1477 | AND Enantiomer 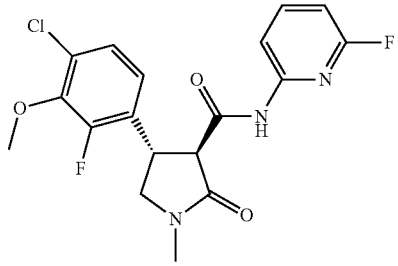 |
| 1478 | AND Enantiomer 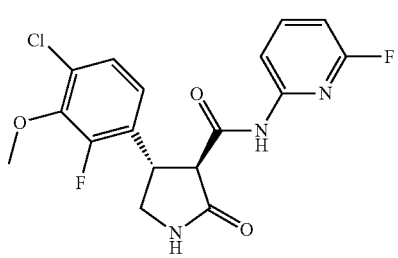 |
| 1479 | AND Enantiomer 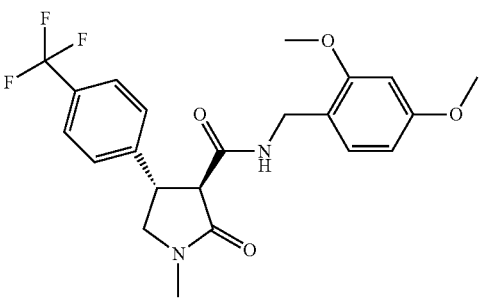 |
| 1480 | AND Enantiomer 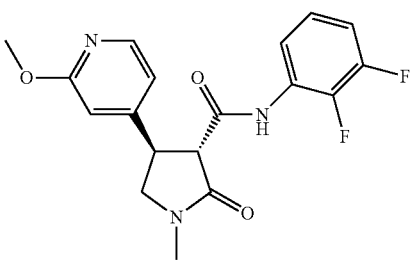 |
| 1481 | AND Enantiomer 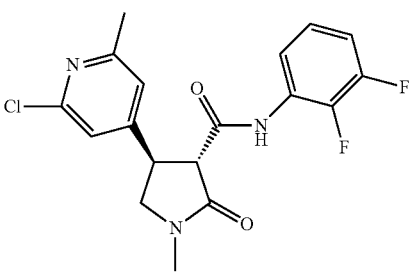 |

INDEX TABLE F
| Ex. # | Structure |
|---|---|
| 1482 | AND Enantiomer 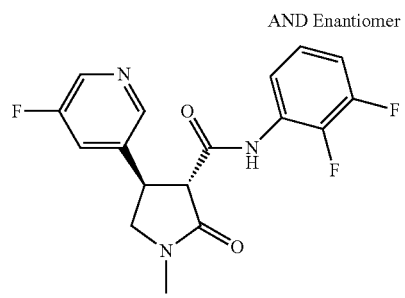 [SMILES: CN1C[C@@H](c2cncc(F)c2)[C@H](C(=O)Nc2cccc(F)c2F)C1=O] |
| 1483 | AND Enantiomer 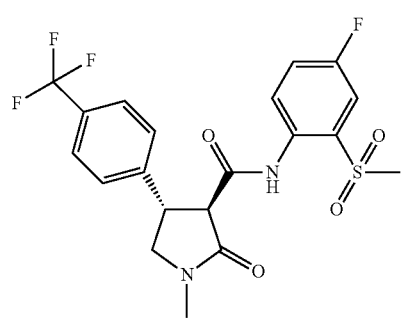 |
| 1484 | AND Enantiomer 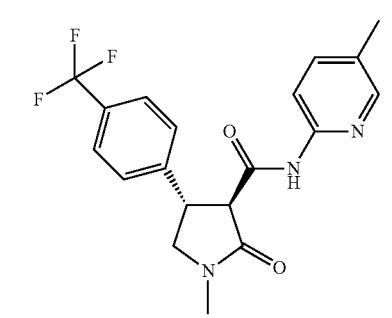 |
| 1485 | AND Enantiomer 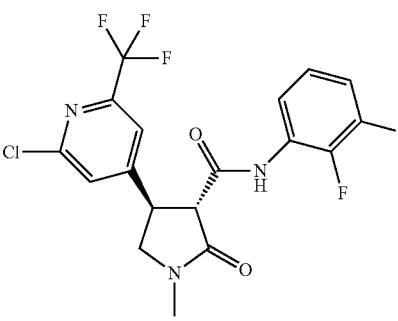 |
| 1486 | AND Enantiomer 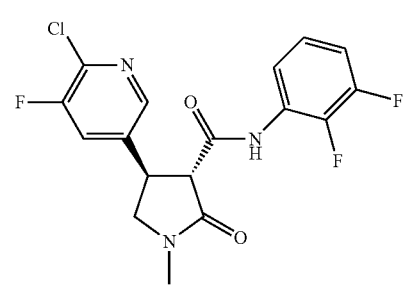 |
| 1487 | AND Enantiomer 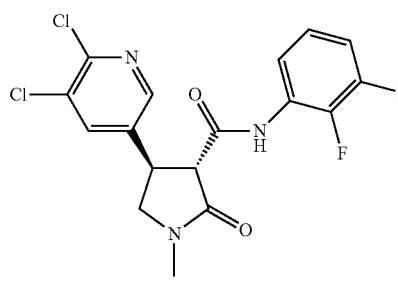 |
| 1488 | AND Enantiomer 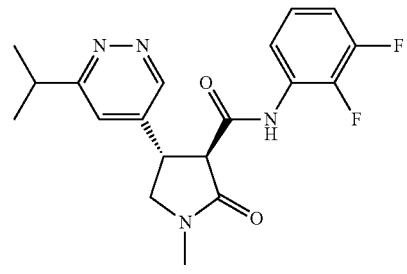 |
| 1489 | AND Enantiomer 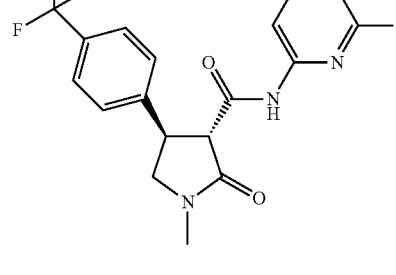 |
| 1490 | AND Enantiomer 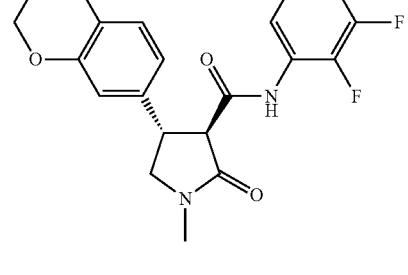 |

| Ex. # | Structure |
|---|---|
| 1491 | AND Enantiomer 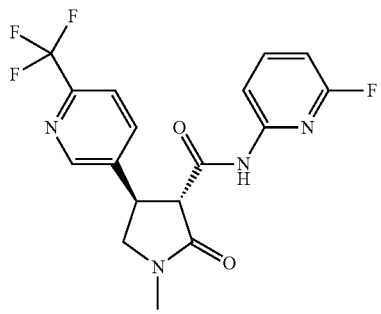 |
| 1492 | AND Enantiomer 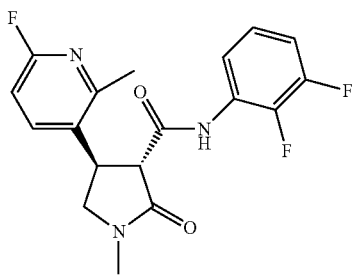 |
| 1493 | AND Enantiomer 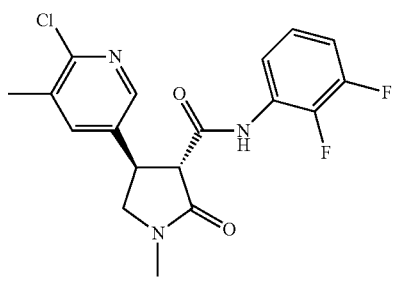 |
| 1494 | AND Enantiomer 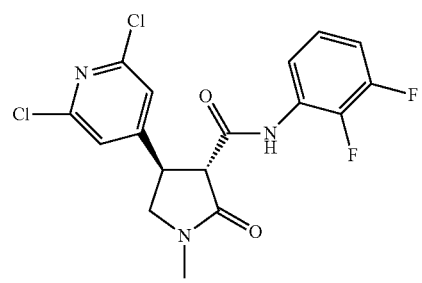 |
| Ex. # | Structure |
|---|---|
| 1495 | AND Enantiomer 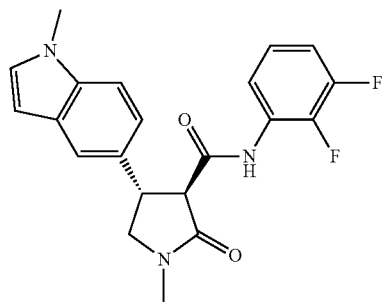 |
| 1496 | AND Enantiomer 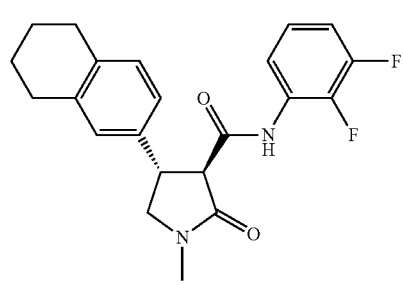 |
| 1497 | AND Enantiomer 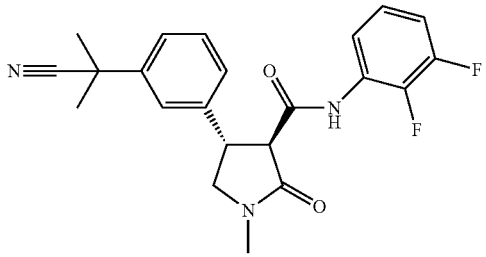 |
| 1498 | AND Enantiomer 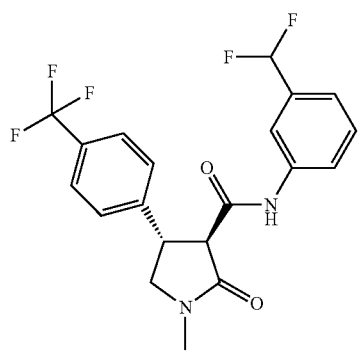 |

INDEX TABLE F
| Ex. # | Structure |
|---|---|
| 1499 | AND Enantiomer 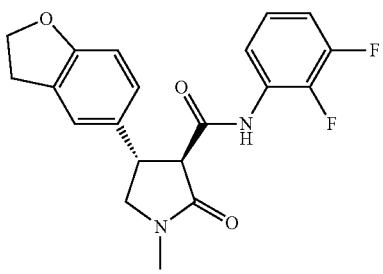 |
| 1500 | AND Enantiomer 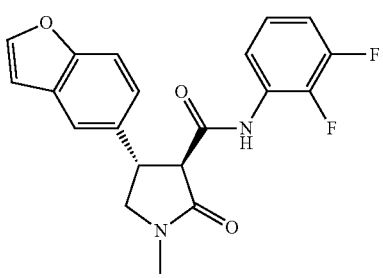 |
| 1501 | AND Enantiomer 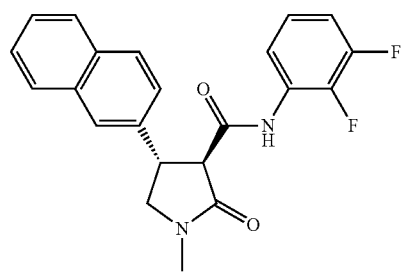 |
| 1502 | AND Enantiomer 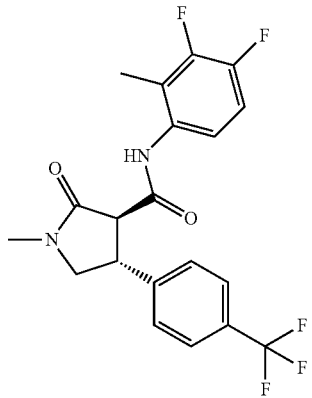 |
| 1503 | AND Enantiomer 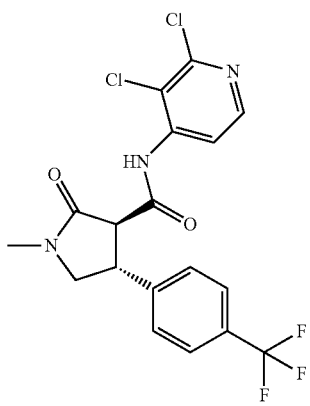 |
| 1504 | AND Enantiomer 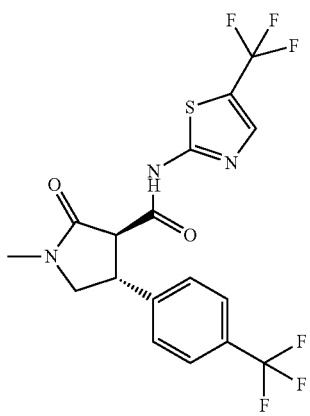 |
| 1505 | AND Enantiomer 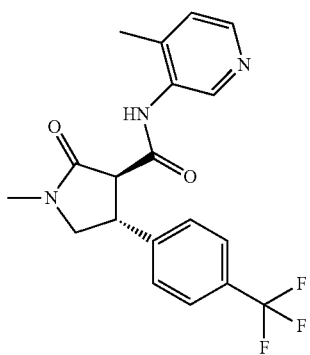 |

INDEX TABLE F
| Ex. # | Structure |
|---|---|
| 1506 | AND Enantiomer 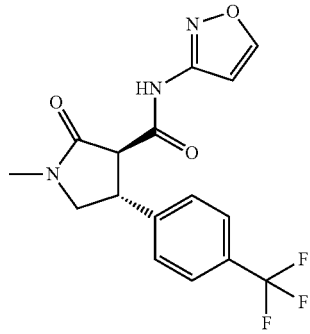 |
| 1507 | AND Enantiomer 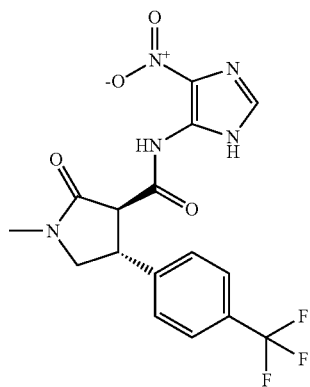 |
| 1508 | AND Enantiomer 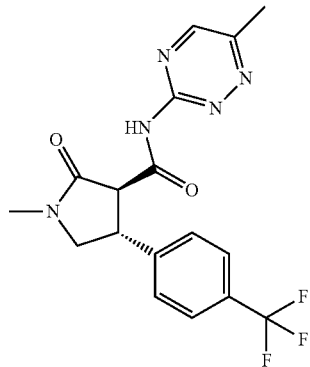 |
| 1509 | AND Enantiomer 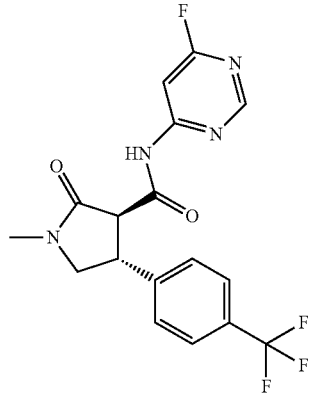 |
| 1510 | AND Enantiomer 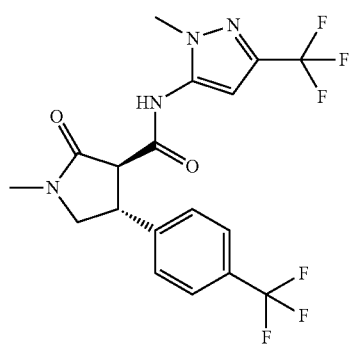 |
| 1511 | AND Enantiomer 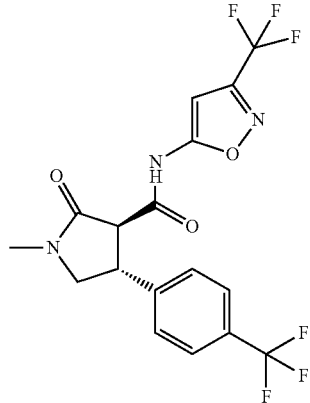 |

INDEX TABLE F
| Ex. # | Structure |
|---|---|
| 1512 | AND Enantiomer 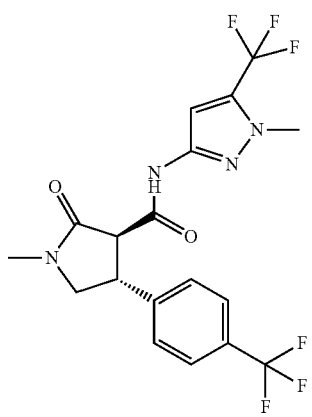 |
| 1513 | AND Enantiomer 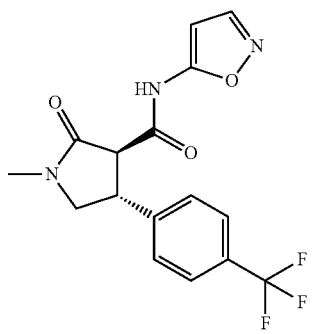 |
| 1514 | AND Enantiomer 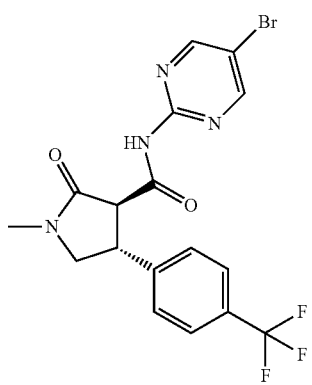 |
INDEX TABLE F
| Ex. # | Structure |
|---|---|
| 1515 | AND Enantiomer 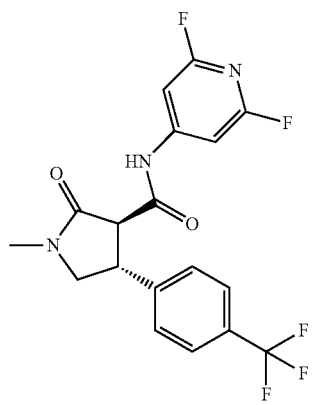 |
| 1516 | AND Enantiomer 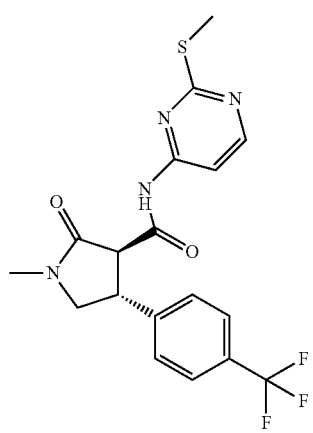 |
| 1517 | AND Enantiomer 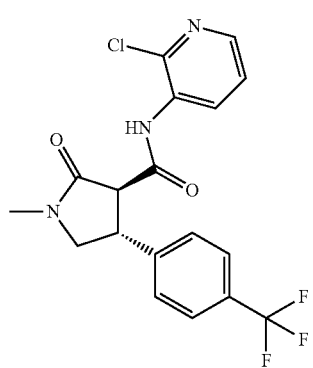 |

INDEX TABLE F
| Ex. # | Structure |
|---|---|
| 1518 | AND Enantiomer 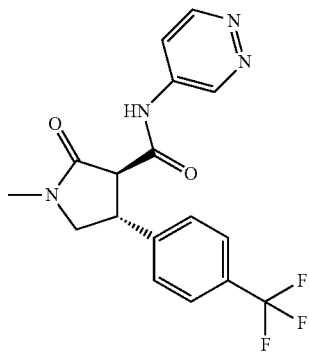 |
| 1519 | AND Enantiomer 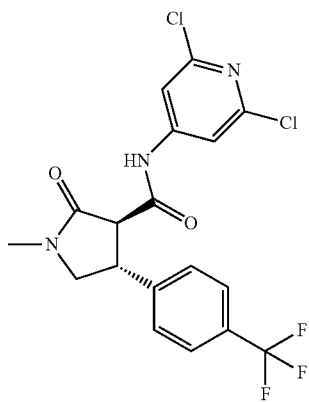 |
| 1520 | AND Enantiomer 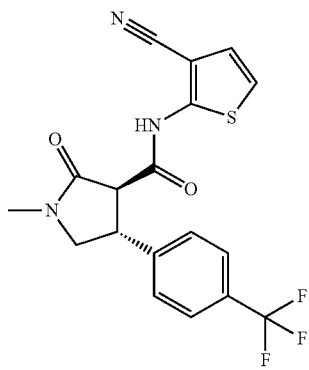 |
| 1521 | AND Enantiomer 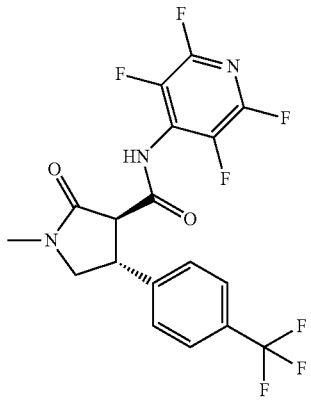 |
| 1522 | AND Enantiomer 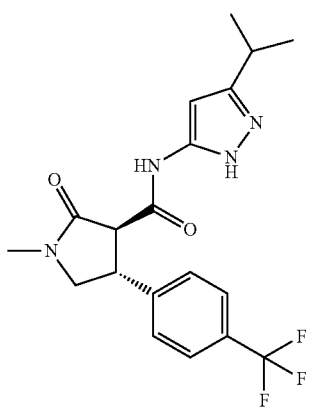 |
| 1523 | AND Enantiomer 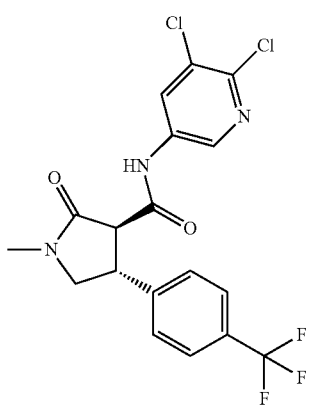 |

INDEX TABLE F
| Ex. # | Structure |
|---|---|
| 1524 | AND Enantiomer 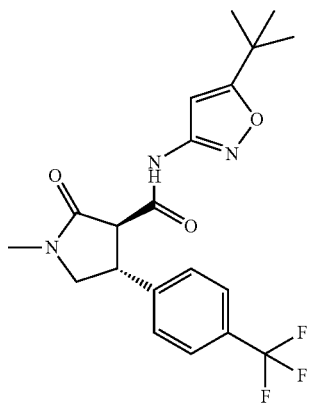 |
| 1525 | AND Enantiomer 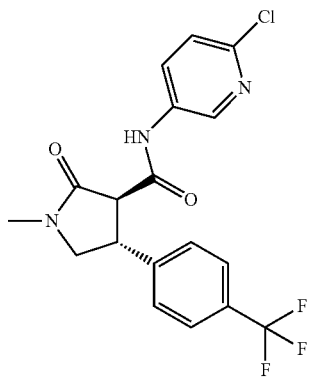 |
| 1526 | AND Enantiomer 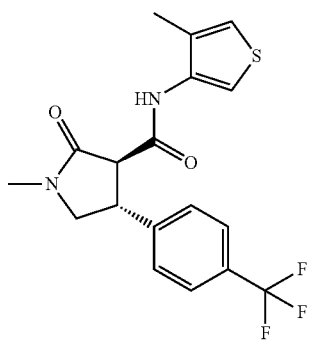 |
| 1527 | AND Enantiomer 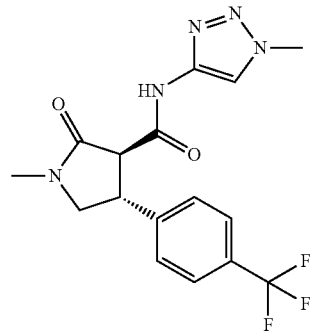 |
| 1528 | AND Enantiomer 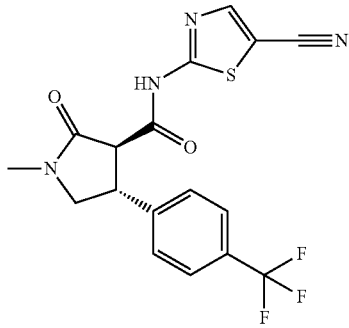 |
| 1529 | AND Enantiomer 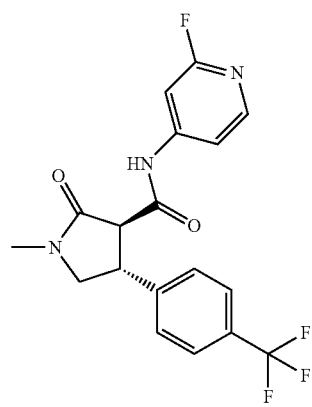 |

INDEX TABLE F
| Ex. # | Structure |
|---|---|
| 1530 | AND Enantiomer 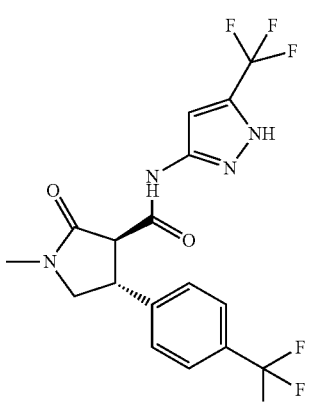 |
| 1531 | AND Enantiomer 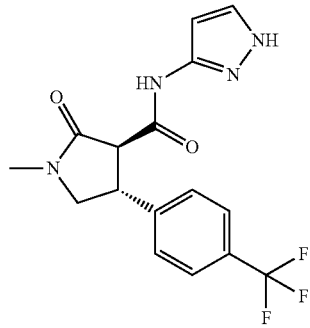 |
| 1532 | AND Enantiomer 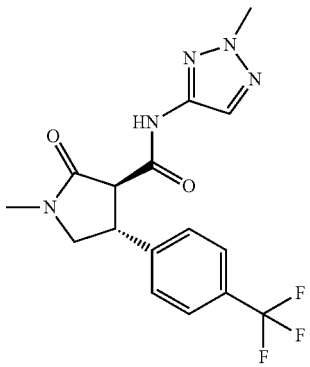 |
| 1533 | AND Enantiomer 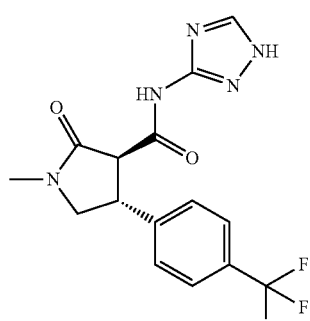 |
| 1534 | AND Enantiomer 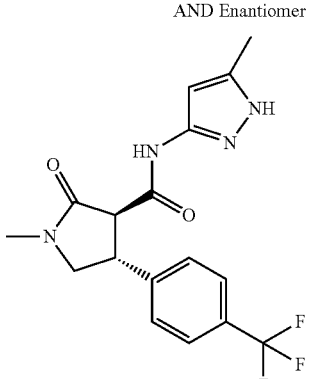 |
| 1535 | AND Enantiomer 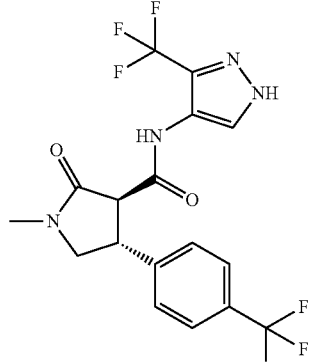 |
| 1536 | AND Enantiomer 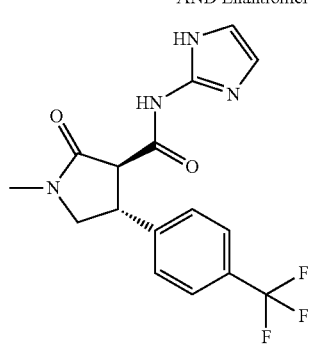 |

INDEX TABLE F
| Ex. # | Structure |
|---|---|
| 1537 | AND Enantiomer 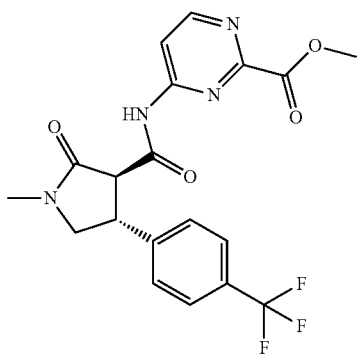 |
| 1538 | AND Enantiomer 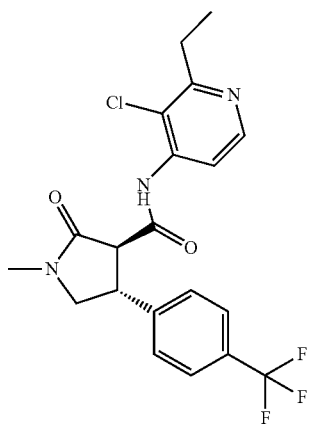 |
| 1539 | AND Enantiomer 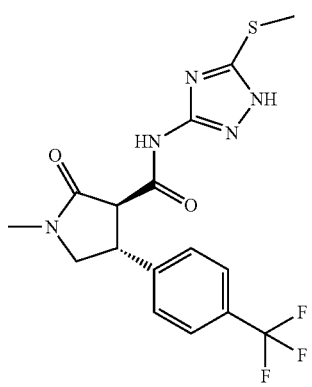 |
| 1540 | AND Enantiomer 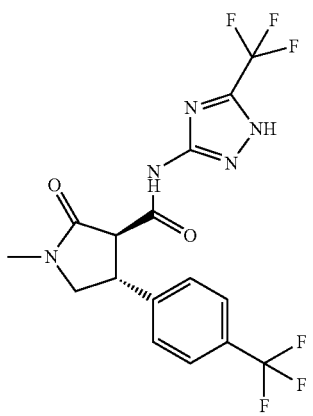 |
| 1541 | AND Enantiomer 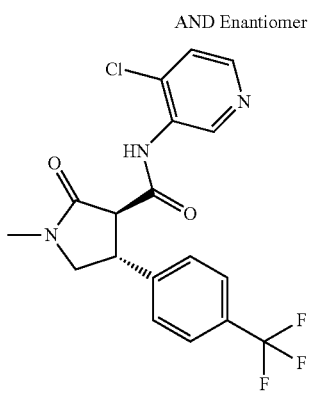 [SMILES: CN1C[C@@H](c2ccc(C(F)(F)F)cc2)[C@H](C(=O)Nc2cnccc2Cl)C1=O] |
| 1542 | AND Enantiomer 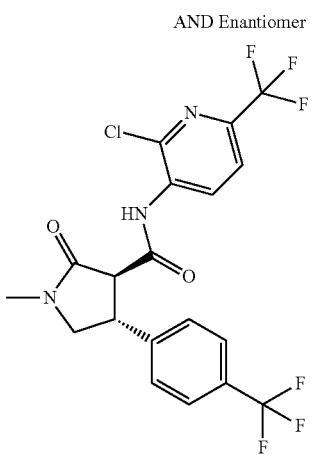 [SMILES: CN1C[C@@H](c2ccc(C(F)(F)F)cc2)[C@H](C(=O)Nc2ccc(C(F)(F)F)nc2Cl)C1=O] |

INDEX TABLE F
| Ex. # | Structure |
|---|---|
| 1543 | AND Enantiomer |
| 1544 | AND Enantiomer |
| 1545 | AND Enantiomer |
| 1546 | AND Enantiomer |
| 1547 | AND Enantiomer |
| 1548 | AND Enantiomer |
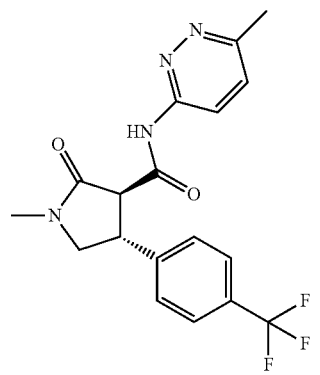

INDEX TABLE F

| Ex. # | Structure |
|---|---|
| 1549 | AND Enantiomer |
| 1550 | AND Enantiomer |
| 1551 | AND Enantiomer |
| 1552 | AND Enantiomer |
| 1553 | AND Enantiomer |
| 1554 | AND Enantiomer |
| 1555 | AND Enantiomer |

317
-continued
| INDEX TABLE F | |
|---|---|
| Ex. # | Structure |
1556  AND Enantiomer
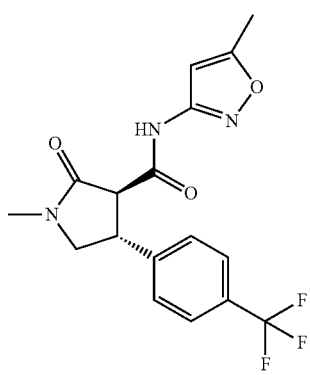
1557  AND Enantiomer
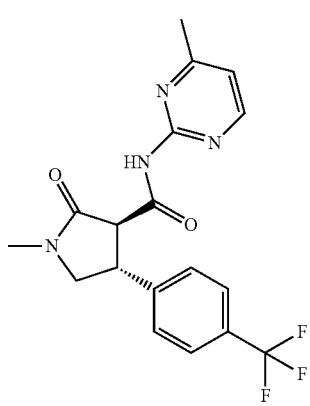
1558  AND Enantiomer
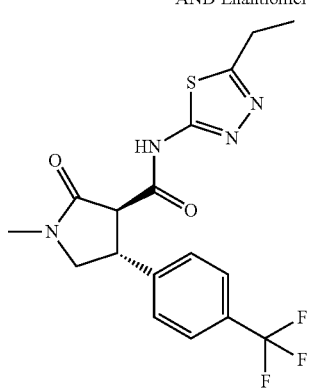
318
-continued
| INDEX TABLE F | |
|---|---|
| Ex. # | Structure |
1559  AND Enantiomer
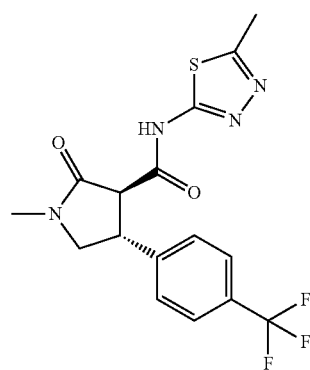
1560  AND Enantiomer
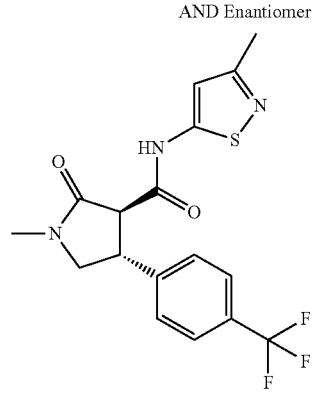 [SMILES: Cc1cc(NC(=O)[C@@H]2C(=O)N(C)C[C@H]2c2ccc(C(F)(F)F)cc2)sn1]
1561  AND Enantiomer
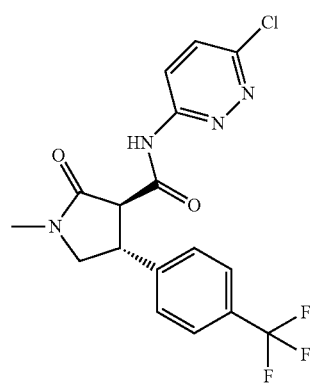

INDEX TABLE F

| Ex. # | Structure |
|---|---|
| 1562 | AND Enantiomer |
| 1563 | AND Enantiomer |
| 1564 | AND Enantiomer |
| 1565 | AND Enantiomer |
| 1566 | AND Enantiomer |
| 1567 | AND Enantiomer |
| 1568 | AND Enantiomer |

INDEX TABLE F
| Ex. # | Structure |
|---|---|
| 1569 | AND Enantiomer 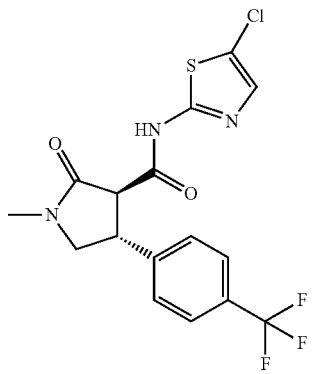 |
| 1570 | AND Enantiomer 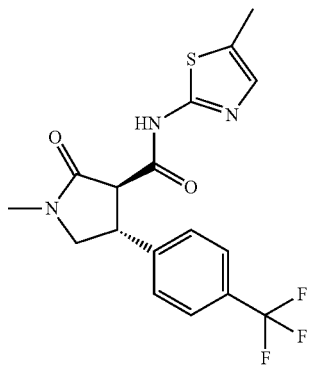 |
| 1571 | AND Enantiomer 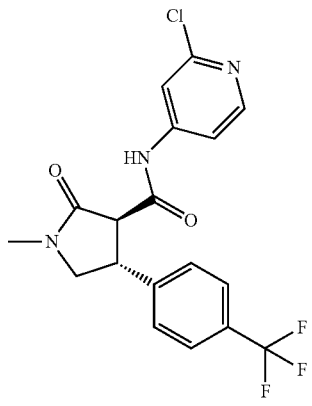 |
| 1572 | AND Enantiomer 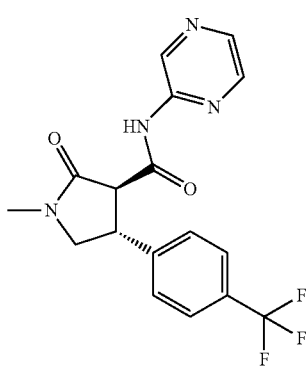 |
| 1573 | AND Enantiomer 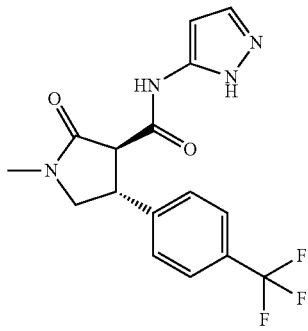 |
| 1574 | AND Enantiomer 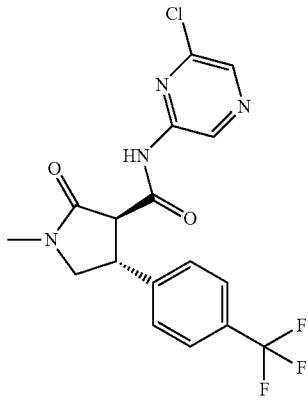 |

INDEX TABLE F
| Ex. # | Structure |
|---|---|
| 1575 | AND Enantiomer 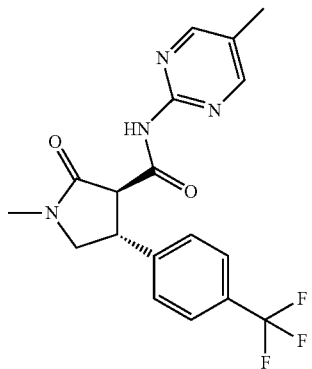 |
| 1576 | AND Enantiomer 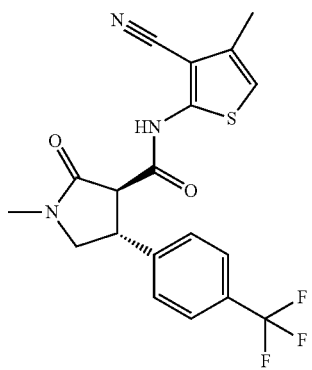 |
| 1577 | AND Enantiomer 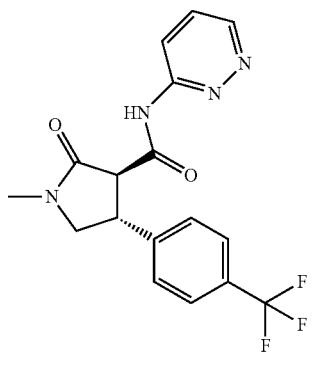 |
INDEX TABLE F
| Ex. # | Structure |
|---|---|
| 1578 | AND Enantiomer 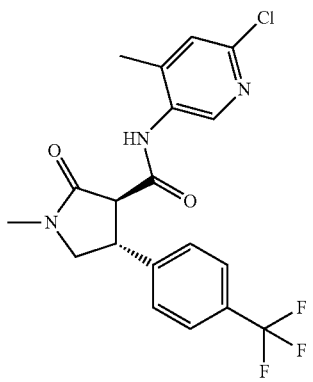 |
| 1579 | AND Enantiomer 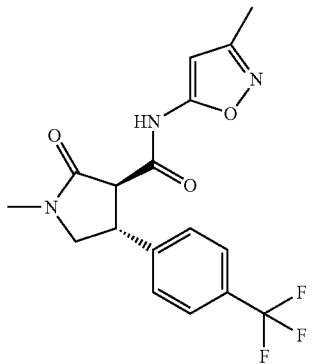 |
| 1580 | AND Enantiomer 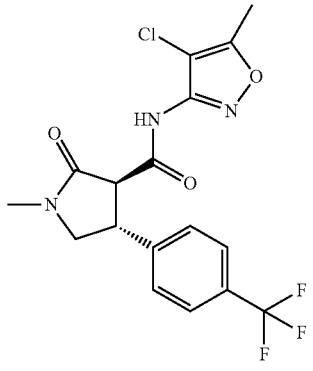 |

INDEX TABLE F
| Ex. # | Structure |
|---|---|
| 1581 | AND Enantiomer 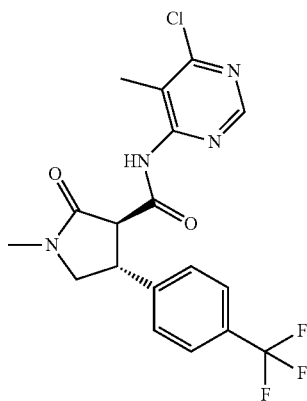 |
| 1582 | AND Enantiomer 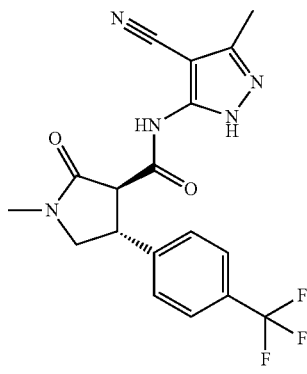 |
| 1583 | AND Enantiomer 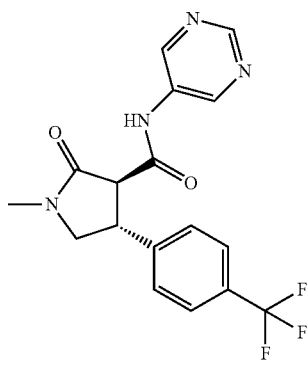 |
| 1584 | AND Enantiomer 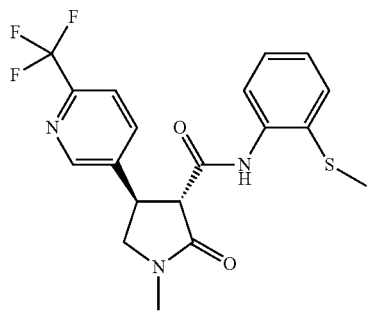 |
| 1585 | AND Enantiomer 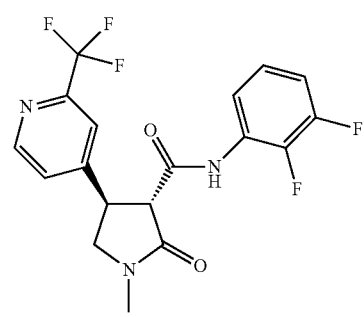 |
| 1586 | AND Enantiomer 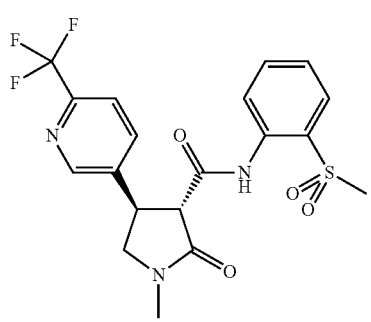 |
| 1587 | AND Enantiomer 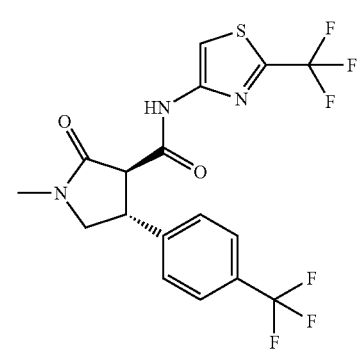 |

INDEX TABLE F

| Ex. # | Structure |
|---|---|
| 1588 | AND Enantiomer |
| 1589 | AND Enantiomer |
| 1590 | AND Enantiomer |
| 1591 | AND Enantiomer |
| 1592 | AND Enantiomer |
| 1593 | AND Enantiomer |
| 1594 | AND Enantiomer |
| 1595 | AND Enantiomer |

INDEX TABLE F
| Ex. # | Structure |
|---|---|
| 1596 | AND Enantiomer 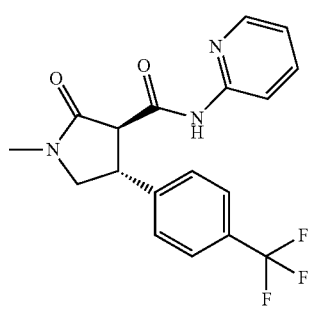 |
| 1597 | AND Enantiomer 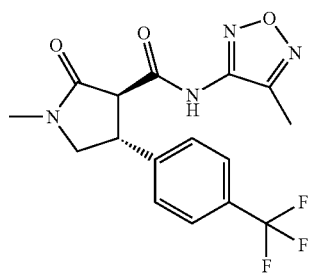 |
| 1598 | AND Enantiomer 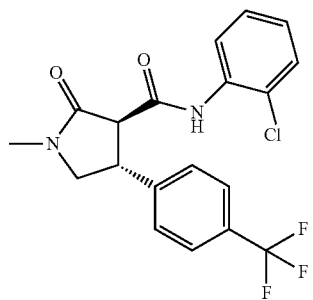 |
| 1599 | AND Enantiomer 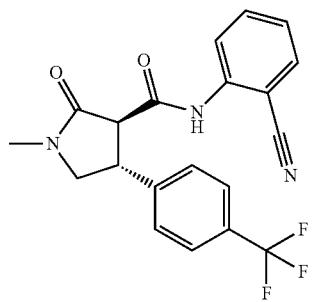 |
INDEX TABLE F
| Ex. # | Structure |
|---|---|
| 1600 | AND Enantiomer 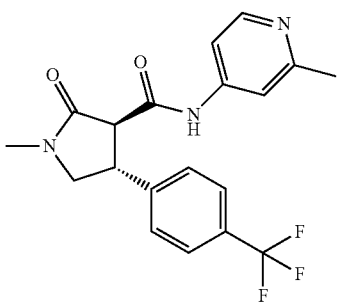 |
| 1601 | AND Enantiomer 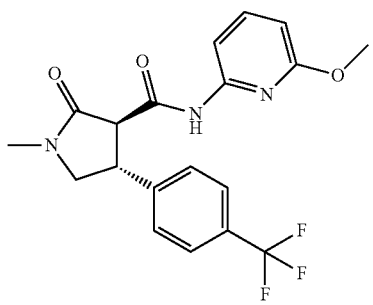 |
| 1602 | AND Enantiomer 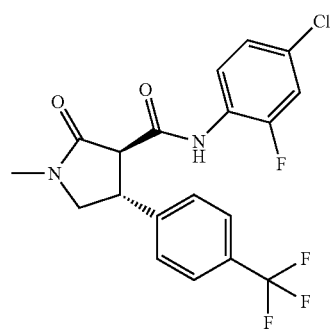 |
| 1603 | AND Enantiomer 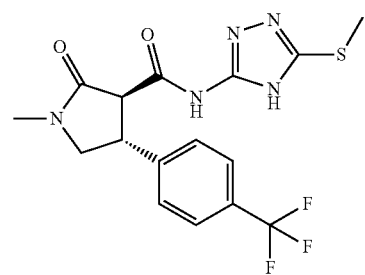 |

331
-continued
INDEX TABLE F
| Ex. # | Structure |
|---|---|
| 1604 | AND Enantiomer 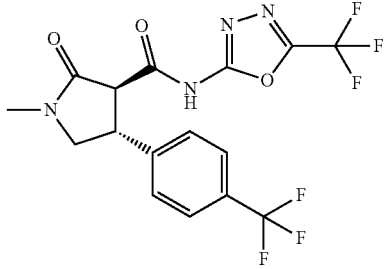 |
| 1605 | AND Enantiomer 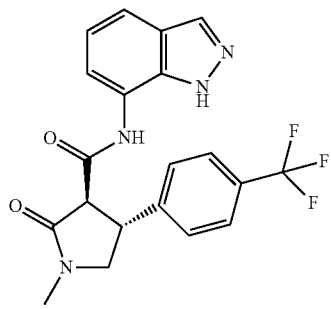 |
| 1606 | AND Enantiomer 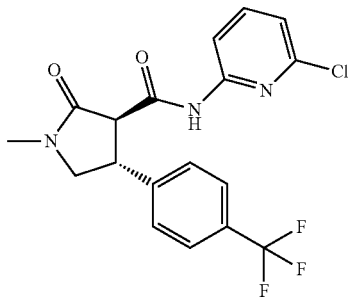 |
| 1607 | AND Enantiomer 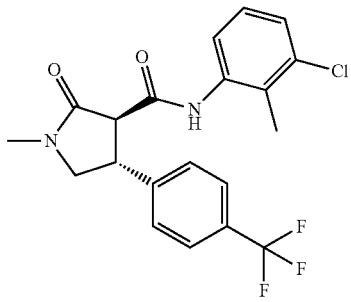 |
332
-continued
INDEX TABLE F
| Ex. # | Structure |
|---|---|
| 1608 | AND Enantiomer 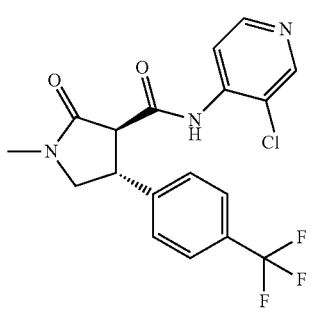 |
| 1609 | AND Enantiomer 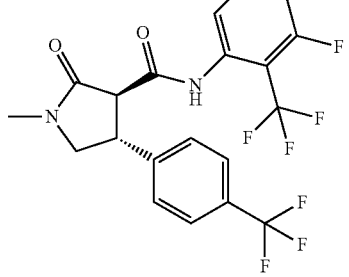 |
| 1610 | AND Enantiomer 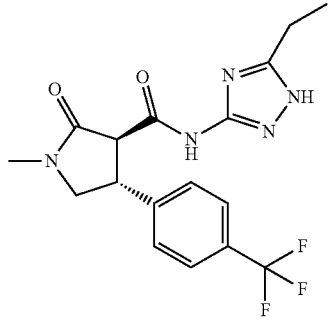 |
| 1611 | AND Enantiomer 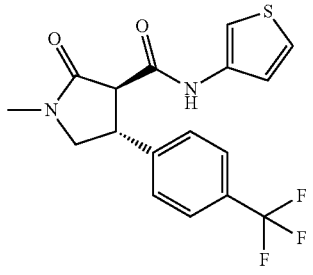 |

INDEX TABLE F
| Ex. # | Structure |
|---|---|
| 1612 | AND Enantiomer 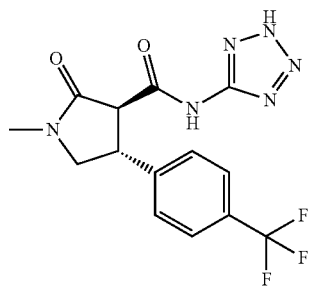 |
| 1613 | AND Enantiomer 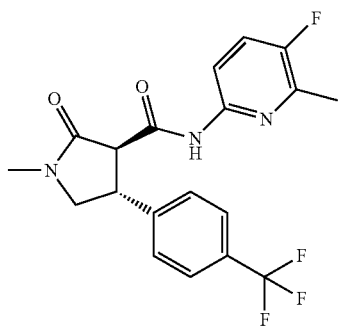 |
| 1614 | AND Enantiomer 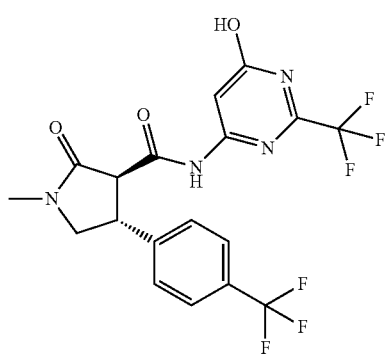 |
| 1615 | AND Enantiomer 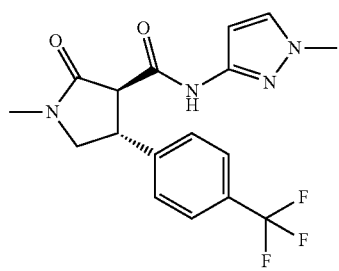 |
INDEX TABLE F
| Ex. # | Structure |
|---|---|
| 1616 | AND Enantiomer 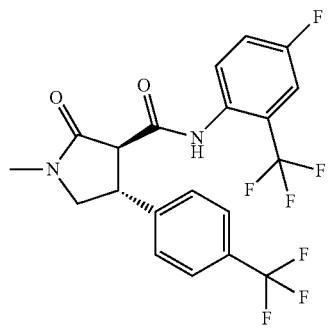 |
| 1617 | AND Enantiomer 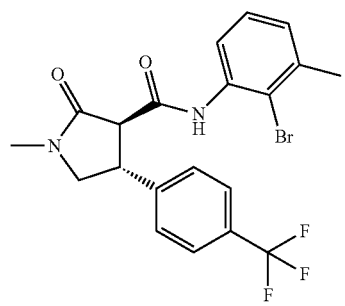 |
| 1618 | AND Enantiomer 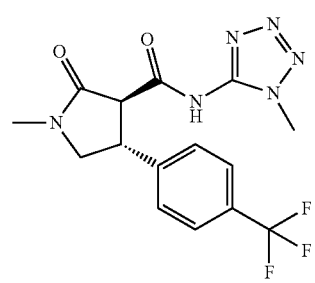 |
| 1619 | AND Enantiomer 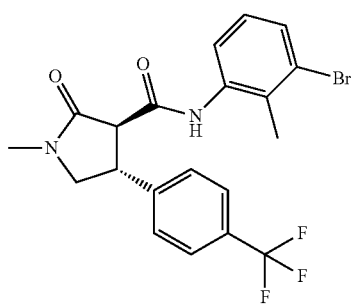 |

INDEX TABLE F
| Ex. # | Structure |
|---|---|
| 1620 | AND Enantiomer 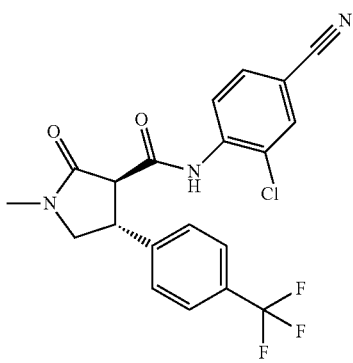 |
| 1621 | AND Enantiomer 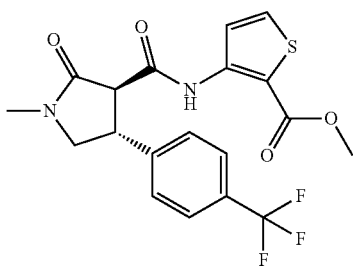 |
| 1622 | AND Enantiomer 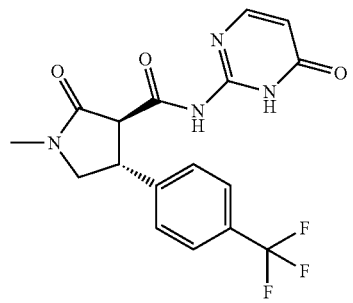 |
| 1623 | AND Enantiomer 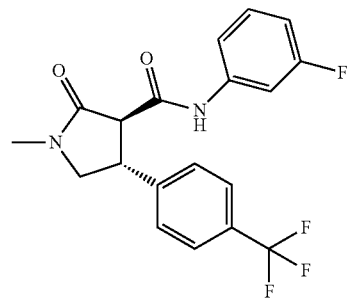 |
INDEX TABLE F
| Ex. # | Structure |
|---|---|
| 1624 | AND Enantiomer 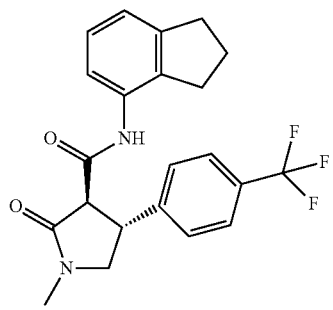 |
| 1625 | AND Enantiomer 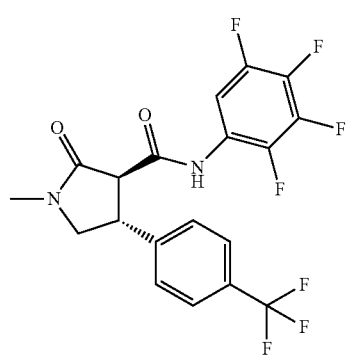 |
| 1626 | AND Enantiomer 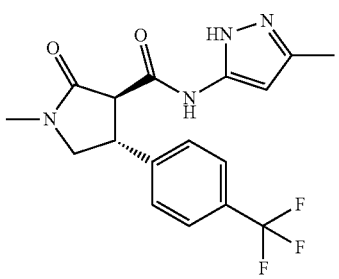 |
| 1627 | AND Enantiomer 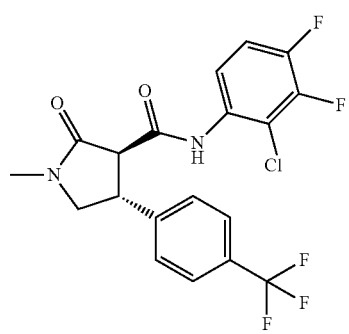 |

INDEX TABLE F
| Ex. # | Structure |
|---|---|
| 1628 | AND Enantiomer 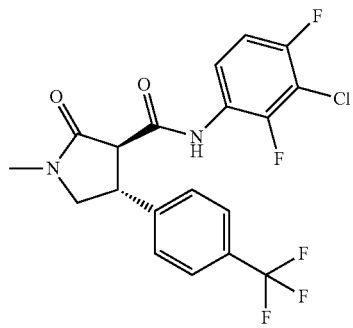 |
| 1629 | AND Enantiomer 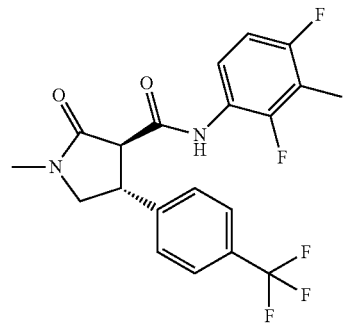 |
| 1630 | AND Enantiomer 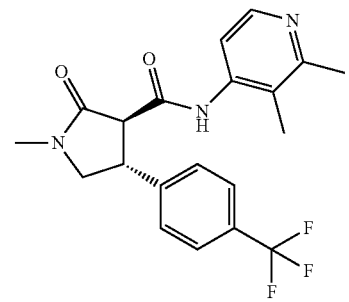 |
| 1631 | AND Enantiomer 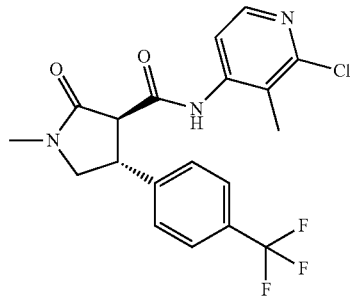 |
INDEX TABLE F
| Ex. # | Structure |
|---|---|
| 1632 | AND Enantiomer 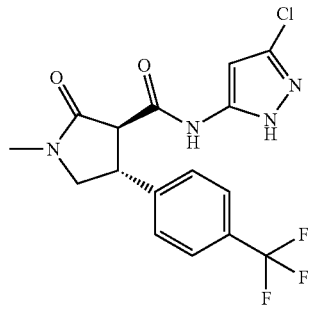 |
| 1633 | AND Enantiomer 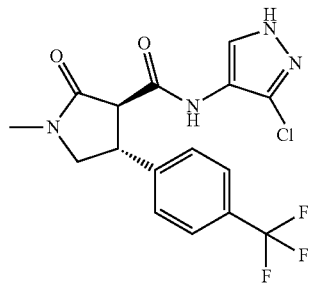 |
| 1634 | AND Enantiomer 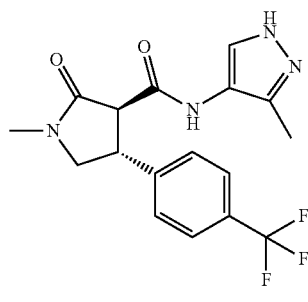 |
| 1635 | AND Enantiomer 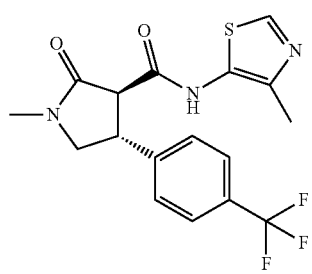 |

INDEX TABLE F

| Ex. # | Structure |
|---|---|
| 1636 | AND Enantiomer |
| 1637 | AND Enantiomer |
| 1638 | AND Enantiomer |
| 1639 | AND Enantiomer |
| 1640 | AND Enantiomer |
| 1641 | AND Enantiomer |
| 1642 | AND Enantiomer |
| 1643 | AND Enantiomer |

INDEX TABLE F
| Ex. # | Structure |
|---|---|
| 1644 | AND Enantiomer 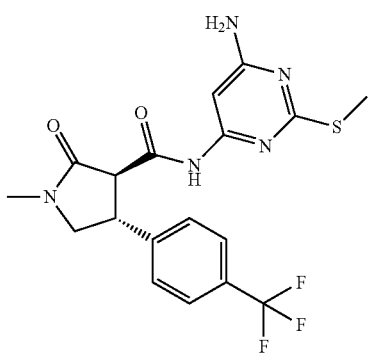 |
| 1645 | AND Enantiomer 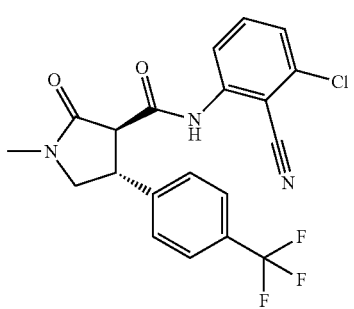 |
| 1646 | AND Enantiomer 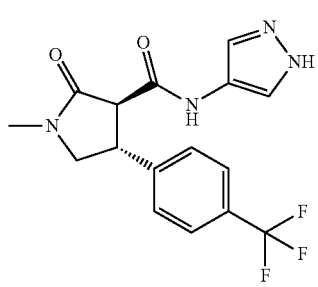 |
| 1647 | AND Enantiomer 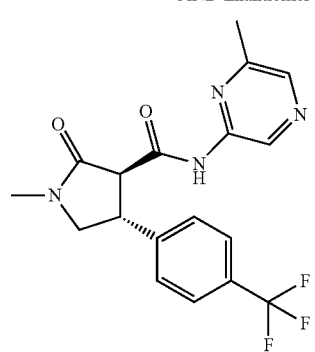 |
INDEX TABLE F
| Ex. # | Structure |
|---|---|
| 1648 | AND Enantiomer 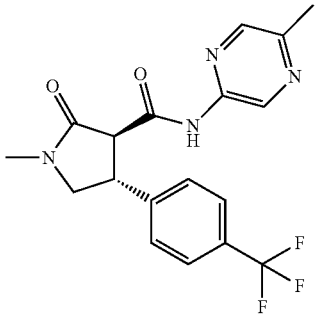 |
| 1649 | AND Enantiomer 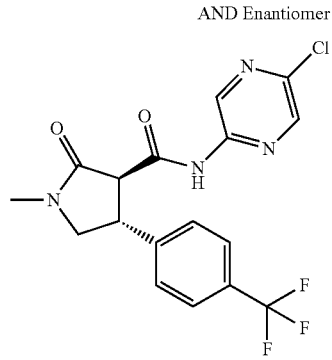 [SMILES: CN1C[C@@H](c2ccc(C(F)(F)F)cc2)[C@H](C(=O)Nc2cnc(Cl)cn2)C1=O] |
| 1650 | AND Enantiomer 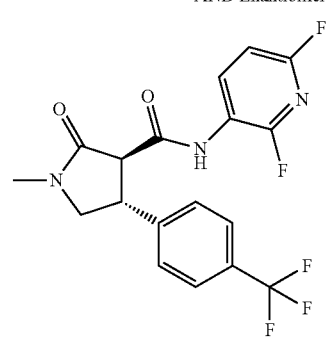 |
| 1651 | AND Enantiomer 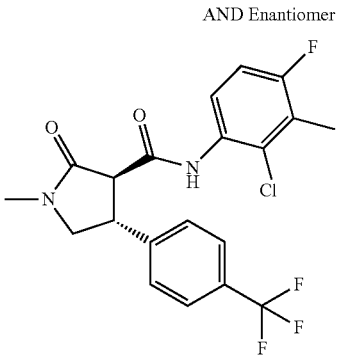 |

INDEX TABLE F

| Ex. # | Structure |
|---|---|
| 1652 | AND Enantiomer |
| 1653 | AND Enantiomer |
| 1654 | AND Enantiomer |
| 1655 | AND Enantiomer |
| 1656 | AND Enantiomer |
| 1657 | AND Enantiomer |
| 1658 | AND Enantiomer |
| 1659 | AND Enantiomer |

INDEX TABLE F

| Ex. # | Structure |
|---|---|
| 1660 | AND Enantiomer |
| 1661 | AND Enantiomer |
| 1662 | AND Enantiomer |
| 1663 | AND Enantiomer |
| 1664 | AND Enantiomer |
| 1665 | AND Enantiomer |
| 1666 | AND Enantiomer |
| 1667 | AND Enantiomer |

INDEX TABLE F
| Ex. # | Structure |
|---|---|
| 1668 | AND Enantiomer 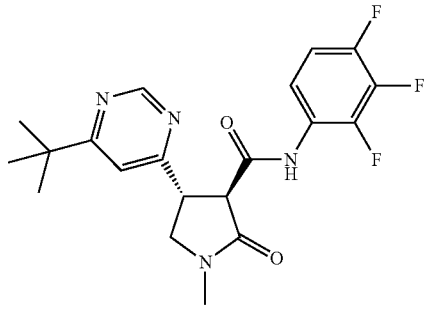 |
| 1669 | AND Enantiomer 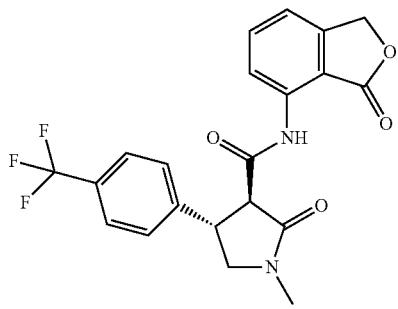 |
| 1670 | AND Enantiomer 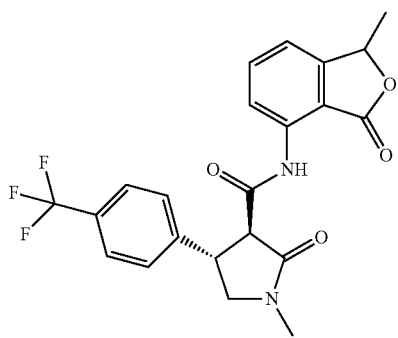 |
| 1671 | AND Enantiomer 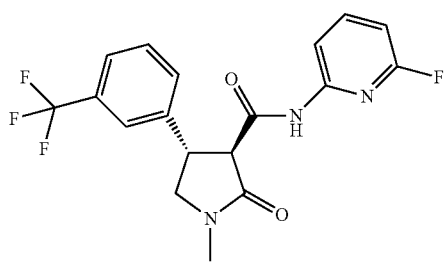 |
| 1672 | AND Enantiomer 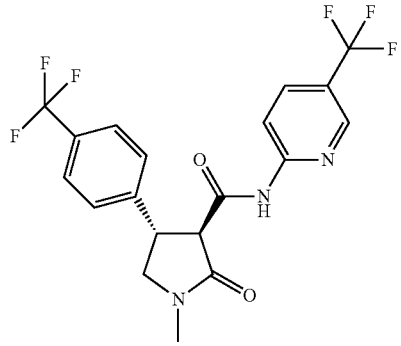 |
| 1673 | AND Enantiomer 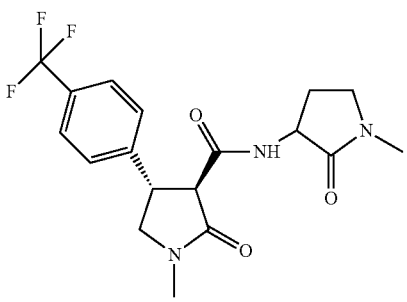 |
| 1674 | AND Enantiomer 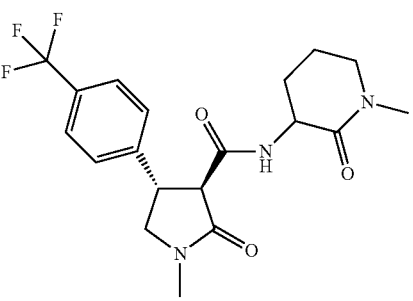 |
| 1675 | AND Enantiomer 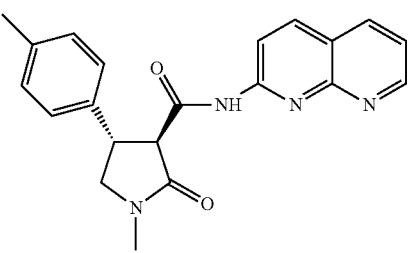 |

INDEX TABLE F
| Ex. # | Structure |
|---|---|
| 1676 | 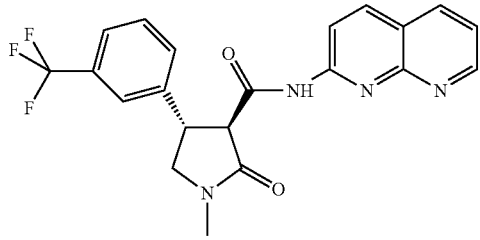 AND Enantiomer |
| 1677 | 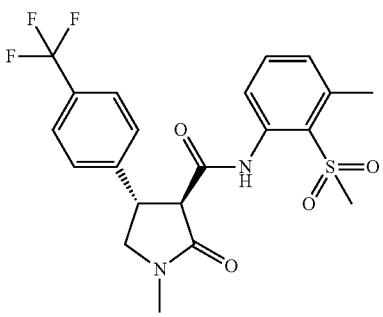 AND Enantiomer |
| 1678 | 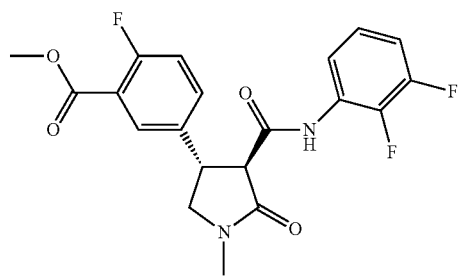 AND Enantiomer |
| 1679 | AND Enantiomer |
INDEX TABLE F
| Ex. # | Structure |
|---|---|
| 1680 | 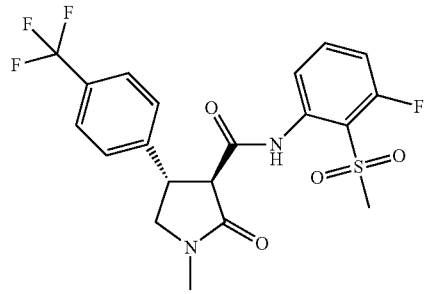 AND Enantiomer |
| 1681 | 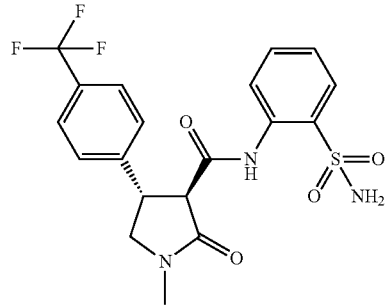 AND Enantiomer |
| 1682 | 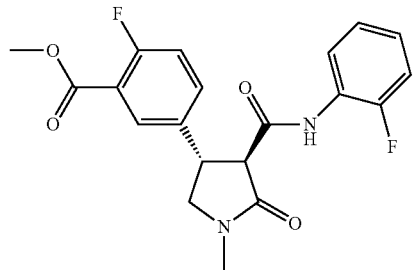 AND Enantiomer |
| 1683 | 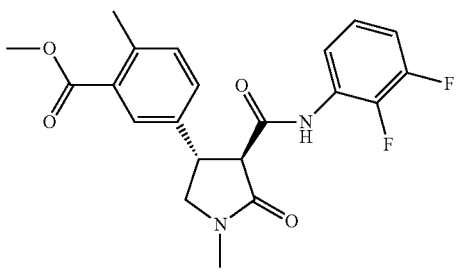 AND Enantiomer |

INDEX TABLE F

| Ex. # | Structure |
|---|---|
| 1684 | 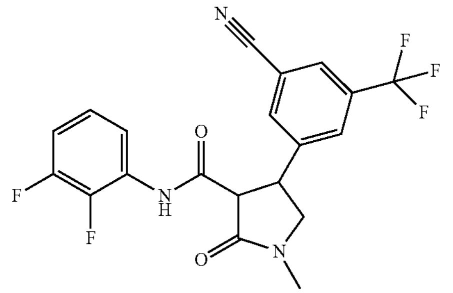 [SMILES: CN1CC(c2cc(C#N)cc(C(F)(F)F)c2)C(C(=O)Nc2cccc(F)c2F)C1=O] |
| 1685 | 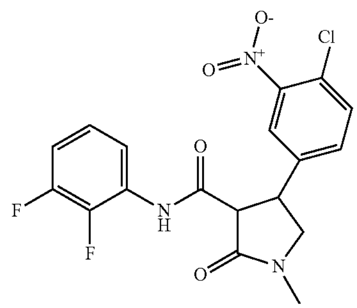 [SMILES: CN1CC(c2ccc(Cl)c([N+](=O)[O-])c2)C(C(=O)Nc2cccc(F)c2F)C1=O] |
| 1686 | 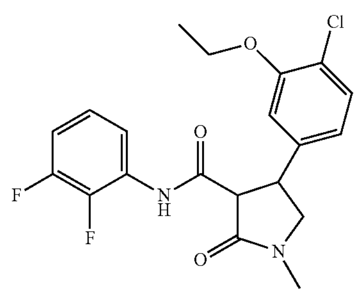 [SMILES: CCOc1cc(C2CN(C)C(=O)C2C(=O)Nc2cccc(F)c2F)ccc1Cl] |
| 1687 | 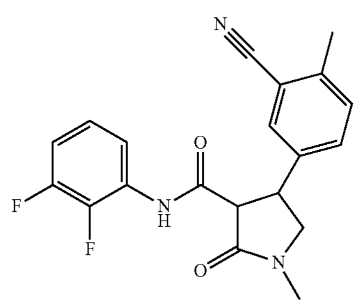 [SMILES: Cc1ccc(C2CN(C)C(=O)C2C(=O)Nc2cccc(F)c2F)cc1C#N] |
| 1688 | 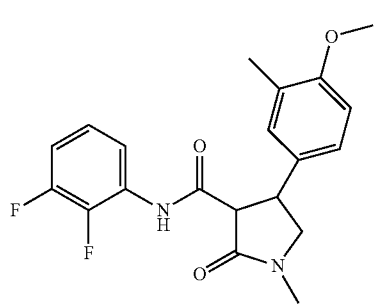 [SMILES: COc1ccc(C2CN(C)C(=O)C2C(=O)Nc2cccc(F)c2F)cc1C] |
| 1689 | |
| 1690 | |
| 1691 | |
| 1692 | |
| 1693 | |

INDEX TABLE F

| Ex. # | Structure |
|---|---|
| 1694 | 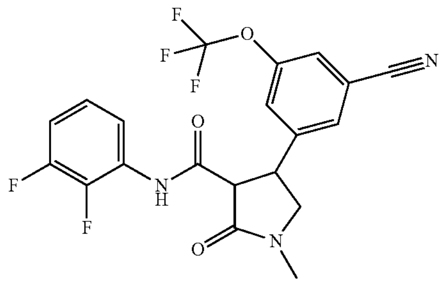 [SMILES: CN1CC(c2cc(C#N)cc(OC(F)(F)F)c2)C(C(=O)Nc2cccc(F)c2F)C1=O] |
| 1695 | 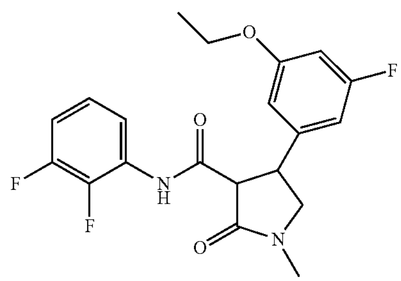 [SMILES: CCOc1cc(F)cc(C2CN(C)C(=O)C2C(=O)Nc2cccc(F)c2F)c1] |
| 1696 | 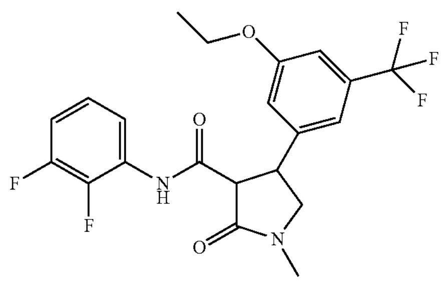 [SMILES: CCOc1cc(C2CN(C)C(=O)C2C(=O)Nc2cccc(F)c2F)cc(C(F)(F)F)c1] |
| 1697 | 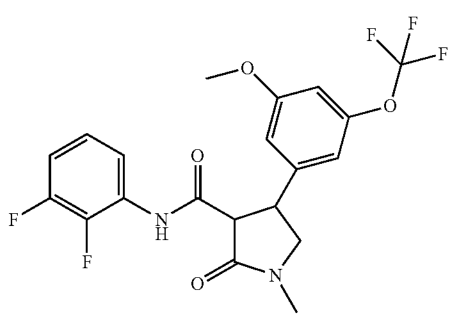 [SMILES: COc1cc(OC(F)(F)F)cc(C2CN(C)C(=O)C2C(=O)Nc2cccc(F)c2F)c1] |
| 1698 | 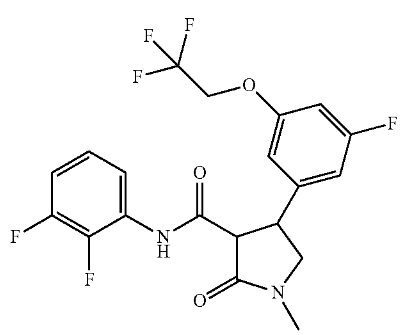 [SMILES: CN1CC(c2cc(F)cc(OCC(F)(F)F)c2)C(C(=O)Nc2cccc(F)c2F)C1=O] |

INDEX TABLE F

| Ex. # | Structure |
|---|---|
| 1699 | |
| 1700 | |
| 1701 | |
| 1702 | |
| 1703 | |

INDEX TABLE F

| Ex. # | Structure |
|---|---|
| 1704 | 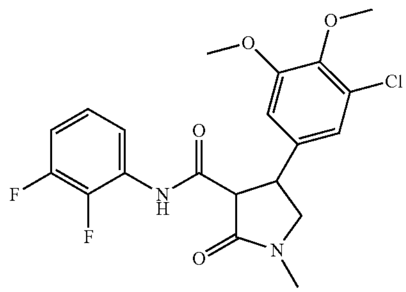 [SMILES: COc1cc(C2CN(C)C(=O)C2C(=O)Nc2cccc(F)c2F)cc(Cl)c1OC] |
| 1705 | 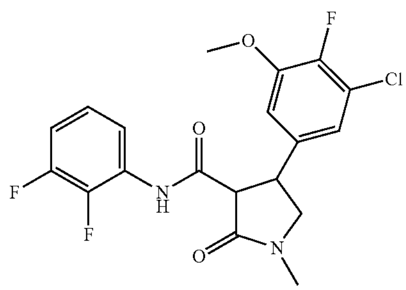 [SMILES: COc1cc(C2CN(C)C(=O)C2C(=O)Nc2cccc(F)c2F)cc(Cl)c1F] |
| 1706 | 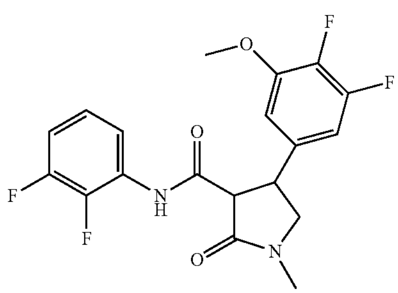 [SMILES: COc1cc(C2CN(C)C(=O)C2C(=O)Nc2cccc(F)c2F)cc(F)c1F] |
| 1707 | 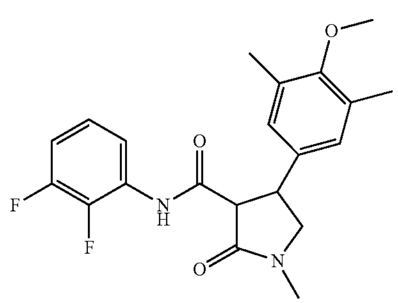 [SMILES: COc1c(C)cc(C2CN(C)C(=O)C2C(=O)Nc2cccc(F)c2F)cc1C] |
| 1708 | 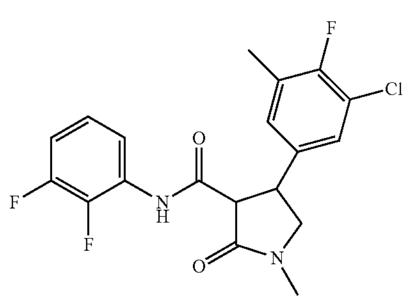 [SMILES: Cc1cc(C2CN(C)C(=O)C2C(=O)Nc2cccc(F)c2F)cc(Cl)c1F] |

INDEX TABLE F

| Ex. # | Structure |
|---|---|
| 1709 | 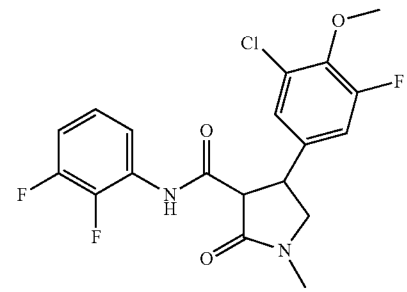 [SMILES: COc1c(F)cc(C2CN(C)C(=O)C2C(=O)Nc2cccc(F)c2F)cc1Cl] |
| 1710 | 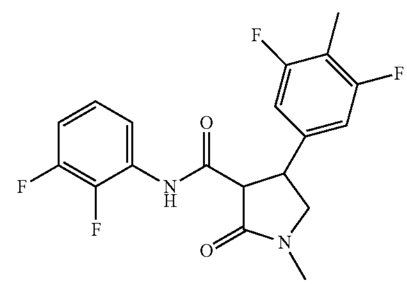 [SMILES: Cc1c(F)cc(C2CN(C)C(=O)C2C(=O)Nc2cccc(F)c2F)cc1F] |
| 1711 | 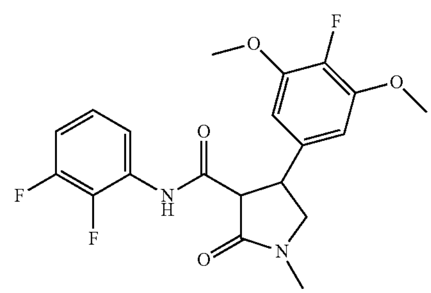 [SMILES: COc1cc(C2CN(C)C(=O)C2C(=O)Nc2cccc(F)c2F)cc(OC)c1F] |
| 1712 | 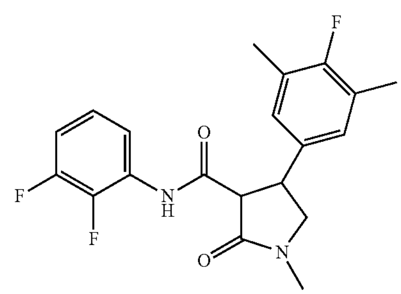 [SMILES: Cc1cc(C2CN(C)C(=O)C2C(=O)Nc2cccc(F)c2F)cc(C)c1F] |
| 1713 | 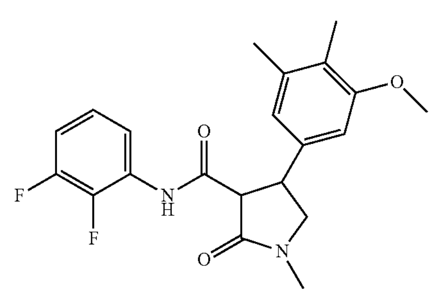 [SMILES: COc1cc(C2CN(C)C(=O)C2C(=O)Nc2cccc(F)c2F)cc(C)c1C] |

INDEX TABLE F

| Ex. # | Structure |
|---|---|
| 1714 | |
| 1715 | |
| 1716 | |
| 1717 | |
| 1718 | 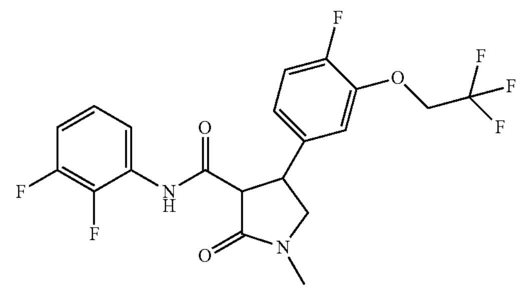 [SMILES: CN1CC(c2ccc(F)c(OCC(F)(F)F)c2)C(C(=O)Nc2cccc(F)c2F)C1=O] |
| 1719 | 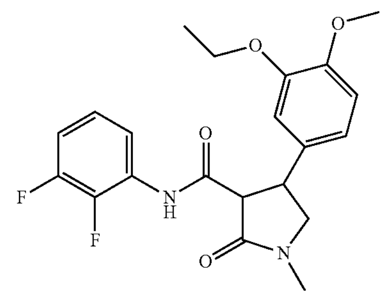 [SMILES: CCOc1cc(C2CN(C)C(=O)C2C(=O)Nc2cccc(F)c2F)ccc1OC] |
| 1720 | 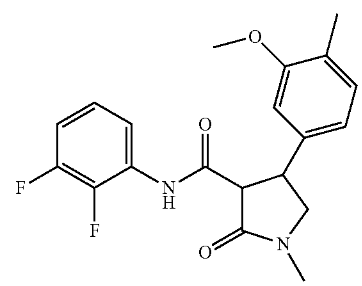 [SMILES: COc1cc(C2CN(C)C(=O)C2C(=O)Nc2cccc(F)c2F)ccc1C] |
| 1721 | 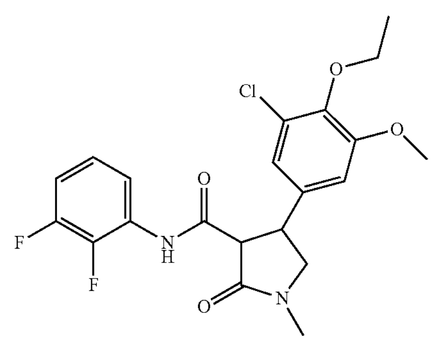 [SMILES: CCOc1c(Cl)cc(C2CN(C)C(=O)C2C(=O)Nc2cccc(F)c2F)cc1OC] |
| 1722 | 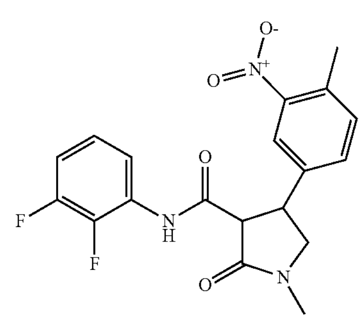 [SMILES: Cc1ccc(C2CN(C)C(=O)C2C(=O)Nc2cccc(F)c2F)cc1[N+](=O)[O-]] |

INDEX TABLE F

| Ex. # | Structure |
|---|---|
| 1723 | 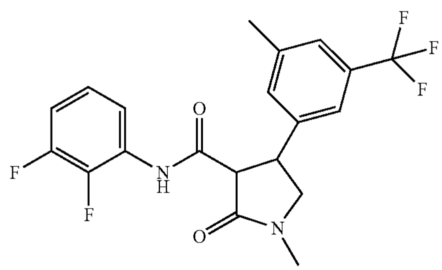 [SMILES: Cc1cc(C2CN(C)C(=O)C2C(=O)Nc2cccc(F)c2F)cc(C(F)(F)F)c1] |
| 1724 | 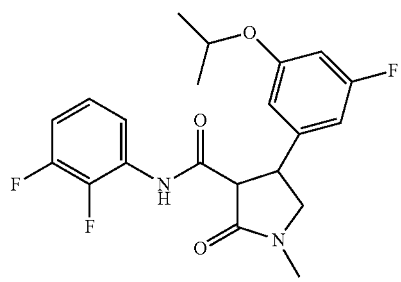 [SMILES: CC(C)Oc1cc(F)cc(C2CN(C)C(=O)C2C(=O)Nc2cccc(F)c2F)c1] |
| 1725 | 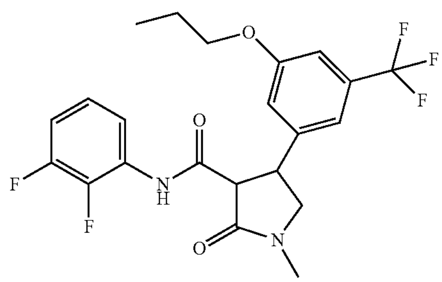 [SMILES: CCCOc1cc(C2CN(C)C(=O)C2C(=O)Nc2cccc(F)c2F)cc(C(F)(F)F)c1] |
| 1726 | 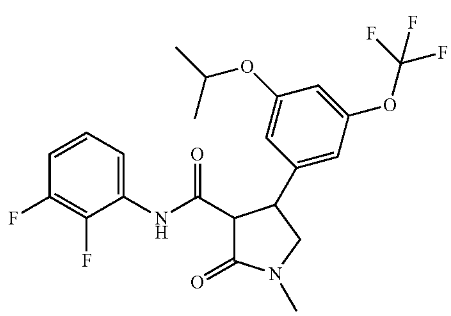 [SMILES: CC(C)Oc1cc(OC(F)(F)F)cc(C2CN(C)C(=O)C2C(=O)Nc2cccc(F)c2F)c1] |
| 1727 | AND Enantiomer |
| 1728 | AND Enantiomer |
| 1729 | AND Enantiomer |
| 1730 | AND Enantiomer |
| 1731 | AND Enantiomer |

361
-continued
INDEX TABLE F
| Ex. # | Structure |
|---|---|
| 1732 | AND Enantiomer 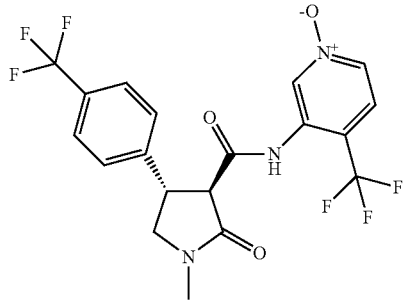 |
| 1733 | AND Enantiomer 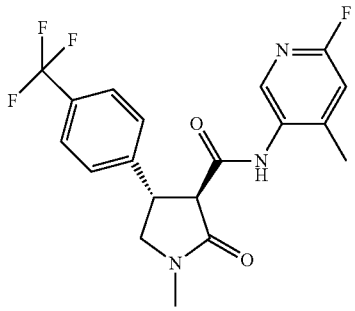 |
| 1734 | AND Enantiomer 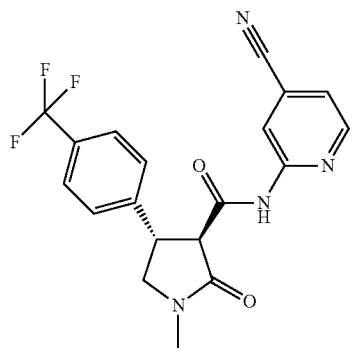 |
| 1735 | AND Enantiomer 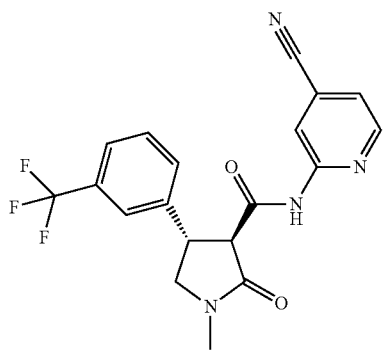 |
362
-continued
INDEX TABLE F
| Ex. # | Structure |
|---|---|
| 1736 | AND Enantiomer 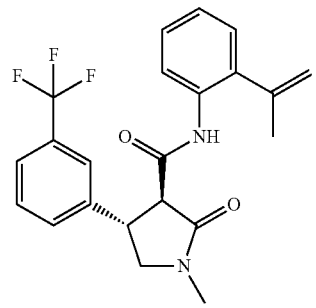 |
| 1737 | AND Enantiomer 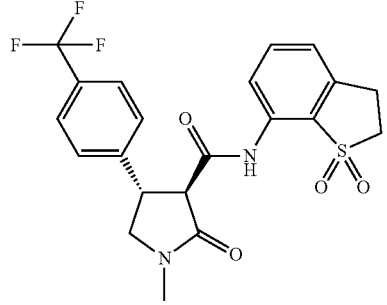 |
| 1738 | AND Enantiomer 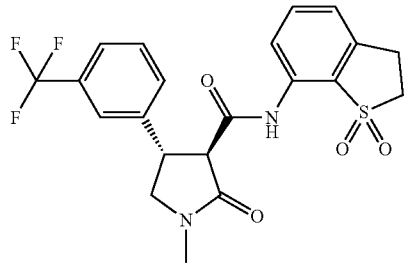 |
| 1739 | AND Enantiomer 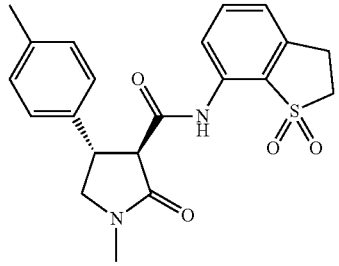 |

INDEX TABLE F
| Ex. # | Structure |
|---|---|
| 1740 | AND Enantiomer 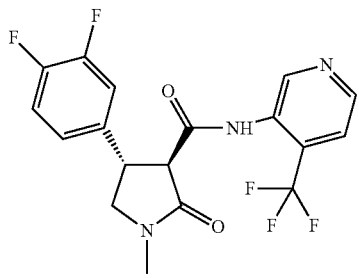 |
| 1741 | AND Enantiomer 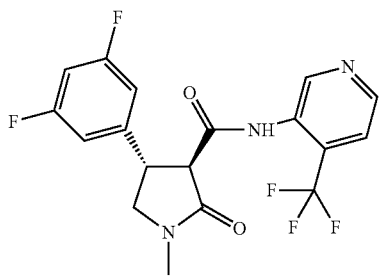 |
| 1742 | AND Enantiomer 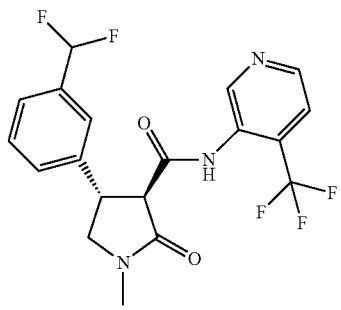 |
| 1743 | AND Enantiomer 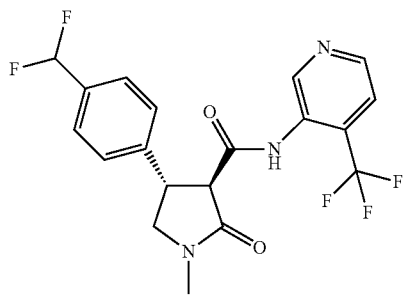 |
INDEX TABLE F
| Ex. # | Structure |
|---|---|
| 1744 | AND Enantiomer 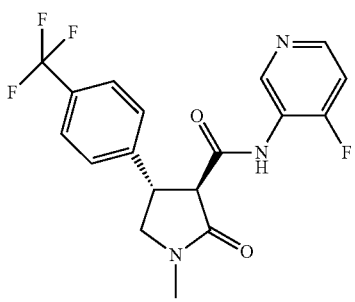 |
| 1745 | AND Enantiomer 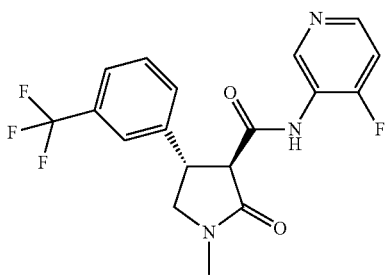 |
| 1746 | AND Enantiomer 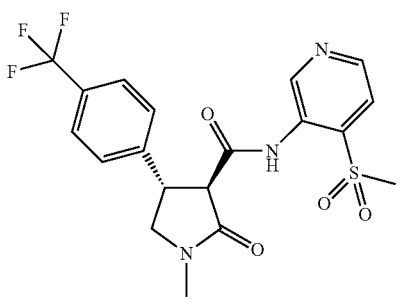 |
| 1747 | AND Enantiomer 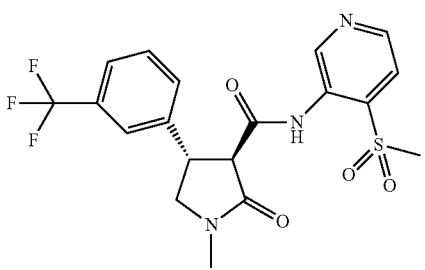 |

INDEX TABLE F

| Ex. # | Structure |
|---|---|
| 1748 | AND Enantiomer |
| 1749 | AND Enantiomer |
| 1750 | AND Enantiomer |
| 1751 | AND Enantiomer |
| 1752 | AND Enantiomer |
| 1753 | AND Enantiomer |
| 1754 | AND Enantiomer |
| 1755 | AND Enantiomer |

INDEX TABLE F
| Ex. # | Structure |
|---|---|
| 1756 | AND Enantiomer 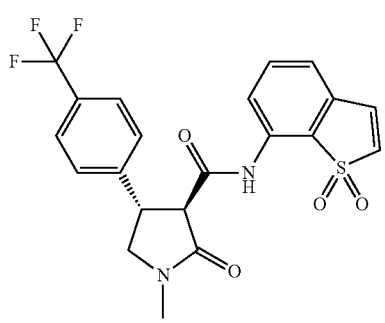 |
| 1757 | AND Enantiomer 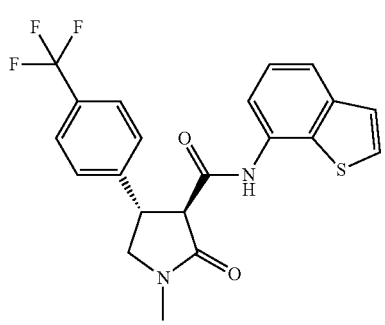 |
| 1758 | AND Enantiomer 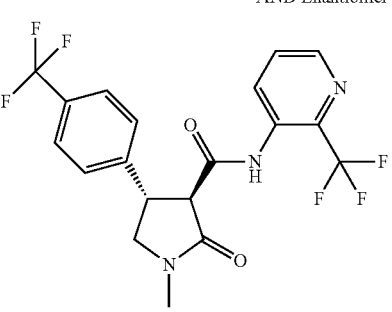 |
| 1759 | AND Enantiomer 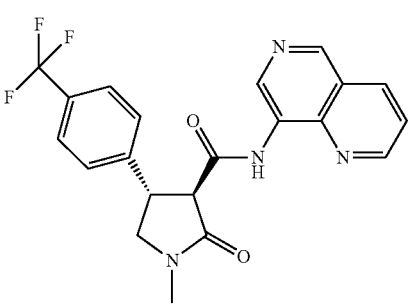 |
INDEX TABLE F
| Ex. # | Structure |
|---|---|
| 1760 | AND Enantiomer 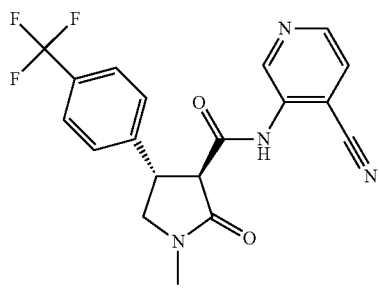 |
| 1761 | AND Enantiomer 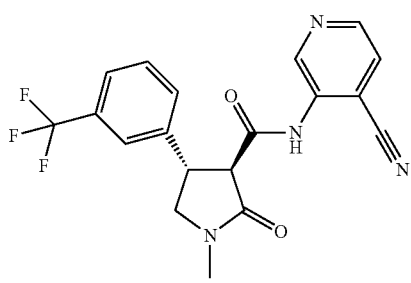 |
| 1762 | AND Enantiomer 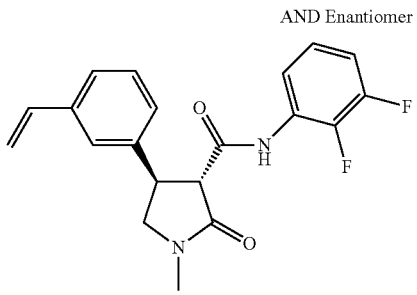 [SMILES: C=Cc1cccc([C@@H]2CN(C)C(=O)[C@H]2C(=O)Nc2cccc(F)c2F)c1] |
| 1763 | AND Enantiomer 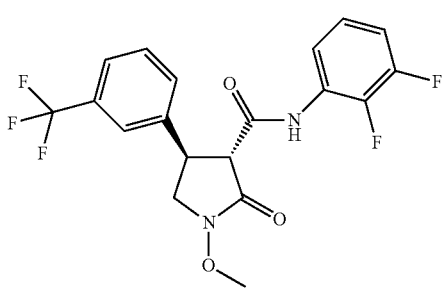 |

INDEX TABLE F
| Ex. # | Structure |
|---|---|
| 1764 | AND Enantiomer 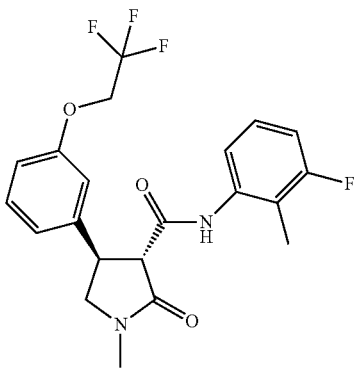 |
| 1765 | AND Enantiomer 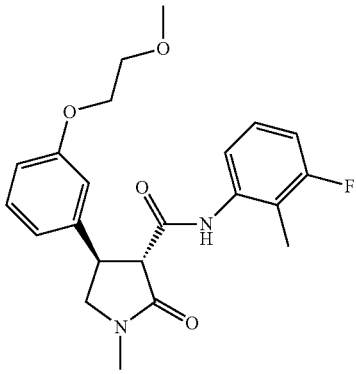 |
| 1766 | AND Enantiomer 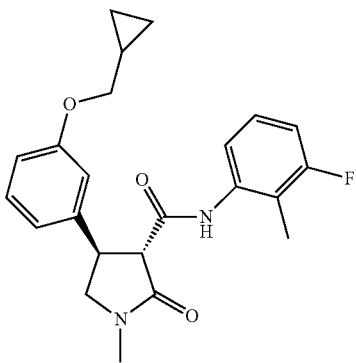 |
| 1767 | AND Enantiomer 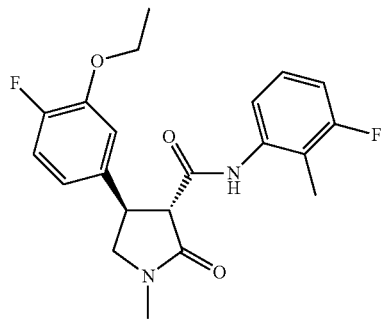 |
INDEX TABLE F
| Ex. # | Structure |
|---|---|
| 1768 | 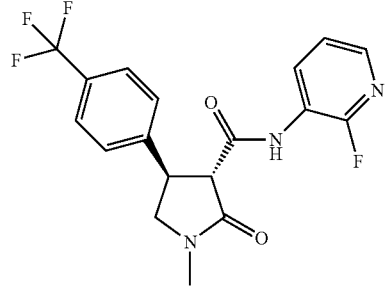 [SMILES: CN1C[C@@H](c2ccc(C(F)(F)F)cc2)[C@H](C(=O)Nc2cccnc2F)C1=O] |
| 1769 | AND Enantiomer 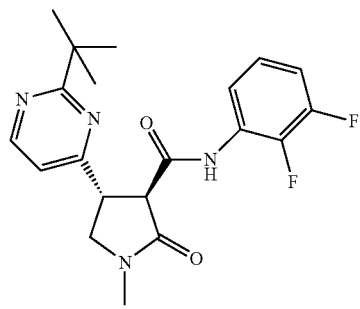 |
| 1770 | AND Enantiomer 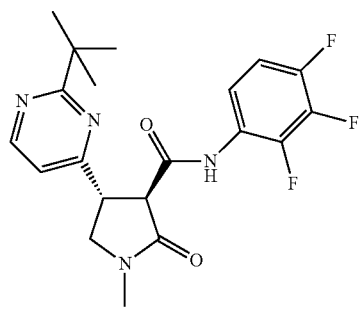 |
| 1771 | 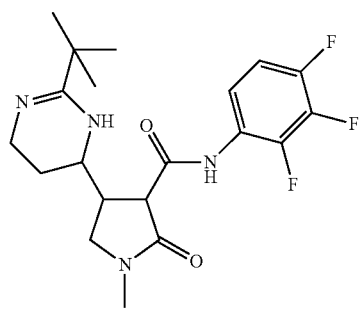 [SMILES: CN1CC(C2CCN=C(C(C)(C)C)N2)C(C(=O)Nc2ccc(F)c(F)c2F)C1=O] |

371
-continued
INDEX TABLE F
| Ex. # | Structure |
|---|---|
| 1772 | AND Enantiomer 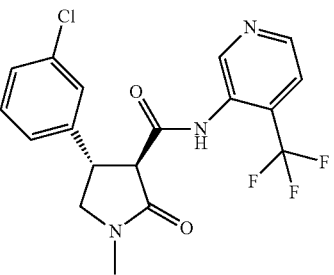 |
| 1773 | 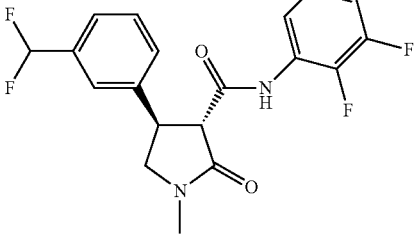 |
| 1774 | 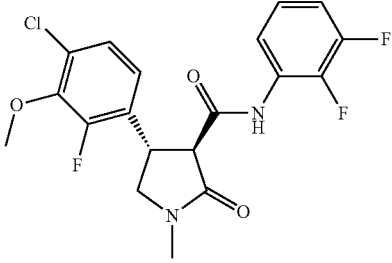 [SMILES: COc1c(Cl)ccc([C@H]2CN(C)C(=O)[C@@H]2C(=O)Nc2cccc(F)c2F)c1F] |
| 1775 | 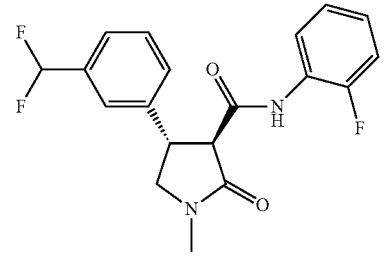 [SMILES: CN1C[C@H](c2cccc(C(F)F)c2)[C@@H](C(=O)Nc2ccccc2F)C1=O] |
| 1776 | 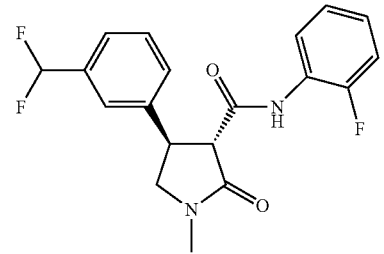 [SMILES: CN1C[C@@H](c2cccc(C(F)F)c2)[C@H](C(=O)Nc2ccccc2F)C1=O] |
372
-continued
INDEX TABLE F
| Ex. # | Structure |
|---|---|
| 1777 | 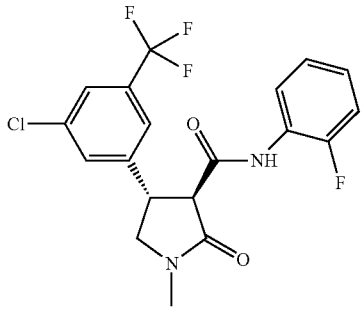 |
| 1778 | 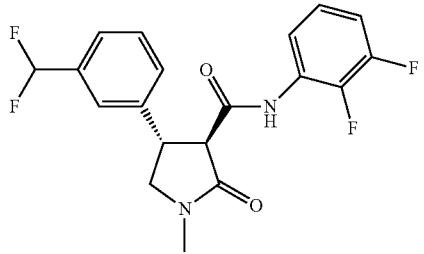 [SMILES: CN1C[C@H](c2cccc(C(F)F)c2)[C@@H](C(=O)Nc2cccc(F)c2F)C1=O] |
| 1779 | 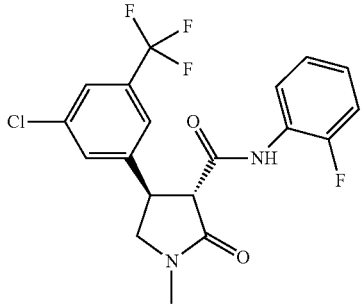 [SMILES: CN1C[C@@H](c2cc(Cl)cc(C(F)(F)F)c2)[C@H](C(=O)Nc2ccccc2F)C1=O] |
| 1780 | 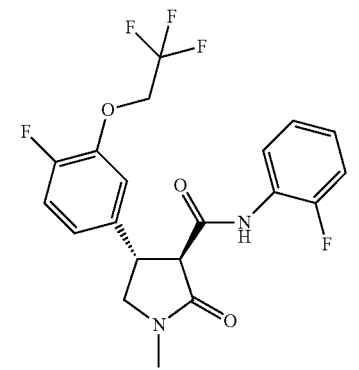 [SMILES: CN1C[C@H](c2ccc(F)c(OCC(F)(F)F)c2)[C@@H](C(=O)Nc2ccccc2F)C1=O] |

INDEX TABLE F
| Ex. # | Structure |
|---|---|
| 1781 | 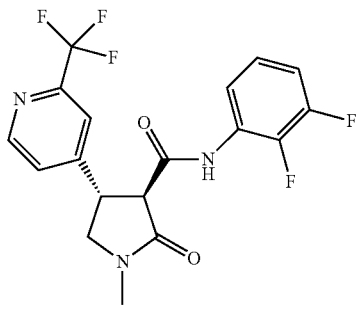 [SMILES: CN1C[C@H](c2ccnc(C(F)(F)F)c2)[C@@H](C(=O)Nc2cccc(F)c2F)C1=O] |
| 1782 | 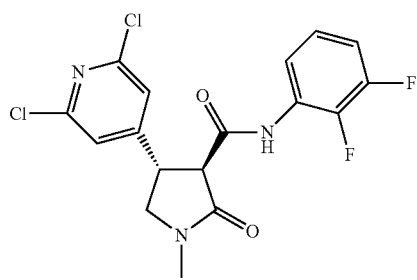 [SMILES: CN1C[C@H](c2cc(Cl)nc(Cl)c2)[C@@H](C(=O)Nc2cccc(F)c2F)C1=O] |
| 1783 | AND Enantiomer 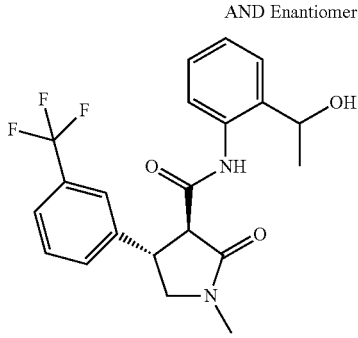 [SMILES: CC(O)c1ccccc1NC(=O)[C@H]1C(=O)N(C)C[C@@H]1c1cccc(C(F)(F)F)c1] |
| 1784 | AND Enantiomer 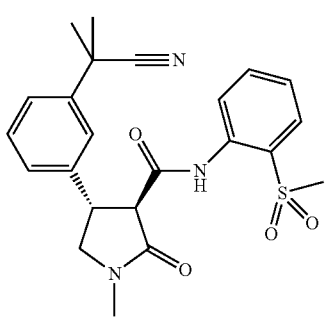 |
| 1785 | AND Enantiomer 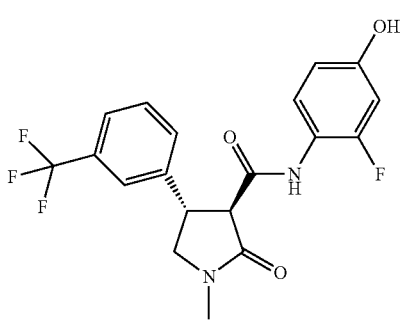 |
| 1786 | AND Enantiomer 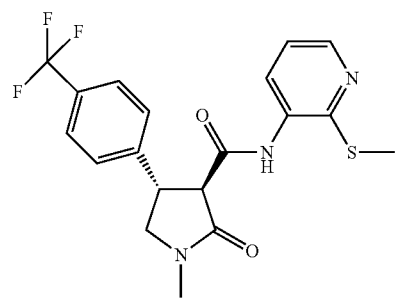 |
| 1787 | AND Enantiomer 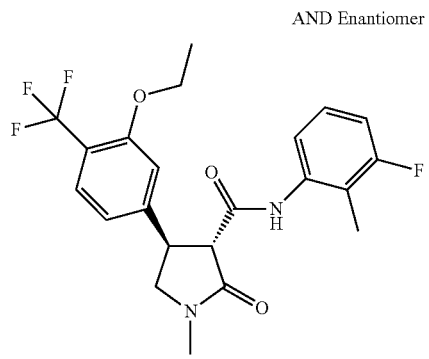 [SMILES: CCOc1cc([C@@H]2CN(C)C(=O)[C@H]2C(=O)Nc2cccc(F)c2C)ccc1C(F)(F)F] |
| 1788 | AND Enantiomer 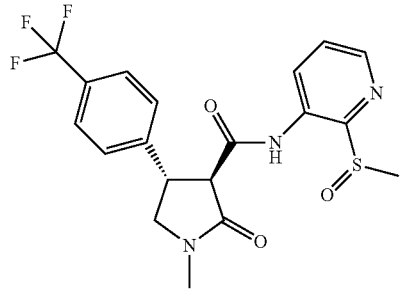 |

INDEX TABLE F-continued
| Ex. # | Structure |
|---|---|
| 1789 | AND Enantiomer 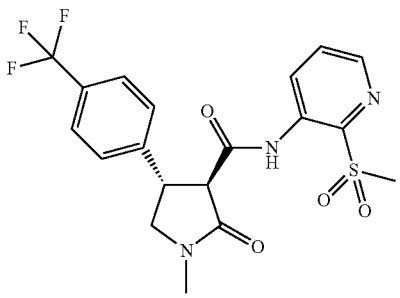 |
| 1790 | AND Enantiomer 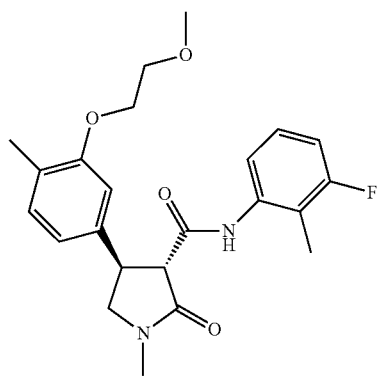 |
| 1791 | AND Enantiomer 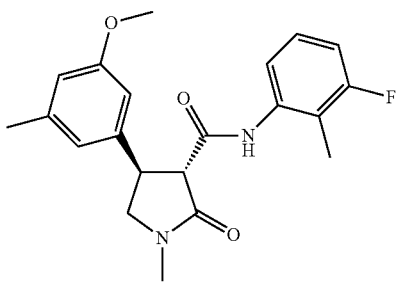 |
| 1792 | AND Enantiomer 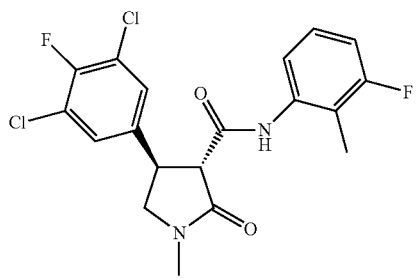 |
| 1793 | AND Enantiomer 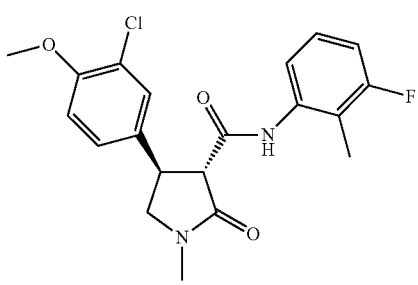 |
| 1794 | AND Enantiomer 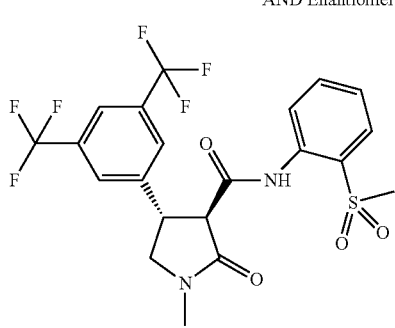 |
| 1795 | AND Enantiomer 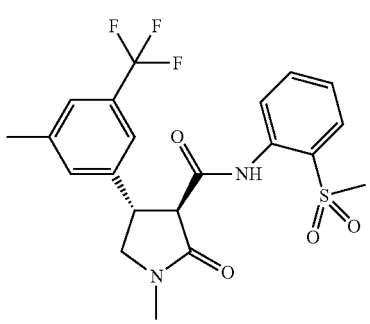 |
| 1796 | AND Enantiomer 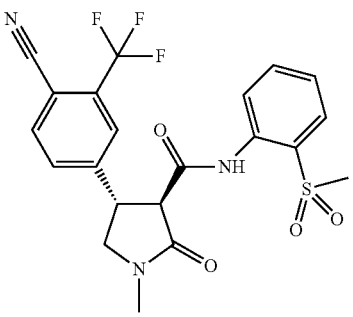 |

INDEX TABLE F
| Ex. # | Structure |
|---|---|
| 1797 | AND Enantiomer 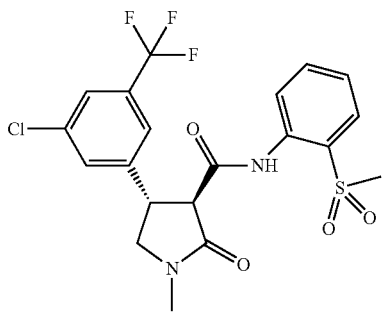 |
| 1798 | AND Enantiomer 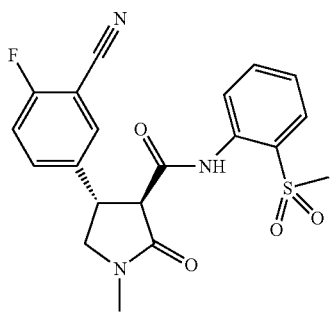 |
| 1799 | AND Enantiomer 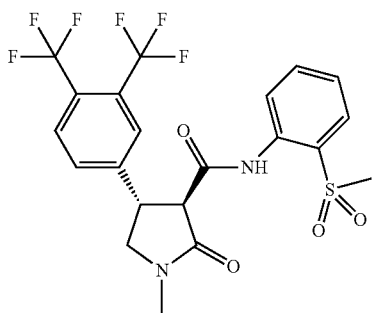 |
| 1800 | AND Enantiomer 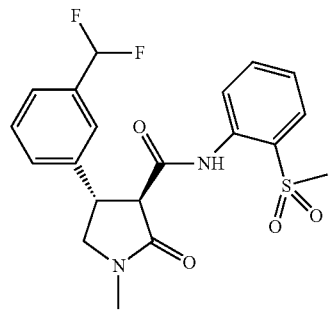 |
| 1801 | AND Enantiomer 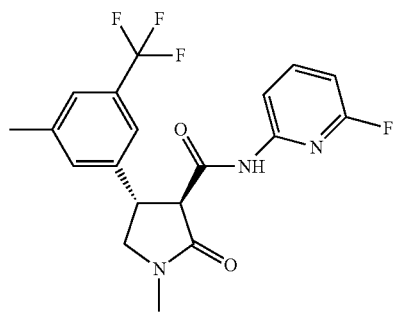 |
| 1802 | AND Enantiomer 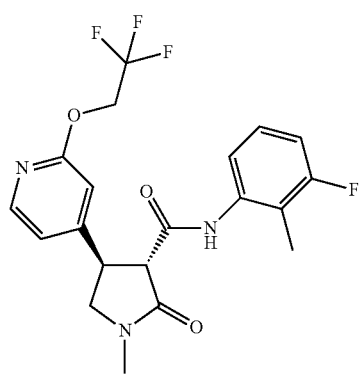 |
| 1803 | AND Enantiomer 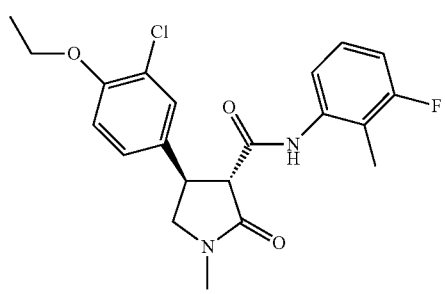 |
| 1804 | AND Enantiomer 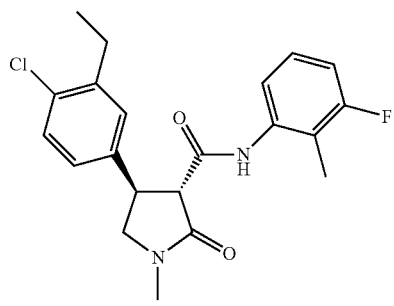 |

TABLE: INDEX TABLE F (continued)

| Ex. # | Structure |
|---|---|
| 1805 | AND Enantiomer |
| 1806 | AND Enantiomer |
| 1807 | AND Enantiomer |
| 1808 | AND Enantiomer |
| 1809 | AND Enantiomer |
| 1810 | 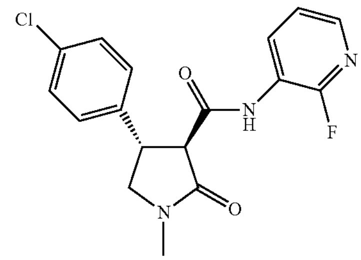 [SMILES: CN1C[C@H](c2ccc(Cl)cc2)[C@@H](C(=O)Nc2cccnc2F)C1=O] |
| 1811 | 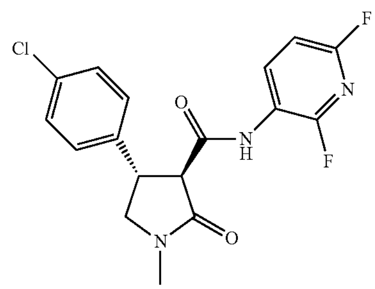 [SMILES: CN1C[C@H](c2ccc(Cl)cc2)[C@@H](C(=O)Nc2ccc(F)nc2F)C1=O] |
| 1812 | 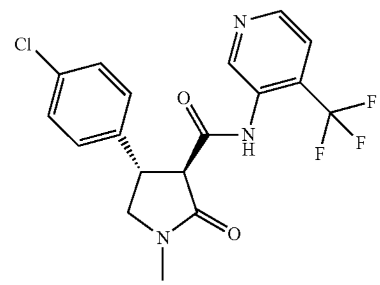 [SMILES: CN1C[C@H](c2ccc(Cl)cc2)[C@@H](C(=O)Nc2cnccc2C(F)(F)F)C1=O] |
| 1813 | AND Enantiomer |
| 1814 | AND Enantiomer |

INDEX TABLE F
| Ex. # | Structure |
|---|---|
| 1815 | AND Enantiomer 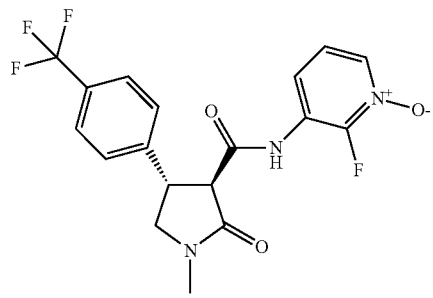 |
| 1816 | 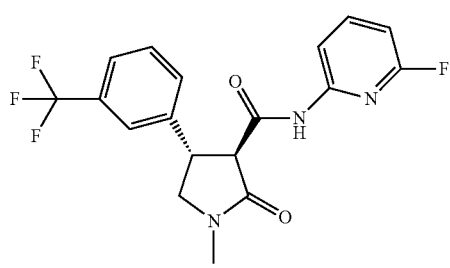 [SMILES: CN1C[C@H](c2cccc(C(F)(F)F)c2)[C@@H](C(=O)Nc2cccc(F)n2)C1=O] |
| 1817 | 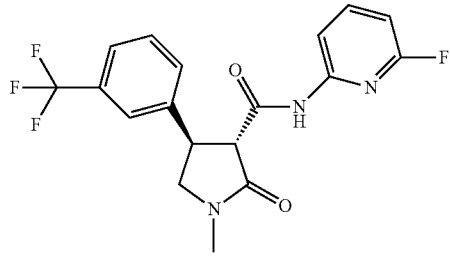 [SMILES: CN1C[C@@H](c2cccc(C(F)(F)F)c2)[C@H](C(=O)Nc2cccc(F)n2)C1=O] |
| 1818 | AND Enantiomer 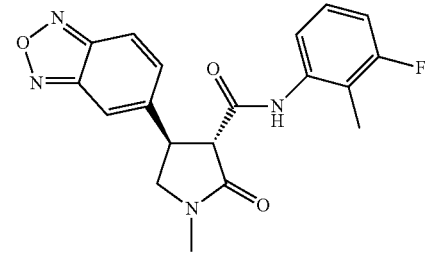 |
| 1819 | AND Enantiomer 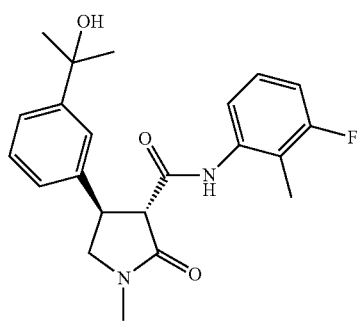 |
INDEX TABLE F
| Ex. # | Structure |
|---|---|
| 1820 | AND Enantiomer 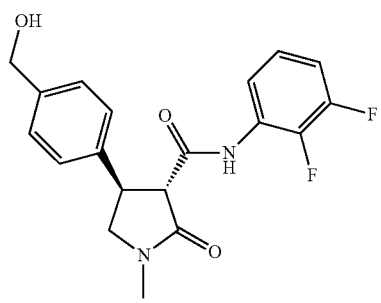 |
| 1821 | AND Enantiomer 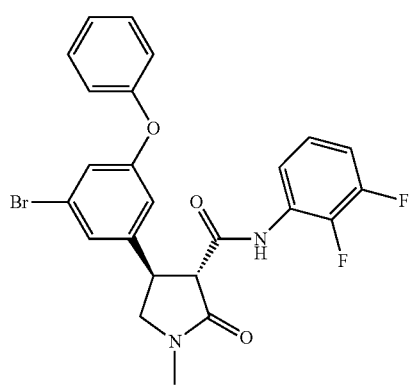 |
| 1822 | AND Enantiomer 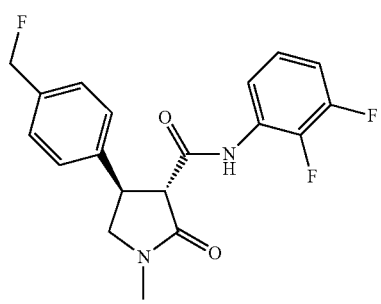 |
| 1823 | 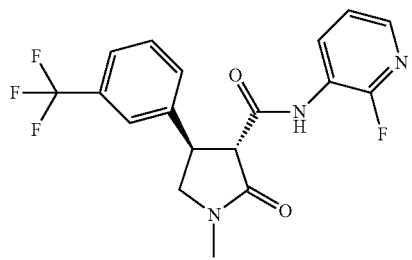 [SMILES: CN1C[C@@H](c2cccc(C(F)(F)F)c2)[C@H](C(=O)Nc2cccnc2F)C1=O] |

INDEX TABLE F
| Ex. # | Structure |
|---|---|
| 1824 | AND Enantiomer 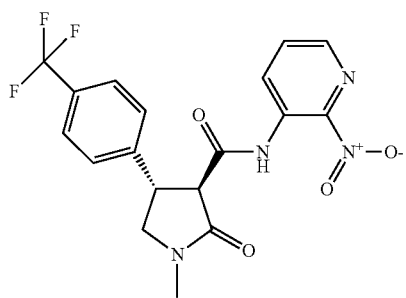 |
| 1825 | AND Enantiomer 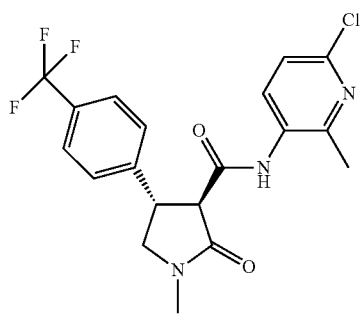 |
| 1826 | AND Enantiomer 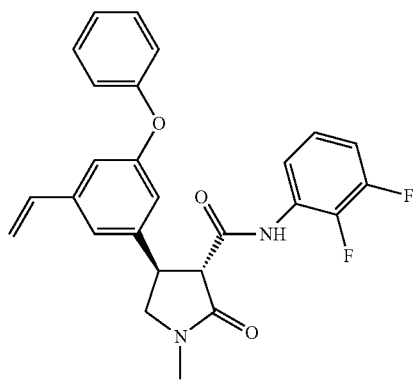 |
| 1827 | AND Enantiomer 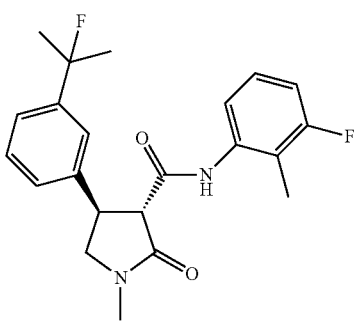 |
| 1828 | AND Enantiomer 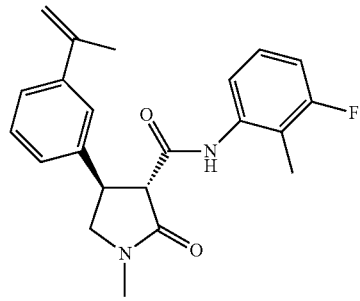 |
| 1829 | AND Enantiomer 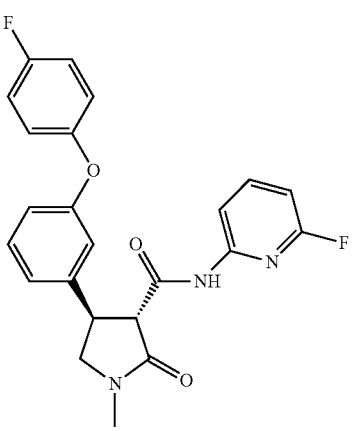 |
| 1830 | AND Enantiomer 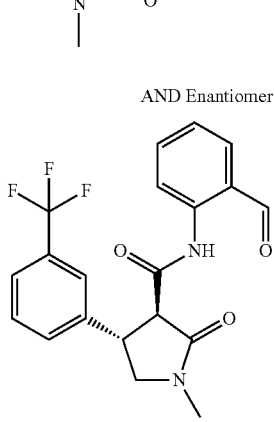 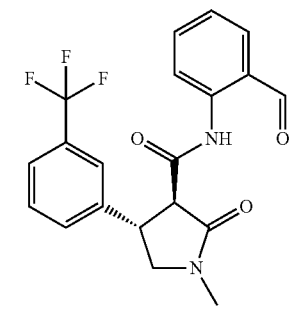 |
| 1831 | AND Enantiomer 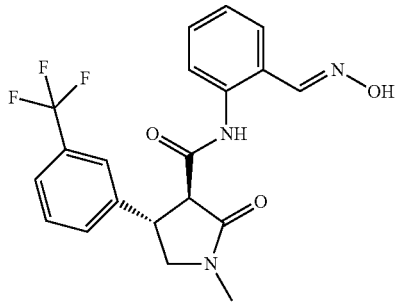 |

385
-continued
INDEX TABLE F
| Ex. # | Structure |
|---|---|
| 1832 | AND Enantiomer 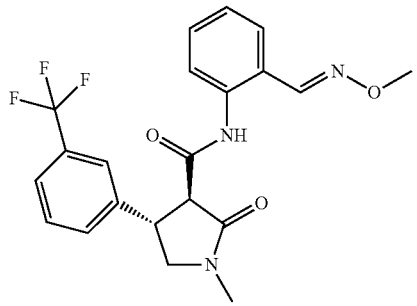 |
| 1833 | AND Enantiomer 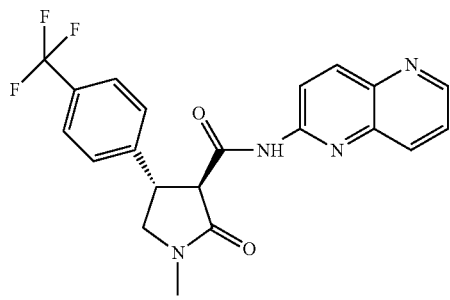 |
| 1834 | AND Enantiomer 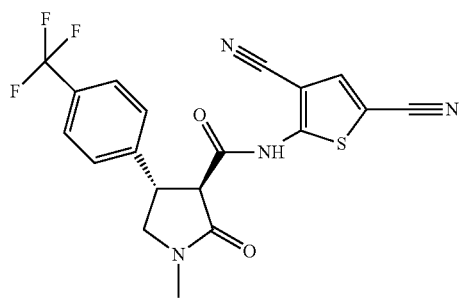 |
| 1835 | AND Enantiomer 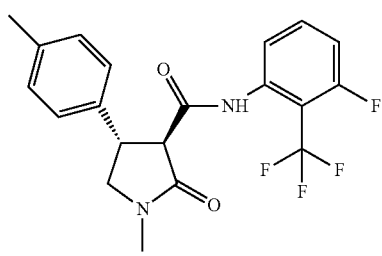 |
386
-continued
INDEX TABLE F
| Ex. # | Structure |
|---|---|
| 1836 | AND Enantiomer 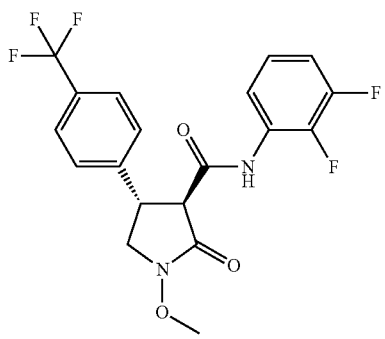 |
| 1837 | AND Enantiomer 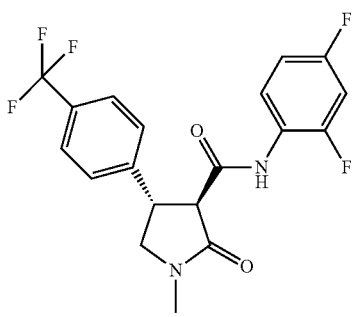 |
| 1838 | AND Enantiomer 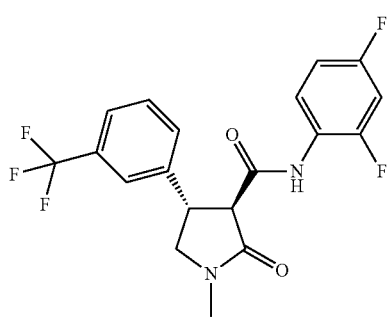 |
| 1839 | AND Enantiomer 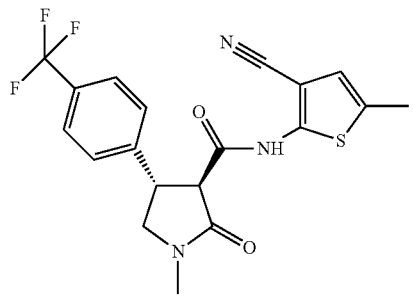 |

INDEX TABLE F

| Ex. # | Structure |
|---|---|
| 1840 | AND Enantiomer |
| 1841 | AND Enantiomer |
| 1842 | AND Enantiomer |
| 1843 | AND Enantiomer |
| 1844 | AND Enantiomer |
| 1845 | AND Enantiomer |
| 1846 | AND Enantiomer |
| 1847 | AND Enantiomer |

INDEX TABLE F
| Ex. # | Structure |
|---|---|
| 1848 | AND Enantiomer 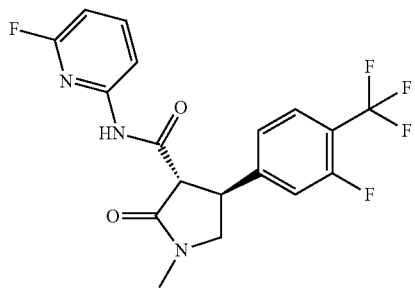 |
| 1849 | AND Enantiomer 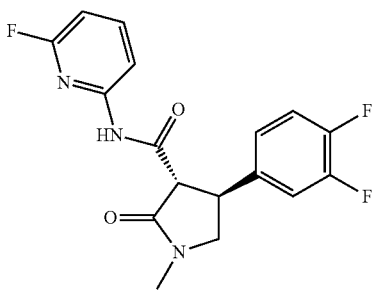 |
| 1850 | 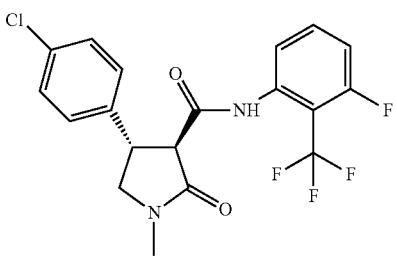 [SMILES: CN1C[C@H](c2ccc(Cl)cc2)[C@@H](C(=O)Nc2cccc(F)c2C(F)(F)F)C1=O] |
| 1851 | 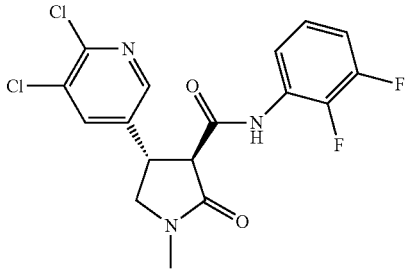 [SMILES: CN1C[C@H](c2cnc(Cl)c(Cl)c2)[C@@H](C(=O)Nc2cccc(F)c2F)C1=O] |
INDEX TABLE F
| Ex. # | Structure |
|---|---|
| 1852 | AND Enantiomer 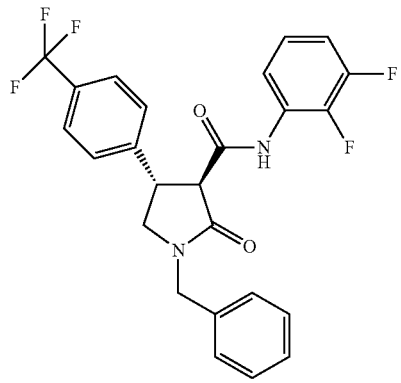 |
| 1853 | AND Enantiomer 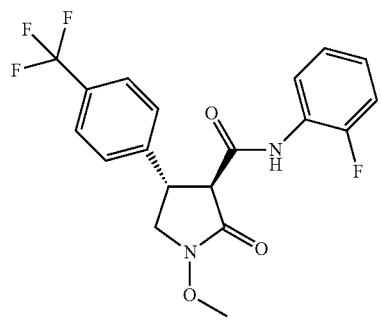 |
| 1854 | AND Enantiomer 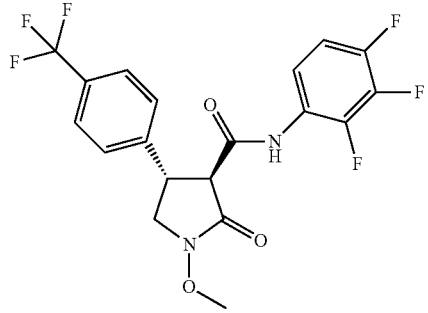 |
| 1855 | AND Enantiomer 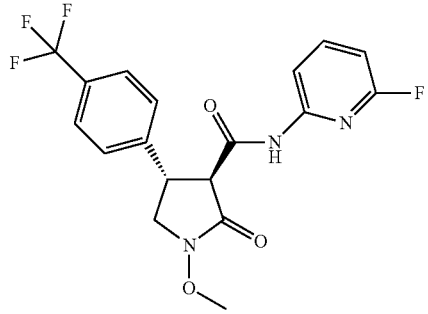 |

INDEX TABLE F
| Ex. # | Structure |
|---|---|
| 1856 | AND Enantiomer 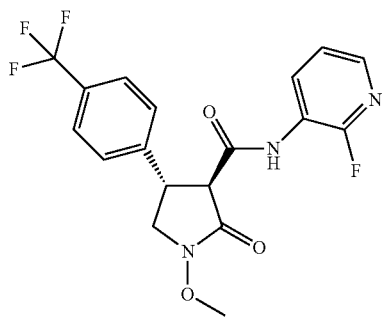 |
| 1857 | AND Enantiomer 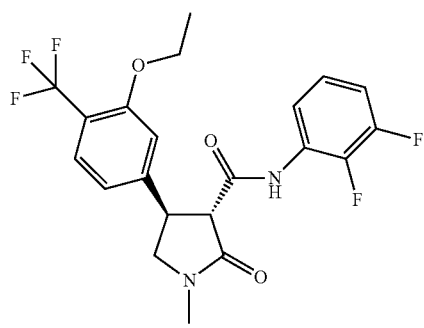 |
| 1858 | 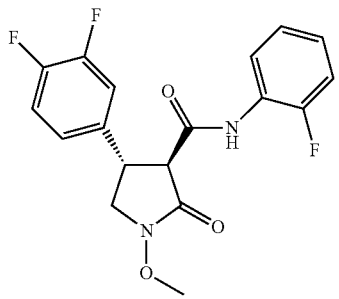 [SMILES: CON1C[C@H](c2ccc(F)c(F)c2)[C@@H](C(=O)Nc2ccccc2F)C1=O] |
| 1859 | AND Enantiomer 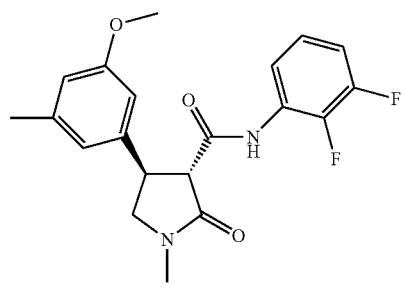 |
INDEX TABLE F
| Ex. # | Structure |
|---|---|
| 1860 | AND Enantiomer 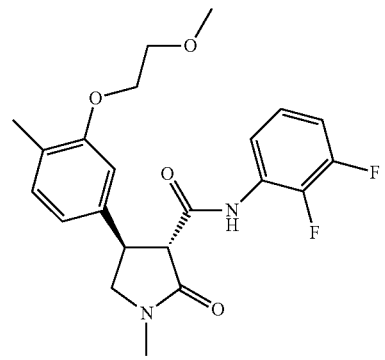 |
| 1861 | 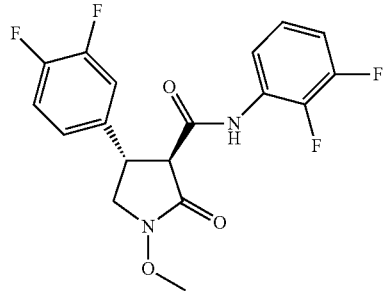 [SMILES: CON1C[C@H](c2ccc(F)c(F)c2)[C@@H](C(=O)Nc2cccc(F)c2F)C1=O] |
| 1862 | 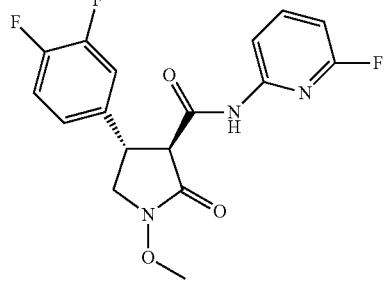 |
| 1863 | 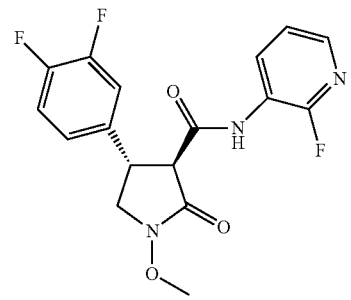 [SMILES: CON1C[C@H](c2ccc(F)c(F)c2)[C@@H](C(=O)Nc2cccnc2F)C1=O] |

INDEX TABLE F
| Ex. # | Structure |
|---|---|
| 1864 | AND Enantiomer 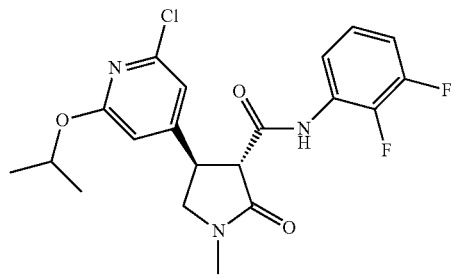 |
| 1865 | AND Enantiomer 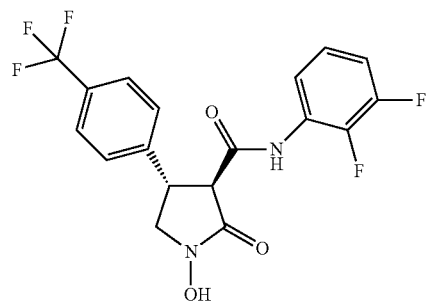 |
| 1866 | 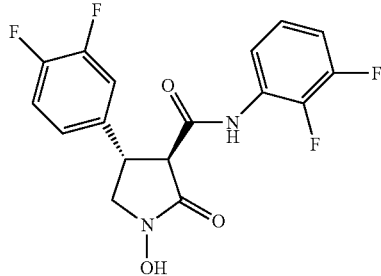 [SMILES: O=C(Nc1cccc(F)c1F)[C@H]1C(=O)N(O)C[C@@H]1c1ccc(F)c(F)c1] |
| 1867 | AND Enantiomer 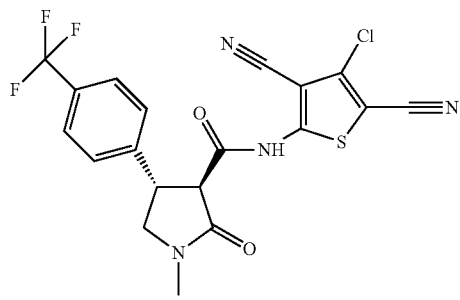 |
| 1868 | AND Enantiomer 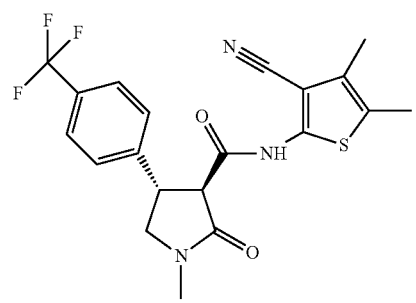 |
| 1869 | AND Enantiomer 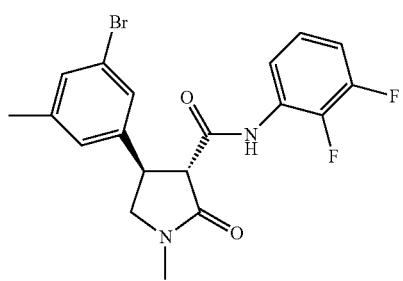 |
| 1870 | AND Enantiomer 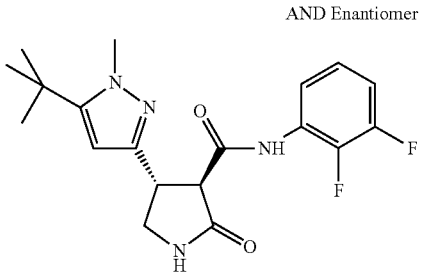 [SMILES: Cn1nc([C@H]2CNC(=O)[C@@H]2C(=O)Nc2cccc(F)c2F)cc1C(C)(C)C] |
| 1871 | AND Enantiomer 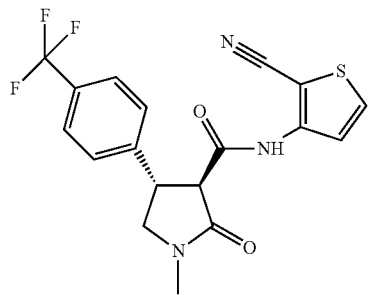 |

INDEX TABLE F

| Ex. # | Structure |
|---|---|
| 1872 | AND Enantiomer, 4-(trifluoromethyl)phenyl / 2-chlorothiophen-3-yl amide, N-methyl-2-oxopyrrolidine |
| 1873 | AND Enantiomer, 4-(trifluoromethyl)phenyl / 4-chlorothiophen-3-yl amide, N-methyl-2-oxopyrrolidine |
| 1874 | AND Enantiomer, 4-(trifluoromethyl)phenyl / 2,3-difluorophenyl amide, N-(2-cyanoethyl)-2-oxopyrrolidine |

Characterization Data for Compounds 1403-1874

| Ex. # | M − 1 | M + 1 |
|---|---|---|
| 1403 | 413 | 415 |
| 1404 | 361 |  |
| 1405 | 397 | 399 |
| 1406 |  | 413 |
| 1407 | 378 | 380 |
| 1408 |  | 380 |
| 1409 | 367 | 369 |
| 1410 |  | 391 |
| 1411 | 443 |  |
| 1412 | 397 |  |
| 1413 |  | 402 |
| 1414 |  | 415 |
| 1415 |  | 395 |
| 1416 | 391 | 406 |
| 1417 | 354 | 388 |
| 1418 | 336 |  |
| 1419 | 418 | 382 |
| 1420 |  | 361 |
| 1421 |  | 377 |
| 1422 | 387 | 387 |
| 1423 | 405 | 422 |
| 1424 |  | 445 |
| 1425 | 413 | 426 |
| 1426 | 405 | 449 |
| 1427 | 387 | 384 |
| 1428 | 401 | 382 |
| 1429 |  | 378 |
| 1430 | 415 | 421 |
| 1431 | 361 | 409 |
| 1432 | 361 | 442 |
| 1433 | 379 | 389 |
| 1434 | 379 | 415 |
| 1435 | 413 | 432 |
| 1436 | 413 | 450 |
| 1437 | 393 | 378 |
| 1438 |  | 385 |
| 1439 | 435 | 437 |
| 1440 | 435 | 437 |
| 1441 | 435 | 437 |
| 1442 | 409 | 411 |
| 1443 | 447 | 449 |
| 1444 | 400 | 402 |
| 1445 |  | 419 |
| 1446 |  | 407 |
| 1447 | 425 | 427 |
| 1448 |  | 405 |
| 1449 |  | 403 |
| 1450 | 380 | 382 |
| 1451 | 465 | 467 |
| 1452 |  | 400 |
| 1453 |  | 373 |
| 1454 |  | 363 |
| 1455 |  | 357 |
| 1456 | 427 | 429 |
| 1457 |  | 339 |
| 1458 |  | 400 |
| 1459 | 439 | 441 |
| 1460 | 403 | 405 |
| 1461 | 364 | 366 |
| 1462 | 364 | 366 |
| 1463 |  | 380 |
| 1464 |  | 363 |
| 1465 | 391 | 393 |
| 1466 | 378 | 380 |
| 1467 | 450 | 452 |
| 1468 | 354 | 356 |
| 1469 | 420 | 422 |
| 1470 | 462 | 464 |
| 1471 | 336 | 338 |
| 1472 | 397 | 399 |
| 1473 |  | 397 |
| 1474 | 393 | 395 |
| 1475 | 377 | 379 |
| 1476 |  | 413 |
| 1477 |  | 396 |
| 1478 | 380 | 382 |
| 1479 | 435 |  |
| 1480 |  | 362 |
| 1481 |  | 380 |
| 1482 | 348 | 350 |
| 1483 | 457 | 459 |
| 1484 | 376 | 378 |
| 1485 | 432 | 434 |
| 1486 | 382 | 384 |
| 1487 | 398 | 400 |
| 1488 |  | 375 |
| 1489 | 380 | 382 |
| 1490 | 387 | 389 |
| 1491 | 381 | 383 |

| Ex. # | M − 1 | M + 1 |
|---|---|---|
| 1492 | 362 | 364 |
| 1493 | 378 | 381 |
| 1494 | 398 | 400 |
| 1495 |  | 384 |
| 1496 |  | 385 |
| 1497 |  | 398 |
| 1498 | 411 | 416 |
| 1499 | 371 | 373 |
| 1500 |  | 371 |
| 1501 |  | 381 |
| 1502 |  | 413 |
| 1503 |  | 432 |
| 1504 |  | 438 |
| 1505 |  | 378 |
| 1506 |  | 354 |
| 1507 |  | 398 |
| 1508 |  | 380 |
| 1509 |  | 383 |
| 1510 |  | 435 |
| 1511 |  | 422 |
| 1512 |  | 435 |
| 1513 |  | 354 |
| 1514 |  | 443 |
| 1515 |  | 400 |
| 1516 |  | 411 |
| 1517 |  | 398 |
| 1518 |  | 365 |
| 1519 |  | 432 |
| 1520 |  | 394 |
| 1521 |  | 436 |
| 1522 |  | 395 |
| 1523 |  | 432 |
| 1524 |  | 410 |
| 1525 |  | 398 |
| 1526 |  | 383 |
| 1527 |  | 368 |
| 1528 |  | 395 |
| 1529 |  | 382 |
| 1530 |  | 421 |
| 1531 |  | 368 |
| 1532 |  | 367 |
| 1533 |  | 353 |
| 1534 |  | 354 |
| 1535 |  | 421 |
| 1536 |  | 353 |
| 1537 |  | 423 |
| 1538 |  | 426 |
| 1539 |  | 400 |
| 1540 |  | 422 |
| 1541 |  | 398 |
| 1542 |  | 466 |
| 1543 |  | 379 |
| 1544 |  | 399 |
| 1545 |  | 409 |
| 1546 |  | 426 |
| 1547 |  | 433 |
| 1548 |  | 439 |
| 1549 |  | 394 |
| 1550 |  | 422 |
| 1551 |  | 378 |
| 1552 |  | 399 |
| 1553 |  | 368 |
| 1554 |  | 370 |
| 1555 |  | 382 |
| 1556 |  | 368 |
| 1557 |  | 379 |
| 1558 |  | 399 |
| 1559 |  | 385 |
| 1560 |  | 384 |
| 1561 |  | 399 |
| 1562 |  | 354 |
| 1563 |  | 432 |
| 1564 |  | 365 |
| 1565 |  | 395 |
| 1566 |  | 446 |
| 1567 |  | 433 |
| 1568 |  | 409 |

| Ex. # | M − 1 | M + 1 |
|---|---|---|
| 1569 |  | 404 |
| 1570 |  | 384 |
| 1571 |  | 398 |
| 1572 |  | 365 |
| 1573 |  | 353 |
| 1574 |  | 399 |
| 1575 |  | 379 |
| 1576 |  | 408 |
| 1577 |  | 365 |
| 1578 |  | 412 |
| 1579 |  | 368 |
| 1580 |  | 402 |
| 1581 |  | 413 |
| 1582 |  | 392 |
| 1583 |  | 365 |
| 1584 | 408 | 410 |
| 1585 | 398 | 400 |
| 1586 | 440 | 442 |
| 1587 |  | 438 |
| 1588 |  | 381 |
| 1589 |  | 394 |
| 1590 |  | 411 |
| 1591 |  | 395 |
| 1592 |  | 422 |
| 1593 |  | 395 |
| 1594 |  | 476 |
| 1595 |  | 384 |
| 1596 |  | 364 |
| 1597 |  | 369 |
| 1598 |  | 397 |
| 1599 |  | 388 |
| 1600 |  | 378 |
| 1601 |  | 394 |
| 1602 |  | 415 |
| 1603 |  | 400 |
| 1604 |  | 423 |
| 1605 |  | 403 |
| 1606 |  | 398 |
| 1607 |  | 411 |
| 1608 |  | 398 |
| 1609 |  | 449 |
| 1610 |  | 382 |
| 1611 |  | 369 |
| 1612 |  | 355 |
| 1613 |  | 396 |
| 1614 |  | 449 |
| 1615 |  | 367 |
| 1616 |  | 449 |
| 1617 |  | 455 |
| 1618 |  | 369 |
| 1619 |  | 455 |
| 1620 |  | 422 |
| 1621 |  | 427 |
| 1622 |  | 381 |
| 1623 |  | 381 |
| 1624 |  | 403 |
| 1625 |  | 435 |
| 1626 |  | 367 |
| 1627 |  | 433 |
| 1628 |  | 433 |
| 1629 |  | 413 |
| 1630 |  | 392 |
| 1631 |  | 412 |
| 1632 |  | 387 |
| 1633 |  | 387 |
| 1634 |  | 367 |
| 1635 |  | 384 |
| 1636 |  | 422 |
| 1637 |  | 406 |
| 1638 |  | 432 |
| 1639 |  | 442 |
| 1640 |  | 395 |
| 1641 |  | 379 |
| 1642 |  | 412 |
| 1643 |  | 368 |
| 1644 |  | 426 |
| 1645 |  | 422 |

| Ex. # | M − 1 | M + 1 |
|---|---|---|
| 1646 | | 353 |
| 1647 | | 379 |
| 1648 | | 379 |
| 1649 | | 399 |
| 1650 | | 400 |
| 1651 | | 429 |
| 1652 | | 382 |
| 1653 | | 382 |
| 1654 | | 396 |
| 1655 | | 383 |
| 1656 | | 416 |
| 1657 | | 383 |
| 1658 | | 387 |
| 1659 | | 370 |
| 1660 | | 367 |
| 1661 | 473 | 475 |
| 1662 | | 347 |
| 1663 | | 365 |
| 1664 | | 455 |
| 1665 | 467 | 469 |
| 1666 | 416 | 418 |
| 1667 | 387 | 389 |
| 1668 | 405 | 407 |
| 1669 | 417 | 419 |
| 1670 | | 433 |
| 1671 | 380 | 382 |
| 1672 | 430 | 432 |
| 1673 | 382 | 384 |
| 1674 | 396 | 398 |
| 1675 | | 361 |
| 1676 | 413 | 415 |
| 1677 | | 456 |
| 1678 | 405 | 407 |
| 1679 | | 401 |
| 1680 | | 459 |
| 1681 | | 442 |
| 1682 | 387 | 389 |
| 1683 | 401 | 403 |
| 1684 | | 424 |
| 1685 | | 410 |
| 1686 | | 409 |
| 1687 | | 370 |
| 1688 | | 375 |
| 1689 | | 419 |
| 1690 | | 395 |
| 1691 | | 370 |
| 1692 | | 389 |
| 1693 | | 473 |
| 1694 | | 440 |
| 1695 | | 393 |
| 1696 | | 443 |
| 1697 | | 445 |
| 1698 | | 447 |
| 1699 | | 379 |
| 1700 | | 393 |
| 1701 | | 447 |
| 1702 | | 397 |
| 1703 | | 401 |
| 1704 | | 425 |
| 1705 | | 413 |
| 1706 | | 397 |
| 1707 | | 389 |
| 1708 | | 397 |
| 1709 | | 413 |
| 1710 | | 381 |
| 1711 | | 409 |
| 1712 | | 377 |
| 1713 | | 389 |
| 1714 | | 467 |
| 1715 | | 389 |
| 1716 | | 419 |
| 1717 | | 393 |
| 1718 | | 447 |
| 1719 | | 405 |
| 1720 | | 375 |
| 1721 | | 439 |
| 1722 | | 390 |

| Ex. # | M − 1 | M + 1 |
|---|---|---|
| 1723 | | 413 |
| 1724 | | 407 |
| 1725 | | 457 |
| 1726 | | 473 |
| 1727 | 399 | 401 |
| 1728 | | 381 |
| 1729 | 407 | 409 |
| 1730 | 415 | 417 |
| 1731 | 407 | 409 |
| 1732 | 446 | 448 |
| 1733 | 394 | 396 |
| 1734 | 387 | 389 |
| 1735 | 387 | 389 |
| 1736 | | 403 |
| 1737 | 451 | 453 |
| 1738 | 451 | 453 |
| 1739 | 397 | 399 |
| 1740 | 398 | 400 |
| 1741 | 398 | 400 |
| 1742 | 412 | 414 |
| 1743 | 412 | 414 |
| 1744 | 380 | 382 |
| 1745 | 380 | 382 |
| 1746 | 440 | 442 |
| 1747 | 440 | 442 |
| 1748 | 397 | 399 |
| 1749 | 408 | 410 |
| 1750 | 408 | 410 |
| 1751 | 424 | 426 |
| 1752 | 424 | 426 |
| 1753 | | 444 |
| 1754 | 455 | 457 |
| 1755 | 394 | 396 |
| 1756 | | 451 |
| 1757 | 417 | 419 |
| 1758 | 430 | 432 |
| 1759 | 413 | 415 |
| 1760 | 387 | 398 |
| 1761 | 387 | 389 |
| 1762 | | 357 |
| 1763 | 413 | 415 |
| 1764 | 423 | 425 |
| 1765 | 399 | 401 |
| 1766 | 395 | 397 |
| 1767 | 387 | 389 |
| 1768 | 380 | 382 |
| 1769 | | 389 |
| 1770 | 405 | |
| 1771 | 409 | 411 |
| 1772 | 396 | 398 |
| 1773 | 413 | 415 |
| 1774 | 361 | 363 |
| 1775 | 361 | 363 |
| 1776 | 379 | 381 |
| 1777 | 379 | 381 |
| 1778 | 413 | 415 |
| 1779 | 413 | 415 |
| 1780 | 427 | 429 |
| 1781 | 398 | 400 |
| 1782 | | 400 |
| 1783 | | 407 |
| 1784 | 438 | 440 |
| 1785 | 395 | 397 |
| 1786 | 408 | 410 |
| 1787 | 437 | 439 |
| 1788 | 424 | 426 |
| 1789 | 440 | 442 |
| 1790 | | 415 |
| 1791 | 369 | 371 |
| 1792 | 411 | 413 |
| 1793 | 389 | 391 |
| 1794 | 507 | 509 |
| 1795 | 453 | 455 |
| 1796 | 464 | 466 |
| 1797 | 473 | 475 |
| 1798 | 414 | 416 |
| 1799 | 507 | 509 |

-continued

| Ex. # | M − 1 | M + 1 |
|---|---|---|
| 1800 | 421 | 423 |
| 1801 | 394 | 396 |
| 1802 | 424 | 426 |
| 1803 | 403 | 405 |
| 1804 |  | 389 |
| 1805 | 392 | 394 |
| 1806 |  | 397 |
| 1807 | 395 | 397 |
| 1808 | 395 | 397 |
| 1809 | 380 | 382 |
| 1810 | 346 | 348 |
| 1811 | 364 | 366 |
| 1812 | 396 | 398 |
| 1813 | 446 | 448 |
| 1814 | 396 | 398 |
| 1815 | 396 | 398 |
| 1816 | 380 | 382 |
| 1817 | 380 | 382 |
| 1818 |  | 369 |
| 1819 | 383 |  |
| 1820 |  | 361 |
| 1821 | 499 | 501 |
| 1822 |  | 363 |
| 1823 | 380 | 382 |
| 1824 | 407 | 409 |
| 1825 | 410 | 412 |
| 1826 | 447 | 449 |
| 1827 | 385 |  |
| 1828 |  | 367 |
| 1829 |  | 424 |
| 1830 |  | 391 |
| 1831 |  | 406 |
| 1832 |  | 420 |
| 1833 |  | 415 |
| 1834 | 417 | 419 |
| 1835 | 393 | 395 |
| 1836 |  | 415 |
| 1837 | 397 | 399 |
| 1838 | 397 | 399 |
| 1839 | 406 | 408 |
| 1840 | 404 | 406 |
| 1841 |  | 364 |
| 1842 |  | 450 |
| 1843 |  | 450 |
| 1844 |  | 370 |
| 1845 |  | 416 |
| 1846 |  | 342 |
| 1847 |  | 407 |
| 1848 |  | 400 |
| 1849 |  | 350 |
| 1850 | 413 | 415 |
| 1851 | 398 |  |
| 1852 | 473 |  |
| 1853 |  | 397 |
| 1854 | 431 |  |
| 1855 |  | 398 |
| 1856 | 396 |  |
| 1857 | 441 | 443 |
| 1858 |  | 365 |
| 1859 | 373 | 375 |
| 1860 |  | 419 |
| 1861 |  | 383 |
| 1862 |  | 366 |
| 1863 |  | 366 |
| 1864 | 422 | 424 |
| 1865 | 399 |  |
| 1866 | 367 |  |
| 1867 | 451 |  |
| 1868 | 420 | 422 |
| 1869 | 423 | 425 |
| 1870 | 375 | 377 |
| 1871 | 392 | 394 |
| 1872 | 401 | 403 |
| 1873 |  | 403 |
| 1874 | 436 | 438 |

BIOLOGICAL EXAMPLES

Test A

Seeds of plant species selected from barnyardgrass (*Echinochloa crus-galli*), kochia (*Kochia scoparia*), ragweed (common ragweed, *Ambrosia elatior*), ryegrass, Italian (Italian ryegrass, *Lolium multiflorum*), crabgrass, large (*Digitaria sanguinalis*), giant foxtail (*Setaria faberii*), green foxtail (*Setaria viridis*), morningglory (*Ipomoea* spp.), pigweed (*Amaranthus retroflexus*), velvetleaf (*Abutilon theophrasti*), wheat (*Triticum aestivum*), and corn (*Zea mays*) were planted into a blend of loam soil and sand and treated preemergence with a directed soil spray using test chemicals formulated in a non-phytotoxic solvent mixture which included a surfactant.

At the same time, plants selected from these crop and weed species and also blackgrass (*Alopecurus myosuroides*), and galium (catchweed bedstraw, *Galium aparine*) were planted in pots containing the same blend of loam soil and sand and treated with postemergence applications of test chemicals formulated in the same manner. Plants ranged in height from 2 to 10 cm and were in the one- to two-leaf stage for the postemergence treatment. Treated plants and untreated controls were maintained in a greenhouse for approximately 10 d, after which time all treated plants were compared to untreated controls and visually evaluated for injury. Plant response ratings, summarized in Table A, are based on a 0 to 100 scale where 0 is no effect and 100 is complete control. A dash (-) response means no test result.

TABLE A

| 1000 g ai/ha | Compounds | | | | | | |
|---|---|---|---|---|---|---|---|
| Postemergence | 355 | 357 | 358 | 511 | 512 | 713 | 784 |
| Barnyardgrass | 0 | 0 | 0 | 90 | 80 | 0 | 90 |
| Blackgrass | — | — | — | 20 | 0 | — | 20 |
| Corn | 0 | 0 | 0 | 0 | 0 | 0 | 0 |
| Crabgrass, Large | 0 | 0 | 40 | — | — | 0 | — |
| Foxtail, Giant | 0 | 0 | 30 | 90 | 90 | 0 | 90 |
| Galium | — | — | — | 0 | 0 | — | 0 |
| Kochia | — | — | — | 0 | 0 | — | 0 |
| Morningglory | 0 | 0 | 0 | — | — | 0 | 0 |
| Pigweed | 0 | 0 | 0 | 0 | 0 | 0 | 0 |
| Ragweed | — | — | — | 0 | 0 | — | 0 |
| Ryegrass, Italian | — | — | — | 0 | 0 | — | 0 |
| Velvetleaf | 0 | 0 | 0 | — | — | 0 | — |
| Wheat | 0 | 0 | 0 | 0 | 0 | 0 | 0 |

TABLE A-continued

| 500 g ai/ha | Compounds | | | | | | | | | | | | |
|---|---|---|---|---|---|---|---|---|---|---|---|---|---|
| Postemergence | 352 | 353 | 354 | 356 | 360 | 361 | 362 | 363 | 364 | 365 | 366 | 367 | 368 |
| Barnyardgrass | 0 | 0 | 0 | 0 | 0 | 0 | 0 | 0 | 0 | 0 | 0 | 0 | 90 |
| Blackgrass | — | — | — | — | — | — | — | — | — | — | — | — | 60 |
| Corn | 0 | 0 | 0 | 0 | 0 | 0 | 0 | 0 | 0 | 0 | 0 | 0 | 20 |
| Crabgrass, Large | 0 | 0 | 0 | 0 | 0 | 0 | 0 | 0 | 0 | 0 | 0 | 0 | — |
| Foxtail, Giant | 0 | 0 | 0 | 0 | 0 | 0 | 0 | 0 | 0 | 0 | 0 | 0 | 80 |
| Galium | — | — | — | — | — | — | — | — | — | — | — | — | 50 |
| Kochia | — | — | — | — | — | — | — | — | — | — | — | — | 0 |
| Morningglory | 0 | 0 | 0 | 0 | 0 | 0 | 0 | 0 | 0 | 0 | 0 | 0 | — |
| Pigweed | 0 | 0 | 0 | 0 | 0 | 0 | 0 | 0 | 0 | 0 | 0 | 0 | 0 |
| Ragweed | — | — | — | — | — | — | — | — | — | — | — | — | 30 |
| Ryegrass, Italian | — | — | — | — | — | — | — | — | — | — | — | — | 50 |
| Velvetleaf | 0 | 0 | 0 | 0 | 0 | 0 | 0 | 10 | 0 | 0 | 0 | 0 | — |
| Wheat | 0 | 0 | 0 | 0 | 0 | 0 | 0 | 0 | 0 | 0 | 0 | 0 | 30 |

| 500 g ai/ha | Compounds | | | | | | | | | | | | |
|---|---|---|---|---|---|---|---|---|---|---|---|---|---|
| Postemergence | 369 | 370 | 371 | 372 | 373 | 374 | 375 | 376 | 377 | 378 | 379 | 380 | 381 | 382 |
| Barnyardgrass | 90 | 90 | 90 | 80 | 80 | 90 | 90 | 90 | 90 | 90 | 50 | 80 | 30 | 20 |
| Blackgrass | 70 | 40 | 60 | 30 | 40 | 50 | 70 | 40 | 70 | 70 | 0 | 40 | 0 | 0 |
| Corn | 50 | 20 | 60 | 20 | 50 | 20 | 80 | 30 | 50 | 80 | 0 | 0 | 0 | 0 |
| Foxtail, Giant | 80 | 70 | 90 | 70 | 70 | 50 | 90 | 90 | 80 | 80 | 20 | 70 | 20 | 20 |
| Galium | 70 | 60 | 30 | 20 | 30 | 40 | 50 | 30 | 70 | 70 | 0 | 50 | 0 | 0 |
| Kochia | 60 | 0 | 40 | 40 | 40 | 0 | 60 | 20 | 60 | 70 | 0 | 0 | 0 | 0 |
| Pigweed | 0 | 0 | 20 | 30 | 30 | 0 | 50 | 0 | 30 | 50 | 0 | 0 | 0 | 0 |
| Ragweed | 30 | 50 | 30 | 0 | 0 | 0 | 20 | 20 | 60 | 50 | 0 | 0 | 0 | 0 |
| Ryegrass, Italian | 50 | 20 | 30 | 40 | 20 | 0 | 20 | 20 | 50 | 70 | 0 | 0 | 0 | 0 |
| Wheat | 60 | 20 | 40 | 20 | 70 | 40 | 80 | 0 | 50 | 50 | 0 | 20 | 0 | 0 |

| 500 g ai/ha | Compounds | | | | | | | | | | | |
|---|---|---|---|---|---|---|---|---|---|---|---|---|
| Postemergence | 383 | 384 | 386 | 387 | 388 | 389 | 390 | 391 | 392 | 393 | 394 | 395 | 396 |
| Barnyardgrass | 90 | 0 | 80 | 70 | 70 | 70 | 70 | 80 | 90 | 90 | 90 | 0 | 90 |
| Blackgrass | 0 | 0 | 70 | 50 | 50 | 0 | 0 | 70 | 70 | 70 | 20 | 0 | 60 |
| Corn | 0 | 0 | 80 | 0 | 0 | 50 | 0 | 70 | 80 | 80 | 0 | 0 | 80 |
| Foxtail, Giant | 50 | 0 | 80 | 70 | 80 | 70 | 80 | 90 | 90 | 90 | 60 | 0 | 90 |
| Galium | 0 | 0 | 60 | 0 | 30 | 0 | 0 | 60 | 70 | 70 | 20 | 0 | 60 |
| Kochia | 30 | 0 | 0 | 0 | 0 | 0 | 0 | 60 | 70 | 60 | 0 | 0 | 70 |
| Pigweed | 0 | 0 | 10 | 0 | 0 | 20 | 20 | 50 | 70 | 70 | 0 | 0 | 70 |
| Ragweed | 20 | 0 | 30 | 0 | 0 | 0 | 0 | 30 | 20 | 0 | 0 | 0 | 0 |
| Ryegrass, Italian | 30 | 0 | 50 | 0 | 0 | 0 | 10 | 40 | 80 | 70 | 0 | 0 | 70 |
| Wheat | 0 | 0 | 50 | 0 | 0 | 0 | 0 | 50 | 70 | 70 | 0 | 0 | 70 |

| 500 g ai/ha | Compounds | | | | | | | | | | | | |
|---|---|---|---|---|---|---|---|---|---|---|---|---|---|
| Postemergence | 397 | 398 | 399 | 400 | 401 | 402 | 403 | 404 | 405 | 406 | 407 | 408 | 409 | 410 |
| Barnyardgrass | 90 | 90 | 90 | 90 | 90 | 90 | 90 | 90 | 90 | 90 | 70 | 0 | 70 | 50 |
| Blackgrass | 70 | 60 | 60 | 60 | 50 | 70 | 60 | 60 | 60 | 50 | 50 | 0 | 20 | 20 |
| Corn | 70 | 70 | 70 | 80 | 40 | 80 | 90 | 80 | 80 | 70 | 40 | 0 | 0 | 0 |
| Foxtail, Giant | 80 | 90 | 90 | 70 | 70 | 90 | 90 | 90 | 80 | 80 | 70 | 0 | 80 | 40 |
| Galium | 60 | 60 | 50 | 60 | 60 | 60 | 60 | 50 | 60 | 50 | 0 | 0 | 0 | 0 |
| Kochia | 50 | 80 | 60 | 70 | 60 | 60 | 60 | 70 | 50 | 50 | 40 | 0 | 30 | 0 |
| Pigweed | 70 | 60 | 40 | 50 | 40 | 50 | 50 | 60 | 50 | 30 | 0 | 0 | 20 | 20 |
| Ragweed | 20 | 0 | 0 | 50 | 50 | 60 | 30 | 50 | 50 | 20 | 0 | 0 | 0 | 0 |
| Ryegrass, Italian | 60 | 50 | 40 | 90 | 60 | 50 | 70 | 70 | 60 | 40 | 0 | 0 | 0 | 0 |
| Wheat | 50 | 70 | 60 | 70 | 70 | 80 | 80 | 80 | 80 | 70 | 0 | 0 | 0 | 0 |

| 500 g ai/ha | Compounds | | | | | | | | | | | | |
|---|---|---|---|---|---|---|---|---|---|---|---|---|---|
| Postemergence | 411 | 412 | 413 | 414 | 415 | 416 | 417 | 418 | 419 | 420 | 421 | 422 | 423 | 424 |
| Barnyardgrass | 70 | 0 | 0 | 0 | 0 | 0 | 0 | 0 | 80 | 90 | 90 | 60 | 0 | 70 |
| Blackgrass | 0 | 0 | 0 | 0 | 0 | 0 | 0 | 0 | 0 | 0 | 50 | 50 | 0 | 0 |
| Corn | 0 | 0 | 0 | 0 | 0 | 0 | 0 | 0 | 20 | 0 | 70 | 0 | 0 | 0 |
| Foxtail, Giant | 80 | 0 | 0 | 0 | 0 | 0 | 0 | 0 | 90 | 80 | 90 | 60 | 0 | 70 |
| Galium | 50 | 0 | 0 | 0 | 0 | 0 | 0 | 0 | 0 | 0 | 60 | 70 | 0 | 0 |
| Kochia | 0 | 0 | 0 | 0 | 10 | 0 | 0 | 0 | 0 | 20 | 0 | 20 | 60 | 0 | 0 |
| Pigweed | 0 | 0 | 0 | 0 | 0 | 0 | 0 | 0 | 0 | 0 | 30 | 60 | 0 | 0 |
| Ragweed | 0 | 0 | 0 | 0 | 0 | 0 | 0 | 0 | 0 | 0 | 30 | 0 | 0 | 0 |
| Ryegrass, Italian | 0 | 0 | 0 | 0 | 0 | 0 | 0 | 0 | 20 | 0 | 40 | 0 | 0 | 0 |
| Wheat | 0 | 0 | 0 | 0 | 0 | 0 | 0 | 0 | 20 | 0 | 40 | 0 | 0 | 0 |

TABLE A-continued

| 500 g ai/ha | Compounds | | | | | | | | | | | | | |
|---|---|---|---|---|---|---|---|---|---|---|---|---|---|---|
| Postemergence | 425 | 426 | 427 | 428 | 429 | 430 | 431 | 432 | 433 | 434 | 435 | 436 | 437 | 438 |
| Barnyardgrass | 30 | 70 | 80 | 90 | 90 | 90 | 90 | 30 | 90 | 90 | 90 | 90 | 90 | 90 |
| Blackgrass | 0 | 0 | 40 | 70 | 70 | 70 | 60 | 0 | 40 | 50 | 50 | 40 | 30 | 70 |
| Corn | 0 | 0 | 20 | 60 | 80 | 70 | 70 | 0 | 30 | 70 | 20 | 40 | 20 | 50 |
| Foxtail, Giant | 30 | 60 | 80 | 90 | 90 | 80 | 90 | 30 | 80 | 90 | 80 | 90 | 90 | 90 |
| Galium | 0 | 0 | 50 | 60 | 70 | 60 | 60 | 0 | 50 | 60 | 60 | 60 | 50 | 50 |
| Kochia | 0 | 0 | 20 | 70 | 70 | 50 | 50 | 0 | 50 | 70 | 50 | 70 | 30 | 70 |
| Pigweed | 0 | 0 | 0 | 20 | 80 | 50 | 60 | 0 | 20 | 70 | 50 | 60 | 20 | 60 |
| Ragweed | 0 | 0 | 20 | 0 | 50 | 30 | 60 | 0 | 50 | 20 | 60 | 20 | 0 | 30 |
| Ryegrass, Italian | 0 | 0 | 20 | 30 | 80 | 50 | 40 | 20 | 60 | 50 | 40 | 50 | 20 | 60 |
| Wheat | 0 | 0 | 20 | 60 | 60 | 50 | 60 | 0 | 60 | 70 | 60 | 40 | 40 | 70 |

| 500 g ai/ha | Compounds | | | | | | | | | | | | | |
|---|---|---|---|---|---|---|---|---|---|---|---|---|---|---|
| Postemergence | 439 | 440 | 441 | 442 | 443 | 444 | 445 | 446 | 447 | 448 | 449 | 450 | 451 | 452 |
| Barnyardgrass | 90 | 90 | 90 | 90 | 80 | 90 | 90 | 90 | 80 | 90 | 80 | 90 | 0 | 70 |
| Blackgrass | 60 | 50 | 80 | 70 | 70 | 60 | 60 | 50 | 30 | 30 | 20 | 40 | 0 | 60 |
| Corn | 20 | 20 | 70 | 70 | 80 | 70 | 90 | 30 | 0 | 0 | 0 | 60 | 0 | 0 |
| Foxtail, Giant | 90 | 90 | 80 | 80 | 80 | 80 | 90 | 90 | 80 | 80 | 80 | 80 | 0 | 80 |
| Galium | 50 | 40 | 50 | 60 | 50 | 70 | 60 | 50 | 50 | 50 | 50 | 60 | 0 | 50 |
| Kochia | 70 | 40 | 70 | 60 | 30 | 80 | 30 | 60 | 40 | 50 | 40 | 50 | 0 | 70 |
| Pigweed | 50 | 20 | 60 | 70 | 50 | 80 | 30 | 60 | 30 | 40 | 20 | 60 | 0 | 70 |
| Ragweed | 20 | 0 | 50 | 40 | 20 | 40 | 30 | 20 | 0 | 0 | 0 | 30 | 0 | 30 |
| Ryegrass, Italian | 30 | 60 | 60 | 80 | 60 | 80 | 40 | 30 | 20 | 20 | 20 | 50 | 0 | 20 |
| Wheat | 40 | 50 | 80 | 70 | 60 | 50 | 70 | 50 | 0 | 0 | 0 | 30 | 0 | 20 |

| 500 g ai/ha | Compounds | | | | | | | | | | | |
|---|---|---|---|---|---|---|---|---|---|---|---|---|
| Postemergence | 453 | 454 | 455 | 456 | 457 | 460 | 461 | 462 | 463 | 464 | 465 | 466 |
| Barnyardgrass | 80 | 80 | 80 | 0 | 0 | 70 | 90 | 80 | 70 | 90 | 90 | 90 |
| Blackgrass | 30 | 50 | 0 | 0 | 0 | 40 | 0 | 40 | 70 | 70 | 70 | 60 |
| Corn | 40 | 70 | 0 | 0 | 0 | 40 | 0 | 0 | 0 | 90 | 90 | 30 |
| Foxtail, Giant | 80 | 80 | 80 | 0 | 0 | 80 | 80 | 70 | 70 | 90 | 90 | 80 |
| Galium | 40 | 30 | 70 | 0 | 0 | 60 | 20 | 10 | 0 | 70 | 60 | 0 |
| Kochia | 30 | 0 | 70 | 0 | 0 | 30 | 0 | 0 | 0 | 60 | 60 | 0 |
| Pigweed | 0 | 0 | 60 | 0 | 0 | 40 | 0 | 0 | 0 | 50 | 20 | 0 |
| Ragweed | 0 | 0 | 0 | 0 | 0 | 0 | 0 | 0 | 0 | 30 | 30 | 30 |
| Ryegrass, Italian | 0 | 40 | 0 | 0 | 0 | 30 | 20 | 0 | 30 | 80 | 70 | 20 |
| Wheat | 30 | 40 | 30 | 0 | 0 | 20 | 0 | 0 | 0 | 70 | 70 | 20 |

| 500 g ai/ha | Compounds | | | | | | | | | | | | | |
|---|---|---|---|---|---|---|---|---|---|---|---|---|---|---|
| Postemergence | 467 | 468 | 469 | 470 | 471 | 472 | 473 | 474 | 475 | 476 | 477 | 478 | 479 | 480 |
| Barnyardgrass | 90 | 30 | 80 | 70 | 70 | 90 | 90 | 90 | 90 | 90 | 70 | 60 | 50 | 30 |
| Blackgrass | 0 | 20 | 40 | 50 | 0 | 60 | 60 | 50 | 40 | 50 | 30 | 20 | 40 | 0 |
| Corn | 20 | 0 | 0 | 0 | 0 | 80 | 40 | 20 | 60 | 30 | 40 | 0 | 0 | 0 |
| Foxtail, Giant | 80 | 0 | 60 | 80 | 70 | 90 | 90 | 90 | 90 | 80 | 70 | 60 | 60 | 50 |
| Galium | 0 | 30 | 0 | 0 | 0 | 50 | 60 | 50 | 60 | 60 | 0 | 0 | 0 | 0 |
| Kochia | 0 | 20 | 0 | 0 | 0 | 70 | 80 | 60 | 60 | 60 | 0 | 0 | 0 | 0 |
| Pigweed | 0 | 0 | 0 | 0 | 0 | 60 | 90 | 30 | 70 | 40 | 0 | 0 | 0 | 0 |
| Ragweed | 20 | 0 | 0 | 0 | 0 | 0 | 50 | 0 | 30 | 0 | 0 | 0 | 0 | 0 |
| Ryegrass, Italian | 40 | 0 | 20 | 20 | 0 | 60 | 40 | 30 | 50 | 40 | 0 | 20 | 0 | 0 |
| Wheat | 30 | 20 | 0 | 0 | 0 | 60 | 40 | 30 | 30 | 30 | 40 | 20 | 40 | 30 |

| 500 g ai/ha | Compounds | | | | | | | | | | | | | |
|---|---|---|---|---|---|---|---|---|---|---|---|---|---|---|
| Postemergence | 481 | 482 | 483 | 484 | 485 | 486 | 487 | 488 | 489 | 490 | 491 | 492 | 493 | 494 |
| Barnyardgrass | 20 | 20 | 60 | 50 | 50 | 40 | 90 | 90 | 90 | 80 | 80 | 90 | 90 | 80 |
| Blackgrass | 0 | 0 | 0 | 0 | 0 | 0 | 30 | 70 | 70 | 40 | 50 | 70 | 50 | 0 |
| Corn | 0 | 0 | 0 | 0 | 20 | 0 | 20 | 80 | 80 | 80 | 90 | 80 | 70 | 0 |
| Foxtail, Giant | 20 | 20 | 70 | 40 | 70 | 50 | 90 | 90 | 90 | 80 | 80 | 90 | 90 | 60 |
| Galium | 0 | 0 | 0 | 0 | 30 | 20 | 0 | 50 | 40 | 40 | 30 | 60 | 40 | 0 |
| Kochia | 0 | 0 | 20 | 0 | 30 | 0 | 30 | 60 | 40 | 20 | 20 | 60 | 20 | 0 |
| Pigweed | 0 | 0 | 0 | 0 | 40 | 40 | 20 | 50 | 20 | 20 | 20 | 60 | 0 | 0 |
| Ragweed | 0 | 0 | 0 | 0 | 0 | 0 | 0 | 20 | 30 | 20 | 20 | 70 | 20 | 0 |
| Ryegrass, Italian | 0 | 0 | 0 | 0 | 0 | 0 | 20 | 60 | 50 | 30 | 30 | 50 | 50 | 0 |
| Wheat | 20 | 0 | 0 | 0 | 20 | 0 | 20 | 60 | 70 | 50 | 60 | 60 | 30 | 0 |

TABLE A-continued

| 500 g ai/ha | Compounds | | | | | | | | | | | | | |
|---|---|---|---|---|---|---|---|---|---|---|---|---|---|---|
| Postemergence | 495 | 496 | 497 | 498 | 499 | 500 | 501 | 502 | 503 | 504 | 505 | 506 | 507 | 508 |
| Barnyardgrass | 80 | 80 | 80 | 70 | 80 | 50 | 80 | 60 | 90 | 90 | 0 | 90 | 60 | 90 |
| Blackgrass | 20 | 0 | 30 | 0 | 0 | 0 | 40 | 20 | 70 | 60 | 0 | 60 | 0 | 0 |
| Corn | 30 | 0 | 40 | 0 | 0 | 20 | 30 | 30 | 80 | 70 | 0 | 60 | 0 | 20 |
| Foxtail, Giant | 70 | 50 | 50 | 40 | 30 | 50 | 80 | 50 | 90 | 90 | 0 | 80 | 20 | 40 |
| Galium | 0 | 30 | 50 | 0 | 40 | 0 | 0 | 50 | 70 | 70 | 0 | 50 | 20 | 20 |
| Kochia | 30 | 0 | 30 | 0 | 0 | 20 | 0 | 20 | 0 | 60 | 0 | 0 | 70 | 20 |
| Pigweed | 0 | 0 | 0 | 0 | 0 | 0 | 0 | 0 | 0 | 70 | 10 | 20 | 0 | 20 |
| Ragweed | 0 | 0 | 0 | 0 | 0 | 40 | 0 | 0 | 30 | 40 | 0 | 0 | 20 | 0 |
| Ryegrass, Italian | 20 | 0 | 20 | 0 | 0 | 0 | 20 | 30 | 70 | 40 | 0 | 40 | 0 | 0 |
| Wheat | 20 | 0 | 40 | 0 | 0 | 20 | 0 | 0 | 40 | 60 | 0 | 30 | 0 | 20 |

| 500 g ai/ha | Compounds | | | | | | | | | | | | | |
|---|---|---|---|---|---|---|---|---|---|---|---|---|---|---|
| Postemergence | 509 | 510 | 513 | 514 | 515 | 516 | 517 | 518 | 519 | 520 | 521 | 522 | 523 | 524 |
| Barnyardgrass | 90 | 70 | 90 | 90 | 20 | 70 | 30 | 50 | 90 | 90 | 90 | 80 | 90 | 70 |
| Blackgrass | 20 | 40 | 40 | 50 | 0 | 0 | 0 | 0 | 50 | 70 | 40 | 50 | 70 | 20 |
| Corn | 0 | 0 | 60 | 80 | 0 | 0 | 0 | 0 | 80 | 70 | 40 | 20 | 80 | 0 |
| Foxtail, Giant | 40 | 30 | 80 | 90 | 0 | 70 | 0 | 70 | 90 | 80 | 90 | 90 | 90 | 70 |
| Galium | 40 | 0 | 40 | 50 | 0 | 0 | 0 | 20 | 50 | 60 | 60 | 60 | 60 | 0 |
| Kochia | 20 | 40 | 50 | 50 | 0 | 0 | 0 | 0 | 20 | 70 | 20 | 50 | 50 | 0 |
| Pigweed | 0 | 0 | 60 | 30 | 0 | 0 | 0 | 0 | 0 | 50 | 50 | 40 | 60 | 0 |
| Ragweed | 0 | 30 | 20 | 20 | 0 | 0 | 0 | 0 | 0 | 30 | 0 | 0 | 50 | 0 |
| Ryegrass, Italian | 0 | 20 | 30 | 40 | 0 | 0 | 0 | 0 | 60 | 80 | 40 | 40 | 70 | 0 |
| Wheat | 0 | 0 | 30 | 40 | 0 | 0 | 0 | 0 | 50 | 70 | 50 | 20 | 70 | 0 |

| 500 g ai/ha | Compounds | | | | | | | | | | | | |
|---|---|---|---|---|---|---|---|---|---|---|---|---|---|
| Postemergence | 525 | 526 | 527 | 534 | 535 | 536 | 537 | 538 | 539 | 540 | 541 | 544 | |
| Barnyardgrass | 40 | 20 | 20 | 0 | 0 | 0 | 0 | 0 | 90 | 70 | 90 | 70 | |
| Blackgrass | 30 | 0 | 0 | 0 | 0 | 0 | 0 | 0 | 80 | 60 | 60 | 0 | |
| Corn | 0 | 0 | 0 | 0 | 0 | 0 | 0 | 0 | 90 | 60 | 60 | 20 | |
| Foxtail, Giant | 60 | 40 | 20 | 0 | 0 | 30 | 0 | 0 | 90 | 90 | 90 | 60 | |
| Galium | 0 | 0 | 0 | 0 | 0 | 0 | 0 | 0 | 70 | 70 | 50 | 0 | |
| Kochia | 0 | 0 | 0 | 0 | 0 | 0 | 0 | 0 | 70 | 0 | 30 | 0 | |
| Pigweed | 0 | 0 | 0 | 0 | 0 | 0 | 0 | 0 | 50 | 0 | 0 | 0 | |
| Ragweed | 0 | 0 | 0 | 0 | 0 | 0 | 0 | 0 | 50 | 20 | 30 | 0 | |
| Ryegrass, Italian | 0 | 0 | 0 | 0 | 0 | 0 | 0 | 0 | 70 | 30 | 40 | 0 | |
| Wheat | 0 | 0 | 0 | 0 | 0 | 0 | 0 | 0 | 70 | 60 | 80 | 0 | |

| 500 g ai/ha | Compounds | | | | | | | | | | | | |
|---|---|---|---|---|---|---|---|---|---|---|---|---|---|
| Postemergence | 545 | 546 | 547 | 549 | 550 | 551 | 552 | 553 | 554 | 557 | 558 | 559 | 560 |
| Barnyardgrass | 80 | 90 | 90 | 90 | 90 | 80 | 90 | 90 | 90 | 0 | 100 | 100 | 100 |
| Blackgrass | 0 | 20 | 0 | 20 | 50 | 0 | 70 | 60 | 70 | 0 | 60 | 60 | 50 |
| Corn | 0 | 20 | 0 | 0 | 20 | 0 | 50 | 90 | 70 | 0 | 20 | 30 | 30 |
| Foxtail, Giant | 70 | 90 | 90 | 90 | 90 | 80 | 80 | 90 | 80 | 0 | 90 | 90 | 90 |
| Galium | 0 | 0 | 20 | 0 | 60 | 0 | 60 | 60 | 60 | 0 | 60 | 60 | 60 |
| Kochia | 0 | 0 | 50 | 20 | 50 | 0 | 30 | 50 | 50 | 0 | 70 | 70 | 80 |
| Pigweed | 0 | 0 | 0 | 0 | 0 | 0 | 0 | 30 | 0 | 0 | 0 | 0 | 20 |
| Ragweed | 0 | 0 | 30 | 0 | 0 | 0 | 20 | 40 | 30 | 0 | 40 | 0 | 20 |
| Ryegrass, Italian | 0 | 0 | 0 | 0 | 20 | 0 | 50 | 70 | 90 | 0 | 40 | 30 | 60 |
| Wheat | 0 | 0 | 0 | 20 | 30 | 0 | 40 | 60 | 50 | 0 | 40 | 50 | 50 |

| 500 g ai/ha | Compounds | | | | | | | | | | | | | |
|---|---|---|---|---|---|---|---|---|---|---|---|---|---|---|
| Postemergence | 561 | 562 | 563 | 564 | 565 | 566 | 567 | 568 | 569 | 570 | 571 | 572 | 573 | 574 |
| Barnyardgrass | 90 | 90 | 90 | 90 | 90 | 90 | 100 | 100 | 90 | 100 | 100 | 90 | 100 | 90 |
| Blackgrass | 70 | 70 | 50 | 70 | 60 | 70 | 80 | 90 | 80 | 80 | 80 | 80 | 70 | 70 |
| Corn | 60 | 80 | 50 | 80 | 20 | 40 | 90 | 90 | 60 | 80 | 80 | 80 | 90 | 80 |
| Foxtail, Giant | 90 | 90 | 90 | 90 | 90 | 90 | 90 | 90 | 90 | 90 | 90 | 90 | 90 | 80 |
| Galium | 60 | 70 | 70 | 70 | 60 | 80 | 50 | 60 | 60 | 60 | 70 | 60 | 70 | 50 |
| Kochia | 80 | 80 | 80 | 80 | 60 | 80 | 50 | 70 | 50 | 70 | 60 | 60 | 60 | 60 |
| Pigweed | 70 | 80 | 40 | 70 | 60 | 60 | 20 | 60 | 50 | 20 | 30 | 40 | 40 | 40 |
| Ragweed | 40 | 60 | 50 | 60 | 50 | 40 | 0 | 30 | 60 | 0 | 0 | 20 | 60 | 0 |
| Ryegrass, Italian | 60 | 80 | 40 | 70 | 30 | 60 | 70 | 90 | 60 | 80 | 60 | 60 | 90 | 70 |
| Wheat | 70 | 80 | 40 | 60 | 40 | 40 | 60 | 70 | 70 | 60 | 70 | 70 | 70 | 70 |

TABLE A-continued

| 500 g ai/ha | Compounds | | | | | | | | | | | | | |
|---|---|---|---|---|---|---|---|---|---|---|---|---|---|---|
| Postemergence | 575 | 576 | 577 | 587 | 588 | 589 | 590 | 591 | 592 | 593 | 594 | 595 | 596 | 597 |
| Barnyardgrass | 90 | 90 | 100 | 90 | 80 | 80 | 90 | 90 | 90 | 90 | 90 | 90 | 90 | 30 |
| Blackgrass | 80 | 50 | 80 | 60 | 50 | 40 | 70 | 60 | 60 | 60 | 60 | 40 | 50 | 20 |
| Corn | 80 | 80 | 80 | 70 | 70 | 60 | 70 | 80 | 70 | 70 | 70 | 60 | 60 | 20 |
| Foxtail, Giant | 90 | 90 | 90 | 90 | 80 | 80 | 90 | 90 | 90 | 90 | 90 | 90 | 90 | 30 |
| Galium | 70 | 60 | 50 | 0 | 30 | 0 | 30 | 50 | 30 | 20 | 20 | 20 | 50 | 20 |
| Kochia | 20 | 60 | 40 | 20 | 70 | 0 | 30 | 60 | 40 | 0 | 40 | 30 | 60 | 0 |
| Pigweed | 20 | 50 | 0 | 0 | 40 | 0 | 0 | 70 | 0 | 0 | 40 | 30 | 20 | 0 |
| Ragweed | 0 | 50 | 30 | 0 | 50 | 0 | 0 | 30 | 0 | 0 | 50 | 0 | 0 | 0 |
| Ryegrass, Italian | 70 | 60 | 30 | 30 | 50 | 40 | 30 | 70 | 0 | 30 | 30 | 40 | 40 | 0 |
| Wheat | 70 | 70 | 70 | 60 | 40 | 50 | 70 | 60 | 70 | 40 | 70 | 50 | 50 | 20 |

| 500 g ai/ha | Compounds | | | | | | | | | | | |
|---|---|---|---|---|---|---|---|---|---|---|---|---|
| Postemergence | 598 | 599 | 600 | 601 | 602 | 605 | 606 | 607 | 608 | 609 | 610 | 611 |
| Barnyardgrass | 80 | 20 | 90 | 70 | 0 | 80 | 70 | 60 | 40 | 80 | 90 | 90 |
| Blackgrass | 0 | 0 | 0 | 0 | 0 | 20 | 40 | 0 | 40 | 40 | 70 | 70 |
| Corn | 0 | 0 | 0 | 20 | 0 | 0 | 0 | 0 | 20 | 30 | 50 | 70 |
| Foxtail, Giant | 20 | 0 | 30 | 50 | 0 | 80 | 90 | 60 | 70 | 90 | 90 | 90 |
| Galium | 30 | 0 | 0 | 0 | 0 | 0 | 70 | 0 | 50 | 40 | 60 | 60 |
| Kochia | 20 | 0 | 0 | 0 | 0 | 0 | 0 | 0 | 60 | 60 | 60 | 70 |
| Pigweed | 0 | 0 | 0 | 0 | 0 | 0 | 70 | 0 | 30 | 30 | 50 | 30 |
| Ragweed | 20 | 0 | 0 | 0 | 0 | 0 | 0 | 0 | 20 | 0 | 30 | 30 |
| Ryegrass, Italian | 0 | 0 | 0 | 0 | 0 | 0 | 0 | 0 | 30 | 40 | 40 | 70 |
| Wheat | 0 | 0 | 0 | 20 | 0 | 30 | 0 | 20 | 0 | 20 | 20 | 60 |

| 500 g ai/ha | Compounds | | | | | | | | | | | |
|---|---|---|---|---|---|---|---|---|---|---|---|---|
| Postemergence | 612 | 613 | 614 | 616 | 617 | 618 | 619 | 620 | 621 | 622 | 623 | 624 | 625 |
| Barnyardgrass | 90 | 90 | 90 | 90 | 90 | 90 | 0 | 60 | 90 | 90 | 90 | 90 | 90 |
| Blackgrass | 60 | 60 | 70 | 60 | 60 | 60 | 0 | 0 | 20 | 60 | 60 | 50 | 40 |
| Corn | 90 | 80 | 20 | 80 | 80 | 80 | 0 | 0 | 20 | 70 | 70 | 40 | 50 |
| Foxtail, Giant | 90 | 90 | 90 | 90 | 90 | 90 | 0 | 50 | 90 | 90 | 90 | 90 | 90 |
| Galium | 50 | 60 | 40 | 70 | 60 | 60 | 0 | 20 | 40 | 70 | 60 | 50 | 60 |
| Kochia | 40 | 70 | 50 | 70 | 60 | 60 | 0 | 0 | 20 | 60 | 70 | 60 | 50 |
| Pigweed | 50 | 70 | 30 | 60 | 50 | 30 | 0 | 0 | 0 | 50 | 60 | 60 | 50 |
| Ragweed | 20 | 30 | 0 | 20 | 50 | 20 | 0 | 0 | 0 | 40 | 0 | 0 | 20 |
| Ryegrass, Italian | 70 | 60 | 20 | 80 | 50 | 50 | 0 | 0 | 20 | 50 | 60 | 30 | 30 |
| Wheat | 30 | 50 | 40 | 70 | 60 | 70 | 0 | 0 | 50 | 70 | 70 | 70 | 50 |

| 500 g ai/ha | Compounds | | | | | | | | | |
|---|---|---|---|---|---|---|---|---|---|---|
| Postemergence | 630 | 631 | 632 | 633 | 634 | 635 | 636 | 637 | 638 | 639 |
| Barnyardgrass | 90 | 0 | 90 | 90 | 80 | 90 | 90 | 90 | 90 | 90 |
| Blackgrass | 20 | 0 | 60 | 50 | 0 | 70 | 60 | 60 | 70 | 60 |
| Corn | 20 | 0 | 80 | 60 | 0 | 70 | 80 | 70 | 80 | 80 |
| Foxtail, Giant | 30 | 0 | 90 | 90 | 80 | 90 | 90 | 90 | 90 | 90 |
| Galium | 40 | 0 | 50 | 50 | 60 | 60 | 50 | 50 | 60 | 50 |
| Kochia | 0 | 0 | 60 | 60 | 0 | 80 | 60 | 30 | 40 | 70 |
| Pigweed | 0 | 0 | 40 | 0 | 0 | 80 | 50 | 60 | 50 | 50 |
| Ragweed | 0 | 0 | 30 | 0 | 0 | 40 | 30 | 20 | 0 | 30 |
| Ryegrass, Italian | 0 | 0 | 50 | 50 | 20 | 30 | 70 | 20 | 40 | 50 |
| Wheat | 20 | 0 | 60 | 40 | 0 | 40 | 60 | 70 | 70 | 60 |

| 500 g ai/ha | Compounds | | | | | | | | | | | | |
|---|---|---|---|---|---|---|---|---|---|---|---|---|---|
| Postemergence | 640 | 641 | 642 | 643 | 644 | 645 | 646 | 647 | 648 | 649 | 650 | 651 | 652 | 653 |
| Barnyardgrass | 90 | 90 | 90 | 90 | 90 | 90 | 90 | 90 | 80 | 70 | 90 | 90 | 90 | 90 |
| Blackgrass | 50 | 60 | 40 | 60 | 70 | 70 | 80 | 60 | 50 | 60 | 50 | 70 | 70 | 70 |
| Corn | 0 | 50 | 70 | 70 | 80 | 60 | 80 | 40 | 0 | 0 | 90 | 90 | 60 | 30 |
| Foxtail, Giant | 90 | 90 | 70 | 90 | 90 | 90 | 90 | 90 | 50 | 60 | 90 | 80 | 90 | 90 |
| Galium | 50 | 50 | 70 | 50 | 60 | 50 | 50 | 50 | 60 | 70 | 70 | 60 | 50 | 50 |
| Kochia | 40 | 20 | 50 | 20 | 70 | 50 | 70 | 20 | 0 | 60 | 40 | 40 | 0 | 0 |
| Pigweed | 20 | 20 | 20 | 0 | 30 | 0 | 20 | 0 | 50 | 30 | 0 | 30 | 20 | 0 |
| Ragweed | 0 | 20 | 40 | 30 | 40 | 20 | 40 | 10 | 30 | 60 | 30 | 20 | 0 | 0 |
| Ryegrass, Italian | 0 | 40 | 50 | 30 | 80 | 50 | 70 | 0 | 50 | 40 | 70 | 70 | 70 | 60 |
| Wheat | 50 | 30 | 20 | 50 | 80 | 50 | 70 | 50 | 0 | 0 | 70 | 60 | 40 | 60 |

TABLE A-continued

| 500 g ai/ha | Compounds | | | | | | | | | | | | | |
|---|---|---|---|---|---|---|---|---|---|---|---|---|---|---|
| Postemergence | 654 | 655 | 656 | 657 | 658 | 659 | 660 | 661 | 662 | 663 | 664 | 665 | 666 | 667 |
| Barnyardgrass | 90 | 90 | 90 | 90 | 90 | 90 | 80 | 90 | 90 | 90 | 90 | 90 | 90 | 90 |
| Blackgrass | 50 | 30 | 30 | 30 | 70 | 50 | 40 | 70 | 80 | 70 | 60 | 70 | 60 | 70 |
| Corn | 70 | 30 | 20 | 0 | 30 | 50 | 0 | 90 | 90 | 80 | 90 | 70 | 80 | 80 |
| Foxtail, Giant | 90 | 60 | 60 | 60 | 60 | 90 | 90 | 90 | 90 | 90 | 90 | 90 | 90 | 90 |
| Galium | 60 | 50 | 60 | 30 | 60 | 20 | 0 | 60 | 70 | 60 | 60 | 50 | 40 | 50 |
| Kochia | 50 | 40 | 30 | 0 | 30 | 20 | 0 | 70 | 70 | 60 | 70 | 50 | 30 | 60 |
| Pigweed | 20 | 0 | 0 | 0 | 0 | 0 | 0 | 0 | 50 | 20 | 20 | 20 | 0 | 0 |
| Ragweed | 20 | 0 | 0 | 0 | 40 | 0 | 0 | 50 | 60 | 40 | 20 | 30 | 0 | 50 |
| Ryegrass, Italian | 60 | 30 | 0 | 0 | 60 | 60 | 0 | 80 | 70 | 70 | 70 | 80 | 60 | 80 |
| Wheat | 40 | 10 | 20 | 0 | 30 | 50 | 0 | 80 | 80 | 70 | 70 | 70 | 60 | 70 |

| 500 g ai/ha | Compounds | | | | | | | | |
|---|---|---|---|---|---|---|---|---|---|
| Postemergence | 668 | 674 | 675 | 676 | 677 | 678 | 679 | 680 | 681 |
| Barnyardgrass | 90 | 70 | 70 | 80 | 90 | 80 | 70 | 60 | 90 |
| Blackgrass | 70 | 0 | 20 | 40 | 20 | 60 | 60 | 20 | 30 |
| Corn | 80 | 0 | 0 | 50 | 40 | 30 | 50 | 20 | 30 |
| Foxtail, Giant | 90 | 80 | 80 | 80 | 70 | 60 | 30 | 30 | 30 |
| Galium | 70 | 0 | 0 | 40 | 40 | 30 | 60 | 20 | 50 |
| Kochia | 20 | 0 | 0 | 0 | 40 | 0 | 0 | 0 | 40 |
| Pigweed | 0 | 0 | 0 | 0 | 20 | 0 | 40 | 0 | 0 |
| Ragweed | 0 | 0 | 0 | 0 | 30 | 0 | 20 | 0 | 0 |
| Ryegrass, Italian | 70 | 0 | 0 | 20 | 30 | 20 | 20 | 0 | 20 |
| Wheat | 60 | 0 | 0 | 20 | 20 | 20 | 20 | 0 | 0 |

| 500 g ai/ha | Compounds | | | | | | | | | | | | | |
|---|---|---|---|---|---|---|---|---|---|---|---|---|---|---|
| Postemergence | 682 | 683 | 684 | 685 | 686 | 687 | 688 | 689 | 690 | 691 | 692 | 693 | 694 | 695 |
| Barnyardgrass | 20 | 20 | 70 | 70 | 90 | 90 | 90 | 90 | 80 | 80 | 80 | 80 | 70 | 90 |
| Blackgrass | 0 | 20 | 20 | 20 | 40 | 40 | 60 | 60 | 70 | 60 | 60 | 50 | 30 | 40 |
| Corn | 0 | 20 | 20 | 0 | 50 | 70 | 70 | 80 | 80 | 90 | 50 | 70 | 0 | 80 |
| Foxtail, Giant | 80 | 80 | 80 | 80 | 90 | 90 | 90 | 90 | 80 | 80 | 80 | 80 | 80 | 80 |
| Galium | 0 | 0 | 0 | 0 | 20 | 20 | 50 | 50 | 70 | 70 | 60 | 70 | 0 | 40 |
| Kochia | 0 | 0 | 0 | 0 | 30 | 30 | 60 | 60 | 70 | 80 | 60 | 70 | 0 | 50 |
| Pigweed | 0 | 0 | 0 | 0 | 20 | 20 | 50 | 60 | 70 | 70 | 50 | 70 | 50 | 30 |
| Ragweed | 0 | 0 | 0 | 0 | 20 | 30 | 50 | 50 | 70 | 60 | 30 | 10 | 0 | 40 |
| Ryegrass, Italian | 0 | 0 | 0 | 0 | 40 | 40 | 60 | 60 | 60 | 60 | 60 | 70 | 50 | 20 |
| Wheat | 20 | 20 | 20 | 20 | 30 | 60 | 70 | 60 | 60 | 60 | 50 | 50 | 0 | 40 |

| 500 g ai/ha | Compounds | | | | | | | | | | |
|---|---|---|---|---|---|---|---|---|---|---|---|
| Postemergence | 696 | 697 | 698 | 699 | 700 | 701 | 702 | 703 | 704 | 705 | 706 |
| Barnyardgrass | 80 | 90 | 80 | 80 | 70 | 70 | 70 | 70 | 90 | 0 | 50 |
| Blackgrass | 40 | 40 | 40 | 60 | 50 | 0 | 0 | 0 | 30 | 0 | 0 |
| Corn | 70 | 80 | 80 | 60 | 70 | 0 | 0 | 0 | 0 | 0 | 0 |
| Foxtail, Giant | 80 | 80 | 80 | 80 | 90 | 70 | 80 | 90 | 90 | 0 | 30 |
| Galium | 70 | 50 | 50 | 60 | 60 | 0 | 40 | 0 | 40 | 0 | 0 |
| Kochia | 40 | 60 | 60 | 50 | 60 | 0 | 0 | 0 | 20 | 0 | 0 |
| Pigweed | 60 | 50 | 60 | 20 | 30 | 0 | 0 | 0 | 20 | 0 | 0 |
| Ragweed | 40 | 50 | 40 | 30 | 30 | 0 | 0 | 0 | 20 | 0 | 0 |
| Ryegrass, Italian | 40 | 30 | 30 | 30 | 40 | 0 | 0 | 0 | 20 | 0 | 0 |
| Wheat | 50 | 40 | 40 | 20 | 60 | 0 | 0 | 0 | 0 | 0 | 0 |

| 500 g ai/ha | Compounds | | | | |
|---|---|---|---|---|---|
| Postemergence | 711 | 712 | 714 | 715 | 716 |
| Barnyardgrass | 0 | 0 | 0 | 0 | 0 |
| Blackgrass | 0 | 0 | — | — | — |
| Corn | 0 | 0 | 0 | 0 | 0 |
| Crabgrass, Large | — | — | 0 | 0 | 0 |
| Foxtail, Giant | 0 | 0 | 0 | 0 | 0 |
| Galium | 0 | 0 | — | — | — |
| Kochia | 0 | 0 | — | — | — |
| Morningglory | — | — | 0 | 0 | 0 |
| Pigweed | 0 | 0 | 0 | 0 | 0 |
| Ragweed | 0 | 0 | — | — | — |
| Ryegrass, Italian | 0 | 0 | — | — | — |
| Velvetleaf | — | — | 0 | 0 | 0 |
| Wheat | 0 | 0 | 0 | 0 | 0 |

TABLE A-continued

| 500 g ai/ha Postemergence | 1000 | 1001 | 1002 | 1013 | 1014 | 1015 | 1016 | 1017 | 1018 | 1019 | 1020 | 1021 | 1022 | 1023 |
|---|---|---|---|---|---|---|---|---|---|---|---|---|---|---|
| Barnyardgrass | 100 | 0 | 90 | 90 | 90 | 90 | 90 | 90 | 90 | 0 | 90 | 100 | 100 | 90 |
| Blackgrass | 0 | 0 | 0 | 40 | 50 | 50 | 0 | 40 | 50 | 0 | 20 | 50 | 0 | 20 |
| Corn | 20 | 0 | 0 | 90 | 90 | 90 | 0 | 90 | 90 | 0 | 30 | 80 | 20 | 50 |
| Crabgrass, Large | — | — | — | — | — | — | — | — | — | — | — | — | — | — |
| Foxtail, Giant | 50 | 0 | 50 | 90 | 90 | 80 | 80 | 90 | 90 | 0 | 90 | 90 | 70 | 90 |
| Galium | 0 | 0 | 0 | 70 | 60 | 70 | 0 | 70 | 60 | 0 | 60 | 70 | 50 | 60 |
| Kochia | 40 | 0 | 40 | 60 | 50 | 50 | 0 | 60 | 50 | 0 | 50 | 70 | 60 | 50 |
| Morningglory | — | — | — | — | — | — | — | — | — | — | — | — | — | — |
| Pigweed | 0 | 0 | 0 | 40 | 30 | 50 | 0 | 40 | 60 | 0 | 30 | 50 | 0 | 30 |
| Ragweed | 0 | 0 | 0 | 40 | 30 | 40 | 0 | 40 | 30 | 0 | 0 | 60 | 0 | 0 |
| Ryegrass, Italian | 0 | 0 | 0 | 60 | 60 | 50 | 0 | 50 | 60 | 0 | 30 | 70 | 30 | 30 |
| Velvetleaf | — | — | — | — | — | — | — | — | — | — | — | — | — | — |
| Wheat | 0 | 0 | 0 | 60 | 80 | 60 | 0 | 60 | 50 | 0 | 30 | 60 | 30 | 20 |

| 500 g ai/ha Postemergence | Compounds | | | | | | | | | | | | |
|---|---|---|---|---|---|---|---|---|---|---|---|---|---|
| | 1024 | 1025 | 1026 | 1027 | 1028 | 1029 | 1030 | 1031 | 1032 | 1033 | 1034 | 1035 | 1036 | 1037 |
| Barnyardgrass | 90 | 70 | 90 | 90 | 90 | 90 | 90 | 0 | 0 | 90 | 90 | 90 | 90 | 90 |
| Blackgrass | 20 | 0 | 0 | 40 | 40 | 40 | 60 | 0 | 0 | 40 | 30 | 60 | 0 | 20 |
| Corn | 70 | 20 | 30 | 0 | 30 | 70 | 50 | 0 | 0 | 40 | 50 | 60 | 20 | 30 |
| Crabgrass, Large | — | — | — | — | — | — | — | — | — | — | — | — | — | — |
| Foxtail, Giant | 90 | 60 | 20 | 60 | 80 | 90 | 90 | 0 | 0 | 80 | 80 | 90 | 60 | 30 |
| Galium | 60 | 30 | 50 | 70 | 50 | 40 | 60 | 0 | 0 | 60 | 60 | 50 | 30 | 60 |
| Kochia | 60 | 50 | 0 | 30 | 0 | 0 | 0 | 0 | 0 | 0 | 30 | 20 | 0 | 20 |
| Morningglory | — | — | — | — | — | — | — | — | — | — | — | — | — | — |
| Pigweed | 50 | 30 | 0 | 0 | 0 | 0 | 0 | 0 | 0 | 0 | 0 | 0 | 0 | 0 |
| Ragweed | 0 | 0 | 0 | 0 | 0 | 0 | 0 | 0 | 0 | 30 | 40 | 0 | 10 | 30 |
| Ryegrass, Italian | 30 | 30 | 0 | 30 | 40 | 40 | 0 | 0 | 0 | 20 | 60 | 60 | 60 | 50 |
| Velvetleaf | — | — | — | — | — | — | — | — | — | — | — | — | — | — |
| Wheat | 30 | 0 | 30 | 0 | 40 | 60 | 60 | 0 | 0 | 0 | 50 | 70 | 20 | 30 |

| 500 g ai/ha Postemergence | Compounds | | | | | | | | | | | | |
|---|---|---|---|---|---|---|---|---|---|---|---|---|---|
| | 1038 | 1039 | 1040 | 1041 | 1042 | 1043 | 1044 | 1045 | 1046 | 1047 | 1048 | 1049 | 1053 | 1054 |
| Barnyardgrass | 90 | 90 | 90 | 50 | 90 | 80 | 80 | 90 | 90 | 80 | 80 | 50 | 0 | 0 |
| Blackgrass | 50 | 40 | 70 | 40 | 70 | 30 | — | 60 | 50 | 0 | 30 | 0 | 0 | 0 |
| Corn | 80 | 70 | 80 | 30 | 70 | 60 | 50 | 40 | 60 | 0 | 40 | 0 | 0 | 0 |
| Crabgrass, Large | — | — | — | — | — | — | — | — | — | — | — | — | — | — |
| Foxtail, Giant | 90 | 90 | 90 | 50 | 90 | 80 | 90 | 90 | 90 | 80 | 80 | 80 | 0 | 0 |
| Galium | 70 | 60 | 70 | 60 | 50 | 40 | 60 | 50 | 50 | 50 | 60 | 40 | 0 | 0 |
| Kochia | 80 | 60 | 70 | — | 60 | 40 | 50 | 0 | 0 | 20 | 60 | 30 | 0 | 0 |
| Morningglory | — | — | — | — | — | — | — | — | — | — | — | — | — | — |
| Pigweed | 20 | 20 | 60 | 20 | 40 | 30 | 30 | 0 | 20 | 0 | 60 | 50 | 0 | 0 |
| Ragweed | 30 | 40 | 40 | — | 30 | 10 | 40 | 30 | 0 | 0 | 50 | 40 | 0 | 0 |
| Ryegrass, Italian | 50 | 60 | 60 | 20 | 50 | 20 | 30 | 50 | 60 | 0 | 40 | 0 | 0 | 0 |
| Velvetleaf | — | — | — | — | — | — | — | — | — | — | — | — | — | — |
| Wheat | 60 | 60 | 30 | 30 | 30 | 0 | 20 | 40 | 30 | 0 | 20 | 0 | 0 | 0 |

| 500 g ai/ha Postemergence | Compounds | | | | | | | | | | | | |
|---|---|---|---|---|---|---|---|---|---|---|---|---|---|
| | 1055 | 1056 | 1057 | 1058 | 1059 | 1073 | 1094 | 1095 | 1096 | 1097 | 1098 | 1099 | 1100 | 1101 |
| Barnyardgrass | 0 | 50 | 0 | 90 | 90 | 90 | 80 | 0 | 0 | 0 | 90 | 80 | 70 | 80 |
| Blackgrass | 0 | 0 | 0 | 40 | 0 | 30 | 30 | 0 | 0 | 0 | 30 | 40 | 20 | 30 |
| Corn | 0 | 0 | 0 | 30 | 20 | 50 | 0 | 0 | 0 | 0 | 70 | 60 | 20 | 70 |
| Crabgrass, Large | — | — | — | — | — | — | — | — | — | — | — | — | — | — |
| Foxtail, Giant | 0 | 20 | 0 | 0 | 40 | 40 | 80 | 0 | 0 | 0 | 90 | 80 | 70 | 80 |
| Galium | 0 | 0 | 0 | 60 | 0 | — | 20 | 0 | 0 | 0 | 40 | 60 | 20 | 60 |
| Kochia | 0 | 0 | 0 | 20 | 0 | 40 | 0 | 0 | 0 | 0 | 60 | 60 | 20 | 60 |
| Morningglory | — | — | — | — | — | — | — | — | — | — | — | — | — | — |
| Pigweed | 0 | 0 | 0 | 0 | 0 | 20 | 20 | 0 | 0 | 0 | 0 | 50 | 0 | 50 |
| Ragweed | 0 | 0 | 90 | 0 | 0 | 30 | 0 | 0 | 0 | 0 | 0 | 40 | 0 | 0 |
| Ryegrass, Italian | 0 | 0 | 0 | 0 | 20 | 40 | 20 | 0 | 0 | 0 | 50 | 60 | 20 | 60 |
| Velvetleaf | — | — | — | — | — | — | — | — | — | — | — | — | — | — |
| Wheat | 0 | 0 | 0 | 0 | 0 | 30 | 30 | 0 | 0 | 0 | 50 | 50 | 20 | 50 |

| 500 g ai/ha Postemergence | Compounds | | | | | | | | | | | | |
|---|---|---|---|---|---|---|---|---|---|---|---|---|---|
| | 1102 | 1111 | 1112 | 1113 | 1114 | 1115 | 1116 | 1117 | 1118 | 1119 | 1120 | 1121 | 1122 | 1123 |
| Barnyardgrass | 80 | 0 | 0 | 0 | 90 | 90 | 60 | 90 | 90 | 90 | 90 | 90 | 90 | 90 |
| Blackgrass | 50 | 0 | 0 | 0 | 60 | 40 | 30 | 40 | 60 | 70 | 50 | 60 | 60 | 80 |
| Corn | 60 | 0 | 0 | 0 | 70 | 50 | 0 | 40 | 20 | 30 | 60 | 90 | 90 | 80 |
| Crabgrass, Large | — | — | — | — | — | — | — | — | — | — | — | — | — | — |
| Foxtail, Giant | 90 | 50 | 0 | 0 | 90 | 90 | 0 | 70 | 50 | 70 | 90 | 90 | 90 | 90 |

TABLE A-continued

| | | | | | | | | | | | | | |
|---|---|---|---|---|---|---|---|---|---|---|---|---|---|
| Galium | 30 | 0 | 0 | 0 | 20 | 30 | 40 | 40 | 60 | 50 | 60 | 60 | 60 | 50 |
| Kochia | 0 | 0 | 0 | 0 | 20 | 40 | 30 | 40 | 30 | 60 | 70 | 70 | 60 | 70 |
| Morningglory | — | — | — | — | — | — | — | — | — | — | — | — | — | — |
| Pigweed | 0 | 0 | 0 | 0 | 0 | 20 | 0 | 0 | 20 | 20 | 20 | 40 | 40 | 20 |
| Ragweed | 20 | 0 | 0 | 0 | 0 | 30 | 0 | 30 | 20 | 60 | 50 | 40 | 50 | 50 |
| Ryegrass, Italian | 30 | 0 | 0 | 0 | 40 | 40 | 20 | 40 | 50 | 30 | 40 | 70 | 60 | 50 |
| Velvetleaf | — | — | — | — | — | — | — | — | — | — | — | — | — | — |
| Wheat | 50 | 0 | 0 | 0 | 30 | 30 | 20 | 70 | 20 | 50 | 50 | 60 | 70 | 60 |

| 500 g ai/ha | Compounds | | | | | | | | | | | | |
|---|---|---|---|---|---|---|---|---|---|---|---|---|---|
| Postemergence | 1124 | 1125 | 1126 | 1127 | 1128 | 1129 | 1130 | 1131 | 1132 | 1133 | 1134 | 1135 | 1136 | 1137 |
| Barnyardgrass | 90 | 90 | 90 | 40 | 90 | 90 | 20 | 90 | 90 | 90 | 80 | 0 | 90 | 0 |
| Blackgrass | 0 | 50 | 40 | 20 | 50 | 0 | 0 | 60 | 50 | 70 | 50 | 0 | 30 | 0 |
| Corn | 0 | 60 | 90 | 0 | 50 | 0 | 0 | 80 | 80 | 80 | 20 | 0 | 0 | 0 |
| Crabgrass, Large | — | — | — | — | — | — | — | — | — | — | — | — | — | — |
| Foxtail, Giant | 90 | 90 | 90 | 50 | 90 | 90 | 30 | 90 | 90 | 90 | 80 | 0 | 90 | 0 |
| Galium | 60 | 50 | 40 | 40 | 70 | 0 | 0 | 60 | 30 | 70 | 70 | 0 | 20 | 0 |
| Kochia | 70 | 40 | 70 | 0 | 70 | 0 | 0 | 70 | 0 | 70 | 30 | 0 | 0 | 0 |
| Morningglory | — | — | — | — | — | — | — | — | — | — | — | — | — | — |
| Pigweed | 60 | 0 | 30 | 0 | 0 | 0 | 0 | 80 | 0 | 70 | 20 | 0 | 0 | 0 |
| Ragweed | 50 | 0 | 40 | 0 | 50 | 0 | 0 | 80 | 0 | 70 | 30 | 0 | 0 | 0 |
| Ryegrass, Italian | 0 | 60 | 50 | 0 | 30 | 0 | 0 | 50 | 30 | 40 | 20 | 0 | 0 | 0 |
| Velvetleaf | — | — | — | — | — | — | — | — | — | — | — | — | — | — |
| Wheat | 0 | 40 | 70 | 0 | 0 | 0 | 0 | 70 | 70 | 70 | 20 | 0 | 0 | 0 |

| 500 g ai/ha | Compounds | | | | | | | | | | | | |
|---|---|---|---|---|---|---|---|---|---|---|---|---|---|
| Postemergence | 1138 | 1139 | 1140 | 1151 | 1152 | 1153 | 1154 | 1155 | 1156 | 1157 | 1158 | 1159 | 1160 | 1177 |
| Barnyardgrass | 90 | 90 | 90 | 90 | 0 | 90 | 90 | 90 | 90 | 90 | 90 | 90 | 90 | 90 |
| Blackgrass | 60 | 60 | 70 | 60 | 0 | 30 | 90 | 0 | 40 | 50 | 40 | 0 | 50 | 70 |
| Corn | 80 | 80 | 70 | 80 | 0 | 0 | 90 | 30 | 60 | 50 | 60 | 20 | 80 | 40 |
| Crabgrass, Large | — | — | — | — | — | — | — | — | — | — | — | — | — | — |
| Foxtail, Giant | 90 | 70 | 90 | 80 | 40 | 90 | 60 | 70 | 90 | 90 | 80 | 70 | 90 | 70 |
| Galium | 50 | 60 | 50 | 60 | 20 | 40 | 70 | 60 | 50 | 60 | 30 | 20 | 60 | 50 |
| Kochia | 0 | 0 | 40 | 60 | 0 | 0 | 60 | 0 | 20 | 50 | 0 | 0 | 20 | 0 |
| Morningglory | — | — | — | — | — | — | — | — | — | — | — | — | — | — |
| Pigweed | 0 | 0 | 0 | 80 | 0 | 0 | 70 | 0 | 0 | 0 | 0 | 20 | 0 | 0 |
| Ragweed | 0 | 40 | 30 | 30 | 0 | 0 | 40 | 40 | 0 | 50 | 0 | 0 | 0 | 0 |
| Ryegrass, Italian | 50 | 50 | 70 | 50 | 0 | 0 | 50 | 20 | 30 | 40 | 50 | 0 | 20 | 40 |
| Velvetleaf | — | — | — | — | — | — | — | — | — | — | — | — | — | — |
| Wheat | 70 | 70 | 70 | 60 | 0 | 0 | 80 | 50 | 50 | 70 | 50 | 0 | 50 | 30 |

| 500 g ai/ha | Compounds | | | | | | | | | | | | |
|---|---|---|---|---|---|---|---|---|---|---|---|---|---|
| Postemergence | 1178 | 1179 | 1180 | 1181 | 1182 | 1194 | 1195 | 1196 | 1197 | 1198 | 1199 | 1200 | 1201 | 1202 |
| Barnyardgrass | 30 | 0 | 0 | 0 | 0 | 20 | 20 | 90 | — | 90 | 100 | 0 | 100 | — |
| Blackgrass | 20 | 0 | 0 | 0 | 0 | 0 | 0 | 0 | 50 | 60 | 0 | 0 | 0 | 40 |
| Corn | 0 | 0 | 0 | 0 | 0 | 0 | 0 | 0 | 90 | 20 | 0 | 0 | 0 | 30 |
| Crabgrass, Large | — | — | — | — | — | — | — | — | — | — | — | — | — | — |
| Foxtail, Giant | 30 | 0 | 0 | 0 | 0 | 20 | 20 | 80 | 90 | 90 | 90 | 0 | 90 | 90 |
| Galium | 30 | 0 | 0 | 0 | 0 | 0 | 0 | 0 | 60 | 50 | 40 | 0 | 50 | 40 |
| Kochia | 40 | — | 0 | — | 0 | 0 | 0 | 0 | 80 | 60 | 40 | 0 | 70 | 40 |
| Morningglory | — | — | — | — | — | — | — | — | — | — | — | — | — | — |
| Pigweed | 0 | 0 | 0 | 0 | 0 | 0 | 0 | 0 | 70 | 70 | 20 | 0 | 60 | 20 |
| Ragweed | 20 | 0 | 0 | 0 | 0 | 0 | 0 | 0 | 60 | 30 | 0 | 0 | 30 | 20 |
| Ryegrass, Italian | 0 | 0 | 0 | 0 | 0 | 0 | 0 | 0 | 60 | 30 | 20 | 0 | 0 | 0 |
| Velvetleaf | — | — | — | — | — | — | — | — | — | — | — | — | — | — |
| Wheat | 0 | 0 | 0 | 0 | 0 | 0 | 0 | 0 | 60 | 60 | 0 | 0 | 0 | 50 |

| 500 g ai/ha | Compounds | | | | | | | | | | | | |
|---|---|---|---|---|---|---|---|---|---|---|---|---|---|
| Postemergence | 1203 | 1204 | 1205 | 1206 | 1207 | 1208 | 1209 | 1210 | 1211 | 1212 | 1213 | 1214 | 1215 | 1216 |
| Barnyardgrass | — | — | 50 | 100 | 100 | 100 | — | — | 100 | 100 | 100 | 90 | — | — |
| Blackgrass | 60 | 70 | 20 | 0 | 0 | 0 | 30 | 50 | 40 | 30 | 40 | 80 | 0 | 0 |
| Corn | 70 | 80 | 80 | 0 | 0 | 50 | 0 | 50 | 90 | 20 | 80 | 90 | 0 | 0 |
| Crabgrass, Large | — | — | — | — | — | — | — | — | — | — | — | — | — | — |
| Foxtail, Giant | 90 | 90 | 80 | 80 | 90 | 90 | 90 | 90 | 80 | 90 | 90 | 90 | 90 | 80 |
| Galium | 60 | 60 | 40 | 50 | 40 | 50 | 30 | 0 | 60 | 60 | 60 | 60 | 0 | 0 |
| Kochia | 60 | 80 | 0 | 50 | 60 | 70 | 50 | 0 | 30 | 80 | 60 | 80 | 30 | 40 |
| Morningglory | — | — | — | — | — | — | — | — | — | — | — | — | — | — |
| Pigweed | 20 | 80 | 0 | 30 | 20 | 60 | 0 | 0 | 30 | 70 | 0 | 60 | 0 | 0 |
| Ragweed | 30 | 60 | 0 | 0 | 30 | 40 | 0 | 0 | 0 | 30 | 0 | 30 | 0 | 0 |
| Ryegrass, Italian | 0 | 80 | 30 | 0 | 0 | 0 | 20 | 60 | 70 | 20 | 50 | 80 | 0 | 0 |

TABLE A-continued

| | | | | | | | | | | | | | | |
|---|---|---|---|---|---|---|---|---|---|---|---|---|---|---|
| Velvetleaf | — | — | — | — | — | — | — | — | — | — | — | — | — | — |
| Wheat | 50 | 70 | 40 | 0 | 0 | 20 | 20 | 60 | 60 | 40 | 50 | 80 | 0 | 0 |

| 500 g ai/ha | Compounds | | | | | | | | | | | | | |
|---|---|---|---|---|---|---|---|---|---|---|---|---|---|---|
| Postemergence | 1217 | 1218 | 1219 | 1220 | 1221 | 1222 | 1223 | 1224 | 1225 | 1226 | 1227 | 1228 | 1229 | 1230 |
| Barnyardgrass | — | — | 60 | 80 | 60 | 0 | 50 | 90 | 90 | 100 | 70 | 90 | 100 | 70 |
| Blackgrass | 0 | 0 | 0 | 40 | 70 | 0 | 50 | 0 | 40 | 30 | 0 | 40 | 40 | 0 |
| Corn | 0 | 0 | 0 | 70 | 60 | 0 | 0 | 0 | 90 | 70 | 0 | 70 | 0 | 0 |
| Crabgrass, Large | — | — | — | — | — | — | — | — | — | — | — | — | — | — |
| Foxtail, Giant | 90 | 50 | 80 | 80 | 90 | 70 | 90 | 70 | 90 | 80 | 0 | 80 | 90 | 80 |
| Galium | 0 | 0 | 0 | 40 | 60 | 0 | 40 | 40 | 70 | 80 | 0 | 60 | 50 | 60 |
| Kochia | 0 | 20 | — | — | — | — | — | 0 | — | 60 | 30 | 60 | 80 | 70 |
| Morningglory | — | — | — | — | — | — | — | — | — | — | — | — | — | — |
| Pigweed | 0 | 0 | 0 | 20 | 0 | 0 | 0 | 20 | 40 | 60 | 30 | 50 | 60 | 60 |
| Ragweed | 0 | 0 | 20 | 30 | 20 | 0 | 20 | 0 | 50 | 50 | 0 | 0 | 0 | 0 |
| Ryegrass, Italian | 0 | 0 | 20 | 30 | 70 | 0 | 60 | 0 | 30 | 0 | 0 | 30 | 40 | 0 |
| Velvetleaf | — | — | — | — | — | — | — | — | — | — | — | — | — | — |
| Wheat | 0 | 0 | 0 | 40 | 60 | 0 | 30 | 0 | 70 | 0 | 0 | 30 | 50 | 0 |

| 500 g ai/ha | Compounds | | | | | | | | | | | | | |
|---|---|---|---|---|---|---|---|---|---|---|---|---|---|---|
| Postemergence | 1231 | 1232 | 1233 | 1234 | 1235 | 1236 | 1238 | 1239 | 1240 | 1241 | 1242 | 1243 | 1244 | 1245 |
| Barnyardgrass | 80 | 80 | 80 | 90 | 100 | 100 | 80 | 80 | 0 | 30 | 40 | 0 | 80 | 90 |
| Blackgrass | 40 | 40 | 40 | 60 | 40 | 30 | 50 | 80 | 0 | 0 | 0 | 0 | 50 | 60 |
| Corn | 80 | 70 | 80 | 100 | 100 | 90 | 40 | 70 | 0 | 20 | 0 | 0 | 40 | 0 |
| Crabgrass, Large | — | — | — | — | — | — | — | — | — | — | — | — | — | — |
| Foxtail, Giant | 90 | 90 | 90 | 90 | 90 | 90 | 80 | 90 | 0 | 20 | 50 | 0 | 90 | 60 |
| Galium | 70 | 60 | 60 | 60 | 70 | 60 | 50 | 60 | 0 | 0 | 20 | 0 | 20 | 50 |
| Kochia | — | — | — | 50 | 50 | 30 | 50 | 70 | 0 | 0 | 0 | 0 | 0 | 40 |
| Morningglory | — | — | — | — | — | — | — | — | — | — | — | — | — | — |
| Pigweed | 50 | 40 | 20 | 50 | 50 | 40 | 30 | 50 | 0 | 0 | 0 | 0 | 0 | 0 |
| Ragweed | 30 | 50 | 30 | 30 | 30 | 40 | 20 | 60 | 0 | 0 | 0 | 0 | 0 | 50 |
| Ryegrass, Italian | 50 | 60 | 50 | 70 | 30 | 50 | 60 | 50 | 0 | 0 | 0 | 0 | 30 | 0 |
| Velvetleaf | — | — | — | — | — | — | — | — | — | — | — | — | — | — |
| Wheat | 70 | 40 | 70 | 50 | 70 | 20 | 30 | 60 | 0 | 0 | 0 | 20 | 40 | 20 |

| 500 g ai/ha | Compounds | | | | | | | | | | | | | |
|---|---|---|---|---|---|---|---|---|---|---|---|---|---|---|
| Postemergence | 1246 | 1247 | 1248 | 1249 | 1250 | 1251 | 1252 | 1253 | 1254 | 1255 | 1256 | 1257 | 1260 | 1280 |
| Barnyardgrass | 80 | 70 | 50 | 100 | 90 | 100 | 90 | 100 | 90 | 100 | 90 | 0 | 90 | 40 |
| Blackgrass | 40 | 0 | 0 | 50 | 60 | 40 | 50 | 50 | 40 | 60 | 20 | 0 | 80 | 0 |
| Corn | 40 | 0 | 0 | 90 | 70 | 80 | 90 | 70 | 50 | 90 | 50 | 0 | 90 | 0 |
| Crabgrass, Large | — | — | — | — | — | — | — | — | — | — | — | — | — | — |
| Foxtail, Giant | 20 | 30 | 20 | 80 | 80 | 80 | 80 | 90 | 80 | 80 | 80 | 0 | 90 | 30 |
| Galium | 60 | 20 | 0 | 50 | 60 | 50 | 60 | 60 | 50 | 60 | 50 | 0 | 70 | 0 |
| Kochia | 20 | 0 | 0 | 70 | 20 | 70 | 60 | 70 | 40 | 50 | 70 | 0 | 70 | 0 |
| Morningglory | — | — | — | — | — | — | — | — | — | — | — | — | — | — |
| Pigweed | 20 | 0 | 0 | 80 | 30 | 80 | 50 | 30 | 20 | 30 | 50 | 0 | 70 | 0 |
| Ragweed | 60 | 0 | 0 | 60 | 0 | 50 | 50 | 0 | 0 | 40 | 20 | 0 | 70 | 0 |
| Ryegrass, Italian | 0 | 0 | 0 | 70 | 50 | 40 | 70 | 60 | 70 | 40 | 70 | 0 | 80 | 0 |
| Velvetleaf | — | — | — | — | — | — | — | — | — | — | — | — | — | — |
| Wheat | 40 | 0 | 0 | 70 | 70 | 60 | 70 | 50 | 40 | 60 | 50 | 0 | 90 | 0 |

| 500 g ai/ha | Compounds | | | | | | | | | | | | | |
|---|---|---|---|---|---|---|---|---|---|---|---|---|---|---|
| Postemergence | 1281 | 1298 | 1299 | 1300 | 1301 | 1302 | 1303 | 1304 | 1305 | 1306 | 1307 | 1308 | 1309 | 1310 |
| Barnyardgrass | 80 | 80 | 90 | 90 | 90 | 90 | 30 | 0 | 80 | 90 | 90 | 80 | 90 | 90 |
| Blackgrass | 0 | 0 | 60 | 50 | 0 | 20 | 0 | 0 | 0 | 0 | 0 | 50 | 60 | 40 |
| Corn | 0 | 0 | 80 | 60 | 0 | 0 | 0 | 0 | 0 | 0 | 0 | 80 | 20 | 50 |
| Crabgrass, Large | — | — | — | — | — | — | — | — | — | — | — | — | — | — |
| Foxtail, Giant | 30 | 90 | 90 | 90 | 20 | 80 | 60 | 0 | 90 | 20 | 20 | 80 | 70 | 90 |
| Galium | 50 | 20 | 50 | 40 | 60 | 30 | 0 | 0 | 0 | 40 | 40 | 50 | 50 | 60 |
| Kochia | 30 | 0 | 60 | 0 | 50 | 20 | — | 0 | 0 | 60 | 40 | 0 | 50 | 50 |
| Morningglory | — | — | — | — | — | — | — | — | — | — | — | — | — | — |
| Pigweed | 0 | 0 | 0 | 0 | 0 | 0 | 0 | 0 | 0 | 0 | 0 | 0 | 0 | 30 |
| Ragweed | 0 | 0 | 20 | 0 | 0 | 0 | 0 | 0 | 0 | 0 | 0 | 20 | 30 | 40 |
| Ryegrass, Italian | 0 | 0 | 60 | 30 | 0 | 20 | 0 | 0 | 0 | 0 | 0 | 20 | 40 |  |
| Velvetleaf | — | — | — | — | — | — | — | — | — | — | — | — | — | — |
| Wheat | 0 | 20 | 40 | 50 | 0 | 0 | 0 | 0 | 20 | 0 | 0 | 40 | 20 | 60 |

TABLE A-continued

| 500 g ai/ha | Compounds | | | | | | | | | | | | | |
|---|---|---|---|---|---|---|---|---|---|---|---|---|---|---|
| Postemergence | 1311 | 1312 | 1313 | 1314 | 1316 | 1317 | 1318 | 1319 | 1320 | 1321 | 1323 | 1324 | 1325 | 1326 |
| Barnyardgrass | — | — | — | — | 90 | 90 | 90 | 90 | 50 | 90 | 90 | 90 | 90 | 90 |
| Blackgrass | 60 | 70 | 0 | 60 | 80 | 80 | 70 | 80 | 0 | 50 | 60 | 60 | — | 0 |
| Corn | 80 | 90 | 0 | 70 | 80 | 80 | 80 | 80 | 0 | 70 | 70 | 80 | 50 | 0 |
| Crabgrass, Large | — | — | — | — | — | — | — | — | — | — | — | — | — | — |
| Foxtail, Giant | 90 | 90 | 90 | 90 | 90 | 90 | 90 | 90 | 20 | 90 | 90 | 90 | 90 | 0 |
| Galium | 60 | 60 | 40 | 50 | 60 | 60 | 60 | 60 | 40 | 50 | 60 | 50 | 90 | 20 |
| Kochia | 50 | 70 | 50 | 60 | 40 | 30 | 40 | 60 | 0 | 50 | 70 | 70 | 80 | 0 |
| Morningglory | — | — | — | — | — | — | — | — | — | — | — | — | — | — |
| Pigweed | 20 | 40 | 0 | 30 | 60 | 20 | 40 | 50 | 0 | 0 | 0 | 20 | 90 | 0 |
| Ragweed | 30 | 70 | 0 | 50 | 70 | 20 | 60 | 0 | 0 | 20 | 50 | 40 | 0 | 0 |
| Ryegrass, Italian | 80 | 50 | 0 | 0 | 80 | 80 | 40 | 60 | 0 | 50 | 70 | 50 | 0 | 20 |
| Velvetleaf | — | — | — | — | — | — | — | — | — | — | — | — | — | — |
| Wheat | 80 | 80 | 0 | 60 | 80 | 60 | 80 | 60 | 0 | 50 | 70 | 70 | 0 | 0 |

| 500 g ai/ha | Compounds | | | | | | | | | | | | | |
|---|---|---|---|---|---|---|---|---|---|---|---|---|---|---|
| Postemergence | 1327 | 1328 | 1329 | 1330 | 1331 | 1332 | 1334 | 1335 | 1336 | 1355 | 1356 | 1357 | 1358 | 1359 |
| Barnyardgrass | 90 | 90 | 90 | 90 | 90 | 60 | 50 | 0 | 0 | 0 | 0 | 0 | 0 | 0 |
| Blackgrass | 20 | 0 | 60 | 70 | 50 | 30 | 0 | 0 | 0 | — | — | — | — | — |
| Corn | 0 | 0 | 50 | 0 | 70 | 0 | 30 | 0 | 0 | 0 | 0 | 0 | 0 | 0 |
| Crabgrass, Large | — | — | — | — | — | — | — | — | — | 0 | 0 | 0 | 30 | 0 |
| Foxtail, Giant | 70 | 40 | 90 | 90 | 90 | 60 | 50 | 0 | 0 | 0 | 0 | 0 | 0 | 0 |
| Galium | 50 | 30 | 60 | 30 | 0 | 20 | 50 | 0 | 0 | — | — | — | — | — |
| Kochia | 30 | 0 | 50 | 20 | 0 | 0 | 0 | 0 | 0 | — | — | — | — | — |
| Morningglory | — | — | — | — | — | — | — | — | — | 0 | 0 | 0 | 0 | 0 |
| Pigweed | 0 | 0 | 0 | 0 | 0 | 0 | 40 | 0 | 0 | 0 | 0 | 0 | 0 | 0 |
| Ragweed | 20 | 0 | 0 | 20 | 0 | 20 | 20 | 0 | 0 | — | — | — | — | — |
| Ryegrass, Italian | 40 | 30 | 50 | 20 | 0 | 0 | 20 | 0 | 0 | — | — | — | — | — |
| Velvetleaf | — | — | — | — | — | — | — | — | — | 0 | 0 | 0 | 0 | 0 |
| Wheat | 0 | 0 | 20 | 70 | 50 | 20 | 0 | 0 | 0 | 0 | 0 | 0 | 0 | 0 |

| 500 g ai/ha | Compounds | | | | | | | | | | | | | |
|---|---|---|---|---|---|---|---|---|---|---|---|---|---|---|
| Postemergence | 1360 | 1361 | 1362 | 1370 | 1371 | 1372 | 1373 | 1374 | 1376 | 1377 | 1378 | 1379 | 1380 | 1381 |
| Barnyardgrass | 0 | 0 | 0 | — | 90 | — | — | 50 | 90 | 90 | 80 | 100 | 80 | 80 |
| Blackgrass | — | — | — | 80 | 60 | 70 | 60 | 0 | 70 | 60 | 40 | 30 | 60 | 60 |
| Corn | 0 | 0 | 0 | 80 | 90 | 90 | 90 | 0 | 30 | 80 | 80 | 70 | 80 | 60 |
| Crabgrass, Large | 0 | 0 | 0 | — | — | — | — | — | — | — | — | — | — | — |
| Foxtail, Giant | 0 | 0 | 0 | 90 | 90 | 90 | 90 | 0 | 80 | 80 | 90 | 80 | 90 | 90 |
| Galium | — | — | — | 50 | 70 | 70 | 60 | 0 | 30 | 60 | 70 | 60 | 50 | 60 |
| Kochia | — | — | — | 50 | 80 | 80 | 80 | 0 | 20 | 70 | — | 60 | — | — |
| Morningglory | 0 | 0 | 0 | — | — | — | — | — | — | — | — | — | — | — |
| Pigweed | 0 | 0 | 0 | 30 | 60 | 80 | 90 | 0 | 20 | 40 | 70 | 50 | 60 | 70 |
| Ragweed | — | — | — | 30 | 60 | 60 | 70 | 0 | 0 | 60 | 70 | 60 | 50 | 60 |
| Ryegrass, Italian | — | — | — | 70 | 50 | 30 | 50 | 0 | 30 | 60 | 60 | 30 | 60 | 60 |
| Velvetleaf | 0 | 0 | 0 | — | — | — | — | — | — | — | — | — | — | — |
| Wheat | 0 | 0 | 0 | 70 | 60 | 90 | 60 | 0 | 60 | 60 | 70 | 50 | 40 | 50 |

| 500 g ai/ha | Compounds | | | | | | | | | | | | |
|---|---|---|---|---|---|---|---|---|---|---|---|---|---|
| Postemergence | 1382 | 1383 | 1384 | 1385 | 1386 | 1387 | 1388 | 1389 | 1390 | 1391 | 1392 | 1394 | 1395 |
| Barnyardgrass | 80 | 100 | 90 | 90 | 90 | 80 | 100 | 100 | 90 | 100 | 40 | 90 | 90 |
| Blackgrass | 0 | 50 | 30 | 20 | 80 | 40 | 90 | 50 | 60 | 70 | 0 | 60 | 0 |
| Corn | 0 | 90 | 90 | 20 | 80 | 10 | 80 | 90 | 70 | 80 | 20 | 70 | 70 |
| Crabgrass, Large | — | — | — | — | — | — | — | — | — | — | — | — | — |
| Foxtail, Giant | 70 | 90 | 90 | 90 | 90 | 80 | 90 | 80 | 90 | 90 | 30 | 90 | 90 |
| Galium | 30 | 60 | 70 | 50 | 60 | 50 | 50 | 70 | 60 | 70 | 0 | 60 | 0 |
| Kochia | 0 | 70 | 60 | 0 | 70 | 50 | 50 | 80 | 70 | 80 | 0 | 0 | 0 |
| Morningglory | — | — | — | — | — | — | — | — | — | — | — | — | — |
| Pigweed | 0 | 70 | 20 | 0 | 70 | 60 | 50 | 70 | 80 | 90 | 0 | 20 | 0 |
| Ragweed | 0 | 60 | 40 | 0 | 50 | 30 | 50 | 20 | 30 | 60 | 0 | 20 | 0 |
| Ryegrass, Italian | 0 | 50 | 30 | 20 | 60 | 40 | 90 | 80 | 50 | 60 | 0 | 20 | 20 |
| Velvetleaf | — | — | — | — | — | — | — | — | — | — | — | — | — |
| Wheat | 0 | 80 | 50 | 20 | 60 | 0 | 60 | 70 | 50 | 60 | 30 | 60 | 40 |

| 125 g ai/ha | Compounds | | | | | | | | | | | | |
|---|---|---|---|---|---|---|---|---|---|---|---|---|---|
| Postemergence | 352 | 353 | 354 | 356 | 360 | 361 | 362 | 363 | 364 | 365 | 366 | 367 | 368 |
| Barnyardgrass | 0 | 0 | 0 | 0 | 0 | 0 | 0 | 0 | 0 | 0 | 0 | 0 | 90 |
| Blackgrass | — | — | — | — | — | — | — | — | — | — | — | — | 0 |
| Corn | 0 | 0 | 0 | 0 | 0 | 0 | 0 | 0 | 0 | 0 | 0 | 0 | 0 |
| Crabgrass, Large | 0 | 0 | 0 | 0 | 0 | 0 | 0 | 0 | 0 | 0 | 0 | 0 | — |

TABLE A-continued

| | | | | | | | | | | | | | |
|---|---|---|---|---|---|---|---|---|---|---|---|---|---|
| Foxtail, Giant | 0 | 0 | 0 | 0 | 0 | 0 | 0 | 0 | 0 | 0 | 0 | 0 | 20 |
| Galium | — | — | — | — | — | — | — | — | — | — | — | — | 30 |
| Kochia | — | — | — | — | — | — | — | — | — | — | — | — | 0 |
| Morningglory | 0 | 0 | 0 | 0 | 0 | 0 | 0 | 0 | 0 | 0 | 0 | 0 | — |
| Pigweed | 0 | 0 | 0 | 0 | 0 | 0 | 0 | 0 | 0 | 0 | 0 | 0 | 0 |
| Ragweed | — | — | — | — | — | — | — | — | — | — | — | — | 0 |
| Ryegrass, Italian | — | — | — | — | — | — | — | — | — | — | — | — | 20 |
| Velvetleaf | 0 | 0 | 0 | 0 | 0 | 0 | 0 | 0 | — | 0 | 0 | 0 | — |
| Wheat | 0 | 0 | 0 | 0 | 0 | 0 | 0 | 0 | 0 | 0 | 0 | 0 | 0 |

| 125 g ai/ha | Compounds | | | | | | | | | | | | |
|---|---|---|---|---|---|---|---|---|---|---|---|---|---|
| Postemergence | 369 | 370 | 371 | 372 | 373 | 374 | 375 | 376 | 377 | 378 | 379 | 380 | 381 | 382 |
| Barnyardgrass | 90 | 80 | 80 | 80 | 80 | 80 | 90 | 90 | 90 | 80 | 0 | 50 | 0 | 0 |
| Blackgrass | 30 | 0 | 30 | 20 | 20 | 0 | 50 | 0 | 50 | 50 | 0 | 30 | 0 | 0 |
| Corn | 0 | 0 | 20 | 0 | 20 | 0 | 30 | 0 | 0 | 50 | 0 | 0 | 0 | 0 |
| Foxtail, Giant | 20 | 40 | 50 | 50 | 40 | 20 | 90 | 90 | 80 | 80 | 0 | 30 | 0 | 0 |
| Galium | 60 | 20 | 30 | 0 | 30 | 0 | 40 | 30 | 60 | 60 | 0 | 20 | 0 | 0 |
| Kochia | 20 | 0 | 20 | 0 | 0 | 0 | 30 | 0 | 30 | 50 | 0 | 0 | 0 | 0 |
| Pigweed | 0 | 0 | 0 | 20 | 20 | 0 | 20 | 0 | 0 | 0 | 0 | 0 | 0 | 0 |
| Ragweed | 0 | 0 | 0 | 0 | 0 | 0 | 0 | 0 | 40 | 20 | 0 | 0 | 0 | 0 |
| Ryegrass, Italian | 20 | 0 | 20 | 20 | 30 | 0 | 0 | 0 | 30 | 40 | 0 | 0 | 0 | 0 |
| Wheat | 0 | 0 | 0 | 0 | 20 | 0 | 30 | 0 | 0 | 40 | 0 | 0 | 0 | 0 |

| 125 g ai/ha | Compounds | | | | | | | | | | | | |
|---|---|---|---|---|---|---|---|---|---|---|---|---|
| Postemergence | 383 | 384 | 386 | 387 | 388 | 389 | 390 | 391 | 392 | 393 | 394 | 395 | 396 |
| Barnyardgrass | 70 | 0 | 70 | 70 | 30 | 50 | 50 | 60 | 80 | 80 | 40 | 0 | 70 |
| Blackgrass | 0 | 0 | 50 | 0 | 10 | 0 | 0 | 50 | 70 | 60 | 0 | 0 | 50 |
| Corn | 0 | 0 | 40 | 0 | 0 | 30 | 0 | 40 | 70 | 80 | 0 | 0 | 70 |
| Foxtail, Giant | 30 | 0 | 70 | 50 | 50 | 60 | 60 | 90 | 90 | 90 | 0 | 0 | 80 |
| Galium | 0 | 0 | 50 | 0 | 0 | 0 | 0 | 60 | 70 | 70 | 0 | 0 | 60 |
| Kochia | 0 | 0 | 0 | 0 | 0 | 0 | 0 | 0 | 50 | 60 | 0 | 0 | 60 |
| Pigweed | 0 | 0 | 0 | 0 | 0 | 0 | 0 | 30 | 60 | 50 | 0 | 0 | 60 |
| Ragweed | 0 | 0 | 0 | 0 | 0 | 0 | 0 | 20 | 50 | 0 | 0 | 0 | 0 |
| Ryegrass, Italian | 20 | 0 | 20 | 0 | 0 | 0 | 0 | 30 | 50 | 40 | 0 | 0 | 50 |
| Wheat | 0 | 0 | 30 | 0 | 0 | 0 | 0 | 0 | 20 | 20 | 0 | 0 | 20 |

| 125 g ai/ha | Compounds | | | | | | | | | | | | |
|---|---|---|---|---|---|---|---|---|---|---|---|---|---|
| Postemergence | 397 | 398 | 399 | 400 | 401 | 402 | 403 | 404 | 405 | 406 | 407 | 408 | 409 | 410 |
| Barnyardgrass | 70 | 90 | 90 | 90 | 90 | 90 | 90 | 90 | 90 | 90 | 60 | 0 | 60 | 20 |
| Blackgrass | 60 | 40 | 40 | 60 | 0 | 50 | 50 | 40 | 50 | 30 | 30 | 0 | 10 | 0 |
| Corn | 50 | 60 | 50 | 20 | 0 | 70 | 70 | 40 | 30 | 20 | 0 | 0 | 0 | 0 |
| Foxtail, Giant | 70 | 80 | 90 | 50 | 30 | 90 | 90 | 90 | 80 | 80 | 70 | 0 | 60 | 0 |
| Galium | 60 | 50 | 50 | 40 | 50 | 50 | 50 | 50 | 60 | 50 | 0 | 0 | 0 | 0 |
| Kochia | 20 | 60 | 50 | 60 | 50 | 20 | 40 | 60 | 40 | 40 | 0 | 0 | 0 | 0 |
| Pigweed | 40 | 50 | 30 | 30 | 0 | 40 | 50 | 20 | 40 | 20 | 0 | 0 | 0 | 0 |
| Ragweed | 0 | 0 | 0 | 40 | 30 | 20 | 0 | 30 | 0 | 20 | 0 | 0 | 0 | 0 |
| Ryegrass, Italian | 40 | 20 | 40 | 20 | 30 | 30 | 50 | 40 | 30 | 30 | 0 | 0 | 0 | 0 |
| Wheat | 40 | 20 | 40 | 30 | 20 | 50 | 70 | 50 | 60 | 40 | 0 | 0 | 0 | 0 |

| 125 g ai/ha | Compounds | | | | | | | | | | | | |
|---|---|---|---|---|---|---|---|---|---|---|---|---|---|
| Postemergence | 411 | 412 | 413 | 414 | 415 | 416 | 417 | 418 | 419 | 420 | 421 | 422 | 423 | 424 |
| Barnyardgrass | 40 | 0 | 0 | 0 | 0 | 0 | 0 | 0 | 60 | 80 | 70 | 50 | 0 | 50 |
| Blackgrass | 0 | 0 | 0 | 0 | 0 | 0 | 0 | 0 | 0 | 0 | 20 | 30 | 0 | 0 |
| Corn | 0 | 0 | 0 | 0 | 0 | 0 | 0 | 0 | 0 | 0 | 0 | 0 | 0 | 0 |
| Foxtail, Giant | 40 | 0 | 0 | 0 | 0 | 0 | 0 | 0 | 20 | 70 | 80 | 50 | 0 | 40 |
| Galium | 30 | 0 | 0 | 0 | 0 | 0 | 0 | 0 | 0 | 0 | 50 | 30 | 0 | 0 |
| Kochia | 0 | 0 | 0 | 0 | 0 | 0 | 0 | 0 | 20 | 0 | 0 | 50 | 0 | 0 |
| Pigweed | 0 | 0 | 0 | 0 | 0 | 0 | 0 | 0 | 0 | 0 | 0 | 40 | 0 | 0 |
| Ragweed | 0 | 0 | 0 | 0 | 0 | 0 | 0 | 0 | 0 | 0 | 0 | 20 | 0 | 0 |
| Ryegrass, Italian | 0 | 0 | 0 | 0 | 0 | 0 | 0 | 0 | 0 | 0 | 20 | 0 | 0 | 0 |
| Wheat | 0 | 0 | 0 | 0 | 0 | 0 | 0 | 0 | 0 | 0 | 0 | 0 | 0 | 0 |

| 125 g ai/ha | Compounds | | | | | | | | | | | | |
|---|---|---|---|---|---|---|---|---|---|---|---|---|---|
| Postemergence | 425 | 426 | 427 | 428 | 429 | 430 | 431 | 432 | 433 | 434 | 435 | 436 | 437 | 438 |
| Barnyardgrass | 20 | 30 | 60 | 90 | 90 | 80 | 80 | 20 | 90 | 90 | 80 | 90 | 90 | 90 |
| Blackgrass | 0 | 0 | 20 | 40 | 50 | 20 | 60 | 0 | 30 | 50 | 30 | 30 | 0 | 40 |
| Corn | 0 | 0 | 0 | 30 | 70 | 50 | 60 | 0 | 0 | 0 | 0 | 0 | 0 | 0 |
| Foxtail, Giant | 20 | 20 | 50 | 80 | 90 | 80 | 80 | 40 | 80 | 90 | 80 | 80 | 90 | 90 |
| Galium | 0 | 0 | 40 | 50 | 70 | 50 | 60 | 0 | 50 | 60 | 50 | 60 | 30 | 40 |
| Kochia | 0 | 0 | 0 | 30 | 60 | 20 | 40 | 0 | 40 | 70 | 20 | 40 | 20 | 70 |

TABLE A-continued

| | | | | | | | | | | | | | | |
|---|---|---|---|---|---|---|---|---|---|---|---|---|---|---|
| Pigweed | 0 | 0 | 0 | 0 | 70 | 30 | 50 | 0 | 20 | 60 | 20 | 20 | 0 | 0 |
| Ragweed | 0 | 0 | 0 | 0 | 30 | 0 | 20 | 0 | 0 | 20 | 40 | 0 | 0 | 0 |
| Ryegrass, Italian | 0 | 0 | 0 | 30 | 60 | 30 | 60 | 0 | 30 | 0 | 40 | 20 | 0 | 40 |
| Wheat | 0 | 0 | 0 | 30 | 50 | 20 | 40 | 0 | 30 | 20 | 0 | 20 | 0 | 30 |

| 125 g ai/ha | Compounds | | | | | | | | | | | | | |
|---|---|---|---|---|---|---|---|---|---|---|---|---|---|---|
| Postemergence | 439 | 440 | 441 | 442 | 443 | 444 | 445 | 446 | 447 | 448 | 449 | 450 | 451 | 452 |
| Barnyardgrass | 90 | 90 | 80 | 80 | 80 | 80 | 90 | 80 | 80 | 80 | 30 | 80 | 0 | 20 |
| Blackgrass | 0 | 30 | 50 | 60 | 60 | 70 | 40 | 50 | 0 | 0 | 0 | 20 | 0 | 0 |
| Corn | 0 | 0 | 60 | 50 | 40 | 60 | 70 | 20 | 0 | 0 | 0 | 20 | 0 | 0 |
| Foxtail, Giant | 90 | 90 | 80 | 80 | 80 | 80 | 90 | 90 | 80 | 60 | 30 | 80 | 0 | 60 |
| Galium | 40 | 40 | 50 | 60 | 40 | 60 | 60 | 50 | 40 | 30 | 0 | 50 | 0 | 50 |
| Kochia | 30 | 30 | 40 | 20 | 20 | 40 | 20 | 60 | 0 | 30 | 20 | 20 | 0 | 50 |
| Pigweed | 40 | 0 | 40 | 60 | 20 | 50 | 20 | 50 | 0 | 20 | 0 | 50 | 0 | 50 |
| Ragweed | 0 | 0 | 20 | 0 | 20 | 20 | 20 | 0 | 0 | 0 | 0 | 20 | 0 | 0 |
| Ryegrass, Italian | 0 | 0 | 60 | 60 | 30 | 50 | 40 | 20 | 0 | 0 | 0 | 0 | 0 | 0 |
| Wheat | 0 | 0 | 50 | 40 | 40 | 50 | 30 | 0 | 0 | 0 | 0 | 0 | 0 | 0 |

| 125 g ai/ha | Compounds | | | | | | | | | | | | |
|---|---|---|---|---|---|---|---|---|---|---|---|---|---|
| Postemergence | 453 | 454 | 455 | 456 | 457 | 460 | 461 | 462 | 463 | 464 | 465 | 466 | |
| Barnyardgrass | 80 | 60 | 70 | 0 | 0 | 60 | 80 | 70 | 50 | 90 | 90 | 80 | |
| Blackgrass | 0 | 0 | 0 | 0 | 0 | 20 | 0 | 20 | 20 | 60 | 40 | 30 | |
| Corn | 0 | 50 | 0 | 0 | 0 | 20 | 0 | 0 | 0 | 90 | 80 | 0 | |
| Foxtail, Giant | 80 | 70 | 70 | 0 | 0 | 90 | 80 | 60 | 70 | 90 | 90 | 20 | |
| Galium | 30 | 0 | 30 | 0 | 0 | 50 | 0 | 0 | 0 | 60 | 60 | 0 | |
| Kochia | 20 | 0 | 60 | 0 | 0 | 0 | 0 | 0 | 0 | 50 | 50 | 0 | |
| Pigweed | 0 | 0 | 50 | 0 | 0 | 20 | 0 | 0 | 0 | 40 | 0 | 0 | |
| Ragweed | 0 | 0 | 0 | 0 | 0 | 0 | 0 | 0 | 0 | 30 | 0 | 0 | |
| Ryegrass, Italian | 0 | 0 | 0 | 0 | 0 | 30 | 0 | 0 | 0 | 70 | 60 | 0 | |
| Wheat | 0 | 20 | 0 | 0 | 0 | 0 | 0 | 0 | 0 | 70 | 60 | 0 | |

| 125 g ai/ha | Compounds | | | | | | | | | | | | | |
|---|---|---|---|---|---|---|---|---|---|---|---|---|---|---|
| Postemergence | 467 | 468 | 469 | 470 | 471 | 472 | 473 | 474 | 475 | 476 | 477 | 478 | 479 | 480 |
| Barnyardgrass | 80 | 0 | 70 | 60 | 50 | 90 | 90 | 90 | 90 | 90 | 40 | 30 | 0 | 0 |
| Blackgrass | 0 | 0 | 0 | 30 | 0 | 30 | 40 | 30 | 30 | 20 | 0 | 0 | 0 | 0 |
| Corn | 0 | 0 | 0 | 0 | 0 | 40 | 0 | 0 | 0 | 0 | 0 | 0 | 0 | 0 |
| Foxtail, Giant | 40 | 0 | 20 | 40 | 50 | 80 | 70 | 90 | 90 | 80 | 40 | 20 | 0 | 20 |
| Galium | 0 | 20 | 0 | 0 | 0 | 50 | 60 | 40 | 50 | 30 | 0 | 0 | 0 | 0 |
| Kochia | 0 | 0 | 0 | 0 | 0 | 60 | 40 | 50 | 40 | 30 | 0 | 0 | 0 | 0 |
| Pigweed | 0 | 0 | 0 | 0 | 0 | 60 | 50 | 30 | 50 | 20 | 0 | 0 | 0 | 0 |
| Ragweed | 0 | 0 | 0 | 0 | 0 | 0 | 50 | 0 | 20 | 0 | 0 | 0 | 0 | 0 |
| Ryegrass, Italian | 0 | 0 | 0 | 0 | 0 | 40 | 0 | 20 | 20 | 30 | 0 | 0 | 0 | 0 |
| Wheat | 0 | 0 | 0 | 0 | 0 | 30 | 0 | 0 | 0 | 0 | 0 | 0 | 0 | 0 |

| 125 g ai/ha | Compounds | | | | | | | | | | | | | |
|---|---|---|---|---|---|---|---|---|---|---|---|---|---|---|
| Postemergence | 481 | 482 | 483 | 484 | 485 | 486 | 487 | 488 | 489 | 490 | 491 | 492 | 493 | 494 |
| Barnyardgrass | 0 | 0 | 20 | 0 | 20 | 0 | 80 | 90 | 90 | 80 | 90 | 90 | 90 | 30 |
| Blackgrass | 0 | 0 | 0 | 0 | 0 | 0 | 0 | 60 | 50 | 20 | 20 | 50 | 20 | 0 |
| Corn | 0 | 0 | 0 | 0 | 0 | 0 | 0 | 70 | 70 | 80 | 60 | 70 | 0 | 0 |
| Foxtail, Giant | 0 | 0 | 20 | 0 | 20 | 0 | 80 | 90 | 90 | 80 | 80 | 90 | 90 | 20 |
| Galium | 0 | 0 | 0 | 0 | 0 | 0 | 0 | 50 | 0 | 20 | 0 | 50 | 30 | 0 |
| Kochia | 0 | 0 | 0 | 0 | 0 | 0 | 0 | 30 | 0 | 0 | 0 | 40 | 0 | 0 |
| Pigweed | 0 | 0 | 0 | 0 | 0 | 0 | 0 | 40 | 0 | 0 | 0 | 40 | 0 | 0 |
| Ragweed | 0 | 0 | 0 | 0 | 0 | 0 | 0 | 20 | 0 | 0 | 0 | 30 | 20 | 0 |
| Ryegrass, Italian | 0 | 0 | 0 | 0 | 0 | 0 | 0 | 30 | 30 | 0 | 0 | 20 | 20 | 0 |
| Wheat | 0 | 0 | 0 | 0 | 0 | 0 | 0 | 50 | 30 | 30 | 30 | 20 | 0 | 0 |

| 125 g ai/ha | Compounds | | | | | | | | | | | | | |
|---|---|---|---|---|---|---|---|---|---|---|---|---|---|---|
| Postemergence | 495 | 496 | 497 | 498 | 499 | 500 | 501 | 502 | 503 | 504 | 505 | 506 | 507 | 508 |
| Barnyardgrass | 20 | 60 | 60 | 30 | 30 | 0 | 50 | 0 | 90 | 80 | 0 | 70 | 20 | 70 |
| Blackgrass | 0 | 0 | 30 | 0 | 0 | 0 | 30 | 0 | 30 | 40 | 0 | 30 | 0 | 0 |
| Corn | 0 | 0 | 0 | 0 | 0 | 0 | 0 | 0 | 20 | 70 | 0 | 0 | 0 | 0 |
| Foxtail, Giant | 20 | 20 | 20 | 20 | 20 | 0 | 70 | 20 | 90 | 90 | 0 | 80 | 0 | 0 |
| Galium | 0 | 0 | 0 | 0 | 0 | 0 | 0 | 20 | 30 | 70 | 0 | 40 | 0 | 0 |
| Kochia | 30 | 0 | 30 | 0 | 0 | 0 | 0 | 0 | 0 | 30 | 0 | 0 | 30 | 0 |
| Pigweed | 0 | 0 | 0 | 0 | 0 | 0 | 0 | 0 | 0 | 60 | 0 | 0 | 0 | 0 |
| Ragweed | 0 | 0 | 0 | 0 | 0 | 0 | 0 | 0 | 30 | 30 | 0 | 0 | 0 | 0 |
| Ryegrass, Italian | 0 | 0 | 0 | 0 | 0 | 0 | 0 | 0 | 40 | 40 | 0 | 20 | 0 | 0 |
| Wheat | 0 | 0 | 0 | 0 | 0 | 0 | 0 | 0 | 0 | 20 | 0 | 0 | 0 | 0 |

TABLE A-continued

| 125 g ai/ha | Compounds | | | | | | | | | | | | | |
|---|---|---|---|---|---|---|---|---|---|---|---|---|---|---|
| Postemergence | 509 | 510 | 513 | 514 | 515 | 516 | 517 | 518 | 519 | 520 | 521 | 522 | 523 | 524 |
| Barnyardgrass | 60 | 60 | 80 | 80 | 0 | 0 | 20 | 0 | 90 | 90 | 90 | 60 | 90 | 30 |
| Blackgrass | 0 | 0 | 20 | 20 | 0 | 0 | 0 | 0 | 50 | 70 | 30 | 30 | 50 | 0 |
| Corn | 0 | 0 | 20 | 30 | 0 | 0 | 0 | 0 | 60 | 60 | 30 | 0 | 20 | 0 |
| Foxtail, Giant | 0 | 10 | 80 | 70 | 0 | 0 | 0 | 20 | 90 | 80 | 70 | 90 | 80 | 30 |
| Galium | 0 | 0 | 0 | 40 | 0 | 0 | 0 | 0 | 30 | 60 | 50 | 30 | 50 | 0 |
| Kochia | 0 | 0 | 20 | 30 | 0 | 0 | 0 | 0 | 0 | 60 | 0 | 20 | 20 | 0 |
| Pigweed | 0 | 0 | 30 | 0 | 0 | 0 | 0 | 0 | 0 | 40 | 40 | 20 | 30 | 0 |
| Ragweed | 0 | 0 | 10 | 0 | 0 | 0 | 0 | 0 | 0 | 30 | 0 | 0 | 50 | 0 |
| Ryegrass, Italian | 0 | 0 | 0 | 20 | 0 | 0 | 0 | 0 | 40 | 40 | 20 | 20 | 30 | 0 |
| Wheat | 0 | 0 | 0 | 30 | 0 | 0 | 0 | 0 | 30 | 50 | 20 | 0 | 0 | 0 |

| 125 g ai/ha | Compounds | | | | | | | | | | | |
|---|---|---|---|---|---|---|---|---|---|---|---|---|
| Postemergence | 525 | 526 | 527 | 534 | 535 | 536 | 537 | 538 | 539 | 540 | 541 | 544 |
| Barnyardgrass | 40 | 10 | 0 | 0 | 0 | 0 | 0 | 0 | 90 | 60 | 90 | 20 |
| Blackgrass | 0 | 0 | 0 | 0 | 0 | 0 | 0 | 0 | 50 | 50 | 30 | 0 |
| Corn | 0 | 0 | 0 | 0 | 0 | 0 | 0 | 0 | 70 | 30 | 0 | 0 |
| Foxtail, Giant | 20 | 20 | 0 | 0 | 0 | 0 | 0 | 0 | 90 | 70 | 80 | 0 |
| Galium | 0 | 0 | 0 | 0 | 0 | 0 | 0 | 0 | 70 | 60 | 30 | 0 |
| Kochia | 0 | 0 | 0 | 0 | 0 | 0 | 0 | 0 | 40 | 0 | 0 | 0 |
| Pigweed | 0 | 0 | 0 | 0 | 0 | 0 | 0 | 0 | 20 | 0 | 0 | 0 |
| Ragweed | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 0 | 0 | 20 | 0 |
| Wheat | 0 | 0 | 0 | 0 | 0 | 0 | 0 | 0 | 50 | 0 | 20 | 0 |

| 125 g ai/ha | Compounds | | | | | | | | | | | |
|---|---|---|---|---|---|---|---|---|---|---|---|---|
| Postemergence | 545 | 546 | 547 | 549 | 550 | 551 | 552 | 553 | 554 | 557 | 558 | 559 | 560 |
| Barnyardgrass | 0 | 80 | 70 | 40 | 80 | 10 | 80 | 90 | 80 | 0 | 80 | 90 | 90 |
| Blackgrass | 0 | 0 | 0 | 0 | 0 | 0 | 30 | 50 | 60 | 0 | 20 | 20 | 30 |
| Corn | 0 | 0 | 0 | 0 | 0 | 0 | 20 | 80 | 40 | 0 | 0 | 0 | 0 |
| Foxtail, Giant | 0 | 70 | 80 | 20 | 80 | 50 | 70 | 70 | 70 | 0 | 70 | 90 | 90 |
| Galium | 0 | 0 | 0 | 0 | 0 | 0 | 40 | 60 | 60 | 0 | 30 | 50 | 40 |
| Kochia | 0 | 0 | 0 | 0 | 0 | 0 | 0 | 30 | 20 | 0 | 20 | 30 | 40 |
| Pigweed | 0 | 0 | 0 | 0 | 0 | 0 | 0 | 20 | 0 | 0 | 0 | 0 | 0 |
| Ragweed | 0 | 0 | 0 | 0 | 0 | 0 | 0 | 30 | 0 | 0 | 0 | 0 | 0 |
| Ryegrass, Italian | 0 | 0 | 0 | 0 | 0 | 0 | 30 | 60 | 40 | 0 | 0 | 0 | 0 |
| Wheat | 0 | 0 | 0 | 0 | 0 | 0 | 0 | 40 | 20 | 0 | 0 | 0 | 0 |

| 125 g ai/ha | Compounds | | | | | | | | | | | | | |
|---|---|---|---|---|---|---|---|---|---|---|---|---|---|---|
| Postemergence | 561 | 562 | 563 | 564 | 565 | 566 | 567 | 568 | 569 | 570 | 571 | 572 | 573 | 574 |
| Barnyardgrass | 90 | 90 | 90 | 90 | 80 | 90 | 90 | 100 | 90 | 100 | 90 | 90 | 90 | 90 |
| Blackgrass | 50 | 60 | 40 | 40 | 40 | 20 | 60 | 60 | 60 | 60 | 70 | 70 | 70 | 60 |
| Corn | 10 | 40 | 20 | 70 | 0 | 0 | 70 | 60 | 20 | 60 | 60 | 60 | 80 | 60 |
| Foxtail, Giant | 90 | 90 | 90 | 90 | 80 | 90 | 90 | 90 | 90 | 90 | 90 | 90 | 90 | 80 |
| Galium | 60 | 60 | 70 | 70 | 60 | 60 | 40 | 60 | 40 | 50 | 50 | 50 | 60 | 40 |
| Kochia | 70 | 70 | 70 | 80 | 20 | 80 | 20 | 70 | 20 | 50 | 30 | 20 | 50 | 30 |
| Pigweed | 60 | 70 | 0 | 40 | 20 | 30 | 20 | 30 | 0 | 20 | 20 | 30 | 30 | 20 |
| Ragweed | 20 | 50 | 0 | 50 | 0 | 0 | 0 | 30 | 30 | 0 | 0 | 0 | 20 | 0 |
| Ryegrass, Italian | 20 | 70 | 40 | 60 | 20 | 30 | 70 | 70 | 40 | 50 | 60 | 30 | 70 | 50 |
| Wheat | 30 | 50 | 20 | 40 | 0 | 0 | 30 | 30 | 30 | 30 | 60 | 60 | 70 | 40 |

| 125 g ai/ha | Compounds | | | | | | | | | | | | | |
|---|---|---|---|---|---|---|---|---|---|---|---|---|---|---|
| Postemergence | 575 | 576 | 577 | 587 | 588 | 589 | 590 | 591 | 592 | 593 | 594 | 595 | 596 | 597 |
| Barnyardgrass | 90 | 90 | 90 | 80 | 80 | 60 | 90 | 90 | 80 | 90 | 90 | 90 | 90 | 0 |
| Blackgrass | 70 | 50 | 70 | 20 | 20 | 20 | 50 | 50 | 30 | 50 | 50 | 20 | 20 | 0 |
| Corn | 70 | 80 | 60 | 40 | 0 | 10 | 50 | 70 | 50 | 30 | 60 | 30 | 20 | 0 |
| Foxtail, Giant | 90 | 90 | 90 | 80 | 80 | 80 | 90 | 90 | 80 | 90 | 90 | 90 | 90 | 0 |
| Galium | 50 | 50 | 30 | 0 | 0 | 0 | 20 | 40 | 20 | 0 | 0 | 0 | 30 | 0 |
| Kochia | 0 | 30 | 0 | 0 | 0 | 0 | 0 | 20 | 0 | 0 | 0 | 0 | 40 | 0 |
| Pigweed | 0 | 0 | 0 | 0 | 0 | 20 | 0 | 20 | 0 | 0 | 0 | 20 | 0 | 0 |
| Ragweed | 0 | 30 | 0 | 0 | 0 | 0 | 0 | 0 | 0 | 0 | 0 | 0 | 0 | 0 |
| Ryegrass, Italian | 60 | 30 | 30 | 0 | 0 | 20 | 30 | 0 | 0 | 0 | 20 | 20 | 0 | 0 |
| Wheat | 40 | 60 | 40 | 40 | 0 | 0 | 20 | 50 | 30 | 0 | 30 | 30 | 0 | 0 |

TABLE A-continued

| 125 g ai/ha | Compounds | | | | | | | | | | | |
|---|---|---|---|---|---|---|---|---|---|---|---|---|
| Postemergence | 598 | 599 | 600 | 601 | 602 | 605 | 606 | 607 | 608 | 609 | 610 | 611 |
| Barnyardgrass | 10 | 0 | 0 | 20 | 0 | 0 | 50 | 20 | 0 | 50 | 70 | 90 |
| Blackgrass | 0 | 0 | 0 | 0 | 0 | 0 | 0 | 0 | 20 | 30 | 50 | 50 |
| Corn | 0 | 0 | 0 | 0 | 0 | 0 | 0 | 0 | 0 | 20 | 20 | 50 |
| Foxtail, Giant | 0 | 0 | 0 | 20 | 0 | 20 | 70 | 20 | 40 | 70 | 90 | 90 |
| Galium | 0 | 0 | 0 | 0 | 0 | 0 | 60 | 0 | 50 | 40 | 50 | 50 |
| Kochia | 0 | 0 | 0 | 0 | 0 | 0 | 0 | 0 | 50 | 20 | 50 | 60 |
| Pigweed | 0 | 0 | 0 | 0 | 0 | 0 | 50 | 0 | 30 | 0 | 50 | 20 |
| Ragweed | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 30 | 30 | 0 | 40 |
| Wheat | 0 | 0 | 0 | 0 | 0 | 0 | 0 | 0 | 0 | 0 | 0 | 40 |

| 125 g ai/ha | Compounds | | | | | | | | | | | | | |
|---|---|---|---|---|---|---|---|---|---|---|---|---|---|---|
| Postemergence | 612 | 613 | 614 | 615 | 616 | 617 | 618 | 619 | 620 | 621 | 622 | 623 | 624 | 625 |
| Barnyardgrass | 70 | 70 | 80 | 0 | 90 | 90 | 90 | 0 | 20 | 90 | 90 | 90 | 80 | 80 |
| Blackgrass | 40 | 40 | 30 | 0 | 50 | 40 | 50 | 0 | 0 | 0 | 30 | 50 | 40 | 30 |
| Corn | 50 | 50 | 0 | 0 | 70 | 80 | 80 | 0 | 0 | 0 | 50 | 60 | 0 | 10 |
| Foxtail, Giant | 70 | 90 | 80 | 0 | 90 | 90 | 90 | 0 | 30 | 70 | 80 | 90 | 80 | 90 |
| Galium | 30 | 60 | 30 | 0 | 60 | 60 | 50 | 0 | 0 | 30 | 60 | 50 | 30 | 30 |
| Kochia | 20 | 60 | 0 | 0 | 50 | 50 | 40 | 0 | 0 | 0 | 40 | 40 | 0 | 30 |
| Pigweed | 20 | 50 | 0 | 0 | 40 | 30 | 0 | 0 | 0 | 0 | 40 | 60 | 20 | 20 |
| Ragweed | 0 | 20 | 0 | 0 | 0 | 20 | 0 | 0 | 0 | 0 | 0 | 20 | 0 | 0 |
| Ryegrass, Italian | 20 | 60 | 0 | 0 | 50 | 20 | 40 | 0 | 0 | 0 | 30 | 30 | 30 | 20 |
| Wheat | 30 | 40 | 0 | 0 | 60 | 50 | 50 | 0 | 0 | 0 | 30 | 40 | 20 | 0 |

| 125 g ai/ha | Compounds | | | | | | | | | |
|---|---|---|---|---|---|---|---|---|---|---|
| Postemergence | 630 | 631 | 632 | 633 | 634 | 635 | 636 | 637 | 638 | 639 |
| Barnyardgrass | 80 | 0 | 90 | 90 | 40 | 80 | 90 | 90 | 90 | 90 |
| Blackgrass | 0 | 0 | 50 | 20 | 0 | 40 | 60 | 50 | 50 | 60 |
| Corn | 0 | 0 | 20 | 0 | 0 | 40 | 70 | 70 | 70 | 40 |
| Foxtail, Giant | 30 | 0 | 90 | 90 | 50 | 90 | 90 | 90 | 90 | 90 |
| Galium | 0 | 0 | 50 | 0 | 30 | 40 | 50 | 50 | 60 | 40 |
| Kochia | 0 | 0 | 60 | 40 | 0 | 60 | 50 | 0 | 20 | 60 |
| Pigweed | 0 | 0 | 0 | 0 | 0 | 60 | 30 | 50 | 20 | 20 |
| Ragweed | 0 | 0 | 20 | 0 | 0 | 0 | 0 | 0 | 0 | 0 |
| Ryegrass, Italian | 0 | 0 | 30 | 0 | 0 | 0 | 50 | 20 | 30 | 30 |
| Wheat | 0 | 0 | 30 | 0 | 0 | 20 | 60 | 70 | 60 | 60 |

| 125 g ai/ha | Compounds | | | | | | | | | | | | | |
|---|---|---|---|---|---|---|---|---|---|---|---|---|---|---|
| Postemergence | 640 | 641 | 642 | 643 | 644 | 645 | 646 | 647 | 648 | 649 | 650 | 651 | 652 | 653 |
| Barnyardgrass | 90 | 90 | 70 | 90 | 90 | 90 | 90 | 80 | 70 | 60 | 90 | 90 | 90 | 60 |
| Blackgrass | 0 | 30 | 20 | 50 | 60 | 60 | 70 | 20 | 30 | 20 | 50 | 60 | 60 | 50 |
| Corn | 0 | 0 | 50 | 0 | 70 | 20 | 70 | 10 | 0 | 0 | 40 | 80 | 30 | 0 |
| Foxtail, Giant | 80 | 90 | 20 | 90 | 90 | 90 | 90 | 90 | 10 | 30 | 90 | 80 | 80 | 60 |
| Galium | 40 | 40 | 50 | 0 | 50 | 50 | 40 | 20 | 20 | 50 | 50 | 60 | 30 | 40 |
| Kochia | 0 | 0 | 20 | 0 | 20 | 0 | 60 | 0 | 0 | 30 | 0 | 0 | 0 | 0 |
| Pigweed | 0 | 0 | 0 | 0 | 20 | 0 | 20 | 0 | 30 | 0 | 0 | 0 | 0 | 0 |
| Ragweed | 0 | 0 | 0 | 0 | 0 | 10 | 0 | 0 | 0 | 20 | 0 | 0 | 0 | 0 |
| Ryegrass, Italian | 0 | 0 | 40 | 30 | 50 | 20 | 60 | 0 | 30 | 30 | 60 | 50 | 50 | 40 |
| Wheat | 0 | 0 | 0 | 0 | 50 | 30 | 40 | 20 | 0 | 0 | 30 | 40 | 0 | 30 |

| 125 g ai/ha | Compounds | | | | | | | | | | | | | |
|---|---|---|---|---|---|---|---|---|---|---|---|---|---|---|
| Postemergence | 654 | 655 | 656 | 657 | 658 | 659 | 660 | 661 | 662 | 663 | 664 | 665 | 666 | 667 |
| Barnyardgrass | 90 | 70 | 90 | 90 | 70 | 70 | 50 | 90 | 90 | 90 | 90 | 90 | 90 | 90 |
| Blackgrass | 30 | 20 | 0 | 0 | 40 | 40 | 0 | 50 | 60 | 60 | 50 | 40 | 60 | 60 |
| Corn | 20 | 0 | 0 | 0 | 0 | 0 | 0 | 50 | 80 | 30 | 50 | 40 | 60 | 70 |
| Foxtail, Giant | 70 | 40 | 20 | 0 | 0 | 90 | 80 | 90 | 90 | 90 | 90 | 90 | 90 | 90 |
| Galium | 40 | 30 | 0 | 0 | 60 | 0 | 0 | 50 | 60 | 50 | 50 | 50 | 30 | 50 |
| Kochia | 20 | 30 | 20 | 0 | 0 | 20 | 0 | 60 | 70 | 20 | 60 | 0 | 0 | 50 |
| Pigweed | 0 | 0 | 0 | 0 | 0 | 0 | 0 | 20 | 0 | 20 | 0 | 0 | 0 | 0 |
| Ragweed | 0 | 0 | 0 | 0 | 0 | 0 | 0 | 10 | 20 | 30 | 10 | 0 | 0 | 0 |

TABLE A-continued

| | | | | | | | | | | | | | | |
|---|---|---|---|---|---|---|---|---|---|---|---|---|---|---|
| Ryegrass, Italian | 30 | 0 | 0 | 0 | 30 | 0 | 0 | 30 | 40 | 40 | 30 | 30 | 20 | 60 |
| Wheat | 0 | 0 | 0 | 0 | 0 | 0 | 0 | 30 | 80 | 50 | 50 | 30 | 20 | 40 |

| 125 g ai/ha | Compounds | | | | | | | | |
|---|---|---|---|---|---|---|---|---|---|
| Postemergence | 668 | 674 | 675 | 676 | 677 | 678 | 679 | 680 | 681 |
| Barnyardgrass | 90 | 30 | 40 | 50 | 80 | 70 | 40 | 30 | 40 |
| Blackgrass | 60 | 0 | 0 | 20 | 0 | 30 | 30 | 20 | 0 |
| Corn | 20 | 0 | 0 | 0 | 0 | 10 | 20 | 20 | 0 |
| Foxtail, Giant | 90 | 30 | 50 | 20 | 20 | 20 | 0 | 0 | 0 |
| Galium | 20 | 0 | 0 | 0 | 0 | 0 | 40 | 0 | 30 |
| Kochia | 20 | 0 | 0 | 0 | 0 | 0 | 0 | 0 | 0 |
| Pigweed | 0 | 0 | 0 | 0 | 0 | 0 | 0 | 0 | 0 |
| Ragweed | 0 | 0 | 0 | 0 | 0 | 0 | 0 | 0 | 0 |
| Ryegrass, Italian | 0 | 0 | 0 | 0 | 0 | 0 | 0 | 0 | 0 |
| Wheat | 20 | 0 | 0 | 0 | 0 | 0 | 0 | 0 | 0 |

| 125 g ai/ha | Compounds | | | | | | | | | | | | |
|---|---|---|---|---|---|---|---|---|---|---|---|---|---|
| Postemergence | 682 | 683 | 684 | 685 | 686 | 687 | 688 | 689 | 690 | 691 | 692 | 693 | 694 | 695 |
| Barnyardgrass | 0 | 0 | 40 | 40 | 90 | 90 | 90 | 90 | 80 | 80 | 70 | 70 | 50 | 80 |
| Blackgrass | 0 | 0 | 0 | 0 | 20 | 30 | 50 | 50 | 60 | 50 | 50 | 10 | 10 | 0 |
| Corn | 0 | 20 | 0 | 30 | 0 | 0 | 40 | 60 | 70 | 60 | 0 | 40 | 0 | 80 |
| Foxtail, Giant | 20 | 80 | 40 | 40 | 80 | 80 | 90 | 80 | 80 | 80 | 70 | 80 | 50 | 80 |
| Galium | 0 | 0 | 0 | 0 | 0 | 0 | 40 | 50 | 70 | 70 | 0 | 60 | 0 | 50 |
| Kochia | 0 | 0 | 0 | 0 | 0 | 0 | 40 | 30 | 50 | 70 | 40 | 60 | 0 | 30 |
| Pigweed | 0 | 0 | 0 | 0 | 0 | 0 | 30 | 30 | 60 | 40 | 40 | 10 | 20 | 20 |
| Ragweed | 0 | 0 | 0 | 0 | 20 | 30 | 30 | 0 | 60 | 50 | 0 | 0 | 0 | 20 |
| Ryegrass, Italian | 0 | 0 | 0 | 0 | 20 | 20 | 40 | 30 | 50 | 50 | 50 | 50 | 0 | 0 |
| Wheat | 0 | 0 | 0 | 0 | 0 | 0 | 20 | 20 | 50 | 50 | 0 | 0 | 0 | 20 |

| 125 g ai/ha | Compounds | | | | | | | | | |
|---|---|---|---|---|---|---|---|---|---|---|
| Postemergence | 696 | 697 | 698 | 699 | 700 | 701 | 702 | 703 | 704 | 705 | 706 |
| Barnyardgrass | 80 | 80 | 70 | 50 | 70 | 60 | 70 | 60 | 70 | 0 | 0 |
| Blackgrass | 30 | 30 | 30 | 30 | 0 | 0 | 0 | 0 | 0 | 0 | 0 |
| Corn | 40 | 70 | 80 | 30 | 0 | 0 | 0 | 0 | 0 | 0 | 0 |
| Foxtail, Giant | 80 | 80 | 80 | 50 | 70 | 60 | 30 | 50 | 70 | 0 | 0 |
| Galium | 50 | 50 | 50 | 50 | 40 | 0 | 0 | 0 | 20 | 0 | 0 |
| Kochia | 30 | 60 | 50 | 30 | 30 | 0 | 0 | 0 | 0 | 0 | 0 |
| Pigweed | 30 | 50 | 40 | 20 | 0 | 0 | 0 | 0 | 0 | 0 | 0 |
| Ragweed | 20 | 30 | 20 | 0 | 20 | 0 | 0 | 0 | 0 | 0 | 0 |
| Ryegrass, Italian | 30 | 20 | 30 | 0 | 30 | 0 | 0 | 0 | 0 | 0 | 0 |
| Wheat | 30 | 20 | 30 | 0 | 0 | 0 | 0 | 0 | 0 | 0 | 0 |

| 125 g ai/ha | Compounds | | | | |
|---|---|---|---|---|---|
| Postemergence | 711 | 712 | 714 | 715 | 716 |
| Barnyardgrass | 0 | 0 | 0 | 0 | 0 |
| Blackgrass | 0 | 0 | — | — | — |
| Corn | 0 | 0 | 0 | 0 | 0 |
| Crabgrass, Large | — | — | 0 | 0 | 0 |
| Foxtail, Giant | 0 | 0 | 0 | 0 | 0 |
| Galium | 0 | 0 | — | — | — |
| Kochia | 0 | 0 | — | — | — |
| Morningglory | — | — | 0 | 0 | 0 |
| Pigweed | 0 | 0 | 0 | 0 | 0 |
| Ragweed | 0 | 0 | — | — | — |
| Ryegrass, Italian | 0 | 0 | — | — | — |
| Velvetleaf | — | — | 0 | 0 | 0 |
| Wheat | 0 | 0 | 0 | 0 | 0 |

| 125 g ai/ha | Compounds | | | | | | | | | | | | |
|---|---|---|---|---|---|---|---|---|---|---|---|---|---|
| Postemergence | 717 | 718 | 719 | 720 | 721 | 722 | 723 | 724 | 725 | 726 | 727 | 728 | 729 | 730 |
| Barnyardgrass | 90 | 70 | 90 | 90 | 10 | 20 | 0 | 0 | 70 | 90 | 80 | 90 | 0 | 100 |
| Blackgrass | 0 | 20 | 60 | 20 | 0 | 0 | 0 | 0 | 0 | 50 | 30 | 0 | 0 | 50 |
| Corn | 0 | 0 | 90 | 0 | 0 | 0 | 0 | 0 | 0 | 60 | 0 | 0 | 0 | 20 |
| Crabgrass, Large | — | — | — | — | — | — | — | — | — | — | — | — | — | — |
| Foxtail, Giant | 30 | 30 | 90 | 20 | 0 | 0 | 0 | 0 | 0 | 90 | 40 | 0 | 0 | 90 |
| Galium | 40 | 40 | 60 | 50 | 20 | 0 | 0 | 0 | 20 | 50 | 0 | 20 | 0 | 50 |
| Kochia | 20 | 30 | 60 | 50 | 0 | 0 | 0 | 0 | 0 | 30 | 0 | 20 | 0 | 70 |
| Morningglory | — | — | — | — | — | — | — | — | — | — | — | — | — | — |
| Pigweed | 0 | 0 | 50 | 0 | 0 | 0 | 0 | 0 | 0 | 50 | 0 | 0 | 0 | 20 |
| Ragweed | 0 | 0 | 30 | 0 | 0 | 0 | 0 | 0 | 0 | 30 | 0 | 20 | 0 | 20 |

TABLE A-continued

| | | | | | | | | | | | | | |
|---|---|---|---|---|---|---|---|---|---|---|---|---|---|
| Ryegrass, Italian | 0 | 0 | 50 | 0 | 0 | 0 | 0 | 0 | 0 | 40 | 0 | 20 | 0 | 40 |
| Velvetleaf | — | — | — | — | — | — | — | — | — | — | — | — | — | — |
| Wheat | 0 | 0 | 80 | 0 | 0 | 0 | 0 | 0 | 0 | 30 | 0 | 0 | 0 | 30 |

| 125 g ai/ha | Compounds |||||||||||||
|---|---|---|---|---|---|---|---|---|---|---|---|---|---|
| Postemergence | 731 | 732 | 733 | 734 | 735 | 736 | 737 | 738 | 739 | 740 | 741 | 742 | 743 | 744 |
| Barnyardgrass | 70 | 90 | 90 | 90 | 90 | 90 | 40 | 80 | 90 | 90 | 0 | 90 | 90 | 60 |
| Blackgrass | 0 | 50 | 0 | 20 | 50 | 60 | 30 | 0 | 0 | 30 | 0 | 40 | 30 | 20 |
| Corn | 0 | 70 | 0 | 40 | 80 | 90 | 40 | 20 | 20 | 70 | 0 | 70 | 60 | 40 |
| Crabgrass, Large | — | — | — | — | — | — | — | — | — | — | — | — | — | — |
| Foxtail, Giant | 50 | 90 | 80 | 90 | 90 | 90 | 70 | 70 | 90 | 90 | 0 | 90 | 90 | 80 |
| Galium | 20 | 30 | 20 | 30 | 40 | 50 | 30 | 50 | 50 | 50 | 0 | 50 | 50 | 30 |
| Kochia | 0 | 20 | 0 | 0 | 30 | 20 | 0 | 20 | 30 | 40 | 0 | 30 | 30 | 30 |
| Morningglory | — | — | — | — | — | — | — | — | — | — | — | — | — | — |
| Pigweed | 0 | 0 | 0 | 0 | 20 | 20 | 20 | 20 | 20 | 40 | 0 | 0 | 0 | 0 |
| Ragweed | 0 | 0 | 0 | 10 | 0 | 0 | 0 | 0 | 30 | 0 | 0 | 20 | 0 | 20 |
| Ryegrass, Italian | 0 | 50 | 20 | 20 | 60 | 80 | 50 | 0 | 20 | 50 | 0 | 60 | 40 | 30 |
| Velvetleaf | — | — | — | — | — | — | — | — | — | — | — | — | — | — |
| Wheat | 0 | 80 | 20 | 50 | 50 | 50 | 40 | 0 | 0 | 50 | 0 | 60 | 50 | 50 |

| 125 g ai/ha | Compounds |||||||||||||
|---|---|---|---|---|---|---|---|---|---|---|---|---|---|
| Postemergence | 745 | 746 | 747 | 748 | 749 | 750 | 751 | 752 | 753 | 754 | 755 | 756 | 757 | 758 |
| Barnyardgrass | 90 | 20 | 40 | 40 | 0 | 70 | 60 | 60 | 50 | 60 | 0 | 90 | 90 | 70 |
| Blackgrass | 40 | 20 | 30 | 0 | 0 | 0 | 20 | 0 | 0 | 0 | 0 | 0 | 60 | 0 |
| Corn | 90 | 0 | 0 | 0 | 0 | 0 | 0 | 0 | 0 | 0 | 0 | 50 | 70 | 20 |
| Crabgrass, Large | — | — | — | — | — | — | — | — | — | — | — | — | — | — |
| Foxtail, Giant | 90 | 50 | 70 | 0 | 0 | 20 | 30 | 50 | 0 | 60 | 0 | 80 | 90 | 80 |
| Galium | 60 | 50 | 60 | 0 | 0 | 0 | 40 | 70 | 0 | 0 | 0 | 50 | 50 | 40 |
| Kochia | 70 | 0 | 20 | 0 | 0 | 0 | 0 | 40 | 0 | 0 | 0 | 20 | 20 | 0 |
| Morningglory | — | — | — | — | — | — | — | — | — | — | — | — | — | — |
| Pigweed | 70 | 0 | 30 | 0 | 0 | 0 | 0 | 0 | 0 | 0 | 0 | 0 | 20 | 0 |
| Ragweed | 40 | 0 | 0 | 0 | 0 | 0 | 0 | 20 | 0 | 0 | 0 | 20 | 0 | 0 |
| Ryegrass, Italian | 50 | 0 | 0 | 0 | 0 | 0 | 0 | 20 | 0 | 0 | 0 | 40 | 20 | 0 |
| Velvetleaf | — | — | — | — | — | — | — | — | — | — | — | — | — | — |
| Wheat | 60 | 0 | 0 | 0 | 0 | 0 | 0 | 0 | 0 | 0 | 0 | 30 | 60 | 0 |

| 125 g ai/ha | Compounds |||||||||||||
|---|---|---|---|---|---|---|---|---|---|---|---|---|---|
| Postemergence | 759 | 760 | 761 | 762 | 763 | 764 | 765 | 766 | 767 | 768 | 769 | 770 | 771 | 772 |
| Barnyardgrass | 70 | 80 | 70 | 90 | 0 | 80 | 70 | 10 | 70 | 70 | 50 | 60 | 90 | 0 |
| Blackgrass | 0 | 0 | 0 | 0 | 0 | 0 | 0 | 0 | 0 | 0 | 0 | 0 | 70 | 0 |
| Corn | 0 | 0 | 0 | 0 | 0 | 0 | 0 | 0 | 0 | 30 | 0 | 50 | 40 | 0 |
| Crabgrass, Large | — | — | — | — | — | — | — | — | — | — | — | — | — | — |
| Foxtail, Giant | 20 | 80 | 60 | 20 | 0 | 0 | 0 | 0 | 0 | 80 | 70 | 70 | 90 | 30 |
| Galium | 0 | 0 | 0 | 0 | 0 | 0 | 0 | 0 | 0 | 30 | 50 | 60 | 50 | 0 |
| Kochia | 0 | 0 | 0 | 0 | 0 | 0 | 0 | 0 | 0 | 0 | 0 | 40 | 50 | — |
| Morningglory | — | — | — | — | — | — | — | — | — | — | — | — | — | — |
| Pigweed | 0 | 0 | 0 | 0 | 0 | 0 | 0 | 0 | 0 | 0 | 0 | 30 | 0 | 0 |
| Ragweed | 0 | 0 | 0 | 0 | 0 | 0 | 0 | 0 | 0 | 0 | 0 | 0 | 20 | 0 |
| Ryegrass, Italian | 0 | 0 | 0 | 0 | 0 | 30 | 40 | 0 | 0 | 30 | 30 | 0 | 20 | 0 |
| Velvetleaf | — | — | — | — | — | — | — | — | — | — | — | — | — | — |
| Wheat | 0 | 0 | 0 | 0 | 0 | 0 | 0 | 0 | 0 | 0 | 0 | 0 | 30 | 0 |

| 125 g ai/ha | Compounds |||||||||||||
|---|---|---|---|---|---|---|---|---|---|---|---|---|---|
| Postemergence | 773 | 774 | 775 | 776 | 777 | 778 | 779 | 780 | 781 | 782 | 783 | 785 | 786 | 787 |
| Barnyardgrass | 0 | 0 | 50 | 80 | 70 | 80 | 90 | 60 | 90 | 90 | 0 | 90 | 80 | 30 |
| Blackgrass | 0 | 0 | 0 | 30 | 0 | 10 | 70 | 50 | 70 | 70 | 0 | 20 | 0 | 0 |
| Corn | 0 | 0 | 20 | 30 | 40 | 0 | 80 | 40 | 60 | 60 | 0 | 0 | 0 | 0 |
| Crabgrass, Large | — | — | — | — | — | — | — | — | — | — | — | — | — | — |
| Foxtail, Giant | 0 | 0 | 60 | 80 | 30 | 70 | 80 | 60 | 80 | 90 | 0 | 70 | 40 | 20 |
| Galium | 0 | 0 | 40 | 20 | 0 | 60 | 60 | 50 | 60 | 70 | 0 | 50 | 10 | 60 |
| Kochia | — | 0 | 40 | 20 | 0 | 60 | 30 | 30 | 0 | 10 | 0 | 0 | 0 | 60 |
| Morningglory | — | — | — | — | — | — | — | — | — | — | — | — | — | — |
| Pigweed | 0 | 0 | 0 | 0 | 0 | 10 | 0 | 0 | 0 | 0 | 0 | 0 | 0 | 60 |
| Ragweed | 0 | 0 | 20 | 0 | 0 | 0 | 20 | 0 | 0 | 0 | 0 | 0 | 0 | 50 |
| Ryegrass, Italian | 0 | 0 | 20 | 20 | 0 | 20 | 40 | 0 | 20 | 40 | 0 | 30 | 0 | 20 |
| Velvetleaf | — | — | — | — | — | — | — | — | — | — | — | — | — | — |
| Wheat | 0 | 0 | 20 | 30 | 30 | 0 | 80 | 30 | 50 | 60 | 0 | 0 | 0 | 0 |

TABLE A-continued

| 125 g ai/ha | Compounds | | | | | | | | | | | | | |
|---|---|---|---|---|---|---|---|---|---|---|---|---|---|---|
| Postemergence | 788 | 789 | 790 | 791 | 792 | 793 | 794 | 795 | 796 | 797 | 798 | 799 | 800 | 801 |
| Barnyardgrass | 80 | 80 | 80 | 60 | 0 | 0 | 30 | 70 | 90 | 90 | 80 | 70 | 80 | 90 |
| Blackgrass | 20 | 40 | 40 | 0 | 0 | 0 | 0 | 0 | 30 | 0 | 40 | 30 | 20 | 60 |
| Corn | 20 | 20 | 30 | 0 | 0 | 0 | 0 | 0 | 90 | 70 | 40 | 20 | 20 | 60 |
| Crabgrass, Large | — | — | — | — | — | — | — | — | — | — | — | — | — | — |
| Foxtail, Giant | 70 | 30 | 50 | 30 | 0 | 0 | 30 | 50 | 90 | 90 | 70 | 80 | 80 | 90 |
| Galium | 50 | 40 | 50 | 60 | 0 | 0 | 0 | 0 | 40 | 30 | 20 | 50 | 30 | 60 |
| Kochia | 40 | 0 | 40 | 20 | 0 | 0 | 0 | 0 | 0 | 0 | 0 | 30 | 0 | 40 |
| Morningglory | — | — | — | — | — | — | — | — | — | — | — | — | — | — |
| Pigweed | 60 | 0 | 20 | 0 | 0 | 0 | 0 | 0 | 20 | 20 | 20 | 20 | 40 | 30 |
| Ragweed | 40 | 0 | 30 | 0 | 0 | 0 | 0 | 0 | 0 | 0 | 0 | 0 | 0 | 50 |
| Ryegrass, Italian | 20 | 0 | 0 | 0 | 0 | 0 | 0 | 0 | 40 | 40 | 40 | 20 | 20 | 60 |
| Velvetleaf | — | — | — | — | — | — | — | — | — | — | — | — | — | — |
| Wheat | 0 | 20 | 20 | 0 | 0 | 0 | 0 | 0 | 60 | 60 | 20 | 20 | 20 | 30 |

| 125 g ai/ha | Compounds | | | | | | | | | | | | | |
|---|---|---|---|---|---|---|---|---|---|---|---|---|---|---|
| Postemergence | 802 | 803 | 804 | 805 | 806 | 807 | 808 | 809 | 810 | 811 | 812 | 813 | 814 | 815 |
| Barnyardgrass | 80 | 80 | 70 | 0 | 0 | 80 | 70 | 0 | 70 | 40 | 90 | 80 | 0 | 100 |
| Blackgrass | 60 | 50 | 20 | 0 | 0 | 0 | 0 | 0 | 0 | 0 | 80 | 80 | 0 | 50 |
| Corn | 70 | 90 | 50 | 0 | 0 | 70 | 0 | 0 | 0 | 0 | 80 | 40 | 0 | 50 |
| Crabgrass, Large | — | — | — | — | — | — | — | — | — | — | — | — | — | — |
| Foxtail, Giant | 90 | 90 | 80 | 0 | 0 | 80 | 80 | 0 | 80 | 60 | 90 | 80 | 0 | 90 |
| Galium | 60 | 60 | 50 | 0 | 0 | 0 | 0 | 0 | 0 | 0 | 50 | 30 | 0 | 50 |
| Kochia | 40 | 70 | 70 | 0 | 0 | 0 | 0 | 0 | 0 | 0 | 20 | 0 | 0 | 40 |
| Morningglory | — | — | — | — | — | — | — | — | — | — | — | — | — | — |
| Pigweed | 40 | 40 | 60 | 0 | 0 | 0 | 0 | 0 | 0 | 0 | 0 | 0 | 0 | 20 |
| Ragweed | 30 | 30 | 0 | 0 | 0 | 0 | 0 | 0 | 0 | 0 | 0 | 0 | 0 | 0 |
| Ryegrass, Italian | 40 | 40 | 0 | 0 | 0 | 0 | 0 | 0 | 0 | 0 | 30 | 20 | 0 | 60 |
| Velvetleaf | — | — | — | — | — | — | — | — | — | — | — | — | — | — |
| Wheat | 30 | 40 | 20 | 0 | 0 | 30 | 0 | 0 | 0 | 0 | 60 | 30 | 0 | 30 |

| 125 g ai/ha | Compounds | | | | | | | | | | | | | |
|---|---|---|---|---|---|---|---|---|---|---|---|---|---|---|
| Postemergence | 816 | 817 | 818 | 819 | 820 | 821 | 822 | 823 | 824 | 825 | 826 | 827 | 828 | 829 |
| Barnyardgrass | 90 | 90 | 90 | 100 | 90 | 90 | 90 | 90 | 90 | 80 | 100 | 70 | 70 | 80 |
| Blackgrass | 60 | 40 | 30 | 60 | 40 | 70 | 0 | 20 | 20 | 40 | 80 | 40 | 50 | 40 |
| Corn | 90 | 50 | 40 | 40 | 30 | 40 | 20 | 0 | 0 | 20 | 80 | 20 | 40 | 30 |
| Crabgrass, Large | — | — | — | — | — | — | — | — | — | — | — | — | — | — |
| Foxtail, Giant | 90 | 90 | 90 | 90 | 90 | 80 | 90 | 90 | 90 | 90 | 90 | 80 | 90 | 90 |
| Galium | 60 | 40 | 50 | 50 | 30 | 50 | 20 | 30 | 40 | 30 | 50 | 40 | 30 | 30 |
| Kochia | 30 | 0 | 40 | 30 | 20 | 30 | 0 | 20 | 0 | 0 | 30 | 0 | 0 | 0 |
| Morningglory | — | — | — | — | — | — | — | — | — | — | — | — | — | — |
| Pigweed | 0 | 0 | 20 | 30 | 20 | 0 | 0 | 20 | 0 | 0 | 30 | 0 | 0 | 0 |
| Ragweed | 0 | 0 | 0 | 0 | 20 | 0 | 0 | 20 | 30 | 20 | 50 | 0 | 0 | 0 |
| Ryegrass, Italian | 60 | 30 | 40 | 70 | 30 | 20 | 20 | 0 | 30 | 20 | 60 | 0 | 20 | 20 |
| Velvetleaf | — | — | — | — | — | — | — | — | — | — | — | — | — | — |
| Wheat | 30 | 50 | 0 | 30 | 40 | 0 | 0 | 0 | 0 | 40 | 60 | 20 | 20 | 30 |

| 125 g ai/ha | Compounds | | | | | | | | | | | | | |
|---|---|---|---|---|---|---|---|---|---|---|---|---|---|---|
| Postemergence | 830 | 831 | 832 | 833 | 834 | 835 | 836 | 837 | 838 | 839 | 840 | 841 | 842 | 843 |
| Barnyardgrass | 90 | 30 | 70 | 90 | 90 | 90 | 100 | 90 | 90 | 60 | 80 | 80 | 90 | 40 |
| Blackgrass | 20 | 0 | 0 | 40 | 60 | 40 | 70 | — | — | — | — | 30 | 30 | 0 |
| Corn | 0 | 0 | 0 | 20 | 40 | 30 | 70 | 60 | 70 | 30 | 30 | 0 | 20 | 0 |
| Crabgrass, Large | — | — | — | — | — | — | — | — | — | — | — | — | — | — |
| Foxtail, Giant | 70 | 20 | 0 | 90 | 90 | 90 | 90 | 90 | 90 | 60 | 90 | 90 | 90 | 70 |
| Galium | 30 | 20 | 50 | 40 | 60 | 30 | 50 | 50 | 50 | 80 | 50 | 40 | 50 | 30 |
| Kochia | 30 | 0 | 20 | 30 | 40 | 0 | 50 | 20 | 70 | 70 | 0 | 30 | 30 | 40 |
| Morningglory | — | — | — | — | — | — | — | — | — | — | — | — | — | — |
| Pigweed | 0 | 0 | 0 | 0 | 20 | 20 | 30 | 30 | 80 | 80 | 0 | 0 | 30 | 20 |
| Ragweed | 0 | 0 | 20 | 0 | 0 | 0 | 0 | 10 | 40 | 60 | 0 | 0 | 30 | 0 |
| Ryegrass, Italian | 20 | 20 | 20 | 60 | 60 | 50 | 60 | 50 | 30 | 50 | 0 | 20 | 20 | 0 |
| Velvetleaf | — | — | — | — | — | — | — | — | — | — | — | — | — | — |
| Wheat | 0 | 0 | 0 | 0 | 30 | 0 | 40 | 0 | 30 | 50 | 20 | 0 | 30 | 0 |

| 125 g ai/ha | Compounds | | | | | | | | | | | | | |
|---|---|---|---|---|---|---|---|---|---|---|---|---|---|---|
| Postemergence | 844 | 845 | 846 | 847 | 848 | 849 | 850 | 851 | 852 | 853 | 854 | 855 | 856 | 857 |
| Barnyardgrass | 0 | 80 | 90 | 0 | 90 | 90 | 90 | 90 | 90 | 90 | 0 | 90 | 80 | 70 |
| Blackgrass | 0 | 40 | 50 | 0 | 0 | 30 | 0 | 0 | 0 | 20 | 0 | 60 | 60 | 30 |
| Corn | 0 | 30 | 60 | 0 | 0 | 70 | 30 | 0 | 0 | 0 | 0 | 70 | 80 | 40 |
| Crabgrass, Large | — | — | — | — | — | — | — | — | — | — | — | — | — | — |

TABLE A-continued

| | | | | | | | | | | | | | | |
|---|---|---|---|---|---|---|---|---|---|---|---|---|---|---|
| Foxtail, Giant | 0 | 90 | 90 | 0 | 70 | 90 | 80 | 90 | 80 | 90 | 50 | 90 | 90 | 70 |
| Galium | 0 | 20 | 0 | 0 | 30 | 60 | 30 | 30 | 0 | 0 | 0 | 0 | 40 | 20 |
| Kochia | 0 | 0 | 40 | 0 | 0 | 0 | 0 | 0 | 0 | 0 | 0 | 0 | 30 | 20 |
| Morningglory | — | — | — | — | — | — | — | — | — | — | — | — | — | — |
| Pigweed | 0 | 0 | 0 | 0 | 0 | 0 | 0 | 0 | 0 | 0 | 0 | 20 | 20 | 30 |
| Ragweed | 0 | 0 | 0 | 0 | 0 | 0 | 0 | 0 | 0 | 0 | 0 | 0 | 0 | 0 |
| Ryegrass, Italian | 0 | 30 | 70 | 0 | 0 | 0 | 0 | 0 | 0 | 0 | 0 | 20 | 40 | 20 |
| Velvetleaf | — | — | — | — | — | — | — | — | — | — | — | — | — | — |
| Wheat | 0 | 0 | 0 | 0 | 0 | 30 | 20 | 20 | 0 | 0 | 0 | 50 | 50 | 30 |

| 125 g ai/ha | Compounds | | | | | | | | | | | | | |
|---|---|---|---|---|---|---|---|---|---|---|---|---|---|---|
| Postemergence | 858 | 859 | 860 | 861 | 862 | 863 | 864 | 865 | 866 | 867 | 868 | 869 | 870 | 871 |
| Barnyardgrass | 80 | 80 | 30 | 90 | 30 | 70 | 90 | 0 | 60 | 90 | 20 | 80 | 0 | 50 |
| Blackgrass | 0 | 30 | 0 | 70 | 0 | 0 | 50 | 0 | 0 | 30 | 0 | 0 | 0 | 0 |
| Corn | 20 | 50 | 0 | 80 | 20 | 30 | 60 | 0 | 30 | 60 | 0 | 0 | 0 | 20 |
| Crabgrass, Large | — | — | — | — | — | — | — | — | — | — | — | — | — | — |
| Foxtail, Giant | 80 | 80 | 60 | 90 | 60 | 20 | 70 | 0 | 70 | 80 | 0 | 60 | 0 | 40 |
| Galium | 30 | 50 | 20 | 60 | 60 | 30 | 20 | 0 | 20 | 30 | 0 | 0 | 0 | 50 |
| Kochia | 20 | 20 | 0 | 60 | 40 | 40 | 0 | 0 | 20 | 0 | 0 | 0 | 0 | 0 |
| Morningglory | — | — | — | — | — | — | — | — | — | — | — | — | — | — |
| Pigweed | 20 | 20 | 0 | 50 | 60 | 50 | 20 | 0 | 0 | 0 | 0 | 0 | 0 | 0 |
| Ragweed | 0 | 0 | 0 | 0 | 0 | 0 | 0 | 0 | 0 | 0 | 0 | 0 | 0 | 0 |
| Ryegrass, Italian | 20 | 20 | 0 | 40 | 20 | 0 | 50 | 0 | 20 | 20 | 0 | 0 | 0 | 20 |
| Velvetleaf | — | — | — | — | — | — | — | — | — | — | — | — | — | — |
| Wheat | 20 | 20 | 20 | 50 | 0 | 0 | 50 | 0 | 0 | 20 | 0 | 0 | 0 | 20 |

| 125 g ai/ha | Compounds | | | | | | | | | | | | | |
|---|---|---|---|---|---|---|---|---|---|---|---|---|---|---|
| Postemergence | 872 | 873 | 874 | 875 | 876 | 877 | 878 | 879 | 880 | 881 | 882 | 883 | 885 | 886 |
| Barnyardgrass | 90 | 90 | 90 | 90 | 60 | 60 | 100 | 100 | 90 | 90 | 80 | 90 | 70 | 90 |
| Blackgrass | 20 | 50 | 60 | 20 | 0 | 0 | 60 | 70 | 0 | 0 | 40 | 0 | 0 | 20 |
| Corn | 30 | 70 | 50 | 20 | 0 | 0 | 50 | 60 | 20 | 0 | 80 | 0 | 0 | 40 |
| Crabgrass, Large | — | — | — | — | — | — | — | — | — | — | — | — | — | — |
| Foxtail, Giant | 80 | 90 | 90 | 90 | 40 | 70 | 80 | 80 | 80 | 80 | 70 | 70 | 40 | 90 |
| Galium | 50 | 50 | 20 | 40 | 0 | 20 | 50 | 50 | 60 | 0 | 50 | 0 | 20 | 0 |
| Kochia | 50 | 60 | 20 | 40 | 50 | 20 | 20 | 60 | 20 | 30 | 60 | 30 | 0 | 0 |
| Morningglory | — | — | — | — | — | — | — | — | — | — | — | — | — | — |
| Pigweed | 30 | 30 | 0 | 0 | 0 | 0 | 0 | 20 | 50 | 0 | 30 | 0 | 0 | 0 |
| Ragweed | 0 | 30 | 20 | 20 | 0 | 20 | 20 | 20 | 40 | 0 | 0 | 0 | 0 | 0 |
| Ryegrass, Italian | 0 | 40 | 20 | 20 | 0 | 20 | 40 | 70 | 50 | 30 | 40 | 0 | 0 | 20 |
| Velvetleaf | — | — | — | — | — | — | — | — | — | — | — | — | — | — |
| Wheat | 20 | 30 | 20 | 0 | 0 | 30 | 60 | 70 | 40 | 0 | 0 | 0 | 0 | 0 |

| 125 g ai/ha | Compounds | | | | | | | | | | | | | |
|---|---|---|---|---|---|---|---|---|---|---|---|---|---|---|
| Postemergence | 887 | 888 | 889 | 890 | 891 | 892 | 893 | 894 | 895 | 896 | 897 | 898 | 899 | 900 |
| Barnyardgrass | 80 | 90 | 70 | 90 | 50 | 90 | 100 | 90 | 90 | 90 | 90 | 80 | 80 | 80 |
| Blackgrass | 0 | 20 | 20 | 20 | 0 | 0 | 30 | 0 | 60 | 40 | 30 | 50 | 40 | 40 |
| Corn | 0 | 0 | 20 | 20 | 20 | 0 | 80 | 60 | 80 | 20 | 30 | 70 | 40 | 50 |
| Crabgrass, Large | — | — | — | — | — | — | — | — | — | — | — | — | — | — |
| Foxtail, Giant | 70 | 30 | 40 | 70 | 40 | 90 | 90 | 90 | 90 | 90 | 80 | 80 | 90 | 80 |
| Galium | 0 | 0 | 30 | 50 | 30 | 20 | 50 | 40 | 70 | 40 | 40 | 0 | 0 | 20 |
| Kochia | 0 | 0 | 0 | 60 | 0 | 40 | 60 | 50 | 70 | 20 | 30 | 0 | 0 | 30 |
| Morningglory | — | — | — | — | — | — | — | — | — | — | — | — | — | — |
| Pigweed | 0 | 0 | 0 | 0 | 0 | 0 | 20 | 0 | 40 | 20 | 0 | 40 | 0 | 50 |
| Ragweed | 0 | 0 | 0 | 0 | 0 | 0 | 30 | 0 | 0 | 0 | 20 | 0 | 20 | 10 |
| Ryegrass, Italian | 0 | 0 | 40 | 0 | 0 | 60 | 60 | 50 | 60 | 50 | 20 | 50 | 30 | 40 |
| Velvetleaf | — | — | — | — | — | — | — | — | — | — | — | — | — | — |
| Wheat | 0 | 0 | 0 | 0 | 0 | 0 | 30 | 20 | 40 | 30 | 30 | 40 | 30 | 50 |

| 125 g ai/ha | Compounds | | | | | | | | | | | | | |
|---|---|---|---|---|---|---|---|---|---|---|---|---|---|---|
| Postemergence | 901 | 902 | 903 | 904 | 905 | 906 | 907 | 908 | 909 | 910 | 911 | 912 | 913 | 914 |
| Barnyardgrass | 60 | 60 | 80 | 80 | 70 | 0 | 50 | 20 | 50 | 90 | 90 | 80 | 90 | 0 |
| Blackgrass | 20 | 0 | 0 | 30 | 0 | — | 0 | 0 | 0 | 50 | 50 | 30 | 0 | 0 |
| Corn | 40 | 0 | 0 | 0 | 0 | 0 | 0 | 0 | 0 | 70 | 80 | 30 | 0 | 0 |
| Crabgrass, Large | — | — | — | — | — | — | — | — | — | — | — | — | — | — |
| Foxtail, Giant | 90 | 30 | 80 | 80 | 60 | 0 | 60 | 30 | 40 | 90 | 90 | 90 | 30 | 70 |
| Galium | 0 | 0 | 10 | 30 | 0 | 0 | 0 | 0 | 0 | 30 | 40 | 0 | 30 | 60 |
| Kochia | 30 | 0 | 0 | 30 | 0 | 0 | 0 | 0 | 0 | 20 | 50 | 0 | 0 | 70 |
| Morningglory | — | — | — | — | — | — | — | — | — | — | — | — | — | — |
| Pigweed | 0 | 0 | 0 | 0 | 0 | 0 | 0 | 0 | 0 | 0 | 0 | 0 | 0 | 80 |
| Ragweed | 0 | 0 | 0 | 0 | 0 | 0 | 0 | 0 | 0 | 10 | 0 | 0 | 30 | 20 |
| Ryegrass, Italian | 0 | 0 | 0 | 0 | 0 | 0 | 0 | 0 | 0 | 50 | 70 | 20 | 0 | 0 |

TABLE A-continued

| | | | | | | | | | | | | | | |
|---|---|---|---|---|---|---|---|---|---|---|---|---|---|---|
| Velvetleaf | — | — | — | — | — | — | — | — | — | — | — | — | — | — |
| Wheat | 20 | 0 | 0 | 0 | 0 | 0 | 0 | 0 | 0 | 0 | 50 | 20 | 0 | 0 |

| 125 g ai/ha | Compounds | | | | | | | | | | | | | |
|---|---|---|---|---|---|---|---|---|---|---|---|---|---|---|
| Postemergence | 915 | 916 | 917 | 918 | 919 | 920 | 921 | 922 | 923 | 924 | 925 | 926 | 927 | 928 |
| Barnyardgrass | 90 | 30 | 0 | 0 | 0 | 40 | 90 | 90 | 0 | 90 | 40 | 40 | 0 | 90 |
| Blackgrass | 40 | 0 | 0 | 40 | 0 | 0 | 20 | 0 | 0 | 0 | 0 | 0 | 0 | 30 |
| Corn | 0 | 0 | 0 | 0 | 0 | 0 | 20 | 0 | 0 | 0 | 0 | 0 | 0 | 40 |
| Crabgrass, Large | — | — | — | — | — | — | — | — | — | — | — | — | — | — |
| Foxtail, Giant | 90 | 0 | 0 | 0 | 0 | 20 | 90 | 50 | 0 | 90 | 40 | 40 | 0 | 90 |
| Galium | 50 | 30 | 0 | 0 | 0 | 0 | 0 | 0 | 0 | 0 | 0 | 0 | 0 | 50 |
| Kochia | 20 | 0 | 0 | 0 | 0 | 0 | 0 | 0 | 0 | 0 | 0 | 0 | 0 | 40 |
| Morningglory | — | — | — | — | — | — | — | — | — | — | — | — | — | — |
| Pigweed | 60 | 0 | 0 | 0 | 0 | 0 | 0 | 0 | 0 | 0 | 0 | 0 | 0 | 20 |
| Ragweed | 30 | 0 | 0 | 0 | 0 | 0 | 0 | 0 | 0 | 0 | 0 | 0 | 0 | 0 |
| Ryegrass, Italian | 30 | 0 | 0 | 0 | 0 | 0 | 20 | 0 | 0 | 0 | 0 | 0 | 0 | 50 |
| Velvetleaf | — | — | — | — | — | — | — | — | — | — | — | — | — | — |
| Wheat | 40 | 0 | 0 | 0 | 0 | 0 | 20 | 0 | 0 | 0 | 0 | 0 | 0 | 40 |

| 125 g ai/ha | Compounds | | | | | | | | | | | | | |
|---|---|---|---|---|---|---|---|---|---|---|---|---|---|---|
| Postemergence | 929 | 930 | 931 | 932 | 933 | 934 | 935 | 936 | 937 | 938 | 939 | 940 | 941 | 942 |
| Barnyardgrass | 90 | 80 | 80 | 90 | 90 | 60 | 70 | 60 | 70 | 80 | 80 | 10 | 50 | 60 |
| Blackgrass | 40 | 20 | 20 | 40 | 20 | 0 | 60 | 30 | 30 | 40 | 0 | 0 | 0 | 70 |
| Corn | 40 | 40 | 70 | 20 | 40 | 20 | 40 | 30 | 20 | 60 | 0 | 0 | 0 | 0 |
| Crabgrass, Large | — | — | — | — | — | — | — | — | — | — | — | — | — | — |
| Foxtail, Giant | 90 | 80 | 90 | 90 | 90 | 90 | 90 | 90 | 90 | 80 | 90 | 0 | 60 | 80 |
| Galium | 50 | 40 | 40 | 40 | 50 | 60 | 40 | 40 | 70 | 50 | 20 | 0 | 20 | 50 |
| Kochia | 40 | 20 | 30 | 30 | 50 | 20 | 30 | 20 | 30 | 40 | 0 | 0 | 0 | 30 |
| Morningglory | — | — | — | — | — | — | — | — | — | — | — | — | — | — |
| Pigweed | 20 | 30 | 20 | 40 | 0 | 20 | 20 | 20 | 60 | 50 | 0 | 0 | 0 | 70 |
| Ragweed | 20 | 0 | 0 | 0 | 0 | 0 | 0 | 0 | 20 | 0 | 0 | 0 | 0 | 0 |
| Ryegrass, Italian | 50 | 30 | 30 | 30 | 40 | 0 | 20 | 0 | 20 | 20 | 0 | 0 | 0 | 0 |
| Velvetleaf | — | — | — | — | — | — | — | — | — | — | — | — | — | — |
| Wheat | 30 | 30 | 30 | 30 | 20 | 0 | 30 | 30 | 20 | 40 | 20 | 0 | 0 | 20 |

| 125 g ai/ha | Compounds | | | | | | | | | | | | | |
|---|---|---|---|---|---|---|---|---|---|---|---|---|---|---|
| Postemergence | 943 | 944 | 945 | 946 | 947 | 948 | 949 | 950 | 951 | 952 | 953 | 954 | 955 | 956 |
| Barnyardgrass | 70 | 80 | 80 | 60 | 20 | 70 | 90 | 90 | 70 | 60 | 90 | 60 | 90 | 90 |
| Blackgrass | 40 | 60 | 0 | 0 | 0 | 0 | 0 | 0 | 0 | 0 | 0 | 0 | 0 | 40 |
| Corn | 20 | 30 | 0 | 0 | 0 | 0 | 0 | 0 | 0 | 0 | 0 | 0 | 0 | 50 |
| Crabgrass, Large | — | — | — | — | — | — | — | — | — | — | — | — | — | — |
| Foxtail, Giant | 90 | 90 | 0 | 0 | 30 | 70 | 20 | 0 | 0 | 50 | 90 | 60 | 80 | 80 |
| Galium | 70 | 20 | 20 | 0 | 0 | 0 | 0 | 20 | 0 | 0 | 20 | 0 | 20 | 40 |
| Kochia | 30 | 0 | 0 | 0 | 0 | 0 | 0 | 0 | 0 | 0 | 30 | 0 | 20 | 30 |
| Morningglory | — | — | — | — | — | — | — | — | — | — | — | — | — | — |
| Pigweed | 40 | 30 | 0 | 0 | 0 | 0 | 0 | 0 | 0 | 0 | 0 | 0 | 0 | 0 |
| Ragweed | 0 | 40 | 0 | 0 | 0 | 0 | 0 | 0 | 0 | 0 | 0 | 0 | 0 | 20 |
| Ryegrass, Italian | 0 | 30 | 0 | 0 | 0 | 0 | 0 | 20 | 0 | 0 | 0 | 0 | 30 | 50 |
| Velvetleaf | — | — | — | — | — | — | — | — | — | — | — | — | — | — |
| Wheat | 0 | 40 | 0 | 0 | 0 | 0 | 0 | 0 | 0 | 0 | 0 | 0 | 0 | 30 |

| 125 g ai/ha | Compounds | | | | | | | | | | | | | |
|---|---|---|---|---|---|---|---|---|---|---|---|---|---|---|
| Postemergence | 957 | 958 | 959 | 960 | 961 | 962 | 963 | 964 | 965 | 966 | 967 | 968 | 969 | 970 |
| Barnyardgrass | 80 | 70 | 90 | 50 | 90 | 90 | 90 | 60 | 80 | 60 | 80 | 20 | 50 | 0 |
| Blackgrass | 20 | 30 | 30 | 20 | 30 | 20 | 0 | 0 | 30 | 20 | 0 | 0 | 0 | 0 |
| Corn | 0 | 0 | 30 | 0 | 20 | 0 | 0 | 0 | 30 | 0 | 0 | 0 | 50 | 0 |
| Crabgrass, Large | — | — | — | — | — | — | — | — | — | — | — | — | — | — |
| Foxtail, Giant | 0 | 90 | 80 | 20 | 30 | 90 | 90 | 60 | 70 | 40 | 80 | 0 | 50 | 0 |
| Galium | 40 | 30 | 40 | 0 | 30 | 30 | 30 | 40 | 40 | 20 | 0 | 0 | 20 | 0 |
| Kochia | 20 | 0 | 50 | 0 | 50 | 20 | 20 | 0 | 0 | 0 | 0 | 0 | 0 | 0 |
| Morningglory | — | — | — | — | — | — | — | — | — | — | — | — | — | — |
| Pigweed | 0 | 0 | 0 | 0 | 0 | 0 | 0 | 0 | 0 | 0 | 0 | 0 | 0 | 0 |
| Ragweed | 0 | 0 | 0 | 0 | 20 | 0 | 0 | 0 | 0 | 0 | 0 | 0 | 0 | 0 |
| Ryegrass, Italian | 20 | 0 | 30 | 30 | 20 | 20 | 20 | 0 | 0 | 0 | 0 | 0 | 20 | 0 |
| Velvetleaf | — | — | — | — | — | — | — | — | — | — | — | — | — | — |
| Wheat | 0 | 0 | 20 | 0 | 0 | 30 | 0 | 0 | 20 | 0 | 0 | 0 | 30 | 0 |

TABLE A-continued

| 125 g ai/ha | Compounds | | | | | | | | | | | | | |
|---|---|---|---|---|---|---|---|---|---|---|---|---|---|---|
| Postemergence | 971 | 972 | 973 | 974 | 975 | 976 | 977 | 978 | 979 | 980 | 981 | 982 | 983 | 984 |
| Barnyardgrass | 80 | 50 | 30 | — | — | — | — | — | — | — | — | — | — | 100 |
| Blackgrass | 50 | 0 | 60 | 70 | 50 | 40 | 0 | 60 | 60 | 0 | 0 | 70 | 30 | 30 |
| Corn | 70 | 60 | 0 | 70 | 20 | 60 | 0 | 60 | 30 | 0 | 0 | 60 | 20 | 80 |
| Crabgrass, Large | — | — | — | — | — | — | — | — | — | — | — | — | — | — |
| Foxtail, Giant | 80 | 60 | 70 | 90 | 90 | 90 | 90 | 90 | 90 | 90 | 70 | 90 | 90 | 90 |
| Galium | 40 | 30 | 50 | 50 | 50 | 0 | 40 | 50 | 40 | 0 | 0 | — | 30 | 30 |
| Kochia | 40 | 0 | — | 70 | 40 | 30 | 70 | 0 | 30 | 0 | 0 | 50 | 50 | 50 |
| Morningglory | — | — | — | — | — | — | — | — | — | — | — | — | — | — |
| Pigweed | 50 | 30 | 0 | 40 | 30 | 0 | 30 | 0 | 40 | 0 | 0 | 0 | 0 | 0 |
| Ragweed | 0 | 30 | 0 | 20 | 0 | 0 | 20 | 0 | 20 | 0 | 0 | 20 | 0 | 0 |
| Ryegrass, Italian | 50 | 20 | 20 | 70 | 20 | 20 | 0 | 50 | 20 | 0 | 0 | 60 | 20 | 20 |
| Velvetleaf | — | — | — | — | — | — | — | — | — | — | — | — | — | — |
| Wheat | 50 | 40 | 0 | 70 | 20 | 40 | 0 | 70 | 50 | 0 | 0 | 70 | 30 | 20 |

| 125 g ai/ha | Compounds | | | | | | | | | | | | | |
|---|---|---|---|---|---|---|---|---|---|---|---|---|---|---|
| Postemergence | 985 | 986 | 987 | 988 | 989 | 990 | 991 | 992 | 993 | 994 | 995 | 996 | 997 | 998 |
| Barnyardgrass | 0 | 80 | 80 | 80 | 80 | 90 | 30 | 0 | 90 | 100 | 60 | 0 | 0 | 0 |
| Blackgrass | 0 | 40 | 0 | 30 | 0 | 0 | 0 | 0 | 70 | 60 | 50 | 0 | 0 | 0 |
| Corn | 0 | 80 | 0 | 20 | 0 | 40 | 0 | 0 | 80 | 70 | 30 | 0 | 0 | 0 |
| Crabgrass, Large | — | — | — | — | — | — | — | — | — | — | — | — | — | — |
| Foxtail, Giant | 0 | 90 | 60 | 80 | 50 | 80 | 80 | 0 | 90 | 90 | 80 | 0 | 0 | 0 |
| Galium | 0 | 30 | 40 | 50 | 20 | 60 | 0 | 0 | 60 | 50 | 40 | 0 | 0 | 0 |
| Kochia | 0 | 30 | 0 | 10 | 0 | 40 | — | — | 20 | 40 | 0 | — | 0 | 0 |
| Morningglory | — | — | — | — | — | — | — | — | — | — | — | — | — | — |
| Pigweed | 0 | 0 | 0 | 0 | 0 | 30 | 0 | 0 | 30 | 0 | 0 | 0 | 0 | 0 |
| Ragweed | 0 | 0 | 0 | 0 | 0 | 0 | 0 | 0 | 0 | 20 | 0 | 0 | 0 | 0 |
| Ryegrass, Italian | 0 | 30 | 0 | 20 | 0 | 20 | 0 | 0 | 50 | 70 | 30 | 0 | 0 | 0 |
| Velvetleaf | — | — | — | — | — | — | — | — | — | — | — | — | — | — |
| Wheat | 0 | 20 | 0 | 30 | 0 | 0 | 0 | 0 | 50 | 70 | 20 | 0 | 0 | 0 |

| 125 g ai/ha | Compounds | | | | | | | | | | | | | |
|---|---|---|---|---|---|---|---|---|---|---|---|---|---|---|
| Postemergence | 999 | 1000 | 1001 | 1002 | 1003 | 1004 | 1005 | 1006 | 1007 | 1008 | 1009 | 1010 | 1011 | 1012 |
| Barnyardgrass | 100 | 60 | 0 | 50 | 0 | 0 | 0 | 0 | 0 | 0 | 0 | 0 | 0 | 0 |
| Blackgrass | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 10 | 0 | 0 | 0 | 0 | 0 | 0 |
| Crabgrass, Large | — | — | — | — | — | — | — | — | — | — | — | — | — | — |
| Foxtail, Giant | 40 | 0 | 0 | 0 | 0 | 0 | 0 | 0 | 0 | 0 | 0 | 0 | 0 | 0 |
| Galium | 0 | 0 | 0 | 0 | 0 | 0 | 0 | 0 | 0 | 0 | 0 | 0 | 0 | 0 |
| Kochia | 40 | 40 | 0 | 0 | 0 | 0 | 0 | 0 | 0 | 0 | 0 | 0 | 0 | 0 |
| Morningglory | — | — | — | — | — | — | — | — | — | — | — | — | — | — |
| Pigweed | 0 | 0 | 0 | 0 | 0 | 0 | 0 | 0 | 0 | 0 | 0 | 0 | 0 | 0 |
| Ragweed | 0 | 0 | 0 | 0 | 0 | 0 | 0 | 10 | 0 | 0 | 0 | 0 | 0 | 0 |
| Ryegrass, Italian | 0 | 0 | 0 | 0 | 0 | 0 | 0 | 0 | 0 | 0 | 0 | 0 | 0 | 0 |
| Velvetleaf | — | — | — | — | — | — | — | — | — | — | — | — | — | — |
| Wheat | 0 | 0 | 0 | 0 | 0 | 0 | 0 | 0 | 0 | 0 | 0 | 0 | 0 | 0 |

| 125 g ai/ha | Compounds | | | | | | | | | | | | | |
|---|---|---|---|---|---|---|---|---|---|---|---|---|---|---|
| Postemergence | 1013 | 1014 | 1015 | 1016 | 1017 | 1018 | 1019 | 1020 | 1021 | 1022 | 1023 | 1024 | 1025 | 1026 |
| Barnyardgrass | 90 | 90 | 90 | 50 | 90 | 90 | 0 | 90 | 100 | 60 | 90 | 90 | 60 | 70 |
| Blackgrass | 0 | 0 | 0 | 0 | 0 | 0 | 0 | 0 | 20 | 0 | 0 | 0 | 0 | 0 |
| Corn | 80 | 70 | 70 | 0 | 80 | 70 | 0 | 0 | 60 | 0 | 0 | 70 | 0 | 0 |
| Crabgrass, Large | — | — | — | — | — | — | — | — | — | — | — | — | — | — |
| Foxtail, Giant | 80 | 90 | 80 | 30 | 90 | 90 | 0 | 90 | 90 | 50 | 70 | 70 | 60 | 0 |
| Galium | 70 | 20 | 40 | 0 | 40 | 30 | 0 | 40 | 50 | 30 | 60 | 60 | 30 | 0 |
| Kochia | 40 | 30 | 0 | 0 | 40 | 30 | 0 | 50 | 70 | 30 | 50 | 50 | 30 | 0 |
| Morningglory | — | — | — | — | — | — | — | — | — | — | — | — | — | — |
| Pigweed | 0 | 30 | 30 | 0 | 0 | 30 | 0 | 30 | 0 | 0 | 0 | 30 | 0 | 0 |
| Ragweed | 0 | 0 | 0 | 0 | 0 | 0 | 0 | 0 | 40 | 0 | 0 | 0 | 0 | 0 |
| Ryegrass, Italian | 0 | 30 | 30 | 0 | 30 | 30 | 0 | 30 | 40 | 0 | 30 | 30 | 0 | 0 |
| Velvetleaf | — | — | — | — | — | — | — | — | — | — | — | — | — | — |
| Wheat | 40 | 30 | 0 | 0 | 20 | 30 | 0 | 0 | 40 | 0 | 0 | 0 | 0 | 20 |

| 125 g ai/ha | Compounds | | | | | | | | | | | | | |
|---|---|---|---|---|---|---|---|---|---|---|---|---|---|---|
| Postemergence | 1027 | 1028 | 1029 | 1030 | 1031 | 1032 | 1033 | 1034 | 1035 | 1036 | 1037 | 1038 | 1039 | 1040 |
| Barnyardgrass | 70 | 80 | 80 | 70 | 0 | 0 | 90 | 90 | 90 | 70 | 70 | 90 | 90 | 80 |
| Blackgrass | 0 | 30 | 30 | 0 | 0 | 0 | 0 | 20 | 40 | 0 | 0 | 30 | 30 | 60 |
| Corn | 0 | 0 | 50 | 20 | 0 | 0 | 0 | 10 | 50 | 0 | 0 | 60 | 70 | 60 |
| Crabgrass, Large | — | — | — | — | — | — | — | — | — | — | — | — | — | — |

TABLE A-continued

| | | | | | | | | | | | | | | |
|---|---|---|---|---|---|---|---|---|---|---|---|---|---|---|
| Foxtail, Giant | 20 | 80 | 80 | 70 | 0 | 0 | 30 | 20 | 50 | 0 | 0 | 90 | 90 | 80 |
| Galium | 50 | 40 | 20 | 40 | 0 | 0 | 40 | 40 | 20 | 20 | 40 | 50 | 40 | 50 |
| Kochia | 0 | 0 | 0 | 0 | 0 | 0 | 0 | 20 | 0 | 0 | 0 | 40 | 40 | 60 |
| Morningglory | — | — | — | — | — | — | — | — | — | — | — | — | — | — |
| Pigweed | 0 | 0 | 0 | 0 | 0 | 0 | 0 | 0 | 0 | 0 | 0 | 0 | 0 | 40 |
| Ragweed | 0 | 0 | 0 | 0 | 0 | 0 | 0 | 10 | 0 | 0 | 20 | 0 | 10 | 0 |
| Ryegrass, Italian | 0 | 0 | 0 | 0 | 0 | 0 | 0 | 0 | 40 | 0 | 0 | 20 | 50 | 30 |
| Velvetleaf | — | — | — | — | — | — | — | — | — | — | — | — | — | — |
| Wheat | 0 | 0 | 30 | 30 | 0 | 0 | 0 | 0 | 20 | 0 | 0 | 20 | 50 | 20 |

| 125 g ai/ha | Compounds | | | | | | | | | | | | | |
|---|---|---|---|---|---|---|---|---|---|---|---|---|---|---|
| Postemergence | 1041 | 1042 | 1043 | 1044 | 1045 | 1046 | 1047 | 1048 | 1049 | 1050 | 1051 | 1052 | 1053 | 1054 |
| Barnyardgrass | 0 | 80 | 50 | 70 | 90 | 90 | 40 | 50 | 30 | 0 | 0 | 80 | 0 | 0 |
| Blackgrass | 0 | 40 | 20 | — | 40 | 30 | 0 | 20 | 0 | 0 | 0 | 20 | 0 | 0 |
| Corn | 0 | 60 | 20 | 0 | 20 | 20 | 0 | 20 | 0 | 0 | 0 | 0 | 0 | 0 |
| Crabgrass, Large | — | — | — | — | — | — | — | — | — | — | — | — | — | — |
| Foxtail, Giant | 0 | 80 | 70 | 60 | 60 | 60 | 50 | 60 | 70 | 0 | 0 | 70 | 0 | 0 |
| Galium | 40 | 30 | 20 | 40 | 40 | 50 | 0 | 0 | 0 | 0 | 50 | 70 | 0 | 0 |
| Kochia | 0 | 30 | 0 | 0 | 0 | 0 | 0 | 30 | 0 | 0 | 0 | 40 | 0 | 0 |
| Morningglory | — | — | — | — | — | — | — | — | — | — | — | — | — | — |
| Pigweed | 0 | 20 | 0 | 30 | 0 | 0 | 0 | 30 | 10 | 0 | 0 | 30 | 0 | 0 |
| Ragweed | 0 | 0 | 0 | 20 | 30 | 0 | 0 | 0 | 0 | 0 | 0 | 30 | 0 | 0 |
| Ryegrass, Italian | 0 | 30 | — | 0 | 50 | 40 | 0 | 30 | 0 | 0 | 0 | 20 | 0 | 0 |
| Velvetleaf | — | — | — | — | — | — | — | — | — | — | — | — | — | — |
| Wheat | 0 | 0 | 0 | 0 | 20 | 20 | 0 | 20 | 0 | 0 | 0 | 0 | 0 | 0 |

| 125 g ai/ha | Compounds | | | | | | | | | | | | | |
|---|---|---|---|---|---|---|---|---|---|---|---|---|---|---|
| Postemergence | 1055 | 1056 | 1057 | 1058 | 1059 | 1060 | 1061 | 1062 | 1063 | 1065 | 1066 | 1067 | 1068 | 1069 |
| Barnyardgrass | 0 | 20 | 0 | 70 | 40 | 100 | 80 | 90 | 90 | 40 | 70 | 60 | 0 | 0 |
| Blackgrass | 0 | 0 | 0 | 30 | 0 | 60 | 0 | 30 | 30 | 50 | 60 | 50 | 0 | 0 |
| Corn | 0 | 0 | 0 | 0 | 0 | 90 | 0 | 0 | 50 | 20 | 40 | 0 | 0 | 0 |
| Crabgrass, Large | — | — | — | — | — | — | — | — | — | — | — | — | — | — |
| Foxtail, Giant | 0 | 0 | 0 | 0 | 0 | 90 | 20 | 90 | 90 | 70 | 90 | 90 | 0 | 0 |
| Galium | 0 | 0 | 0 | 50 | 0 | 40 | 0 | 50 | 50 | 70 | 50 | 50 | 0 | 0 |
| Kochia | 0 | 0 | 0 | 0 | 0 | 0 | 0 | 0 | 0 | 40 | 0 | 30 | 0 | 0 |
| Morningglory | — | — | — | — | — | — | — | — | — | — | — | — | — | — |
| Pigweed | 0 | 0 | 0 | 0 | 0 | 0 | 0 | 0 | 20 | 40 | 0 | 0 | 0 | 0 |
| Ragweed | 0 | 0 | 0 | 80 | 0 | 30 | 0 | 30 | 0 | 0 | 0 | 0 | 0 | 0 |
| Ryegrass, Italian | 0 | 0 | 0 | 0 | 0 | 50 | 0 | 20 | 30 | 40 | 30 | 0 | 0 | 0 |
| Velvetleaf | — | — | — | — | — | — | — | — | — | — | — | — | — | — |
| Wheat | 0 | 0 | 0 | 0 | 0 | 70 | 0 | 30 | 40 | 20 | 50 | 40 | 0 | 0 |

| 125 g ai/ha | Compounds | | | | | | | | | | | | | |
|---|---|---|---|---|---|---|---|---|---|---|---|---|---|---|
| Postemergence | 1070 | 1071 | 1072 | 1073 | 1074 | 1075 | 1076 | 1077 | 1078 | 1079 | 1080 | 1081 | 1082 | 1083 |
| Barnyardgrass | 0 | 90 | 100 | 70 | 90 | 90 | 50 | 90 | 10 | 90 | 50 | 90 | 30 | 90 |
| Blackgrass | 0 | 0 | 20 | 0 | 50 | 50 | 20 | 30 | 0 | 0 | 0 | 0 | 0 | 60 |
| Corn | 0 | 0 | 0 | 20 | 20 | 70 | 0 | 10 | 0 | 0 | 0 | 20 | 30 | 40 |
| Crabgrass, Large | — | — | — | — | — | — | — | — | — | — | — | — | — | — |
| Foxtail, Giant | 0 | 80 | 90 | 0 | 90 | 90 | 50 | 90 | 0 | 20 | 0 | 80 | 0 | 90 |
| Galium | 0 | 0 | 0 | — | — | — | 0 | 70 | 0 | 0 | 0 | 20 | 0 | 70 |
| Kochia | 0 | 0 | 0 | 0 | 20 | 30 | 0 | 0 | 0 | 20 | 0 | 0 | 0 | 40 |
| Morningglory | — | — | — | — | — | — | — | — | — | — | — | — | — | — |
| Pigweed | 0 | 0 | 0 | 0 | 0 | 0 | 0 | 0 | 0 | 0 | 0 | 0 | 0 | 20 |
| Ragweed | 0 | 0 | 0 | 30 | 0 | 40 | 0 | 0 | 0 | 0 | 0 | 0 | 0 | 30 |
| Ryegrass, Italian | 0 | 0 | 30 | 0 | 30 | 70 | 0 | 20 | 0 | 0 | 0 | 0 | 0 | 20 |
| Velvetleaf | — | — | — | — | — | — | — | — | — | — | — | — | — | — |
| Wheat | 0 | 0 | 20 | 0 | 40 | 60 | 0 | 0 | 0 | 30 | 0 | 20 | 0 | 40 |

| 125 g ai/ha | Compounds | | | | | | | | | | | | | |
|---|---|---|---|---|---|---|---|---|---|---|---|---|---|---|
| Postemergence | 1084 | 1085 | 1086 | 1087 | 1088 | 1089 | 1090 | 1091 | 1092 | 1093 | 1094 | 1095 | 1096 | 1097 |
| Barnyardgrass | 60 | 90 | 90 | 90 | 30 | 90 | — | 0 | 90 | 80 | 40 | 0 | 0 | 0 |
| Blackgrass | 20 | 20 | 0 | 30 | 0 | 30 | 20 | 0 | 20 | 0 | 0 | 0 | 0 | 0 |
| Corn | 0 | 20 | 30 | 0 | 0 | 30 | 20 | 0 | 0 | 0 | 0 | 0 | 0 | 0 |
| Crabgrass, Large | — | — | — | — | — | — | — | — | — | — | — | — | — | — |
| Foxtail, Giant | 50 | 60 | 60 | 60 | 20 | 90 | 80 | 0 | 90 | 90 | 30 | 0 | 0 | 0 |
| Galium | 0 | 60 | 20 | 70 | 30 | — | 30 | 0 | — | — | 20 | 0 | 0 | 0 |
| Kochia | 30 | 20 | 0 | 20 | 0 | 0 | 30 | 0 | 20 | 20 | 0 | 0 | 0 | 0 |
| Morningglory | — | — | — | — | — | — | — | — | — | — | — | — | — | — |
| Pigweed | 0 | 20 | 0 | 30 | 0 | 0 | 0 | 30 | 20 | 20 | 0 | 0 | 0 | 0 |
| Ragweed | 0 | 0 | 0 | 0 | 0 | 20 | 0 | 0 | 50 | 30 | 0 | 0 | 0 | 0 |

TABLE A-continued

| | | | | | | | | | | | | | | |
|---|---|---|---|---|---|---|---|---|---|---|---|---|---|---|
| Ryegrass, Italian | 0 | 20 | 0 | 0 | 0 | 0 | 0 | 0 | 0 | 0 | 0 | 0 | 0 | 0 |
| Velvetleaf | — | — | — | — | — | — | — | — | — | — | — | — | — | — |
| Wheat | 20 | 20 | 20 | 0 | 0 | 30 | 20 | 0 | 0 | 0 | 20 | 0 | 0 | 0 |

| 125 g ai/ha | Compounds | | | | | | | | | | | | | |
|---|---|---|---|---|---|---|---|---|---|---|---|---|---|---|
| Postemergence | 1098 | 1099 | 1100 | 1101 | 1102 | 1103 | 1104 | 1105 | 1106 | 1107 | 1108 | 1109 | 1110 | 1111 |
| Barnyardgrass | 80 | 70 | 60 | 70 | 80 | 70 | 30 | 30 | 80 | 0 | 0 | 100 | 90 | 0 |
| Blackgrass | 20 | 20 | 0 | 0 | 20 | 30 | 0 | 0 | 0 | 0 | 0 | 40 | 60 | 0 |
| Corn | 0 | 50 | 0 | 30 | 20 | 0 | 0 | 0 | 0 | 0 | 0 | 80 | 80 | 0 |
| Crabgrass, Large | — | — | — | — | — | — | — | — | — | — | — | — | — | — |
| Foxtail, Giant | 80 | 80 | 70 | 70 | 80 | 80 | 0 | 50 | 60 | 0 | 0 | 90 | 90 | 20 |
| Galium | 30 | 50 | 0 | 50 | 0 | 50 | 0 | 40 | 60 | 0 | 0 | 50 | 50 | 0 |
| Kochia | 20 | 30 | 0 | 30 | 0 | — | 0 | 20 | 60 | 0 | 0 | 70 | 70 | 0 |
| Morningglory | — | — | — | — | — | — | — | — | — | — | — | — | — | — |
| Pigweed | 0 | 20 | 0 | 30 | 0 | 0 | 0 | 0 | 20 | 0 | 0 | 60 | 50 | 0 |
| Ragweed | 0 | 0 | 0 | 0 | 0 | 30 | 0 | 0 | 0 | 0 | 0 | 50 | 30 | 0 |
| Ryegrass, Italian | 40 | 40 | 20 | 20 | 0 | 20 | 0 | 0 | 0 | 0 | 0 | 50 | 60 | 0 |
| Velvetleaf | — | — | — | — | — | — | — | — | — | — | — | — | — | — |
| Wheat | 0 | 20 | 0 | 0 | 20 | 20 | 0 | 0 | 0 | 0 | 0 | 60 | 70 | 0 |

| 125 g ai/ha | Compounds | | | | | | | | | | | | | |
|---|---|---|---|---|---|---|---|---|---|---|---|---|---|---|
| Postemergence | 1112 | 1113 | 1114 | 1115 | 1116 | 1117 | 1118 | 1119 | 1120 | 1121 | 1122 | 1123 | 1124 | 1125 |
| Barnyardgrass | 0 | 0 | 80 | 80 | 30 | 80 | 80 | 80 | 90 | 90 | 90 | 90 | 60 | 90 |
| Blackgrass | 0 | 0 | 20 | 30 | 0 | 0 | 20 | 50 | 30 | 40 | 40 | 30 | 0 | 40 |
| Corn | 0 | 0 | 0 | 40 | 0 | 20 | 0 | 20 | 0 | 50 | 50 | 20 | 0 | 30 |
| Crabgrass, Large | — | — | — | — | — | — | — | — | — | — | — | — | — | — |
| Foxtail, Giant | 0 | 0 | 90 | 70 | 0 | 20 | 0 | 30 | 90 | 90 | 80 | 90 | 60 | 90 |
| Galium | 0 | 0 | 0 | 0 | 0 | 40 | 50 | 40 | 40 | 50 | 50 | 40 | 50 | 40 |
| Kochia | 0 | 0 | 0 | 20 | 0 | 20 | 0 | 40 | 20 | 50 | 60 | 60 | 60 | 0 |
| Morningglory | — | — | — | — | — | — | — | — | — | — | — | — | — | — |
| Pigweed | 0 | 0 | 0 | 20 | 0 | 0 | 0 | 0 | 0 | 20 | 20 | 0 | 0 | 0 |
| Ragweed | 0 | 0 | 0 | 0 | 0 | 0 | 0 | 20 | 0 | 20 | 50 | 30 | 0 | 0 |
| Ryegrass, Italian | 0 | 0 | 0 | 20 | 0 | 0 | 20 | 30 | 20 | 40 | 30 | 30 | 0 | 0 |
| Velvetleaf | — | — | — | — | — | — | — | — | — | — | — | — | — | — |
| Wheat | 0 | 0 | 0 | 20 | 0 | 0 | 20 | 20 | 20 | 30 | 50 | 0 | 0 | 30 |

| 125 g ai/ha | Compounds | | | | | | | | | | | | | |
|---|---|---|---|---|---|---|---|---|---|---|---|---|---|---|
| Postemergence | 1126 | 1127 | 1129 | 1130 | 1131 | 1132 | 1133 | 1134 | 1135 | 1136 | 1137 | 1138 | 1139 | 1140 |
| Barnyardgrass | 90 | 0 | 40 | 0 | 70 | 90 | 80 | 60 | 0 | 30 | 0 | 90 | 60 | 90 |
| Blackgrass | 20 | 0 | 0 | 0 | 40 | 30 | 30 | 20 | 0 | 0 | 0 | 30 | 40 | 30 |
| Corn | 60 | 0 | 0 | 0 | 70 | 60 | 50 | 20 | 0 | 0 | 0 | 50 | 60 | 60 |
| Crabgrass, Large | — | — | — | — | — | — | — | — | — | — | — | — | — | — |
| Foxtail, Giant | 80 | 0 | 70 | 0 | 80 | 80 | 90 | 30 | 0 | 20 | 0 | 50 | 40 | 90 |
| Galium | 50 | 0 | 0 | 0 | 60 | 0 | 70 | 20 | 0 | 0 | 0 | 20 | 50 | 40 |
| Kochia | 50 | 0 | 0 | 0 | 60 | 0 | 30 | 0 | 0 | 0 | 0 | 0 | 0 | 0 |
| Morningglory | — | — | — | — | — | — | — | — | — | — | — | — | — | — |
| Pigweed | 0 | 0 | 0 | 0 | 50 | 0 | 0 | 0 | 0 | 0 | 0 | 0 | 0 | 0 |
| Ragweed | 40 | 0 | 0 | 0 | 50 | 0 | 60 | 0 | 0 | 0 | 0 | 0 | 0 | 0 |
| Ryegrass, Italian | 30 | 0 | 0 | 0 | 0 | 0 | 20 | 20 | 0 | 0 | 0 | 0 | 40 | 50 |
| Velvetleaf | — | — | — | — | — | — | — | — | — | — | — | — | — | — |
| Wheat | 50 | 0 | 0 | 0 | 50 | 30 | 60 | 0 | 0 | 0 | 0 | 30 | 50 | 30 |

| 125 g ai/ha | Compounds | | | | | | | | | | | | | |
|---|---|---|---|---|---|---|---|---|---|---|---|---|---|---|
| Postemergence | 1141 | 1142 | 1143 | 1144 | 1145 | 1146 | 1147 | 1148 | 1149 | 1150 | 1151 | 1152 | 1153 | 1154 |
| Barnyardgrass | 90 | 30 | 50 | 90 | 80 | 40 | 0 | 80 | 90 | 40 | 80 | 0 | 90 | 70 |
| Blackgrass | 30 | 0 | 0 | 40 | 50 | 0 | 0 | 20 | 0 | 0 | 30 | 0 | 0 | 70 |
| Corn | 20 | 0 | 0 | 50 | 50 | 30 | 0 | 0 | 0 | 20 | 60 | 0 | 0 | 90 |
| Crabgrass, Large | — | — | — | — | — | — | — | — | — | — | — | — | — | — |
| Foxtail, Giant | 90 | 60 | 40 | 90 | 90 | 20 | 0 | 80 | 80 | 50 | 70 | 20 | 60 | 90 |
| Galium | 90 | 30 | 0 | 40 | 0 | 0 | 0 | 40 | 50 | 20 | 20 | 0 | 30 | 60 |
| Kochia | 30 | 0 | 0 | 70 | 0 | 0 | 0 | 0 | 30 | 20 | 30 | 0 | 0 | 60 |
| Morningglory | — | — | — | — | — | — | — | — | — | — | — | — | — | — |
| Pigweed | 50 | 30 | 20 | 30 | 0 | 0 | 0 | 20 | 0 | 0 | 20 | 0 | 0 | 60 |
| Ragweed | 30 | 0 | 0 | 70 | 0 | 0 | 0 | 0 | 0 | 0 | 0 | 0 | 0 | 0 |
| Ryegrass, Italian | 50 | 0 | 0 | 60 | 20 | 0 | 0 | 0 | 20 | 0 | 30 | 0 | 0 | 30 |
| Velvetleaf | — | — | — | — | — | — | — | — | — | — | — | — | — | — |
| Wheat | 20 | 0 | 0 | 50 | 40 | 0 | 0 | 0 | 0 | 0 | 40 | 0 | 0 | 40 |

TABLE A-continued

| 125 g ai/ha | Compounds | | | | | | | | | | | | | |
|---|---|---|---|---|---|---|---|---|---|---|---|---|---|---|
| Postemergence | 1155 | 1156 | 1157 | 1158 | 1159 | 1160 | 1161 | 1162 | 1163 | 1164 | 1165 | 1166 | 1167 | 1168 |
| Barnyardgrass | 80 | 90 | 90 | 90 | 90 | 80 | 0 | 60 | 60 | 80 | 80 | 0 | 50 | 0 |
| Blackgrass | 0 | 0 | 0 | 20 | 0 | 0 | 0 | 0 | 20 | 0 | 0 | 0 | 0 | 0 |
| Corn | 20 | 20 | 40 | 20 | 0 | 40 | 0 | 0 | 0 | 0 | 30 | 0 | 0 | 0 |
| Crabgrass, Large | — | — | — | — | — | — | — | — | — | — | — | — | — | — |
| Foxtail, Giant | 30 | 90 | 90 | 80 | 40 | 80 | 0 | 40 | 0 | 0 | 70 | 20 | 30 | 20 |
| Galium | 40 | 40 | 50 | 20 | 20 | 0 | 0 | 50 | 20 | 30 | 60 | 0 | 20 | 30 |
| Kochia | 0 | 0 | 0 | 0 | 0 | 0 | 0 | 0 | 0 | 0 | 30 | 0 | 0 | 0 |
| Morningglory | — | — | — | — | — | — | — | — | — | — | — | — | — | — |
| Pigweed | 0 | 0 | 0 | 0 | 0 | 0 | 0 | 0 | 0 | 0 | 30 | 0 | 0 | 0 |
| Ragweed | 0 | 0 | 0 | 0 | 0 | 0 | 0 | 0 | 0 | 0 | 0 | 0 | 0 | 0 |
| Ryegrass, Italian | 0 | 20 | 0 | 30 | 0 | 20 | 0 | 0 | 0 | 0 | 20 | 0 | 0 | 0 |
| Velvetleaf | — | — | — | — | — | — | — | — | — | — | — | — | — | — |
| Wheat | 20 | 20 | 30 | 30 | 0 | 20 | 0 | 20 | 0 | 0 | 30 | 0 | 50 | 20 |

| 125 g ai/ha | Compounds | | | | | | | | | | | | | |
|---|---|---|---|---|---|---|---|---|---|---|---|---|---|---|
| Postemergence | 1169 | 1170 | 1171 | 1172 | 1173 | 1174 | 1175 | 1176 | 1177 | 1178 | 1179 | 1180 | 1181 | 1182 |
| Barnyardgrass | 80 | 60 | 70 | 0 | 70 | 70 | 90 | 90 | 70 | 0 | 0 | 0 | 0 | 0 |
| Blackgrass | 0 | 20 | 0 | 0 | 0 | 0 | 50 | 70 | 60 | 0 | 0 | 0 | 0 | 0 |
| Corn | 0 | 0 | 0 | 0 | 0 | 50 | 30 | 90 | 20 | 0 | 0 | 0 | 0 | 0 |
| Crabgrass, Large | — | — | — | — | — | — | — | — | — | — | — | — | — | — |
| Foxtail, Giant | 70 | 60 | 60 | 0 | 80 | 80 | 80 | 80 | 50 | 0 | 0 | 0 | 0 | 0 |
| Galium | 0 | 30 | 0 | 0 | 50 | 0 | 40 | 50 | 20 | 30 | 0 | 0 | 0 | 0 |
| Kochia | 20 | — | 0 | 0 | 50 | 0 | 0 | 40 | 0 | 20 | — | 0 | — | 0 |
| Morningglory | — | — | — | — | — | — | — | — | — | — | — | — | — | — |
| Pigweed | 0 | 0 | 0 | 0 | 50 | 0 | 20 | 0 | 0 | 0 | 0 | 0 | 0 | 0 |
| Ragweed | 0 | 0 | 0 | 0 | 10 | 0 | 30 | 30 | 0 | 0 | 0 | 0 | 0 | 0 |
| Ryegrass, Italian | 0 | 0 | 0 | 0 | 20 | 0 | 50 | 30 | 40 | 0 | 0 | 0 | 0 | 0 |
| Velvetleaf | — | — | — | — | — | — | — | — | — | — | — | — | — | — |
| Wheat | 0 | 0 | 0 | 0 | 0 | 30 | 40 | 90 | 20 | 0 | 0 | 0 | 0 | 0 |

| 125 g ai/ha | Compounds | | | | | | | | | | | | | |
|---|---|---|---|---|---|---|---|---|---|---|---|---|---|---|
| Postemergence | 1183 | 1184 | 1185 | 1186 | 1187 | 1188 | 1189 | 1190 | 1191 | 1192 | 1193 | 1194 | 1195 | 1196 |
| Barnyardgrass | 90 | 80 | 50 | 100 | 100 | 100 | 100 | 60 | 0 | 100 | 70 | 0 | 0 | 70 |
| Blackgrass | 50 | 60 | 50 | 80 | 40 | 70 | 40 | 0 | 0 | 0 | 0 | 0 | 0 | 0 |
| Corn | 60 | 40 | 20 | 80 | 0 | 50 | 20 | 0 | 0 | 40 | 0 | 0 | 0 | 0 |
| Crabgrass, Large | — | — | — | — | — | — | — | — | — | — | — | — | — | — |
| Foxtail, Giant | 80 | 80 | 60 | 90 | 80 | 80 | 80 | 20 | 0 | 70 | 30 | 0 | 0 | 30 |
| Galium | 0 | 20 | 0 | 60 | 50 | 60 | 50 | 20 | 0 | 50 | 0 | 0 | 0 | 0 |
| Kochia | 0 | 0 | 0 | 60 | 20 | 50 | 20 | 0 | 0 | 40 | 0 | 0 | 0 | 0 |
| Morningglory | — | — | — | — | — | — | — | — | — | — | — | — | — | — |
| Pigweed | 0 | 0 | 0 | 0 | 0 | 20 | 0 | 0 | 0 | 20 | 0 | 0 | 0 | 0 |
| Ragweed | 0 | 0 | 0 | 70 | 0 | 40 | 40 | 0 | 0 | 0 | 0 | 0 | 0 | 0 |
| Ryegrass, Italian | 50 | 30 | 20 | 50 | 20 | 40 | 20 | 0 | 0 | 0 | 0 | 0 | 0 | 0 |
| Velvetleaf | — | — | — | — | — | — | — | — | — | — | — | — | — | — |
| Wheat | 50 | 60 | 40 | 60 | 20 | 40 | 20 | 0 | 0 | 0 | 0 | 0 | 0 | 0 |

| 125 g ai/ha | Compounds | | | | | | | | | | | | | |
|---|---|---|---|---|---|---|---|---|---|---|---|---|---|---|
| Postemergence | 1197 | 1198 | 1199 | 1200 | 1201 | 1202 | 1203 | 1204 | 1205 | 1206 | 1207 | 1208 | 1209 | 1210 |
| Barnyardgrass | — | 80 | 70 | 0 | 70 | — | — | — | 40 | 70 | 70 | 100 | — | — |
| Blackgrass | 50 | 20 | 0 | 0 | 0 | 0 | 20 | 50 | 0 | 0 | 0 | 0 | 0 | 0 |
| Corn | 80 | 0 | 0 | 0 | 0 | 20 | 40 | 70 | 70 | 0 | 0 | 20 | 0 | 0 |
| Crabgrass, Large | — | — | — | — | — | — | — | — | — | — | — | — | — | — |
| Foxtail, Giant | 90 | 80 | 70 | 0 | 70 | 70 | 90 | 90 | 80 | 50 | 50 | 70 | 80 | 90 |
| Galium | 60 | 40 | 20 | 0 | 30 | 0 | 50 | 50 | 20 | 30 | 20 | 40 | 0 | 0 |
| Kochia | 70 | 60 | 20 | 0 | 40 | 30 | 40 | 80 | 0 | 50 | 20 | 70 | 0 | 0 |
| Morningglory | — | — | — | — | — | — | — | — | — | — | — | — | — | — |
| Pigweed | 50 | 40 | 0 | 0 | 20 | 0 | 0 | 70 | 0 | 0 | 0 | 30 | 0 | 0 |
| Ragweed | 50 | 0 | 0 | 0 | 0 | 0 | 20 | 20 | 0 | 0 | 0 | 0 | 0 | 0 |
| Ryegrass, Italian | 30 | 0 | 0 | 0 | 0 | 0 | 0 | 70 | 0 | 0 | 0 | 0 | 0 | 30 |
| Velvetleaf | — | — | — | — | — | — | — | — | — | — | — | — | — | — |
| Wheat | 50 | 0 | 0 | 0 | 0 | 0 | 0 | 60 | 30 | 0 | 0 | 0 | 0 | 0 |

| 125 g ai/ha | Compounds | | | | | | | | | | | | | |
|---|---|---|---|---|---|---|---|---|---|---|---|---|---|---|
| Postemergence | 1211 | 1212 | 1213 | 1214 | 1215 | 1216 | 1217 | 1218 | 1219 | 1220 | 1221 | 1222 | 1223 | 1224 |
| Barnyardgrass | 100 | 80 | 100 | 90 | — | — | — | — | 30 | 70 | 30 | 0 | 30 | 70 |
| Blackgrass | 30 | 0 | 20 | 80 | 0 | 0 | 0 | 0 | 0 | 30 | 60 | 0 | 30 | 0 |
| Corn | 80 | 0 | 50 | 80 | 0 | 0 | 0 | 0 | 0 | 30 | 0 | 0 | 0 | 0 |
| Crabgrass, Large | — | — | — | — | — | — | — | — | — | — | — | — | — | — |

TABLE A-continued

| | | | | | | | | | | | | | |
|---|---|---|---|---|---|---|---|---|---|---|---|---|---|
| Foxtail, Giant | 80 | 70 | 90 | 90 | 70 | 20 | 90 | 0 | 50 | 80 | 90 | 20 | 90 | 30 |
| Galium | 50 | 50 | 50 | 60 | 0 | 0 | 0 | 0 | 0 | 30 | 40 | 0 | 20 | 0 |
| Kochia | 0 | 60 | 50 | 60 | 0 | 0 | 0 | 0 | — | — | — | — | — | 0 |
| Morningglory | — | — | — | — | — | — | — | — | — | — | — | — | — | — |
| Pigweed | 30 | 50 | 0 | 30 | 0 | 0 | 0 | 0 | 0 | 20 | 0 | 0 | 0 | 0 |
| Ragweed | 0 | 0 | 0 | 0 | 0 | 0 | 0 | 0 | 20 | 0 | 0 | 0 | 0 | 0 |
| Ryegrass, Italian | 0 | 0 | 0 | 60 | 0 | 0 | 0 | 0 | 0 | 20 | 20 | 0 | 20 | 0 |
| Velvetleaf | — | — | — | — | — | — | — | — | — | — | — | — | — | — |
| Wheat | 30 | 0 | 40 | 70 | 0 | 0 | 0 | 0 | 0 | 20 | 20 | 0 | 0 | 0 |

| 125 g ai/ha | Compounds | | | | | | | | | | | | |
|---|---|---|---|---|---|---|---|---|---|---|---|---|---|
| Postemergence | 1225 | 1226 | 1227 | 1228 | 1229 | 1230 | 1231 | 1232 | 1233 | 1234 | 1235 | 1236 | 1237 | 1238 |
| Barnyardgrass | 90 | 100 | 0 | 90 | 100 | 30 | 80 | 80 | 80 | 90 | 90 | 100 | 20 | 50 |
| Blackgrass | 30 | 20 | 0 | 0 | 0 | 0 | 0 | 0 | 0 | 30 | 30 | 30 | 0 | 30 |
| Corn | 30 | 30 | 0 | 20 | 0 | 0 | 70 | 0 | 70 | 80 | 70 | 60 | 0 | 20 |
| Crabgrass, Large | — | — | — | — | — | — | — | — | — | — | — | — | — | — |
| Foxtail, Giant | 90 | 80 | 0 | 80 | 90 | 60 | 80 | 80 | 80 | 80 | 80 | 30 | 20 | 60 |
| Galium | 50 | 80 | 0 | 20 | 40 | 20 | 50 | 20 | 20 | 50 | 50 | 50 | 0 | 20 |
| Kochia | — | 60 | 0 | 60 | 70 | 30 | — | — | — | 40 | 30 | 20 | 0 | 30 |
| Morningglory | — | — | — | — | — | — | — | — | — | — | — | — | — | — |
| Pigweed | 30 | 20 | 20 | 20 | 40 | 30 | 0 | 0 | 0 | 20 | 0 | 20 | 0 | 0 |
| Ragweed | 40 | 0 | 0 | 0 | 0 | 0 | 0 | 0 | 0 | 30 | 0 | 0 | 0 | 0 |
| Ryegrass, Italian | 30 | 0 | 0 | 0 | 0 | 0 | 40 | 30 | 40 | 40 | 0 | 0 | 0 | 20 |
| Velvetleaf | — | — | — | — | — | — | — | — | — | — | — | — | — | — |
| Wheat | 30 | 0 | 0 | 0 | 0 | 0 | 50 | 0 | 40 | 40 | 40 | 0 | 0 | 0 |

| 125 g ai/ha | Compounds | | | | | | | | | | | | |
|---|---|---|---|---|---|---|---|---|---|---|---|---|---|
| Postemergence | 1239 | 1240 | 1241 | 1242 | 1243 | 1244 | 1245 | 1246 | 1247 | 1248 | 1249 | 1250 | 1251 | 1252 |
| Barnyardgrass | 90 | 0 | 0 | 20 | 0 | 50 | 40 | 50 | 40 | 0 | 100 | 70 | 80 | 80 |
| Blackgrass | 70 | 0 | 0 | 0 | 0 | 0 | 30 | 0 | 0 | 0 | 40 | 20 | 0 | 50 |
| Corn | 50 | 0 | 0 | 0 | 0 | 0 | 0 | 0 | 0 | 0 | 70 | 40 | 20 | 80 |
| Crabgrass, Large | — | — | — | — | — | — | — | — | — | — | — | — | — | — |
| Foxtail, Giant | 90 | 0 | 0 | 20 | 0 | 50 | 20 | 20 | 0 | 0 | 80 | 80 | 70 | 80 |
| Galium | 60 | 0 | 0 | 0 | 0 | 0 | 30 | 50 | 0 | 0 | 50 | 40 | 50 | 50 |
| Kochia | 40 | 0 | 0 | 0 | 0 | 0 | 0 | 0 | 0 | 0 | 40 | 0 | 50 | 20 |
| Morningglory | — | — | — | — | — | — | — | — | — | — | — | — | — | — |
| Pigweed | 50 | 0 | 0 | 0 | 0 | 0 | 0 | 0 | 0 | 0 | 30 | 0 | 70 | 0 |
| Ragweed | 20 | 0 | 0 | 0 | 0 | 0 | 0 | 10 | 0 | 0 | 0 | 0 | 0 | 0 |
| Ryegrass, Italian | 20 | 0 | 0 | 0 | 0 | 0 | 0 | 0 | 0 | 0 | 30 | 20 | 20 | 70 |
| Velvetleaf | — | — | — | — | — | — | — | — | — | — | — | — | — | — |
| Wheat | 30 | 0 | 0 | 0 | 0 | 0 | 0 | 0 | 0 | 0 | 50 | 40 | 30 | 70 |

| 125 g ai/ha | Compounds | | | | | | | | | | | | |
|---|---|---|---|---|---|---|---|---|---|---|---|---|---|
| Postemergence | 1253 | 1254 | 1255 | 1256 | 1257 | 1258 | 1259 | 1260 | 1261 | 1262 | 1263 | 1264 | 1265 | 1266 |
| Barnyardgrass | 90 | 80 | 90 | 50 | 0 | 70 | 80 | 90 | 90 | 90 | 0 | 0 | 90 | 90 |
| Blackgrass | 30 | 0 | 0 | 0 | 0 | 0 | 0 | 70 | 60 | 50 | 0 | 0 | 50 | 60 |
| Corn | 0 | 20 | 60 | 0 | 0 | 40 | 70 | 90 | 80 | 60 | 0 | 0 | 70 | 90 |
| Crabgrass, Large | — | — | — | — | — | — | — | — | — | — | — | — | — | — |
| Foxtail, Giant | 80 | 80 | 80 | 60 | 0 | 60 | 70 | 80 | 90 | 80 | 0 | 0 | 80 | 80 |
| Galium | 50 | 30 | 40 | 40 | 0 | 80 | 80 | 70 | 60 | 70 | 0 | 0 | 60 | 60 |
| Kochia | 60 | 0 | 20 | 20 | 0 | 0 | 0 | 60 | 50 | 50 | 0 | 0 | 70 | 70 |
| Morningglory | — | — | — | — | — | — | — | — | — | — | — | — | — | — |
| Pigweed | 0 | 0 | 0 | 20 | 0 | 30 | 60 | 50 | 30 | 70 | 0 | 0 | 70 | 70 |
| Ragweed | 0 | 0 | 0 | 0 | 0 | 0 | 0 | 50 | 30 | 30 | 0 | 0 | 30 | 50 |
| Ryegrass, Italian | 40 | 0 | 20 | 20 | 0 | 0 | 0 | 60 | 50 | 20 | 0 | 0 | 30 | 70 |
| Velvetleaf | — | — | — | — | — | — | — | — | — | — | — | — | — | — |
| Wheat | 0 | 20 | 40 | 20 | 0 | 0 | 20 | 90 | 50 | 30 | 0 | 0 | 50 | 50 |

| 125 g ai/ha | Compounds | | | | | | | | | | | | |
|---|---|---|---|---|---|---|---|---|---|---|---|---|---|
| Postemergence | 1267 | 1268 | 1269 | 1270 | 1271 | 1272 | 1273 | 1274 | 1275 | 1276 | 1277 | 1278 | 1279 | 1280 |
| Barnyardgrass | 90 | 90 | 90 | 90 | 60 | 70 | 60 | 90 | 90 | 100 | 80 | 100 | 50 | 0 |
| Blackgrass | 0 | 0 | 40 | 40 | 30 | 40 | 20 | 30 | 0 | 0 | 0 | 0 | 20 | 0 |
| Corn | 0 | 0 | 80 | 20 | 40 | 50 | 60 | 30 | 0 | 0 | 0 | 0 | 0 | 0 |
| Crabgrass, Large | — | — | — | — | — | — | — | — | — | — | — | — | — | — |
| Foxtail, Giant | 90 | 90 | 80 | 80 | 80 | 80 | 80 | 90 | 70 | 60 | 70 | 80 | 20 | 0 |
| Galium | 0 | 0 | 60 | 70 | 60 | 60 | 50 | 60 | 0 | 0 | 0 | 0 | 30 | 0 |
| Kochia | 0 | 0 | 40 | 60 | 40 | 20 | 60 | 70 | 0 | 0 | 0 | 20 | 0 | 0 |
| Morningglory | — | — | — | — | — | — | — | — | — | — | — | — | — | — |
| Pigweed | 0 | 0 | 30 | 60 | 30 | 0 | 40 | 20 | 0 | 0 | 0 | 0 | 0 | 0 |

TABLE A-continued

| | | | | | | | | | | | | | | |
|---|---|---|---|---|---|---|---|---|---|---|---|---|---|---|
| Ragweed | 0 | 0 | 0 | 0 | 0 | 0 | 0 | 30 | 0 | 0 | 30 | 30 | 0 | 0 |
| Ryegrass, Italian | 0 | 20 | 30 | 30 | 30 | 30 | 40 | 20 | 0 | 0 | 0 | 0 | 0 | 0 |
| Velvetleaf | — | — | — | — | — | — | — | — | — | — | — | — | — | — |
| Wheat | 0 | 0 | 60 | 40 | 60 | 50 | 30 | 60 | 0 | 0 | 0 | 0 | 0 | 0 |

| 125 g ai/ha | Compounds | | | | | | | | | | | | |
|---|---|---|---|---|---|---|---|---|---|---|---|---|---|
| Postemergence | 1281 | 1282 | 1283 | 1284 | 1285 | 1286 | 1287 | 1288 | 1289 | 1290 | 1291 | 1292 | 1293 | 1294 |
| Barnyardgrass | 20 | 100 | 0 | 0 | 80 | 90 | 90 | 0 | 0 | 0 | 90 | 0 | 20 | 20 |
| Blackgrass | 0 | 0 | 0 | 0 | 0 | 40 | 20 | 0 | 0 | 0 | 0 | 0 | 0 | 0 |
| Corn | 0 | 30 | 0 | 0 | 0 | 80 | 0 | 0 | 0 | 0 | 30 | 0 | 0 | 0 |
| Crabgrass, Large | — | — | — | — | — | — | — | — | — | — | — | — | — | — |
| Foxtail, Giant | 20 | 80 | 0 | 0 | 70 | 90 | 80 | 0 | 0 | 0 | 80 | 0 | 0 | 20 |
| Galium | 0 | 70 | 0 | 0 | 30 | 40 | 40 | 0 | 0 | 0 | 20 | 0 | 0 | 0 |
| Kochia | 0 | 60 | 0 | 0 | 0 | 30 | 30 | 0 | 0 | 0 | 0 | 0 | 0 | 0 |
| Morningglory | — | — | — | — | — | — | — | — | — | — | — | — | — | — |
| Pigweed | 0 | 20 | 0 | 0 | 20 | 20 | 0 | 0 | 0 | 0 | 0 | 0 | 0 | 0 |
| Ragweed | 0 | 40 | 0 | 0 | 0 | 0 | 0 | 0 | 0 | 0 | 0 | 0 | 0 | 0 |
| Ryegrass, Italian | 0 | 40 | 0 | 0 | 0 | 0 | 0 | 0 | 0 | 0 | 0 | 0 | 0 | 0 |
| Velvetleaf | — | — | — | — | — | — | — | — | — | — | — | — | — | — |
| Wheat | 0 | 50 | 0 | 0 | 0 | 0 | 0 | 0 | 0 | 0 | 30 | 0 | 0 | 0 |

| 125 g ai/ha | Compounds | | | | | | | | | | | | |
|---|---|---|---|---|---|---|---|---|---|---|---|---|---|
| Postemergence | 1295 | 1296 | 1297 | 1298 | 1299 | 1300 | 1301 | 1302 | 1303 | 1304 | 1305 | 1306 | 1307 | 1308 |
| Barnyardgrass | 0 | 30 | 20 | 80 | 90 | 80 | 20 | 60 | 0 | 0 | 60 | 20 | 40 | 80 |
| Blackgrass | 0 | 0 | 0 | 0 | 20 | 30 | 0 | 0 | 0 | 0 | 0 | 0 | 0 | 30 |
| Corn | 0 | 0 | 0 | 0 | 40 | 20 | 0 | 0 | 0 | 0 | 0 | 0 | 0 | 20 |
| Crabgrass, Large | — | — | — | — | — | — | — | — | — | — | — | — | — | — |
| Foxtail, Giant | 0 | 30 | 20 | 70 | 90 | 80 | 20 | 30 | 40 | 0 | 80 | 0 | 0 | 20 |
| Galium | 0 | 0 | 0 | 0 | 40 | 20 | 20 | 0 | 0 | 0 | 0 | 20 | 30 | 30 |
| Kochia | 0 | 0 | 0 | 0 | 0 | 0 | 0 | 0 | — | 0 | 0 | 0 | 0 | 0 |
| Morningglory | — | — | — | — | — | — | — | — | — | — | — | — | — | — |
| Pigweed | 0 | 0 | 0 | 0 | 0 | 0 | 0 | 0 | 0 | 0 | 0 | 0 | 0 | 0 |
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 0 | 20 | 0 | 0 | 0 | 0 | 0 | 0 | 0 | 0 | 0 |
| Velvetleaf | — | — | — | — | — | — | — | — | — | — | — | — | — | — |
| Wheat | 0 | 0 | 0 | 0 | 30 | 0 | 0 | 0 | 0 | 0 | 0 | 0 | 0 | 20 |

| 125 g ai/ha | Compounds | | | | | | | | | | | | |
|---|---|---|---|---|---|---|---|---|---|---|---|---|---|
| Postemergence | 1309 | 1310 | 1311 | 1312 | 1313 | 1314 | 1316 | 1317 | 1318 | 1319 | 1320 | 1321 | 1323 | 1324 |
| Barnyardgrass | 90 | 90 | — | — | — | — | 90 | 90 | 80 | 90 | 0 | 90 | 90 | 90 |
| Blackgrass | 0 | 0 | 60 | 50 | 0 | 0 | 70 | 80 | 70 | 70 | 0 | 30 | 50 | 40 |
| Corn | 0 | 0 | 70 | 40 | 0 | 30 | 80 | 80 | 60 | 70 | 0 | 40 | 50 | 60 |
| Crabgrass, Large | — | — | — | — | — | — | — | — | — | — | — | — | — | — |
| Foxtail, Giant | 30 | 80 | 90 | 90 | 90 | 90 | 90 | 90 | 90 | 90 | 0 | 90 | 90 | 90 |
| Galium | 30 | 50 | 50 | 50 | 0 | 30 | 60 | 60 | 60 | 60 | 30 | 30 | 50 | 30 |
| Kochia | 0 | 0 | 30 | 50 | 20 | 50 | 30 | 20 | 0 | 20 | 0 | 0 | 0 | 30 |
| Morningglory | — | — | — | — | — | — | — | — | — | — | — | — | — | — |
| Pigweed | 0 | 0 | 0 | 0 | 0 | 0 | 50 | 30 | 30 | 0 | 0 | 0 | 0 | 0 |
| Ragweed | 0 | 0 | 0 | 0 | 0 | 0 | 30 | 0 | 10 | 0 | 0 | 0 | 0 | 20 |
| Ryegrass, Italian | 0 | 0 | 40 | 30 | 0 | 0 | 50 | 40 | 20 | 40 | 0 | 20 | 40 | 30 |
| Velvetleaf | — | — | — | — | — | — | — | — | — | — | — | — | — | — |
| Wheat | 20 | 0 | 60 | 30 | 0 | 20 | 60 | 60 | 50 | 60 | 0 | 20 | 50 | 30 |

| 125 g ai/ha | Compounds | | | | | | | | | | | | |
|---|---|---|---|---|---|---|---|---|---|---|---|---|---|
| Postemergence | 1325 | 1326 | 1327 | 1328 | 1329 | 1330 | 1331 | 1332 | 1333 | 1334 | 1335 | 1336 | 1337 | 1338 |
| Barnyardgrass | 90 | 70 | 90 | 60 | 90 | 90 | 90 | 50 | 70 | 0 | 0 | 0 | 30 | 80 |
| Blackgrass | — | 0 | 0 | 0 | 20 | 50 | 20 | 0 | 0 | 0 | 0 | 0 | 0 | 0 |
| Corn | 0 | 0 | 0 | 0 | 30 | 90 | 20 | 0 | 0 | 0 | 0 | 0 | 0 | 0 |
| Crabgrass, Large | — | — | — | — | — | — | — | — | — | — | — | — | — | — |
| Foxtail, Giant | 80 | 0 | 20 | 0 | 90 | 90 | 90 | 40 | 60 | 0 | 0 | 0 | 40 | 80 |
| Galium | 80 | 0 | 30 | 0 | 30 | 30 | 0 | 0 | 0 | 50 | 0 | 0 | 0 | 30 |
| Kochia | 70 | 0 | 0 | 0 | 40 | 0 | 0 | 0 | 0 | 0 | 0 | 0 | 20 | 0 |
| Morningglory | — | — | — | — | — | — | — | — | — | — | — | — | — | — |
| Pigweed | 70 | 0 | 0 | 0 | 0 | 0 | 0 | 0 | 10 | 30 | 0 | 0 | 20 | 0 |
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 0 | 0 | 0 | 0 | 20 | 0 |
| Velvetleaf | — | — | — | — | — | — | — | — | — | — | — | — | — | — |
| Wheat | 0 | 0 | 0 | 0 | 0 | 50 | 0 | 0 | 0 | 0 | 0 | 0 | 20 | 0 |

TABLE A-continued

| 125 g ai/ha | Compounds | | | | | | | | | | | | | |
|---|---|---|---|---|---|---|---|---|---|---|---|---|---|
| Postemergence | 1339 | 1340 | 1341 | 1342 | 1343 | 1344 | 1345 | 1346 | 1347 | 1348 | 1349 | 1350 | 1351 | 1352 |
| Barnyardgrass | 90 | 30 | 90 | 90 | 90 | 0 | 90 | 80 | 90 | 90 | 90 | 90 | 0 | 60 |
| Blackgrass | 0 | 0 | 0 | 0 | 0 | 0 | 20 | 20 | 60 | 50 | 20 | 50 | 0 | 30 |
| Corn | 0 | 20 | 0 | 0 | 0 | 0 | 0 | 40 | 30 | 80 | 0 | 50 | 0 | 0 |
| Crabgrass, Large | — | — | — | — | — | — | — | — | — | — | — | — | — | — |
| Foxtail, Giant | 80 | 50 | 0 | 70 | 90 | 0 | 90 | 90 | 90 | 90 | 80 | 90 | 0 | 80 |
| Galium | 50 | 20 | — | — | — | 0 | 20 | — | 70 | 70 | 60 | — | — | — |
| Kochia | 20 | 20 | 0 | 20 | 50 | 0 | 0 | 30 | 80 | 50 | 30 | 70 | 0 | 0 |
| Morningglory | — | — | — | — | — | — | — | — | — | — | — | — | — | — |
| Pigweed | 30 | 0 | 0 | 0 | 0 | 0 | 0 | 20 | 90 | 0 | 0 | 70 | 0 | 0 |
| Ragweed | 20 | 0 | 0 | 0 | 30 | 0 | 0 | 0 | 70 | 20 | 0 | 60 | 0 | 0 |
| Ryegrass, Italian | 0 | 0 | 0 | 0 | 20 | 0 | 0 | 20 | 40 | 30 | 20 | 20 | 0 | 0 |
| Velvetleaf | — | — | — | — | — | — | — | — | — | — | — | — | — | — |
| Wheat | 0 | 0 | 0 | 0 | 30 | 0 | 0 | 60 | 30 | 60 | 0 | 50 | 0 | 20 |

| 125 g ai/ha | Compounds | | | | | | | | | | | | |
|---|---|---|---|---|---|---|---|---|---|---|---|---|---|
| Postemergence | 1353 | 1354 | 1355 | 1356 | 1357 | 1358 | 1359 | 1360 | 1361 | 1362 | 1366 | 1367 | 1368 | 1369 |
| Barnyardgrass | 90 | 20 | 0 | 0 | 0 | 0 | 0 | 0 | 0 | 0 | 70 | 30 | 50 | 60 |
| Blackgrass | 20 | 0 | — | — | — | — | — | — | — | — | 0 | 0 | 30 | 20 |
| Corn | 0 | 0 | 0 | 0 | 0 | 0 | 0 | 0 | 0 | 0 | 0 | 0 | 0 | 0 |
| Crabgrass, Large | — | — | 0 | 0 | 0 | 0 | 0 | 0 | 0 | 0 | — | — | — | — |
| Foxtail, Giant | 70 | 60 | 0 | 0 | 0 | 0 | 0 | 0 | 0 | 0 | 70 | 30 | 40 | 50 |
| Galium | — | 40 | — | — | — | — | — | — | — | — | 70 | 0 | 30 | 30 |
| Kochia | 20 | 20 | — | — | — | — | — | — | — | — | 0 | 0 | 20 | 20 |
| Morningglory | — | — | 0 | 0 | 0 | 0 | 0 | 0 | 0 | 0 | — | — | — | — |
| Pigweed | 20 | 0 | 0 | 0 | 0 | 0 | 0 | 0 | 0 | 0 | 80 | 20 | 0 | 20 |
| Ragweed | 0 | 0 | — | — | — | — | — | — | — | — | 0 | 0 | 0 | 20 |
| Ryegrass, Italian | 0 | 0 | — | — | — | — | — | — | — | — | 0 | 0 | 40 | 30 |
| Velvetleaf | — | — | 0 | 0 | 0 | 0 | 0 | 0 | 0 | 0 | — | — | — | — |
| Wheat | 0 | 0 | 0 | 0 | 0 | 0 | 0 | 0 | 0 | 0 | 0 | 0 | 0 | 0 |

| 125 g ai/ha | Compounds | | | | | | | | | | | | |
|---|---|---|---|---|---|---|---|---|---|---|---|---|---|
| Postemergence | 1370 | 1371 | 1372 | 1373 | 1374 | 1375 | 1376 | 1377 | 1378 | 1379 | 1380 | 1381 | 1382 | 1383 |
| Barnyardgrass | — | 80 | — | — | 0 | 100 | 90 | 90 | 80 | 100 | 60 | 80 | 0 | 100 |
| Blackgrass | 50 | 40 | 50 | 50 | 0 | 40 | 20 | 20 | 30 | 20 | 40 | 40 | 0 | 40 |
| Corn | 30 | 40 | 70 | 90 | 0 | 30 | 0 | 50 | 80 | 70 | 50 | 40 | 0 | 80 |
| Crabgrass, Large | — | — | — | — | — | — | — | — | — | — | — | — | — | — |
| Foxtail, Giant | 90 | 90 | 90 | 90 | 0 | 90 | 80 | 80 | 80 | 80 | 90 | 90 | 0 | 90 |
| Galium | 40 | 70 | 60 | 60 | 0 | 50 | 0 | 40 | 60 | 40 | 50 | 50 | 0 | 60 |
| Kochia | 50 | 50 | 70 | 80 | 0 | 50 | 0 | 50 | — | 30 | — | — | 0 | 70 |
| Morningglory | — | — | — | — | — | — | — | — | — | — | — | — | — | — |
| Pigweed | 0 | 30 | 60 | 70 | 0 | 0 | 0 | 20 | 30 | 20 | 50 | 70 | 0 | 40 |
| Ragweed | 0 | 20 | 60 | 60 | 0 | 20 | 0 | 20 | 40 | 30 | 40 | 50 | 0 | 50 |
| Ryegrass, Italian | 40 | 30 | 20 | 30 | 0 | 20 | 0 | 30 | 40 | 30 | 50 | 50 | 0 | 40 |
| Velvetleaf | — | — | — | — | — | — | — | — | — | — | — | — | — | — |
| Wheat | 40 | 10 | 70 | 50 | 0 | 30 | 0 | 30 | 60 | 30 | 40 | 30 | 0 | 60 |

| 125 g ai/ha | Compounds | | | | | | | | | | | | |
|---|---|---|---|---|---|---|---|---|---|---|---|---|---|
| Postemergence | 1384 | 1385 | 1386 | 1387 | 1388 | 1389 | 1390 | 1391 | 1392 | 1393 | 1394 | 1395 | 1396 | 1397 |
| Barnyardgrass | 90 | 80 | 90 | 60 | 100 | 90 | 90 | 90 | 0 | 90 | 90 | 90 | 80 | 90 |
| Blackgrass | 0 | 20 | 70 | 0 | 70 | 50 | 30 | 40 | 0 | 30 | 0 | 70 | 50 | 70 |
| Corn | 70 | 0 | 70 | 0 | 60 | 90 | 70 | 0 | 0 | 80 | 40 | 50 | 60 | 90 |
| Crabgrass, Large | — | — | — | — | — | — | — | — | — | — | — | — | — | — |
| Foxtail, Giant | 80 | 70 | 90 | 60 | 90 | 80 | 90 | 90 | 0 | 90 | 80 | 90 | 80 | 90 |
| Galium | 30 | 30 | 60 | 30 | 50 | 60 | 50 | 70 | 0 | 60 | 50 | 0 | 70 | 60 |
| Kochia | 40 | 0 | 70 | 0 | 30 | 60 | 40 | 70 | 0 | 70 | 0 | 0 | 70 | 0 |
| Morningglory | — | — | — | — | — | — | — | — | — | — | — | — | — | — |
| Pigweed | 0 | 0 | 40 | 0 | 40 | 30 | 40 | 70 | 0 | 60 | 0 | 0 | 70 | 0 |
| Ragweed | 40 | 0 | 20 | 0 | 0 | 0 | 0 | 20 | 0 | 50 | 0 | 0 | 50 | 0 |
| Ryegrass, Italian | 30 | 0 | 40 | 0 | 60 | 70 | 20 | 40 | 0 | 20 | 0 | 20 | 40 | 40 |
| Velvetleaf | — | — | — | — | — | — | — | — | — | — | — | — | — | — |
| Wheat | 0 | 0 | 50 | 0 | 50 | 60 | 30 | 30 | 0 | 30 | 0 | 20 | 70 | 70 |

| 125 g ai/ha | Compounds | | | |
|---|---|---|---|---|
| Postemergence | 1398 | 1399 | 1400 | 1402 |
| Barnyardgrass | 100 | 90 | 90 | 90 |
| Blackgrass | 60 | 20 | 70 | 50 |
| Corn | 40 | 0 | 40 | 0 |
| Crabgrass, Large | — | — | — | — |

TABLE A-continued

| | | | | | | | | | | | | | |
|---|---|---|---|---|---|---|---|---|---|---|---|---|---|
| Foxtail, Giant | | 90 | | | 90 | | | 90 | | | 90 | | |
| Galium | | 50 | | | 60 | | | 70 | | | 70 | | |
| Kochia | | 60 | | | 70 | | | 70 | | | 70 | | |
| Morningglory | | — | | | — | | | — | | | — | | |
| Pigweed | | 0 | | | 40 | | | 60 | | | 0 | | |
| Ragweed | | 30 | | | 40 | | | 50 | | | 20 | | |
| Ryegrass, Italian | | 40 | | | 20 | | | 50 | | | 0 | | |
| Velvetleaf | | — | | | — | | | — | | | — | | |
| Wheat | | 60 | | | 20 | | | 60 | | | 40 | | |

| 31 g ai/ha | Compounds | | | | | | | | | | | | |
|---|---|---|---|---|---|---|---|---|---|---|---|---|---|
| Postemergence | 770 | 792 | 793 | 794 | 795 | 796 | 797 | 798 | 799 | 800 | 801 | 802 | 803 | 804 |
| Barnyardgrass | 30 | 0 | 0 | 0 | 20 | 80 | 90 | 40 | 40 | 80 | 80 | 80 | 80 | 20 |
| Blackgrass | 0 | 0 | 0 | 0 | 0 | 0 | 0 | 0 | 0 | 0 | 20 | 20 | 20 | 0 |
| Corn | 0 | 0 | 0 | 0 | 0 | 70 | 60 | 0 | 0 | 0 | 20 | 20 | 20 | 0 |
| Foxtail, Giant | 60 | 0 | 0 | 0 | 0 | 80 | 80 | 20 | 40 | 80 | 70 | 70 | 90 | 60 |
| Galium | 30 | 0 | 0 | 0 | 0 | 0 | 0 | 0 | 0 | 0 | 30 | 0 | 30 | 40 |
| Kochia | 0 | 0 | 0 | 0 | 0 | 0 | 0 | 0 | 0 | 0 | 20 | 20 | 50 | 40 |
| Pigweed | 0 | 0 | 0 | 0 | 0 | 0 | 0 | 0 | 0 | 20 | 30 | 30 | 30 | 50 |
| Ragweed | 0 | 0 | 0 | 0 | 0 | 0 | 0 | 0 | 0 | 0 | 0 | 0 | 30 | 0 |
| Ryegrass, Italian | 0 | 0 | 0 | 0 | 0 | 0 | 0 | 0 | 0 | 0 | 0 | 0 | 0 | 0 |
| Wheat | 0 | 0 | 0 | 0 | 0 | 30 | 0 | 0 | 0 | 0 | 0 | 0 | 0 | 0 |

| 31 g ai/ha | Compounds | | | | | | | | | | | | |
|---|---|---|---|---|---|---|---|---|---|---|---|---|---|
| Postemergence | 805 | 806 | 807 | 808 | 809 | 810 | 811 | 812 | 813 | 814 | 970 | 971 | 972 | 997 |
| Barnyardgrass | 0 | 0 | 70 | 50 | 0 | 40 | 0 | 90 | 40 | 0 | 0 | 50 | 50 | 0 |
| Blackgrass | 0 | 0 | 0 | 0 | 0 | 0 | 0 | 40 | 30 | 0 | 0 | 40 | 0 | 0 |
| Corn | 0 | 0 | 0 | 0 | 0 | 0 | 0 | 30 | 30 | 0 | 0 | 70 | 20 | 0 |
| Foxtail, Giant | 0 | 0 | 70 | 70 | 0 | 60 | 0 | 70 | 70 | 0 | 0 | 80 | 30 | 0 |
| Galium | 0 | 0 | 0 | 0 | 0 | 0 | 0 | 20 | 20 | 0 | 0 | 20 | 0 | 0 |
| Kochia | 0 | 0 | 0 | 0 | 0 | 0 | 0 | 0 | 0 | 0 | 0 | 20 | 0 | 0 |
| Pigweed | 0 | 0 | 0 | 0 | 0 | 0 | 0 | 0 | 0 | 0 | 0 | 20 | 20 | 0 |
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 0 | 0 | 0 | 20 | 0 | 0 |
| Wheat | 0 | 0 | 0 | 0 | 0 | 0 | 0 | 20 | 0 | 0 | 0 | 30 | 20 | 0 |

| 31 g ai/ha | Compounds | | | | | | | | | | | | |
|---|---|---|---|---|---|---|---|---|---|---|---|---|---|
| Postemergence | 1003 | 1004 | 1005 | 1006 | 1007 | 1008 | 1009 | 1010 | 1011 | 1012 | 1050 | 1051 | 1052 | 1060 |
| Barnyardgrass | 0 | 0 | 0 | 0 | 0 | 0 | 0 | 0 | 0 | 0 | 0 | 0 | 30 | 90 |
| Blackgrass | 0 | 0 | 0 | 0 | 0 | 0 | 0 | 0 | 0 | 0 | 0 | 0 | 0 | 50 |
| Corn | 0 | 0 | 0 | 0 | 0 | 0 | 0 | 0 | 0 | 0 | 0 | 0 | 0 | 70 |
| Foxtail, Giant | 0 | 0 | 0 | 0 | 0 | 0 | 0 | 0 | 0 | 0 | 0 | 0 | 30 | 90 |
| Galium | 0 | 0 | 0 | 0 | 0 | 0 | 0 | 0 | 0 | 0 | 0 | 30 | 40 | 0 |
| Kochia | 0 | 0 | 0 | 0 | 0 | 0 | 0 | 0 | 0 | 0 | 0 | 0 | 0 | 0 |
| Pigweed | 0 | 0 | 0 | 0 | 0 | 0 | 0 | 0 | 0 | 0 | 0 | 0 | 0 | 0 |
| Ragweed | 0 | 0 | 0 | 10 | 0 | 0 | 0 | 0 | 0 | 0 | 0 | 0 | 0 | 0 |
| Ryegrass, Italian | 0 | 0 | 0 | 0 | 0 | 0 | 0 | 0 | 0 | 0 | 0 | 0 | 0 | 50 |
| Wheat | 0 | 0 | 0 | 0 | 0 | 0 | 0 | 0 | 0 | 0 | 0 | 0 | 0 | 30 |

| 31 g ai/ha | Compounds | | | | | | | | | | | | |
|---|---|---|---|---|---|---|---|---|---|---|---|---|---|
| Postemergence | 1061 | 1062 | 1063 | 1065 | 1066 | 1067 | 1068 | 1069 | 1070 | 1071 | 1072 | 1074 | 1075 | 1076 |
| Barnyardgrass | 50 | 70 | 70 | 0 | 50 | 20 | 0 | 0 | 0 | 30 | 90 | 80 | 90 | 0 |
| Blackgrass | 0 | 0 | 20 | 0 | 0 | 0 | 0 | 0 | 0 | 0 | 0 | 20 | 40 | 0 |
| Corn | 0 | 0 | 0 | 0 | 0 | 0 | 0 | 0 | 0 | 0 | 0 | 0 | 20 | 0 |
| Foxtail, Giant | 0 | 90 | 80 | 0 | 70 | 30 | 0 | 0 | 0 | 20 | 80 | 70 | 80 | 0 |
| Galium | 0 | 0 | 30 | 40 | 0 | 0 | 0 | 0 | 0 | 0 | 0 | — | — | — |
| Kochia | 0 | 0 | 0 | 0 | 0 | 0 | 0 | 0 | 0 | 0 | 0 | 0 | 30 | 0 |
| Pigweed | 0 | 0 | 0 | 0 | 0 | 0 | 0 | 0 | 0 | 0 | 0 | 0 | 0 | 0 |
| Ragweed | 0 | 30 | 0 | 0 | 0 | 0 | 0 | 0 | 0 | 0 | 0 | 0 | 0 | 0 |
| Ryegrass, Italian | 0 | 0 | 0 | 0 | 30 | 0 | 0 | 0 | 0 | 0 | 0 | 20 | 0 | 0 |
| Wheat | 0 | 0 | 0 | 0 | 0 | 0 | 0 | 0 | 0 | 0 | 0 | 0 | 0 | 0 |

| 31 g ai/ha | Compounds | | | | | | | | | | | | |
|---|---|---|---|---|---|---|---|---|---|---|---|---|---|
| Postemergence | 1077 | 1078 | 1079 | 1080 | 1081 | 1082 | 1083 | 1084 | 1085 | 1086 | 1087 | 1088 | 1089 | 1090 |
| Barnyardgrass | 70 | 0 | 20 | 0 | 30 | 0 | 90 | 10 | 40 | 30 | 20 | 0 | 60 | — |
| Blackgrass | 0 | 0 | 0 | 0 | 0 | 0 | 50 | 0 | 0 | 0 | 0 | 0 | 0 | 0 |
| Corn | 0 | 0 | 0 | 0 | 0 | 0 | 20 | 0 | 20 | 0 | 0 | 0 | 0 | 0 |
| Foxtail, Giant | 50 | 0 | 0 | 0 | 10 | 0 | 80 | 0 | 0 | 10 | 30 | 0 | 80 | 20 |
| Galium | 20 | 0 | 0 | 0 | 0 | 0 | 60 | 0 | 40 | 0 | 30 | 20 | — | 30 |
| Kochia | 0 | 0 | 0 | 0 | 0 | 0 | 20 | 0 | 0 | 0 | 0 | 0 | 0 | 0 |

TABLE A-continued

| | | | | | | | | | | | | | | |
|---|---|---|---|---|---|---|---|---|---|---|---|---|---|---|
| Pigweed | 0 | 0 | 0 | 0 | 0 | 0 | 0 | 0 | 0 | 0 | 0 | 0 | 0 | 0 |
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 0 | 0 | 0 | 0 | 0 | 0 |
| Wheat | 0 | 0 | 0 | 0 | 0 | 0 | 40 | 0 | 0 | 0 | 0 | 0 | 0 | 0 |

| 31 g ai/ha | Compounds | | | | | | | | | | | | | |
|---|---|---|---|---|---|---|---|---|---|---|---|---|---|---|
| Postemergence | 1091 | 1092 | 1093 | 1103 | 1104 | 1105 | 1106 | 1107 | 1108 | 1109 | 1110 | 1141 | 1142 | 1143 |
| Barnyardgrass | 0 | 50 | 40 | 40 | 0 | 0 | 30 | 0 | 0 | 90 | 80 | 60 | 0 | 0 |
| Blackgrass | 0 | 0 | 0 | 20 | 0 | 0 | 0 | 0 | 0 | 20 | 0 | 0 | 0 | 0 |
| Corn | 0 | 0 | 0 | 0 | 0 | 0 | 0 | 0 | 0 | 40 | 30 | 0 | 0 | 0 |
| Foxtail, Giant | 0 | 30 | 30 | 50 | 0 | 0 | 0 | 0 | 0 | 70 | 60 | 60 | 0 | 0 |
| Galium | 0 | — | — | 30 | 0 | 30 | 40 | 0 | 0 | 30 | 20 | 60 | 0 | 0 |
| Kochia | 0 | 0 | 0 | 0 | 0 | 0 | 0 | 0 | 0 | 20 | 30 | 0 | 0 | 0 |
| Pigweed | 0 | 0 | 0 | 0 | 0 | 0 | 10 | 0 | 0 | 20 | 20 | 30 | 0 | 0 |
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 0 | 0 | 40 | 20 | 0 | 0 |
| Wheat | 0 | 0 | 0 | 0 | 0 | 0 | 0 | 0 | 0 | 30 | 30 | 0 | 0 | 0 |

| 31 g ai/ha | Compounds | | | | | | | | | | | | | |
|---|---|---|---|---|---|---|---|---|---|---|---|---|---|---|
| Postemergence | 1144 | 1145 | 1146 | 1147 | 1148 | 1149 | 1150 | 1161 | 1162 | 1163 | 1164 | 1165 | 1166 | 1167 |
| Barnyardgrass | 90 | 60 | 0 | 0 | 50 | 50 | 0 | 0 | 30 | 30 | 30 | 40 | 0 | 0 |
| Blackgrass | 0 | 0 | 0 | 0 | 0 | 0 | 0 | 0 | 0 | 0 | 0 | 0 | 0 | 0 |
| Corn | 20 | 0 | 0 | 0 | 0 | 0 | 0 | 0 | 0 | 0 | 0 | 0 | 0 | 0 |
| Foxtail, Giant | 80 | 50 | 0 | 0 | 50 | 40 | 0 | 0 | 30 | 0 | 0 | 70 | 0 | 0 |
| Galium | 0 | 0 | 0 | 0 | 0 | 20 | 0 | 0 | 0 | 0 | 0 | 20 | 0 | 0 |
| Kochia | 50 | 0 | 0 | 0 | 0 | 0 | 0 | 0 | 0 | 0 | 0 | 30 | 0 | 0 |
| Pigweed | 0 | 0 | 0 | 0 | 0 | 0 | 0 | 0 | 0 | 0 | 0 | 10 | 0 | 0 |
| Ragweed | 20 | 0 | 0 | 0 | 0 | 0 | 0 | 0 | 0 | 0 | 0 | 0 | 0 | 0 |
| Ryegrass, Italian | 30 | 0 | 0 | 0 | 0 | 0 | 0 | 0 | 0 | 0 | 0 | 0 | 0 | 0 |
| Wheat | 30 | 0 | 0 | 0 | 0 | 0 | 0 | 0 | 0 | 0 | 0 | 0 | 0 | 0 |

| 31 g ai/ha | Compounds | | | | | | | | | | | | | |
|---|---|---|---|---|---|---|---|---|---|---|---|---|---|---|
| Postemergence | 1168 | 1169 | 1170 | 1171 | 1172 | 1173 | 1174 | 1175 | 1176 | 1183 | 1184 | 1185 | 1186 | 1187 |
| Barnyardgrass | 0 | 30 | 0 | 20 | 0 | 50 | 70 | 50 | 80 | 80 | 70 | 20 | 100 | 20 |
| Blackgrass | 0 | 0 | 0 | 0 | 0 | 0 | 0 | 0 | 50 | 0 | 30 | 0 | 70 | 0 |
| Corn | 0 | 0 | 0 | 0 | 0 | 0 | 0 | 0 | 50 | 30 | 50 | 0 | 30 | 0 |
| Foxtail, Giant | 0 | 30 | 0 | 30 | 0 | 70 | 40 | 50 | 80 | 70 | 80 | 30 | 90 | 40 |
| Galium | 0 | 0 | 20 | 0 | 0 | 0 | 0 | 20 | 30 | 0 | 0 | 0 | 50 | 20 |
| Kochia | 0 | 0 | 0 | 0 | 0 | 30 | 0 | 0 | 0 | 0 | 0 | 0 | 20 | 0 |
| Pigweed | 0 | 0 | 0 | 0 | 0 | 30 | 0 | 0 | 0 | 0 | 0 | 0 | 0 | 0 |
| Ragweed | 0 | 0 | 0 | 0 | 0 | 0 | 0 | 0 | 0 | 0 | 0 | 0 | 20 | 0 |
| Ryegrass, Italian | 0 | 0 | 0 | 0 | 0 | 0 | 0 | 0 | 20 | 20 | 30 | 0 | 40 | 0 |
| Wheat | 0 | 0 | 0 | 0 | 0 | 0 | 0 | 0 | 50 | 20 | 40 | 0 | 30 | 0 |

| 31 g ai/ha | Compounds | | | | | | | | | | | | | |
|---|---|---|---|---|---|---|---|---|---|---|---|---|---|---|
| Postemergence | 1188 | 1189 | 1190 | 1191 | 1192 | 1193 | 1237 | 1258 | 1259 | 1261 | 1262 | 1263 | 1264 | 1265 |
| Barnyardgrass | 70 | 70 | 0 | 0 | 50 | 0 | 0 | 30 | 30 | 90 | 70 | 0 | 0 | 80 |
| Blackgrass | 30 | 20 | 0 | 0 | 0 | 0 | 0 | 0 | 0 | 40 | 0 | 0 | 0 | 0 |
| Corn | 0 | 0 | 0 | 0 | 0 | 0 | 0 | 0 | 0 | 50 | 20 | 0 | 0 | 30 |
| Foxtail, Giant | 70 | 70 | 0 | 0 | 40 | 0 | 0 | 30 | 30 | 90 | 70 | 0 | 0 | 80 |
| Galium | 50 | 30 | 0 | 0 | 0 | 0 | 0 | 0 | 70 | 60 | 50 | 30 | 0 | 60 |
| Kochia | 0 | 0 | 0 | 0 | 0 | 0 | 0 | 0 | 0 | 20 | 20 | 0 | 0 | 50 |
| Pigweed | 0 | 0 | 0 | 0 | 0 | 0 | 0 | 0 | 40 | 0 | 30 | 0 | 0 | 30 |
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 0 | 20 | 0 | 0 | 0 | 0 |
| Wheat | 0 | 0 | 0 | 0 | 0 | 0 | 0 | 0 | 0 | 20 | 0 | 0 | 0 | 0 |

| 31 g ai/ha | Compounds | | | | | | | | | | | | | |
|---|---|---|---|---|---|---|---|---|---|---|---|---|---|---|
| Postemergence | 1266 | 1267 | 1268 | 1269 | 1270 | 1271 | 1272 | 1273 | 1274 | 1275 | 1276 | 1277 | 1278 | 1279 |
| Barnyardgrass | 90 | 60 | 80 | 90 | 90 | 40 | 40 | 50 | 50 | 30 | 70 | 30 | 70 | 0 |
| Blackgrass | 20 | 0 | 0 | 0 | 0 | 0 | 20 | 0 | 0 | 0 | 0 | 0 | 0 | 0 |
| Corn | 90 | 0 | 0 | 0 | 0 | 30 | 0 | 0 | 30 | 0 | 0 | 0 | 0 | 0 |
| Foxtail, Giant | 80 | 60 | 50 | 60 | 60 | 20 | 50 | 60 | 50 | 20 | 30 | 50 | 50 | 0 |
| Galium | 50 | 0 | 0 | 0 | 60 | 60 | 50 | 40 | 50 | 0 | 0 | 0 | 0 | 0 |
| Kochia | 30 | 0 | 0 | 0 | 0 | 20 | 0 | 0 | 50 | 0 | 0 | 0 | 0 | 0 |
| Pigweed | 20 | 0 | 0 | 0 | 40 | 20 | 0 | 0 | 0 | 0 | 0 | 0 | 0 | 0 |
| Ragweed | 0 | 0 | 0 | 0 | 0 | 0 | 0 | 0 | 0 | 0 | 0 | 30 | 0 | 0 |
| Ryegrass, Italian | 20 | 0 | 0 | 0 | 0 | 0 | 20 | 0 | 0 | 0 | 0 | 0 | 0 | 0 |
| Wheat | 0 | 0 | 0 | 0 | 0 | 20 | 20 | 0 | 20 | 0 | 0 | 0 | 0 | 0 |

TABLE A-continued

| 31 g ai/ha | Compounds | | | | | | | | | | | | | |
|---|---|---|---|---|---|---|---|---|---|---|---|---|---|---|
| Postemergence | 1282 | 1283 | 1284 | 1285 | 1286 | 1287 | 1288 | 1289 | 1290 | 1291 | 1292 | 1293 | 1294 | 1295 |
| Barnyardgrass | 90 | 0 | 0 | 60 | 90 | 80 | 0 | 0 | 0 | 70 | 0 | 0 | 0 | 0 |
| Blackgrass | 0 | 0 | 0 | 0 | 0 | 0 | 0 | 0 | 0 | 0 | 0 | 0 | 0 | 0 |
| Corn | 0 | 0 | 0 | 0 | 20 | 0 | 0 | 0 | 0 | 0 | 0 | 0 | 0 | 0 |
| Foxtail, Giant | 80 | 0 | 0 | 40 | 70 | 70 | 0 | 0 | 0 | 70 | 0 | 0 | 0 | 0 |
| Galium | 40 | 0 | 0 | 20 | 20 | 30 | 0 | 0 | 0 | 0 | 0 | 0 | 0 | 0 |
| Kochia | 0 | 0 | 0 | 0 | 0 | 0 | 0 | 0 | 0 | 0 | 0 | 0 | 0 | 0 |
| Pigweed | 0 | 0 | 0 | 20 | 0 | 0 | 0 | 0 | 0 | 0 | 0 | 0 | 0 | 0 |
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 |

| 31 g ai/ha | Compounds | | | | | | | | | | | | | |
|---|---|---|---|---|---|---|---|---|---|---|---|---|---|---|
| Postemergence | 1296 | 1297 | 1333 | 1337 | 1338 | 1339 | 1340 | 1341 | 1342 | 1343 | 1344 | 1345 | 1346 | 1347 |
| Barnyardgrass | 0 | 0 | 0 | 20 | 70 | 70 | 20 | 40 | 20 | 60 | 0 | 50 | 60 | 70 |
| Blackgrass | 0 | 0 | 0 | 0 | 0 | 0 | 0 | 0 | 0 | 0 | 0 | 0 | 30 | 30 |
| Corn | 0 | 0 | 0 | 0 | 0 | 0 | 0 | 0 | 0 | 0 | 0 | 0 | 0 | 30 |
| Foxtail, Giant | 0 | 0 | 0 | 20 | 50 | 70 | 0 | 0 | 20 | 60 | 0 | 20 | 60 | 70 |
| Galium | 0 | 0 | 0 | 0 | 0 | 30 | 0 | — | — | 0 | 0 | 0 | — | 70 |
| Kochia | 0 | 0 | 0 | 20 | 0 | 0 | 0 | 0 | 0 | 0 | 0 | 0 | 0 | 60 |
| Pigweed | 0 | 0 | 0 | 0 | 0 | 20 | 0 | 0 | 0 | 0 | 0 | 0 | 0 | 50 |
| Ragweed | 0 | 0 | 0 | 0 | 0 | 0 | 0 | 0 | 0 | 0 | 0 | 0 | 0 | 40 |
| Ryegrass, Italian | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 30 | 20 |

| 31 g ai/ha | Compounds | | | | | | | | | | | | |
|---|---|---|---|---|---|---|---|---|---|---|---|---|---|
| Postemergence | 1348 | 1349 | 1350 | 1351 | 1352 | 1353 | 1354 | 1366 | 1367 | 1368 | 1369 | 1375 | 1393 | 1396 |
| Barnyardgrass | 90 | 70 | 60 | 0 | 60 | 40 | 0 | 20 | 0 | 20 | 20 | 70 | 70 | 70 |
| Blackgrass | 50 | 0 | 0 | 0 | 0 | 0 | 0 | 0 | 0 | 0 | 0 | 0 | 20 | 0 |
| Corn | 50 | 0 | 30 | 0 | 0 | 0 | 0 | 0 | 0 | 0 | 0 | 0 | 0 | 20 |
| Foxtail, Giant | 90 | 60 | 70 | 0 | 60 | 30 | 0 | 30 | 0 | 0 | 20 | 70 | 70 | 80 |
| Galium | 50 | 30 | — | — | — | — | 20 | 0 | 0 | 0 | 0 | 20 | 50 | 60 |
| Kochia | 0 | 0 | 50 | 0 | 0 | 0 | 0 | 0 | 0 | 0 | 0 | 30 | 30 | 60 |
| Pigweed | 0 | 0 | 30 | 0 | 0 | 0 | 0 | 0 | 0 | 0 | 20 | 0 | 40 | 30 |
| Ragweed | 0 | 0 | 0 | 0 | 0 | 0 | 0 | 0 | 0 | 0 | 0 | 0 | 0 | 0 |
| Ryegrass, Italian | 20 | 0 | 20 | 0 | 0 | 0 | 0 | 0 | 0 | 0 | 20 | 0 | 0 | 20 |
| Wheat | 40 | 0 | 20 | 0 | 0 | 0 | 0 | 0 | 0 | 0 | 0 | 0 | 0 | 0 |

| 31 g ai/ha | Compounds | | | | |
|---|---|---|---|---|---|
| Postemergence | 1397 | 1398 | 1399 | 1400 | 1402 |
| Barnyardgrass | 90 | 90 | 90 | 70 | 80 |
| Blackgrass | 40 | 20 | 20 | 30 | 0 |
| Corn | 50 | 0 | 0 | 20 | 0 |
| Foxtail, Giant | 80 | 90 | 70 | 70 | 50 |
| Galium | 20 | 30 | 40 | 20 | 60 |
| Kochia | 0 | 20 | 50 | 30 | 30 |
| Pigweed | 0 | 0 | 0 | 50 | 0 |
| Ragweed | 0 | 0 | 0 | 0 | 0 |
| Ryegrass, Italian | 50 | 0 | 20 | 30 | 0 |
| Wheat | 40 | 0 | 0 | 0 | 20 |

| 1000 g ai/ha | Compounds | | | | | | |
|---|---|---|---|---|---|---|---|
| Preemergence | 355 | 357 | 358 | 511 | 512 | 713 | 784 |
| Barnyardgrass | 0 | 0 | 0 | 90 | 80 | 0 | 80 |
| Corn | 0 | 0 | 0 | — | — | 0 | — |
| Crabgrass, Large | 0 | 0 | 50 | — | — | 80 | — |
| Foxtail, Giant | 0 | 0 | 0 | 90 | 90 | 40 | 90 |
| Kochia | — | — | — | 0 | 0 | — | 0 |
| Morningglory | 0 | 0 | 0 | — | — | 0 | — |
| Pigweed | 0 | 0 | 0 | 0 | 0 | 0 | 0 |
| Ragweed | — | — | — | 0 | 0 | — | 0 |
| Ryegrass, Italian | — | — | — | 0 | 0 | — | 0 |
| Velvetleaf | 0 | 0 | 0 | — | — | 0 | — |
| Wheat | 0 | 0 | 0 | — | — | 0 | — |

TABLE A-continued

| 500 g ai/ha | Compounds | | | | | | | | | | | | |
|---|---|---|---|---|---|---|---|---|---|---|---|---|---|
| Preemergence | 352 | 353 | 354 | 356 | 360 | 361 | 362 | 363 | 364 | 365 | 366 | 367 | 368 |
| Barnyardgrass | 0 | 0 | 0 | 0 | 0 | 0 | 0 | 0 | 0 | 0 | 0 | 0 | 90 |
| Corn | 0 | 0 | 0 | 0 | 0 | 0 | 0 | 0 | 0 | 0 | 0 | 0 | — |
| Crabgrass, Large | 0 | 0 | 0 | 0 | 0 | 0 | 0 | 0 | 0 | 0 | 0 | 0 | — |
| Foxtail, Giant | 0 | 0 | 0 | 0 | 0 | 0 | 0 | 0 | 0 | 0 | 0 | 0 | 90 |
| Kochia | — | — | — | — | — | — | — | — | — | — | — | — | 30 |
| Morningglory | 0 | 0 | 0 | 0 | 0 | 0 | 0 | — | 0 | 0 | 0 | 0 | — |
| Pigweed | 0 | 0 | 0 | 0 | 0 | 0 | 0 | 0 | 0 | 0 | 0 | 0 | 0 |
| Ragweed | — | — | — | — | — | — | — | — | — | — | — | — | 60 |
| Ryegrass, Italian | — | — | — | — | — | — | — | — | — | — | — | — | 30 |
| Velvetleaf | 0 | 0 | 0 | 0 | 0 | 0 | 0 | 0 | 0 | 0 | 0 | 0 | — |
| Wheat | 0 | 0 | 0 | 0 | 0 | 0 | 0 | 0 | 0 | 0 | 0 | 0 | — |

| 500 g ai/ha | Compounds | | | | | | | | | | | | |
|---|---|---|---|---|---|---|---|---|---|---|---|---|---|
| Preemergence | 369 | 370 | 371 | 372 | 373 | 374 | 375 | 376 | 377 | 378 | 379 | 380 | 381 | 382 |
| Barnyardgrass | 90 | 90 | 90 | 90 | 90 | 90 | 90 | 90 | 90 | 90 | 30 | 90 | 20 | 50 |
| Foxtail, Giant | 90 | 90 | 90 | 90 | 90 | 90 | 90 | 90 | 90 | 100 | 40 | 90 | 30 | 30 |
| Kochia | 40 | 30 | 60 | 0 | 30 | 0 | 70 | 0 | 80 | 90 | 0 | 40 | 0 | 0 |
| Pigweed | 0 | 0 | 20 | 50 | 20 | 0 | 70 | 0 | 70 | 80 | 0 | 30 | 0 | 0 |
| Ragweed | 60 | 20 | 40 | 30 | 30 | 0 | 70 | 0 | 0 | 50 | 0 | 0 | 0 | 0 |
| Ryegrass, Italian | 20 | 0 | 20 | 30 | 40 | 30 | 50 | 20 | 60 | 80 | 0 | 20 | 0 | 0 |

| 500 g ai/ha | Compounds | | | | | | | | | | | | |
|---|---|---|---|---|---|---|---|---|---|---|---|---|---|
| Preemergence | 383 | 384 | 386 | 387 | 388 | 389 | 390 | 391 | 392 | 393 | 394 | 395 | 396 |
| Barnyardgrass | 90 | 0 | 80 | 80 | 80 | 70 | 80 | 90 | 90 | 90 | 80 | 0 | 90 |
| Foxtail, Giant | 70 | 0 | 90 | 90 | 90 | 90 | 90 | 90 | 90 | 90 | 90 | 0 | 90 |
| Kochia | 20 | 0 | 0 | 0 | 0 | 0 | 0 | 0 | 50 | 70 | 50 | 0 | 80 |
| Pigweed | 0 | 0 | 0 | 0 | 0 | 0 | 0 | 0 | 70 | 80 | 70 | 0 | 90 |
| Ragweed | 0 | 0 | — | 0 | 0 | 0 | 0 | 0 | 80 | 60 | 70 | 0 | 20 |
| Ryegrass, Italian | 20 | 0 | 50 | 0 | 0 | 0 | 0 | 0 | 50 | 80 | 50 | 0 | 70 |

| 500 g ai/ha | Compounds | | | | | | | | | | | | |
|---|---|---|---|---|---|---|---|---|---|---|---|---|---|
| Preemergence | 397 | 398 | 399 | 400 | 401 | 402 | 403 | 404 | 405 | 406 | 407 | 408 | 409 | 410 |
| Barnyardgrass | 90 | 90 | 90 | 100 | 90 | 90 | 90 | 90 | 90 | 90 | 80 | 0 | 80 | 60 |
| Foxtail, Giant | 90 | 90 | 90 | 100 | 90 | 90 | 90 | 90 | 90 | 90 | 90 | 0 | 90 | 80 |
| Kochia | 90 | 90 | 80 | 80 | 80 | 70 | 80 | 70 | 70 | 40 | 0 | 0 | 0 | 0 |
| Pigweed | 90 | 90 | 90 | 60 | 50 | 50 | 60 | 60 | 60 | 50 | 20 | 0 | 10 | 20 |
| Ragweed | 70 | 30 | 50 | 90 | 50 | 70 | 60 | 50 | 70 | 40 | 0 | 0 | 0 | 0 |
| Ryegrass, Italian | 70 | 70 | 60 | 40 | 40 | 40 | 70 | 80 | 30 | 50 | 0 | 0 | 0 | 0 |

| 500 g ai/ha | Compounds | | | | | | | | | | | | |
|---|---|---|---|---|---|---|---|---|---|---|---|---|---|
| Preemergence | 411 | 412 | 413 | 414 | 415 | 416 | 417 | 418 | 419 | 420 | 421 | 422 | 423 | 424 |
| Barnyardgrass | 80 | 70 | 0 | 0 | 0 | 0 | 0 | 0 | 90 | 90 | 90 | 70 | 0 | 90 |
| Foxtail, Giant | 90 | 70 | 0 | 10 | 0 | 50 | 0 | 0 | 90 | 90 | 90 | 70 | 0 | 90 |
| Kochia | 0 | 0 | 0 | 0 | 0 | 0 | 0 | 0 | 0 | 30 | 80 | 0 | 0 | 0 |
| Pigweed | 10 | 0 | 0 | 0 | 0 | 0 | 0 | 0 | 20 | 30 | 40 | 30 | 0 | 0 |
| Ragweed | 0 | 0 | 0 | 0 | 0 | 0 | 0 | 0 | 0 | 0 | 40 | 0 | 0 | 0 |
| Ryegrass, Italian | 0 | 0 | 0 | 0 | 0 | 0 | 0 | 0 | 0 | 0 | 30 | 0 | 0 | 0 |

| 500 g ai/ha | Compounds | | | | | | | | | | | | |
|---|---|---|---|---|---|---|---|---|---|---|---|---|---|
| Preemergence | 425 | 426 | 427 | 428 | 429 | 430 | 431 | 432 | 433 | 434 | 435 | 436 | 437 | 438 |
| Barnyardgrass | 20 | 80 | 90 | 90 | 90 | 90 | 90 | 40 | 90 | 90 | 90 | 100 | 90 | 100 |
| Foxtail, Giant | 70 | 90 | 90 | 90 | 100 | 90 | 100 | 0 | 90 | 100 | 90 | 100 | 100 | 100 |
| Kochia | 0 | 0 | 80 | 50 | 80 | 70 | 70 | 0 | 80 | 80 | 80 | 80 | 70 | 80 |
| Pigweed | 0 | 30 | 40 | 20 | 80 | 50 | 90 | 0 | 70 | 90 | 80 | 90 | 80 | 90 |
| Ragweed | 0 | 0 | 40 | 0 | — | 50 | 70 | 0 | 60 | 60 | 70 | 50 | 60 | 90 |
| Ryegrass, Italian | 0 | 0 | 30 | 30 | 80 | 50 | 70 | 0 | 60 | 90 | 20 | 60 | 50 | 70 |

| 500 g ai/ha | Compounds | | | | | | | | | | | | |
|---|---|---|---|---|---|---|---|---|---|---|---|---|---|
| Preemergence | 439 | 440 | 441 | 442 | 443 | 444 | 445 | 446 | 447 | 448 | 449 | 450 | 451 | 452 |
| Barnyardgrass | 90 | 100 | 90 | 90 | 90 | 90 | 90 | 90 | 90 | 90 | 90 | 90 | 0 | 90 |
| Foxtail, Giant | 100 | 100 | 90 | 90 | 90 | 90 | 90 | 90 | 90 | 90 | 90 | 90 | 0 | 90 |
| Kochia | 70 | 70 | 80 | 90 | 80 | 80 | 50 | 50 | 50 | 50 | 40 | 80 | 0 | 70 |
| Pigweed | 80 | 80 | 70 | 80 | 90 | 80 | 40 | 60 | 30 | 40 | 20 | 80 | 0 | 90 |

TABLE A-continued

| | | | | | | | | | | | | | |
|---|---|---|---|---|---|---|---|---|---|---|---|---|---|
| Ragweed | 60 | 40 | 80 | 60 | 80 | 80 | 30 | 50 | 0 | 20 | 0 | 70 | 0 | 60 |
| Ryegrass, Italian | 50 | 50 | 80 | 80 | 50 | 90 | 90 | 60 | 30 | 20 | 0 | 40 | 0 | 30 |

| 500 g ai/ha | Compounds | | | | | | | | | | | |
|---|---|---|---|---|---|---|---|---|---|---|---|---|
| Preemergence | 453 | 454 | 455 | 456 | 457 | 460 | 461 | 462 | 463 | 464 | 465 | 466 |
| Barnyardgrass | 90 | 80 | 90 | 0 | 0 | 80 | 90 | 90 | 80 | 90 | 100 | 90 |
| Foxtail, Giant | 90 | 90 | 90 | 0 | 0 | 90 | 90 | 90 | 90 | 90 | 100 | 90 |
| Kochia | 30 | 0 | 50 | 0 | 0 | 40 | 50 | 70 | 0 | 80 | 80 | 0 |
| Pigweed | 30 | 0 | 50 | 0 | 0 | 30 | 0 | 0 | 0 | 70 | 70 | 0 |
| Ragweed | 20 | 0 | 0 | 0 | 0 | 20 | 0 | 50 | 0 | — | 70 | 30 |
| Ryegrass, Italian | 0 | 30 | 0 | 0 | 0 | 60 | 20 | 0 | 20 | 90 | 70 | 20 |

| 500 g ai/ha | Compounds | | | | | | | | | | | | |
|---|---|---|---|---|---|---|---|---|---|---|---|---|---|
| Preemergence | 467 | 468 | 469 | 470 | 471 | 472 | 473 | 474 | 475 | 476 | 477 | 478 | 479 | 480 |
| Barnyardgrass | 90 | 20 | 90 | 90 | 90 | 90 | 100 | 90 | 90 | 90 | 90 | 60 | 30 | 0 |
| Foxtail, Giant | 100 | 80 | 90 | 90 | 90 | 90 | 100 | 90 | 90 | 100 | 90 | 80 | 90 | 90 |
| Kochia | 50 | 80 | 0 | 40 | 0 | 80 | 80 | 70 | 70 | 70 | 0 | 0 | 0 | 0 |
| Pigweed | 0 | 50 | 0 | 20 | 0 | 90 | 90 | 90 | 90 | 80 | 0 | 0 | 0 | 0 |
| Ragweed | 70 | 70 | 0 | — | 0 | 50 | 70 | 20 | 60 | 60 | 0 | 0 | 0 | 0 |
| Ryegrass, Italian | 20 | 0 | 0 | 30 | 0 | 80 | 90 | 50 | 40 | 40 | 0 | 0 | 0 | 0 |

| 500 g ai/ha | Compounds | | | | | | | | | | | | |
|---|---|---|---|---|---|---|---|---|---|---|---|---|---|
| Preemergence | 481 | 482 | 483 | 484 | 485 | 486 | 487 | 488 | 489 | 490 | 491 | 492 | 493 | 494 |
| Barnyardgrass | 10 | 10 | 70 | 40 | 80 | 70 | 90 | 90 | 90 | 90 | 90 | 90 | 90 | 90 |
| Foxtail, Giant | 90 | 80 | 90 | 90 | 90 | 90 | 90 | 90 | 90 | 90 | 90 | 90 | 90 | 90 |
| Kochia | 0 | 0 | 0 | 0 | 0 | 0 | 60 | 70 | 50 | 20 | 20 | 70 | 20 | 0 |
| Pigweed | 0 | 0 | 0 | 0 | 0 | 20 | 30 | 70 | 40 | 0 | 0 | 70 | 0 | 0 |
| Ragweed | 0 | 0 | 0 | 0 | 0 | 0 | 30 | 80 | 30 | 0 | 0 | 80 | 30 | 0 |
| Ryegrass, Italian | 0 | 0 | 30 | 0 | 0 | 20 | 40 | 70 | 20 | 50 | 30 | 50 | 20 | 0 |

| 500 g ai/ha | Compounds | | | | | | | | | | | | |
|---|---|---|---|---|---|---|---|---|---|---|---|---|---|
| Preemergence | 495 | 496 | 497 | 498 | 499 | 500 | 501 | 502 | 503 | 504 | 505 | 506 | 507 | 508 |
| Barnyardgrass | 90 | 90 | 90 | 90 | 90 | 40 | 90 | 60 | 90 | 90 | 0 | 90 | 80 | 90 |
| Foxtail, Giant | 90 | 90 | 90 | 80 | 90 | 90 | 90 | 90 | 90 | 90 | 0 | 90 | 50 | 70 |
| Kochia | 30 | 40 | 50 | 0 | 30 | 50 | 30 | 70 | 20 | 80 | 0 | 30 | 70 | 0 |
| Pigweed | 20 | 0 | 20 | 0 | 0 | 20 | 20 | 30 | 40 | 100 | 0 | 60 | 20 | 0 |
| Ragweed | 0 | 0 | 0 | 0 | 0 | 0 | 50 | 50 | 0 | 50 | 0 | 0 | 0 | 0 |
| Ryegrass, Italian | 20 | 0 | 30 | 0 | 0 | 0 | 0 | 30 | 50 | 70 | 0 | 50 | 0 | 0 |

| 500 g ai/ha | Compounds | | | | | | | | | | | | |
|---|---|---|---|---|---|---|---|---|---|---|---|---|---|
| Preemergence | 509 | 510 | 513 | 514 | 515 | 516 | 517 | 518 | 519 | 520 | 521 | 522 | 523 | 524 |
| Barnyardgrass | 90 | 80 | 90 | 90 | 0 | 80 | 0 | 60 | 90 | 90 | 90 | 90 | 90 | 40 |
| Foxtail, Giant | 70 | 70 | 90 | 90 | 70 | 90 | 30 | 90 | 100 | 90 | 90 | 90 | 90 | 70 |
| Kochia | 0 | 50 | 20 | 50 | 0 | 0 | 0 | 0 | 60 | 70 | 70 | 60 | 80 | 0 |
| Pigweed | 0 | 0 | 0 | 40 | 0 | 0 | 0 | 0 | 20 | 80 | 70 | 80 | 90 | 0 |
| Ragweed | 0 | 50 | 0 | 30 | 0 | 0 | 0 | 0 | 30 | 50 | 60 | 30 | 80 | 0 |
| Ryegrass, Italian | 0 | 10 | 30 | 60 | 0 | 0 | 0 | 0 | 70 | 50 | 50 | 60 | 90 | 0 |

| 500 g ai/ha | Compounds | | | | | | | | | | | |
|---|---|---|---|---|---|---|---|---|---|---|---|---|
| Preemergence | 525 | 526 | 527 | 534 | 535 | 536 | 537 | 538 | 539 | 540 | 541 | 544 |
| Barnyardgrass | 50 | 20 | 20 | 0 | 0 | 0 | 0 | 0 | 90 | 90 | 90 | 80 |
| Foxtail, Giant | 70 | 80 | 80 | 0 | 0 | 20 | 0 | 0 | 90 | 90 | 90 | 90 |
| Kochia | 0 | 0 | 0 | 0 | 0 | 0 | 0 | 0 | 70 | 20 | 20 | 0 |
| Pigweed | 0 | 0 | 0 | 0 | 0 | 0 | 0 | 0 | 80 | 60 | 0 | 0 |
| Ragweed | 0 | 0 | 0 | 0 | 0 | 0 | 0 | 0 | 70 | — | 0 | 0 |
| Ryegrass, Italian | 0 | 0 | 0 | 0 | 0 | 0 | 0 | 0 | 50 | 40 | 20 | 0 |

| 500 g ai/ha | Compounds | | | | | | | | | | | |
|---|---|---|---|---|---|---|---|---|---|---|---|---|
| Preemergence | 545 | 546 | 547 | 549 | 550 | 551 | 552 | 553 | 554 | 557 | 558 | 559 | 560 |
| Barnyardgrass | 70 | 90 | 90 | 80 | 90 | 90 | 90 | 90 | 90 | 0 | 100 | 100 | 100 |
| Foxtail, Giant | 90 | 90 | 90 | 90 | 90 | 90 | 90 | 90 | 90 | 0 | 100 | 100 | 100 |
| Kochia | 0 | 0 | 0 | 0 | 40 | 0 | 70 | 80 | 90 | 0 | 80 | 80 | 80 |
| Pigweed | 0 | 0 | 0 | 0 | 0 | 0 | 0 | 40 | 30 | 0 | 70 | 50 | 40 |
| Ragweed | 0 | 0 | 70 | 0 | 0 | 0 | 60 | — | 70 | 0 | 70 | 20 | 0 |
| Ryegrass, Italian | 0 | 0 | 0 | 0 | 20 | 0 | 40 | 70 | 40 | 0 | 60 | 50 | 70 |

TABLE A-continued

| 500 g ai/ha | Compounds | | | | | | | | | | | | | |
|---|---|---|---|---|---|---|---|---|---|---|---|---|---|---|
| Preemergence | 561 | 562 | 563 | 564 | 565 | 566 | 567 | 568 | 569 | 570 | 571 | 572 | 573 | 574 |
| Barnyardgrass | 90 | 90 | 100 | 100 | 90 | 100 | 100 | 100 | 100 | 100 | 90 | 90 | 100 | 90 |
| Foxtail, Giant | 90 | 90 | 100 | 100 | 90 | 100 | 100 | 100 | 100 | 100 | 100 | 90 | 100 | 90 |
| Kochia | 90 | 90 | 80 | 90 | 90 | 80 | 80 | 80 | 90 | 80 | 80 | 80 | 80 | 70 |
| Pigweed | 90 | 90 | 80 | 90 | 80 | 90 | 40 | 60 | 80 | 70 | 80 | 80 | 80 | 50 |
| Ragweed | 80 | 80 | 60 | 90 | 50 | 90 | 60 | 50 | 70 | 0 | 0 | 50 | 50 | 0 |
| Ryegrass, Italian | 40 | 90 | 0 | 90 | 40 | 70 | 80 | 100 | 70 | 90 | 80 | 50 | 90 | 80 |

| 500 g ai/ha | Compounds | | | | | | | | | | | | | |
|---|---|---|---|---|---|---|---|---|---|---|---|---|---|---|
| Preemergence | 575 | 576 | 577 | 587 | 588 | 589 | 590 | 591 | 592 | 593 | 594 | 595 | 596 | 597 |
| Barnyardgrass | 100 | 90 | 100 | 90 | 90 | 90 | 90 | 90 | 90 | 90 | 90 | 90 | 100 | 70 |
| Foxtail, Giant | 100 | 90 | 100 | 90 | 90 | 90 | 90 | 90 | 90 | 90 | 90 | 90 | 100 | 80 |
| Kochia | 70 | 90 | 70 | 0 | 0 | 0 | 20 | 60 | 30 | 0 | 50 | 50 | 70 | 20 |
| Pigweed | 40 | 80 | 40 | — | 0 | 0 | 0 | 40 | 0 | 0 | 20 | 30 | 40 | 0 |
| Ragweed | 0 | 60 | 40 | 0 | 0 | 0 | — | 60 | 20 | 0 | 20 | 30 | 20 | 0 |
| Ryegrass, Italian | 80 | 30 | 80 | 60 | 50 | 40 | 30 | 60 | 50 | 50 | 90 | 40 | 50 | 0 |

| 500 g ai/ha | Compounds | | | | | | | | | | | |
|---|---|---|---|---|---|---|---|---|---|---|---|---|
| Preemergence | 598 | 599 | 600 | 601 | 602 | 605 | 606 | 607 | 608 | 609 | 610 | 611 |
| Barnyardgrass | 60 | 30 | 90 | 80 | 0 | 70 | 80 | 30 | 80 | 90 | 90 | 90 |
| Foxtail, Giant | 60 | 0 | 90 | 80 | 0 | 90 | 90 | 90 | 90 | 90 | 90 | 90 |
| Kochia | 0 | 0 | 20 | 0 | 0 | 0 | 0 | 0 | 70 | 60 | 70 | 60 |
| Pigweed | 0 | 0 | 0 | 0 | 0 | 0 | 0 | 0 | 70 | 80 | 80 | 80 |
| Ragweed | 0 | 0 | 0 | 0 | 0 | 0 | 0 | 0 | 60 | 60 | 70 | — |
| Ryegrass, Italian | 20 | 0 | 0 | 0 | 0 | 20 | 0 | 0 | 50 | 60 | 70 | 60 |

| 500 g ai/ha | Compounds | | | | | | | | | | | |
|---|---|---|---|---|---|---|---|---|---|---|---|---|
| Preemergence | 612 | 613 | 614 | 616 | 617 | 618 | 619 | 620 | 621 | 622 | 623 | 624 | 625 |
| Barnyardgrass | 90 | 90 | 90 | 90 | 90 | 90 | 0 | 80 | 90 | 90 | 90 | 90 | 90 |
| Foxtail, Giant | 90 | 90 | 90 | 100 | 100 | 100 | 0 | 90 | 90 | 90 | 90 | 90 | 90 |
| Kochia | 20 | 70 | 20 | 80 | 70 | 90 | 20 | 20 | 40 | 80 | 70 | 60 | 80 |
| Pigweed | 70 | 70 | 0 | 90 | 90 | 90 | 0 | 0 | 20 | 80 | 80 | 80 | 90 |
| Ragweed | 50 | 60 | 0 | 80 | 60 | 70 | 0 | 0 | 90 | 60 | 80 | 70 | 60 |
| Ryegrass, Italian | 70 | 80 | 20 | 90 | 90 | 90 | 0 | 0 | 40 | 40 | 90 | 40 | 50 |

| 500 g ai/ha | Compounds | | | | | | | | | |
|---|---|---|---|---|---|---|---|---|---|---|
| Preemergence | 630 | 631 | 632 | 633 | 634 | 635 | 636 | 637 | 638 | 639 |
| Barnyardgrass | 90 | 0 | 90 | 90 | 70 | 90 | 90 | 90 | 90 | 90 |
| Foxtail, Giant | 90 | 0 | 90 | 90 | 80 | 90 | 90 | 100 | 100 | 100 |
| Kochia | 50 | 0 | 70 | 50 | 0 | 60 | 70 | 60 | 20 | 80 |
| Pigweed | 0 | 0 | 70 | 50 | 30 | 70 | 80 | 100 | 60 | 80 |
| Ragweed | 30 | 0 | 70 | 50 | 0 | 50 | 70 | 70 | 60 | 70 |
| Ryegrass, Italian | 20 | 0 | 70 | 60 | 0 | 30 | 90 | 90 | 90 | 90 |

| 500 g ai/ha | Compounds | | | | | | | | | | | | | |
|---|---|---|---|---|---|---|---|---|---|---|---|---|---|---|
| Preemergence | 640 | 641 | 642 | 643 | 644 | 645 | 646 | 647 | 648 | 649 | 650 | 651 | 652 | 653 |
| Barnyardgrass | 90 | 0 | 90 | 90 | 90 | 90 | 90 | 90 | 90 | 90 | 90 | 100 | 90 | 90 | 90 |
| Foxtail, Giant | 90 | 100 | 90 | 100 | 90 | 90 | 100 | 100 | 80 | 70 | 100 | 100 | 100 | 100 |
| Kochia | 60 | 50 | 60 | 40 | 80 | 60 | 70 | 0 | 50 | 70 | 70 | 70 | 30 | 70 |
| Pigweed | 90 | 50 | 60 | 20 | 70 | 50 | 70 | 60 | 40 | 60 | 90 | 100 | 30 | 90 |
| Ragweed | 60 | 60 | 50 | 20 | 60 | 20 | 70 | 40 | 20 | 70 | 80 | 90 | 0 | 80 |
| Ryegrass, Italian | 50 | 60 | 80 | 90 | 90 | 60 | 90 | 30 | 40 | 70 | 90 | 90 | 60 | 70 |

| 500 g ai/ha | Compounds | | | | | | | | | | | | | |
|---|---|---|---|---|---|---|---|---|---|---|---|---|---|---|
| Preemergence | 654 | 655 | 656 | 657 | 658 | 659 | 660 | 661 | 662 | 663 | 664 | 665 | 666 | 667 |
| Barnyardgrass | 90 | 90 | 90 | 90 | 90 | 90 | 90 | 90 | 90 | 100 | 90 | 90 | 90 | 90 |
| Foxtail, Giant | 90 | 90 | 90 | 90 | 90 | 90 | 90 | 100 | 100 | 100 | 100 | 100 | 100 | 100 |
| Kochia | 40 | 40 | 50 | 40 | 30 | 0 | 0 | 70 | 90 | 80 | 70 | 70 | 60 | 70 |
| Pigweed | 70 | 60 | 40 | 30 | 50 | 0 | 0 | 40 | 80 | 70 | 60 | 30 | 20 | 50 |
| Ragweed | 30 | 30 | 60 | 20 | 70 | 0 | 0 | 80 | 80 | 70 | 80 | 90 | 70 | 70 |
| Ryegrass, Italian | 80 | 60 | 60 | 30 | 70 | 30 | 20 | 50 | 90 | 90 | 80 | 50 | 50 | 90 |

TABLE A-continued

| 500 g ai/ha | Compounds | | | | | | | | |
|---|---|---|---|---|---|---|---|---|---|
| Preemergence | 668 | 674 | 675 | 676 | 677 | 678 | 679 | 680 | 681 |
| Barnyardgrass | 90 | 80 | 80 | 90 | 90 | 90 | 90 | 90 | 80 |
| Foxtail, Giant | 100 | 90 | 90 | 90 | 90 | 90 | 90 | 90 | 90 |
| Kochia | 70 | 30 | 0 | 0 | 40 | 30 | 60 | 20 | 60 |
| Pigweed | 50 | 0 | 0 | 0 | 0 | 0 | 40 | 0 | 30 |
| Ragweed | 40 | 0 | 0 | 0 | 0 | 0 | 30 | 0 | 0 |
| Ryegrass, Italian | 0 | 0 | 20 | 20 | 40 | 20 | 30 | 20 | 30 |

| 500 g ai/ha | Compounds | | | | | | | | | | | | | |
|---|---|---|---|---|---|---|---|---|---|---|---|---|---|---|
| Preemergence | 682 | 683 | 684 | 685 | 686 | 687 | 688 | 689 | 690 | 691 | 692 | 693 | 694 | 695 |
| Barnyardgrass | 0 | 60 | 90 | 80 | 90 | 90 | 90 | 90 | 90 | 90 | 90 | 90 | 90 | 90 |
| Foxtail, Giant | 90 | 90 | 90 | 90 | 90 | 90 | 90 | 90 | 90 | 90 | 90 | 90 | 90 | 90 |
| Kochia | 0 | 20 | 0 | 0 | 40 | 40 | 50 | 60 | 90 | 90 | 80 | 90 | 0 | 90 |
| Pigweed | 0 | 0 | 0 | 0 | 20 | 30 | 40 | 40 | 90 | 80 | 90 | 80 | 0 | 40 |
| Ragweed | 0 | 0 | 0 | 0 | 0 | 0 | 40 | 30 | 80 | 90 | 70 | 60 | 0 | 40 |
| Ryegrass, Italian | 30 | 0 | 20 | 30 | 20 | 20 | 20 | 20 | 70 | 60 | 60 | 70 | 10 | 30 |

| 500 g ai/ha | Compounds | | | | | | | | | | |
|---|---|---|---|---|---|---|---|---|---|---|---|
| Preemergence | 696 | 697 | 698 | 699 | 700 | 701 | 702 | 703 | 704 | 705 | 706 |
| Barnyardgrass | 90 | 90 | 90 | 90 | 90 | 90 | 90 | 80 | 90 | 0 | 70 |
| Foxtail, Giant | 90 | 90 | 90 | 90 | 90 | 90 | 90 | 90 | 90 | 0 | 80 |
| Kochia | 60 | 80 | 40 | 70 | 70 | 0 | 20 | — | 30 | 0 | 0 |
| Pigweed | 30 | 50 | 50 | 50 | 60 | 0 | 30 | 0 | 30 | 0 | 0 |
| Ragweed | 40 | 60 | 50 | 70 | 60 | 0 | 0 | 0 | 20 | 0 | 0 |
| Ryegrass, Italian | 60 | 50 | 60 | 40 | 30 | 0 | 0 | 0 | 20 | 0 | 0 |

| 500 g ai/ha | Compounds | | | | |
|---|---|---|---|---|---|
| Preemergence | 711 | 712 | 714 | 715 | 716 |
| Barnyardgrass | 0 | 0 | 0 | 0 | 0 |
| Corn | — | — | 0 | 0 | 0 |
| Crabgrass, Large | — | — | 30 | 0 | 0 |
| Foxtail, Giant | 0 | 0 | 20 | 0 | 0 |
| Kochia | 0 | 0 | — | — | — |
| Morningglory | — | — | 0 | 0 | 0 |
| Pigweed | 0 | 0 | 0 | 0 | 0 |
| Ragweed | 0 | 0 | — | — | — |
| Ryegrass, Italian | 0 | 0 | — | — | — |
| Velvetleaf | — | — | 0 | 0 | 0 |
| Wheat | — | — | 0 | 0 | 0 |

| 500 g ai/ha | Compounds | | | | | | | | | | | | | |
|---|---|---|---|---|---|---|---|---|---|---|---|---|---|---|
| Preemergence | 717 | 718 | 719 | 720 | 721 | 722 | 723 | 724 | 725 | 726 | 727 | 728 | 729 | 730 |
| Barnyardgrass | 90 | 90 | 90 | 100 | 80 | 80 | 0 | 0 | 90 | 90 | 90 | 90 | 0 | 100 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 90 | 90 | 90 | 80 | 50 | 0 | 90 | 90 | 90 | 90 | 0 | 100 |
| Kochia | 60 | 60 | 80 | 70 | 0 | 0 | 0 | 0 | 50 | 90 | 0 | 90 | 0 | 80 |
| Morningglory | — | — | — | — | — | — | — | — | — | — | — | — | — | — |
| Pigweed | 30 | 0 | 90 | 0 | 0 | 0 | 0 | 0 | 0 | 90 | 0 | 0 | 0 | 50 |
| Ragweed | 40 | 40 | 70 | 80 | 50 | 0 | 0 | 0 | 0 | 50 | 0 | 30 | 0 | 60 |
| Ryegrass, Italian | 30 | 30 | 90 | 20 | 20 | 0 | 0 | 0 | 20 | 80 | 0 | 60 | 0 | 70 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | | |
|---|---|---|---|---|---|---|---|---|---|---|---|---|---|---|
| Preemergence | 731 | 732 | 733 | 734 | 735 | 736 | 737 | 738 | 739 | 740 | 741 | 742 | 743 | 744 |
| Barnyardgrass | 90 | 100 | 100 | 100 | 90 | 90 | 80 | 100 | 100 | 90 | 0 | 90 | 90 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 90 | 100 | 90 | 90 | 90 | 100 | 100 | 100 | 0 | 90 | 90 | 90 |
| Kochia | 60 | 90 | 80 | 90 | 80 | 70 | 50 | 70 | 80 | 90 | 30 | 90 | 80 | 90 |
| Morningglory | — | — | — | — | — | — | — | — | — | — | — | — | — | — |
| Pigweed | 0 | 20 | 60 | 80 | 20 | 20 | 0 | 50 | 30 | 80 | 40 | 50 | 20 | 50 |
| Ragweed | 70 | 70 | 80 | 50 | 0 | 20 | 0 | 70 | 80 | 50 | 0 | 80 | 40 | 50 |
| Ryegrass, Italian | 40 | 80 | 60 | 90 | 90 | 90 | 70 | 20 | 30 | 80 | 0 | 90 | 90 | 80 |

TABLE A-continued

| | | | | | | | | | | | | | |
|---|---|---|---|---|---|---|---|---|---|---|---|---|---|
| Velvetleaf | — | — | — | — | — | — | — | — | — | — | — | — | — |
| Wheat | — | — | — | — | — | — | — | — | — | — | — | — | — |

| 500 g ai/ha | Compounds | | | | | | | | | | | | |
|---|---|---|---|---|---|---|---|---|---|---|---|---|---|
| Preemergence | 745 | 746 | 747 | 748 | 749 | 750 | 751 | 752 | 753 | 754 | 755 | 756 | 757 | 758 |
| Barnyardgrass | 90 | 0 | 70 | 30 | 20 | 90 | 90 | 90 | 100 | 100 | 0 | 100 | 90 | 100 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 90 | 90 | 90 | 90 | 90 | 90 | 90 | 90 | 0 | 100 | 90 | 100 |
| Kochia | 90 | 60 | 80 | 0 | 20 | 0 | — | 70 | 20 | 0 | 0 | 70 | 70 | 60 |
| Morningglory | — | — | — | — | — | — | — | — | — | — | — | — | — | — |
| Pigweed | 90 | 20 | 50 | 0 | 0 | 0 | 0 | 40 | 0 | 0 | 0 | 70 | 70 | 20 |
| Ragweed | 80 | 0 | 0 | 0 | 0 | 0 | 40 | 60 | 0 | 0 | 0 | 30 | 90 | 0 |
| Ryegrass, Italian | 90 | 40 | 60 | 0 | 20 | 20 | 20 | 30 | 20 | 0 | 0 | 70 | 60 | 70 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | |
|---|---|---|---|---|---|---|---|---|---|---|---|---|---|
| Preemergence | 759 | 760 | 761 | 762 | 763 | 764 | 765 | 766 | 767 | 768 | 769 | 771 | 772 | 773 |
| Barnyardgrass | 100 | 100 | 100 | 100 | 80 | 100 | 100 | 90 | 90 | 90 | 100 | 90 | 40 | 0 |
| Corn | — | — | — | — | — | — | — | — | — | — | — | — | — | — |
| Crabgrass, Large | — | — | — | — | — | — | — | — | — | — | — | — | — | — |
| Foxtail, Giant | 100 | 100 | 90 | 100 | 50 | 80 | 80 | 40 | 90 | 90 | 100 | 90 | 90 | 0 |
| Kochia | 20 | 60 | 80 | 50 | 30 | 0 | 0 | 0 | 0 | 70 | 70 | 80 | 30 | 0 |
| Morningglory | — | — | — | — | — | — | — | — | — | — | — | — | — | — |
| Pigweed | 0 | 0 | 0 | 0 | 30 | 0 | 0 | 0 | 0 | 20 | 80 | 0 | 0 | 0 |
| Ragweed | 0 | 0 | 0 | 50 | 0 | 0 | 30 | 0 | 0 | 0 | 70 | 50 | 0 | 0 |
| Ryegrass, Italian | 20 | 0 | 40 | 70 | 0 | 20 | 60 | 0 | 0 | 20 | 40 | 70 | 0 | 0 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | |
|---|---|---|---|---|---|---|---|---|---|---|---|---|---|
| Preemergence | 774 | 775 | 776 | 777 | 778 | 779 | 780 | 781 | 782 | 783 | 785 | 786 | 787 | 788 |
| Barnyardgrass | 0 | 100 | 90 | 100 | 90 | 90 | 90 | 100 | 90 | 70 | 90 | 90 | 70 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 0 | 100 | 100 | 100 | 90 | 90 | 90 | 100 | 100 | 80 | 90 | 90 | 90 | 100 |
| Kochia | 0 | 80 | 60 | 0 | 80 | 80 | 80 | 90 | 90 | 50 | 40 | 0 | 90 | 80 |
| Morningglory | — | — | — | — | — | — | — | — | — | — | — | — | — | — |
| Pigweed | 0 | 70 | 60 | 40 | 80 | 60 | 50 | 70 | 50 | 0 | 20 | 0 | 80 | 90 |
| Ragweed | 0 | 80 | 80 | 0 | 60 | 70 | 70 | 0 | 20 | 0 | 0 | 0 | 70 | 90 |
| Ryegrass, Italian | 0 | 0 | 50 | 70 | 20 | 40 | 20 | 50 | 60 | 0 | 40 | 0 | 0 | 40 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | |
|---|---|---|---|---|---|---|---|---|---|---|---|---|---|
| Preemergence | 789 | 790 | 791 | 815 | 816 | 817 | 818 | 819 | 820 | 821 | 822 | 823 | 824 | 825 |
| Barnyardgrass | 90 | 90 | 90 | 100 | 90 | 90 | 100 | 100 | 100 | 90 | 100 | 100 | 100 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 90 | 100 | 90 | 90 | 100 | 100 | 100 | 100 | 100 | 100 | 100 | 90 |
| Kochia | 30 | 80 | 60 | 80 | 80 | 70 | 80 | 100 | 80 | 90 | 80 | 70 | 70 | 60 |
| Morningglory | — | — | — | — | — | — | — | — | — | — | — | — | — | — |
| Pigweed | 20 | 40 | 0 | 50 | 60 | 80 | 60 | 30 | 70 | 50 | 50 | 50 | 40 | 30 |
| Ragweed | 0 | 60 | 40 | 0 | 50 | 50 | 0 | 20 | 60 | 0 | 30 | 40 | 50 | 20 |
| Ryegrass, Italian | 0 | 70 | 20 | 80 | 80 | 40 | 90 | 100 | 80 | 90 | 40 | 60 | 40 | 40 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | |
|---|---|---|---|---|---|---|---|---|---|---|---|---|---|
| Preemergence | 826 | 827 | 828 | 829 | 830 | 831 | 832 | 833 | 834 | 835 | 836 | 837 | 838 | 839 |
| Barnyardgrass | 100 | 90 | 90 | 90 | 90 | 70 | 80 | 90 | 90 | 100 | 90 | 90 | 90 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 100 | 90 | 100 | 90 | 90 | 90 | 80 | 100 | 100 | 100 | 90 | 90 | 90 | 90 |
| Kochia | 90 | 60 | 40 | 90 | 90 | 0 | 100 | 80 | 90 | 90 | 90 | 90 | 80 | 90 |
| Morningglory | — | — | — | — | — | — | — | — | — | — | — | — | — | — |
| Pigweed | 60 | 40 | 0 | 60 | 40 | 20 | 30 | 0 | 30 | 40 | 60 | 80 | 90 | 90 |
| Ragweed | 80 | 20 | 0 | 70 | 20 | 0 | 60 | 20 | 20 | 0 | 0 | 70 | 60 | 90 |
| Ryegrass, Italian | 80 | 70 | 70 | 40 | 30 | 50 | 30 | 80 | 80 | 70 | 80 | 70 | 60 | 40 |

TABLE A-continued

| | | | | | | | | | | | | | |
|---|---|---|---|---|---|---|---|---|---|---|---|---|---|
| Velvetleaf | — | — | — | — | — | — | — | — | — | — | — | — | — |
| Wheat | — | — | — | — | — | — | — | — | — | — | — | — | — |

| 500 g ai/ha | Compounds | | | | | | | | | | | | |
|---|---|---|---|---|---|---|---|---|---|---|---|---|---|
| Preemergence | 840 | 841 | 842 | 843 | 844 | 845 | 846 | 847 | 848 | 849 | 850 | 851 | 852 | 853 |
| Barnyardgrass | 90 | 100 | 90 | 80 | 20 | 90 | 90 | 60 | 90 | 90 | 90 | 90 | 90 | 100 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 100 | 90 | 30 | 90 | 90 | 50 | 90 | 90 | 90 | 90 | 90 | 100 |
| Kochia | 70 | 60 | 80 | 70 | 0 | 90 | 70 | 0 | 70 | 80 | 70 | 70 | 20 | 40 |
| Morningglory | — | — | — | — | — | — | — | — | — | — | — | — | — | — |
| Pigweed | 60 | 30 | 70 | 40 | 0 | 0 | 0 | 0 | 50 | 50 | 30 | 90 | 40 | 40 |
| Ragweed | 0 | 0 | 80 | 30 | 0 | 0 | 0 | 0 | 30 | 90 | 0 | 30 | 0 | 20 |
| Ryegrass, Italian | 20 | 40 | 60 | 50 | 0 | 30 | 70 | 0 | 50 | 90 | 70 | 70 | 30 | 60 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | |
|---|---|---|---|---|---|---|---|---|---|---|---|---|---|
| Preemergence | 854 | 855 | 856 | 857 | 858 | 859 | 860 | 861 | 862 | 864 | 865 | 866 | 867 | 868 |
| Barnyardgrass | 80 | 100 | 90 | 90 | 90 | 90 | 90 | 90 | 100 | 90 | 70 | 90 | 90 | 60 |
| Corn | — | — | — | — | — | — | — | — | — | — | — | — | — | — |
| Crabgrass, Large | — | — | — | — | — | — | — | — | — | — | — | — | — | — |
| Foxtail, Giant | 80 | 90 | 90 | 90 | 90 | 90 | 90 | 90 | 90 | 90 | 80 | 90 | 90 | 60 |
| Kochia | 0 | 30 | 50 | 30 | 70 | 60 | 60 | 60 | 70 | 80 | — | 80 | 70 | 0 |
| Morningglory | — | — | — | — | — | — | — | — | — | — | — | — | — | — |
| Pigweed | 0 | — | 50 | 70 | 50 | 80 | 90 | 70 | 90 | 90 | 0 | 50 | 30 | 0 |
| Ragweed | 0 | 0 | 20 | 30 | 30 | 50 | 50 | 70 | 100 | 50 | 0 | 30 | 30 | 0 |
| Ryegrass, Italian | 0 | 30 | 80 | 60 | 70 | 80 | 40 | 90 | 20 | 50 | 0 | 70 | 60 | 0 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | |
|---|---|---|---|---|---|---|---|---|---|---|---|---|---|
| Preemergence | 869 | 870 | 871 | 872 | 873 | 874 | 875 | 876 | 877 | 878 | 879 | 880 | 881 | 882 |
| Barnyardgrass | 90 | 80 | 90 | 100 | 90 | 100 | 90 | 90 | 100 | 100 | 100 | 100 | 90 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 50 | 80 | 90 | 100 | 100 | 90 | 100 | 90 | 100 | 100 | 100 | 90 | 90 |
| Kochia | 0 | 0 | 80 | 80 | 90 | 90 | 80 | 70 | 80 | 90 | 90 | 90 | 60 | 90 |
| Morningglory | — | — | — | — | — | — | — | — | — | — | — | — | — | — |
| Pigweed | 0 | 0 | 30 | 60 | 50 | 30 | 0 | 30 | 0 | 40 | 80 | 90 | 0 | 20 |
| Ragweed | 0 | 0 | 20 | 100 | 90 | 60 | 50 | 80 | 60 | 80 | 90 | 80 | 0 | 60 |
| Ryegrass, Italian | 0 | 0 | 30 | 40 | 80 | 50 | 30 | 30 | 20 | 70 | 90 | 70 | 60 | 30 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | |
|---|---|---|---|---|---|---|---|---|---|---|---|---|---|
| Preemergence | 883 | 885 | 886 | 887 | 888 | 889 | 890 | 891 | 892 | 893 | 894 | 895 | 896 | 897 |
| Barnyardgrass | 90 | 90 | 90 | 90 | 90 | 90 | 90 | 80 | 100 | 100 | 100 | 100 | 90 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 80 | 100 | 90 | 90 | 90 | 90 | 90 | 100 | 90 | 100 | 90 | 100 | 100 |
| Kochia | 60 | 0 | 90 | 20 | 80 | 80 | 90 | 20 | 90 | 90 | 90 | 90 | 50 | 90 |
| Morningglory | — | — | — | — | — | — | — | — | — | — | — | — | — | — |
| Pigweed | 0 | 0 | 0 | 0 | 0 | 0 | 50 | 0 | 40 | 50 | 50 | 50 | 40 | 60 |
| Ragweed | 0 | 0 | 50 | 0 | 0 | 40 | 0 | 0 | 50 | 70 | 40 | 0 | 0 | 60 |
| Ryegrass, Italian | 20 | 20 | 60 | 0 | 60 | 40 | 70 | 30 | 90 | 90 | 60 | 70 | 70 | 50 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | |
|---|---|---|---|---|---|---|---|---|---|---|---|---|---|
| Preemergence | 898 | 899 | 900 | 901 | 902 | 903 | 904 | 905 | 906 | 907 | 908 | 909 | 910 | 911 |
| Barnyardgrass | 90 | 90 | 90 | 90 | 90 | 90 | 90 | 90 | 0 | 80 | 50 | 80 | 100 | 100 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 90 | 90 | 90 | 90 | 90 | 0 | 90 | 80 | 90 | 100 | 100 | |
| Kochia | 90 | 70 | 90 | 80 | 0 | 90 | 90 | 90 | 0 | 20 | 0 | 50 | 90 | 100 |
| Morningglory | — | — | — | — | — | — | — | — | — | — | — | — | — | — |
| Pigweed | 80 | 40 | 90 | 60 | 0 | 0 | 50 | 0 | 0 | 0 | 0 | 0 | 30 | 50 |
| Ragweed | 60 | 60 | 80 | 0 | 0 | 0 | 0 | 0 | 0 | 0 | 20 | 0 | 0 | 60 |
| Ryegrass, Italian | 70 | 20 | 60 | 50 | 20 | 0 | 0 | 0 | 0 | 0 | 0 | 30 | 60 | 90 |

TABLE A-continued

| | | | | | | | | | | | | | |
|---|---|---|---|---|---|---|---|---|---|---|---|---|---|
| Velvetleaf | — | — | — | — | — | — | — | — | — | — | — | — | — |
| Wheat | — | — | — | — | — | — | — | — | — | — | — | — | — |

| 500 g ai/ha | Compounds | | | | | | | | | | | | |
|---|---|---|---|---|---|---|---|---|---|---|---|---|---|
| Preemergence | 912 | 913 | 914 | 915 | 916 | 917 | 918 | 919 | 920 | 921 | 922 | 923 | 924 | 925 |
| Barnyardgrass | 90 | 90 | 90 | 100 | 80 | 80 | 40 | 0 | 90 | 90 | 80 | 70 | 90 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 100 | 90 | 90 | 100 | 80 | 90 | 70 | 0 | 90 | 100 | 90 | 70 | 90 | 90 |
| Kochia | 70 | 40 | 60 | 90 | 60 | 0 | 0 | 0 | 0 | 30 | 0 | 0 | 0 | 0 |
| Morningglory | — | — | — | — | — | — | — | — | — | — | — | — | — | — |
| Pigweed | 0 | 0 | 90 | 90 | 20 | 0 | 0 | 0 | 0 | 0 | 0 | 0 | 0 | 0 |
| Ragweed | 0 | 60 | 0 | 90 | 70 | 0 | 0 | 0 | 0 | 0 | 0 | 0 | 0 | 0 |
| Ryegrass, Italian | 50 | 40 | 60 | 70 | 30 | 0 | 0 | 0 | 0 | 60 | 40 | 0 | 70 | 30 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | |
|---|---|---|---|---|---|---|---|---|---|---|---|---|---|
| Preemergence | 926 | 927 | 928 | 929 | 930 | 931 | 932 | 933 | 934 | 935 | 936 | 937 | 938 | 939 |
| Barnyardgrass | 90 | 70 | 90 | 90 | 90 | 90 | 90 | 100 | 90 | 90 | 90 | 90 | 90 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 70 | 90 | 90 | 90 | 90 | 100 | 100 | 90 | 90 | 90 | 90 | 90 | 90 |
| Kochia | 0 | 0 | 80 | 90 | 90 | 90 | 70 | 90 | 80 | 80 | 90 | 80 | 80 | 60 |
| Morningglory | — | — | — | — | — | — | — | — | — | — | — | — | — | — |
| Pigweed | 0 | 0 | 20 | 50 | 30 | 40 | 30 | 30 | 80 | 20 | 80 | 80 | 90 | 0 |
| Ragweed | 0 | 0 | 0 | 30 | 0 | 30 | 30 | 90 | 30 | 30 | 50 | 80 | 20 | 50 |
| Ryegrass, Italian | 0 | 0 | 70 | 80 | 70 | 70 | 60 | 70 | 60 | 50 | 70 | 50 | 30 | 20 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | |
|---|---|---|---|---|---|---|---|---|---|---|---|---|---|
| Preemergence | 940 | 941 | 942 | 943 | 944 | 945 | 946 | 947 | 948 | 949 | 950 | 951 | 952 | 953 |
| Barnyardgrass | 70 | 90 | 90 | 90 | 90 | 90 | 80 | 60 | 90 | 100 | 100 | 90 | 90 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 90 | 90 | 90 | 70 | 20 | 80 | 90 | 70 | 90 | 70 | 90 | 100 |
| Kochia | 0 | 0 | 90 | 80 | 70 | 0 | 50 | 40 | 0 | 50 | 60 | 20 | 30 | 60 |
| Morningglory | — | — | — | — | — | — | — | — | — | — | — | — | — | — |
| Pigweed | 0 | 0 | 90 | 50 | 20 | 0 | 0 | 0 | 0 | 0 | 0 | 0 | 0 | 0 |
| Ragweed | 0 | 30 | 50 | 30 | 50 | 0 | 0 | 0 | 0 | 0 | 20 | 0 | 0 | 0 |
| Ryegrass, Italian | 0 | 0 | 20 | 50 | 0 | 0 | 0 | 0 | 0 | 0 | 70 | 0 | 0 | 60 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | |
|---|---|---|---|---|---|---|---|---|---|---|---|---|---|
| Preemergence | 954 | 955 | 956 | 957 | 958 | 959 | 960 | 961 | 962 | 963 | 964 | 965 | 966 | 967 |
| Barnyardgrass | 90 | 100 | 100 | 100 | 90 | 100 | 90 | 90 | 90 | 100 | 90 | 90 | 90 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 100 | 100 | 70 | 90 | 100 | 90 | 90 | 90 | 100 | 90 | 90 | 90 | 90 |
| Kochia | 20 | 70 | 90 | 80 | 90 | 90 | 30 | 90 | 70 | 70 | 20 | 60 | 30 | 0 |
| Morningglory | — | — | — | — | — | — | — | — | — | — | — | — | — | — |
| Pigweed | 0 | 0 | 0 | 20 | 30 | 30 | 0 | 30 | 50 | 30 | 0 | 0 | 0 | 0 |
| Ragweed | 0 | 30 | 80 | 30 | 60 | 70 | 0 | 90 | 30 | 0 | 0 | 0 | 0 | 0 |
| Ryegrass, Italian | 0 | 60 | 90 | 40 | 20 | 60 | 0 | 80 | 30 | 40 | 30 | 90 | 60 | 0 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | |
|---|---|---|---|---|---|---|---|---|---|---|---|---|---|
| Preemergence | 968 | 969 | 973 | 974 | 975 | 976 | 977 | 978 | 979 | 980 | 981 | 982 | 983 | 984 |
| Barnyardgrass | 60 | 80 | 90 | 100 | 100 | 100 | 90 | 90 | 90 | 100 | 100 | 90 | 100 | 100 |
| Corn | — | — | — | — | — | — | — | — | — | — | — | — | — | — |
| Crabgrass, Large | — | — | — | — | — | — | — | — | — | — | — | — | — | — |
| Foxtail, Giant | 60 | 90 | 90 | 90 | 90 | 90 | 90 | 90 | 100 | 100 | 100 | 100 | 100 | 100 |
| Kochia | 0 | 0 | 60 | 100 | 90 | 90 | 90 | 90 | 90 | 90 | 90 | 90 | 90 | 90 |
| Morningglory | — | — | — | — | — | — | — | — | — | — | — | — | — | — |
| Pigweed | 0 | 0 | 0 | 60 | 90 | 50 | 70 | 50 | 90 | 0 | 0 | 50 | 40 | 60 |
| Ragweed | 0 | 0 | 70 | 90 | 90 | 90 | 100 | 90 | 90 | 20 | 50 | 80 | 100 | 30 |
| Ryegrass, Italian | 0 | 30 | 30 | 90 | 40 | 80 | 40 | 90 | 60 | 30 | 60 | 90 | 60 | 30 |

TABLE A-continued

| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | | |
|---|---|---|---|---|---|---|---|---|---|---|---|---|---|---|
| Preemergence | 985 | 986 | 987 | 988 | 989 | 990 | 991 | 992 | 993 | 994 | 995 | 996 | 998 | 999 |
| Barnyardgrass | 0 | 90 | 90 | 90 | 90 | 100 | 90 | 0 | 90 | 100 | 90 | 0 | 0 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 0 | 100 | 90 | 90 | 90 | 100 | 90 | 0 | 90 | 100 | 90 | 0 | 0 | 90 |
| Kochia | 0 | 70 | 60 | 80 | 90 | 90 | 60 | 0 | 50 | 60 | 0 | 0 | 0 | 20 |
| Morningglory | — | — | — | — | — | — | — | — | — | — | — | — | — | — |
| Pigweed | 0 | 70 | 20 | 40 | 0 | 80 | 50 | 0 | 80 | 70 | 30 | 0 | 0 | 50 |
| Ragweed | 0 | 70 | 0 | 80 | 40 | 80 | 30 | 0 | 60 | 0 | 20 | 0 | 0 | 30 |
| Ryegrass, Italian | 0 | 80 | 40 | 20 | 0 | 60 | 50 | 0 | 90 | 100 | 50 | 0 | 0 | 50 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | | |
|---|---|---|---|---|---|---|---|---|---|---|---|---|---|---|
| Preemergence | 1000 | 1001 | 1002 | 1013 | 1014 | 1015 | 1016 | 1017 | 1018 | 1019 | 1020 | 1021 | 1022 | 1023 |
| Barnyardgrass | 60 | 0 | 70 | 90 | 90 | 90 | 90 | 90 | 90 | 0 | 90 | 100 | 100 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 0 | 80 | 90 | 90 | 90 | 90 | 90 | 90 | 0 | 90 | 100 | 100 | 90 |
| Kochia | 0 | 0 | 0 | 70 | 70 | 60 | 0 | 70 | 60 | 0 | 20 | 90 | 80 | 0 |
| Morningglory | — | — | — | — | — | — | — | — | — | — | — | — | — | — |
| Pigweed | 40 | 0 | 50 | 40 | 30 | 40 | 0 | 60 | 80 | 0 | 40 | 80 | 70 | 30 |
| Ragweed | 0 | 0 | 0 | 0 | 0 | 50 | 0 | 90 | 40 | 0 | 20 | 70 | 0 | 40 |
| Ryegrass, Italian | 20 | 0 | 0 | 70 | 70 | 90 | 0 | 70 | 70 | 0 | 30 | 20 | 50 | 70 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | | |
|---|---|---|---|---|---|---|---|---|---|---|---|---|---|---|
| Preemergence | 1024 | 1025 | 1026 | 1027 | 1028 | 1029 | 1030 | 1031 | 1032 | 1033 | 1034 | 1035 | 1036 | 1037 |
| Barnyardgrass | 90 | 70 | 90 | 90 | 90 | 90 | 90 | 0 | 70 | 90 | 90 | 90 | 90 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 90 | 90 | 90 | 90 | 90 | 0 | 70 | 90 | 90 | 90 | 90 | 80 |
| Kochia | 40 | 20 | 80 | 90 | 60 | 90 | 70 | 0 | 0 | 60 | 70 | 50 | 90 | 90 |
| Morningglory | — | — | — | — | — | — | — | — | — | — | — | — | — | — |
| Pigweed | 50 | 50 | 0 | 40 | 0 | 0 | 0 | 0 | 0 | 0 | 0 | 0 | 0 | 20 |
| Ragweed | 30 | 0 | 50 | 80 | — | 0 | 0 | 0 | 0 | 10 | 90 | 70 | 50 | 60 |
| Ryegrass, Italian | 90 | 30 | 0 | 0 | 30 | 90 | 70 | 0 | 0 | 50 | 60 | 70 | 20 | 70 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | | |
|---|---|---|---|---|---|---|---|---|---|---|---|---|---|---|
| Preemergence | 1038 | 1039 | 1040 | 1041 | 1042 | 1043 | 1044 | 1045 | 1046 | 1047 | 1048 | 1049 | 1053 | 1054 |
| Barnyardgrass | 100 | 100 | 90 | 60 | 90 | 90 | 90 | 90 | 90 | 80 | 90 | 70 | 60 | 0 |
| Corn | — | — | — | — | — | — | — | — | — | — | — | — | — | — |
| Crabgrass, Large | — | — | — | — | — | — | — | — | — | — | — | — | — | — |
| Foxtail, Giant | 100 | 100 | 90 | 90 | 90 | 90 | 90 | 90 | 90 | 80 | 90 | 90 | 0 | 0 |
| Kochia | 80 | 100 | 80 | — | 70 | 70 | 50 | 20 | 70 | 80 | 90 | 70 | 0 | 0 |
| Morningglory | — | — | — | — | — | — | — | — | — | — | — | — | — | — |
| Pigweed | 30 | 40 | 40 | 20 | 50 | 20 | 30 | 0 | 0 | 20 | 90 | 60 | 0 | 0 |
| Ragweed | 70 | 90 | 80 | — | 40 | 50 | 30 | 30 | 70 | 60 | 80 | 40 | 0 | 0 |
| Ryegrass, Italian | 70 | 80 | 50 | 0 | 50 | 50 | 50 | 70 | 60 | 0 | 40 | 30 | 0 | 0 |
| Velvetleaf | — | — | — | — | — | — | — | — | — | — | — | — | — | — |
| Wheat | — | — | — | — | — | — | — | — | — | — | — | — | — | — |

| 500 g ai/hae | Compounds | | | | | | | | | | | | | |
|---|---|---|---|---|---|---|---|---|---|---|---|---|---|---|
| Preemergence | 1055 | 1056 | 1057 | 1058 | 1059 | 1073 | 1094 | 1095 | 1096 | 1097 | 1098 | 1099 | 1100 | 1101 |
| Barnyardgrass | 0 | 90 | 0 | 100 | 90 | 100 | 80 | 60 | 0 | 0 | 90 | 90 | 90 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 0 | 90 | 0 | 100 | 80 | 100 | 100 | 90 | 0 | 0 | 90 | 90 | 90 | 90 |
| Kochia | 0 | 0 | 0 | 30 | 20 | 70 | 0 | 0 | 0 | 0 | 70 | 70 | 60 | 70 |
| Morningglory | — | — | — | — | — | — | — | — | — | — | — | — | — | — |
| Pigweed | 0 | 0 | 0 | 0 | 0 | 100 | 0 | 30 | 0 | 0 | 0 | 30 | 0 | 20 |
| Ragweed | 0 | 0 | 0 | 0 | 30 | 30 | 0 | 0 | 0 | 0 | 0 | 60 | 0 | 40 |
| Ryegrass, Italian | 0 | 0 | 0 | 40 | 0 | 20 | 0 | 0 | 0 | 0 | 50 | 70 | 30 | 70 |

TABLE A-continued

| | | | | | | | | | | | | | |
|---|---|---|---|---|---|---|---|---|---|---|---|---|---|
| Velvetleaf | — | — | — | — | — | — | — | — | — | — | — | — | — |
| Wheat | — | — | — | — | — | — | — | — | — | — | — | — | — |

| 500 g ai/ha | Compounds | | | | | | | | | | | | |
|---|---|---|---|---|---|---|---|---|---|---|---|---|---|
| Preemergence | 1102 | 1111 | 1112 | 1113 | 1114 | 1115 | 1116 | 1117 | 1118 | 1119 | 1120 | 1121 | 1122 | 1123 |
| Barnyardgrass | 90 | 0 | 0 | 0 | 90 | 90 | 90 | 90 | 90 | 90 | 100 | 100 | 90 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 0 | 0 | 0 | 90 | 90 | 90 | 90 | 90 | 80 | 100 | 100 | 90 | 90 |
| Kochia | 70 | 0 | 0 | 0 | 60 | 70 | 30 | 70 | 70 | 80 | 70 | 100 | 70 | 80 |
| Morningglory | — | — | — | — | — | — | — | — | — | — | — | — | — | — |
| Pigweed | 50 | 0 | 0 | 0 | 0 | 40 | 20 | 0 | 0 | 30 | 50 | 50 | 70 | 50 |
| Ragweed | 50 | 0 | 0 | 0 | 0 | 20 | 20 | 70 | 60 | 70 | 50 | 100 | 80 | 60 |
| Ryegrass, Italian | 60 | 20 | 0 | 0 | 20 | 60 | 20 | 60 | 50 | 30 | 40 | 60 | 90 | 60 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | |
|---|---|---|---|---|---|---|---|---|---|---|---|---|---|
| Preemergence | 1124 | 1125 | 1126 | 1127 | 1128 | 1129 | 1130 | 1131 | 1132 | 1133 | 1134 | 1135 | 1136 | 1137 |
| Barnyardgrass | 90 | 90 | 90 | 30 | 90 | 90 | 0 | 90 | 90 | 90 | 80 | 0 | 90 | 0 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 100 | 90 | 70 | 90 | 90 | 30 | 90 | 100 | 90 | 90 | 0 | 90 | 0 |
| Kochia | 90 | 80 | 80 | 0 | 80 | 50 | 0 | 90 | 0 | 100 | 60 | 0 | 80 | 0 |
| Morningglory | — | — | — | — | — | — | — | — | — | — | — | — | — | — |
| Pigweed | 70 | 40 | 60 | 0 | 0 | 0 | 0 | 90 | 0 | 70 | 30 | 0 | 0 | 0 |
| Ragweed | 60 | — | 50 | 0 | 50 | 0 | 0 | 80 | 0 | 60 | 70 | 0 | 0 | 0 |
| Ryegrass, Italian | 30 | 60 | 70 | 0 | 40 | 50 | 0 | 70 | 50 | 30 | 40 | 0 | 30 | 0 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | |
|---|---|---|---|---|---|---|---|---|---|---|---|---|---|
| Preemergence | 1138 | 1139 | 1140 | 1151 | 1152 | 1153 | 1154 | 1155 | 1156 | 1157 | 1158 | 1159 | 1160 | 1177 |
| Barnyardgrass | 90 | 90 | 100 | 100 | 90 | 90 | 90 | 100 | 90 | 90 | 100 | 90 | 90 | 100 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 100 | 100 | 90 | 90 | 90 | 90 | 100 | 100 | 100 | 90 | 90 | 100 |
| Kochia | 80 | 60 | 80 | 80 | 0 | 70 | 90 | 90 | 80 | 90 | 30 | 30 | 50 | 30 |
| Morningglory | — | — | — | — | — | — | — | — | — | — | — | — | — | — |
| Pigweed | 0 | 0 | 40 | 100 | 80 | 0 | 80 | 30 | 20 | 60 | 0 | 0 | 20 | 20 |
| Ragweed | 0 | 50 | 60 | 60 | 0 | 0 | 90 | 80 | 100 | 80 | 0 | 0 | 0 | 30 |
| Ryegrass, Italian | 50 | 70 | 40 | 70 | 20 | 50 | 50 | 30 | 30 | 90 | 70 | 0 | 0 | 70 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | |
|---|---|---|---|---|---|---|---|---|---|---|---|---|---|
| Preemergence | 1178 | 1179 | 1180 | 1181 | 1182 | 1194 | 1195 | 1196 | 1197 | 1198 | 1199 | 1200 | 1201 | 1202 |
| Barnyardgrass | 50 | 0 | 70 | 0 | 0 | 30 | 80 | 90 | 100 | 100 | 100 | 0 | 70 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 70 | 0 | 50 | 0 | 0 | 20 | 40 | 90 | 100 | 100 | 100 | 0 | 80 | 90 |
| Kochia | 70 | 0 | 30 | 0 | 0 | 0 | 0 | 0 | 100 | 80 | 0 | 0 | 70 | 60 |
| Morningglory | — | — | — | — | — | — | — | — | — | — | — | — | — | — |
| Pigweed | 50 | 0 | 0 | 0 | 0 | 0 | 0 | 0 | 80 | 100 | 60 | 0 | 70 | 0 |
| Ragweed | 50 | 0 | 0 | 0 | 0 | 0 | 0 | 0 | 100 | 100 | 90 | 0 | 70 | 90 |
| Ryegrass, Italian | 20 | 0 | 0 | 0 | 0 | 0 | 0 | 0 | 70 | 60 | 0 | 0 | 0 | 60 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | |
|---|---|---|---|---|---|---|---|---|---|---|---|---|---|
| Preemergence | 1203 | 1204 | 1205 | 1206 | 1207 | 1208 | 1209 | 1210 | 1211 | 1212 | 1213 | 1214 | 1215 | 1216 |
| Barnyardgrass | 90 | 90 | 90 | 100 | 100 | 100 | 90 | 100 | 100 | 100 | 100 | 90 | 100 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 100 | 90 | 100 | 100 | 100 | 100 | 100 | 100 | 100 | 90 | 90 | 80 |
| Kochia | 50 | 80 | 30 | 100 | 90 | 100 | 90 | 10 | 70 | 100 | 80 | 60 | 90 | — |
| Morningglory | — | — | — | — | — | — | — | — | — | — | — | — | — | — |
| Pigweed | 20 | 100 | 30 | 90 | 60 | 90 | 0 | 0 | 70 | 90 | 80 | 70 | 0 | 0 |
| Ragweed | 80 | 90 | 0 | 60 | 90 | 100 | 90 | 0 | 50 | 90 | 70 | 70 | 0 | 20 |
| Ryegrass, Italian | 20 | 90 | 70 | 0 | 20 | 70 | 50 | 50 | 80 | 70 | 70 | 90 | 0 | 0 |

TABLE A-continued

| | | | | | | | | | | | | | | |
|---|---|---|---|---|---|---|---|---|---|---|---|---|---|---|
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | | |
|---|---|---|---|---|---|---|---|---|---|---|---|---|---|---|
| Preemergence | 1217 | 1218 | 1219 | 1220 | 1221 | 1222 | 1223 | 1224 | 1225 | 1226 | 1227 | 1228 | 1229 | 1230 |
| Barnyardgrass | 100 | 100 | 90 | 90 | 100 | 20 | 90 | 80 | 90 | 100 | 40 | 90 | 100 | 50 |
| Corn | — | — | — | — | — | — | — | — | — | — | — | — | — | — |
| Crabgrass, Large | — | — | — | — | — | — | — | — | — | — | — | — | — | — |
| Foxtail, Giant | 100 | 90 | 90 | 90 | 100 | 60 | 90 | 90 | 90 | 100 | 90 | 90 | 100 | 90 |
| Kochia | 0 | 0 | 0 | 50 | 50 | 40 | 20 | 0 | 70 | 70 | 0 | 0 | 90 | 90 |
| Morningglory | — | — | — | — | — | — | — | — | — | — | — | — | — | — |
| Pigweed | 0 | 0 | 0 | 40 | 50 | 0 | 0 | 70 | 50 | 90 | 60 | 60 | 90 | 30 |
| Ragweed | 0 | 0 | 0 | 40 | 70 | 0 | 20 | 20 | 60 | 30 | 0 | 0 | 70 | 0 |
| Ryegrass, Italian | 0 | 0 | 0 | 50 | 80 | 0 | 0 | 20 | 40 | 80 | 70 | 60 | 40 | 0 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | | |
|---|---|---|---|---|---|---|---|---|---|---|---|---|---|---|
| Preemergence | 1231 | 1232 | 1233 | 1234 | 1235 | 1236 | 1238 | 1239 | 1240 | 1241 | 1242 | 1243 | 1244 | 1245 |
| Barnyardgrass | 90 | 90 | 90 | 100 | 100 | 100 | 90 | 90 | 0 | 0 | 60 | 0 | 90 | 80 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 90 | 100 | 100 | 100 | 90 | 90 | 0 | 0 | 80 | 0 | 90 | 90 |
| Kochia | 90 | 80 | 70 | 80 | 80 | 90 | 60 | — | 0 | 0 | 0 | 0 | 0 | 20 |
| Morningglory | — | — | — | — | — | — | — | — | — | — | — | — | — | — |
| Pigweed | 70 | 90 | 40 | 90 | 90 | 90 | 60 | 60 | 0 | 0 | 0 | 0 | 0 | 0 |
| Ragweed | 60 | 80 | 50 | 60 | 90 | 30 | 50 | 70 | 0 | 0 | 0 | 0 | 0 | 20 |
| Ryegrass, Italian | 90 | 60 | 70 | 80 | 60 | 80 | 50 | 50 | 0 | 0 | 0 | 0 | 50 | 60 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | | |
|---|---|---|---|---|---|---|---|---|---|---|---|---|---|---|
| Preemergence | 1246 | 1247 | 1248 | 1249 | 1250 | 1251 | 1252 | 1253 | 1254 | 1255 | 1256 | 1257 | 1260 | 1280 |
| Barnyardgrass | 80 | 90 | 90 | 100 | 100 | 100 | 100 | 100 | 100 | 100 | 100 | 0 | 100 | 50 |
| Corn | — | — | — | — | — | — | — | — | — | — | — | — | — | — |
| Crabgrass, Large | — | — | — | — | — | — | — | — | — | — | — | — | — | — |
| Foxtail, Giant | 70 | 80 | 50 | 100 | 100 | 100 | 100 | 100 | 100 | 100 | 100 | 0 | 90 | 80 |
| Kochia | 80 | 30 | 0 | 90 | 40 | 90 | 80 | 80 | 70 | 80 | 70 | 0 | 90 | 0 |
| Morningglory | — | — | — | — | — | — | — | — | — | — | — | — | — | — |
| Pigweed | 0 | 0 | 0 | 90 | 30 | 90 | 90 | 80 | 70 | 90 | 70 | 0 | 90 | 30 |
| Ragweed | 60 | 0 | 0 | 70 | 0 | 80 | 70 | 60 | 30 | 70 | 30 | 0 | 90 | 0 |
| Ryegrass, Italian | 50 | 20 | 0 | 100 | 50 | 60 | 90 | 60 | 40 | 40 | 60 | 0 | 60 | 0 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | | |
|---|---|---|---|---|---|---|---|---|---|---|---|---|---|---|
| Preemergence | 1281 | 1298 | 1299 | 1300 | 1301 | 1302 | 1303 | 1304 | 1305 | 1306 | 1307 | 1308 | 1309 | 1310 |
| Barnyardgrass | 90 | 90 | 90 | 90 | 90 | 90 | 30 | 0 | 90 | 90 | 90 | 90 | 90 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 90 | 90 | 90 | 90 | 90 | 0 | 90 | 90 | 90 | 90 | 90 | 90 |
| Kochia | 60 | 80 | 70 | 60 | 60 | 60 | 0 | 0 | 0 | 70 | 90 | 50 | 60 | 70 |
| Morningglory | — | — | — | — | — | — | — | — | — | — | — | — | — | — |
| Pigweed | 40 | 0 | 60 | 40 | 30 | 30 | 30 | 0 | 0 | 0 | 0 | 20 | 20 | 40 |
| Ragweed | 60 | 20 | 70 | 80 | 20 | 50 | 0 | 0 | 0 | 60 | 60 | 70 | 50 | 40 |
| Ryegrass, Italian | 20 | 0 | 70 | 60 | 0 | 0 | 0 | 0 | 0 | 0 | 0 | 0 | 20 | 70 |
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | | |
|---|---|---|---|---|---|---|---|---|---|---|---|---|---|---|
| Preemergence | 1311 | 1312 | 1313 | 1314 | 1316 | 1317 | 1318 | 1319 | 1320 | 1321 | 1323 | 1324 | 1325 | 1326 |
| Barnyardgrass | 100 | 100 | 100 | 100 | 90 | 90 | 90 | 90 | 60 | 100 | 90 | 100 | 90 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 100 | 100 | 80 | 100 | 90 | 100 | 90 | 90 | 80 | 100 | 90 | 100 | 90 | 90 |
| Kochia | 100 | 80 | 100 | 80 | 80 | 80 | 80 | 80 | 60 | 80 | 90 | 90 | 90 | 100 |
| Morningglory | — | — | — | — | — | — | — | — | — | — | — | — | — | — |
| Pigweed | 20 | 60 | 0 | 70 | 80 | 60 | 80 | 60 | 0 | 0 | 40 | 40 | 90 | 0 |
| Ragweed | 90 | 100 | 0 | 100 | 70 | 40 | 90 | 20 | 0 | 50 | 70 | 90 | 70 | 0 |
| Ryegrass, Italian | 80 | 70 | 0 | 40 | 90 | 90 | 60 | 90 | 0 | 40 | 70 | 60 | 0 | 20 |

TABLE A-continued

| | | | | | | | | | | | | | |
|---|---|---|---|---|---|---|---|---|---|---|---|---|---|
| Velvetleaf | — | — | — | — | — | — | — | — | — | — | — | — | — | — |
| Wheat | — | — | — | — | — | — | — | — | — | — | — | — | — | — |

| 500 g ai/ha | Compounds | | | | | | | | | | | | |
|---|---|---|---|---|---|---|---|---|---|---|---|---|---|
| Preemergence | 1327 | 1328 | 1329 | 1330 | 1331 | 1332 | 1334 | 1335 | 1336 | 1355 | 1356 | 1357 | 1358 | 1359 |
| Barnyardgrass | 90 | 90 | 100 | 90 | 90 | 90 | 80 | 0 | 0 | 0 | 0 | 0 | 0 | 0 |
| Corn | — | — | — | — | — | — | — | — | — | 0 | 0 | 0 | 0 | 0 |
| Crabgrass, Large | — | — | — | — | — | — | — | — | — | 0 | 0 | 0 | 80 | 20 |
| Foxtail, Giant | 90 | 90 | 90 | 90 | 100 | 90 | 80 | 0 | 0 | 0 | 0 | 0 | 0 | 0 |
| Kochia | 90 | 50 | 50 | 90 | 0 | 0 | 20 | 0 | 0 | — | — | — | — | — |
| Morningglory | — | — | — | — | — | — | — | — | — | 0 | 0 | 0 | — | 0 |
| Pigweed | 30 | 0 | 30 | 0 | 0 | 0 | 30 | 0 | 0 | 0 | 0 | 0 | 0 | 0 |
| Ragweed | 0 | 0 | 20 | 50 | 0 | 0 | 30 | 0 | 0 | — | — | — | — | — |
| Ryegrass, Italian | 20 | 30 | 40 | 50 | 80 | 0 | 20 | 0 | 0 | — | — | — | — | — |
| Velvetleaf | — | — | — | — | — | — | — | — | — | 0 | 0 | 0 | 0 | 0 |
| Wheat | — | — | — | — | — | — | — | — | — | 0 | 0 | 0 | 50 | 0 |

| 500 g ai/ha | Compounds | | | | | | | | | | | | |
|---|---|---|---|---|---|---|---|---|---|---|---|---|---|
| Preemergence | 1360 | 1361 | 1362 | 1370 | 1371 | 1372 | 1373 | 1374 | 1376 | 1377 | 1378 | 1379 | 1380 | 1381 |
| Barnyardgrass | 0 | 0 | 0 | 90 | 100 | 100 | 100 | 0 | 100 | 100 | 90 | 100 | 100 | 100 |
| Corn | 0 | 0 | 0 | — | — | — | — | — | — | — | — | — | — | — |
| Crabgrass, Large | 0 | 0 | 0 | — | — | — | — | — | — | — | — | — | — | — |
| Foxtail, Giant | 0 | 0 | 0 | 90 | 90 | 100 | 100 | 0 | 100 | 100 | 90 | 100 | 100 | 100 |
| Kochia | — | — | — | 80 | 90 | 90 | 100 | 0 | 0 | 80 | 90 | 90 | 90 | 80 |
| Morningglory | 0 | 0 | 0 | — | — | — | — | — | — | — | — | — | — | — |
| Pigweed | 0 | 0 | 0 | 20 | 90 | 90 | 100 | 0 | 0 | 40 | 70 | 90 | 90 | 100 |
| Ragweed | — | — | — | 80 | 80 | 90 | 100 | 0 | 0 | 30 | 90 | 90 | 80 | 80 |
| Ryegrass, Italian | — | — | — | 90 | 50 | 60 | 90 | 0 | 70 | 50 | 90 | 50 | 50 | 50 |
| Velvetleaf | 0 | 0 | 0 | — | — | — | — | — | — | — | — | — | — | — |
| Wheat | 0 | 0 | 0 | — | — | — | — | — | — | — | — | — | — | — |

| 500 g ai/ha | Compounds | | | | | | | | | | | | |
|---|---|---|---|---|---|---|---|---|---|---|---|---|---|
| Preemergence | 1382 | 1383 | 1384 | 1385 | 1386 | 1387 | 1388 | 1389 | 1390 | 1391 | 1392 | 1394 | 1395 |
| Barnyardgrass | 70 | 100 | 90 | 90 | 100 | 90 | 100 | 100 | 90 | 100 | 60 | 90 | 90 |
| Corn | — | — | — | — | — | — | — | — | — | — | — | — | — |
| Crabgrass, Large | — | — | — | — | — | — | — | — | — | — | — | — | — |
| Foxtail, Giant | 90 | 100 | 90 | 90 | 90 | 90 | 100 | 100 | 90 | 100 | 60 | 90 | 90 |
| Kochia | 60 | 90 | 70 | 20 | 90 | 60 | 90 | 90 | 90 | 90 | 0 | 60 | 0 |
| Morningglory | — | — | — | — | — | — | — | — | — | — | — | — | — |
| Pigweed | 20 | 80 | 30 | 0 | 90 | 60 | 70 | 80 | 90 | 90 | 0 | 30 | 0 |
| Ragweed | 0 | 80 | 0 | 0 | 80 | 0 | 70 | 30 | 70 | 90 | 0 | 80 | 0 |
| Ryegrass, Italian | 0 | 70 | 70 | 0 | 70 | 0 | 100 | 90 | 30 | 70 | 0 | 60 | 40 |
| Velvetleaf | — | — | — | — | — | — | — | — | — | — | — | — | — |
| Wheat | — | — | — | — | — | — | — | — | — | — | — | — | — |

| 125 g ai/ha | Compounds | | | | | | | | | | | | |
|---|---|---|---|---|---|---|---|---|---|---|---|---|---|
| Preemergence | 352 | 353 | 354 | 356 | 360 | 361 | 362 | 363 | 364 | 365 | 366 | 367 | 368 |
| Barnyardgrass | 0 | 0 | 0 | 0 | 0 | 0 | 0 | 0 | 0 | 0 | 0 | 0 | 90 |
| Corn | 0 | 0 | 0 | 0 | 0 | 0 | 0 | 0 | 0 | 0 | 0 | 0 | — |
| Crabgrass, Large | 0 | 0 | 0 | 0 | 0 | 0 | 0 | 0 | 0 | 0 | 0 | 0 | — |
| Foxtail, Giant | 0 | 0 | 0 | 0 | 0 | 0 | 0 | 0 | 0 | 0 | 0 | 0 | 90 |
| Kochia | — | — | — | — | — | — | — | — | — | — | — | — | 0 |
| Morningglory | 0 | 0 | 0 | 0 | 0 | 0 | 0 | — | 0 | 0 | 0 | 0 | — |
| Pigweed | 0 | 0 | 0 | 0 | 0 | 0 | 0 | 0 | 0 | 0 | 0 | 0 | 0 |
| Ragweed | — | — | — | — | — | — | — | — | — | — | — | — | 30 |
| Ryegrass, Italian | — | — | — | — | — | — | — | — | — | — | — | — | 0 |
| Velvetleaf | 0 | 0 | 0 | 0 | 0 | 0 | 0 | 0 | 0 | 0 | 0 | 0 | — |
| Wheat | 0 | 0 | 0 | 0 | 0 | 0 | 0 | 0 | 0 | 0 | 0 | 0 | — |

| 125 g ai/ha | Compounds | | | | | | | | | | | | |
|---|---|---|---|---|---|---|---|---|---|---|---|---|---|
| Preemergence | 369 | 370 | 371 | 372 | 373 | 374 | 375 | 376 | 377 | 378 | 379 | 380 | 381 | 382 |
| Barnyardgrass | 90 | 90 | 90 | 90 | 90 | 90 | 90 | 90 | 90 | 90 | 20 | 0 | 70 | 0 | 0 |
| Foxtail, Giant | 90 | 90 | 90 | 80 | 80 | 90 | 90 | 90 | 90 | 90 | 0 | 50 | 0 | 0 |
| Kochia | 50 | 0 | 20 | 0 | 0 | 0 | 20 | 0 | 50 | 80 | 0 | 0 | 0 | 0 |
| Pigweed | 0 | 0 | 0 | 0 | 0 | 0 | 20 | 0 | 50 | 60 | 0 | 0 | 0 | 0 |
| Ragweed | 60 | 0 | 30 | 0 | 0 | 0 | 0 | 0 | 0 | 10 | 0 | 0 | 0 | 0 |
| Ryegrass, Italian | 0 | 0 | 0 | 0 | 30 | 0 | 20 | 0 | 20 | 50 | 0 | 0 | 0 | 0 |

TABLE A-continued

| 125 g ai/ha | Compounds | | | | | | | | | | | | |
|---|---|---|---|---|---|---|---|---|---|---|---|---|---|
| Preemergence | 383 | 384 | 386 | 387 | 388 | 389 | 390 | 391 | 392 | 393 | 394 | 395 | 396 |
| Barnyardgrass | 50 | 0 | 80 | 70 | 60 | 70 | 60 | 80 | 90 | 90 | 40 | 0 | 90 |
| Foxtail, Giant | 50 | 0 | 80 | 70 | 80 | 80 | 80 | 90 | 90 | 90 | 70 | 0 | 90 |
| Kochia | 0 | 0 | 0 | 0 | 0 | 0 | 0 | 30 | 50 | 60 | 0 | 0 | 80 |
| Pigweed | 0 | 0 | 0 | 0 | 0 | 0 | 0 | 70 | 70 | 50 | 0 | 0 | 90 |
| Ragweed | 0 | 0 | 0 | 0 | 0 | 0 | 0 | 80 | 70 | 0 | 0 | 0 | 0 |
| Ryegrass, Italian | 0 | 0 | 30 | 0 | 0 | 0 | 0 | 20 | 40 | 20 | 0 | 0 | 60 |

| 125 g ai/ha | Compounds | | | | | | | | | | | | |
|---|---|---|---|---|---|---|---|---|---|---|---|---|---|
| Preemergence | 397 | 398 | 399 | 400 | 401 | 402 | 403 | 404 | 405 | 406 | 407 | 408 | 409 | 410 |
| Barnyardgrass | 80 | 90 | 90 | 90 | 90 | 90 | 90 | 90 | 90 | 90 | 70 | 0 | 70 | 50 |
| Foxtail, Giant | 90 | 90 | 90 | 90 | 80 | 90 | 90 | 90 | 90 | 90 | 80 | 0 | 80 | 70 |
| Kochia | 70 | 70 | 80 | 60 | 50 | 40 | 70 | 60 | 50 | 0 | 0 | 0 | 0 | 0 |
| Pigweed | 90 | 70 | 70 | 60 | 20 | 30 | 30 | 30 | 50 | 20 | 0 | 0 | 0 | 0 |
| Ragweed | 50 | 20 | 50 | 70 | 0 | — | 50 | 0 | 20 | 0 | 0 | 0 | 0 | 0 |
| Ryegrass, Italian | 30 | 30 | 20 | 30 | 0 | 20 | 20 | 0 | 0 | 20 | 0 | 0 | 0 | 0 |

| 125 g ai/ha | Compounds | | | | | | | | | | | | |
|---|---|---|---|---|---|---|---|---|---|---|---|---|---|
| Preemergence | 411 | 412 | 413 | 414 | 415 | 416 | 417 | 418 | 419 | 420 | 421 | 422 | 423 | 424 |
| Barnyardgrass | 70 | 40 | 0 | 0 | 0 | 0 | 0 | 0 | 60 | 70 | 90 | 40 | 0 | 30 |
| Foxtail, Giant | 80 | 60 | 0 | 0 | 0 | 0 | 0 | 0 | 80 | 90 | 90 | 60 | 0 | 70 |
| Kochia | 0 | 0 | 0 | 0 | 0 | 0 | 0 | 0 | 0 | 0 | 70 | 0 | 0 | 0 |
| Pigweed | 0 | 0 | 0 | 0 | 0 | 0 | 0 | 0 | 0 | 0 | 20 | 20 | 0 | 0 |
| Ragweed | 0 | 0 | 0 | 0 | 0 | 0 | 0 | 0 | 0 | 0 | 30 | 0 | 0 | 0 |
| Ryegrass, Italian | 0 | 0 | 0 | 0 | 0 | 0 | 0 | 0 | 0 | 0 | 0 | 0 | 0 | 0 |

| 125 g ai/ha | Compounds | | | | | | | | | | | | |
|---|---|---|---|---|---|---|---|---|---|---|---|---|---|
| Preemergence | 425 | 426 | 427 | 428 | 429 | 430 | 431 | 432 | 433 | 434 | 435 | 436 | 437 | 438 |
| Barnyardgrass | 0 | 50 | 40 | 90 | 90 | 80 | 90 | 30 | 90 | 90 | 80 | 90 | 90 | 90 |
| Foxtail, Giant | 40 | 80 | 90 | 90 | 90 | 90 | 90 | 0 | 90 | 90 | 90 | 90 | 90 | 100 |
| Kochia | 0 | 0 | 30 | 50 | 70 | 30 | 30 | 0 | 70 | 70 | 60 | 70 | 60 | 70 |
| Pigweed | 0 | 0 | 0 | 0 | 80 | 0 | 70 | 0 | 20 | 80 | 60 | 80 | 20 | 80 |
| Ragweed | 0 | 0 | 0 | 0 | 50 | 30 | 40 | 0 | 70 | 50 | 20 | 0 | 0 | 60 |
| Ryegrass, Italian | 0 | 0 | 0 | 20 | 70 | 40 | 70 | 0 | 20 | 60 | 0 | 40 | 0 | 50 |

| 125 g ai/ha | Compounds | | | | | | | | | | | | |
|---|---|---|---|---|---|---|---|---|---|---|---|---|---|
| Preemergence | 439 | 440 | 441 | 442 | 443 | 444 | 445 | 446 | 447 | 448 | 449 | 450 | 451 | 452 |
| Barnyardgrass | 90 | 90 | 90 | 90 | 90 | 90 | 90 | 90 | 70 | 90 | 50 | 90 | 0 | 60 |
| Foxtail, Giant | 90 | 90 | 90 | 90 | 90 | 90 | 90 | 90 | 90 | 90 | 80 | 90 | 0 | 90 |
| Kochia | 70 | 60 | 70 | 80 | 30 | 60 | 50 | 50 | 50 | 20 | 20 | 50 | 0 | 60 |
| Pigweed | 50 | 20 | 50 | 70 | 80 | 80 | 30 | 40 | 30 | 20 | 0 | 70 | 0 | 80 |
| Ragweed | 0 | 20 | 30 | 20 | 80 | 50 | 20 | 50 | 0 | 0 | 0 | 20 | 0 | 20 |
| Ryegrass, Italian | 0 | 0 | 70 | 60 | 40 | 40 | 30 | 20 | 20 | 0 | 20 | 0 | 0 | 0 |

| 125 g ai/ha | Compounds | | | | | | | | | | | |
|---|---|---|---|---|---|---|---|---|---|---|---|---|
| Preemergence | 453 | 454 | 455 | 456 | 457 | 460 | 461 | 462 | 463 | 464 | 465 | 466 |
| Barnyardgrass | 80 | 70 | 70 | 0 | 0 | 80 | 70 | 80 | 50 | 90 | 90 | 90 |
| Foxtail, Giant | 90 | 80 | 80 | 0 | 0 | 90 | 90 | 80 | 80 | 90 | 100 | 70 |
| Kochia | 0 | 0 | 20 | 0 | 0 | 0 | 0 | 30 | 0 | 70 | 80 | 0 |
| Pigweed | 20 | 0 | 0 | 0 | 0 | 30 | 0 | 0 | 0 | 70 | 50 | 0 |
| Ragweed | 0 | 0 | 0 | 0 | 0 | 0 | 0 | 10 | 0 | 50 | 40 | 0 |
| Ryegrass, Italian | 0 | 0 | 0 | 0 | 0 | 40 | 20 | 0 | 0 | 70 | 70 | 0 |

| 125 g ai/ha | Compounds | | | | | | | | | | | | |
|---|---|---|---|---|---|---|---|---|---|---|---|---|---|
| Preemergence | 467 | 468 | 469 | 470 | 471 | 472 | 473 | 474 | 475 | 476 | 477 | 478 | 479 | 480 |
| Barnyardgrass | 90 | 0 | 80 | 90 | 70 | 90 | 80 | 90 | 90 | 90 | 20 | 20 | 0 | 0 |
| Foxtail, Giant | 90 | 0 | 80 | 90 | 90 | 90 | 90 | 90 | 90 | 90 | 90 | 70 | 80 | 70 |
| Kochia | 30 | 40 | 0 | 70 | 0 | 80 | 80 | 60 | 70 | 50 | 0 | 0 | 0 | 0 |
| Pigweed | 0 | 0 | 0 | 0 | 0 | 80 | 80 | 30 | 60 | 30 | 0 | 0 | 0 | 0 |
| Ragweed | 30 | 0 | 0 | 0 | 0 | 0 | 20 | 0 | 50 | 0 | 0 | 0 | 0 | 0 |
| Ryegrass, Italian | 0 | 0 | 0 | 0 | 0 | 50 | 0 | 0 | 20 | 0 | 0 | 0 | 0 | 0 |

TABLE A-continued

| 125 g ai/ha | Compounds | | | | | | | | | | | | | |
|---|---|---|---|---|---|---|---|---|---|---|---|---|---|---|
| Preemergence | 481 | 482 | 483 | 484 | 485 | 486 | 487 | 488 | 489 | 490 | 491 | 492 | 493 | 494 |
| Barnyardgrass | 0 | 0 | 0 | 0 | 30 | 30 | 90 | 90 | 90 | 80 | 90 | 90 | 90 | 70 |
| Foxtail, Giant | 50 | 70 | 70 | 50 | 70 | 60 | 90 | 90 | 90 | 90 | 90 | 90 | 90 | 80 |
| Kochia | 0 | 0 | 0 | 0 | 0 | 0 | 30 | 70 | 20 | 0 | 0 | 60 | 0 | 0 |
| Pigweed | 0 | 0 | 0 | 0 | 0 | 0 | 0 | 50 | 0 | 0 | 0 | 0 | 0 | 0 |
| Ragweed | 0 | 0 | 0 | 0 | 0 | 0 | 30 | 70 | 30 | 0 | 0 | 30 | 0 | 0 |
| Ryegrass, Italian | 0 | 0 | 0 | 0 | 0 | 0 | 20 | 30 | 30 | 20 | 20 | 50 | 0 | 0 |

| 125 g ai/ha | Compounds | | | | | | | | | | | | | |
|---|---|---|---|---|---|---|---|---|---|---|---|---|---|---|
| Preemergence | 495 | 496 | 497 | 498 | 499 | 500 | 501 | 502 | 503 | 504 | 505 | 506 | 507 | 508 |
| Barnyardgrass | 30 | 60 | 90 | 30 | 30 | 0 | 80 | 0 | 90 | 90 | 0 | 90 | 40 | 70 |
| Foxtail, Giant | 90 | 30 | 90 | 40 | 30 | 80 | 80 | 80 | 90 | 90 | 0 | 90 | 0 | 40 |
| Kochia | 20 | 0 | 20 | 0 | 0 | 50 | 0 | 0 | 0 | 80 | 0 | 0 | 0 | 0 |
| Pigweed | 0 | 0 | 30 | 0 | 0 | 0 | 0 | 0 | 0 | 80 | 0 | 30 | 0 | 0 |
| Ragweed | 0 | 0 | 0 | 0 | 0 | 0 | 0 | 0 | 0 | 40 | 0 | 0 | 0 | 0 |
| Ryegrass, Italian | 0 | 0 | 0 | 0 | 0 | 0 | 0 | 0 | 0 | 40 | 0 | 20 | 0 | 0 |

| 125 g ai/ha | Compounds | | | | | | | | | | | | | |
|---|---|---|---|---|---|---|---|---|---|---|---|---|---|---|
| Preemergence | 509 | 510 | 513 | 514 | 515 | 516 | 517 | 518 | 519 | 520 | 521 | 522 | 523 | 524 |
| Barnyardgrass | 60 | 60 | 40 | 90 | 0 | 40 | 0 | 0 | 90 | 90 | 90 | 90 | 90 | 20 |
| Foxtail, Giant | 40 | 60 | 90 | 90 | 0 | 70 | 0 | 70 | 90 | 90 | 90 | 90 | 90 | 40 |
| Kochia | 0 | 30 | 0 | 0 | 0 | 0 | 0 | 0 | 40 | 50 | 0 | 60 | 0 | 0 |
| Pigweed | 0 | 0 | 0 | 0 | 0 | 0 | 0 | 0 | 30 | 60 | 70 | 80 | 0 | 0 |
| Ragweed | 0 | 30 | 0 | 0 | 0 | 0 | 0 | 0 | 0 | 0 | 40 | 0 | 60 | 0 |
| Ryegrass, Italian | 0 | 0 | 20 | 20 | 0 | 0 | 0 | 0 | 50 | 30 | 30 | 30 | 40 | 0 |

| 125 g ai/ha | Compounds | | | | | | | | | | | |
|---|---|---|---|---|---|---|---|---|---|---|---|---|
| Preemergence | 525 | 526 | 527 | 534 | 535 | 536 | 537 | 538 | 539 | 540 | 541 | 544 |
| Barnyardgrass | 30 | 0 | 0 | 0 | 0 | 0 | 0 | 0 | 90 | 80 | 90 | 30 |
| Foxtail, Giant | 30 | 70 | 80 | 0 | 0 | 0 | 0 | 0 | 90 | 90 | 90 | 70 |
| Kochia | 0 | 0 | 0 | 0 | 0 | 0 | 0 | 0 | 60 | 0 | 0 | 0 |
| Pigweed | 0 | 0 | 0 | 0 | 0 | 0 | 0 | 0 | 40 | 0 | 0 | 0 |
| Ragweed | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 30 | 0 | 0 | 0 |

| 125 g ai/ha | Compounds | | | | | | | | | | | |
|---|---|---|---|---|---|---|---|---|---|---|---|---|
| Preemergence | 545 | 546 | 547 | 549 | 550 | 551 | 552 | 553 | 554 | 557 | 558 | 559 | 560 |
| Barnyardgrass | 20 | 80 | 90 | 40 | 40 | 30 | 90 | 90 | 90 | 0 | 90 | 90 | 90 |
| Foxtail, Giant | 80 | 90 | 90 | 90 | 90 | 80 | 90 | 90 | 90 | 0 | 90 | 90 | 100 |
| Kochia | 0 | 0 | 0 | 0 | 0 | 0 | 0 | 60 | 70 | 0 | 70 | 60 | 60 |
| Pigweed | 0 | 0 | 0 | 0 | 0 | 0 | 0 | 30 | 0 | 0 | 30 | 20 | 0 |
| Ragweed | 0 | 0 | 0 | 0 | 0 | 0 | 0 | 40 | 20 | 0 | 50 | 0 | 0 |
| Ryegrass, Italian | 0 | 0 | 0 | 0 | 0 | 0 | 20 | 70 | 20 | 0 | 0 | 0 | 0 |

| 125 g ai/ha | Compounds | | | | | | | | | | | | |
|---|---|---|---|---|---|---|---|---|---|---|---|---|---|
| Preemergence | 561 | 562 | 563 | 564 | 565 | 566 | 567 | 568 | 569 | 570 | 571 | 572 | 573 | 574 |
| Barnyardgrass | 90 | 90 | 90 | 90 | 80 | 90 | 100 | 90 | 90 | 100 | 90 | 90 | 90 | 90 |
| Foxtail, Giant | 90 | 90 | 90 | 90 | 90 | 90 | 100 | 100 | 100 | 100 | 90 | 90 | 90 | 90 |
| Kochia | 70 | 70 | 70 | 80 | 70 | 70 | 60 | 70 | 60 | 60 | 60 | 70 | 70 | 40 |
| Pigweed | 80 | 90 | 70 | 90 | 70 | 80 | 20 | 30 | 50 | 40 | 30 | 40 | 40 | 20 |
| Ragweed | 80 | 70 | 50 | 80 | 50 | 60 | 50 | 20 | 60 | 0 | 0 | 0 | 0 | 0 |
| Ryegrass, Italian | 0 | 60 | 0 | 40 | 0 | 20 | 60 | 70 | 30 | 60 | 60 | 50 | 80 | 40 |

| 125 g ai/ha | Compounds | | | | | | | | | | | | |
|---|---|---|---|---|---|---|---|---|---|---|---|---|---|
| Preemergence | 575 | 576 | 577 | 587 | 588 | 589 | 590 | 591 | 592 | 593 | 594 | 595 | 596 | 597 |
| Barnyardgrass | 90 | 90 | 90 | 90 | 90 | 80 | 90 | 90 | 90 | 90 | 90 | 90 | 90 | 20 |
| Foxtail, Giant | 90 | 90 | 90 | 90 | 90 | 80 | 90 | 90 | 90 | 90 | 90 | 90 | 100 | 20 |
| Kochia | 0 | 20 | 50 | 0 | 0 | 0 | 0 | 30 | 0 | 0 | 0 | 40 | 20 | 0 |
| Pigweed | 0 | 20 | 0 | 0 | 0 | 0 | 0 | 0 | 0 | — | 0 | 30 | 0 | 0 |
| Ragweed | 0 | 20 | 0 | 0 | 0 | 0 | 0 | 0 | 0 | 0 | 0 | 0 | 0 | 0 |
| Ryegrass, Italian | 60 | 20 | 40 | 20 | 80 | 0 | 0 | 20 | 0 | 0 | 30 | 20 | 40 | 0 |

TABLE A-continued

| 125 g ai/ha | Compounds | | | | | | | | | | | |
|---|---|---|---|---|---|---|---|---|---|---|---|---|
| Preemergence | 598 | 599 | 600 | 601 | 602 | 605 | 606 | 607 | 608 | 609 | 610 | 611 |
| Barnyardgrass | 0 | 0 | 30 | 60 | 0 | 30 | 50 | 0 | 0 | 90 | 90 | 90 |
| Foxtail, Giant | 0 | 0 | 30 | 70 | 0 | 90 | 80 | 80 | 90 | 90 | 90 | 90 |
| Kochia | 0 | 0 | 0 | 0 | 0 | 0 | 0 | 0 | 50 | 60 | 60 | 40 |
| Pigweed | 0 | 0 | 0 | 0 | 0 | 0 | 0 | 0 | 70 | 60 | 80 | 70 |
| Ragweed | 0 | 0 | 0 | 0 | 0 | 0 | 0 | 0 | 50 | 60 | 0 | 0 |
| Ryegrass, Italian | 0 | 0 | 0 | 0 | 0 | 0 | 0 | 0 | 0 | 50 | 40 | 60 |

| 125 g ai/ha | Compounds | | | | | | | | | | | | |
|---|---|---|---|---|---|---|---|---|---|---|---|---|---|
| Preemergence | 612 | 613 | 614 | 616 | 617 | 618 | 619 | 620 | 621 | 622 | 623 | 624 | 625 |
| Barnyardgrass | 90 | 90 | 50 | 90 | 90 | 90 | 0 | 70 | 90 | 90 | 90 | 90 | 80 |
| Foxtail, Giant | 90 | 90 | 90 | 90 | 90 | 90 | 0 | 80 | 90 | 90 | 90 | 90 | 90 |
| Kochia | 20 | 60 | 0 | 70 | 70 | 90 | 20 | 0 | 0 | 80 | 60 | 40 | 50 |
| Pigweed | 70 | 70 | 0 | 80 | 90 | 50 | 0 | 0 | 0 | 80 | 80 | 80 | 50 |
| Ragweed | 50 | 60 | 0 | 80 | 30 | — | 0 | 0 | 0 | 60 | 80 | 60 | 20 |
| Ryegrass, Italian | 50 | 70 | 0 | 80 | 70 | 50 | 0 | 0 | 0 | 40 | 80 | 40 | 30 |

| 125 g ai/ha | Compounds | | | | | | | | | |
|---|---|---|---|---|---|---|---|---|---|---|
| Preemergence | 630 | 631 | 632 | 633 | 634 | 635 | 636 | 637 | 638 | 639 |
| Barnyardgrass | 90 | 0 | 90 | 90 | 20 | 90 | 90 | 90 | 90 | 90 |
| Foxtail, Giant | 80 | 0 | 90 | 90 | 60 | 90 | 90 | 90 | 90 | 90 |
| Kochia | 0 | 0 | 50 | 30 | 0 | 60 | 50 | 40 | 0 | 70 |
| Pigweed | 0 | 0 | 0 | 0 | 0 | 60 | 40 | 80 | 40 | 50 |
| Ragweed | 0 | 0 | 60 | 0 | 0 | 40 | 20 | 40 | 30 | 50 |
| Ryegrass, Italian | 0 | 0 | 60 | 30 | 0 | 20 | 90 | 50 | 30 | 60 |

| 125 g ai/ha | Compounds | | | | | | | | | | | | |
|---|---|---|---|---|---|---|---|---|---|---|---|---|---|
| Preemergence | 640 | 641 | 642 | 643 | 644 | 645 | 646 | 647 | 648 | 649 | 650 | 651 | 652 | 653 |
| Barnyardgrass | 90 | 90 | 90 | 90 | 90 | 90 | 90 | 90 | 70 | 80 | 100 | 90 | 90 | 90 |
| Foxtail, Giant | 90 | 90 | 90 | 100 | 90 | 90 | 90 | 90 | 60 | 50 | 100 | 90 | 100 | 90 |
| Kochia | 50 | 20 | 40 | 0 | 50 | 0 | 60 | 0 | 0 | 60 | 30 | 60 | 0 | 0 |
| Pigweed | 80 | 20 | 50 | 0 | 60 | 0 | 60 | 0 | 0 | 50 | 50 | 40 | 0 | 70 |
| Ragweed | 40 | 0 | 0 | 0 | 50 | 0 | 60 | 0 | 0 | 20 | 0 | 50 | 0 | 50 |
| Ryegrass, Italian | 20 | 20 | 50 | 20 | 60 | 20 | 60 | 30 | 30 | 30 | 40 | 90 | 60 | 70 |

| 125 g ai/ha | Compounds | | | | | | | | | | | | | |
|---|---|---|---|---|---|---|---|---|---|---|---|---|---|---|
| Preemergence | 654 | 655 | 656 | 657 | 658 | 659 | 660 | 661 | 662 | 663 | 664 | 665 | 666 | 667 |
| Barnyardgrass | 90 | 90 | 90 | 90 | 90 | 90 | 60 | 90 | 90 | 90 | 90 | 90 | 90 | 90 |
| Foxtail, Giant | 90 | 90 | 90 | 90 | 90 | 90 | 80 | 90 | 100 | 90 | 90 | 100 | 100 | 90 |
| Kochia | 0 | 30 | 60 | 20 | 0 | 0 | 0 | 50 | 70 | 70 | 70 | 60 | 20 | 40 |
| Pigweed | 40 | 50 | 30 | 20 | 0 | 0 | 0 | 0 | 70 | 30 | 60 | 30 | 0 | 20 |
| Ragweed | 0 | 0 | 20 | 20 | 50 | 0 | 0 | 70 | 80 | 30 | 20 | 20 | 0 | 60 |
| Ryegrass, Italian | 40 | 40 | 30 | 20 | 0 | 0 | 0 | 30 | 40 | 30 | 20 | 20 | 20 | 80 |

| 125 g ai/ha | Compounds | | | | | | | | |
|---|---|---|---|---|---|---|---|---|---|
| Preemergence | 668 | 674 | 675 | 676 | 677 | 678 | 679 | 680 | 681 |
| Barnyardgrass | 90 | 60 | 70 | 70 | 60 | 90 | 80 | 30 | 70 |
| Foxtail, Giant | 90 | 70 | 70 | 80 | 40 | 80 | 90 | 60 | 90 |
| Kochia | 20 | 0 | 0 | 0 | 0 | 20 | 0 | 30 | 0 | 20 |
| Pigweed | 20 | 0 | 0 | 0 | 0 | 0 | 0 | 0 | 0 |
| Ragweed | 0 | 0 | 0 | 0 | 0 | 0 | 0 | 0 | 0 |
| Ryegrass, Italian | 0 | 0 | 0 | 0 | 20 | 0 | 20 | 0 | 0 |

| 125 g ai/ha | Compounds | | | | | | | | | | | | | |
|---|---|---|---|---|---|---|---|---|---|---|---|---|---|---|
| Preemergence | 682 | 683 | 684 | 685 | 686 | 687 | 688 | 689 | 690 | 691 | 692 | 693 | 694 | 695 |
| Barnyardgrass | 0 | 20 | 60 | 60 | 90 | 90 | 90 | 90 | 90 | 90 | 70 | 80 | 70 | 90 |
| Foxtail, Giant | 90 | 90 | 90 | 90 | 90 | 90 | 90 | 90 | 90 | 90 | 80 | 90 | 90 | 90 |
| Kochia | 0 | 0 | 0 | 0 | 0 | 0 | 30 | 20 | 80 | 80 | 70 | 80 | 0 | 30 |
| Pigweed | 0 | 0 | 0 | 0 | 0 | 0 | 30 | 20 | 80 | 70 | 80 | 70 | 0 | 30 |
| Ragweed | 0 | 0 | 0 | 0 | 0 | 0 | 20 | 0 | 70 | 60 | 50 | 50 | 0 | 20 |
| Ryegrass, Italian | 20 | 0 | 0 | 20 | 0 | 0 | 0 | 0 | 60 | 50 | 20 | 60 | 0 | 40 |

TABLE A-continued

| 125 g ai/ha | Compounds | | | | | | | | | | |
|---|---|---|---|---|---|---|---|---|---|---|---|
| Preemergence | 696 | 697 | 698 | 699 | 700 | 701 | 702 | 703 | 704 | 705 | 706 |
| Barnyardgrass | 80 | 90 | 80 | 90 | 90 | 60 | 70 | 20 | 40 | 0 | 0 |
| Foxtail, Giant | 90 | 90 | 90 | 90 | 90 | 90 | 90 | 80 | 90 | 0 | 0 |
| Kochia | 40 | 30 | 50 | 0 | 30 | 0 | 20 | 0 | 0 | 0 | 0 |
| Pigweed | 20 | 50 | 50 | 30 | 40 | 0 | 0 | 0 | 0 | 0 | 0 |
| Ragweed | 0 | 50 | 0 | 0 | 0 | 0 | 0 | 0 | 0 | 0 | 0 |
| Ryegrass, Italian | 30 | 40 | 30 | 20 | 0 | 0 | 0 | 0 | 0 | 0 | 0 |

| 125 g ai/ha | Compounds | | | | |
|---|---|---|---|---|---|
| Preemergence | 711 | 712 | 714 | 715 | 716 |
| Barnyardgrass | 0 | 0 | 0 | 0 | 0 |
| Corn | — | — | 0 | 0 | 0 |
| Crabgrass, Large | — | — | 20 | 0 | 0 |
| Foxtail, Giant | 0 | 0 | 0 | 0 | 0 |
| Kochia | 0 | 0 | — | — | — |
| Morningglory | — | — | 0 | 0 | 0 |
| Pigweed | 0 | 0 | 0 | 0 | 0 |
| Ragweed | 0 | 0 | — | — | — |
| Ryegrass, Italian | 0 | 0 | — | — | — |
| Velvetleaf | — | — | 0 | 0 | 0 |
| Wheat | — | — | 0 | 0 | 0 |

| 125 g ai/ha | Compounds | | | | | | | | | | | | |
|---|---|---|---|---|---|---|---|---|---|---|---|---|---|
| Preemergence | 717 | 718 | 719 | 720 | 721 | 722 | 723 | 724 | 725 | 726 | 727 | 728 | 729 | 730 |
| Barnyardgrass | 90 | 90 | 90 | 90 | 30 | 20 | 0 | 0 | 90 | 90 | 70 | 80 | 0 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 80 | 70 | 90 | 60 | 30 | 50 | 0 | 0 | 90 | 90 | 80 | 30 | 0 | 90 |
| Foxtail, Green | — | — | — | — | — | — | — | — | — | — | — | — | — | — |
| Kochia | 0 | 0 | 70 | 20 | 0 | 0 | 0 | 0 | 0 | 70 | 0 | 30 | 0 | 70 |
| Morningglory | — | — | — | — | — | — | — | — | — | — | — | — | — | — |
| Pigweed | 0 | 0 | 50 | 0 | 0 | 0 | 0 | 0 | 0 | 80 | 0 | 0 | 0 | 30 |
| Ragweed | 0 | 0 | 20 | 0 | 0 | 0 | 0 | 0 | 0 | 30 | 0 | 0 | 0 | 50 |
| Ryegrass, Italian | 0 | 30 | 70 | 0 | 0 | 0 | 0 | 0 | 0 | 50 | 0 | 20 | 0 | 20 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | |
|---|---|---|---|---|---|---|---|---|---|---|---|---|---|
| Preemergence | 731 | 732 | 733 | 734 | 735 | 736 | 737 | 738 | 739 | 740 | 741 | 742 | 743 | 744 |
| Barnyardgrass | 80 | 90 | 90 | 90 | 90 | 90 | 70 | 90 | 90 | 90 | 0 | 90 | 90 | 20 |
| Corn | — | — | — | — | — | — | — | — | — | — | — | — | — | — |
| Crabgrass, Large | — | — | — | — | — | — | — | — | — | — | — | — | — | — |
| Foxtail, Giant | 40 | 90 | 90 | 90 | 90 | 90 | 90 | 90 | 90 | 100 | 0 | 90 | 90 | 90 |
| Foxtail, Green | — | — | — | — | — | — | — | — | — | — | — | — | — | — |
| Kochia | 0 | 70 | 20 | 20 | 20 | 20 | 40 | 0 | 30 | 80 | 0 | 60 | 60 | 60 |
| Morningglory | — | — | — | — | — | — | — | — | — | — | — | — | — | — |
| Pigweed | 0 | 0 | 20 | 20 | 0 | 0 | 0 | 0 | 0 | 70 | 0 | 20 | 0 | 20 |
| Ragweed | 0 | 0 | 70 | 20 | 0 | 0 | 0 | 0 | 50 | 40 | 0 | 20 | 0 | 0 |
| Ryegrass, Italian | 20 | 80 | 40 | 40 | 80 | 90 | 40 | 0 | 0 | 60 | 0 | 50 | 90 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | |
|---|---|---|---|---|---|---|---|---|---|---|---|---|---|
| Preemergence | 745 | 746 | 747 | 748 | 749 | 750 | 751 | 752 | 753 | 754 | 755 | 756 | 757 | 758 |
| Barnyardgrass | 90 | 0 | 0 | 0 | 0 | 80 | 90 | 30 | 70 | 80 | 0 | 100 | 90 | 100 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 80 | 90 | 40 | 50 | 50 | 80 | 90 | 70 | 70 | 0 | 100 | 90 | 100 |
| Foxtail, Green | — | — | — | — | — | — | — | — | — | — | — | — | — | — |
| Kochia | 90 | 0 | 60 | 0 | 0 | 0 | 20 | 60 | 20 | 0 | 0 | 70 | 70 | 0 |
| Morningglory | — | — | — | — | — | — | — | — | — | — | — | — | — | — |
| Pigweed | 80 | 0 | 50 | 0 | 0 | 0 | 20 | 0 | 0 | 0 | 0 | 40 | 30 | 0 |
| Ragweed | 80 | 0 | 20 | 0 | 0 | 0 | 20 | 40 | 0 | 0 | 0 | 0 | 20 | 0 |
| Ryegrass, Italian | 70 | 0 | 0 | 0 | 0 | 0 | 0 | 20 | 0 | 0 | 0 | 30 | 30 | 30 |
| Velvetleaf | — | — | — | — | — | — | — | — | — | — | — | — | — | — |
| Wheat | — | — | — | — | — | — | — | — | — | — | — | — | — | — |

TABLE A-continued

| 125 g ai/ha | Compounds | | | | | | | | | | | | | |
|---|---|---|---|---|---|---|---|---|---|---|---|---|---|
| Preemergence | 759 | 760 | 761 | 762 | 763 | 764 | 765 | 766 | 767 | 768 | 769 | 770 | 771 | 772 |
| Barnyardgrass | 90 | 100 | 90 | 100 | 80 | 100 | 100 | 70 | 90 | 90 | 70 | 90 | 90 | 0 |
| Corn | — | — | — | — | — | — | — | — | — | — | — | — | — | — |
| Crabgrass, Large | — | — | — | — | — | — | — | — | — | — | — | — | — | — |
| Foxtail, Giant | 70 | 100 | 60 | 70 | 0 | 70 | 30 | 0 | 0 | 90 | 90 | 90 | 90 | 50 |
| Foxtail, Green | — | — | — | — | — | — | — | — | — | — | — | — | — | — |
| Kochia | 0 | 0 | 30 | 0 | 30 | 0 | 0 | 0 | 0 | 60 | 30 | 0 | 50 | 0 |
| Morningglory | — | — | — | — | — | — | — | — | — | — | — | — | — | — |
| Pigweed | 0 | 0 | 0 | 0 | 0 | 0 | 0 | 0 | 0 | 0 | 30 | 90 | 0 | 0 |
| Ragweed | 0 | 0 | 0 | 0 | 0 | 0 | 0 | 0 | 0 | 0 | 30 | 0 | 0 | 0 |
| Ryegrass, Italian | 0 | 0 | 0 | 20 | 0 | 0 | 0 | 0 | 0 | 0 | 0 | 0 | 40 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | | |
|---|---|---|---|---|---|---|---|---|---|---|---|---|---|
| Preemergence | 773 | 774 | 775 | 776 | 777 | 778 | 779 | 780 | 781 | 782 | 783 | 785 | 786 | 787 |
| Barnyardgrass | 0 | 0 | 60 | 90 | 70 | 70 | 90 | 80 | 80 | 80 | 0 | 90 | 80 | 20 |
| Corn | — | — | — | — | — | — | — | — | — | — | — | — | — | — |
| Crabgrass, Large | — | — | — | — | — | — | — | — | — | — | — | — | — | — |
| Foxtail, Giant | 0 | 0 | 80 | 90 | 80 | 90 | 90 | 90 | 90 | 90 | 0 | 90 | 90 | 70 |
| Foxtail, Green | — | — | — | — | — | — | — | — | — | — | — | — | — | — |
| Kochia | 0 | 0 | 30 | 50 | 0 | 80 | 70 | 40 | 50 | 80 | 30 | 20 | 0 | 80 |
| Morningglory | — | — | — | — | — | — | — | — | — | — | — | — | — | — |
| Pigweed | 0 | 0 | 30 | 30 | 0 | 30 | 40 | 0 | 0 | 0 | 0 | 0 | 0 | 50 |
| Ragweed | 0 | 0 | 50 | 30 | 0 | 40 | 20 | 40 | 0 | 0 | 0 | 0 | 0 | 70 |
| Ryegrass, Italian | 0 | 0 | 0 | 20 | 40 | 0 | 40 | 0 | 20 | 40 | 0 | 0 | 0 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | | |
|---|---|---|---|---|---|---|---|---|---|---|---|---|---|
| Preemergence | 788 | 789 | 790 | 791 | 792 | 793 | 794 | 795 | 796 | 797 | 798 | 799 | 800 | 801 |
| Barnyardgrass | 90 | 90 | 90 | 90 | 0 | 0 | 90 | 80 | 90 | 90 | 80 | 40 | 90 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 60 | 70 | 50 | 0 | 0 | 90 | 70 | 90 | 90 | 90 | 90 | 90 | 90 |
| Foxtail, Green | — | — | — | — | — | — | — | — | — | — | — | — | — | — |
| Kochia | 80 | — | 70 | 50 | 0 | 0 | 0 | 0 | 20 | 20 | 20 | 40 | 0 | 70 |
| Morningglory | — | — | — | — | — | — | — | — | — | — | — | — | — | — |
| Pigweed | 80 | 0 | 0 | 0 | 0 | 0 | 0 | 0 | 40 | 20 | 40 | 40 | 20 | 30 |
| Ragweed | 80 | 0 | 20 | 0 | 0 | 0 | 0 | 0 | 0 | 0 | 0 | 0 | 0 | 60 |
| Ryegrass, Italian | 0 | 0 | 30 | 0 | 0 | 0 | 0 | 0 | 20 | 50 | 0 | 0 | 40 | 20 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | | |
|---|---|---|---|---|---|---|---|---|---|---|---|---|---|
| Preemergence | 802 | 803 | 804 | 805 | 806 | 807 | 808 | 809 | 810 | 811 | 812 | 813 | 814 | 815 |
| Barnyardgrass | 90 | 90 | 90 | 0 | 0 | 100 | 100 | 90 | 90 | 40 | 90 | 80 | 0 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 80 | 0 | 0 | 100 | 90 | 20 | 90 | 40 | 90 | 90 | 0 | 90 |
| Foxtail, Green | — | — | — | — | — | — | — | — | — | — | — | — | — | — |
| Kochia | 50 | 70 | 20 | 0 | 0 | 50 | 0 | 0 | 0 | 0 | 0 | 0 | 0 | 70 |
| Morningglory | — | — | — | — | — | — | — | — | — | — | — | — | — | — |
| Pigweed | 50 | 60 | 60 | 0 | 0 | 40 | 0 | 0 | 0 | 0 | 0 | 0 | 0 | 30 |
| Ragweed | 60 | 60 | 0 | 0 | 0 | 0 | 0 | 0 | 0 | 0 | 0 | 0 | 0 | 0 |
| Ryegrass, Italian | 40 | 0 | 50 | 0 | 0 | 70 | 30 | 0 | 20 | 0 | 20 | 20 | 0 | 80 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | | |
|---|---|---|---|---|---|---|---|---|---|---|---|---|---|
| Preemergence | 816 | 817 | 818 | 819 | 820 | 821 | 822 | 823 | 824 | 825 | 826 | 827 | 828 | 829 |
| Barnyardgrass | 90 | 90 | 90 | 90 | 90 | 90 | 90 | 90 | 90 | 70 | 90 | 90 | 70 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 90 | 100 | 90 | 90 | 90 | 100 | 90 | 90 | 100 | 90 | 90 | 90 |
| Foxtail, Green | — | — | — | — | — | — | — | — | — | — | — | — | — | — |
| Kochia | 60 | 50 | 70 | 70 | 70 | 70 | 70 | 0 | 60 | 20 | 70 | 30 | 40 | 60 |
| Morningglory | — | — | — | — | — | — | — | — | — | — | — | — | — | — |
| Pigweed | 0 | 0 | 20 | 30 | 40 | 50 | 0 | 0 | 0 | 0 | 0 | 20 | 0 | 0 |

TABLE A-continued

| | | | | | | | | | | | | | | |
|---|---|---|---|---|---|---|---|---|---|---|---|---|---|---|
| Ragweed | 20 | 20 | 0 | 0 | 20 | 0 | 0 | 0 | 20 | 20 | 20 | 0 | 0 | 30 |
| Ryegrass, Italian | 70 | 20 | 60 | 80 | 60 | 80 | 20 | 30 | 20 | 20 | 70 | 30 | 50 | 20 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | | |
|---|---|---|---|---|---|---|---|---|---|---|---|---|---|---|
| Preemergence | 830 | 831 | 832 | 833 | 834 | 835 | 836 | 837 | 838 | 839 | 840 | 841 | 842 | 843 |
| Barnyardgrass | 90 | 50 | 40 | 90 | 90 | 90 | 90 | 90 | 90 | 80 | 80 | 90 | 90 | 60 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 0 | 90 | 90 | 90 | 90 | 90 | 90 | 90 | 90 | 90 | 90 | 90 |
| Foxtail, Green | — | — | — | — | — | — | — | — | — | — | — | — | — | — |
| Kochia | 70 | 0 | 90 | 70 | 80 | 80 | 90 | 90 | 70 | 90 | 0 | 40 | 80 | 60 |
| Morningglory | — | — | — | — | — | — | — | — | — | — | — | — | — | — |
| Pigweed | 20 | 20 | 0 | 0 | 0 | 20 | 30 | 20 | 80 | 90 | 30 | 0 | 40 | 0 |
| Ragweed | 0 | 0 | 40 | 0 | 0 | 0 | 0 | 70 | 40 | 80 | 0 | 0 | 70 | 0 |
| Ryegrass, Italian | 0 | 30 | 0 | 70 | 70 | 30 | 90 | 50 | 20 | 0 | 0 | 0 | 30 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | | |
|---|---|---|---|---|---|---|---|---|---|---|---|---|---|---|
| Preemergence | 844 | 845 | 846 | 847 | 848 | 849 | 850 | 851 | 852 | 853 | 854 | 855 | 856 | 857 |
| Barnyardgrass | 0 | 90 | 90 | 0 | 90 | 90 | 90 | 90 | 90 | 90 | 0 | 90 | 90 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 0 | 80 | 90 | 0 | 90 | 90 | 90 | 90 | 90 | 90 | 50 | 90 | 90 | 80 |
| Foxtail, Green | — | — | — | — | — | — | — | — | — | — | — | — | — | — |
| Kochia | 0 | 40 | 20 | 0 | 40 | 80 | 30 | 20 | 0 | 40 | 0 | 20 | 40 | 0 |
| Morningglory | — | — | — | — | — | — | — | — | — | — | — | — | — | — |
| Pigweed | 0 | 0 | 0 | 0 | 40 | 40 | 20 | 60 | 20 | 40 | 0 | 30 | 20 | 60 |
| Ragweed | 0 | 0 | 0 | 0 | 0 | 80 | 0 | 0 | 0 | 0 | 0 | 0 | 0 | 0 |
| Ryegrass, Italian | 0 | 0 | 60 | 0 | 40 | 80 | 70 | 0 | 0 | 0 | 0 | 0 | 50 | 40 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | | |
|---|---|---|---|---|---|---|---|---|---|---|---|---|---|---|
| Preemergence | 858 | 859 | 860 | 861 | 862 | 863 | 864 | 865 | 866 | 867 | 868 | 869 | 870 | 871 |
| Barnyardgrass | 90 | 90 | 90 | 90 | 90 | 50 | 90 | 0 | 30 | 90 | 30 | 60 | 50 | 20 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 90 | 90 | 90 | 90 | 90 | 0 | 90 | 90 | 20 | 90 | 20 | 80 |
| Foxtail, Green | — | — | — | — | — | — | — | — | — | — | — | — | — | — |
| Kochia | 60 | 50 | 0 | 30 | 70 | 80 | 60 | 0 | 20 | 50 | 0 | 0 | 0 | 80 |
| Morningglory | — | — | — | — | — | — | — | — | — | — | — | — | — | — |
| Pigweed | 20 | 60 | 60 | 50 | 80 | 70 | 90 | 0 | 0 | 0 | 0 | 0 | 0 | 0 |
| Ragweed | 0 | 0 | 0 | 0 | 90 | 0 | 20 | 0 | 0 | 0 | 0 | 0 | 0 | 0 |
| Ryegrass, Italian | 30 | 20 | 20 | 30 | 0 | 0 | 0 | 0 | 50 | 60 | 0 | 0 | 0 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | | |
|---|---|---|---|---|---|---|---|---|---|---|---|---|---|---|
| Preemergence | 872 | 873 | 874 | 875 | 876 | 877 | 878 | 879 | 880 | 881 | 882 | 883 | 885 | 886 |
| Barnyardgrass | 90 | 90 | 90 | 90 | 60 | 90 | 100 | 100 | 90 | 80 | 90 | 90 | 70 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 90 | 90 | 80 | 90 | 100 | 100 | 100 | 80 | 70 | 60 | 50 | 90 |
| Foxtail, Green | — | — | — | — | — | — | — | — | — | — | — | — | — | — |
| Kochia | 0 | 80 | 60 | 50 | 0 | 60 | 70 | 80 | 70 | 30 | 70 | 30 | 0 | 80 |
| Morningglory | — | — | — | — | — | — | — | — | — | — | — | — | — | — |
| Pigweed | 0 | 40 | 20 | 0 | 0 | 0 | 0 | 70 | 70 | 0 | 20 | 0 | 0 | 0 |
| Ragweed | 60 | 40 | 20 | 0 | 0 | 0 | 30 | 50 | 50 | 0 | 30 | 0 | 0 | 0 |
| Ryegrass, Italian | 0 | 50 | 40 | 0 | 0 | 0 | 30 | 60 | 20 | 30 | 0 | 0 | 0 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | | |
|---|---|---|---|---|---|---|---|---|---|---|---|---|---|---|
| Preemergence | 887 | 888 | 889 | 890 | 891 | 892 | 893 | 894 | 895 | 896 | 897 | 898 | 899 | 900 |
| Barnyardgrass | 90 | 90 | 90 | 90 | 60 | 100 | 90 | 90 | 90 | 90 | 80 | 90 | 90 | 90 |
| Corn | — | — | — | — | — | — | — | — | — | — | — | — | — | — |
| Crabgrass, Large | — | — | — | — | — | — | — | — | — | — | — | — | — | — |

TABLE A-continued

| | | | | | | | | | | | | | | |
|---|---|---|---|---|---|---|---|---|---|---|---|---|---|---|
| Foxtail, Giant | 80 | 80 | 90 | 90 | 80 | 100 | 90 | 90 | 90 | 90 | 90 | 90 | 90 | 90 |
| Foxtail, Green | — | — | — | — | — | — | — | — | — | — | — | — | — | — |
| Kochia | 0 | 60 | 80 | 40 | 0 | 70 | 80 | 60 | 90 | 30 | 60 | 70 | — | 90 |
| Morningglory | — | — | — | — | — | — | — | — | — | — | — | — | — | — |
| Pigweed | 0 | 0 | 0 | 30 | 0 | 0 | 30 | 20 | 50 | 20 | 30 | 60 | 20 | 80 |
| Ragweed | 0 | 0 | 30 | 0 | 0 | 20 | 40 | 0 | 0 | 0 | 20 | 60 | 20 | 50 |
| Ryegrass, Italian | 0 | 0 | 30 | 50 | 0 | 30 | 40 | 50 | 90 | 40 | 20 | 40 | 30 | 60 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | | |
|---|---|---|---|---|---|---|---|---|---|---|---|---|---|---|
| Preemergence | 901 | 902 | 903 | 904 | 905 | 906 | 907 | 908 | 909 | 910 | 911 | 912 | 913 | 914 |
| Barnyardgrass | 90 | 40 | 90 | 90 | 70 | 0 | 70 | 0 | 70 | 90 | 90 | 80 | 80 | 70 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 30 | 90 | 90 | 90 | 0 | 80 | 30 | 90 | 90 | 90 | 90 | 50 | 90 |
| Foxtail, Green | — | — | — | — | — | — | — | — | — | — | — | — | — | — |
| Kochia | 80 | 0 | 20 | 90 | 10 | 0 | 0 | 0 | 0 | 60 | 90 | 60 | 0 | 60 |
| Morningglory | — | — | — | — | — | — | — | — | — | — | — | — | — | — |
| Pigweed | 30 | 0 | 0 | 0 | 0 | 0 | 0 | 0 | 0 | 0 | 20 | 0 | 0 | 90 |
| Ragweed | 0 | 0 | 0 | 0 | 0 | 0 | 0 | 0 | 0 | 0 | 0 | 0 | 0 | 0 |
| Ryegrass, Italian | 20 | 0 | 0 | 0 | 0 | 0 | 0 | 0 | 0 | 50 | 70 | 40 | 0 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | | |
|---|---|---|---|---|---|---|---|---|---|---|---|---|---|---|
| Preemergence | 915 | 916 | 917 | 918 | 919 | 920 | 921 | 922 | 923 | 924 | 925 | 926 | 927 | 928 |
| Barnyardgrass | 100 | 30 | 20 | 0 | 0 | 70 | 90 | 60 | 0 | 90 | 30 | 30 | 0 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 70 | 30 | 20 | 0 | 80 | 90 | 90 | 0 | 90 | 80 | 80 | 0 | 90 |
| Foxtail, Green | — | — | — | — | — | — | — | — | — | — | — | — | — | — |
| Kochia | 80 | 40 | 0 | 0 | 0 | 0 | 0 | 0 | 0 | 0 | 0 | 0 | 0 | 80 |
| Morningglory | — | — | — | — | — | — | — | — | — | — | — | — | — | — |
| Pigweed | 80 | 0 | 0 | 0 | 0 | 0 | 0 | 0 | 0 | 0 | 0 | 0 | 0 | 0 |
| Ragweed | 80 | 0 | 0 | 0 | 0 | 0 | 0 | 0 | 0 | 0 | 0 | 0 | 0 | 0 |
| Ryegrass, Italian | 40 | 0 | 0 | 0 | 0 | 0 | 50 | 20 | 0 | 20 | 30 | 0 | 0 | 40 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | | |
|---|---|---|---|---|---|---|---|---|---|---|---|---|---|---|
| Preemergence | 929 | 930 | 931 | 932 | 933 | 934 | 935 | 936 | 937 | 938 | 939 | 940 | 941 | 942 |
| Barnyardgrass | 90 | 90 | 90 | 90 | 90 | 70 | 70 | 70 | 90 | 90 | 90 | 30 | 80 | 70 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 90 | 90 | 90 | 90 | 90 | 90 | 90 | 90 | 90 | 40 | 90 | 90 |
| Foxtail, Green | — | — | — | — | — | — | — | — | — | — | — | — | — | — |
| Kochia | 70 | 70 | 90 | 40 | 50 | 50 | 70 | 60 | 80 | 70 | 30 | 0 | 0 | 70 |
| Morningglory | — | — | — | — | — | — | — | — | — | — | — | — | — | — |
| Pigweed | 20 | 20 | 30 | 0 | 30 | 0 | 20 | 20 | 50 | 80 | 0 | 0 | 0 | 80 |
| Ragweed | 0 | 0 | 0 | 0 | — | 0 | 30 | 60 | 40 | 20 | 0 | 0 | 0 | 40 |
| Ryegrass, Italian | 40 | 40 | 40 | 30 | 50 | 0 | 20 | 40 | 20 | 20 | 0 | 0 | 0 | 40 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | | |
|---|---|---|---|---|---|---|---|---|---|---|---|---|---|---|
| Preemergence | 943 | 944 | 945 | 946 | 947 | 948 | 949 | 950 | 951 | 952 | 953 | 954 | 955 | 956 |
| Barnyardgrass | 90 | 90 | 60 | 60 | 30 | 70 | 70 | 100 | 90 | 50 | 90 | 70 | 100 | 100 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 0 | 0 | 50 | 70 | 60 | 60 | 70 | 80 | 90 | 90 | 100 | 100 |
| Foxtail, Green | — | — | — | — | — | — | — | — | — | — | — | — | — | — |
| Kochia | 70 | 0 | 0 | 0 | 0 | 0 | 20 | 50 | 0 | 30 | 60 | 0 | 30 | 90 |
| Morningglory | — | — | — | — | — | — | — | — | — | — | — | — | — | — |
| Pigweed | 40 | 0 | 0 | 0 | 0 | 0 | 0 | 0 | 0 | 0 | 0 | 0 | 0 | 0 |
| Ragweed | 0 | 50 | 0 | 0 | 0 | 0 | 0 | 0 | 0 | 0 | 0 | 0 | 0 | 20 |
| Ryegrass, Italian | 0 | 0 | 0 | 0 | 0 | 0 | 0 | 20 | 0 | 0 | 0 | 0 | 70 | 40 |
| Velvetleaf | — | — | — | — | — | — | — | — | — | — | — | — | — | — |
| Wheat | — | — | — | — | — | — | — | — | — | — | — | — | — | — |

TABLE A-continued

| 125 g ai/ha | Compounds | | | | | | | | | | | | | |
|---|---|---|---|---|---|---|---|---|---|---|---|---|---|---|
| Preemergence | 957 | 958 | 959 | 960 | 961 | 962 | 963 | 964 | 965 | 966 | 967 | 968 | 969 | 970 |
| Barnyardgrass | 70 | 90 | 90 | 80 | 90 | 90 | 90 | 90 | 90 | 80 | 80 | 20 | 50 | 0 |
| Corn | — | — | — | — | — | — | — | — | — | — | — | — | — | — |
| Crabgrass, Large | — | — | — | — | — | — | — | — | — | — | — | — | — | — |
| Foxtail, Giant | 20 | 90 | 90 | 70 | 70 | 90 | 100 | 90 | 90 | 80 | 80 | 30 | 90 | 80 |
| Foxtail, Green | — | — | — | — | — | — | — | — | — | — | — | — | — | — |
| Kochia | 30 | 0 | 70 | 20 | 70 | 50 | 40 | 0 | 0 | 30 | 0 | 0 | 0 | 0 |
| Morningglory | — | — | — | — | — | — | — | — | — | — | — | — | — | — |
| Pigweed | 20 | 0 | 0 | 0 | 0 | 0 | 0 | 0 | 0 | 0 | 0 | 0 | 0 | 0 |
| Ragweed | 0 | 20 | 70 | 0 | 60 | 20 | 0 | 0 | 0 | 0 | 0 | 0 | 0 | 0 |
| Ryegrass, Italian | 0 | 0 | 20 | 0 | 30 | 0 | 20 | 0 | 70 | 20 | 0 | 0 | 40 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | | |
|---|---|---|---|---|---|---|---|---|---|---|---|---|---|---|
| Preemergence | 971 | 972 | 973 | 974 | 975 | 976 | 977 | 978 | 979 | 980 | 981 | 982 | 983 | 984 |
| Barnyardgrass | 90 | 80 | 90 | 90 | 90 | 90 | 90 | 90 | 90 | 90 | 90 | 90 | 90 | 100 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 80 | 90 | 90 | 90 | 90 | 90 | 90 | 90 | 90 | 90 | 90 | 100 | 100 |
| Foxtail, Green | — | — | — | — | — | — | — | — | — | — | — | — | — | — |
| Kochia | 0 | 0 | 0 | 90 | 50 | 70 | 90 | 40 | 50 | 0 | 0 | 50 | 90 | 90 |
| Morningglory | — | — | — | — | — | — | — | — | — | — | — | — | — | — |
| Pigweed | 20 | 0 | 0 | 20 | 20 | 0 | 40 | 0 | 40 | 0 | 0 | 0 | 0 | 40 |
| Ragweed | 20 | 20 | 0 | 90 | — | — | 70 | 90 | 50 | 0 | 0 | — | 70 | 0 |
| Ryegrass, Italian | 80 | 90 | 0 | 70 | 30 | 50 | 0 | 60 | 50 | 20 | 0 | 90 | 30 | 70 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | | |
|---|---|---|---|---|---|---|---|---|---|---|---|---|---|---|
| Preemergence | 985 | 986 | 987 | 988 | 989 | 990 | 991 | 992 | 993 | 994 | 995 | 996 | 997 | 998 |
| Barnyardgrass | 0 | 90 | 60 | 90 | 70 | 100 | 70 | 0 | 90 | 90 | 80 | 0 | 0 | 0 |
| Corn | — | — | — | — | — | — | — | — | — | — | — | — | — | — |
| Crabgrass, Large | — | — | — | — | — | — | — | — | — | — | — | — | — | — |
| Foxtail, Giant | 0 | 100 | 90 | 90 | 70 | 100 | 90 | 0 | 90 | 100 | 90 | 0 | 0 | 0 |
| Foxtail, Green | — | — | — | — | — | — | — | — | — | — | — | — | — | — |
| Kochia | 0 | 30 | 0 | 30 | 0 | 70 | 0 | 0 | 0 | 40 | — | 0 | 0 | 0 |
| Morningglory | — | — | — | — | — | — | — | — | — | — | — | — | — | — |
| Pigweed | 0 | 60 | 0 | 30 | 0 | 40 | 60 | 0 | 40 | 30 | 20 | 0 | 0 | 0 |
| Ragweed | 0 | 50 | 0 | 50 | 0 | 50 | 0 | 0 | 0 | 0 | 0 | 0 | 0 | 0 |
| Ryegrass, Italian | 0 | 60 | 0 | 0 | 0 | 0 | 0 | 0 | 80 | 70 | 20 | 0 | 0 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | | |
|---|---|---|---|---|---|---|---|---|---|---|---|---|---|---|
| Preemergence | 999 | 1000 | 1001 | 1002 | 1003 | 1004 | 1005 | 1006 | 1007 | 1008 | 1009 | 1010 | 1011 | 1012 |
| Barnyardgrass | 70 | 0 | 0 | 20 | 0 | 0 | 0 | 0 | 0 | 0 | 0 | 0 | 0 | 0 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 70 | 0 | 30 | 60 | 30 | 0 | 0 | 0 | 0 | 0 | 0 | 0 | 0 |
| Foxtail, Green | — | — | — | — | — | — | — | — | — | — | — | — | — | — |
| Kochia | 0 | 0 | 0 | 0 | 0 | 0 | 0 | 0 | 0 | 0 | 0 | 0 | 0 | 0 |
| Morningglory | — | — | — | — | — | — | — | — | — | — | — | — | — | — |
| Pigweed | 0 | 20 | 0 | 20 | 0 | 0 | 0 | 0 | 0 | 0 | 0 | 0 | 0 | 0 |
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 0 | 0 | 0 | 0 | 0 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | | |
|---|---|---|---|---|---|---|---|---|---|---|---|---|---|---|
| Preemergence | 1013 | 1014 | 1015 | 1016 | 1017 | 1018 | 1019 | 1020 | 1021 | 1022 | 1023 | 1024 | 1025 | 1026 |
| Barnyardgrass | 90 | 90 | 90 | 90 | 90 | 90 | 0 | 90 | 100 | 60 | 90 | 70 | 70 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 90 | 90 | 90 | 90 | 0 | 90 | 100 | 100 | 90 | 90 | 90 | 30 |
| Foxtail, Green | — | — | — | — | — | — | — | — | — | — | — | — | — | — |
| Kochia | 50 | 20 | 0 | 0 | 0 | 0 | 0 | 30 | 70 | 70 | 0 | 30 | 0 | 30 |
| Morningglory | — | — | — | — | — | — | — | — | — | — | — | — | — | — |
| Pigweed | 30 | 30 | 0 | 0 | 50 | 30 | 0 | 30 | 70 | 30 | 30 | 30 | 0 | 0 |

TABLE A-continued

| | | | | | | | | | | | | | | |
|---|---|---|---|---|---|---|---|---|---|---|---|---|---|---|
| Ragweed | 0 | 0 | 0 | 0 | 0 | 0 | 0 | 0 | 70 | 0 | 0 | 0 | 0 | 50 |
| Ryegrass, Italian | 30 | 0 | 40 | 0 | 0 | 0 | 0 | 0 | 0 | 0 | 50 | 0 | 0 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | |
|---|---|---|---|---|---|---|---|---|---|---|---|---|---|
| Preemergence | 1027 | 1028 | 1029 | 1030 | 1031 | 1032 | 1033 | 1034 | 1035 | 1036 | 1037 | 1038 | 1039 | 1040 |
| Barnyardgrass | 90 | 90 | 90 | 70 | 0 | 20 | 90 | 90 | 90 | 90 | 80 | 100 | 90 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 40 | 90 | 90 | 90 | 0 | 0 | 70 | 80 | 90 | 70 | 20 | 100 | 90 | 90 |
| Foxtail, Green | — | — | — | — | — | — | — | — | — | — | — | — | — | — |
| Kochia | 80 | 0 | 0 | 0 | 0 | 0 | 0 | 60 | 0 | 70 | 40 | 80 | 80 | 50 |
| Morningglory | — | — | — | — | — | — | — | — | — | — | — | — | — | — |
| Pigweed | 0 | 0 | 0 | 0 | 0 | 0 | 0 | 0 | 0 | 0 | 0 | 20 | 20 | 30 |
| Ragweed | 70 | 0 | 0 | 0 | 0 | 0 | 0 | 30 | 20 | 0 | 0 | 20 | 10 | — |
| Ryegrass, Italian | 30 | 30 | 70 | 70 | 0 | 0 | 0 | 20 | — | 20 | 50 | 30 | 60 | 50 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | |
|---|---|---|---|---|---|---|---|---|---|---|---|---|---|
| Preemergence | 1041 | 1042 | 1043 | 1044 | 1045 | 1046 | 1047 | 1048 | 1049 | 1050 | 1051 | 1052 | 1053 | 1054 |
| Barnyardgrass | 30 | 90 | 80 | 90 | 90 | 90 | 30 | 90 | 30 | 0 | 20 | 90 | 0 | 0 |
| Corn | — | — | — | — | — | — | — | — | — | — | — | — | — | — |
| Crabgrass, Large | — | — | — | — | — | — | — | — | — | — | — | — | — | — |
| Foxtail, Giant | 80 | 90 | 70 | 70 | 80 | 80 | 60 | 90 | 80 | 0 | 90 | 90 | 0 | 0 |
| Foxtail, Green | — | — | — | — | — | — | — | — | — | — | — | — | — | — |
| Kochia | 30 | 20 | 60 | 0 | 0 | 60 | 60 | 90 | 30 | 0 | 0 | 70 | 0 | 0 |
| Morningglory | — | — | — | — | — | — | — | — | — | — | — | — | — | — |
| Pigweed | 0 | 30 | 0 | 0 | 0 | 0 | 0 | 80 | 0 | 0 | 40 | 80 | 0 | 0 |
| Ragweed | 20 | 20 | 0 | 0 | 0 | 40 | 40 | 50 | 20 | 0 | 0 | 20 | 0 | 0 |
| Ryegrass, Italian | 0 | 30 | 20 | 0 | 30 | 60 | 0 | 20 | 0 | 0 | 0 | 30 | 0 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | |
|---|---|---|---|---|---|---|---|---|---|---|---|---|---|
| Preemergence | 1055 | 1056 | 1057 | 1058 | 1059 | 1060 | 1061 | 1062 | 1063 | 1065 | 1066 | 1067 | 1068 | 1069 |
| Barnyardgrass | 0 | 90 | 0 | 90 | 70 | 100 | 80 | 100 | 100 | 70 | 100 | 100 | 0 | 0 |
| Corn | — | — | — | — | — | — | — | — | — | — | — | — | — | — |
| Crabgrass, Large | — | — | — | — | — | — | — | — | — | — | — | — | — | — |
| Foxtail, Giant | 0 | 60 | 0 | 90 | 70 | 100 | 70 | — | — | 100 | 100 | 100 | 0 | 50 |
| Foxtail, Green | — | — | — | — | — | — | — | 100 | 100 | — | — | — | — | — |
| Kochia | 0 | 0 | 0 | 0 | 0 | 0 | 0 | 20 | 20 | 70 | 20 | 70 | 0 | 0 |
| Morningglory | — | — | — | — | — | — | — | — | — | — | — | — | — | — |
| Pigweed | 0 | 0 | 0 | 0 | 0 | 30 | 0 | 0 | 0 | 70 | 20 | 0 | 0 | 0 |
| Ragweed | 0 | 0 | 0 | 0 | 0 | 30 | 0 | 0 | 30 | 0 | 0 | 60 | 0 | 0 |
| Ryegrass, Italian | 0 | 0 | 0 | 0 | 0 | 60 | 0 | 20 | 0 | 30 | 50 | 70 | 0 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | |
|---|---|---|---|---|---|---|---|---|---|---|---|---|---|
| Preemergence | 1070 | 1071 | 1072 | 1073 | 1074 | 1075 | 1076 | 1077 | 1078 | 1079 | 1080 | 1081 | 1082 | 1083 |
| Barnyardgrass | 0 | 90 | 100 | 100 | 100 | 100 | 90 | 100 | 0 | 80 | 0 | 90 | 0 | 100 |
| Corn | — | — | — | — | — | — | — | — | — | — | — | — | — | — |
| Crabgrass, Large | — | — | — | — | — | — | — | — | — | — | — | — | — | — |
| Foxtail, Giant | 60 | 100 | 100 | 100 | 100 | 100 | 100 | 100 | 0 | 100 | 0 | 100 | 0 | 100 |
| Foxtail, Green | — | — | — | — | — | — | — | — | — | — | — | — | — | — |
| Kochia | 0 | 0 | 0 | 0 | 20 | 30 | 0 | 20 | 0 | 0 | 10 | 30 | 0 | 90 |
| Morningglory | — | — | — | — | — | — | — | — | — | — | — | — | — | — |
| Pigweed | 0 | 0 | 0 | 100 | 20 | 20 | 20 | 0 | 0 | 0 | 0 | 0 | 0 | 20 |
| Ragweed | 0 | 0 | 0 | 10 | 10 | 20 | 0 | 0 | 0 | 0 | 0 | 0 | 0 | 80 |
| Ryegrass, Italian | 0 | 0 | 0 | 0 | 50 | 80 | 0 | 10 | 0 | 0 | 0 | 0 | 0 | 60 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | |
|---|---|---|---|---|---|---|---|---|---|---|---|---|---|
| Preemergence | 1084 | 1085 | 1086 | 1087 | 1088 | 1089 | 1090 | 1091 | 1092 | 1093 | 1094 | 1095 | 1096 | 1097 |
| Barnyardgrass | 70 | 90 | 80 | 90 | 30 | 90 | 90 | 0 | 90 | 90 | 0 | 0 | 0 | 0 |
| Corn | — | — | — | — | — | — | — | — | — | — | — | — | — | — |
| Crabgrass, Large | | | | | | | | | | | | | | |

TABLE A-continued

| | | | | | | | | | | | | | | |
|---|---|---|---|---|---|---|---|---|---|---|---|---|---|---|
| Foxtail, Giant | 100 | 100 | 100 | 100 | 100 | 100 | 100 | 100 | 100 | 100 | 90 | 0 | 0 | 0 |
| Foxtail, Green | — | — | — | — | — | — | — | — | — | — | — | — | — | — |
| Kochia | 20 | 0 | 0 | 60 | 20 | 20 | 30 | 40 | 0 | 50 | 0 | 0 | 0 | 0 |
| Morningglory | — | — | — | — | — | — | — | — | — | — | — | — | — | — |
| Pigweed | 0 | 0 | 0 | 0 | 0 | 0 | 0 | 0 | 0 | 80 | 0 | 0 | 0 | 0 |
| Ragweed | 10 | 0 | 0 | 0 | 0 | 60 | 0 | 0 | 40 | 20 | 0 | 0 | 0 | 0 |
| Ryegrass, Italian | 10 | 0 | 30 | 30 | 0 | 10 | 0 | 0 | 0 | 0 | 0 | 0 | 0 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | |
|---|---|---|---|---|---|---|---|---|---|---|---|---|---|
| Preemergence | 1098 | 1099 | 1100 | 1101 | 1102 | 1103 | 1104 | 1105 | 1106 | 1107 | 1108 | 1109 | 1110 | 1111 |
| Barnyardgrass | 90 | 90 | 90 | 90 | 90 | 70 | 50 | 60 | 90 | 0 | 0 | 100 | 100 | 0 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 90 | 90 | 90 | 90 | 70 | 90 | 90 | 0 | 0 | 100 | 100 | 0 |
| Foxtail, Green | — | — | — | — | — | — | — | — | — | — | — | — | — | — |
| Kochia | 20 | 60 | 50 | 60 | 20 | — | 0 | 70 | 60 | 0 | 0 | 70 | 70 | 0 |
| Morningglory | — | — | — | — | — | — | — | — | — | — | — | — | — | — |
| Pigweed | 0 | 0 | 0 | 0 | 20 | 0 | 0 | 0 | 20 | 0 | 0 | 90 | 90 | 0 |
| Ragweed | 0 | 20 | 0 | 0 | 0 | 20 | 0 | 20 | 30 | 0 | 0 | 50 | 40 | 0 |
| Ryegrass, Italian | 20 | 50 | 0 | 30 | 30 | 0 | 0 | 0 | 0 | 0 | 0 | 80 | 50 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | |
|---|---|---|---|---|---|---|---|---|---|---|---|---|---|
| Preemergence | 1112 | 1113 | 1114 | 1115 | 1116 | 1117 | 1118 | 1119 | 1120 | 1121 | 1122 | 1123 | 1124 | 1125 |
| Barnyardgrass | 0 | 0 | 90 | 90 | 90 | 90 | 80 | 90 | 90 | 90 | 90 | 90 | 60 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 0 | 0 | 90 | 90 | 20 | 50 | 60 | 50 | 90 | 90 | 90 | 90 | 90 | 90 |
| Foxtail, Green | — | — | — | — | — | — | — | — | — | — | — | — | — | — |
| Kochia | 0 | 0 | — | 70 | 0 | 40 | 0 | 70 | 40 | 80 | 60 | 60 | 70 | 50 |
| Morningglory | — | — | — | — | — | — | — | — | — | — | — | — | — | — |
| Pigweed | 0 | 0 | 0 | 0 | 0 | 0 | 0 | 0 | 0 | 0 | 30 | 0 | 50 | 0 |
| Ragweed | 0 | 0 | 0 | 0 | 0 | 20 | 20 | 70 | 40 | 50 | 70 | 20 | 0 | 0 |
| Ryegrass, Italian | 0 | 0 | 0 | 50 | 0 | 0 | 40 | 20 | 20 | 50 | 70 | 40 | 0 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | |
|---|---|---|---|---|---|---|---|---|---|---|---|---|---|
| Preemergence | 1126 | 1127 | 1129 | 1130 | 1131 | 1132 | 1133 | 1134 | 1135 | 1136 | 1137 | 1138 | 1139 | 1140 |
| Barnyardgrass | 90 | 0 | 80 | 0 | 90 | 90 | 90 | 30 | 0 | 30 | 0 | 90 | 90 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 0 | 90 | 0 | 90 | 100 | 90 | 70 | 0 | 30 | 0 | 90 | 90 | 100 |
| Foxtail, Green | — | — | — | — | — | — | — | — | — | — | — | — | — | — |
| Kochia | 70 | 0 | 0 | 0 | 100 | 0 | 60 | 50 | 0 | 0 | 0 | 0 | 30 | 80 |
| Morningglory | — | — | — | — | — | — | — | — | — | — | — | — | — | — |
| Pigweed | 30 | 0 | 0 | 0 | 80 | 0 | 30 | 0 | 0 | 0 | 0 | 0 | 0 | 0 |
| Ragweed | 60 | 0 | 0 | 0 | 60 | 0 | 40 | 0 | 0 | 0 | 0 | 0 | 50 | 30 |
| Ryegrass, Italian | 0 | 0 | 20 | 0 | 0 | 30 | 20 | 0 | 0 | 0 | 0 | 30 | 30 | 30 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | |
|---|---|---|---|---|---|---|---|---|---|---|---|---|---|
| Preemergence | 1141 | 1142 | 1143 | 1144 | 1145 | 1146 | 1147 | 1148 | 1149 | 1150 | 1151 | 1152 | 1153 | 1154 |
| Barnyardgrass | 80 | 30 | 40 | 90 | 90 | 70 | 20 | 90 | 90 | 70 | 90 | 20 | 80 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 80 | 90 | 90 | 80 | 20 | 90 | 90 | 90 | 100 | 70 | 90 | 90 |
| Foxtail, Green | — | — | — | — | — | — | — | — | — | — | — | — | — | — |
| Kochia | 0 | 0 | 0 | 60 | 50 | 0 | 0 | 0 | 20 | 0 | 70 | 0 | 60 | 70 |
| Morningglory | — | — | — | — | — | — | — | — | — | — | — | — | — | — |
| Pigweed | 60 | 60 | 0 | 80 | 0 | 0 | 0 | 0 | 40 | 0 | 80 | 60 | 0 | 60 |
| Ragweed | 0 | 0 | 0 | 20 | 0 | 0 | 0 | 0 | 0 | 0 | 0 | 0 | 0 | 20 |
| Ryegrass, Italian | 40 | 0 | 0 | 50 | 30 | 30 | 0 | 20 | 20 | 0 | 70 | 0 | 30 | 30 |
| Velvetleaf | — | — | — | — | — | — | — | — | — | — | — | — | — | — |
| Wheat | — | — | — | — | — | — | — | — | — | — | — | — | — | — |

TABLE A-continued

| 125 g ai/ha | Compounds | | | | | | | | | | | | | |
|---|---|---|---|---|---|---|---|---|---|---|---|---|---|---|
| Preemergence | 1155 | 1156 | 1157 | 1158 | 1159 | 1160 | 1161 | 1162 | 1163 | 1164 | 1165 | 1166 | 1167 | 1168 |
| Barnyardgrass | 90 | 90 | 90 | 90 | 60 | 90 | 0 | 90 | 90 | 80 | 90 | 20 | 0 | 0 |
| Corn | — | — | — | — | — | — | — | — | — | — | — | — | — | — |
| Crabgrass, Large | — | — | — | — | — | — | — | — | — | — | — | — | — | — |
| Foxtail, Giant | 70 | 90 | 90 | 100 | 70 | 90 | 20 | 90 | 60 | 30 | 90 | 80 | 50 | 30 |
| Foxtail, Green | — | — | — | — | — | — | — | — | — | — | — | — | — | — |
| Kochia | 60 | 70 | 90 | 30 | 0 | 0 | 0 | 0 | 20 | 20 | 70 | 0 | 0 | 0 |
| Morningglory | — | — | — | — | — | — | — | — | — | — | — | — | — | — |
| Pigweed | 0 | 0 | 30 | 0 | 0 | 0 | 0 | 0 | 0 | 0 | 50 | 0 | 0 | 0 |
| Ragweed | 40 | 100 | 0 | 0 | 0 | 0 | 0 | 0 | 0 | 0 | 30 | 0 | 0 | 0 |
| Ryegrass, Italian | 0 | 20 | 30 | 60 | 0 | 0 | 0 | 20 | 0 | 0 | 0 | 0 | 0 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | | |
|---|---|---|---|---|---|---|---|---|---|---|---|---|---|---|
| Preemergence | 1169 | 1170 | 1171 | 1172 | 1173 | 1174 | 1175 | 1176 | 1177 | 1178 | 1179 | 1180 | 1181 | 1182 |
| Barnyardgrass | 90 | 40 | 80 | 0 | 90 | 100 | 90 | 90 | 70 | 20 | 0 | 20 | 0 | 0 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 70 | 90 | 0 | 80 | 90 | 90 | 90 | 70 | 20 | 0 | 0 | 0 | 0 |
| Foxtail, Green | — | — | — | — | — | — | — | — | — | — | — | — | — | — |
| Kochia | 30 | 0 | 30 | 0 | 20 | 0 | 50 | 40 | 30 | 40 | 0 | 0 | 0 | 0 |
| Morningglory | — | — | — | — | — | — | — | — | — | — | — | — | — | — |
| Pigweed | 0 | 0 | 40 | 0 | 0 | 0 | 40 | 40 | 0 | 20 | 0 | 0 | 0 | 0 |
| Ragweed | 0 | 0 | 0 | 0 | 40 | 0 | 20 | 0 | 0 | 0 | 0 | 0 | 0 | 0 |
| Ryegrass, Italian | 0 | 0 | 60 | 0 | 30 | 40 | 20 | 50 | 30 | 0 | 0 | 0 | 0 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | | |
|---|---|---|---|---|---|---|---|---|---|---|---|---|---|---|
| Preemergence | 1183 | 1184 | 1185 | 1186 | 1187 | 1188 | 1189 | 1190 | 1191 | 1192 | 1193 | 1194 | 1195 | 1196 |
| Barnyardgrass | 90 | 100 | 100 | 100 | 100 | 100 | 100 | 90 | 0 | 100 | 90 | 0 | 0 | 50 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 90 | 100 | 100 | 100 | 100 | 90 | 0 | 100 | 80 | 0 | 0 | 70 |
| Foxtail, Green | — | — | — | — | — | — | — | — | — | — | — | — | — | — |
| Kochia | 0 | 0 | 0 | 80 | 70 | 80 | 70 | 0 | 0 | 50 | 0 | 0 | 0 | 0 |
| Morningglory | — | — | — | — | — | — | — | — | — | — | — | — | — | — |
| Pigweed | 0 | 0 | 0 | 70 | 20 | 80 | 40 | 0 | 0 | 30 | 0 | 0 | 0 | 0 |
| Ragweed | 0 | 0 | 0 | 60 | 50 | 70 | 50 | 0 | 0 | 0 | 0 | 0 | 0 | 0 |
| Ryegrass, Italian | 50 | 50 | 60 | 70 | 40 | 60 | 60 | 0 | 0 | 0 | 0 | 0 | 0 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | | |
|---|---|---|---|---|---|---|---|---|---|---|---|---|---|---|
| Preemergence | 1197 | 1198 | 1199 | 1200 | 1201 | 1202 | 1203 | 1204 | 1205 | 1206 | 1207 | 1208 | 1209 | 1210 |
| Barnyardgrass | 100 | 70 | 90 | 0 | 0 | 90 | 80 | 90 | 90 | 70 | 60 | 90 | 90 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 100 | 100 | 90 | 0 | 70 | 50 | 80 | 90 | 100 | 80 | 80 | 100 | 90 | 100 |
| Foxtail, Green | — | — | — | — | — | — | — | — | — | — | — | — | — | — |
| Kochia | 100 | 80 | 0 | 0 | 30 | 20 | 20 | 80 | 30 | 60 | 30 | 70 | 60 | 0 |
| Morningglory | — | — | — | — | — | — | — | — | — | — | — | — | — | — |
| Pigweed | 80 | 70 | 0 | 0 | 20 | 0 | 0 | 70 | 0 | 50 | 0 | 60 | 0 | 0 |
| Ragweed | 100 | 70 | 30 | 0 | 60 | 0 | 30 | 90 | 0 | 0 | 30 | 40 | 60 | 0 |
| Ryegrass, Italian | 70 | 30 | 0 | 0 | 0 | 0 | 0 | 70 | 40 | 0 | 0 | 20 | 0 | 20 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | | |
|---|---|---|---|---|---|---|---|---|---|---|---|---|---|---|
| Preemergence | 1211 | 1212 | 1213 | 1214 | 1215 | 1216 | 1217 | 1218 | 1219 | 1220 | 1221 | 1222 | 1223 | 1224 |
| Barnyardgrass | 100 | 80 | 100 | 90 | 90 | 0 | 90 | 30 | 70 | 90 | 90 | 0 | 90 | 40 |
| Corn | — | — | — | — | — | — | — | — | — | — | — | — | — | — |
| Crabgrass, Large | — | — | — | — | — | — | — | — | — | — | — | — | — | — |
| Foxtail, Giant | 100 | 90 | 100 | 90 | 60 | 30 | 90 | 80 | 80 | 90 | 90 | 0 | 90 | 80 |
| Foxtail, Green | — | — | — | — | — | — | — | — | — | — | — | — | — | — |
| Kochia | 20 | 100 | 70 | 50 | 0 | 0 | 0 | 0 | 0 | 40 | 40 | 0 | 0 | 0 |
| Morningglory | — | — | — | — | — | — | — | — | — | — | — | — | — | — |
| Pigweed | 50 | 80 | 50 | 60 | 0 | 0 | 0 | 0 | 0 | 20 | 0 | 0 | 0 | 50 |

TABLE A-continued

| 125 g ai/ha | | | | | | | | | | | | | |
|---|---|---|---|---|---|---|---|---|---|---|---|---|---|
| Ragweed | 50 | 40 | 50 | 0 | 0 | 0 | 0 | 0 | 0 | 30 | 20 | 0 | 0 | 0 |
| Ryegrass, Italian | 50 | 0 | 20 | 60 | 0 | 0 | 0 | 0 | 0 | 30 | 20 | 0 | 0 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | |
|---|---|---|---|---|---|---|---|---|---|---|---|---|---|
| Preemergence | 1225 | 1226 | 1227 | 1228 | 1229 | 1230 | 1231 | 1232 | 1233 | 1234 | 1235 | 1236 | 1237 | 1238 |
| Barnyardgrass | 90 | 90 | 0 | 90 | 90 | 0 | 90 | 90 | 90 | 100 | 100 | 90 | 70 | 80 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 100 | 50 | 90 | 100 | 40 | 90 | 90 | 90 | 100 | 100 | 90 | 60 | 90 |
| Foxtail, Green | — | — | — | — | — | — | — | — | — | — | — | — | — | — |
| Kochia | 60 | 60 | 0 | 0 | 90 | 70 | 70 | 70 | 70 | 70 | 60 | 20 | 0 | 60 |
| Morningglory | — | — | — | — | — | — | — | — | — | — | — | — | — | — |
| Pigweed | 30 | 80 | 30 | 20 | 60 | 20 | 40 | 70 | 40 | 70 | 30 | 60 | 0 | 0 |
| Ragweed | 50 | 0 | 0 | 0 | 60 | 0 | 30 | 60 | 30 | 40 | 70 | 0 | 0 | 0 |
| Ryegrass, Italian | 20 | 80 | 20 | 30 | 0 | 0 | 40 | 20 | 40 | 40 | 50 | 30 | 0 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | |
|---|---|---|---|---|---|---|---|---|---|---|---|---|---|
| Preemergence | 1239 | 1240 | 1241 | 1242 | 1243 | 1244 | 1245 | 1246 | 1247 | 1248 | 1249 | 1250 | 1251 | 1252 |
| Barnyardgrass | 80 | 0 | 0 | 20 | 0 | 80 | 50 | 60 | 70 | 70 | 100 | 100 | 100 | 100 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 0 | 0 | 30 | 0 | 90 | 80 | 50 | 20 | 0 | 100 | 100 | 100 | 90 |
| Foxtail, Green | — | — | — | — | — | — | — | — | — | — | — | — | — | — |
| Kochia | 90 | 0 | 0 | 0 | 0 | 0 | 0 | 60 | 0 | 0 | — | 0 | 80 | 80 |
| Morningglory | — | — | — | — | — | — | — | — | — | — | — | — | — | — |
| Pigweed | 20 | 0 | 0 | 0 | 0 | 0 | 0 | 0 | 0 | 0 | 80 | 30 | 90 | 70 |
| Ragweed | 0 | 0 | 0 | 0 | 0 | 0 | — | 40 | 0 | 0 | 30 | 0 | 70 | 60 |
| Ryegrass, Italian | 50 | 0 | 0 | 0 | 0 | 0 | 0 | 0 | 0 | 0 | 30 | 50 | 50 | 80 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | |
|---|---|---|---|---|---|---|---|---|---|---|---|---|---|
| Preemergence | 1253 | 1254 | 1255 | 1256 | 1257 | 1258 | 1259 | 1260 | 1261 | 1262 | 1263 | 1264 | 1265 | 1266 |
| Barnyardgrass | 90 | 100 | 100 | 100 | 0 | 30 | 60 | 90 | 90 | 90 | 0 | 0 | 90 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 100 | 90 | 100 | 90 | 0 | 70 | 90 | 90 | 90 | 90 | 0 | 0 | 90 | 90 |
| Foxtail, Green | — | — | — | — | — | — | — | — | — | — | — | — | — | — |
| Kochia | 80 | 20 | 60 | 30 | 0 | 0 | 0 | 80 | 80 | 60 | 0 | 0 | 70 | 80 |
| Morningglory | — | — | — | — | — | — | — | — | — | — | — | — | — | — |
| Pigweed | 50 | 20 | 60 | 30 | 0 | 0 | 30 | 90 | 20 | 50 | 0 | 0 | 80 | 80 |
| Ragweed | 40 | 0 | 20 | 0 | 0 | 0 | 0 | 80 | 50 | 0 | 0 | 0 | 0 | 60 |
| Ryegrass, Italian | 20 | 0 | 20 | 20 | 0 | 0 | 30 | 50 | 30 | 0 | 0 | 0 | 60 | 40 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | |
|---|---|---|---|---|---|---|---|---|---|---|---|---|---|
| Preemergence | 1267 | 1268 | 1269 | 1270 | 1271 | 1272 | 1273 | 1274 | 1275 | 1276 | 1277 | 1278 | 1279 | 1280 |
| Barnyardgrass | 90 | 90 | 90 | 90 | 90 | 90 | 80 | 90 | 100 | 100 | 100 | 100 | 70 | 0 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 90 | 90 | 90 | 90 | 90 | 90 | 100 | 100 | 100 | 100 | 20 | 0 |
| Foxtail, Green | — | — | — | — | — | — | — | — | — | — | — | — | — | — |
| Kochia | 0 | 0 | 50 | 60 | 40 | 20 | 50 | 70 | 20 | 60 | 0 | 30 | 0 | 0 |
| Morningglory | — | — | — | — | — | — | — | — | — | — | — | — | — | — |
| Pigweed | 0 | 0 | 0 | 40 | 50 | 0 | 20 | 70 | 0 | 30 | 0 | 90 | 0 | 0 |
| Ragweed | 0 | 0 | 0 | 30 | 20 | 0 | 0 | 80 | 20 | 80 | 0 | 100 | 0 | 0 |
| Ryegrass, Italian | 0 | 20 | 30 | 40 | 90 | 60 | 40 | 20 | 0 | 30 | 0 | 30 | 0 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | |
|---|---|---|---|---|---|---|---|---|---|---|---|---|---|
| Preemergence | 1281 | 1282 | 1283 | 1284 | 1285 | 1286 | 1287 | 1288 | 1289 | 1290 | 1291 | 1292 | 1293 | 1294 |
| Barnyardgrass | 40 | 100 | 0 | 0 | 90 | 100 | 100 | 0 | 30 | 0 | 100 | 50 | 20 | 50 |
| Corn | — | — | — | — | — | — | — | — | — | — | — | — | — | — |
| Crabgrass, Large | — | — | — | — | — | — | — | — | — | — | — | — | — | — |

TABLE A-continued

| | | | | | | | | | | | | | |
|---|---|---|---|---|---|---|---|---|---|---|---|---|---|
| Foxtail, Giant | 40 | 100 | 0 | 0 | 100 | 100 | 100 | 0 | 50 | 0 | 100 | 80 | 20 | 30 |
| Foxtail, Green | — | — | — | — | — | — | — | — | — | — | — | — | — | — |
| Kochia | 0 | 70 | 0 | 0 | 30 | 60 | 70 | 0 | 0 | 0 | 40 | 60 | 0 | 0 |
| Morningglory | — | — | — | — | — | — | — | — | — | — | — | — | — | — |
| Pigweed | 30 | 80 | 0 | 0 | 0 | 20 | 40 | 0 | 0 | 0 | 100 | 40 | 0 | 0 |
| Ragweed | 0 | 90 | 0 | 0 | 30 | 50 | 0 | 0 | 0 | 0 | 0 | 0 | 0 | 0 |
| Ryegrass, Italian | 0 | 70 | 0 | 0 | 0 | 60 | 40 | 0 | 0 | 0 | 20 | 40 | 0 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | |
|---|---|---|---|---|---|---|---|---|---|---|---|---|---|
| Preemergence | 1295 | 1296 | 1297 | 1298 | 1299 | 1300 | 1301 | 1302 | 1303 | 1304 | 1305 | 1306 | 1307 | 1308 |
| Barnyardgrass | 0 | 70 | 20 | 80 | 90 | 90 | 30 | 60 | 0 | 0 | 70 | 60 | 80 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 40 | 60 | 80 | 90 | 90 | 90 | 90 | 90 | 40 | 0 | 90 | 30 | 50 | 90 |
| Foxtail, Green | — | — | — | — | — | — | — | — | — | — | — | — | — | — |
| Kochia | 0 | 0 | 0 | 0 | 70 | 0 | 30 | 0 | 0 | 0 | 0 | 0 | 20 | 0 |
| Morningglory | — | — | — | — | — | — | — | — | — | — | — | — | — | — |
| Pigweed | 0 | 0 | 0 | 0 | 20 | 0 | 0 | 0 | 0 | 0 | 0 | 0 | 0 | 0 |
| Ragweed | 0 | 0 | 0 | 0 | 30 | 0 | 0 | 0 | 0 | 0 | 0 | 40 | — | 0 |
| Ryegrass, Italian | 0 | 0 | 0 | 0 | 30 | 0 | 0 | 0 | 0 | 0 | 0 | 0 | 0 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | |
|---|---|---|---|---|---|---|---|---|---|---|---|---|---|
| Preemergence | 1309 | 1310 | 1311 | 1312 | 1313 | 1314 | 1316 | 1317 | 1318 | 1319 | 1320 | 1321 | 1323 | 1324 |
| Barnyardgrass | 90 | 90 | 100 | 90 | 90 | 100 | 90 | 90 | 90 | 90 | 0 | 90 | 90 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 80 | 90 | 100 | 90 | 20 | 90 | 90 | 90 | 90 | 90 | 0 | 90 | 90 | 90 |
| Foxtail, Green | — | — | — | — | — | — | — | — | — | — | — | — | — | — |
| Kochia | 60 | 70 | 70 | 50 | 90 | 80 | 80 | 60 | 70 | 80 | 0 | 50 | 80 | 90 |
| Morningglory | — | — | — | — | — | — | — | — | — | — | — | — | — | — |
| Pigweed | 0 | 0 | 0 | 20 | 0 | 0 | 70 | 0 | 70 | 0 | 0 | 0 | 0 | 0 |
| Ragweed | 40 | 0 | — | 70 | 0 | 80 | 0 | 0 | 0 | 0 | 0 | 50 | 0 | 90 |
| Ryegrass, Italian | 0 | 0 | 70 | 60 | 0 | 20 | 70 | 20 | 40 | 30 | 0 | 0 | 20 | 20 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | |
|---|---|---|---|---|---|---|---|---|---|---|---|---|---|
| Preemergence | 1325 | 1326 | 1327 | 1328 | 1329 | 1330 | 1331 | 1332 | 1333 | 1334 | 1335 | 1336 | 1337 | 1338 |
| Barnyardgrass | 90 | 80 | 90 | 70 | 90 | 90 | 90 | 70 | 70 | 20 | 0 | 0 | 80 | 100 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 60 | 70 | 50 | 90 | 90 | 90 | 80 | 90 | 40 | 0 | 0 | 80 | 90 |
| Foxtail, Green | — | — | — | — | — | — | — | — | — | — | — | — | — | — |
| Kochia | 80 | 30 | 100 | 30 | 50 | 20 | 0 | 0 | 30 | 0 | 0 | 0 | 0 | 0 |
| Morningglory | — | — | — | — | — | — | — | — | — | — | — | — | — | — |
| Pigweed | 60 | 0 | 0 | 0 | 0 | 0 | 0 | 0 | 0 | 20 | 0 | 0 | 0 | 0 |
| Ragweed | 10 | 0 | 0 | 0 | 0 | 0 | 0 | 0 | 0 | 0 | 0 | 0 | 0 | 0 |
| Ryegrass, Italian | 0 | 20 | 20 | 0 | 0 | 50 | 20 | 0 | 0 | 0 | 0 | 0 | 70 | 0 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | |
|---|---|---|---|---|---|---|---|---|---|---|---|---|---|
| Preemergence | 1339 | 1340 | 1341 | 1342 | 1343 | 1344 | 1345 | 1346 | 1347 | 1348 | 1349 | 1350 | 1351 | 1352 |
| Barnyardgrass | 90 | 90 | 60 | 90 | 90 | 0 | 100 | 90 | 100 | 100 | 100 | 90 | 0 | 90 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 70 | 100 | 100 | 0 | 100 | 100 | 100 | 100 | 100 | 100 | 0 | 100 |
| Foxtail, Green | — | — | — | — | — | — | — | — | — | — | — | — | — | — |
| Kochia | 50 | 0 | 0 | 0 | 40 | 0 | 40 | 80 | 90 | 80 | 20 | 70 | 0 | 60 |
| Morningglory | — | — | — | — | — | — | — | — | — | — | — | — | — | — |
| Pigweed | 0 | 20 | 0 | 20 | 30 | 0 | 0 | 90 | 100 | 100 | 0 | 90 | 0 | 80 |
| Ragweed | 0 | 0 | 0 | 0 | 0 | 0 | 60 | 90 | 90 | 20 | 0 | 80 | 0 | 30 |
| Ryegrass, Italian | 20 | 0 | 0 | 0 | 30 | 0 | 0 | 30 | 30 | 60 | 0 | 30 | 0 | 40 |
| Velvetleaf | — | — | — | — | — | — | — | — | — | — | — | — | — | — |
| Wheat | — | — | — | — | — | — | — | — | — | — | — | — | — | — |

TABLE A-continued

| 125 g ai/ha | Compounds | | | | | | | | | | | | | |
|---|---|---|---|---|---|---|---|---|---|---|---|---|---|---|
| Preemergence | 1353 | 1354 | 1355 | 1356 | 1357 | 1358 | 1359 | 1360 | 1361 | 1362 | 1366 | 1367 | 1368 | 1369 |
| Barnyardgrass | 70 | 80 | 0 | 0 | 0 | 0 | 0 | 0 | 0 | 0 | 70 | 80 | 100 | 100 |
| Corn | — | — | 0 | 0 | 0 | 0 | 0 | 0 | 0 | 0 | — | — | — | — |
| Crabgrass, Large | — | — | 0 | 0 | 0 | 20 | 0 | 0 | 0 | 0 | — | — | — | — |
| Foxtail, Giant | 100 | 100 | 0 | 0 | 0 | 0 | 0 | 0 | 0 | 0 | 90 | — | — | — |
| Foxtail, Green | — | — | — | — | — | — | — | — | — | — | — | 60 | 100 | 100 |
| Kochia | 80 | 20 | — | — | — | — | — | — | — | — | 0 | 0 | 0 | 0 |
| Morningglory | — | — | 0 | 0 | 0 | 0 | 0 | 0 | 0 | 0 | — | — | — | — |
| Pigweed | 30 | 20 | 0 | 0 | 0 | 0 | 0 | 0 | 0 | 0 | 0 | 0 | 0 | 0 |
| Ragweed | 0 | 0 | — | — | — | — | — | — | — | — | 0 | 0 | 0 | 70 |
| Ryegrass, Italian | 20 | 20 | — | — | — | — | — | — | — | — | 10 | 0 | 0 | 0 |
| Velvetleaf | — | — | 0 | 0 | 0 | 0 | 0 | 0 | 0 | 0 | — | — | — | — |
| Wheat | — | — | 0 | 0 | 0 | 0 | 0 | 0 | 0 | 0 | — | — | — | — |

| 125 g ai/ha | Compounds | | | | | | | | | | | | | |
|---|---|---|---|---|---|---|---|---|---|---|---|---|---|---|
| Preemergence | 1370 | 1371 | 1372 | 1373 | 1374 | 1375 | 1376 | 1377 | 1378 | 1379 | 1380 | 1381 | 1382 | 1383 |
| Barnyardgrass | 90 | 90 | 90 | 90 | 0 | 100 | 90 | 80 | 90 | 100 | 90 | 90 | 0 | 100 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 90 | 100 | 0 | 100 | 90 | 100 | 90 | 100 | 100 | 100 | 0 | 100 |
| Foxtail, Green | — | — | — | — | — | — | — | — | — | — | — | — | — | — |
| Kochia | — | 80 | 90 | 100 | 0 | 70 | 0 | 70 | 80 | 90 | 80 | 80 | 0 | 90 |
| Morningglory | — | — | — | — | — | — | — | — | — | — | — | — | — | — |
| Pigweed | 0 | 70 | 90 | 90 | 0 | 0 | 0 | 20 | 70 | 80 | 80 | 90 | 20 | 80 |
| Ragweed | 40 | 70 | 90 | 100 | 0 | 70 | 0 | 0 | 50 | 70 | 70 | 70 | 0 | 80 |
| Ryegrass, Italian | 80 | 0 | 60 | 60 | 0 | 70 | 20 | 20 | 80 | 20 | 50 | 30 | 0 | 70 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | | | | | | | | | | | |
|---|---|---|---|---|---|---|---|---|---|---|---|---|---|---|
| Preemergence | 1384 | 1385 | 1386 | 1387 | 1388 | 1389 | 1390 | 1391 | 1392 | 1393 | 1394 | 1395 | 1396 | 1397 |
| Barnyardgrass | 90 | 90 | 90 | 50 | 100 | 100 | 90 | 90 | 0 | 90 | 90 | 90 | 90 | 100 |
| Corn | — | — | — | — | — | — | — | — | — | — | — | — | — | — |
| Crabgrass, Large | — | — | — | — | — | — | — | — | — | — | — | — | — | — |
| Foxtail, Giant | 90 | 90 | 90 | 80 | 100 | 100 | 90 | 100 | 0 | 90 | 90 | 90 | 90 | 100 |
| Foxtail, Green | — | — | — | — | — | — | — | — | — | — | — | — | — | — |
| Kochia | 30 | 0 | 80 | 30 | 80 | 70 | 80 | 90 | 0 | 70 | 40 | 0 | 70 | 60 |
| Morningglory | — | — | — | — | — | — | — | — | — | — | — | — | — | — |
| Pigweed | 30 | 0 | 80 | 0 | 30 | 70 | 80 | 90 | 0 | 80 | 0 | 0 | 90 | 0 |
| Ragweed | 0 | 0 | 60 | 0 | 0 | 0 | 70 | 90 | 0 | 90 | 20 | 0 | 60 | 0 |
| Ryegrass, Italian | 30 | 0 | 50 | 0 | 90 | 80 | 30 | 30 | 0 | 20 | 50 | 50 | 40 | 70 |
| Velvetleaf | — | — | — | — | — | — | — | — | — | — | — | — | — | — |
| Wheat | — | — | — | — | — | — | — | — | — | — | — | — | — | — |

| 125 g ai/ha | Compounds | | | |
|---|---|---|---|---|
| Preemergence | 1398 | 1399 | 1400 | 1402 |
| Barnyardgrass | 100 | 90 | 90 | 90 |
| Corn | — | — | — | — |
| Crabgrass, Large | — | — | — | — |
| Foxtail, Giant | 100 | 90 | 90 | 100 |
| Foxtail, Green | — | — | — | — |
| Kochia | 90 | 70 | 70 | 80 |
| Morningglory | — | — | — | — |
| Pigweed | 50 | 30 | 80 | 90 |
| Ragweed | 90 | 60 | 70 | 0 |
| Ryegrass, Italian | 70 | 40 | 30 | 0 |
| Velvetleaf | — | — | — | — |
| Wheat | — | — | — | — |

| 31 g ai/ha | Compounds | | | | | | | | | | | | | |
|---|---|---|---|---|---|---|---|---|---|---|---|---|---|---|
| Preemergence | 770 | 792 | 793 | 794 | 795 | 796 | 797 | 798 | 799 | 800 | 801 | 802 | 803 | 804 |
| Barnyardgrass | 70 | 0 | 0 | 70 | 30 | 70 | 80 | 20 | 0 | 80 | 80 | 80 | 70 | 70 |
| Foxtail, Giant | 90 | 0 | 0 | 30 | 0 | 90 | 90 | 70 | 70 | 80 | 80 | 90 | 90 | 70 |
| Foxtail, Green | — | — | — | — | — | — | — | — | — | — | — | — | — | — |
| Kochia | 0 | 0 | 0 | 0 | 0 | 0 | 0 | 0 | 0 | 0 | 40 | 0 | 50 | 0 |
| Pigweed | 40 | 0 | 0 | 0 | 0 | 20 | 0 | 30 | 30 | 0 | 30 | 40 | 40 | 0 |
| Ragweed | 0 | 0 | 0 | 0 | 0 | 0 | 0 | 0 | 0 | 0 | 20 | 0 | 30 | 0 |
| Ryegrass, Italian | 0 | 0 | 0 | 0 | 0 | 0 | 0 | 0 | 0 | 0 | 0 | 0 | 0 | 40 |

TABLE A-continued

| 31 g ai/ha | Compounds | | | | | | | | | | | | | |
|---|---|---|---|---|---|---|---|---|---|---|---|---|---|---|
| Preemergence | 805 | 806 | 807 | 808 | 809 | 810 | 811 | 812 | 813 | 814 | 970 | 971 | 972 | 997 |
| Barnyardgrass | 0 | 0 | 100 | 100 | 90 | 90 | 0 | 70 | 20 | 0 | 0 | 70 | 70 | 0 |
| Foxtail, Giant | 0 | 0 | 100 | 70 | 0 | 70 | 0 | 80 | 70 | 0 | 20 | 70 | 80 | 0 |
| Foxtail, Green | — | — | — | — | — | — | — | — | — | — | — | — | — | — |
| Kochia | 0 | 0 | 0 | 0 | 0 | 0 | 0 | 0 | 0 | 0 | 0 | 0 | 0 | 0 |
| Pigweed | 0 | 0 | 0 | 0 | 0 | 0 | 0 | 0 | 0 | 0 | 0 | 20 | 0 | 0 |
| Ragweed | 0 | 0 | 0 | 0 | 0 | 0 | 0 | 0 | 0 | 0 | 0 | 0 | 0 | 0 |
| Ryegrass, Italian | 0 | 0 | 20 | 0 | 0 | 0 | 0 | 0 | 0 | 0 | 0 | 50 | 50 | 0 |

| 31 g ai/ha | Compounds | | | | | | | | | | | | | |
|---|---|---|---|---|---|---|---|---|---|---|---|---|---|---|
| Preemergence | 1003 | 1004 | 1005 | 1006 | 1007 | 1008 | 1009 | 1010 | 1011 | 1012 | 1050 | 1051 | 1052 | 1060 |
| Barnyardgrass | 0 | 0 | 0 | 0 | 0 | 0 | 0 | 0 | 0 | 0 | 0 | 0 | 30 | 90 |
| Foxtail, Giant | 0 | 0 | 0 | 0 | 0 | 0 | 0 | 0 | 0 | 0 | 0 | 30 | 80 | 90 |
| Foxtail, Green | — | — | — | — | — | — | — | — | — | — | — | — | — | — |
| Kochia | 0 | 0 | 0 | 0 | 0 | 0 | 0 | 0 | 0 | 0 | 0 | 0 | 20 | 0 |
| Pigweed | 0 | 0 | 0 | 0 | 0 | 0 | 0 | 0 | 0 | 0 | 0 | 0 | 40 | 0 |
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 0 | 0 | 0 | 0 | 0 | 50 |

| 31 g ai/ha | Compounds | | | | | | | | | | | | | |
|---|---|---|---|---|---|---|---|---|---|---|---|---|---|---|
| Preemergence | 1061 | 1062 | 1063 | 1065 | 1066 | 1067 | 1068 | 1069 | 1070 | 1071 | 1072 | 1074 | 1075 | 1076 |
| Barnyardgrass | 40 | 100 | 100 | 0 | 50 | 30 | 0 | 0 | 0 | 40 | 90 | 90 | 100 | 0 |
| Foxtail, Giant | 20 | — | — | 90 | 100 | 90 | 0 | 0 | 0 | 90 | 90 | 100 | 100 | 80 |
| Foxtail, Green | — | 100 | 100 | — | — | — | — | — | — | — | — | — | — | — |
| Kochia | 0 | 0 | 10 | 0 | 0 | 0 | 0 | 0 | 0 | 0 | 0 | 0 | 0 | 0 |
| Pigweed | 0 | 0 | 0 | 30 | 0 | 0 | 0 | 0 | 0 | 0 | 0 | 0 | 0 | 0 |
| Ragweed | 0 | 70 | 0 | 0 | 0 | 0 | 0 | 0 | 0 | 0 | 0 | 0 | 30 | 10 |
| Ryegrass, Italian | 0 | 10 | 0 | 0 | 20 | 20 | 0 | 0 | 0 | 0 | 0 | 0 | 50 | 0 |

| 31 g ai/ha | Compounds | | | | | | | | | | | | | |
|---|---|---|---|---|---|---|---|---|---|---|---|---|---|---|
| Preemergence | 1077 | 1078 | 1079 | 1080 | 1081 | 1082 | 1083 | 1084 | 1085 | 1086 | 1087 | 1088 | 1089 | 1090 |
| Barnyardgrass | 80 | 0 | 0 | 0 | 10 | 0 | 90 | 0 | 0 | 80 | 0 | 0 | 90 | 10 |
| Foxtail, Giant | 100 | 0 | 20 | 0 | 100 | 0 | 100 | 30 | 90 | 90 | 90 | 0 | 100 | 60 |
| Foxtail, Green | — | — | — | — | — | — | — | — | — | — | — | — | — | — |
| Kochia | 0 | 0 | 0 | 0 | 20 | 0 | 20 | 0 | 0 | 0 | 0 | 30 | 0 | 20 |
| Pigweed | 0 | 0 | 0 | 0 | 0 | 0 | 0 | 0 | 0 | 0 | 0 | 0 | 0 | 0 |
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 20 | 0 | 0 | 0 | 0 | 0 | 0 | 30 |

| 31 g ai/ha | Compounds | | | | | | | | | | | | | |
|---|---|---|---|---|---|---|---|---|---|---|---|---|---|---|
| Preemergence | 1091 | 1092 | 1093 | 1103 | 1104 | 1105 | 1106 | 1107 | 1108 | 1109 | 1110 | 1141 | 1142 | 1143 |
| Barnyardgrass | 0 | 40 | 40 | 20 | 0 | 30 | 50 | 0 | 0 | 100 | 90 | 30 | 0 | 0 |
| Foxtail, Giant | 50 | 90 | 100 | 70 | 0 | 20 | 60 | 0 | 0 | 100 | 90 | 80 | 30 | 20 |
| Foxtail, Green | — | — | — | — | — | — | — | — | — | — | — | — | — | — |
| Kochia | 20 | 70 | 0 | 0 | 0 | 0 | 0 | 0 | 0 | 0 | 0 | 0 | 0 | 0 |
| Pigweed | 10 | 0 | 0 | 0 | 0 | 0 | 0 | 0 | 0 | 70 | 60 | 30 | 0 | 0 |
| Ragweed | 100 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 0 | 60 | 30 | 0 | 0 | 0 |

| 31 g ai/ha | Compounds | | | | | | | | | | | | |
|---|---|---|---|---|---|---|---|---|---|---|---|---|---|
| Preemergence | 1144 | 1145 | 1146 | 1147 | 1148 | 1149 | 1150 | 1161 | 1162 | 1163 | 1164 | 1165 | 1166 | 1167 |
| Barnyardgrass | 90 | 80 | 50 | 0 | 30 | 70 | 0 | 0 | 40 | 70 | 60 | 70 | 0 | 0 |
| Foxtail, Giant | 90 | 90 | 20 | 0 | 90 | 80 | 30 | 0 | 50 | 10 | 30 | 70 | 20 | 0 |
| Foxtail, Green | — | — | — | — | — | — | — | — | — | — | — | — | — | — |
| Kochia | 50 | 0 | 0 | 0 | 0 | 0 | 0 | 0 | 0 | 0 | 0 | 0 | 0 | 0 |
| Pigweed | 30 | 0 | 0 | 0 | 0 | 0 | 0 | 0 | 0 | 0 | 0 | 40 | 0 | 0 |
| Ragweed | 0 | 0 | 0 | 0 | 0 | 0 | 0 | 0 | 0 | 0 | 0 | 0 | 0 | 0 |
| Ryegrass, Italian | 50 | 0 | 0 | 0 | 0 | 0 | 0 | 0 | 0 | 0 | 0 | 0 | 0 | 0 |

| 31 g ai/ha | Compounds | | | | | | | | | | | | |
|---|---|---|---|---|---|---|---|---|---|---|---|---|---|
| Preemergence | 1168 | 1169 | 1170 | 1171 | 1172 | 1173 | 1174 | 1175 | 1176 | 1183 | 1184 | 1185 | 1186 | 1187 |
| Barnyardgrass | 0 | 70 | 0 | 40 | 0 | 60 | 80 | 50 | 90 | 90 | 90 | 70 | 90 | 70 |
| Foxtail, Giant | 0 | 70 | 0 | 70 | 0 | 30 | 80 | 70 | 90 | 80 | 80 | 50 | 100 | 90 |
| Foxtail, Green | — | — | — | — | — | — | — | — | — | — | — | — | — | — |
| Kochia | 0 | 30 | 0 | 0 | 0 | 0 | 0 | 20 | 0 | 0 | 0 | 0 | 70 | 50 |

TABLE A-continued

| | | | | | | | | | | | | | | |
|---|---|---|---|---|---|---|---|---|---|---|---|---|---|---|
| Pigweed | 0 | 0 | 0 | 0 | 0 | 0 | 0 | 0 | 0 | 0 | 0 | 0 | 30 | 0 |
| Ragweed | 0 | 0 | 0 | 0 | 0 | 0 | 0 | 0 | 0 | 0 | 0 | 0 | 0 | 0 |
| Ryegrass, Italian | 0 | 0 | 0 | 0 | 0 | 0 | 0 | 0 | 40 | 20 | 40 | 0 | 20 | 0 |

| 31 g ai/ha | Compounds | | | | | | | | | | | | |
|---|---|---|---|---|---|---|---|---|---|---|---|---|---|
| Preemergence | 1188 | 1189 | 1190 | 1191 | 1192 | 1193 | 1237 | 1258 | 1259 | 1261 | 1262 | 1263 | 1264 | 1265 |
| Barnyardgrass | 90 | 90 | 50 | 0 | 70 | 40 | 0 | 0 | 0 | 90 | 70 | 0 | 0 | 80 |
| Foxtail, Giant | 90 | 90 | 60 | 0 | 30 | 0 | 20 | 40 | 40 | 90 | 90 | 0 | 0 | 90 |
| Foxtail, Green | — | — | — | — | — | — | — | — | — | — | — | — | — | — |
| Kochia | 60 | 40 | 0 | 0 | 0 | 0 | 0 | 0 | 0 | 70 | 20 | 0 | 0 | 30 |
| Pigweed | 40 | 0 | 0 | 0 | 0 | 0 | 0 | 0 | 30 | 0 | 0 | 0 | 0 | 0 |
| Ragweed | 30 | 0 | 0 | 0 | 0 | 0 | 0 | 0 | 0 | 50 | 0 | 0 | 0 | 0 |
| Ryegrass, Italian | 0 | 20 | 0 | 0 | 0 | 0 | 0 | 0 | 0 | 20 | 0 | 0 | 0 | 50 |

| 31 g ai/ha | Compounds | | | | | | | | | | | | |
|---|---|---|---|---|---|---|---|---|---|---|---|---|---|
| Preemergence | 1266 | 1267 | 1268 | 1269 | 1270 | 1271 | 1272 | 1273 | 1274 | 1275 | 1276 | 1277 | 1278 | 1279 |
| Barnyardgrass | 80 | 90 | 90 | 70 | 70 | 90 | 90 | 60 | 30 | 70 | 90 | 80 | 80 | 0 |
| Foxtail, Giant | 90 | 90 | 70 | 90 | 90 | 80 | 90 | 80 | 80 | 90 | 90 | 90 | 100 | 0 |
| Foxtail, Green | — | — | — | — | — | — | — | — | — | — | — | — | — | — |
| Kochia | 40 | 0 | 0 | 0 | 40 | 30 | 0 | 0 | 30 | 0 | 30 | 0 | 30 | 0 |
| Pigweed | 20 | 0 | 0 | 0 | 0 | 0 | 0 | 0 | 30 | 0 | 0 | 0 | 0 | 0 |
| Ragweed | 20 | 0 | 0 | 0 | 0 | 0 | 0 | 0 | 20 | 0 | 20 | 0 | 20 | 0 |
| Ryegrass, Italian | 0 | 0 | 0 | 0 | 0 | 70 | 20 | 0 | 0 | 0 | 0 | 0 | 0 | 0 |

| 31 g ai/ha | Compounds | | | | | | | | | | | | |
|---|---|---|---|---|---|---|---|---|---|---|---|---|---|
| Preemergence | 1282 | 1283 | 1284 | 1285 | 1286 | 1287 | 1288 | 1289 | 1290 | 1291 | 1292 | 1293 | 1294 | 1295 |
| Barnyardgrass | 100 | 0 | 0 | 40 | 100 | 90 | 0 | 20 | 0 | 100 | 0 | 0 | 0 | 0 |
| Foxtail, Giant | 100 | 0 | 0 | 90 | 100 | 100 | 0 | 50 | 0 | 100 | 70 | 0 | 0 | 0 |
| Foxtail, Green | — | — | — | — | — | — | — | — | — | — | — | — | — | — |
| Kochia | 30 | 0 | 0 | 20 | 0 | 20 | 0 | 0 | 0 | 0 | 60 | 0 | 0 | 0 |
| Pigweed | 60 | 0 | 0 | 0 | 0 | 0 | 0 | 0 | 0 | 0 | 40 | 0 | 0 | 0 |
| Ragweed | 0 | 0 | 0 | 30 | 0 | 0 | 0 | 0 | 0 | 0 | 0 | 0 | 0 | 0 |
| Ryegrass, Italian | 30 | 0 | 0 | 0 | 20 | 0 | 0 | 0 | 0 | 0 | 0 | 0 | 0 | 0 |

| 31 g ai/ha | Compounds | | | | | | | | | | | | |
|---|---|---|---|---|---|---|---|---|---|---|---|---|---|
| Preemergence | 1296 | 1297 | 1333 | 1337 | 1338 | 1339 | 1340 | 1341 | 1342 | 1343 | 1344 | 1345 | 1346 | 1347 |
| Barnyardgrass | 20 | 20 | 40 | 50 | 90 | 90 | 90 | 0 | 60 | 90 | 0 | 80 | 40 | 80 |
| Foxtail, Giant | 20 | 0 | 90 | 40 | 80 | 80 | 40 | 10 | 90 | 100 | 0 | 90 | 90 | 100 |
| Foxtail, Green | — | — | — | — | — | — | — | — | — | — | — | — | — | — |
| Kochia | 0 | 0 | 0 | 0 | 0 | 0 | 0 | 30 | 0 | 0 | 0 | 0 | 10 | 90 |
| Pigweed | 0 | 0 | 0 | 0 | 0 | 0 | 0 | 0 | 0 | 0 | 0 | 0 | 80 | 90 |
| Ragweed | 0 | 0 | 0 | 0 | 0 | 0 | 0 | 20 | 0 | 90 | 0 | 0 | 0 | 30 |
| Ryegrass, Italian | 0 | 0 | 0 | 20 | 0 | 0 | 0 | 0 | 0 | 0 | 0 | 0 | 10 | 0 |

| 31 g ai/ha | Compounds | | | | | | | | | | | | |
|---|---|---|---|---|---|---|---|---|---|---|---|---|---|
| Preemergence | 1348 | 1349 | 1350 | 1351 | 1352 | 1353 | 1354 | 1366 | 1367 | 1368 | 1369 | 1375 | 1393 | 1396 |
| Barnyardgrass | 90 | 20 | 90 | 0 | 80 | 0 | 0 | 60 | 0 | 0 | 0 | 90 | 40 | 90 |
| Foxtail, Giant | 100 | 100 | 100 | 0 | 100 | 80 | 30 | 50 | — | — | — | 90 | 80 | 90 |
| Foxtail, Green | — | — | — | — | — | — | — | — | 0 | 0 | 20 | — | — | — |
| Kochia | 0 | 0 | 30 | 0 | 20 | 60 | 0 | 0 | 0 | 0 | 0 | 50 | 40 | 30 |
| Pigweed | 0 | 0 | 70 | 0 | 0 | 0 | 0 | 0 | 0 | 0 | 0 | 0 | 30 | 70 |
| Ragweed | 80 | 0 | 50 | 0 | 0 | 40 | 20 | 0 | 0 | 0 | 50 | 40 | 30 | 30 |
| Ryegrass, Italian | 20 | 0 | 30 | 0 | 0 | 10 | 0 | 0 | 0 | 0 | 0 | 0 | 0 | 0 |

| 31 g ai/ha | Compounds | | | | |
|---|---|---|---|---|---|
| Preemergence | 1397 | 1398 | 1399 | 1400 | 1402 |
| Barnyardgrass | 100 | 100 | 80 | 90 | 100 |
| Foxtail, Giant | 100 | 100 | 90 | 90 | 100 |
| Foxtail, Green | — | — | — | — | — |
| Kochia | 0 | 100 | 20 | 60 | 20 |
| Pigweed | 0 | 0 | 30 | 80 | 20 |
| Ragweed | 0 | 50 | 50 | 0 | 30 |
| Ryegrass, Italian | 50 | 0 | 0 | 0 | 0 |

Test B

Plant species in the flooded paddy test selected from rice (*Oryza sativa*), sedge, umbrella (small-flower umbrella sedge, *Cyperus difformis*), ducksalad (*Heteranthera limosa*), and barnyardgrass (*Echinochloa crus-galli*) were grown to the 2-leaf stage for testing. At time of treatment, test pots were flooded to 3 cm above the soil surface, treated by application of test compounds directly to the paddy water, and then maintained at that water depth for the duration of the test. Treated plants and controls were maintained in a greenhouse for 13 to 15 d, after which time all species were compared to controls and visually evaluated. Plant response ratings, summarized in Table B, are based on a scale of 0 to 100 where 0 is no effect and 100 is complete control. A dash (-) response means no test result.

TABLE B

| 1000 g ai/ha | Compounds | | |
|---|---|---|---|
| Flood | 365 | 366 | 367 |
| Barnyardgrass | 0 | 0 | 0 |
| Ducksalad | 0 | 0 | 0 |
| Rice | 0 | 0 | 0 |
| Sedge, Umbrella | 0 | 0 | 0 |

| 500 g ai/ha | Compounds | | | | | | | | | | | |
|---|---|---|---|---|---|---|---|---|---|---|---|---|
| Flood | 386 | 387 | 388 | 389 | 390 | 407 | 408 | 409 | 410 | 411 | 412 | 413 |
| Barnyardgrass | 60 | 50 | 0 | 60 | 50 | 60 | 0 | 40 | 0 | 20 | 0 | 0 |
| Ducksalad | 70 | 75 | 75 | 100 | 65 | 100 | 0 | 40 | 30 | 98 | 30 | 0 |
| Rice | 15 | 20 | 0 | 15 | 0 | 10 | 0 | 30 | 0 | 0 | 0 | 0 |
| Sedge, Umbrella | 0 | 0 | 0 | 0 | 0 | 0 | 0 | 0 | 0 | 0 | 0 | 0 |

| 500 g ai/ha | Compounds | | | | | | | | | | | | |
|---|---|---|---|---|---|---|---|---|---|---|---|---|---|
| Flood | 414 | 415 | 416 | 419 | 420 | 421 | 422 | 423 | 424 | 425 | 426 | 427 | 534 | 535 |
| Barnyardgrass | 0 | 0 | 0 | 40 | 65 | 75 | 0 | 0 | 0 | 0 | 0 | 40 | 0 | 0 |
| Ducksalad | 40 | 0 | 50 | 50 | 85 | 100 | 50 | 20 | 30 | 30 | 40 | 100 | 0 | 20 |
| Rice | 0 | 0 | 15 | 0 | 25 | 15 | 0 | 0 | 0 | 0 | 0 | 0 | 20 | 0 |
| Sedge, Umbrella | 0 | 0 | 0 | 0 | 0 | 0 | 0 | 0 | 0 | 0 | 0 | 0 | 0 | 50 |

| 500 g ai/ha | Compounds | | | | | | | | | | | | |
|---|---|---|---|---|---|---|---|---|---|---|---|---|---|
| Flood | 536 | 537 | 538 | 634 | 635 | 674 | 675 | 676 | 695 | 696 | 697 | 698 | 699 | 700 |
| Barnyardgrass | 30 | 30 | 0 | 20 | 60 | 60 | 60 | 80 | 80 | 75 | 90 | 50 | 60 | 85 |
| Ducksalad | 0 | 0 | 0 | 40 | 100 | 65 | 75 | 85 | 100 | 90 | 90 | 90 | 90 | 100 |
| Rice | 15 | 20 | 0 | 15 | 10 | 20 | 15 | 15 | 0 | 35 | 0 | 0 | 0 | 0 |
| Sedge, Umbrella | 0 | 50 | 0 | 0 | 0 | 0 | 0 | 0 | 0 | 0 | 0 | 0 | 0 | 0 |

| 500 g ai/ha | Compounds | | | | | | | |
|---|---|---|---|---|---|---|---|---|
| Flood | 701 | 702 | 703 | 704 | 705 | 706 | 711 | 712 |
| Barnyardgrass | 65 | 50 | 30 | 30 | 0 | 0 | 0 | 0 |
| Ducksalad | 100 | 100 | 98 | 85 | 0 | 0 | 60 | 0 |
| Rice | 0 | 20 | 0 | 0 | 0 | 15 | 0 | 0 |
| Sedge, Umbrella | 0 | 0 | 0 | 0 | 0 | 0 | 0 | 0 |

| 250 g ai/ha | Compounds | | | | | | | | | | | | |
|---|---|---|---|---|---|---|---|---|---|---|---|---|---|
| Flood | 352 | 353 | 354 | 360 | 361 | 362 | 368 | 369 | 370 | 371 | 372 | 373 | 374 | 375 |
| Barnyardgrass | 0 | 0 | 0 | 0 | 0 | 0 | 55 | 20 | 60 | 60 | 60 | 60 | 60 | 70 |
| Ducksalad | 0 | 0 | 0 | 0 | 0 | 0 | 100 | 100 | 100 | 100 | 100 | 100 | 95 | 100 |
| Rice | 0 | 0 | 20 | 0 | 0 | 0 | 15 | 0 | 0 | 20 | 35 | 20 | 30 | 30 |
| Sedge, Umbrella | 0 | 0 | 20 | 0 | 0 | 0 | 0 | 0 | 30 | 0 | 0 | 0 | 0 | 0 |

| 250 g ai/ha | Compounds | | | | | | | | | | | | |
|---|---|---|---|---|---|---|---|---|---|---|---|---|---|
| Flood | 376 | 377 | 378 | 379 | 380 | 381 | 382 | 383 | 391 | 392 | 393 | 394 | 396 | 397 |
| Barnyardgrass | 70 | 60 | 70 | 0 | 0 | 0 | 0 | 0 | 40 | 60 | 65 | 0 | 40 | 65 |
| Ducksalad | 100 | 100 | 30 | 0 | 0 | 0 | 0 | 30 | 100 | 90 | 90 | 40 | 40 | 75 |
| Rice | 0 | 25 | 0 | 0 | 0 | 0 | 0 | 0 | 20 | 0 | 0 | 30 | 0 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | |
|---|---|---|---|---|---|---|---|---|---|---|---|---|---|
| Flood | 398 | 399 | 400 | 401 | 402 | 403 | 404 | 405 | 406 | 429 | 430 | 431 | 432 | 433 |
| Barnyardgrass | 60 | 65 | 65 | 70 | 100 | 75 | 80 | 70 | 70 | 65 | 65 | 40 | 20 | 70 |
| Ducksalad | 80 | 100 | 100 | 100 | 90 | 100 | 100 | 85 | 80 | 100 | 100 | 100 | 0 | 98 |

TABLE B-continued

| | | | | | | | | | | | | | | |
|---|---|---|---|---|---|---|---|---|---|---|---|---|---|---|
| Rice | 20 | 0 | 20 | 25 | 0 | 0 | 30 | 0 | 0 | 15 | 20 | 25 | 15 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds |
|---|---|
| Flood | 434 435 436 437 438 439 440 441 442 443 444 445 446 447 |

| | | | | | | | | | | | | | | |
|---|---|---|---|---|---|---|---|---|---|---|---|---|---|---|
| Barnyardgrass | 70 | 60 | 60 | 65 | 85 | 40 | 70 | 70 | 75 | 70 | 75 | 70 | 75 | 40 |
| Ducksalad | 100 | 90 | 100 | 100 | 100 | 100 | 95 | 90 | 100 | 80 | 100 | 100 | 100 | 98 |
| Rice | 0 | 0 | 0 | 0 | 20 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds |
|---|---|
| Flood | 448 449 450 451 452 453 454 455 456 457 460 461 |

| | | | | | | | | | | | | |
|---|---|---|---|---|---|---|---|---|---|---|---|---|
| Barnyardgrass | 40 | 40 | 45 | 0 | 0 | 30 | 40 | 75 | 0 | 0 | 40 | 60 |
| Ducksalad | 95 | 98 | 75 | 0 | 100 | 95 | 60 | 100 | 0 | 0 | 100 | 100 |
| Rice | 0 | 0 | 0 | 0 | 0 | 0 | 15 | 0 | 0 | 0 | 0 | 0 |
| Sedge, Umbrella | 0 | 0 | 0 | 0 | 0 | 0 | 0 | 0 | 0 | 0 | 0 | 0 |

| 250 g ai/ha | Compounds |
|---|---|
| Flood | 462 463 464 465 466 467 468 469 470 471 472 473 474 475 |

| | | | | | | | | | | | | | | |
|---|---|---|---|---|---|---|---|---|---|---|---|---|---|---|
| Barnyardgrass | 40 | 25 | 70 | 80 | 0 | 20 | 35 | 40 | 0 | 0 | 60 | 40 | 30 | 20 |
| Ducksalad | 85 | 70 | 100 | 100 | 0 | 80 | 85 | 70 | 85 | 70 | 75 | 75 | 80 | 100 |
| Rice | 0 | 0 | 20 | 0 | 0 | 0 | 0 | 0 | 0 | 20 | 20 | 0 | 0 | 15 |
| Sedge, Umbrella | 0 | 0 | 0 | 0 | 0 | 0 | 0 | 0 | 0 | 0 | 0 | 0 | 0 | 0 |

| 250 g ai/ha | Compounds |
|---|---|
| Flood | 476 477 478 479 480 481 482 483 484 485 486 487 488 489 |

| | | | | | | | | | | | | | | |
|---|---|---|---|---|---|---|---|---|---|---|---|---|---|---|
| Barnyardgrass | 0 | 0 | 0 | 0 | 0 | 0 | 0 | 0 | 0 | 0 | 0 | 75 | 65 | 65 |
| Ducksalad | 80 | 0 | 0 | 20 | 0 | 0 | 0 | 30 | 0 | 40 | 0 | 95 | 90 | 100 |
| Rice | 0 | 0 | 0 | 0 | 0 | 0 | 0 | 0 | 0 | 0 | 0 | 0 | 30 | 20 |
| Sedge, Umbrella | 0 | 0 | 0 | 0 | 0 | 0 | 0 | 0 | 0 | 0 | 0 | 0 | 0 | 0 |

| 250 g ai/ha | Compounds |
|---|---|
| Flood | 490 491 492 493 494 495 496 497 498 499 500 501 502 503 |

| | | | | | | | | | | | | | | |
|---|---|---|---|---|---|---|---|---|---|---|---|---|---|---|
| Barnyardgrass | 50 | 0 | 65 | 60 | 20 | 35 | 60 | 70 | 45 | 50 | 0 | 20 | 0 | 45 |
| Ducksalad | 85 | 40 | 100 | 80 | 30 | 75 | 85 | 90 | 90 | 80 | 65 | 85 | 70 | 85 |
| Rice | 30 | 0 | 25 | 25 | 0 | 0 | 0 | 20 | 0 | 15 | 0 | 0 | 0 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds |
|---|---|
| Flood | 504 505 506 507 508 509 513 514 515 516 517 518 519 520 |

| | | | | | | | | | | | | | | |
|---|---|---|---|---|---|---|---|---|---|---|---|---|---|---|
| Barnyardgrass | 40 | 0 | 40 | 0 | 0 | 0 | 30 | 50 | 0 | 0 | 0 | 0 | 65 | 65 |
| Ducksalad | 80 | 0 | 75 | 75 | 50 | 50 | 90 | 100 | 0 | 0 | 0 | 65 | 85 | 100 |
| Rice | 0 | 0 | 0 | 0 | 0 | 0 | 30 | 20 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds |
|---|---|
| Flood | 521 522 523 539 540 541 544 545 546 547 549 |

| | | | | | | | | | | | |
|---|---|---|---|---|---|---|---|---|---|---|---|
| Barnyardgrass | 40 | 40 | 50 | 65 | 55 | 35 | 25 | 0 | 70 | 0 | 25 |
| Ducksalad | 85 | 100 | 50 | 95 | 75 | 75 | 45 | 0 | 85 | 0 | 90 |
| Rice | 0 | 0 | 0 | 0 | 0 | 0 | 0 | 0 | 20 | 0 | 0 |
| Sedge, Umbrella | 0 | 0 | 0 | 0 | 0 | 0 | 0 | 0 | 0 | 0 | 0 |

| 250 g ai/ha | Compounds |
|---|---|
| Flood | 550 551 552 553 554 587 588 589 590 591 592 593 594 595 |

| | | | | | | | | | | | | | | |
|---|---|---|---|---|---|---|---|---|---|---|---|---|---|---|
| Barnyardgrass | 55 | 20 | 60 | 65 | 55 | 55 | 30 | 60 | 60 | 65 | 55 | 60 | 70 | 50 |
| Ducksalad | 95 | 85 | 100 | 100 | 100 | 75 | 70 | 70 | 90 | 100 | 80 | 80 | 90 | 80 |
| Rice | 50 | 15 | 10 | 10 | 25 | 20 | 30 | 20 | 0 | 35 | 0 | 15 | 35 | 20 |
| Sedge, Umbrella | 0 | 0 | 0 | 0 | 0 | 0 | 0 | 0 | 0 | 0 | 0 | 0 | 0 | 70 |

TABLE B-continued

| 250 g ai/ha | Compounds | | | | | | | | | | | |
|---|---|---|---|---|---|---|---|---|---|---|---|---|
| Flood | 596 | 597 | 598 | 599 | 600 | 601 | 602 | 605 | 606 | 607 | 608 | 609 |
| Barnyardgrass | 95 | 0 | 0 | 0 | 0 | 40 | 0 | 0 | 50 | 0 | 0 | 45 |
| Ducksalad | 100 | 50 | 65 | 50 | 85 | 75 | 30 | 50 | 0 | 50 | 90 | 100 |
| Rice | 0 | 0 | 0 | 0 | 15 | 0 | 0 | 0 | 0 | 0 | 20 | 15 |
| Sedge, Umbrella | 0 | 0 | 0 | 0 | 0 | 0 | 0 | 0 | 40 | 0 | 0 | 0 |

| 250 g ai/ha | Compounds | | | | | | | | | | | |
|---|---|---|---|---|---|---|---|---|---|---|---|---|
| Flood | 610 | 611 | 612 | 613 | 614 | 616 | 617 | 618 | 619 | 620 | 621 | 622 | 623 |
| Barnyardgrass | 65 | 85 | 65 | 80 | 65 | 70 | 90 | 85 | 0 | 10 | 50 | 70 | 40 |
| Ducksalad | 100 | 100 | 100 | 98 | 100 | 100 | 100 | 100 | 0 | 65 | 100 | 100 | 50 |
| Rice | 0 | 40 | 15 | 10 | 10 | 10 | 10 | 10 | 0 | 0 | 20 | 0 | 0 |
| Sedge, Umbrella | 0 | 0 | 85 | 75 | 0 | 0 | 0 | 0 | 0 | 0 | 0 | 0 | 0 |

| 250 g ai/ha | Compounds | | | | | | | | | | | |
|---|---|---|---|---|---|---|---|---|---|---|---|---|
| Flood | 624 | 625 | 627 | 630 | 631 | 632 | 633 | 636 | 637 | 638 | 639 | 640 | 641 | 642 |
| Barnyardgrass | 70 | 40 | 0 | 20 | 0 | 80 | 90 | 70 | 80 | 85 | 80 | 30 | 70 | 30 |
| Ducksalad | 100 | 100 | 0 | 95 | 0 | 100 | 100 | 100 | 100 | 100 | 100 | 100 | 100 | 100 |
| Rice | 20 | 0 | 0 | 0 | 0 | 30 | 20 | 0 | 10 | 10 | 0 | 25 | 0 | 30 |
| Sedge, Umbrella | 0 | 0 | 0 | 0 | 0 | 50 | 0 | 0 | 0 | 0 | 0 | 0 | 0 | 0 |

| 250 g ai/ha | Compounds | | | | | | | | | | | |
|---|---|---|---|---|---|---|---|---|---|---|---|---|
| Flood | 643 | 644 | 645 | 646 | 647 | 648 | 649 | 650 | 651 | 652 | 653 | 654 | 655 | 656 |
| Barnyardgrass | 80 | 85 | 80 | 80 | 75 | 20 | 60 | 80 | 60 | 40 | 30 | 35 | 20 | 50 |
| Ducksalad | 100 | 98 | 100 | 98 | 90 | 100 | 100 | 100 | 100 | 65 | 40 | 90 | 100 | 100 |
| Rice | 15 | 15 | 0 | 25 | 40 | 20 | 0 | 0 | 0 | 0 | 0 | 0 | 30 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | |
|---|---|---|---|---|---|---|---|---|---|---|---|---|
| Flood | 657 | 658 | 659 | 660 | 661 | 662 | 663 | 664 | 665 | 666 | 667 | 668 |
| Barnyardgrass | 40 | 50 | 60 | 45 | 80 | 80 | 70 | 85 | 70 | 75 | 75 | 70 |
| Ducksalad | 100 | 100 | 80 | 60 | 100 | 95 | 98 | 100 | 90 | 85 | 90 | 98 |
| Rice | 0 | 0 | 15 | 15 | 10 | 20 | 0 | 0 | 25 | 0 | 10 | 0 |
| Sedge, Umbrella | 0 | 0 | 0 | 0 | 0 | 0 | 0 | 0 | 0 | 0 | 0 | 0 |

| 250 g ai/ha | Compounds | | | | | | | | | | | |
|---|---|---|---|---|---|---|---|---|---|---|---|---|
| Flood | 677 | 678 | 679 | 680 | 681 | 682 | 683 | 684 | 685 | 686 | 687 | 688 |
| Barnyardgrass | 30 | 40 | 30 | 20 | 35 | 0 | 35 | 0 | 30 | 35 | 35 | 35 |
| Ducksalad | 100 | 75 | 55 | 30 | 25 | 0 | 0 | 0 | 0 | 90 | 80 | 100 |
| Rice | 0 | 10 | 0 | 15 | 0 | 0 | 25 | 0 | 0 | 0 | 0 | 0 |
| Sedge, Umbrella | 0 | 0 | 0 | 0 | 0 | 0 | 0 | 0 | 0 | 0 | 0 | 0 |

| 250 g ai/ha | Compounds | | | | | | | | |
|---|---|---|---|---|---|---|---|---|---|
| Flood | 689 | 690 | 691 | 692 | 693 | 694 | 714 | 715 | 716 |
| Barnyardgrass | 40 | 50 | 70 | 0 | 75 | 0 | 0 | 0 | 0 |
| Ducksalad | 98 | 75 | 95 | 20 | 70 | 20 | 0 | 0 | 0 |
| Rice | 0 | 0 | 25 | 0 | 20 | 0 | 0 | 0 | 0 |
| Sedge, Umbrella | 0 | 0 | 0 | 0 | 0 | 0 | 0 | 0 | 0 |

| 125 g ai/ha Flood | Compound 445 |
|---|---|
| Barnyardgrass | 65 |
| Ducksalad | 95 |
| Rice | 0 |
| Sedge, Umbrella | 0 |

| 62 g ai/ha Flood | Compound 445 |
|---|---|
| Barnyardgrass | 60 |
| Ducksalad | 85 |
| Rice | 0 |
| Sedge, Umbrella | 0 |

TABLE B-continued

|  | 31 g ai/ha Flood | | | | | | | Compound 445 | | | | | | |
|---|---|---|---|---|---|---|---|---|---|---|---|---|---|---|
| Barnyardgrass | | | | | | | | 35 | | | | | | |
| Ducksalad | | | | | | | | 70 | | | | | | |
| Rice | | | | | | | | 0 | | | | | | |
| Sedge, Umbrella | | | | | | | | 0 | | | | | | |

| 250 g ai/ha | Compounds | | | | | | | | | | | | | |
|---|---|---|---|---|---|---|---|---|---|---|---|---|---|---|
| Flood | 717 | 718 | 719 | 720 | 721 | 722 | 723 | 724 | 725 | 726 | 727 | 728 | 729 | 730 |
| Barnyardgrass | 60 | 40 | 85 | 30 | 0 | 0 | 0 | 0 | 0 | 55 | 0 | 0 | 60 | 75 |
| Ducksalad | 100 | 100 | 100 | 100 | 100 | 0 | 0 | 0 | 100 | 100 | 75 | 85 | 100 | 95 |
| Rice | 0 | 0 | 0 | 0 | 0 | 0 | 0 | 0 | 0 | 0 | 25 | 0 | 0 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| Flood | 731 | 732 | 733 | 734 | 735 | 736 | 737 | 738 | 739 | 740 | 741 | 742 | 743 | 744 |
| Barnyardgrass | 60 | 45 | 20 | 60 | 60 | 40 | 0 | 40 | 60 | 60 | 0 | 60 | 65 | 60 |
| Ducksalad | 100 | 100 | 60 | 100 | 40 | 40 | 0 | 100 | 100 | 100 | 90 | 100 | 95 | 85 |
| Rice | 20 | 0 | 0 | 0 | 0 | 0 | 0 | 0 | 0 | 50 | 0 | 0 | 20 | 0 |
| Sedge, Umbrella | 0 | 0 | 0 | 0 | 0 | 0 | 0 | 0 | 0 | 0 | 40 | 0 | 0 | 0 |

| 250 g ai/ha | Compounds | | | | | | | | | | | | | |
|---|---|---|---|---|---|---|---|---|---|---|---|---|---|---|
| Flood | 745 | 746 | 747 | 748 | 749 | 750 | 751 | 752 | 753 | 754 | 755 | 756 | 757 | 758 |
| Barnyardgrass | 70 | 0 | 0 | 0 | 0 | 0 | 40 | 0 | 0 | 0 | 0 | 50 | 75 | 45 |
| Ducksalad | 100 | 95 | 90 | 75 | 20 | 90 | 100 | 0 | 60 | 40 | 0 | 100 | 100 | 100 |
| Rice | 40 | 0 | 15 | 25 | 0 | 0 | 30 | 0 | 0 | 0 | 0 | 0 | 80 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| Flood | 759 | 760 | 761 | 762 | 763 | 764 | 765 | 766 | 767 | 768 | 769 | 770 | 771 | 772 |
| Barnyardgrass | 0 | 50 | 0 | 0 | 0 | 50 | 40 | 0 | 0 | 60 | 0 | 0 | 90 | 0 |
| Ducksalad | 0 | 80 | 95 | 98 | 60 | 90 | 100 | 85 | 100 | 85 | 80 | 0 | 100 | 75 |
| Rice | 0 | 0 | 0 | 0 | 0 | 0 | 20 | 0 | 0 | 15 | 15 | 0 | 20 | 0 |
| Sedge, Umbrella | 0 | 0 | 0 | 0 | 0 | 0 | 0 | 60 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| Flood | 773 | 774 | 775 | 776 | 777 | 778 | 779 | 780 | 781 | 782 | 783 | 785 | 786 | 787 |
| Barnyardgrass | 0 | 0 | 35 | 80 | 30 | 0 | 60 | 20 | 65 | 65 | 0 | 40 | 0 | 0 |
| Ducksalad | 0 | 0 | 75 | 80 | 0 | 100 | 100 | 90 | 100 | 100 | 0 | 90 | 70 | 50 |
| Rice | 0 | 0 | 0 | 0 | 20 | 0 | 0 | 0 | 0 | 0 | 0 | 0 | 0 | 0 |
| Sedge, Umbrella | 0 | 0 | 65 | 0 | 0 | 0 | 0 | 0 | 0 | 0 | 0 | 0 | 40 | 0 |

| 250 g ai/ha | Compounds | | | | | | | | | | | | | |
|---|---|---|---|---|---|---|---|---|---|---|---|---|---|---|
| Flood | 788 | 789 | 790 | 791 | 792 | 793 | 794 | 795 | 796 | 797 | 798 | 799 | 800 | 801 |
| Barnyardgrass | 20 | 20 | 40 | 0 | 0 | 0 | 40 | 0 | 70 | 90 | 75 | 65 | 95 | 90 |
| Ducksalad | 60 | 100 | 100 | 100 | 0 | 25 | 30 | 70 | 90 | 90 | 50 | 80 | 95 | 90 |
| Rice | 0 | 0 | 0 | 0 | 0 | 0 | 20 | 0 | 40 | 25 | 40 | 30 | 30 | 30 |
| Sedge, Umbrella | 0 | 0 | 0 | 0 | 0 | 25 | 0 | 0 | 0 | 0 | 0 | 0 | 0 | 40 |

| 250 g ai/ha | Compounds | | | | | | | | | | | | | |
|---|---|---|---|---|---|---|---|---|---|---|---|---|---|---|
| Flood | 802 | 803 | 804 | 805 | 806 | 807 | 808 | 809 | 810 | 811 | 812 | 813 | 814 | 815 |
| Barnyardgrass | 90 | 90 | 30 | 0 | 0 | 95 | 70 | 0 | 60 | 20 | 85 | 70 | 0 | 65 |
| Ducksalad | 100 | 100 | 80 | 0 | 75 | 100 | 100 | 0 | 90 | 40 | 90 | 100 | 50 | 75 |
| Rice | 20 | 55 | 60 | 0 | 0 | 0 | 15 | 0 | 0 | 0 | 0 | 20 | 0 | 20 |
| Sedge, Umbrella | 0 | 0 | 0 | 0 | 0 | 0 | 0 | 0 | 0 | 40 | 0 | 0 | 60 | 0 |

| 250 g ai/ha | Compounds | | | | | | | | | | | | | |
|---|---|---|---|---|---|---|---|---|---|---|---|---|---|---|
| Flood | 816 | 817 | 818 | 819 | 820 | 821 | 822 | 823 | 824 | 825 | 826 | 827 | 828 | 829 |
| Barnyardgrass | 55 | 60 | 55 | 65 | 60 | 60 | 75 | 40 | 65 | 0 | 65 | 30 | 0 | 55 |
| Ducksalad | 75 | 90 | 80 | 100 | 75 | 80 | 85 | 90 | 95 | 80 | 100 | 75 | 30 | 70 |
| Rice | 30 | 0 | 0 | 0 | 0 | 0 | 0 | 0 | 0 | 25 | 0 | 0 | 0 | 0 |
| Sedge, Umbrella | 0 | 0 | 0 | 0 | 0 | 0 | 0 | 0 | 0 | 0 | 0 | 0 | 0 | 0 |

TABLE B-continued

| 250 g ai/ha | Compounds | | | | | | | | | | | | | |
|---|---|---|---|---|---|---|---|---|---|---|---|---|---|---|
| Flood | 830 | 831 | 832 | 833 | 834 | 835 | 836 | 837 | 838 | 839 | 840 | 841 | 842 | 843 |
| Barnyardgrass | 20 | 0 | 0 | 45 | 60 | 50 | 65 | 0 | 40 | 0 | 0 | 40 | 65 | 0 |
| Ducksalad | 100 | 70 | 100 | 85 | 65 | 70 | 95 | 70 | 100 | 70 | 80 | 80 | 100 | 20 |
| Rice | 0 | 0 | 15 | 0 | 0 | 20 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | |
|---|---|---|---|---|---|---|---|---|---|---|---|---|---|
| Flood | 844 | 845 | 846 | 847 | 848 | 849 | 850 | 851 | 852 | 853 | 854 | 855 | 856 | 857 |
| Barnyardgrass | 0 | 30 | 60 | 0 | 60 | 75 | 70 | 0 | 40 | 70 | 0 | 70 | 50 | 60 |
| Ducksalad | 0 | 0 | 60 | 90 | 100 | 100 | 90 | 90 | 40 | 40 | 0 | 75 | 75 | 80 |
| Rice | 0 | 20 | 0 | 0 | 0 | 15 | 0 | 0 | 0 | 20 | 0 | 0 | 0 | 0 |
| Sedge, Umbrella | 0 | 0 | 0 | 0 | 0 | 0 | 0 | 0 | 0 | 0 | 0 | 0 | 0 | 80 |

| 250 g ai/ha | Compounds | | | | | | | | | | | | |
|---|---|---|---|---|---|---|---|---|---|---|---|---|---|
| Flood | 858 | 859 | 860 | 861 | 862 | 863 | 864 | 865 | 866 | 867 | 868 | 869 | 870 | 871 |
| Barnyardgrass | 45 | 65 | 0 | 70 | 0 | 0 | 50 | 0 | 35 | 65 | 0 | 0 | 0 | 0 |
| Ducksalad | 100 | 100 | 90 | 100 | 90 | 0 | 90 | 60 | 90 | 100 | 0 | 60 | 0 | 0 |
| Rice | 0 | 0 | 0 | 50 | 0 | 0 | 40 | 30 | 35 | 30 | 0 | 0 | 0 | 0 |
| Sedge, Umbrella | 0 | 0 | 0 | 0 | 0 | 0 | 50 | 30 | 35 | 30 | 0 | 0 | 0 | 0 |

| 250 g ai/ha | Compounds | | | | | | | | | | | | |
|---|---|---|---|---|---|---|---|---|---|---|---|---|---|
| Flood | 872 | 873 | 874 | 875 | 876 | 877 | 878 | 879 | 880 | 881 | 882 | 883 | 885 | 886 |
| Barnyardgrass | 0 | 85 | 65 | 70 | 0 | 55 | 85 | 90 | 60 | 45 | 45 | 0 | 0 | 75 |
| Ducksalad | 85 | 100 | 100 | 100 | 85 | 100 | 100 | 100 | 100 | 100 | 100 | 80 | 60 | 50 |
| Rice | 0 | 0 | 0 | 0 | 0 | 0 | 0 | 0 | 0 | 15 | 0 | 20 | 0 | 0 |
| Sedge, Umbrella | 40 | 50 | 0 | 0 | 0 | 0 | 0 | 50 | 0 | 0 | 0 | 0 | 0 | 0 |

| 250 g ai/ha | Compounds | | | | | | | | | | | | |
|---|---|---|---|---|---|---|---|---|---|---|---|---|---|
| Flood | 887 | 888 | 889 | 890 | 891 | 892 | 893 | 894 | 895 | 896 | 897 | 898 | 899 | 900 |
| Barnyardgrass | 50 | 70 | 60 | 60 | 0 | 65 | 90 | 70 | 75 | 45 | 45 | 55 | 55 | 70 |
| Ducksalad | 65 | 75 | 75 | 90 | 100 | 80 | 90 | 100 | 85 | 25 | 45 | 70 | 10 | 40 |
| Rice | 0 | 0 | 0 | 0 | 20 | 0 | 10 | 0 | 0 | 20 | 0 | 0 | 0 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | |
|---|---|---|---|---|---|---|---|---|---|---|---|---|---|
| Flood | 901 | 902 | 903 | 904 | 905 | 906 | 907 | 908 | 909 | 910 | 911 | 912 | 913 | 914 |
| Barnyardgrass | 60 | 0 | 0 | 0 | 0 | 0 | 0 | 0 | 40 | 70 | 80 | 50 | 0 | 0 |
| Ducksalad | 60 | 75 | 0 | 0 | 0 | 0 | 50 | 0 | 70 | 85 | 75 | 50 | 90 | 50 |
| Rice | 0 | 0 | 0 | 0 | 0 | 0 | 0 | 0 | 0 | 0 | 0 | 0 | 0 | 15 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | |
|---|---|---|---|---|---|---|---|---|---|---|---|---|---|
| Flood | 915 | 916 | 917 | 918 | 919 | 920 | 921 | 922 | 923 | 924 | 925 | 926 | 927 | 928 |
| Barnyardgrass | 40 | 0 | 0 | 0 | 0 | 0 | 85 | 0 | 0 | 50 | 0 | 0 | 0 | 55 |
| Ducksalad | 100 | 100 | 40 | 30 | 0 | 0 | 90 | 0 | 0 | 70 | 0 | 0 | 0 | 80 |
| Rice | 20 | 0 | 0 | 15 | 0 | 0 | 20 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | |
|---|---|---|---|---|---|---|---|---|---|---|---|---|---|
| Flood | 929 | 930 | 931 | 932 | 933 | 934 | 935 | 936 | 937 | 938 | 939 | 940 | 941 | 942 |
| Barnyardgrass | 40 | 50 | 65 | 0 | 60 | 0 | 0 | 0 | 0 | 40 | 0 | 0 | 0 | 0 |
| Ducksalad | 60 | 80 | 60 | 30 | 60 | 60 | 70 | 85 | 45 | 60 | 40 | 0 | 35 | 40 |
| Rice | 0 | 0 | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | |
|---|---|---|---|---|---|---|---|---|---|---|---|---|---|
| Flood | 943 | 944 | 945 | 946 | 947 | 948 | 949 | 950 | 951 | 952 | 953 | 954 | 955 | 956 |
| Barnyardgrass | 0 | 40 | 0 | 0 | 0 | 0 | 30 | 65 | 30 | 0 | 20 | 0 | 70 | 70 |
| Ducksalad | 50 | 75 | 85 | 0 | 65 | 0 | 100 | 95 | 90 | 40 | 40 | 35 | 90 | 100 |

TABLE B-continued

| | | | | | | | | | | | | | | |
|---|---|---|---|---|---|---|---|---|---|---|---|---|---|---|
| Rice | 0 | 0 | 0 | 0 | 0 | 0 | 15 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| Flood | 957 | 958 | 959 | 960 | 961 | 962 | 963 | 964 | 965 | 966 | 967 | 968 | 969 | 970 |
| Barnyardgrass | 30 | 55 | 60 | 20 | 40 | 60 | 65 | 0 | 20 | 0 | 0 | 0 | 0 | 0 |
| Ducksalad | 100 | 100 | 100 | 100 | 100 | 90 | 90 | 75 | 85 | 60 | 35 | 30 | 0 | 0 |
| Rice | 0 | 15 | 20 | 0 | 20 | 10 | 0 | 15 | 0 | 0 | 0 | 0 | 0 | 0 |
| Sedge, Umbrella | 0 | 0 | 0 | 65 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| Flood | 971 | 972 | 973 | 974 | 975 | 976 | 977 | 978 | 979 | 980 | 981 | 982 | 983 | 984 |
| Barnyardgrass | 60 | 80 | 0 | 60 | 40 | 65 | 15 | 65 | 60 | 60 | 0 | 75 | 30 | 55 |
| Ducksalad | 85 | 85 | 100 | 100 | 90 | 95 | 100 | 100 | 100 | 0 | 0 | 100 | 100 | 85 |
| Rice | 45 | 50 | 0 | 15 | 0 | 20 | 15 | 30 | 0 | 30 | 0 | 20 | 0 | 15 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| Flood | 985 | 986 | 987 | 988 | 989 | 990 | 991 | 992 | 993 | 994 | 995 | 996 | 997 | 998 |
| Barnyardgrass | 0 | 55 | 90 | 75 | 15 | 50 | 0 | 0 | 70 | 75 | 25 | 0 | 0 | 0 |
| Ducksalad | 40 | 75 | 75 | 100 | 100 | 100 | 40 | 0 | 85 | 100 | 70 | 70 | 0 | 0 |
| Rice | 0 | 20 | 35 | 20 | 0 | 55 | 15 | 0 | 40 | 20 | 0 | 0 | 0 | 0 |
| Sedge, Umbrella | 0 | 0 | 0 | 0 | 0 | 0 | 0 | 0 | 60 | 0 | 30 | 0 | 0 | 0 |

| 250 g ai/ha | Compounds | | | | | | | | | | | | | |
|---|---|---|---|---|---|---|---|---|---|---|---|---|---|---|
| Flood | 999 | 1000 | 1001 | 1002 | 1003 | 1004 | 1005 | 1006 | 1007 | 1008 | 1009 | 1010 | 1011 | 1012 |
| Barnyardgrass | 0 | 0 | 0 | 0 | 0 | 0 | 0 | 0 | 0 | 0 | 0 | 0 | 0 | 0 |
| Ducksalad | 85 | 90 | 0 | 60 | 0 | 60 | 0 | 0 | 0 | 95 | 0 | 0 | 0 | 0 |
| Rice | 0 | 0 | 0 | 0 | 0 | 0 | 0 | 0 | 0 | 0 | 0 | 0 | 0 | 20 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| Flood | 1013 | 1014 | 1015 | 1016 | 1017 | 1018 | 1019 | 1020 | 1021 | 1022 | 1023 | 1024 | 1025 | 1026 |
| Barnyardgrass | 55 | 100 | 95 | 0 | 70 | 65 | 0 | 75 | 80 | 0 | 40 | 40 | 0 | 0 |
| Ducksalad | 100 | 85 | 90 | 0 | 90 | 90 | 0 | 90 | 98 | 75 | 65 | 70 | 0 | 100 |
| Rice | 70 | 70 | 40 | 30 | 30 | 0 | 0 | 20 | 15 | 0 | 20 | 0 | 0 | 20 |
| Sedge, Umbrella | 100 | 0 | 35 | 0 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| Flood | 1027 | 1028 | 1029 | 1030 | 1031 | 1032 | 1033 | 1034 | 1035 | 1037 | 1038 | 1039 | 1040 | 1041 |
| Barnyardgrass | 40 | 20 | 0 | 30 | 0 | 0 | 50 | 60 | 50 | 25 | 65 | 65 | 60 | 0 |
| Ducksalad | 100 | 80 | 85 | 70 | 0 | 20 | 100 | 100 | 100 | 100 | 100 | 90 | 75 | 100 |
| Rice | 30 | 10 | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| Flood | 1042 | 1043 | 1044 | 1045 | 1046 | 1047 | 1048 | 1049 | 1050 | 1051 | 1052 | 1053 | 1054 | 1055 |
| Barnyardgrass | 30 | 0 | 0 | 75 | 60 | 0 | 30 | 20 | 0 | 0 | 85 | 0 | 0 | 0 |
| Ducksalad | 75 | 90 | 0 | 100 | 100 | 0 | 50 | 70 | 85 | 75 | 100 | 0 | 0 | 30 |
| Rice | 0 | 0 | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| Flood | 1056 | 1057 | 1058 | 1059 | 1060 | 1061 | 1065 | 1066 | 1067 | 1068 | 1069 | 1070 | 1071 | 1072 |
| Barnyardgrass | 0 | 30 | 35 | 0 | 75 | 60 | 0 | 45 | 20 | 0 | 20 | 0 | 40 | 70 |
| Ducksalad | 0 | 85 | 0 | 0 | 90 | 95 | 100 | 75 | 85 | 90 | 35 | 80 | 98 | 80 |
| Rice | 20 | 0 | 25 | 0 | 20 | 15 | 0 | 0 | 0 | 0 | 0 | 0 | 0 | 15 |
| Sedge, Umbrella | 0 | 0 | 0 | 0 | 0 | 0 | 0 | 0 | 0 | 0 | 0 | 0 | 0 | 0 |

TABLE B-continued

| 250 g ai/ha | Compounds | | | | | | | | | | | | | |
|---|---|---|---|---|---|---|---|---|---|---|---|---|---|
| Flood | 1073 | 1074 | 1075 | 1076 | 1077 | 1078 | 1079 | 1080 | 1081 | 1082 | 1083 | 1084 | 1085 | 1086 |
| Barnyardgrass | 55 | 75 | 75 | 20 | 85 | 30 | 60 | 50 | 90 | 0 | 90 | 75 | 60 | 45 |
| Ducksalad | 100 | 100 | 100 | 90 | 90 | 0 | 30 | 40 | 80 | 70 | 95 | 100 | 30 | 40 |
| Rice | 15 | 35 | 35 | 40 | 15 | 0 | 20 | 15 | 40 | 35 | 40 | 20 | 25 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|
| Flood | 1087 | 1088 | 1089 | 1090 | 1091 | 1092 | 1093 | 1094 | 1095 | 1096 | 1097 | 1098 | 1099 | 1100 |
| Barnyardgrass | 70 | 30 | 90 | 80 | 0 | 60 | 60 | 45 | 0 | 0 | 0 | 0 | 0 | 0 |
| Ducksalad | 30 | 75 | 85 | 95 | 0 | 85 | 80 | 0 | 50 | 65 | 0 | 90 | 100 | 75 |
| Rice | 25 | 0 | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|
| Flood | 1101 | 1102 | 1103 | 1104 | 1105 | 1106 | 1107 | 1108 | 1109 | 1110 | 1111 | 1112 | 1113 | 1114 |
| Barnyardgrass | 30 | 60 | 75 | 40 | 50 | 70 | 0 | 40 | 85 | 90 | 20 | 0 | 0 | 45 |
| Ducksalad | 60 | 85 | 90 | 100 | 100 | 100 | 80 | 85 | 90 | 100 | 70 | 0 | 30 | 85 |
| Rice | 0 | 0 | 25 | 20 | 20 | 40 | 0 | 20 | 50 | 50 | 0 | 15 | 20 | 0 |
| Sedge, Umbrella | 0 | 0 | 0 | 0 | 0 | 0 | 0 | 75 | 0 | 0 | 0 | 40 | 0 | 0 |

| 250 g ai/ha | Compounds | | | | | | | | | | | | | |
|---|---|---|---|---|---|---|---|---|---|---|---|---|---|
| Flood | 1115 | 1116 | 1117 | 1118 | 1119 | 1120 | 1121 | 1122 | 1123 | 1124 | 1125 | 1126 | 1127 | 1129 |
| Barnyardgrass | 45 | 50 | 60 | 65 | 60 | 65 | 70 | 70 | 70 | 0 | 70 | 75 | 0 | 20 |
| Ducksalad | 90 | 100 | 100 | 100 | 100 | 100 | 100 | 100 | 100 | 95 | 100 | 100 | 100 | 70 |
| Rice | 30 | 20 | 20 | 40 | 20 | 20 | 10 | 25 | 25 | 0 | 0 | 0 | 0 | 0 |
| Sedge, Umbrella | 0 | 75 | 0 | 0 | 50 | 0 | 0 | 30 | 0 | 0 | 0 | 0 | 0 | 0 |

| 250 g ai/ha | Compounds | | | | | | | | | | | | | |
|---|---|---|---|---|---|---|---|---|---|---|---|---|---|
| Flood | 1130 | 1131 | 1132 | 1133 | 1134 | 1135 | 1136 | 1137 | 1138 | 1139 | 1140 | 1141 | 1142 | 1143 |
| Barnyardgrass | 0 | 60 | 60 | 50 | 0 | 0 | 0 | 0 | 60 | 0 | 75 | 50 | 0 | 0 |
| Ducksalad | 0 | 70 | 90 | 85 | 0 | 40 | 85 | 0 | 75 | 30 | 100 | 90 | 0 | 0 |
| Rice | 0 | 30 | 15 | 0 | 0 | 0 | 0 | 0 | 0 | 20 | 0 | 0 | 0 | 0 |
| Sedge, Umbrella | 0 | 0 | 40 | 0 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|
| Flood | 1144 | 1145 | 1146 | 1147 | 1148 | 1149 | 1150 | 1151 | 1152 | 1153 | 1154 | 1155 | 1156 | 1157 |
| Barnyardgrass | 85 | 75 | 45 | 0 | 50 | 45 | 0 | 0 | 0 | 30 | 30 | 50 | 40 | 55 |
| Ducksalad | 100 | 60 | 0 | 0 | 70 | 75 | 0 | 0 | 0 | 70 | 100 | 100 | 100 | 98 |
| Rice | 20 | 30 | 0 | 15 | 60 | 30 | 0 | 0 | 0 | 0 | 30 | 20 | 20 | 0 |
| Sedge, Umbrella | 0 | 40 | 50 | 0 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|
| Flood | 1158 | 1159 | 1160 | 1161 | 1162 | 1163 | 1164 | 1165 | 1166 | 1167 | 1168 | 1169 | 1170 | 1171 |
| Barnyardgrass | 60 | 0 | 0 | 0 | 35 | 30 | 40 | 95 | 40 | 0 | 40 | 0 | 30 | 30 |
| Ducksalad | 80 | 70 | 80 | 0 | 80 | 95 | 95 | 90 | 30 | 0 | 0 | 0 | 40 | 0 |
| Rice | 0 | 0 | 20 | 15 | 15 | 0 | 0 | 45 | 25 | 0 | 30 | 0 | 0 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|
| Flood | 1172 | 1173 | 1174 | 1175 | 1176 | 1177 | 1178 | 1179 | 1180 | 1181 | 1182 | 1183 | 1184 | 1185 |
| Barnyardgrass | 0 | 60 | 70 | 65 | 95 | 70 | 20 | 0 | 0 | 0 | 0 | 95 | 90 | 60 |
| Ducksalad | 0 | 90 | 90 | 90 | 95 | 95 | 90 | 40 | 85 | 35 | 0 | 95 | 95 | 50 |
| Rice | 0 | 25 | 20 | 10 | 0 | 20 | 20 | 0 | 0 | 0 | 0 | 10 | 15 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|
| Flood | 1186 | 1187 | 1188 | 1189 | 1190 | 1191 | 1192 | 1193 | 1194 | 1195 | 1196 | 1197 | 1198 | 1199 |
| Barnyardgrass | 75 | 60 | 65 | 75 | 55 | 0 | 100 | 75 | 0 | 20 | 0 | 70 | 20 | 40 |
| Ducksalad | 60 | 85 | 100 | 100 | 90 | 90 | 95 | 90 | 0 | 0 | 30 | 100 | 40 | 95 |

TABLE B-continued

| | | | | | | | | | | | | | |
|---|---|---|---|---|---|---|---|---|---|---|---|---|---|
| Rice | 30 | 0 | 15 | 15 | 40 | 10 | 30 | 30 | 0 | 20 | 0 | 0 | 0 | 0 |
| Sedge, Umbrella | 0 | 0 | 0 | 0 | 0 | 0 | 30 | 0 | 0 | 0 | 0 | 0 | 30 | 0 |

| 250 g ai/ha | Compounds | | | | | | | | | | | | |
|---|---|---|---|---|---|---|---|---|---|---|---|---|---|
| Flood | 1200 | 1201 | 1202 | 1203 | 1204 | 1205 | 1206 | 1207 | 1208 | 1209 | 1210 | 1211 | 1212 | 1213 |
| Barnyardgrass | 0 | 0 | 0 | 30 | 70 | 40 | 0 | 0 | 45 | 0 | 50 | 85 | 0 | 70 |
| Ducksalad | 0 | 50 | 100 | 100 | 100 | 100 | 95 | 100 | 95 | 50 | 30 | 100 | 95 | 100 |
| Rice | 0 | 0 | 0 | 0 | 0 | 20 | 15 | 0 | 15 | 0 | 20 | 60 | 0 | 20 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | |
|---|---|---|---|---|---|---|---|---|---|---|---|---|---|
| Flood | 1214 | 1215 | 1216 | 1217 | 1218 | 1219 | 1220 | 1221 | 1222 | 1223 | 1224 | 1225 | 1226 | 1227 |
| Barnyardgrass | 70 | 0 | 0 | 0 | 0 | 0 | 70 | 85 | 0 | 80 | 0 | 80 | 60 | 0 |
| Ducksalad | 100 | 70 | 0 | 40 | 40 | 60 | 95 | 100 | 65 | 90 | 70 | 100 | 100 | 80 |
| Rice | 15 | 0 | 0 | 25 | 0 | 0 | 10 | 0 | 15 | 30 | 0 | 20 | 20 | 15 |
| Sedge, Umbrella | 60 | 0 | 0 | 0 | 0 | 40 | 0 | 0 | 70 | 0 | 0 | 0 | 0 | 0 |

| 250 g ai/ha | Compounds | | | | | | | | | | | | |
|---|---|---|---|---|---|---|---|---|---|---|---|---|---|
| Flood | 1228 | 1229 | 1230 | 1231 | 1232 | 1233 | 1234 | 1235 | 1236 | 1237 | 1238 | 1239 | 1240 | 1241 |
| Barnyardgrass | 50 | 50 | 25 | 85 | 55 | 80 | 90 | 100 | 65 | 0 | 0 | 40 | 0 | 0 |
| Ducksalad | 100 | 90 | 70 | 100 | 95 | 100 | 100 | 90 | 100 | 65 | 0 | 100 | 0 | 0 |
| Rice | 30 | 0 | 0 | 0 | 0 | 15 | 75 | 80 | 35 | 0 | 0 | 20 | 0 | 0 |
| Sedge, Umbrella | 0 | 0 | 0 | 0 | 0 | 0 | 0 | 75 | 0 | 0 | 0 | 0 | 0 | 0 |

| 250 g ai/ha | Compounds | | | | | | | | | | | | |
|---|---|---|---|---|---|---|---|---|---|---|---|---|---|
| Flood | 1242 | 1243 | 1244 | 1245 | 1246 | 1247 | 1248 | 1249 | 1250 | 1251 | 1252 | 1253 | 1254 | 1255 |
| Barnyardgrass | 0 | 0 | 20 | 0 | 0 | 20 | 15 | 60 | 50 | 0 | 65 | 40 | 60 | 65 |
| Ducksalad | 75 | 0 | 30 | 90 | 100 | 55 | 70 | 100 | 100 | 90 | 100 | 100 | 100 | 100 |
| Rice | 0 | 0 | 0 | 0 | 0 | 0 | 0 | 0 | 0 | 0 | 0 | 30 | 0 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | |
|---|---|---|---|---|---|---|---|---|---|---|---|---|---|
| Flood | 1256 | 1257 | 1258 | 1259 | 1260 | 1261 | 1262 | 1263 | 1264 | 1265 | 1266 | 1267 | 1268 | 1269 |
| Barnyardgrass | 0 | 20 | 40 | 0 | 80 | 75 | 65 | 0 | 0 | 60 | 60 | 90 | 85 | 60 |
| Ducksalad | 50 | 0 | 0 | 0 | 100 | 100 | 100 | 30 | 0 | 90 | 100 | 90 | 95 | 90 |
| Rice | 0 | 0 | 0 | 0 | 50 | 50 | 10 | 0 | 0 | 45 | 50 | 0 | 20 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | |
|---|---|---|---|---|---|---|---|---|---|---|---|---|---|
| Flood | 1270 | 1271 | 1272 | 1273 | 1274 | 1275 | 1276 | 1277 | 1278 | 1279 | 1280 | 1281 | 1282 | 1283 |
| Barnyardgrass | 60 | 40 | 50 | 30 | 20 | 75 | 65 | 40 | 60 | 40 | 0 | 0 | 90 | 0 |
| Ducksalad | 80 | 90 | 80 | 90 | 100 | 90 | 90 | 60 | 90 | 100 | 0 | 50 | 100 | 0 |
| Rice | 15 | 0 | 20 | 0 | 0 | 20 | 25 | 25 | 35 | 30 | 0 | 0 | 30 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | |
|---|---|---|---|---|---|---|---|---|---|---|---|---|---|
| Flood | 1284 | 1285 | 1286 | 1287 | 1288 | 1289 | 1290 | 1291 | 1292 | 1293 | 1294 | 1295 | 1296 | 1297 |
| Barnyardgrass | 0 | 60 | 70 | 75 | 0 | 0 | 0 | 90 | 0 | 0 | 0 | 0 | 15 | 0 |
| Ducksalad | 0 | 90 | 95 | 80 | 0 | 0 | 0 | 100 | 0 | 0 | 0 | 0 | 0 | 0 |
| Rice | 0 | 25 | 0 | 15 | 0 | 0 | 10 | 30 | 15 | 0 | 0 | 0 | 30 | 30 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | |
|---|---|---|---|---|---|---|---|---|---|---|---|---|---|
| Flood | 1298 | 1299 | 1300 | 1301 | 1302 | 1303 | 1304 | 1305 | 1306 | 1307 | 1308 | 1309 | 1310 | 1311 |
| Barnyardgrass | 50 | 65 | 65 | 0 | 20 | 0 | 0 | 20 | 20 | 30 | 65 | 60 | 30 | 80 |
| Ducksalad | 80 | 85 | 80 | 20 | 80 | 0 | 0 | 70 | 100 | 100 | 100 | 100 | 80 | 100 |
| Rice | 15 | 20 | 25 | 0 | 15 | 0 | 0 | 0 | 0 | 20 | 40 | 20 | 15 | 0 |
| Sedge, Umbrella | 0 | 40 | 0 | 0 | 0 | 0 | 0 | 0 | 0 | 0 | 0 | 0 | 0 | 0 |

TABLE B-continued

| 250 g ai/ha | Compounds | | | | | | | | | | | | | |
|---|---|---|---|---|---|---|---|---|---|---|---|---|---|---|
| Flood | 1312 | 1313 | 1314 | 1316 | 1317 | 1318 | 1319 | 1320 | 1321 | 1323 | 1324 | 1325 | 1326 | 1327 |
| Barnyardgrass | 40 | 25 | 65 | 75 | 85 | 65 | 90 | 0 | 90 | 90 | 75 | 15 | 0 | 30 |
| Ducksalad | 100 | 70 | 100 | 90 | 100 | 85 | 90 | 50 | 85 | 85 | 65 | 100 | 70 | 100 |
| Rice | 0 | 0 | 0 | 0 | 0 | 0 | 0 | 0 | 0 | 10 | 0 | 0 | 0 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| Flood | 1328 | 1329 | 1330 | 1331 | 1332 | 1333 | 1334 | 1335 | 1336 | 1337 | 1338 | 1339 | 1340 | 1341 |
| Barnyardgrass | 0 | 60 | 85 | 70 | 0 | 45 | 0 | 0 | 0 | 20 | 90 | 95 | 40 | 30 |
| Ducksalad | 50 | 70 | 90 | 20 | 100 | 80 | 90 | 0 | 40 | 20 | 100 | 100 | 80 | 90 |
| Rice | 0 | 0 | 0 | 0 | 0 | 20 | 0 | 0 | 0 | 20 | 25 | 60 | 20 | 0 |
| Sedge, Umbrella | 0 | 0 | 0 | 0 | 0 | 70 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| Flood | 1342 | 1343 | 1344 | 1345 | 1346 | 1347 | 1348 | 1349 | 1350 | 1351 | 1352 | 1353 | 1354 | 1358 |
| Barnyardgrass | 50 | 95 | 0 | 90 | 90 | 90 | 90 | 90 | 90 | 0 | 60 | 60 | 0 | 0 |
| Ducksalad | 85 | 98 | 0 | 95 | 90 | 98 | 98 | 95 | 90 | 40 | 70 | 40 | 0 | 0 |
| Rice | 0 | 0 | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | | | | | | | | | | |
|---|---|---|---|---|---|---|---|---|---|---|---|---|---|---|
| Flood | 1366 | 1370 | 1371 | 1372 | 1373 | 1374 | 1375 | 1376 | 1377 | 1378 | 1379 | 1380 | 1381 | 1382 |
| Barnyardgrass | 40 | 60 | 60 | 80 | 85 | 0 | 70 | 40 | 60 | 85 | 55 | 60 | 65 | 30 |
| Ducksalad | 80 | 70 | 100 | 85 | 100 | 0 | 95 | 70 | 90 | 95 | 100 | 100 | 100 | 90 |
| Rice | 0 | 20 | 0 | 40 | 0 | 20 | 0 | 0 | 15 | 45 | 0 | 0 | 0 | 0 |
| Sedge, Umbrella | 0 | 0 | 0 | 0 | 0 | 0 | 0 | 0 | 0 | 0 | 0 | 0 | 0 | 20 |

| 250 g ai/ha | Compounds | | | | | | | | | | | | | |
|---|---|---|---|---|---|---|---|---|---|---|---|---|---|---|
| Flood | 1383 | 1384 | 1385 | 1386 | 1387 | 1388 | 1389 | 1390 | 1391 | 1392 | 1393 | 1394 | 1395 | 1396 |
| Barnyardgrass | 65 | 65 | 0 | 55 | 0 | 65 | 60 | 0 | 0 | 0 | 85 | 40 | 90 | 80 |
| Ducksalad | 100 | 100 | 40 | 100 | 0 | 80 | 100 | 50 | 75 | 30 | 100 | 75 | 80 | 100 |
| Rice | 25 | 40 | 0 | 0 | 0 | 0 | 15 | 0 | 0 | 0 | 55 | 10 | 10 | 25 |
| Sedge, Umbrella | 0 | 0 | 0 | 0 | 0 | 0 | 0 | 0 | 0 | 0 | 0 | 0 | 0 | 0 |

| 250 g ai/ha | Compounds | | | | |
|---|---|---|---|---|---|
| Flood | 1397 | 1398 | 1399 | 1400 | 1402 |
| Barnyardgrass | 75 | 80 | 85 | 80 | 90 |
| Ducksalad | 100 | 100 | 100 | 100 | 95 |
| Rice | 0 | 15 | 15 | 0 | 0 |
| Sedge, Umbrella | 0 | 0 | 0 | 0 | 0 |

Test C

Seeds of plant species selected from blackgrass (*Alopecurus myosuroides*), ryegrass, Italian (Italian ryegrass, *Lolium multiflorum*), wheat (winter wheat, *Triticum aestivum*), galium (catchweed bedstraw, *Galium aparine*), corn (*Zea mays*), crabgrass, large (large crabgrass, *Digitaria sanguinalis*), foxtail, giant (giant foxtail, *Setaria faberii*), johnsongrass (*Sorghum halepense*), lambsquarters (*Chenopodium album*), morningglory (*Ipomoea coccinea*), nutsedge, yellow (yellow nutsedge, *Cyperus esculentus*), pigweed (*Amaranthus retroflexus*), ragweed (common ragweed, *Ambrosia elatior*), soybean (*Glycine max*), barnyardgrass (*Echinochloa crus-galli*), oilseed rape (*Brassica napus*), waterhemp (common waterhemp, *Amaranthus rudis*) and velvetleaf (*Abutilon theophrasti*) were planted into a blend of loam soil and sand and treated preemergence with test chemicals formulated in a non-phytotoxic solvent mixture which included a surfactant.

At the same time, plants selected from these crop and weed species and also kochia (*Kochia scoparia*), oat, wild (wild oat, *Avena fatua*), and chickweed (common chickweed, *Stellaria media*) were planted in pots containing Sunshine Redi-Earth® planting medium comprising spaghnum peat moss, vermiculite, starter nutrients and dolomitic limestone and treated with postemergence applications of test chemicals formulated in the same manner. Plants ranged in height from 2 to 18 cm (1- to 4-leaf stage) for postemergence treatments. Treated plants and controls were maintained in a greenhouse for 13 to 15 d, after which time all species were compared to controls and visually evaluated. Plant response ratings, summarized in Table C, are based on a scale of 0 to 100 where 0 is no effect and 100 is complete control. A dash (-) response means no test result.

Plant species in the flooded paddy test consisted of rice (*Oryza sativa*), sedge, umbrella (small-flower umbrella sedge, *Cyperus difformis*), ducksalad (*Heteranthera limosa*), and barnyardgrass (*Echinochloa crus-galli*) grown to the 2-leaf stage for testing. At time of treatment, test pots were flooded to 3 cm above the soil surface, treated by application of test compounds directly to the paddy water, and then maintained at that water depth for the duration of the test. Treated plants and controls were maintained in a greenhouse for 13 to 15 d, after which time all species were compared to controls and visually evaluated. Plant response ratings, summarized in Table C, are based on a scale of 0 to 100 where 0 is no effect and 100 is complete control. A dash (-) response means no test result.

TABLE C

| | Compounds | | | | | | Compounds | | | | |
|---|---|---|---|---|---|---|---|---|---|---|---|
| 250 g ai/ha | 596 | 635 | 639 | 640 | 641 | 125 g ai/ha | 596 | 635 | 639 | 640 | 641 |
| | Postemergence | | | | | | | | | | |
| Barnyardgrass | 65 | 65 | 85 | 10 | 65 | Barnyardgrass | 45 | 65 | 70 | 10 | 35 |
| Blackgrass | 10 | 40 | 10 | 0 | 0 | Blackgrass | 0 | 5 | 5 | 0 | 0 |
| Chickweed | 80 | 90 | 90 | 35 | 55 | Chickweed | 25 | 85 | 50 | 60 | 50 |
| Corn | 10 | 40 | 35 | 0 | 10 | Corn | 0 | 5 | 0 | 0 | 0 |
| Crabgrass, Large | 75 | 70 | 80 | 35 | 70 | Crabgrass, Large | 65 | 50 | 70 | 10 | 70 |
| Foxtail, Giant | 80 | 60 | 85 | 65 | 80 | Foxtail, Giant | 50 | 50 | 80 | 10 | 65 |
| Galium | 60 | 55 | 70 | 65 | 65 | Galium | 60 | 60 | 70 | 60 | 60 |
| Johnsongrass | 10 | 5 | 0 | 0 | 0 | Johnsongrass | 0 | 5 | 0 | 0 | 0 |
| Kochia | 60 | 60 | 85 | 75 | 40 | Kochia | 35 | 50 | 80 | 30 | 0 |
| Lambsquarters | 55 | 85 | 70 | 40 | 30 | Lambsquarters | 40 | 75 | 65 | 70 | 5 |
| Morningglory | 50 | 45 | 75 | 40 | 40 | Morningglory | 25 | 45 | 60 | 55 | 35 |
| Nutsedge, Yellow | 10 | 0 | 10 | 10 | 0 | Nutsedge, Yellow | 10 | 0 | 0 | 0 | 0 |
| Oat, Wild | 5 | 5 | 0 | 5 | 0 | Oat, Wild | 0 | 0 | 0 | 0 | 0 |
| Oilseed Rape | 30 | 80 | 50 | 60 | 55 | Oilseed Rape | 30 | 10 | 40 | 50 | 45 |
| Pigweed | 30 | 75 | 45 | 55 | 50 | Pigweed | 35 | 75 | 40 | 35 | 25 |
| Ragweed | 15 | 80 | 65 | 55 | 30 | Ragweed | 0 | 70 | 50 | 30 | 40 |
| Ryegrass, Italian | 0 | 20 | 10 | 5 | 10 | Ryegrass, Italian | 0 | 15 | 5 | 0 | 10 |
| Soybean | 0 | 10 | 25 | 5 | 15 | Soybean | 10 | 5 | 15 | 10 | 5 |
| Velvetleaf | 55 | 30 | 60 | 30 | 50 | Velvetleaf | 50 | 10 | 50 | 25 | — |
| Waterhemp | 30 | 70 | 25 | 30 | 30 | Waterhemp | 20 | 55 | 30 | 10 | 25 |
| Wheat | 0 | 5 | 0 | 0 | 0 | Wheat | 0 | 0 | 0 | 0 | 0 |

| | Compounds | | | | | | Compounds | | | | |
|---|---|---|---|---|---|---|---|---|---|---|---|
| 62 g ai/ha | 596 | 635 | 639 | 640 | 641 | 31 g ai/ha | 596 | 635 | 639 | 640 | 641 |
| | Postemergence | | | | | | | | | | |
| Barnyardgrass | 30 | 10 | 40 | 0 | 10 | Barnyardgrass | 0 | 0 | 20 | 0 | 0 |
| Blackgrass | 0 | 0 | 0 | 0 | 0 | Blackgrass | 0 | 0 | 0 | 0 | 0 |
| Chickweed | 20 | 85 | 40 | 0 | 0 | Chickweed | 20 | 80 | 40 | 25 | 0 |
| Corn | 0 | 0 | 0 | 0 | 0 | Corn | 0 | 0 | 0 | 0 | 0 |
| Crabgrass, Large | 65 | 60 | 70 | 0 | 50 | Crabgrass, Large | 30 | 20 | 60 | 0 | 10 |
| Foxtail, Giant | 20 | 30 | 60 | 0 | 10 | Foxtail, Giant | 10 | 15 | 35 | 0 | 0 |
| Galium | 45 | 50 | 50 | 55 | 60 | Galium | 40 | 50 | 50 | 50 | 40 |
| Johnsongrass | 0 | 0 | 0 | 0 | 0 | Johnsongrass | 0 | 0 | 0 | 0 | 0 |
| Kochia | 30 | 20 | 50 | 30 | 0 | Kochia | 30 | 40 | 40 | 20 | 0 |
| Lambsquarters | 35 | 80 | 75 | 20 | 15 | Lambsquarters | 35 | 75 | 40 | 30 | 5 |
| Morningglory | 10 | 40 | 25 | 40 | 15 | Morningglory | 0 | 25 | 30 | 35 | 0 |
| Nutsedge, Yellow | 0 | 0 | 0 | 0 | 0 | Nutsedge, Yellow | 0 | 0 | 0 | 0 | 0 |
| Oat, Wild | 0 | 0 | 0 | 0 | 0 | Oat, Wild | 0 | 0 | 0 | 0 | 0 |
| Oilseed Rape | 0 | 45 | 30 | 15 | 45 | Oilseed Rape | 0 | 50 | 30 | 20 | 20 |
| Pigweed | 10 | 60 | 45 | 35 | 0 | Pigweed | 10 | 65 | 10 | 10 | 0 |
| Ragweed | 0 | 60 | 10 | 25 | 0 | Ragweed | 0 | 25 | 0 | 0 | 0 |
| Ryegrass, Italian | 0 | 0 | 0 | 0 | 0 | Ryegrass, Italian | 0 | 0 | 0 | 0 | 0 |
| Soybean | 0 | 0 | 10 | 10 | 0 | Soybean | 0 | 0 | 0 | 65 | 0 |
| Velvetleaf | 35 | 0 | 60 | 70 | 40 | Velvetleaf | 35 | 0 | 35 | 5 | 40 |
| Waterhemp | 0 | 60 | 25 | 20 | 10 | Waterhemp | 0 | 35 | 10 | 5 | 10 |
| Wheat | 0 | 0 | 0 | 0 | 0 | Wheat | 0 | 0 | 0 | 0 | 0 |

| | Compounds | | | | | | | | | | | |
|---|---|---|---|---|---|---|---|---|---|---|---|---|
| 250 g ai/ha | 392 | 393 | 396 | 397 | 399 | 421 | 428 | 429 | 431 | 445 | 446 | 450 | 464 |
| | Preemergence | | | | | | | | | | | | |
| Barnyardgrass | 95 | 95 | 98 | 98 | 98 | 95 | 98 | 98 | 98 | 95 | 95 | 95 | 98 |
| Blackgrass | 60 | 90 | 80 | 90 | 90 | 70 | 30 | 95 | 98 | 80 | 55 | 60 | 85 |
| Corn | 75 | 70 | 75 | 75 | 60 | 75 | 70 | 90 | 65 | 85 | 10 | 65 | 90 |
| Crabgrass, Large | 95 | 98 | 100 | 100 | 100 | 95 | 98 | 98 | 100 | 100 | 100 | 95 | 100 |
| Foxtail, Giant | 95 | 95 | 98 | 98 | 98 | 90 | 95 | — | — | 95 | 95 | 95 | — |
| Galium | — | — | 100 | 90 | 90 | 45 | — | 100 | 90 | 65 | 95 | 95 | 95 |
| Johnsongrass | 90 | 85 | — | — | — | 0 | 75 | 90 | 90 | 85 | 65 | 50 | 95 |
| Lambsquarters | 75 | 85 | 98 | 75 | 98 | 70 | 65 | 85 | 65 | 50 | 95 | 65 | 90 |
| Morningglory | 15 | 10 | 70 | 70 | 55 | 20 | 0 | 60 | 10 | 25 | 0 | 10 | 40 |
| Nutsedge, Yellow | 0 | 0 | 20 | 70 | 0 | 0 | 30 | 0 | 0 | 0 | 0 | 0 | 0 |
| Oilseed Rape | 90 | 85 | 85 | 85 | 85 | 35 | 15 | 90 | 90 | 55 | 95 | 60 | 90 |
| Pigweed | 90 | 90 | 95 | 95 | 95 | 60 | 40 | 100 | 85 | 60 | 85 | 80 | 70 |
| Ragweed | 70 | 65 | 85 | 70 | 80 | 60 | 0 | 75 | 60 | 35 | 85 | 60 | 90 |
| Ryegrass, Italian | 90 | 45 | 80 | 60 | 50 | 65 | 45 | 65 | 70 | 85 | 45 | 30 | 85 |

TABLE C-continued

| | | | | | | | | | | | | | |
|---|---|---|---|---|---|---|---|---|---|---|---|---|---|
| Soybean | 5 | 30 | 0 | 20 | 0 | 10 | 15 | 10 | — | 0 | 25 | 0 | 0 |
| Velvetleaf | 70 | 80 | 60 | 45 | 60 | 40 | 10 | 45 | 30 | 10 | 30 | 50 | 60 |
| Waterhemp | 90 | 90 | 95 | 95 | 98 | 85 | 35 | 90 | 90 | 100 | 98 | 85 | 95 |
| Wheat | 75 | 70 | 90 | 70 | 75 | 40 | 80 | 60 | 90 | 65 | 30 | 60 | 90 |

| | Compounds | | | | | | | | | | | | |
|---|---|---|---|---|---|---|---|---|---|---|---|---|---|
| 250 g ai/ha | 465 | 488 | 492 | 523 | 591 | 596 | 612 | 613 | 616 | 617 | 618 | 622 | 624 | 635 |

Preemergence

| | | | | | | | | | | | | | |
|---|---|---|---|---|---|---|---|---|---|---|---|---|---|
| Barnyardgrass | 100 | 95 | 95 | 100 | 95 | 95 | 98 | 98 | 95 | 95 | 98 | 95 | 95 | 95 |
| Blackgrass | 90 | 85 | 10 | 90 | 90 | 90 | 95 | 95 | 80 | 90 | 80 | 85 | 90 | 90 |
| Corn | 90 | 85 | 85 | 85 | 80 | 35 | 70 | 85 | 85 | 80 | 85 | 80 | 65 | 85 |
| Crabgrass, Large | 100 | 100 | 95 | 98 | 95 | 100 | 100 | 98 | 95 | 100 | 100 | 100 | 98 | 98 |
| Foxtail, Giant | — | 95 | 95 | 98 | 95 | 100 | 95 | 98 | 95 | 98 | 95 | 95 | 95 | 95 |
| Galium | 98 | 85 | 85 | 80 | 80 | 85 | 90 | 90 | 90 | 85 | 90 | 90 | 85 | 80 |
| Johnsongrass | 85 | 90 | 90 | 70 | 85 | 75 | 90 | 90 | 90 | 75 | 85 | 65 | 25 | 85 |
| Lambsquarters | 100 | 60 | 50 | 65 | 70 | 75 | 70 | 75 | 60 | 80 | 75 | 75 | 60 | 85 |
| Morningglory | 50 | 60 | 45 | 35 | 65 | 20 | 55 | 50 | 10 | 40 | 5 | 20 | 35 | 50 |
| Nutsedge, Yellow | 0 | 0 | 0 | 40 | 0 | 0 | 35 | 20 | 0 | 35 | 10 | 0 | 50 | 25 |
| Oilseed Rape | 90 | 90 | 85 | 60 | 85 | 90 | 90 | 90 | 85 | 90 | 90 | 85 | 85 | 90 |
| Pigweed | 55 | 85 | 80 | 90 | 75 | 55 | 90 | 90 | 80 | 75 | 75 | 90 | 90 | 85 |
| Ragweed | 80 | 70 | 45 | 70 | 70 | 75 | 65 | 65 | 75 | 70 | 80 | 85 | 80 | 80 |
| Ryegrass, Italian | 65 | 65 | 20 | 20 | 75 | 20 | 85 | 95 | 85 | 90 | 55 | 70 | 30 | 40 |
| Soybean | 15 | 10 | 0 | 45 | 0 | 100 | 0 | 0 | 15 | 20 | 0 | 45 | 40 | 60 |
| Velvetleaf | 65 | 20 | 5 | 45 | 20 | 55 | 60 | 70 | 35 | 45 | 60 | 70 | 65 | 40 |
| Waterhemp | 80 | 80 | 65 | 80 | 70 | 65 | 95 | 90 | 85 | 80 | 85 | 90 | 100 | 85 |
| Wheat | 95 | 90 | 35 | 80 | 70 | 70 | 90 | 70 | 85 | 80 | 80 | 80 | 80 | 65 |

| | Compounds | | | | | | | | | | | | |
|---|---|---|---|---|---|---|---|---|---|---|---|---|---|
| 250 g ai/ha | 636 | 637 | 639 | 640 | 641 | 644 | 646 | 651 | 653 | 662 | 663 | 665 | 667 | 695 |

Preemergence

| | | | | | | | | | | | | | |
|---|---|---|---|---|---|---|---|---|---|---|---|---|---|
| Barnyardgrass | 95 | 95 | 100 | 95 | 95 | 98 | 98 | 100 | 90 | 100 | 100 | 100 | 100 | 90 |
| Blackgrass | 90 | 90 | 90 | 50 | 70 | 95 | 98 | 85 | 90 | 98 | 95 | 90 | 95 | 90 |
| Corn | 90 | 85 | 85 | 0 | 10 | 85 | 75 | 70 | 20 | 85 | 60 | 70 | 85 | 80 |
| Crabgrass, Large | 100 | 100 | 100 | 100 | 100 | 100 | 100 | 100 | 100 | 100 | 100 | 100 | 98 | 95 |
| Foxtail, Giant | 90 | 95 | 100 | 95 | 95 | 98 | 98 | 100 | 100 | 98 | 100 | 98 | 100 | 90 |
| Galium | 90 | 85 | 95 | 90 | 85 | 98 | 100 | 90 | 40 | 90 | 90 | 90 | 90 | 90 |
| Johnsongrass | 90 | 85 | 90 | 40 | 60 | 85 | 90 | 80 | 55 | 90 | 40 | 45 | 90 | 85 |
| Lambsquarters | 65 | 70 | 70 | 70 | 65 | 85 | 80 | 100 | 60 | 100 | 85 | 85 | 100 | 80 |
| Morningglory | 65 | 45 | 40 | 0 | 0 | 0 | 10 | 0 | 0 | 25 | 40 | 10 | 10 | 10 |
| Nutsedge, Yellow | 60 | 65 | 20 | 0 | 0 | 15 | 35 | 0 | 25 | 0 | 50 | 0 | 25 | 0 |
| Oilseed Rape | 90 | 85 | 90 | 80 | 90 | 90 | 90 | 90 | 85 | 90 | 80 | 85 | 90 | 80 |
| Pigweed | 85 | 85 | 75 | 80 | 70 | 70 | 75 | 85 | 85 | 80 | 75 | 50 | 70 | 70 |
| Ragweed | 80 | 75 | 80 | 85 | 45 | 85 | 70 | 85 | 60 | 85 | 85 | 75 | 80 | 80 |
| Ryegrass, Italian | 90 | 35 | 70 | 40 | 70 | 80 | 90 | 85 | 25 | 95 | 75 | 60 | 98 | 30 |
| Soybean | 0 | 5 | 20 | 0 | 100 | — | 0 | — | 40 | 0 | 0 | 10 | 0 | 0 |
| Velvetleaf | 55 | 65 | 55 | 40 | 45 | 60 | 60 | 70 | 50 | 75 | 55 | 70 | 40 | 55 |
| Waterhemp | 85 | 90 | 80 | 85 | 70 | 80 | 85 | 85 | 80 | 90 | 90 | 85 | 75 | 85 |
| Wheat | 75 | 90 | 85 | 60 | 70 | 90 | 90 | 75 | 40 | 90 | 90 | 90 | 50 | 60 |

| | Compounds | | | | Compounds | | | | |
|---|---|---|---|---|---|---|---|---|---|
| 250 g ai/ha | 697 | 698 | 700 | 125 g ai/ha | 691 | 695 | 697 | 698 | 700 |

Preemergence

| | | | | | | | | | |
|---|---|---|---|---|---|---|---|---|---|
| Barnyardgrass | 90 | 90 | 95 | Barnyardgrass | 100 | 90 | 90 | 90 | 90 |
| Blackgrass | 90 | 70 | 85 | Blackgrass | 75 | 90 | 90 | 50 | 60 |
| Corn | 75 | 80 | 50 | Corn | 65 | 70 | 80 | 80 | 10 |
| Crabgrass, Large | 95 | 95 | 98 | Crabgrass, Large | 100 | 95 | 90 | 95 | 95 |
| Foxtail, Giant | 90 | 90 | 90 | Foxtail, Giant | 98 | 90 | 90 | 85 | 90 |
| Galium | 90 | 90 | 40 | Galium | 95 | 85 | 85 | 100 | 50 |
| Johnsongrass | 85 | 85 | 60 | Johnsongrass | — | 80 | 85 | 80 | 10 |
| Lambsquarters | 60 | 80 | 85 | Lambsquarters | 90 | 65 | 65 | 70 | 80 |
| Morningglory | 30 | 25 | 0 | Morningglory | 40 | 5 | 25 | 20 | 0 |
| Nutsedge, Yellow | 0 | 0 | 0 | Nutsedge, Yellow | 20 | 0 | 0 | 0 | 0 |
| Oilseed Rape | 85 | 85 | 50 | Oilseed Rape | 80 | 85 | 80 | 80 | 60 |
| Pigweed | 85 | 90 | 65 | Pigweed | 100 | 65 | 85 | 90 | 50 |
| Ragweed | 80 | 55 | 75 | Ragweed | 85 | 75 | 80 | 40 | 75 |
| Ryegrass, Italian | 50 | 30 | 45 | Ryegrass, Italian | 55 | 30 | 45 | 0 | 35 |
| Soybean | 10 | 0 | 0 | Soybean | 15 | 0 | 0 | 0 | 15 |
| Velvetleaf | 35 | 65 | 40 | Velvetleaf | 50 | 30 | 65 | 50 | 20 |
| Waterhemp | 85 | 90 | 70 | Waterhemp | 95 | 70 | 85 | 85 | 75 |
| Wheat | 35 | 30 | 70 | Wheat | 80 | 35 | 10 | 0 | 0 |

TABLE C-continued

| Compounds | | | | | | | | | | | | | |
|---|---|---|---|---|---|---|---|---|---|---|---|---|---|
| 125 g ai/ha | 392 | 393 | 396 | 397 | 399 | 421 | 428 | 429 | 431 | 445 | 446 | 450 | 464 |
| Preemergence | | | | | | | | | | | | | |
| Barnyardgrass | 90 | 95 | 98 | 98 | 100 | 90 | 95 | 95 | 95 | 90 | 90 | 90 | 95 |
| Blackgrass | 70 | 70 | 80 | 90 | 70 | 70 | 30 | 90 | 90 | 80 | 50 | 45 | 85 |
| Corn | 55 | 55 | 65 | 60 | 65 | 60 | 55 | 65 | 50 | 80 | 0 | 20 | 75 |
| Crabgrass, Large | 95 | 95 | 98 | 100 | 100 | 90 | 98 | 98 | 100 | 95 | 100 | 90 | 100 |
| Foxtail, Giant | 95 | 95 | 98 | 98 | 98 | 85 | 90 | — | — | 90 | 90 | 90 | — |
| Galium | — | — | 100 | 90 | 90 | 55 | — | 100 | 100 | 45 | 90 | 90 | 95 |
| Johnsongrass | 85 | 85 | — | — | — | 0 | 65 | 95 | 85 | 80 | 50 | 20 | 85 |
| Lambsquarters | 75 | 75 | 70 | 75 | 85 | 60 | 35 | 75 | 50 | 40 | 55 | 65 | 80 |
| Morningglory | 0 | 10 | 60 | 60 | 30 | 15 | 0 | 20 | 10 | 35 | 0 | 20 | 20 |
| Nutsedge, Yellow | 0 | 0 | 30 | 50 | 0 | 0 | 0 | 0 | 0 | 0 | 0 | 0 | 0 |
| Oilseed Rape | 85 | 80 | 80 | 80 | 70 | 30 | 0 | 90 | 85 | 10 | 90 | 20 | 80 |
| Pigweed | 85 | 85 | 90 | 95 | 90 | 35 | 0 | 90 | 75 | 65 | 80 | 80 | 60 |
| Ragweed | 60 | 40 | 85 | 70 | 65 | 40 | 0 | 75 | 40 | 35 | 75 | 20 | 75 |
| Ryegrass, Italian | 55 | 30 | 30 | 60 | 75 | 35 | 40 | 85 | 15 | 50 | 0 | 0 | 70 |
| Soybean | 15 | 15 | 0 | 0 | 0 | 0 | 0 | 0 | 0 | 0 | 10 | 0 | 0 |
| Velvetleaf | 60 | 50 | 65 | 30 | 50 | 20 | 0 | 30 | 40 | 10 | 10 | 10 | 45 |
| Waterhemp | 90 | 85 | 95 | 98 | 90 | 80 | 10 | 90 | 85 | 25 | 80 | 75 | 80 |
| Wheat | 80 | 35 | 70 | 45 | 80 | 25 | 50 | 70 | 70 | 40 | 0 | 40 | 70 |

| Compounds | | | | | | | | | | | | | |
|---|---|---|---|---|---|---|---|---|---|---|---|---|---|
| 125 g ai/ha | 465 | 488 | 492 | 523 | 591 | 596 | 610 | 612 | 613 | 616 | 617 | 618 | 622 | 624 |
| Preemergence | | | | | | | | | | | | | |
| Barnyardgrass | 98 | 95 | 90 | 98 | 95 | 95 | 95 | 95 | 95 | 95 | 95 | 95 | 90 | 95 |
| Blackgrass | 80 | 90 | 10 | 20 | 90 | 70 | 90 | 90 | 95 | 80 | 85 | 60 | 80 | 90 |
| Corn | 65 | 70 | 55 | 65 | 60 | 0 | 10 | 65 | 65 | 80 | 75 | 75 | 85 | 5 |
| Crabgrass, Large | 100 | 95 | 95 | 100 | 90 | 100 | 98 | 98 | 95 | 95 | 100 | 100 | 100 | 100 |
| Foxtail, Giant | — | 90 | 90 | 98 | 90 | 95 | 95 | 95 | 95 | 90 | 95 | 90 | 95 | 90 |
| Galium | 90 | 85 | 0 | 80 | 50 | 40 | 90 | 90 | 90 | 85 | 85 | 85 | 90 | 80 |
| Johnsongrass | 80 | 85 | 80 | 60 | 75 | 70 | 35 | 85 | 90 | 75 | 65 | 85 | 50 | 0 |
| Lambsquarters | 85 | 60 | 40 | 70 | 35 | 70 | 80 | 40 | 50 | 70 | 70 | 70 | 70 | 70 |
| Morningglory | 25 | 55 | 20 | 25 | 40 | 10 | 35 | 25 | 55 | 10 | 25 | 10 | 25 | 30 |
| Nutsedge, Yellow | 0 | 0 | 0 | 0 | 0 | 0 | 0 | 25 | 10 | 0 | 20 | 0 | 0 | 25 |
| Oilseed Rape | 85 | 85 | 85 | 30 | 30 | 30 | 80 | 70 | 90 | 70 | 90 | 90 | 85 | 85 |
| Pigweed | 60 | 70 | 75 | 90 | 60 | 40 | 85 | 90 | 85 | 80 | 45 | 60 | 85 | 85 |
| Ragweed | 75 | 40 | 35 | 40 | 35 | 50 | 70 | 55 | 40 | 50 | 40 | 65 | 85 | 75 |
| Ryegrass, Italian | 65 | 70 | 25 | 5 | 35 | 30 | 30 | 50 | 75 | 90 | 50 | 45 | 35 | 30 |
| Soybean | — | 0 | 40 | 30 | 0 | 0 | — | 10 | 0 | 0 | 0 | 0 | 85 | 15 |
| Velvetleaf | 55 | 10 | 5 | 30 | 20 | 30 | 40 | 30 | 40 | 40 | 20 | 55 | 70 | 45 |
| Waterhemp | 80 | 75 | 40 | 65 | 65 | 25 | 80 | 90 | 85 | 85 | 70 | 65 | 90 | 90 |
| Wheat | 80 | 85 | 5 | 50 | 30 | 50 | 30 | 25 | 65 | 50 | 45 | 75 | 70 | 45 |

| Compounds | | | | | | | | | | | | | |
|---|---|---|---|---|---|---|---|---|---|---|---|---|---|
| 125 g ai/ha | 635 | 636 | 637 | 639 | 640 | 641 | 644 | 646 | 651 | 653 | 662 | 663 | 665 | 667 |
| Preemergence | | | | | | | | | | | | | |
| Barnyardgrass | 95 | 95 | 95 | 95 | 90 | 90 | 98 | 98 | 100 | 80 | 98 | 98 | 98 | 98 |
| Blackgrass | 70 | 90 | 90 | 85 | 20 | 30 | 90 | 85 | 60 | 60 | 95 | 85 | 90 | 85 |
| Corn | 75 | 85 | 75 | 80 | 0 | 0 | 65 | 65 | 70 | 0 | 80 | 20 | 75 | 80 |
| Crabgrass, Large | 95 | 100 | 100 | 100 | 98 | 100 | 98 | 98 | 100 | 100 | 100 | 100 | 100 | 98 |
| Foxtail, Giant | 95 | 90 | 95 | 95 | 95 | 90 | 98 | 95 | 98 | 95 | 95 | 98 | 98 | 98 |
| Galium | 80 | 90 | 80 | 85 | 85 | 90 | 90 | 90 | 90 | 30 | 100 | 85 | 90 | 98 |
| Johnsongrass | 65 | 85 | 75 | 80 | 0 | 10 | 85 | 85 | 70 | 40 | 90 | 20 | 25 | 85 |
| Lambsquarters | 80 | 55 | 55 | 40 | 50 | 40 | 85 | 75 | 85 | 50 | 100 | 65 | 70 | 90 |
| Morningglory | 30 | 35 | 40 | 35 | 0 | 0 | 0 | 0 | 0 | 0 | 30 | 30 | 20 | 0 |
| Nutsedge, Yellow | 0 | 0 | 0 | 0 | 0 | 0 | 0 | 0 | 0 | 0 | 0 | 0 | 0 | 0 |
| Oilseed Rape | 90 | 85 | 85 | 85 | 5 | 85 | 85 | 85 | 90 | 30 | 90 | 65 | 80 | 85 |
| Pigweed | 85 | 80 | 85 | 65 | 70 | 60 | 55 | 65 | 50 | 50 | 75 | 70 | 50 | 50 |
| Ragweed | 80 | 65 | 75 | 75 | 70 | 30 | 70 | 60 | 60 | 35 | 80 | 70 | 70 | 70 |
| Ryegrass, Italian | 20 | 50 | 30 | 60 | 5 | 35 | 65 | 80 | 75 | 20 | 80 | 50 | 65 | 95 |
| Soybean | 5 | 0 | 0 | 10 | 0 | 10 | 0 | 10 | 0 | 5 | 0 | 0 | 0 | 0 |
| Velvetleaf | 15 | 55 | 45 | 65 | 10 | 25 | 40 | 55 | 70 | 35 | 70 | 30 | 60 | 50 |
| Waterhemp | 85 | 85 | 85 | 75 | 70 | 45 | 65 | 75 | 50 | 50 | 85 | 85 | 65 | 60 |
| Wheat | 10 | 65 | 90 | 80 | 45 | 35 | 85 | 85 | 55 | 0 | 90 | 55 | 50 | 55 |

TABLE C-continued

| | Compounds | | | | | | | | | | | | |
|---|---|---|---|---|---|---|---|---|---|---|---|---|---|
| 62 g ai/ha | 392 | 393 | 396 | 397 | 399 | 421 | 428 | 429 | 431 | 445 | 446 | 450 | 464 |
| | Preemergence | | | | | | | | | | | | |
| Barnyardgrass | 90 | 90 | 95 | 95 | 98 | 80 | 95 | 95 | 95 | 90 | 90 | 90 | 95 |
| Blackgrass | 45 | 55 | 50 | 70 | 80 | 45 | 0 | 90 | 85 | 65 | 0 | 0 | 85 |
| Corn | 65 | 40 | 50 | 15 | 40 | 0 | 25 | 40 | 35 | 75 | 0 | 5 | 70 |
| Crabgrass, Large | 95 | 95 | 98 | 98 | 98 | 95 | 95 | 98 | 100 | 95 | 100 | 90 | 100 |
| Foxtail, Giant | 95 | 95 | 98 | 95 | 95 | 85 | 90 | — | — | 90 | 90 | 90 | — |
| Galium | — | — | 90 | 80 | 85 | 0 | — | 100 | 90 | 0 | 90 | 90 | 95 |
| Johnsongrass | 85 | 80 | — | — | — | 0 | 50 | 95 | 75 | 80 | 40 | 0 | 80 |
| Lambsquarters | 70 | 75 | 75 | 70 | 85 | 35 | 10 | 75 | 40 | 30 | 50 | 50 | 80 |
| Morningglory | 0 | 10 | 40 | 55 | 40 | 0 | 0 | 30 | 10 | 10 | 0 | 0 | 20 |
| Nutsedge, Yellow | 0 | 0 | 0 | 10 | 0 | 0 | 0 | 0 | 0 | 0 | 0 | 0 | 0 |
| Oilseed Rape | 80 | 40 | 70 | 70 | 30 | 25 | 0 | 80 | 60 | 0 | 85 | 30 | 85 |
| Pigweed | 80 | 75 | 80 | 90 | 75 | 0 | 0 | 85 | 60 | 10 | 75 | 60 | 45 |
| Ragweed | 45 | 35 | 80 | 75 | 50 | 30 | 0 | 40 | 40 | 40 | 40 | 10 | 70 |
| Ryegrass, Italian | 40 | 30 | 55 | 60 | 50 | 40 | 40 | 85 | 10 | 40 | 0 | 0 | 55 |
| Soybean | 100 | 10 | 0 | 0 | 0 | 0 | 0 | — | — | 0 | 20 | 5 | 0 |
| Velvetleaf | 40 | 35 | 40 | 25 | 20 | 20 | 0 | 40 | 25 | 0 | 0 | 0 | 30 |
| Waterhemp | 85 | 80 | 90 | 90 | 80 | 30 | 0 | 85 | 75 | 35 | 100 | 60 | 75 |
| Wheat | 35 | 20 | 10 | 45 | 15 | 0 | 15 | 60 | 5 | 30 | 0 | 30 | 50 |

| | Compounds | | | | | | | | | | | | |
|---|---|---|---|---|---|---|---|---|---|---|---|---|---|
| 62 g ai/ha | 465 | 488 | 492 | 523 | 591 | 596 | 610 | 612 | 613 | 616 | 617 | 618 | 622 | 623 |
| | Preemergence | | | | | | | | | | | | |
| Barnyardgrass | 95 | 90 | 90 | 95 | 90 | 95 | 90 | 95 | 95 | 90 | 90 | 95 | 95 | 95 |
| Blackgrass | 50 | 50 | 5 | 0 | 85 | 40 | 50 | 90 | 85 | 45 | 20 | 10 | 0 | 90 |
| Corn | 55 | 60 | 10 | 20 | 70 | 0 | 10 | 30 | 55 | 65 | 40 | 50 | 45 | 65 |
| Crabgrass, Large | 100 | 95 | 95 | 95 | 90 | 100 | 95 | 95 | 95 | 90 | 95 | 100 | 95 | 95 |
| Foxtail, Giant | — | 90 | 90 | 90 | 90 | 90 | 95 | 90 | 95 | 90 | 90 | 90 | 90 | 90 |
| Galium | 85 | 85 | 0 | 80 | 50 | 85 | 0 | 90 | 85 | 85 | 0 | 90 | 90 | 90 |
| Johnsongrass | 65 | 80 | 55 | 30 | 55 | 25 | 10 | 60 | 85 | 85 | 30 | 60 | 60 | 70 |
| Lambsquarters | 75 | 50 | 35 | 70 | 20 | 60 | 75 | 45 | 60 | 35 | 55 | 50 | 35 | 50 |
| Morningglory | 20 | 25 | 10 | 35 | 30 | 0 | 35 | 0 | 40 | 0 | 0 | 0 | 0 | 15 |
| Nutsedge, Yellow | 0 | 0 | 0 | 0 | 0 | 0 | 0 | 0 | 0 | 0 | 0 | 0 | 0 | 0 |
| Oilseed Rape | 10 | 45 | 50 | 0 | 20 | 0 | 50 | 50 | 70 | 60 | 85 | 85 | 85 | 85 |
| Pigweed | 25 | 75 | 25 | 100 | 45 | 25 | 75 | 80 | 80 | 80 | 20 | 60 | 85 | 85 |
| Ragweed | 60 | 25 | 10 | 15 | 20 | 20 | 40 | 10 | 25 | 25 | 10 | 40 | 70 | 75 |
| Ryegrass, Italian | 70 | 35 | 5 | 5 | 10 | 0 | 0 | 40 | 25 | 35 | 45 | 50 | 50 | 55 |
| Soybean | — | 0 | 0 | 25 | 0 | 0 | 0 | 0 | 0 | 0 | 10 | 10 | 20 | 0 |
| Velvetleaf | 5 | 0 | 0 | 0 | 0 | 20 | 5 | 10 | 40 | 10 | 10 | 5 | 25 | 60 |
| Waterhemp | 70 | 40 | 10 | 65 | 30 | 0 | 75 | 85 | 75 | 80 | 25 | 60 | 85 | 90 |
| Wheat | 70 | 35 | 0 | 30 | 10 | 45 | 0 | 55 | 45 | 10 | 15 | 30 | 40 | 35 |

| | Compounds | | | | | | | | | | | | |
|---|---|---|---|---|---|---|---|---|---|---|---|---|---|
| 62 g ai/ha | 624 | 635 | 636 | 637 | 639 | 640 | 641 | 644 | 646 | 651 | 653 | 662 | 663 | 665 |
| | Preemergence | | | | | | | | | | | | |
| Barnyardgrass | 90 | 90 | 90 | 90 | 95 | 90 | 90 | 95 | 95 | 98 | 55 | 98 | 90 | 95 |
| Blackgrass | 70 | 60 | 85 | 90 | 85 | 0 | 45 | 70 | 80 | 45 | 15 | 75 | 60 | 60 |
| Corn | 0 | 70 | 80 | 55 | 40 | 0 | 0 | 50 | 45 | 55 | 0 | 70 | 10 | 10 |
| Crabgrass, Large | 100 | 95 | 98 | 100 | 98 | 100 | 100 | 95 | 95 | 100 | 95 | 98 | 98 | 100 |
| Foxtail, Giant | 90 | 90 | 90 | 90 | 90 | 95 | 90 | 95 | 95 | 98 | 95 | 95 | 95 | 95 |
| Galium | 85 | 5 | 85 | 80 | 80 | 80 | 30 | 85 | 90 | 50 | 100 | 100 | 90 | 90 |
| Johnsongrass | 0 | 75 | 85 | 70 | 65 | 0 | 0 | 70 | 40 | 50 | 0 | 70 | 10 | 25 |
| Lambsquarters | 40 | 40 | 40 | 55 | 25 | 35 | 40 | 75 | 60 | 55 | 35 | 85 | 60 | 45 |
| Morningglory | 0 | 25 | 25 | 35 | 10 | 0 | 0 | 0 | 0 | 0 | 0 | 0 | 35 | 15 |
| Nutsedge, Yellow | 0 | 0 | 75 | 85 | 0 | 0 | 0 | 0 | 0 | 0 | 0 | 0 | 0 | 0 |
| Oilseed Rape | 80 | 50 | 60 | 80 | 60 | 0 | 85 | 50 | 80 | 80 | 0 | 85 | 20 | 60 |
| Pigweed | 85 | 70 | 70 | 80 | 55 | 50 | 25 | 55 | 10 | 40 | 20 | 60 | 60 | 60 |
| Ragweed | 55 | 70 | 65 | 60 | 60 | 40 | 25 | 35 | 30 | 25 | 5 | 75 | 55 | 55 |
| Ryegrass, Italian | 40 | 5 | 30 | 30 | 60 | 5 | 10 | 55 | 20 | 40 | 10 | 70 | 70 | 60 |
| Soybean | 0 | 85 | 75 | 0 | 0 | 0 | 0 | 10 | 0 | — | — | 0 | 10 | 10 |
| Velvetleaf | 30 | 10 | 50 | 10 | 30 | 0 | 35 | 15 | 25 | 45 | 25 | 50 | 15 | 35 |
| Waterhemp | 90 | 80 | 75 | 80 | 65 | 75 | 0 | 65 | 60 | 40 | 30 | 80 | 60 | 40 |
| Wheat | 35 | 0 | 45 | 50 | 65 | 20 | 0 | 80 | 80 | 50 | 0 | 70 | 50 | 50 |

TABLE C-continued

| 62 g ai/ha | Compounds | | | | | | |
|---|---|---|---|---|---|---|---|
| | 667 | 690 | 691 | 695 | 697 | 698 | 700 |
| | Preemergence | | | | | | |
| Barnyardgrass | 95 | 98 | 98 | 90 | 90 | 90 | 85 |
| Blackgrass | 80 | 55 | 5 | 20 | 75 | 0 | 55 |
| Corn | 70 | 70 | 55 | 25 | 65 | 70 | 0 |
| Crabgrass, Large | 95 | 100 | 100 | 90 | 95 | 90 | 95 |
| Foxtail, Giant | 98 | 98 | 98 | 85 | 85 | 90 | 85 |
| Galium | 100 | 98 | 95 | 80 | 85 | 90 | 0 |
| Johnsongrass | 80 | — | — | 80 | 75 | 75 | 0 |
| Lambsquarters | 70 | 85 | 90 | 40 | 40 | 35 | 25 |
| Morningglory | 0 | 0 | 20 | 0 | 10 | 0 | 0 |
| Nutsedge, Yellow | 0 | 50 | 0 | 0 | 0 | 0 | 0 |
| Oilseed Rape | 85 | 80 | 50 | 40 | 70 | 30 | 30 |
| Pigweed | 50 | 90 | 90 | 60 | 80 | 85 | 15 |
| Ragweed | 100 | 80 | 70 | 70 | 80 | 40 | 50 |
| Ryegrass, Italian | 70 | 45 | 35 | 60 | 55 | 0 | 20 |
| Soybean | 10 | 0 | 15 | 0 | 10 | 0 | 0 |
| Velvetleaf | 30 | 50 | 40 | 10 | 25 | 40 | 0 |
| Waterhemp | 10 | 95 | 95 | 75 | 80 | 85 | 65 |
| Wheat | 10 | 45 | 60 | 5 | 0 | 0 | 0 |

| 31 g ai/ha | Compounds | | | | | | | | | | | | |
|---|---|---|---|---|---|---|---|---|---|---|---|---|---|
| | 392 | 393 | 396 | 397 | 399 | 421 | 428 | 429 | 431 | 445 | 446 | 450 | 464 |
| | Preemergence | | | | | | | | | | | | |
| Barnyardgrass | 90 | 90 | 85 | 90 | 95 | 60 | 90 | 85 | 90 | 85 | 90 | 90 | 90 |
| Blackgrass | 20 | 10 | 50 | 55 | 50 | 40 | 0 | 70 | 60 | 40 | 0 | 0 | 80 |
| Corn | 45 | 0 | 0 | 25 | 35 | 0 | 15 | 0 | 0 | 55 | 0 | 5 | 50 |
| Crabgrass, Large | 90 | 95 | 95 | 98 | 98 | 90 | 90 | 95 | 98 | 95 | 100 | 90 | 95 |
| Foxtail, Giant | 90 | 90 | 95 | 95 | 95 | 80 | 85 | — | — | 85 | 85 | 90 | — |
| Galium | — | — | 90 | 40 | 80 | 0 | — | 100 | 95 | 0 | 0 | 50 | 90 |
| Johnsongrass | 70 | 70 | — | — | — | 0 | 5 | 75 | 70 | 40 | 20 | 0 | 35 |
| Lambsquarters | 60 | 55 | 50 | 30 | 90 | 10 | 0 | 60 | 10 | 0 | 60 | 55 | 45 |
| Morningglory | 0 | 0 | 10 | 5 | 40 | 0 | 0 | 35 | 0 | 0 | 0 | 0 | 10 |
| Nutsedge, Yellow | 0 | 0 | 0 | 0 | 0 | 0 | 0 | 0 | 0 | 0 | 0 | 0 | 0 |
| Oilseed Rape | 70 | 0 | 30 | 20 | 35 | 10 | 0 | 80 | 10 | 0 | 0 | 30 | 80 |
| Pigweed | 75 | 70 | 85 | 55 | 70 | 0 | 10 | 75 | 40 | 0 | 50 | 55 | 45 |
| Ragweed | 70 | 35 | 65 | 20 | 50 | 0 | 0 | 0 | 50 | 35 | 25 | 5 | 70 |
| Ryegrass, Italian | 5 | 5 | 60 | 0 | 55 | 10 | 45 | 70 | 10 | 20 | 0 | 0 | 20 |
| Soybean | 0 | 10 | 0 | 0 | 0 | 0 | 0 | 0 | 0 | 100 | 0 | 0 | 0 |
| Velvetleaf | 10 | 25 | 40 | 5 | 30 | 25 | 0 | 10 | 25 | 0 | 10 | 0 | 40 |
| Waterhemp | 80 | 80 | 95 | 85 | 80 | 0 | 0 | 80 | 80 | 0 | 100 | 55 | 75 |
| Wheat | 10 | 0 | 5 | 0 | 0 | 0 | 45 | 50 | 5 | 0 | 0 | 0 | 45 |

| 31 g ai/ha | Compounds | | | | | | | | | | | | |
|---|---|---|---|---|---|---|---|---|---|---|---|---|---|
| | 465 | 488 | 492 | 523 | 591 | 596 | 610 | 612 | 613 | 616 | 617 | 618 | 622 | 623 |
| | Preemergence | | | | | | | | | | | | | |
| Barnyardgrass | 90 | 95 | 80 | 65 | 90 | 90 | 60 | 85 | 90 | 90 | 85 | 95 | 90 | 90 |
| Blackgrass | 20 | 0 | 0 | 0 | 30 | 0 | 50 | 70 | 85 | 30 | 20 | 0 | 0 | 60 |
| Corn | 40 | 25 | 0 | 0 | 45 | 0 | 20 | 40 | 40 | 55 | 0 | 30 | 5 | 60 |
| Crabgrass, Large | 100 | 90 | 90 | 90 | 90 | 95 | 95 | 98 | 95 | 90 | 95 | 100 | 100 | 95 |
| Foxtail, Giant | — | 85 | 90 | 85 | 85 | 90 | 90 | 90 | 95 | 90 | 90 | 90 | 90 | 90 |
| Galium | 80 | 80 | 85 | 0 | 5 | 30 | 0 | 80 | 90 | 90 | 0 | 0 | 80 | 85 |
| Johnsongrass | 10 | 70 | 0 | 0 | 35 | 20 | 0 | 40 | 75 | 60 | 25 | 20 | 25 | 50 |
| Lambsquarters | 75 | 20 | 25 | 20 | 10 | 10 | 60 | 45 | 25 | 25 | 30 | 50 | 75 | 60 |
| Morningglory | 5 | 0 | 0 | 20 | 10 | 0 | 25 | 0 | 40 | 0 | 0 | 0 | 0 | 25 |
| Nutsedge, Yellow | 0 | 0 | 0 | 0 | 0 | 0 | 0 | 0 | 0 | 0 | 0 | 0 | 0 | 0 |
| Oilseed Rape | 30 | 40 | 0 | 0 | 5 | 0 | 30 | 30 | 15 | 60 | 30 | 60 | 60 | 30 |
| Pigweed | 10 | 20 | 0 | 75 | 10 | 20 | 35 | 60 | 70 | 75 | 10 | 40 | 75 | 85 |
| Ragweed | 0 | 0 | 0 | 5 | 0 | 10 | 5 | 10 | 25 | 25 | 10 | 40 | 45 | 45 |
| Ryegrass, Italian | 10 | 5 | 0 | 0 | 0 | 0 | 0 | 20 | 10 | 30 | 10 | 45 | 25 | 45 |
| Soybean | 5 | 0 | 50 | 10 | 0 | 0 | 0 | 0 | 0 | 0 | 0 | 0 | 0 | 0 |
| Velvetleaf | 15 | 0 | 0 | 0 | 0 | 10 | 5 | 0 | 30 | 0 | 10 | 0 | 0 | 5 |
| Waterhemp | 60 | 25 | 0 | 55 | 5 | 0 | 60 | 75 | 70 | 50 | 20 | 60 | 75 | 85 |
| Wheat | 20 | 35 | 0 | 0 | 0 | 15 | 0 | 20 | 25 | 0 | 0 | 20 | 30 | 40 |

TABLE C-continued

| | Compounds | | | | | | | | | | | | | |
|---|---|---|---|---|---|---|---|---|---|---|---|---|---|---|
| 31 g ai/ha | 624 | 635 | 636 | 637 | 639 | 640 | 641 | 644 | 646 | 651 | 653 | 662 | 663 | 665 |
| Preemergence | | | | | | | | | | | | | | |
| Barnyardgrass | 75 | 85 | 90 | 90 | 90 | 80 | 85 | 90 | 90 | 95 | 20 | 95 | 95 | 85 |
| Blackgrass | 50 | 30 | 90 | 70 | 40 | 0 | 0 | 70 | 80 | 40 | 0 | 70 | 20 | 60 |
| Corn | 0 | 0 | 60 | 35 | 5 | 0 | 0 | 30 | 35 | 25 | 0 | 55 | 0 | 0 |
| Crabgrass, Large | 95 | 90 | 95 | 95 | 98 | 95 | 98 | 95 | 95 | 98 | 90 | 98 | 95 | 98 |
| Foxtail, Giant | 85 | 85 | 85 | 90 | 90 | 85 | 90 | 95 | 95 | 95 | 85 | 95 | 95 | 90 |
| Galium | 50 | 5 | 85 | 0 | 85 | 98 | 0 | 10 | 90 | 60 | 0 | 90 | 90 | 90 |
| Johnsongrass | 0 | 25 | 80 | 45 | 20 | 0 | 0 | 35 | 35 | 20 | 0 | 60 | 0 | 10 |
| Lambsquarters | 35 | 40 | 40 | 25 | 20 | 25 | 0 | 50 | 40 | 35 | 15 | 100 | 70 | 10 |
| Morningglory | 0 | 0 | 5 | 10 | 20 | 0 | 0 | 0 | 0 | 0 | 0 | 0 | 0 | 0 |
| Nutsedge, Yellow | 0 | 0 | 0 | 0 | 0 | 0 | 0 | 0 | 0 | 0 | 0 | 0 | 0 | 0 |
| Oilseed Rape | 75 | 25 | 80 | 10 | 0 | 0 | 80 | 0 | 15 | 75 | 0 | 70 | 30 | 30 |
| Pigweed | 80 | 70 | 60 | 70 | 40 | 40 | 0 | 0 | 0 | 35 | 30 | 70 | 70 | 0 |
| Ragweed | 25 | 40 | 20 | 55 | 5 | 0 | 0 | 25 | 20 | 20 | 0 | 70 | 50 | 40 |
| Ryegrass, Italian | 10 | 0 | 70 | 55 | 25 | 0 | 0 | 50 | 30 | 15 | 0 | 50 | 10 | 30 |
| Soybean | 0 | 20 | 0 | 0 | 0 | 0 | 0 | 10 | 0 | 5 | — | 0 | 0 | 10 |
| Velvetleaf | 10 | 0 | 5 | 0 | 0 | 0 | 0 | 5 | 15 | 25 | 0 | 35 | 5 | 20 |
| Waterhemp | 85 | 75 | 65 | 75 | 50 | 55 | 0 | 10 | 65 | 20 | 35 | 60 | 50 | 50 |
| Wheat | 0 | 0 | 35 | 60 | 0 | 0 | 5 | 30 | 35 | 50 | 0 | 35 | 0 | 15 |

| | Compounds | | | | | | |
|---|---|---|---|---|---|---|---|
| 31 g ai/ha | 667 | 690 | 691 | 695 | 697 | 698 | 700 |
| Preemergence | | | | | | | |
| Barnyardgrass | 95 | 95 | 90 | 90 | 85 | 75 | 75 |
| Blackgrass | 50 | 50 | 0 | 0 | 70 | 0 | 20 |
| Corn | 55 | 20 | 40 | 0 | 40 | 40 | 0 |
| Crabgrass, Large | 95 | 98 | 100 | 90 | 90 | 90 | 95 |
| Foxtail, Giant | 95 | 95 | 95 | 80 | 85 | 85 | 80 |
| Galium | 10 | 95 | 100 | 50 | 0 | 100 | 0 |
| Johnsongrass | 70 | — | — | 40 | 70 | 75 | 100 |
| Lambsquarters | 50 | 75 | 85 | 25 | 35 | 10 | 0 |
| Morningglory | 0 | 0 | 30 | 0 | 10 | 0 | 0 |
| Nutsedge, Yellow | 0 | 0 | 0 | 0 | 0 | 0 | 0 |
| Oilseed Rape | 35 | 75 | 35 | 0 | 20 | 0 | 0 |
| Pigweed | 40 | 75 | 85 | 50 | 75 | 75 | 0 |
| Ragweed | 25 | 25 | 100 | 35 | 60 | 70 | 10 |
| Ryegrass, Italian | 60 | 40 | 0 | 0 | 15 | 0 | 0 |
| Soybean | — | 0 | 0 | 0 | 0 | 35 | 100 |
| Velvetleaf | 5 | 20 | 25 | 0 | 0 | 25 | 0 |
| Waterhemp | 0 | 90 | 85 | 55 | 80 | 85 | 10 |
| Wheat | 0 | 40 | 10 | 40 | 0 | 0 | 0 |

| | Compounds | | | | | Compounds | |
|---|---|---|---|---|---|---|---|
| 16 g ai/ha | 610 | 623 | 690 | 691 | 8 g ai/ha | 623 | 690 |
| Preemergence | | | | | | | |
| Barnyardgrass | 40 | 90 | 95 | 90 | Barnyardgrass | 90 | 85 |
| Blackgrass | 0 | 40 | 0 | 0 | Blackgrass | 0 | 0 |
| Corn | 0 | 30 | 10 | 0 | Corn | 10 | 20 |
| Crabgrass, Large | 95 | 90 | 98 | 98 | Crabgrass, Large | 90 | 95 |
| Foxtail, Giant | 70 | 90 | 95 | 95 | Foxtail, Giant | 85 | 90 |
| Galium | 30 | 85 | 90 | 100 | Galium | 90 | 100 |
| Johnsongrass | 0 | 15 | — | — | Johnsongrass | 50 | — |
| Lambsquarters | 35 | 30 | 65 | 70 | Lambsquarters | 10 | 65 |
| Morningglory | 0 | 0 | 0 | 0 | Morningglory | 0 | 0 |
| Nutsedge, Yellow | 0 | 0 | 0 | 0 | Nutsedge, Yellow | 0 | 0 |
| Oilseed Rape | 0 | 0 | 50 | 0 | Oilseed Rape | 80 | 0 |
| Pigweed | 30 | 85 | 60 | 35 | Pigweed | 75 | 50 |
| Ragweed | 0 | 20 | 10 | 0 | Ragweed | 0 | 0 |
| Ryegrass, Italian | 0 | 20 | 10 | 0 | Ryegrass, Italian | 0 | 0 |
| Soybean | 0 | 0 | 0 | 0 | Soybean | 0 | 0 |
| Velvetleaf | 0 | 0 | 0 | 10 | Velvetleaf | 0 | 0 |
| Waterhemp | 35 | 75 | 80 | 85 | Waterhemp | 45 | 65 |
| Wheat | 0 | 0 | 5 | 10 | Wheat | 20 | 0 |

TABLE C-continued

| Compounds | | | | | | | | | | | | | |
|---|---|---|---|---|---|---|---|---|---|---|---|---|---|
| 250 g ai/ha | 356 | 363 | 364 | 455 | 487 | 596 | 606 | 611 | 612 | 613 | 618 | 633 | 637 |
| Flood | | | | | | | | | | | | | |
| Barnyardgrass | 0 | 0 | 0 | 50 | 65 | 85 | 40 | 75 | 55 | 60 | 80 | 70 | 75 |
| Ducksalad | 0 | 0 | 0 | 100 | 100 | 100 | 70 | 95 | 55 | 100 | 100 | 100 | 90 |
| Rice | 0 | 0 | 0 | 0 | 0 | 10 | 0 | 15 | 15 | 20 | 15 | 10 | 45 |
| Sedge, Umbrella | 0 | 0 | 0 | 0 | 0 | 0 | 0 | 0 | 0 | 0 | 0 | 0 | 0 |

| Compounds | | | | | | | | | | |
|---|---|---|---|---|---|---|---|---|---|---|
| 250 g ai/ha | 638 | 639 | 643 | 644 | 645 | 650 | 661 | 664 | 695 | 697 |
| Flood | | | | | | | | | | |
| Barnyardgrass | 75 | 75 | 90 | 90 | 75 | 75 | 85 | 70 | 70 | 45 |
| Ducksalad | 75 | 100 | 100 | 100 | 95 | 95 | 100 | 100 | 100 | 100 |
| Rice | 25 | 20 | 10 | 0 | 0 | 0 | 10 | 0 | 15 | 70 |
| Sedge, Umbrella | 0 | 0 | 0 | 0 | 0 | 0 | 0 | 0 | 0 | 0 |

| Compounds | | | | | | | | | | | | | |
|---|---|---|---|---|---|---|---|---|---|---|---|---|---|
| 125 g ai/ha | 363 | 364 | 455 | 465 | 487 | 596 | 606 | 611 | 612 | 613 | 618 | 633 | 637 |
| Flood | | | | | | | | | | | | | |
| Barnyardgrass | 0 | 0 | 0 | 70 | 20 | 75 | 20 | 60 | 0 | 50 | 75 | 55 | 60 |
| Ducksalad | 0 | 0 | 80 | 90 | 85 | 90 | 50 | 80 | 0 | 75 | 95 | 75 | 70 |
| Rice | 0 | 0 | 0 | 0 | 0 | 10 | 0 | 0 | 0 | 10 | 15 | 0 | 15 |
| Sedge, Umbrella | 0 | 0 | 0 | 0 | 0 | 0 | 0 | 0 | 0 | 0 | 0 | 0 | 0 |

| Compounds | | | | | | | | | | |
|---|---|---|---|---|---|---|---|---|---|---|
| 125 g ai/ha | 638 | 639 | 643 | 644 | 645 | 650 | 661 | 664 | 695 | 697 |
| Flood | | | | | | | | | | |
| Barnyardgrass | 60 | 70 | 65 | 75 | 65 | 60 | 80 | 70 | 65 | 45 |
| Ducksalad | 60 | 90 | 75 | 100 | 80 | 90 | 95 | 85 | 80 | 60 |
| Rice | 25 | 20 | 0 | 0 | 0 | 0 | 0 | 0 | 15 | 50 |
| Sedge, Umbrella | 0 | 0 | 0 | 0 | 0 | 0 | 0 | 0 | 0 | 0 |

| Compounds | | | | | | | | | | | | | |
|---|---|---|---|---|---|---|---|---|---|---|---|---|---|
| 62 g ai/ha | 356 | 363 | 364 | 455 | 465 | 487 | 596 | 606 | 611 | 612 | 613 | 618 | 633 |
| Flood | | | | | | | | | | | | | |
| Barnyardgrass | 0 | 0 | 0 | 0 | 45 | 15 | 60 | 0 | 0 | 0 | 30 | 50 | 40 |
| Ducksalad | 0 | 0 | 0 | 40 | 65 | 45 | 60 | 0 | 0 | 0 | 60 | 60 | 60 |
| Rice | 0 | 0 | 0 | 0 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 | 0 | 0 |

| Compounds | | | | | | | | | | | |
|---|---|---|---|---|---|---|---|---|---|---|---|
| 62 g ai/ha | 637 | 638 | 639 | 643 | 644 | 645 | 650 | 661 | 664 | 695 | 697 |
| Flood | | | | | | | | | | | |
| Barnyardgrass | 40 | 55 | 50 | 35 | 60 | 40 | 20 | 70 | 65 | 60 | 30 |
| Ducksalad | 45 | 40 | 75 | 50 | 65 | 60 | 70 | 75 | 70 | 50 | 40 |
| Rice | 15 | 25 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 | 0 |

| Compounds | | | | | | | | | | | | | |
|---|---|---|---|---|---|---|---|---|---|---|---|---|---|
| 31 g ai/ha | 363 | 364 | 455 | 465 | 487 | 596 | 606 | 611 | 612 | 613 | 618 | 633 | 637 |
| Flood | | | | | | | | | | | | | |
| Barnyardgrass | 0 | 0 | 0 | 25 | 0 | 0 | 0 | 0 | 0 | 0 | 35 | 10 | 35 |
| Ducksalad | 0 | 0 | 0 | 45 | 30 | 30 | 0 | 0 | 0 | 0 | 60 | 0 | 30 |
| Rice | 0 | 0 | 0 | 0 | 0 | 0 | 0 | 0 | 0 | 0 | 0 | 0 | 15 |
| Sedge, Umbrella | 0 | 0 | 0 | 0 | 0 | 0 | 0 | 0 | 0 | 0 | 0 | 0 | 0 |

TABLE C-continued

| 31 g ai/ha | Compounds | | | | | | | | | |
|---|---|---|---|---|---|---|---|---|---|---|
| | 638 | 639 | 643 | 644 | 645 | 650 | 661 | 664 | 695 | 697 |
| Flood | | | | | | | | | | |
| Barnyardgrass | 45 | 0 | 0 | 40 | 30 | 20 | 25 | 0 | 20 | 0 |
| Ducksalad | 0 | 50 | 20 | 55 | 30 | 60 | 65 | 45 | 30 | 40 |
| Rice | 20 | 0 | 0 | 0 | 0 | 0 | 0 | 0 | 0 | 0 |
| Sedge, Umbrella | 0 | 0 | 0 | 0 | 0 | 0 | 0 | 0 | 0 | 0 |

| 16 g ai/ha | Compound 465 |
|---|---|
| Flood | |
| Barnyardgrass | 0 |
| Ducksalad | 0 |
| Rice | 0 |
| Sedge, Umbrella | 0 |

Test D

Seeds of plant species selected from bluegrass (annual bluegrass, *Poa annua*), blackgrass (*Alopecurus myosuroides*), canarygrass (littleseed canarygrass, *Phalaris minor*), chickweed (common chickweed, *Stellaria media*), galium (catchweed bedstraw, *Galium aparine*), bromegrass, downy (downy bromegrass, *Bromus tectorum*), field poppy (*Papaver rhoeas*), field violet (*Viola arvensis*), foxtail, green (green foxtail, *Setaria viridis*), deadnettle (henbit deadnettle, *Lamium amplexicaule*), ryegrass, Italian (Italian ryegrass, *Lolium multiflorum*), kochia (*Kochia scoparia*), lambsquarters (*Chenopodium album*), oilseed rape (*Brassica napus*), pigweed (*Amaranthus retroflexus*), chamomile (scentless chamomile, *Matricaria inodora*), Russian thistle (*Salsola kali*), speedwell (bird's-eye speedwell, *Veronica persica*), barley, spring (spring barley, *Hordeum vulgare*), wheat, spring (spring wheat, *Triticum aestivum*), buckwheat, wild (wild buckwheat, *Polygonum convolvulus*), mustard, wild (wild mustard, *Sinapis arvensis*), oat, wild (wild oat, *Avena fatua*), radish, wild (wild radish, *Raphanus raphanistrum*), windgrass (*Apera spica-venti*), barley, winter (winter barley *Hordeum vulgare*), and wheat, winter (winter wheat, *Triticum aestivum*) were planted into a silt loam soil and treated preemergence with test chemicals formulated in a non-phytotoxic solvent mixture which included a surfactant. Treated plants and controls were maintained in a controlled growth environment approximately 21 d after which time all species were compared to controls and visually evaluated. Plant response ratings, summarized in Table D, are based on a scale of 0 to 100 where 0 is no effect and 100 is complete control. A dash (-) response means no test result.

TABLE D

| 250 g ai/ha | Compounds | | | | 125 g ai/ha | Compounds | | | |
|---|---|---|---|---|---|---|---|---|---|
| | 623 | 624 | 636 | 637 | | 623 | 624 | 636 | 637 |
| Preemergence | | | | | | | | | |
| Barley, Spring | 65 | 40 | 75 | 70 | Barley, Spring | 35 | 5 | 60 | 40 |
| Barley, Winter | 65 | 40 | 80 | 60 | Barley, Winter | 40 | 0 | 55 | 50 |
| Blackgrass | 70 | 85 | 75 | 50 | Blackgrass | 45 | 15 | 60 | 45 |
| Bluegrass | 85 | 65 | 100 | 100 | Bluegrass | 70 | 55 | 90 | 75 |
| Bromegrass, Downy | 65 | 20 | 80 | 40 | Bromegrass, Downy | 40 | 20 | 55 | 25 |
| Buckwheat, Wild | 45 | 50 | 80 | 80 | Buckwheat, Wild | 15 | 15 | 90 | 15 |
| Canarygrass | 85 | 45 | 95 | 70 | Canarygrass | 85 | 25 | 90 | 50 |
| Chamomile | 100 | 100 | 100 | 90 | Chamomile | 85 | 90 | 100 | 90 |
| Chickweed | 95 | 85 | 90 | 75 | Chickweed | 95 | 60 | 90 | 65 |
| Deadnettle | 75 | 70 | 75 | 65 | Deadnettle | 75 | 25 | 70 | 25 |
| Field Poppy | 100 | 100 | 100 | 100 | Field Poppy | 85 | 100 | 100 | 100 |
| Field Violet | 15 | 10 | 85 | 0 | Field Violet | 10 | 10 | 35 | 0 |
| Foxtail, Green | 98 | 95 | 100 | 100 | Foxtail, Green | 98 | 90 | 100 | 95 |
| Galium | 80 | 0 | 60 | 10 | Galium | 15 | 0 | 30 | 30 |
| Kochia | 95 | 85 | 75 | 85 | Kochia | 95 | 15 | 75 | 35 |
| Lambsquarters | 95 | 60 | 90 | 75 | Lambsquarters | 80 | 35 | 80 | 40 |
| Mustard, Wild | 85 | 70 | 85 | 15 | Mustard, Wild | 85 | — | 15 | 15 |
| Oat, Wild | 60 | 35 | 85 | 85 | Oat, Wild | 55 | 15 | 80 | 75 |
| Oilseed Rape | 75 | 65 | 65 | 65 | Oilseed Rape | 25 | 35 | 60 | 40 |
| Pigweed | 100 | 98 | 85 | 98 | Pigweed | 95 | 95 | 50 | 100 |
| Radish, Wild | 85 | 75 | 100 | 90 | Radish, Wild | 50 | 0 | 65 | 20 |
| Russian Thistle | 70 | 50 | 60 | 50 | Russian Thistle | 60 | 10 | 50 | 10 |
| Ryegrass, Italian | 65 | 25 | 80 | 20 | Ryegrass, Italian | 40 | 25 | 65 | 20 |
| Speedwell | 90 | 100 | — | 100 | Speedwell | 100 | 100 | — | 100 |
| Wheat, Spring | 45 | 40 | 80 | 70 | Wheat, Spring | 20 | 15 | 45 | 80 |
| Wheat, Winter | 40 | 10 | 65 | 75 | Wheat, Winter | 20 | 5 | 70 | 60 |
| Windgrass | 95 | 95 | 98 | 95 | Windgrass | 95 | 85 | 95 | 85 |

TABLE D-continued

| 62 g ai/ha | Compounds | | | | 31 g ai/ha | Compounds | | | |
| --- | --- | --- | --- | --- | --- | --- | --- | --- | --- |
| | 623 | 624 | 636 | 637 | | 623 | 624 | 636 | 637 |
| Preemergence | | | | | | | | | |
| Barley, Spring | 15 | 0 | 55 | 20 | Barley, Spring | 5 | 0 | 35 | 0 |
| Barley, Winter | 10 | 0 | 45 | 0 | Barley, Winter | 5 | 0 | 5 | 0 |
| Blackgrass | 40 | 5 | 30 | 10 | Blackgrass | 30 | 5 | 25 | 10 |
| Bluegrass | 65 | 25 | 95 | 25 | Bluegrass | 25 | 10 | 35 | 5 |
| Bromegrass, Downy | 30 | 10 | 20 | 10 | Bromegrass, Downy | 15 | 0 | 10 | 0 |
| Buckwheat, Wild | 10 | 0 | 75 | 10 | Buckwheat, Wild | 0 | 0 | 5 | 0 |
| Canarygrass | 70 | 15 | 85 | 0 | Canarygrass | 25 | 0 | 65 | 0 |
| Chamomile | 80 | 95 | 100 | — | Chamomile | 20 | 0 | 90 | 0 |
| Chickweed | 95 | — | 85 | 5 | Chickweed | 65 | 15 | 85 | 0 |
| Deadnettle | 65 | 0 | 35 | 0 | Deadnettle | 25 | 0 | 0 | 0 |
| Field Poppy | 80 | 25 | 95 | 100 | Field Poppy | 80 | 15 | 90 | 100 |
| Field Violet | 0 | 10 | 0 | 0 | Field Violet | 0 | 10 | 0 | 0 |
| Foxtail, Green | 98 | 50 | 100 | 80 | Foxtail, Green | 95 | 40 | 100 | 75 |
| Galium | 5 | 0 | 15 | 20 | Galium | 0 | 0 | 0 | 0 |
| Kochia | 75 | 5 | 25 | 0 | Kochia | 25 | 0 | 5 | 5 |
| Lambsquarters | 60 | 70 | 70 | 60 | Lambsquarters | 55 | 0 | 35 | 50 |
| Mustard, Wild | 15 | 30 | 15 | 5 | Mustard, Wild | 10 | 15 | 0 | 5 |
| Oat, Wild | 30 | 5 | 30 | 30 | Oat, Wild | 25 | 0 | 5 | 20 |
| Oilseed Rape | 20 | 25 | 30 | 40 | Oilseed Rape | 15 | 0 | 10 | 0 |
| Pigweed | 95 | 80 | 10 | 90 | Pigweed | 75 | 35 | 0 | 20 |
| Radish, Wild | 15 | — | 25 | 20 | Radish, Wild | 0 | 0 | — | — |
| Russian Thistle | 25 | 30 | 40 | 0 | Russian Thistle | 15 | 0 | 0 | 0 |
| Ryegrass, Italian | 15 | 0 | 40 | 0 | Ryegrass, Italian | 0 | 0 | 15 | 0 |
| Speedwell | 100 | 90 | — | 60 | Speedwell | 95 | 90 | — | 15 |
| Wheat, Spring | 10 | 10 | 40 | 30 | Wheat, Spring | 5 | 5 | 20 | 5 |
| Wheat, Winter | 20 | 0 | 60 | 40 | Wheat, Winter | 5 | 0 | 5 | 5 |
| Windgrass | 90 | 25 | 95 | 25 | Windgrass | 85 | 15 | 85 | 10 |

Test E

Seeds of plant species selected from corn (*Zea mays*), soybean (*Glycine max*), velvetleaf (*Abutilon theophrasti*), lambsquarters (*Chenopodium album*), poinsettia, wild (wild poinsettia, *Euphorbia heterophylla*), pigweed, palmer (palmer pigweed, *Amaranthus palmeri*), waterhemp (common waterhemp, *Amaranthus rudis*), surinam grass (*Brachiaria decumbens*), crabgrass, large (large crabgrass, *Digitaria sanguinalis*), crabgrass, Brazil (Brazilian crabgrass, *Digitaria horizontalis*), panicum, fall (fall panicum, *Panicum dichotomiflorum*), foxtail, giant (giant foxtail, *Setaria faberii*), foxtail, green (green foxtail, *Setaria viridis*), goosegrass (*Eleusine indica*), johnsongrass (*Sorghum halepense*), ragweed (common ragweed, *Ambrosia elatior*), barnyardgrass (*Echinochloa crus-galli*), sandbur (southern sandbur, *Cenchrus echinatus*), arrowleaf sida (*Sida rhombifolia*), ryegrass, Italian (Italian ryegrass, *Lolium multiflorum*), dayflower, VA (Virginia dayflower, *Commelina virginica*), field bindweed (*Convolvulus arvensis*), morningglory (*Ipomoea coccinea*), nightshade (eastern black nightshade, *Solanum ptycanthum*), kochia (*Kochia scoparia*), nutsedge, yellow (yellow nutsedge, *Cyperus esculentus*), horseweed (*Conyza canadensis*), and beggarticks (hairy beggarticks, *Bidens pilosa*), were planted into a silt loam soil and treated preemergence with test chemicals formulated in a non-phytotoxic solvent mixture which included a surfactant.

At the same time, plants selected from these crop and weed species were planted in pots containing Sunshine Redi-Earth® planting medium comprising spaghnum peat moss, vermiculite, starter nutrients and dolomitic limestone and treated with postemergence applications of a test chemical formulated in the same manner. Plants ranged in height from 2 to 18 cm (1- to 4-leaf stage) for postemergence treatments. Treated plants and controls were maintained in a greenhouse for 14 to 21 d, after which time all species were compared to controls and visually evaluated. Plant response ratings, summarized in Table E, are based on a scale of 0 to 100 where 0 is no effect and 100 is complete control. A dash (-) response means no test result.

TABLE E

| 250 g ai/ha | Compound 623 | 125 g ai/ha | Compound 623 |
| --- | --- | --- | --- |
| Postemergence | | | |
| Corn | 4 | Corn | 1 |
| Crabgrass, Large | 55 | Crabgrass, Large | 30 |
| Foxtail, Giant | 69 | Foxtail, Giant | 78 |
| Pigweed, Palmer | 68 | Pigweed, Palmer | 40 |
| Soybean | 35 | Soybean | 19 |
| Waterhemp | 68 | Waterhemp | 65 |

| 62 g ai/ha | Compound 623 | 31 g ai/ha | Compound 623 |
| --- | --- | --- | --- |
| Postemergence | | | |
| Corn | 1 | Corn | 0 |
| Crabgrass, Large | 10 | Crabgrass, Large | 10 |
| Foxtail, Giant | 56 | Foxtail, Giant | 54 |
| Pigweed, Palmer | 43 | Pigweed, Palmer | 19 |
| Soybean | 20 | Soybean | 0 |
| Waterhemp | 55 | Waterhemp | 45 |

| 16 g ai/ha | Compound 623 |
| --- | --- |
| Postemergence | |
| Corn | 0 |
| Crabgrass, Large | 1 |
| Foxtail, Giant | 5 |
| Pigweed, Palmer | 6 |
| Soybean | 0 |
| Waterhemp | 11 |

TABLE E-continued

| Compounds | | | | | | |
|---|---|---|---|---|---|---|
| 250 g ai/ha | 392 | 596 | 623 | 624 | 636 | 637 |
| Preemergence | | | | | | |
| Arrowleaf Sida | 80 | 50 | 90 | 60 | 90 | 0 |
| Barnyardgrass | 95 | 98 | 98 | 65 | 98 | 95 |
| Beggarticks | 0 | 0 | 35 | 50 | 0 | 0 |
| Corn | 70 | 0 | 65 | 20 | 80 | 70 |
| Crabgrass, Brazil | 98 | 100 | 98 | 100 | 98 | 95 |
| Crabgrass, Large | 98 | 98 | 98 | 90 | 98 | 98 |
| Dayflower, VA | 35 | 35 | 35 | 50 | 65 | 20 |
| Field Bindweed | 70 | 15 | 75 | 10 | 70 | 35 |
| Foxtail, Giant | 98 | 98 | 95 | 85 | 95 | 98 |
| Foxtail, Green | 98 | 95 | 98 | 75 | 98 | 98 |
| Goosegrass | 95 | 65 | 98 | 100 | 95 | 90 |
| Horseweed | 100 | — | 90 | 85 | 95 | — |
| Johnsongrass | 95 | 35 | 95 | — | 98 | 60 |
| Kochia | 90 | 90 | 95 | 30 | 95 | 90 |
| Lambsquarters | 100 | 90 | 95 | 85 | 90 | 80 |
| Morningglory | 0 | 0 | 0 | 40 | 0 | 35 |
| Nightshade | 90 | 60 | 70 | 80 | 50 | 40 |
| Nutsedge, Yellow | 0 | 0 | 80 | 10 | 60 | 35 |
| Panicum, Fall | 98 | 90 | 90 | 60 | 90 | 95 |
| Pigweed, Palmer | 90 | 40 | 95 | 30 | 90 | 65 |
| Poinsettia, Wild | 20 | — | — | 40 | — | 25 |
| Ragweed | 65 | 50 | 85 | 30 | 0 | 85 |
| Ryegrass, Italian | 70 | 50 | 90 | 15 | 95 | 35 |
| Sandbur | 90 | 95 | 90 | 50 | 95 | 90 |
| Soybean | 25 | 0 | 0 | 10 | 0 | 35 |
| Surinam Grass | 30 | 95 | 90 | 70 | 95 | 90 |
| Velvetleaf | 75 | 35 | 65 | 20 | 40 | 35 |
| Waterhemp | 90 | 50 | 95 | 70 | 80 | 85 |

| Compounds | | | | | | |
|---|---|---|---|---|---|---|
| 125 g ai/ha | 392 | 596 | 623 | 624 | 636 | 637 |
| Preemergence | | | | | | |
| Arrowleaf Sida | 65 | 30 | 85 | 40 | 80 | 0 |
| Barnyardgrass | 90 | 98 | 98 | 50 | 98 | 80 |
| Beggarticks | 0 | 0 | 0 | 40 | 0 | 0 |
| Corn | 50 | 0 | 75 | 10 | 80 | 35 |
| Crabgrass, Brazil | 98 | 100 | 98 | 95 | 98 | 98 |
| Crabgrass, Large | 98 | 98 | 98 | 80 | 98 | 98 |
| Dayflower, VA | 0 | 40 | 20 | 30 | 35 | 0 |
| Field Bindweed | 35 | 0 | 70 | 5 | 80 | 0 |
| Foxtail, Giant | 98 | 98 | 95 | 70 | 95 | 98 |
| Foxtail, Green | 95 | 95 | 98 | 65 | 95 | 95 |
| Goosegrass | 95 | 25 | 98 | 80 | 90 | 65 |
| Horseweed | 98 | — | 90 | — | 95 | — |
| Johnsongrass | 50 | 0 | 85 | 35 | 95 | 25 |
| Kochia | 80 | 80 | 95 | 0 | 90 | 90 |
| Lambsquarters | 98 | 80 | 100 | 50 | 90 | 90 |
| Morningglory | 0 | 0 | 0 | 50 | 0 | 35 |
| Nightshade | 90 | 0 | 70 | 80 | 40 | 25 |
| Nutsedge, Yellow | 0 | 0 | 40 | 0 | 0 | 0 |
| Panicum, Fall | 98 | 0 | 90 | 30 | 100 | 90 |
| Pigweed, Palmer | 35 | 0 | 95 | 20 | 80 | 0 |
| Poinsettia, Wild | 35 | — | — | 30 | — | 20 |
| Ragweed | 0 | 25 | 95 | 30 | — | 20 |
| Ryegrass, Italian | 60 | 35 | 60 | 10 | 95 | 35 |
| Sandbur | 60 | 90 | 90 | 50 | 90 | 90 |
| Soybean | 20 | 0 | 0 | 20 | 0 | 25 |
| Surinam Grass | 15 | 95 | 90 | 40 | 95 | 75 |
| Velvetleaf | 50 | 0 | 65 | 10 | 60 | 30 |
| Waterhemp | 70 | 0 | 95 | 75 | 70 | 65 |

| Compounds | | | | | | |
|---|---|---|---|---|---|---|
| 62 g ai/ha | 392 | 596 | 623 | 624 | 636 | 637 |
| Preemergence | | | | | | |
| Arrowleaf Sida | 15 | 30 | 80 | 50 | 65 | 0 |
| Barnyardgrass | 70 | 98 | 95 | 30 | 95 | 70 |
| Beggarticks | 0 | 0 | 0 | 25 | 0 | 0 |
| Corn | 15 | 0 | 60 | 0 | 70 | 0 |
| Crabgrass, Brazil | 98 | 95 | 98 | 80 | 95 | 85 |
| Crabgrass, Large | 95 | 95 | 98 | 85 | 98 | 95 |
| Dayflower, VA | 0 | 40 | 0 | 0 | 0 | 0 |
| Field Bindweed | 0 | 0 | 60 | 10 | 75 | 0 |
| Foxtail, Giant | 95 | 95 | 95 | 50 | 95 | 95 |
| Foxtail, Green | 90 | 95 | 95 | 20 | 95 | 75 |
| Goosegrass | 90 | 5 | 98 | 75 | 80 | 0 |
| Horseweed | 0 | — | 90 | 90 | 90 | — |
| Johnsongrass | 30 | 0 | 60 | 0 | 95 | 0 |
| Kochia | 90 | 25 | 90 | — | 90 | 40 |
| Lambsquarters | 75 | 25 | 90 | 0 | 90 | 0 |
| Morningglory | 0 | 0 | 0 | 20 | 0 | 0 |
| Nightshade | 80 | 0 | 35 | 75 | 0 | 15 |
| Nutsedge, Yellow | 0 | 0 | 20 | 0 | 0 | 0 |
| Panicum, Fall | 98 | 0 | 90 | 0 | 90 | 35 |
| Pigweed, Palmer | 20 | 0 | 90 | 25 | 10 | 0 |
| Poinsettia, Wild | 0 | — | — | 20 | — | 0 |
| Ragweed | 0 | 0 | 90 | 20 | — | 0 |
| Ryegrass, Italian | 10 | 0 | 50 | 0 | 65 | 50 |
| Sandbur | 60 | 90 | 90 | 30 | 90 | 35 |
| Soybean | 0 | 0 | 0 | 10 | 0 | 10 |
| Surinam Grass | 0 | 65 | 90 | 30 | 90 | 50 |
| Velvetleaf | 20 | 0 | 50 | 0 | 35 | 0 |
| Waterhemp | 80 | 0 | 90 | 60 | 80 | 40 |

| Compounds | | | | | | |
|---|---|---|---|---|---|---|
| 31 g ai/ha | 392 | 596 | 623 | 624 | 636 | 637 |
| Preemergence | | | | | | |
| Arrowleaf Sida | 0 | 35 | 20 | 50 | 35 | 0 |
| Barnyardgrass | 85 | 95 | 95 | 0 | 95 | 85 |
| Beggarticks | 0 | 0 | 0 | 20 | 0 | 0 |
| Corn | 0 | 0 | 0 | 0 | 65 | 0 |
| Crabgrass, Brazil | 98 | 100 | 98 | 80 | 95 | 75 |
| Crabgrass, Large | 90 | 95 | 98 | 30 | 98 | 90 |
| Dayflower, VA | 0 | 0 | 0 | 0 | 0 | 0 |
| Field Bindweed | 0 | 0 | 0 | 0 | 0 | 0 |
| Foxtail, Giant | 90 | 95 | 95 | 20 | 95 | 75 |
| Foxtail, Green | 65 | 95 | 95 | 20 | 95 | 65 |
| Goosegrass | 85 | 5 | 95 | 50 | 50 | 0 |
| Horseweed | 0 | — | 80 | 30 | 0 | 0 |
| Johnsongrass | 25 | 0 | 40 | 0 | 90 | 0 |
| Kochia | 85 | 0 | 90 | 0 | 85 | 0 |
| Lambsquarters | 75 | 25 | 90 | 0 | 90 | — |
| Morningglory | 0 | 0 | 0 | 10 | 0 | 0 |
| Nightshade | 20 | 0 | — | 70 | 0 | 0 |
| Nutsedge, Yellow | 0 | 0 | 0 | 0 | 0 | 0 |
| Panicum, Fall | 95 | 0 | 90 | 0 | 90 | 0 |
| Pigweed, Palmer | 0 | 0 | 75 | 0 | 0 | 0 |
| Poinsettia, Wild | 0 | — | — | 20 | — | 0 |
| Ragweed | 0 | 0 | 60 | 20 | 0 | 0 |
| Ryegrass, Italian | 0 | 0 | 25 | 0 | 40 | 0 |
| Sandbur | 0 | 85 | 90 | 10 | 90 | 0 |
| Soybean | 0 | 0 | 0 | 0 | 0 | 0 |
| Surinam Grass | 0 | 35 | 75 | 20 | 40 | 10 |
| Velvetleaf | 0 | 0 | 0 | 0 | 20 | 0 |
| Waterhemp | 35 | 0 | 90 | 50 | 25 | 50 |

Test F

Plant species in the flooded paddy test consisted of one stand of 9 or 10 water seeded rice seedlings (Rice, W. S. Jap, *Oryza sativa* cv. 'Japonica—M202' or Rice, W. S. Ind, 'Indica'), and two stands of 3 or 4 transplanted rice seedlings (*Oryza sativa* cv. 'Japonica—M202'), monochoria (*Monochorea vaginalis*), sedge, umbrella (small-flower umbrella sedge, *Cyperus difformis*), hardstem bulrush (*Scirpus juncoides*), redstem (purple redstem, *Ammannia coccinea*), rice flatsedge (*Cyperus iria*), bearded sprangletop (*Leptochloa fascicularis*), barnyardgrass (*Echinochloa crus-galli*), waterplantain (common waterplantain, *Alisma plantago-aquatica*), and late watergrass (*Echinochloa oryzicola*) grown to the 2 to 2.5 leaf stage for testing. Potted plants were grown in a greenhouse with day/night temperature settings of 30/27° C., and supplemental balanced lighting was provided to maintain a 16-hour photoperiod. At time of treatment, test pots were flooded to 3 cm above the soil surface, treated by application of test compounds directly to the paddy water, and then maintained at that water depth for the duration of the test. Effects of treatments on rice and weeds were visually evaluated by comparison to untreated controls after 21 d. Plant response ratings, summarized in Table F, are based on a scale of 0 to 100 where 0 is no effect and 100 is complete control. A dash (-) response means no test result.

CAS RN 9005-64-5) to give a final dose of 15.625, 62.5 or 250 g/ha of test compound.

The test plants were then grown on under controlled conditions in a glasshouse (at 24/16° C., day/night; 14 hours light; 65% humidity) and watered twice daily. After 13 days the test was evaluated (100=total damage to plant; 0=no damage to plant). A dash (-) means no test result. Results are shown below.

TABLE F

| 250 g ai/ha | Compounds | | | | 250 g ai/ha | Compounds | | | |
|---|---|---|---|---|---|---|---|---|---|
| | 465 | 596 | 617 | 639 | | 465 | 596 | 617 | 639 |
| Flood | | | | | | | | | |
| Barnyardgrass | 100 | 100 | 100 | 100 | Rice, Water Seeded | 60 | 15 | 60 | 75 |
| Bulrush, Hardstem | — | — | — | — | Sedge, Umbrella | 0 | — | 0 | 0 |
| Flatsedge, Rice | 0 | — | 0 | 0 | Sprangletop, Brdd. | 95 | 95 | 90 | 98 |
| Monochoria | 100 | 100 | 100 | 100 | Watergrass, Late | 100 | 100 | 100 | 100 |
| Redstem | 45 | — | 0 | 30 | Waterplantain | 100 | — | 90 | 100 |
| Rice, Transplanted | 15 | 0 | 0 | 40 | | | | | |

| 125 g ai/ha | Compounds | | | | 64 g ai/ha | Compounds | | | |
|---|---|---|---|---|---|---|---|---|---|
| | 465 | 596 | 617 | 639 | | 465 | 596 | 617 | 639 |
| Flood | | | | | | | | | |
| Barnyardgrass | 100 | 100 | 100 | 100 | Barnyardgrass | 100 | 100 | 85 | 100 |
| Bulrush, Hardstem | — | — | — | — | Bulrush, Hardstem | — | — | — | — |
| Flatsedge, Rice | 0 | — | 0 | 0 | Flatsedge, Rice | 0 | — | 0 | 0 |
| Monochoria | 100 | 100 | 70 | 100 | Monochoria | 75 | 100 | 40 | 98 |
| Redstem | 0 | — | 0 | 0 | Redstem | 0 | — | 0 | 0 |
| Rice, Transplanted | 0 | 0 | 0 | 25 | Rice, Transplanted | 0 | 0 | 0 | 15 |
| Rice, Water Seed. | 35 | 10 | 20 | 50 | Rice, Water Seed. | 0 | 10 | 0 | 40 |
| Sedge, Umbrella | 0 | — | 0 | 0 | Sedge, Umbrella | 0 | — | 0 | 0 |
| Sprangletop, Brdd. | 95 | 85 | 85 | 95 | Sprangletop, Brdd. | 85 | 85 | 80 | 85 |
| Watergrass, Late | 100 | 100 | 100 | 100 | Watergrass, Late | 00 | 85 | 100 | 100 |
| Waterplantain | 90 | — | 85 | 98 | Waterplantain | 40 | — | 75 | 80 |

| 32 g ai/ha | Compounds | | | | 16 g ai/ha | Compounds |
|---|---|---|---|---|---|---|
| | 465 | 596 | 617 | 639 | | 596 |
| Flood | | | | | | |
| Barnyardgrass | 100 | 65 | 60 | 90 | Barnyardgrass | 45 |
| Bulrush, Hardstem | — | — | — | — | Monochoria | 25 |
| Flatsedge, Rice | 0 | — | 0 | 0 | Rice, Transplanted | 0 |
| Monochoria | 50 | 45 | 0 | 65 | Rice, Water Seeded | 0 |
| Redstem | 0 | — | 0 | 0 | Sprangletop, Brdd. | 0 |
| Rice, Transplanted | 0 | 0 | 0 | 0 | Watergrass, Late | 15 |
| Rice, Water Seeded | 0 | 0 | 0 | 0 | | |
| Sedge, Umbrella | 0 | — | 0 | 0 | | |
| Sprangletop, Brdd. | 85 | 40 | 0 | 85 | | |
| Watergrass, Late | 85 | 40 | 100 | 100 | | |
| Waterplantain | 0 | — | 0 | 80 | | |

Test G

Pre-Emergence Protocol

Seeds of corn (*Zea mays*), giant foxtail (*Setaria faberi*), barnyardgrass (*Echinochloa crus-galli*), ivy-leaved morning glory (*Ipomoea hederacea*), redroot pigweed (*Amaranthus retroflexus*) and velvetleaf (*Abutilon theophrasti*) were sown in standard soil in pots. After cultivation for one day under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethylene sorbitan monolaurate, CAS RN 9005-64-5) to give a final dose of 15.625, 62.5 or 250 g/ha of test compound.

Post-Emergence Protocol

Seeds of corn (*Zea mays*), giant foxtail (*Setaria faberi*), barnyardgrass (*Echinochloa crus-galli*), ivy-leaved morning glory (*Ipomoea hederacea*), redroot pigweed (*Amaranthus retroflexus*) and velvetleaf (*Abutilon theophrasti*) were sown in standard soil in pots. After cultivation for 8 days under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethylene sorbitan monolaurate, CAS RN 9005-64-5) to give a final dose of 15.625, 62.5 or 250 g/ha of test compound.

The test plants were then grown on under controlled conditions in a glasshouse (at 24/16° C., day/night; 14 hours light; 65% humidity) and watered twice daily. After 13 days the test was evaluated (100=total damage to plant; 0=no damage to plant). A dash (-) means no test result. Results are shown below.

| | Pre-Emergence (250 g ai/ha) | | | | | |
|---|---|---|---|---|---|---|
| Cmpd | Barnyard grass | Corn | Foxtail, Giant | Morning-glory, Ivy-leaved | Pigweed, Redroot | Velvetleaf |
| 1396 | 90 | 80 | 100 | 70 | 80 | 80 |
| 1397 | 90 | 90 | 90 | 80 | 80 | 70 |
| 1398 | 90 | 90 | 90 | 80 | 80 | 80 |
| 1399 | 90 | 60 | 90 | 60 | 80 | 70 |
| 1400 | 80 | 60 | 90 | — | 90 | 60 |
| 1401 | 80 | 20 | 90 | 20 | 90 | 70 |
| 1402 | 90 | 90 | 90 | 80 | 80 | 80 |
| 1403 | 0 | 0 | 0 | 0 | 0 | 0 |
| 1404 | 70 | 0 | 80 | 20 | 20 | 0 |
| 1405 | 0 | 0 | 0 | 0 | 0 | 0 |
| 1406 | 0 | 0 | 0 | 0 | 0 | 0 |
| 1407 | 90 | 0 | 90 | 0 | 0 | 0 |
| 1408 | 20 | 10 | 70 | 0 | 10 | 0 |
| 1409 | 10 | 0 | 40 | 0 | 0 | 0 |
| 1410 | 20 | 0 | 80 | 10 | 10 | 20 |
| 1411 | 0 | 0 | 0 | 0 | 0 | 0 |
| 1412 | 60 | 10 | 80 | 0 | 10 | 10 |
| 1413 | 80 | 0 | 90 | 0 | 20 | 0 |
| 1414 | 80 | 50 | 80 | 20 | 0 | 0 |
| 1415 | 70 | 0 | 80 | 0 | 10 | 0 |
| 1416 | 0 | 0 | 0 | 0 | 0 | 0 |
| 1417 | 80 | 0 | 90 | 30 | 30 | 0 |
| 1418 | 90 | 0 | 80 | 0 | 0 | 0 |
| 1419 | 90 | 50 | 90 | 60 | 70 | 0 |
| 1420 | 80 | 70 | 80 | 0 | 0 | 0 |
| 1421 | 80 | 10 | 90 | 0 | 0 | 0 |
| 1422 | 0 | 0 | 50 | 0 | 0 | 0 |
| 1423 | 30 | 10 | 70 | 0 | 0 | 0 |
| 1424 | 50 | 0 | 70 | 0 | 0 | 0 |
| 1425 | 60 | 0 | 80 | 0 | 0 | 0 |
| 1426 | 20 | 0 | 70 | 0 | 0 | 0 |
| 1427 | 0 | 0 | 0 | 0 | 0 | 0 |
| 1428 | 80 | 70 | 80 | 40 | 80 | 0 |
| 1429 | 70 | 0 | 80 | 0 | 0 | 50 |
| 1430 | 60 | 0 | 80 | 0 | 0 | 0 |
| 1431 | 0 | 0 | 0 | 0 | 0 | 0 |
| 1432 | 0 | 0 | 0 | 0 | 0 | 0 |
| 1433 | 0 | 0 | 0 | 0 | 0 | 0 |
| 1434 | 20 | 0 | 50 | 0 | 0 | 0 |
| 1435 | 0 | 0 | 0 | 0 | 0 | 0 |
| 1436 | 0 | 0 | 0 | 0 | 0 | 0 |
| 1437 | 0 | 0 | 0 | 0 | 0 | 0 |
| 1438 | 0 | 0 | 20 | 0 | 0 | 0 |
| 1439 | 40 | 0 | 50 | 0 | 0 | 0 |
| 1440 | 40 | 0 | 80 | 0 | 0 | 0 |
| 1441 | 0 | 0 | 0 | 0 | 0 | 0 |
| 1442 | 0 | 0 | 30 | 0 | 10 | 10 |
| 1443 | 0 | 0 | 0 | 0 | 0 | 0 |
| 1444 | 60 | 50 | 80 | 40 | 50 | 20 |
| 1445 | 0 | 0 | 0 | 0 | 0 | 0 |
| 1446 | 0 | 0 | 40 | 0 | 0 | 0 |
| 1447 | 10 | 20 | 60 | 0 | 0 | 0 |
| 1448 | 0 | 0 | 60 | 0 | 0 | 0 |
| 1449 | 30 | 0 | 80 | 0 | 0 | 0 |
| 1450 | 70 | 0 | 90 | 0 | 80 | 0 |
| 1451 | 0 | 0 | 0 | 0 | 0 | 0 |
| 1452 | 50 | 0 | 60 | 0 | 0 | 30 |
| 1453 | 90 | 0 | 90 | 0 | 0 | 20 |
| 1454 | 70 | 60 | 90 | 10 | 70 | 60 |
| 1455 | 90 | 10 | 90 | 20 | 0 | 0 |
| 1456 | 80 | 40 | 90 | 40 | 90 | 40 |
| 1457 | 50 | 0 | 90 | 0 | 0 | 0 |
| 1458 | 80 | 50 | 80 | 20 | 70 | 30 |
| 1459 | 60 | 0 | 80 | 0 | 60 | 0 |
| 1460 | 90 | 10 | 90 | 50 | 70 | 0 |
| 1461 | 90 | 0 | 90 | 0 | 0 | 0 |
| 1462 | 80 | 0 | 80 | 50 | 0 | 0 |
| 1463 | 90 | 0 | 90 | 0 | 0 | 0 |
| 1464 | 90 | 80 | 90 | 70 | 0 | 0 |
| 1465 | 70 | 0 | 90 | 0 | 0 | 0 |
| 1466 | 0 | 0 | 0 | 0 | 0 | 0 |
| 1468 | 80 | 0 | 90 | 0 | 0 | 0 |
| 1471 | 90 | 0 | 90 | 20 | 0 | 0 |
| 1472 | 80 | 20 | 80 | 0 | 0 | 0 |
| 1473 | 70 | 10 | 80 | 10 | 70 | 0 |
| 1474 | 80 | 40 | 90 | 10 | 20 | 0 |
| 1475 | 80 | 50 | 90 | 10 | 0 | 0 |
| 1476 | 80 | 50 | 80 | 0 | 0 | 0 |
| 1477 | 80 | 50 | 90 | 0 | 0 | 0 |
| 1478 | 30 | 10 | 40 | 0 | 0 | 0 |
| 1479 | 10 | 0 | 20 | 0 | 0 | 10 |
| 1480 | 90 | 80 | 90 | 70 | 40 | 10 |
| 1481 | 80 | 60 | 90 | 10 | 20 | 10 |
| 1482 | 80 | 30 | 90 | 10 | 10 | 10 |
| 1483 | 70 | 40 | 80 | 0 | 80 | 0 |
| 1484 | 30 | 30 | 30 | 0 | 20 | 0 |
| 1485 | 90 | 80 | 90 | 0 | 60 | 30 |
| 1486 | 90 | 40 | 90 | 0 | 60 | 10 |
| 1487 | 80 | 70 | 90 | 20 | 80 | 30 |
| 1488 | 0 | 0 | 0 | 0 | 0 | 0 |
| 1489 | 0 | 0 | 0 | 0 | 100 | 0 |
| 1490 | 80 | 10 | 90 | 0 | 0 | 0 |
| 1491 | 90 | 0 | 80 | 0 | 0 | 0 |
| 1492 | 80 | 0 | 80 | 0 | 0 | 0 |
| 1493 | 90 | 70 | 90 | 10 | 0 | 0 |
| 1494 | 90 | 60 | 80 | 70 | 30 | 0 |
| 1496 | 80 | 20 | 80 | 0 | 0 | 0 |
| 1497 | 80 | 10 | 80 | 20 | 0 | 0 |
| 1498 | 20 | 0 | 10 | 0 | 0 | 0 |
| 1499 | 90 | 80 | 80 | 100 | 0 | 30 |
| 1500 | 90 | 30 | 80 | 20 | 80 | 20 |
| 1501 | 60 | 0 | 80 | — | 0 | 0 |
| 1502 | 80 | 50 | 90 | 0 | 70 | 10 |
| 1503 | 20 | 0 | 30 | 0 | 0 | 0 |
| 1504 | 0 | 0 | 0 | 0 | 0 | 0 |
| 1505 | 20 | 0 | 30 | 0 | 0 | 0 |
| 1506 | 0 | 0 | 0 | 0 | 0 | 0 |
| 1507 | 0 | 0 | 0 | 0 | 0 | 0 |
| 1508 | 0 | 0 | 0 | 0 | 0 | 0 |
| 1509 | 0 | 0 | 0 | 0 | 0 | 0 |
| 1510 | 0 | 0 | 0 | 0 | 0 | 0 |
| 1511 | 0 | 0 | 0 | 0 | 0 | 0 |
| 1512 | 0 | 0 | 0 | 0 | 0 | 0 |
| 1513 | 0 | 0 | 0 | 0 | 0 | 0 |
| 1514 | 0 | 0 | 0 | 0 | 0 | 0 |
| 1515 | 0 | 0 | 0 | 0 | 0 | 0 |
| 1516 | 0 | 0 | 0 | 0 | 0 | 0 |
| 1517 | 90 | 20 | 80 | 0 | 60 | 0 |
| 1518 | 0 | 0 | 0 | 0 | 0 | 0 |
| 1519 | 0 | 0 | 0 | 0 | 0 | 0 |
| 1520 | 90 | 0 | 80 | 0 | 30 | 0 |
| 1522 | 0 | 0 | 0 | 0 | 0 | 0 |
| 1525 | 40 | 0 | 30 | 0 | 0 | 0 |
| 1526 | 80 | 10 | 90 | 0 | 70 | 0 |
| 1527 | 0 | 0 | 0 | 0 | 0 | 0 |
| 1528 | 0 | 0 | 0 | 0 | 0 | 0 |
| 1529 | 0 | 0 | 0 | 0 | 0 | 0 |
| 1530 | 0 | 0 | 0 | 0 | 0 | 0 |
| 1531 | 0 | 0 | 0 | 0 | 0 | 0 |
| 1532 | 0 | 0 | 0 | 0 | 0 | 0 |
| 1533 | 0 | 0 | 0 | 0 | 0 | 0 |
| 1534 | 0 | 0 | 0 | 0 | 0 | 0 |
| 1535 | 0 | 0 | 0 | 0 | 40 | 0 |
| 1536 | 0 | 0 | 0 | 0 | 0 | 0 |
| 1537 | 0 | 0 | 0 | 0 | 0 | 0 |
| 1538 | 50 | 0 | 60 | 70 | 0 | 0 |
| 1539 | 20 | 0 | 20 | 0 | 0 | 0 |
| 1540 | 0 | 0 | 0 | 0 | 40 | 0 |
| 1541 | 30 | 10 | 70 | 0 | 40 | 0 |

-continued

Pre-Emergence (250 g ai/ha)

| Cmpd | Barnyard grass | Corn | Foxtail, Giant | Morning-glory, Ivy-leaved | Pigweed, Redroot | Velvetleaf |
|---|---|---|---|---|---|---|
| 1542 | 10 | 0 | 10 | 0 | 0 | 0 |
| 1543 | 0 | 0 | 0 | 0 | 0 | 0 |
| 1544 | 0 | 0 | 0 | 0 | 0 | 0 |
| 1545 | 0 | 0 | 0 | 0 | 0 | 0 |
| 1546 | 80 | 40 | 90 | 40 | 70 | 0 |
| 1547 | 0 | 0 | 0 | 0 | 0 | 0 |
| 1548 | 0 | 0 | 0 | 0 | 0 | 0 |
| 1549 | 0 | 0 | 0 | 0 | 0 | 0 |
| 1550 | 0 | 0 | 0 | 0 | 0 | 0 |
| 1551 | 0 | 0 | 0 | 0 | 0 | 0 |
| 1552 | 0 | 0 | 0 | 0 | 0 | 0 |
| 1553 | 0 | 0 | 0 | 0 | 0 | 0 |
| 1554 | 10 | 0 | 20 | 0 | 30 | 0 |
| 1555 | 70 | 20 | 70 | 0 | 70 | 0 |
| 1556 | 0 | 0 | 0 | 0 | 20 | 0 |
| 1557 | 10 | 10 | 20 | 0 | 0 | 0 |
| 1558 | 10 | 0 | 0 | 0 | 10 | 0 |
| 1559 | 0 | 0 | 0 | 0 | 0 | 0 |
| 1560 | 10 | 10 | 10 | 0 | 0 | 0 |
| 1561 | 80 | 20 | 70 | 20 | 30 | 10 |
| 1562 | 20 | 0 | 30 | 0 | 0 | 0 |
| 1563 | 0 | 0 | 0 | 0 | 0 | 0 |
| 1564 | 0 | 10 | 0 | 0 | 0 | 0 |
| 1565 | 10 | 0 | 60 | 0 | 10 | 0 |
| 1566 | 0 | 0 | 0 | 0 | 0 | 0 |
| 1567 | 0 | 0 | 0 | 0 | 0 | 0 |
| 1568 | 0 | 0 | 0 | 0 | 0 | 0 |
| 1569 | 0 | 0 | 0 | 0 | 0 | 0 |
| 1570 | 0 | 0 | 0 | 0 | 0 | 0 |
| 1571 | 0 | 0 | 20 | 0 | 0 | 0 |
| 1572 | 0 | 0 | 0 | 0 | 0 | 0 |
| 1573 | 0 | 0 | 0 | 0 | 0 | 0 |
| 1574 | 60 | 0 | 70 | 0 | 30 | 0 |
| 1575 | 0 | 0 | 0 | 0 | 0 | 0 |
| 1576 | 90 | 20 | 70 | 0 | 20 | 0 |
| 1577 | 0 | 0 | 0 | 0 | 0 | 0 |
| 1578 | 0 | 10 | 60 | 0 | 20 | 10 |
| 1579 | 0 | 0 | 0 | 0 | 0 | 0 |
| 1580 | 0 | 0 | 0 | 0 | 0 | 0 |
| 1581 | 0 | 0 | 0 | 0 | 0 | 0 |
| 1582 | 0 | 0 | 0 | 0 | 0 | 0 |
| 1583 | 0 | 0 | 30 | 0 | 30 | 0 |
| 1584 | 90 | 70 | 90 | 10 | 60 | 20 |
| 1585 | 90 | 80 | 90 | 80 | 20 | 30 |
| 1586 | 90 | 30 | 70 | 10 | 60 | 30 |
| 1587 | 0 | 0 | 0 | 0 | 10 | 0 |
| 1588 | 90 | 80 | 90 | 80 | 70 | 20 |
| 1589 | 0 | 0 | 0 | 0 | 0 | 0 |
| 1590 | 60 | 0 | 80 | 0 | 0 | 0 |
| 1591 | 70 | 0 | 80 | 0 | 0 | 10 |
| 1592 | 50 | 0 | 70 | 10 | 30 | 0 |
| 1593 | 20 | 0 | 70 | 0 | 0 | 0 |
| 1594 | 20 | 10 | 30 | 0 | 0 | 0 |
| 1595 | 0 | 0 | 0 | 0 | 0 | 0 |
| 1596 | 70 | 0 | 80 | 100 | 60 | 20 |
| 1597 | 0 | 0 | 0 | 0 | 0 | 0 |
| 1598 | 80 | 70 | 90 | 40 | 50 | 60 |
| 1599 | 70 | 40 | 80 | 10 | 70 | 20 |
| 1600 | 0 | 0 | 0 | 0 | 0 | 0 |
| 1601 | 70 | 0 | 80 | 0 | 50 | 0 |
| 1602 | 40 | 0 | 70 | 0 | 40 | 10 |
| 1603 | 0 | 0 | 0 | 0 | 0 | 0 |
| 1604 | 0 | 0 | 0 | 0 | 0 | 0 |
| 1605 | 0 | 0 | 0 | 0 | 0 | 0 |
| 1606 | 60 | 10 | 90 | 10 | 0 | 0 |
| 1607 | 80 | 10 | 80 | 20 | 30 | 20 |
| 1608 | 0 | 0 | 0 | 0 | 20 | 0 |
| 1609 | 80 | 40 | 80 | 70 | 70 | 30 |
| 1610 | 0 | 0 | 0 | 0 | 0 | 0 |
| 1611 | 0 | 0 | 0 | 0 | 0 | 0 |
| 1612 | 0 | 0 | 0 | 0 | 0 | 0 |
| 1613 | 70 | 0 | 90 | 0 | 10 | 10 |
| 1614 | 0 | 0 | 0 | 0 | 80 | 70 |
| 1615 | 0 | 0 | 0 | 0 | 0 | 0 |
| 1616 | 60 | 0 | 90 | 20 | 60 | 50 |
| 1617 | 80 | 0 | 90 | 0 | 20 | 10 |
| 1618 | 10 | 20 | 20 | 20 | 20 | 10 |
| 1619 | 10 | 0 | 70 | 10 | 20 | 10 |
| 1620 | 0 | 0 | 0 | 0 | 0 | 0 |
| 1621 | 0 | 0 | 0 | 0 | 0 | 0 |
| 1622 | 0 | 0 | 0 | 0 | 0 | 0 |
| 1623 | 60 | 10 | 80 | 10 | 50 | 50 |
| 1624 | 80 | 0 | 80 | 0 | 20 | 10 |
| 1625 | 40 | 0 | 80 | 10 | 10 | 10 |
| 1626 | 0 | 0 | 0 | 0 | 0 | 0 |
| 1627 | 80 | 70 | 80 | 10 | 60 | 20 |
| 1628 | 70 | 0 | 80 | 20 | 50 | 0 |
| 1629 | 70 | 0 | 80 | 50 | 0 | 0 |
| 1630 | 0 | 0 | 0 | 0 | 0 | 0 |
| 1631 | 0 | 0 | 70 | 30 | 10 | 0 |
| 1632 | 0 | 0 | 0 | 0 | 0 | 0 |
| 1633 | 0 | 0 | 0 | 0 | 0 | 0 |
| 1634 | 0 | 0 | 0 | 0 | 0 | 0 |
| 1635 | 0 | 0 | 0 | 0 | 0 | 0 |
| 1636 | 30 | 0 | 60 | 0 | 0 | 0 |
| 1637 | 80 | 30 | 90 | 0 | 60 | 0 |
| 1638 | 0 | 0 | 0 | 0 | 0 | 0 |
| 1639 | 30 | 0 | 80 | 0 | 30 | 0 |
| 1640 | 0 | 0 | 0 | 0 | 0 | 0 |
| 1641 | 0 | 0 | 0 | 0 | 0 | 0 |
| 1642 | 0 | 10 | 20 | 0 | 0 | 0 |
| 1643 | 0 | 0 | 0 | 0 | 0 | 0 |
| 1644 | 0 | 0 | 0 | 0 | 0 | 0 |
| 1645 | 50 | 0 | 60 | 0 | 10 | 10 |
| 1646 | 0 | 0 | 0 | 0 | 0 | 0 |
| 1647 | 0 | 0 | 70 | 0 | 20 | 10 |
| 1648 | 0 | 0 | 0 | 0 | 0 | 0 |
| 1649 | 0 | 0 | 20 | 0 | 20 | 0 |
| 1650 | 90 | 80 | 90 | 0 | 80 | 50 |
| 1651 | 20 | 0 | 80 | 0 | 20 | 10 |
| 1652 | 0 | 10 | 30 | 0 | 0 | 0 |
| 1653 | 80 | 80 | 90 | 20 | 80 | 50 |
| 1654 | 80 | 20 | 90 | — | 0 | 10 |
| 1655 | 0 | 0 | 30 | 0 | 0 | 0 |
| 1656 | 20 | 0 | 80 | 0 | 0 | 0 |
| 1657 | 20 | 0 | 80 | 0 | 50 | 0 |
| 1658 | 0 | 0 | 0 | 0 | 0 | 0 |
| 1659 | 0 | 0 | 0 | 0 | 0 | 0 |
| 1660 | 0 | 0 | 0 | 0 | 0 | 0 |
| 1661 | 0 | 10 | 80 | 10 | 20 | 0 |
| 1662 | 0 | 0 | 0 | 0 | 0 | 0 |
| 1663 | 0 | 0 | 0 | 0 | 0 | 0 |
| 1664 | 80 | 80 | 90 | 0 | 100 | 20 |
| 1665 | 20 | 0 | 80 | 20 | 20 | 0 |
| 1667 | 20 | 0 | 20 | 30 | 0 | 0 |
| 1668 | 20 | 0 | 20 | — | 0 | 0 |
| 1669 | 10 | 0 | 60 | 10 | 20 | 10 |
| 1670 | 0 | 0 | 50 | 0 | 20 | 0 |
| 1671 | 90 | 80 | 90 | 70 | 50 | 60 |
| 1672 | 0 | 0 | 0 | 0 | 0 | 0 |
| 1673 | 0 | 0 | 0 | 0 | 0 | 0 |
| 1674 | 0 | 0 | 0 | 0 | 0 | 0 |
| 1675 | 0 | 0 | 10 | 0 | 0 | 0 |
| 1676 | 0 | 0 | 0 | 0 | 0 | 0 |
| 1677 | 10 | 0 | 70 | 0 | 0 | 0 |
| 1678 | 0 | 0 | 0 | 0 | 0 | 0 |
| 1679 | 90 | 60 | 90 | 10 | 30 | 60 |
| 1680 | 60 | 0 | 90 | 0 | 70 | 90 |
| 1682 | 0 | 0 | 0 | 0 | 0 | 0 |
| 1683 | 80 | 80 | 90 | 60 | 20 | 30 |
| 1684 | 0 | 10 | 0 | 0 | 10 | 0 |
| 1685 | 80 | 60 | 90 | 30 | 60 | 30 |
| 1686 | 70 | 50 | 90 | 60 | 60 | 40 |
| 1687 | 80 | 90 | 90 | 50 | 30 | 10 |
| 1688 | 90 | 70 | 90 | 10 | 60 | 50 |
| 1690 | 90 | 70 | 90 | 0 | 20 | 30 |

Pre-Emergence (250 g ai/ha)

| Cmpd | Barnyard grass | Corn | Foxtail, Giant | Morning-glory, Ivy-leaved | Pigweed, Redroot | Velvetleaf |
|---|---|---|---|---|---|---|
| 1691 | 80 | 80 | 90 | 50 | 30 | 60 |
| 1692 | 80 | 80 | 90 | 30 | 10 | 20 |
| 1693 | 70 | 40 | 70 | 20 | 10 | 10 |
| 1694 | 0 | 0 | 0 | 0 | 0 | 0 |
| 1696 | 80 | 50 | 90 | 20 | 20 | 0 |
| 1697 | 80 | 50 | 80 | 0 | 20 | 20 |
| 1698 | 80 | 70 | 90 | 20 | 40 | 20 |
| 1699 | 90 | 70 | 90 | 70 | 0 | 0 |
| 1700 | 70 | 30 | 90 | 20 | 0 | 0 |
| 1701 | 70 | 30 | 90 | 20 | 10 | 0 |
| 1702 | 90 | 90 | 90 | 40 | 50 | 70 |
| 1703 | 80 | 80 | 90 | 40 | 10 | 30 |
| 1704 | 80 | 80 | 80 | 30 | 0 | 10 |
| 1705 | 70 | 70 | 80 | 10 | 30 | 20 |
| 1706 | 80 | 40 | 90 | 0 | 20 | 10 |
| 1707 | 90 | 80 | 90 | 30 | 40 | 60 |
| 1708 | 60 | 0 | 90 | 20 | 0 | 0 |
| 1709 | 80 | 90 | 90 | 20 | 50 | 30 |
| 1710 | — | — | — | — | — | — |
| 1711 | 80 | 20 | 90 | 10 | 0 | 0 |
| 1712 | 90 | 70 | 90 | 20 | 10 | 20 |
| 1713 | 90 | 90 | 90 | 0 | 0 | 0 |
| 1714 | 80 | 10 | 80 | 10 | 10 | 0 |
| 1716 | 90 | 60 | 90 | 0 | 10 | 10 |
| 1717 | 90 | 0 | 90 | 0 | 20 | 0 |
| 1718 | 90 | 80 | 90 | 10 | 60 | 50 |
| 1719 | 90 | 60 | 90 | 0 | 20 | 0 |
| 1720 | — | — | — | — | — | — |
| 1721 | 80 | 0 | 90 | 0 | 0 | 0 |
| 1722 | 80 | 70 | 90 | 0 | 30 | 20 |
| 1723 | 90 | 60 | 90 | 10 | 30 | 10 |
| 1724 | 90 | 90 | 90 | 0 | 0 | 0 |
| 1725 | 70 | 30 | 80 | 0 | 20 | 0 |
| 1726 | 70 | 30 | 80 | 0 | 10 | 0 |
| 1727 | 80 | 0 | 80 | 10 | 30 | 0 |
| 1728 | 90 | 80 | 90 | 80 | 80 | 80 |
| 1729 | 0 | 0 | 0 | 0 | 0 | 0 |
| 1730 | 70 | 0 | 90 | 0 | 0 | 0 |
| 1731 | 0 | 0 | 20 | 0 | 0 | 0 |
| 1732 | 0 | 0 | 50 | 0 | 10 | 10 |
| 1733 | 70 | 80 | 90 | 80 | 80 | 80 |
| 1734 | 0 | 0 | 10 | 0 | 0 | 0 |
| 1735 | 0 | 0 | 0 | 0 | 0 | 0 |
| 1736 | 90 | 60 | 90 | 0 | 10 | 10 |
| 1737 | 0 | 0 | 0 | 0 | 0 | 0 |
| 1738 | 70 | 0 | 70 | 0 | 0 | 0 |
| 1739 | 0 | 0 | 0 | 0 | 0 | 0 |
| 1740 | 40 | 10 | 90 | 0 | 40 | 50 |
| 1741 | 70 | 30 | 90 | 0 | 30 | 60 |
| 1742 | 80 | 30 | 90 | 10 | 20 | 30 |
| 1743 | 80 | 80 | 90 | 70 | 80 | 80 |
| 1744 | 0 | 0 | 50 | — | 10 | 0 |
| 1745 | 60 | 0 | 50 | 10 | 20 | 0 |
| 1746 | 50 | 0 | 70 | 10 | 20 | 10 |
| 1747 | 80 | 0 | 70 | 0 | 10 | 0 |
| 1748 | 0 | 0 | 0 | 0 | 0 | 0 |
| 1749 | 0 | 0 | 0 | 0 | 0 | 0 |
| 1750 | 10 | 10 | 70 | 0 | 0 | 0 |
| 1751 | 0 | 0 | 10 | 0 | 10 | 0 |
| 1752 | 20 | 0 | 20 | 0 | 0 | 0 |
| 1753 | 80 | 60 | 90 | 80 | 60 | 0 |
| 1754 | 90 | 80 | 90 | 10 | 60 | 30 |
| 1755 | 90 | 80 | 90 | 80 | 70 | 70 |
| 1757 | 10 | 0 | 70 | 0 | 0 | 0 |
| 1760 | 0 | 0 | 30 | 0 | 0 | 0 |
| 1761 | 70 | 0 | 70 | 0 | 0 | 0 |
| 1762 | 80 | 80 | 80 | 10 | 20 | 10 |
| 1763 | 80 | 80 | 90 | 20 | 0 | 0 |
| 1764 | 80 | 70 | 80 | 20 | 30 | 30 |
| 1765 | 60 | 20 | 90 | 0 | 0 | 0 |
| 1766 | 80 | 20 | 70 | 0 | 0 | 10 |
| 1767 | 80 | 60 | 90 | 20 | 0 | 30 |
| 1768 | 0 | 0 | 0 | 0 | 0 | 0 |
| 1769 | 70 | 0 | 90 | 0 | 0 | 0 |
| 1770 | 70 | 0 | 80 | 30 | 10 | 20 |
| 1771 | 0 | 0 | 0 | 0 | 0 | 0 |
| 1772 | 80 | 60 | 90 | 60 | 10 | 40 |
| 1773 | 90 | 80 | 90 | 80 | 70 | 60 |
| 1783 | 90 | 90 | 90 | 40 | 40 | 70 |
| 1784 | 10 | 0 | 40 | 10 | 0 | 0 |
| 1785 | 0 | 0 | 10 | 0 | 20 | 0 |
| 1786 | 20 | 0 | 80 | 0 | 40 | 30 |
| 1787 | 90 | 40 | 90 | 20 | 20 | 20 |
| 1788 | 20 | 0 | 0 | 0 | 0 | 0 |
| 1789 | 0 | 10 | 0 | 0 | 20 | 20 |
| 1790 | 90 | 90 | 90 | 70 | 10 | 40 |
| 1791 | 90 | 80 | 90 | 80 | 10 | 40 |
| 1792 | 80 | 50 | 90 | 0 | 0 | 0 |
| 1793 | 90 | 40 | 90 | 10 | 0 | 30 |
| 1794 | 80 | 80 | 90 | 10 | 80 | 0 |
| 1795 | 80 | 80 | 90 | 60 | 30 | 10 |
| 1796 | 0 | 0 | 0 | 0 | 20 | 10 |
| 1797 | 80 | 70 | 90 | 20 | 60 | 70 |
| 1798 | 10 | 0 | 30 | 0 | 20 | 10 |
| 1799 | 70 | 80 | 90 | 0 | 40 | 20 |
| 1800 | 80 | 0 | 90 | 0 | 10 | 0 |
| 1801 | 90 | 80 | 90 | 40 | 40 | 20 |
| 1802 | 90 | 70 | 90 | 40 | 30 | 70 |
| 1803 | 90 | 30 | 90 | 0 | 40 | 20 |
| 1804 | 90 | 60 | 90 | 10 | 30 | 30 |
| 1805 | 0 | 0 | 10 | 0 | 30 | 20 |
| 1806 | 20 | 0 | 30 | 0 | 10 | 0 |
| 1807 | 0 | 0 | 0 | 0 | 0 | 0 |
| 1808 | 40 | 0 | 70 | 10 | 20 | 10 |
| 1809 | 90 | 90 | 90 | 80 | 60 | 50 |
| 1810 | 90 | 90 | 90 | 70 | 80 | 70 |
| 1811 | 90 | 80 | 90 | 80 | 80 | 70 |
| 1812 | 70 | 40 | 90 | 40 | 70 | 80 |
| 1813 | 10 | 0 | 90 | 20 | 20 | 30 |
| 1814 | 0 | 0 | 0 | 0 | 0 | 0 |
| 1815 | 0 | 0 | 40 | 0 | 0 | 0 |
| 1816 | 90 | 80 | 90 | 80 | 80 | 60 |
| 1817 | 0 | 0 | 10 | 0 | 0 | 0 |
| 1818 | 90 | 70 | 90 | 40 | 40 | 70 |
| 1819 | 90 | 60 | 90 | 0 | 20 | 10 |
| 1820 | 0 | 0 | 0 | 0 | 0 | 0 |
| 1821 | 0 | 0 | 60 | 0 | 20 | 0 |
| 1822 | 90 | 70 | 90 | 80 | 80 | 80 |
| 1823 | 0 | 0 | 0 | 0 | 0 | 0 |
| 1824 | 70 | 0 | 80 | 0 | 20 | 0 |
| 1825 | 0 | 0 | 70 | 0 | 0 | 0 |
| 1826 | 80 | 20 | 90 | 0 | 20 | 0 |
| 1827 | 90 | 50 | 90 | 20 | 0 | 10 |
| 1828 | 90 | 70 | 90 | 30 | 0 | 30 |
| 1829 | 90 | 60 | 90 | 0 | 30 | 20 |
| 1833 | 0 | 0 | 0 | 0 | 0 | 0 |
| 1836 | 80 | 80 | 90 | 30 | 50 | 30 |

Pre-Emergence (62.5 g ai/ha)

| Cmpd | Barnyard grass | Corn | Foxtail, Giant | Morning-glory, Ivy-leaved | Pigweed, Redroot | Velvetleaf |
|---|---|---|---|---|---|---|
| 1396 | 90 | 80 | 90 | 70 | 80 | 70 |
| 1397 | 90 | 80 | 90 | 70 | 20 | 10 |
| 1398 | 90 | 80 | 90 | 60 | 60 | 60 |
| 1399 | 90 | 10 | 90 | 50 | 30 | 40 |
| 1400 | 80 | 40 | 90 | 0 | 80 | 10 |
| 1401 | 30 | 10 | 70 | 0 | 40 | 30 |
| 1402 | 90 | 80 | 90 | 70 | 80 | 70 |
| 1403 | 0 | 0 | 0 | 0 | 0 | 0 |
| 1404 | 20 | 0 | 70 | 10 | 0 | 0 |

Pre-Emergence (62.5 g ai/ha)

| Cmpd | Barnyard grass | Corn | Foxtail, Giant | Morning-glory, Ivy-leaved | Pigweed, Redroot | Velvetleaf |
|---|---|---|---|---|---|---|
| 1405 | 0 | 0 | 0 | 0 | 0 | 0 |
| 1406 | 0 | 0 | 0 | 0 | 0 | 0 |
| 1407 | 80 | 0 | 80 | 0 | 0 | 0 |
| 1408 | 0 | 0 | 20 | 0 | 0 | 0 |
| 1409 | 0 | 0 | 0 | 0 | 0 | 0 |
| 1410 | 0 | 0 | 0 | 0 | 20 | 10 |
| 1411 | 0 | 0 | 0 | 0 | 0 | 0 |
| 1412 | 30 | 10 | 50 | 0 | 20 | 0 |
| 1413 | 20 | 0 | 60 | 0 | 20 | 0 |
| 1414 | 70 | 20 | 80 | 0 | 0 | 0 |
| 1415 | 50 | 0 | 70 | 0 | 0 | 0 |
| 1416 | 0 | 0 | 0 | 0 | 0 | 0 |
| 1417 | 60 | 0 | 80 | 0 | 0 | 0 |
| 1418 | 80 | 0 | 70 | 0 | 0 | 0 |
| 1419 | 80 | 0 | 80 | 0 | 0 | 0 |
| 1420 | 70 | 50 | 80 | 0 | 0 | 0 |
| 1421 | 60 | 0 | 80 | 0 | 0 | 0 |
| 1422 | 0 | 0 | 10 | 0 | 0 | 0 |
| 1423 | 10 | 20 | 60 | 0 | 0 | 0 |
| 1424 | 10 | 0 | 40 | 0 | 0 | 0 |
| 1425 | 40 | 0 | 80 | 0 | 0 | 0 |
| 1426 | 10 | 0 | 50 | 0 | 0 | 0 |
| 1427 | 0 | 0 | 0 | 0 | 0 | 0 |
| 1428 | 60 | 20 | 80 | 10 | 0 | 0 |
| 1429 | 40 | 0 | 70 | 0 | 0 | 0 |
| 1430 | 20 | 0 | 50 | 0 | 0 | 0 |
| 1431 | 0 | 0 | 0 | 0 | 0 | 0 |
| 1432 | 0 | 0 | 0 | 0 | 0 | 0 |
| 1433 | 0 | 0 | 0 | 0 | 0 | 0 |
| 1434 | 0 | 0 | 20 | 0 | 0 | 0 |
| 1435 | 0 | 0 | 0 | 0 | 0 | 0 |
| 1436 | 0 | 0 | 0 | 0 | 0 | 0 |
| 1437 | 0 | 0 | 0 | 0 | 0 | 0 |
| 1438 | 0 | 0 | 0 | 0 | 0 | 0 |
| 1439 | 0 | 0 | 0 | 0 | 0 | 0 |
| 1440 | 10 | 0 | 50 | 0 | 0 | 0 |
| 1441 | 0 | 0 | 0 | 0 | 0 | 0 |
| 1442 | 0 | 0 | 0 | 0 | 0 | 0 |
| 1443 | 0 | 0 | 0 | 0 | 0 | 0 |
| 1444 | 30 | 0 | 80 | 0 | 40 | 20 |
| 1445 | 0 | 0 | 0 | 0 | 0 | 0 |
| 1446 | 0 | 0 | 0 | 0 | 0 | 0 |
| 1447 | 0 | 0 | 50 | 0 | 0 | 0 |
| 1448 | 0 | 0 | 20 | 0 | 0 | 0 |
| 1449 | 0 | 0 | 70 | 0 | 0 | 0 |
| 1450 | 30 | 0 | 70 | 0 | 0 | 0 |
| 1451 | 0 | 0 | 0 | 0 | 0 | 0 |
| 1452 | 0 | 0 | 0 | 0 | 0 | 0 |
| 1453 | 40 | 0 | 60 | 0 | 0 | 0 |
| 1454 | 60 | 10 | 70 | 10 | 0 | 20 |
| 1455 | 70 | 0 | 70 | 0 | 0 | 30 |
| 1456 | 60 | 0 | 80 | — | 0 | 0 |
| 1457 | 0 | 0 | 20 | 0 | 0 | 0 |
| 1458 | 80 | 0 | 80 | 0 | 0 | 0 |
| 1459 | 60 | 0 | 60 | 0 | — | 0 |
| 1460 | 70 | 0 | 80 | 40 | 40 | 0 |
| 1461 | 60 | 0 | 80 | 0 | 0 | 0 |
| 1462 | 50 | 0 | 70 | 0 | 0 | 0 |
| 1463 | 50 | 0 | 70 | 0 | 0 | 0 |
| 1464 | 90 | 50 | 90 | 30 | 0 | 0 |
| 1465 | 20 | 0 | 70 | 0 | 0 | 0 |
| 1466 | 0 | 0 | 0 | 0 | 0 | 0 |
| 1468 | 70 | 0 | 80 | 0 | 0 | 0 |
| 1471 | 70 | 0 | 80 | 0 | 0 | 0 |
| 1472 | 40 | 0 | 50 | 0 | 0 | 0 |
| 1473 | 40 | 0 | 70 | 0 | 0 | 0 |
| 1474 | 70 | 0 | 80 | 0 | 0 | 0 |
| 1475 | 70 | 30 | 80 | 0 | 0 | 0 |
| 1476 | 70 | 0 | 80 | 0 | 0 | 0 |
| 1477 | 60 | 40 | 80 | 0 | 0 | 0 |
| 1478 | 0 | 0 | 0 | 0 | 0 | 0 |
| 1479 | 0 | 0 | 20 | 0 | 0 | 0 |
| 1480 | 80 | 30 | 90 | 0 | 0 | 0 |
| 1481 | 40 | 30 | 60 | 0 | 0 | 0 |
| 1482 | 30 | 40 | 60 | 0 | 0 | 0 |
| 1483 | 40 | 20 | 60 | 0 | 40 | 0 |
| 1484 | 10 | 10 | 10 | 0 | 0 | 0 |
| 1485 | 90 | 70 | 90 | 0 | 30 | 0 |
| 1486 | 60 | 20 | 90 | 0 | 0 | 0 |
| 1487 | 90 | 20 | 90 | 0 | 0 | 0 |
| 1488 | 0 | 0 | 0 | 0 | 0 | 0 |
| 1489 | 0 | 0 | 0 | 0 | 0 | 0 |
| 1490 | 50 | 0 | 40 | 0 | 0 | 0 |
| 1491 | 20 | 0 | 50 | 0 | 0 | 0 |
| 1492 | 20 | 0 | 20 | 0 | 0 | 0 |
| 1493 | 90 | 0 | 80 | 0 | 0 | 0 |
| 1494 | 80 | 20 | 80 | 0 | 0 | 0 |
| 1496 | 40 | 0 | 50 | 0 | 0 | 0 |
| 1497 | 30 | 0 | 60 | 0 | 0 | 0 |
| 1498 | 0 | 0 | 0 | 0 | 0 | 0 |
| 1499 | 80 | 0 | 80 | 0 | 0 | 0 |
| 1500 | 90 | 0 | 80 | — | 0 | 0 |
| 1501 | 50 | 0 | 70 | 0 | 0 | 0 |
| 1502 | 60 | 0 | 90 | 0 | 20 | 0 |
| 1503 | 0 | 0 | 0 | 0 | — | 0 |
| 1504 | 0 | 0 | 0 | 0 | 0 | 0 |
| 1505 | 0 | 0 | 10 | — | 0 | 0 |
| 1506 | 0 | 0 | 0 | 0 | 0 | 0 |
| 1507 | 0 | 0 | 0 | 0 | 0 | 0 |
| 1508 | 0 | 0 | 0 | 0 | 0 | 0 |
| 1509 | 0 | 0 | 0 | 0 | 0 | 0 |
| 1510 | 0 | 0 | 0 | 0 | 0 | 0 |
| 1511 | 0 | 0 | 0 | 0 | 0 | 0 |
| 1512 | 0 | 0 | 0 | 0 | 0 | 0 |
| 1513 | 0 | 0 | 0 | 0 | 0 | 0 |
| 1514 | 0 | 0 | 0 | 0 | 0 | 0 |
| 1515 | 0 | 0 | 0 | 0 | 0 | 0 |
| 1516 | 0 | 0 | 0 | 0 | 0 | 0 |
| 1517 | 70 | 0 | 70 | 0 | 0 | 0 |
| 1518 | 0 | 0 | 0 | 0 | 0 | 0 |
| 1519 | 0 | 0 | 0 | 0 | 0 | 0 |
| 1520 | 50 | 0 | 60 | 0 | 0 | 0 |
| 1522 | 0 | 0 | 0 | 0 | 0 | 0 |
| 1525 | 0 | 0 | 10 | 0 | 0 | 0 |
| 1526 | 60 | 0 | 50 | — | 50 | 0 |
| 1527 | 0 | 0 | 0 | 0 | 0 | 0 |
| 1528 | 0 | 0 | 0 | 0 | 0 | 0 |
| 1529 | 0 | 0 | 0 | 0 | 0 | 0 |
| 1530 | 0 | 0 | 0 | 0 | 0 | 0 |
| 1531 | 0 | 0 | 0 | 0 | 0 | 0 |
| 1532 | 30 | 0 | 100 | 0 | 0 | 0 |
| 1533 | 0 | 0 | 0 | 0 | 0 | 0 |
| 1534 | 0 | 0 | 0 | 0 | 0 | 0 |
| 1535 | 0 | 0 | 0 | 0 | 20 | 0 |
| 1536 | 0 | 0 | 0 | 0 | 0 | 0 |
| 1537 | 0 | 0 | 0 | 0 | 0 | 0 |
| 1538 | 30 | 0 | 20 | 0 | 0 | 0 |
| 1539 | 10 | 0 | 10 | — | 0 | 0 |
| 1540 | 0 | 0 | 0 | 0 | 0 | 0 |
| 1541 | 0 | 0 | 0 | 0 | 0 | 0 |
| 1542 | 10 | 0 | 10 | 0 | 0 | 0 |
| 1543 | 0 | 0 | 0 | 0 | 0 | 0 |
| 1544 | 0 | 0 | 0 | 0 | 0 | 0 |
| 1545 | 0 | 0 | 0 | 0 | 0 | 0 |
| 1546 | 20 | 10 | 80 | 20 | 30 | 0 |
| 1547 | 0 | 0 | 0 | 0 | 0 | 0 |
| 1548 | 0 | 0 | 0 | 0 | 0 | 0 |
| 1549 | 0 | 0 | 0 | 0 | 0 | 0 |
| 1550 | 0 | 0 | 0 | 0 | 0 | 0 |
| 1551 | 0 | 0 | 0 | 0 | 0 | 0 |
| 1552 | 0 | 0 | 0 | 0 | 0 | 0 |
| 1553 | 0 | 0 | 0 | 0 | 0 | 0 |
| 1554 | 0 | 0 | 0 | 0 | 0 | 0 |
| 1555 | 20 | 0 | 30 | 0 | 30 | 0 |
| 1556 | 0 | 0 | 0 | 0 | 0 | 0 |
| 1557 | 0 | 0 | 0 | 0 | 0 | 0 |

| | Pre-Emergence (62.5 g ai/ha) | | | | | |
|---|---|---|---|---|---|---|
| Cmpd | Barnyard grass | Corn | Foxtail, Giant | Morning-glory, Ivy-leaved | Pigweed, Redroot | Velvetleaf |
| 1558 | 0 | 0 | 0 | 0 | 0 | 0 |
| 1559 | 0 | 0 | 0 | 0 | 0 | 0 |
| 1560 | 0 | 0 | 0 | 0 | 0 | 0 |
| 1561 | 50 | 0 | 60 | 0 | 20 | 0 |
| 1562 | 0 | 0 | — | 0 | 0 | 0 |
| 1563 | 0 | 0 | 0 | 0 | 0 | 0 |
| 1564 | 0 | 0 | 0 | 0 | 0 | 0 |
| 1565 | 0 | 0 | 0 | 0 | 0 | 0 |
| 1566 | 0 | 0 | 0 | 0 | 0 | 0 |
| 1567 | 0 | 0 | 0 | 0 | 0 | 0 |
| 1568 | 0 | 0 | 0 | 0 | 0 | 0 |
| 1569 | 0 | 0 | 0 | 0 | 0 | 0 |
| 1570 | 0 | 0 | 0 | 0 | 0 | 0 |
| 1571 | 0 | 0 | 0 | 0 | 0 | 0 |
| 1572 | 0 | 0 | 0 | 0 | 0 | 0 |
| 1573 | 0 | 0 | 0 | 0 | 0 | 0 |
| 1574 | 0 | 0 | 0 | 0 | 0 | 0 |
| 1575 | 0 | 0 | 0 | 0 | 0 | 0 |
| 1576 | 70 | 0 | 70 | 0 | 0 | 0 |
| 1577 | 0 | 0 | 0 | 0 | 0 | 0 |
| 1578 | 0 | 0 | 0 | 0 | 0 | 0 |
| 1579 | 0 | 0 | 0 | 0 | 0 | 0 |
| 1580 | 0 | 0 | 0 | 0 | 0 | 0 |
| 1581 | 0 | 0 | 0 | 0 | 0 | 0 |
| 1582 | 0 | 0 | 0 | 0 | 0 | 0 |
| 1583 | 0 | 0 | 0 | 0 | 0 | 0 |
| 1584 | 0 | 0 | 50 | 0 | 0 | 0 |
| 1585 | 90 | 80 | 80 | 30 | 0 | 0 |
| 1586 | 0 | 10 | 20 | 0 | 40 | 0 |
| 1587 | 0 | 10 | 0 | 0 | 0 | 0 |
| 1588 | 90 | 60 | 80 | 0 | 40 | 10 |
| 1589 | 0 | 0 | 0 | 0 | 0 | 0 |
| 1590 | 0 | 0 | 50 | 0 | 0 | 0 |
| 1591 | 50 | 10 | 70 | 0 | 0 | 0 |
| 1592 | 10 | 0 | 20 | 0 | 0 | 0 |
| 1593 | 0 | 0 | 10 | 0 | 0 | 0 |
| 1594 | 20 | 10 | 40 | 0 | 0 | 0 |
| 1595 | 0 | 0 | 0 | 0 | 0 | 0 |
| 1596 | 0 | 0 | 40 | 10 | 20 | 0 |
| 1597 | 0 | 0 | 0 | 0 | 0 | 0 |
| 1598 | 70 | 10 | 80 | 20 | 40 | 10 |
| 1599 | 70 | 10 | 60 | 10 | 40 | 30 |
| 1600 | 0 | 0 | 0 | 0 | 0 | 0 |
| 1601 | 10 | 0 | 20 | 0 | 0 | 0 |
| 1602 | 0 | 0 | 30 | 0 | 30 | 0 |
| 1603 | 0 | 0 | 0 | 0 | 0 | 0 |
| 1604 | 0 | 0 | 0 | 0 | 0 | 0 |
| 1605 | 0 | 0 | 0 | 0 | 0 | 0 |
| 1606 | 20 | 0 | 60 | 0 | 0 | 0 |
| 1607 | 40 | 0 | 80 | 10 | 20 | 0 |
| 1608 | 0 | 0 | 0 | 0 | 10 | 0 |
| 1609 | 50 | 10 | 80 | 20 | 40 | 10 |
| 1610 | 0 | 0 | 0 | 0 | 0 | 0 |
| 1611 | 0 | 0 | 0 | 0 | 0 | 0 |
| 1612 | 0 | 0 | 0 | 0 | 0 | 0 |
| 1613 | 0 | 0 | 50 | 0 | 0 | 0 |
| 1614 | 0 | 0 | 0 | 0 | 0 | 0 |
| 1615 | 0 | 0 | 0 | 0 | 0 | 0 |
| 1616 | 0 | 0 | 80 | 0 | 20 | 0 |
| 1617 | 30 | 0 | 80 | 0 | 10 | 0 |
| 1618 | 0 | 0 | 0 | 0 | 0 | 0 |
| 1619 | 0 | 0 | 0 | 0 | 0 | 0 |
| 1620 | 0 | 0 | 0 | 0 | 0 | 0 |
| 1621 | 0 | 0 | 0 | 0 | 0 | 0 |
| 1622 | 0 | 0 | 0 | 0 | 0 | 0 |
| 1623 | 30 | 0 | 60 | 10 | 10 | 0 |
| 1624 | 0 | 0 | 60 | 0 | 0 | 0 |
| 1625 | 0 | 0 | 10 | 10 | 20 | 0 |
| 1626 | 0 | 0 | 0 | 0 | 0 | 0 |
| 1627 | 40 | 10 | 80 | 0 | 50 | 20 |
| 1628 | 0 | 0 | 50 | 0 | 30 | 0 |
| 1629 | 0 | 10 | 50 | 40 | 0 | 0 |
| 1630 | 0 | 0 | 0 | 0 | 0 | 0 |
| 1631 | 0 | 10 | 10 | 20 | 20 | 0 |
| 1632 | 0 | 0 | 0 | 0 | 0 | 0 |
| 1633 | 0 | 0 | 0 | 0 | 0 | 0 |
| 1634 | 0 | 0 | 0 | 0 | 0 | 0 |
| 1635 | 0 | 0 | 0 | 0 | 0 | 0 |
| 1636 | 10 | 0 | 40 | 0 | 0 | 0 |
| 1637 | 30 | 0 | 90 | 0 | 50 | 0 |
| 1638 | 0 | 0 | 0 | 0 | 0 | 0 |
| 1639 | 10 | 0 | 60 | 0 | 20 | 0 |
| 1640 | 0 | 0 | 0 | 0 | 0 | 0 |
| 1641 | 0 | 0 | 0 | 0 | 0 | 0 |
| 1642 | 0 | 0 | 0 | 0 | 0 | 0 |
| 1643 | 0 | 0 | 0 | 0 | 0 | 0 |
| 1644 | 0 | 0 | 0 | 0 | 0 | 0 |
| 1645 | 40 | 0 | 30 | 0 | 10 | 0 |
| 1646 | 0 | 0 | 0 | 0 | 0 | 0 |
| 1647 | 0 | 0 | 0 | 0 | 0 | 0 |
| 1648 | 0 | 0 | 0 | 0 | 0 | 0 |
| 1649 | 0 | 0 | 10 | 0 | 20 | 0 |
| 1650 | 70 | 0 | 90 | 0 | 70 | 0 |
| 1651 | 0 | 0 | 20 | 0 | 10 | 0 |
| 1652 | 0 | 0 | 10 | 0 | 0 | 0 |
| 1653 | 80 | 30 | 90 | 0 | 40 | 10 |
| 1654 | 0 | 0 | 60 | 0 | 0 | 0 |
| 1655 | 0 | 0 | 0 | 0 | 0 | 0 |
| 1656 | 0 | 0 | 0 | 20 | 0 | 0 |
| 1657 | 10 | 0 | 60 | 0 | 20 | 0 |
| 1658 | 0 | 0 | 0 | 0 | 0 | 0 |
| 1659 | 0 | 0 | 0 | 0 | 0 | 0 |
| 1660 | 0 | 0 | 0 | 0 | 0 | 0 |
| 1661 | 0 | 0 | 50 | 0 | 0 | 0 |
| 1662 | 0 | 0 | 0 | 0 | 0 | 0 |
| 1663 | 0 | 0 | 0 | 0 | 0 | 0 |
| 1664 | 40 | 0 | 70 | 0 | 20 | 0 |
| 1665 | 0 | 0 | 0 | 0 | 0 | 0 |
| 1667 | 10 | 0 | 10 | — | 0 | 0 |
| 1668 | 0 | 0 | 0 | 0 | 0 | 0 |
| 1669 | 0 | 0 | 20 | 0 | 10 | 0 |
| 1670 | 0 | 0 | 20 | 0 | 0 | 0 |
| 1671 | 90 | 80 | 90 | 20 | 30 | 30 |
| 1672 | 0 | 0 | 0 | 0 | 0 | 0 |
| 1673 | 0 | 0 | 0 | 0 | 0 | 0 |
| 1674 | 0 | 0 | 0 | 0 | 0 | 0 |
| 1675 | 0 | 0 | 0 | 0 | 0 | 0 |
| 1676 | 0 | 0 | 0 | 0 | 0 | 0 |
| 1677 | 0 | 0 | 40 | 0 | 0 | 0 |
| 1678 | 0 | 0 | 0 | 0 | 0 | 0 |
| 1679 | 80 | 0 | 90 | — | 10 | 10 |
| 1680 | 20 | 0 | 60 | 0 | 20 | 10 |
| 1682 | 0 | 0 | 0 | 0 | 0 | 0 |
| 1683 | 70 | 50 | 80 | 10 | 20 | 10 |
| 1684 | 0 | 0 | 0 | 0 | 0 | 0 |
| 1685 | 70 | 0 | 70 | 20 | 10 | 10 |
| 1686 | 70 | 20 | 70 | 20 | 0 | 0 |
| 1687 | 70 | 40 | 70 | 40 | 10 | 0 |
| 1688 | 70 | 50 | 80 | 0 | 20 | 0 |
| 1690 | 80 | 20 | 80 | 0 | 0 | 0 |
| 1691 | 70 | 20 | 90 | 20 | 20 | 40 |
| 1692 | 70 | 60 | 80 | 0 | 10 | 0 |
| 1693 | 70 | 30 | 50 | 20 | 0 | 0 |
| 1694 | 0 | 0 | 0 | 0 | 0 | 0 |
| 1695 | 90 | 40 | 90 | — | 0 | 0 |
| 1696 | 70 | 40 | 80 | 10 | 0 | 0 |
| 1697 | 70 | 40 | 80 | 0 | 0 | 0 |
| 1698 | 70 | 30 | 70 | 0 | 10 | 10 |
| 1699 | 80 | 30 | 90 | 10 | 0 | 0 |
| 1700 | 50 | 0 | 80 | 10 | 0 | 0 |
| 1701 | 30 | 0 | 80 | 20 | 0 | 0 |
| 1702 | 70 | 70 | 80 | 30 | 0 | 10 |
| 1703 | 80 | 60 | 80 | 0 | 0 | 0 |
| 1704 | 70 | 50 | 80 | 0 | 20 | 0 |
| 1705 | 60 | 10 | 70 | 0 | 0 | 0 |
| 1706 | 60 | 10 | 70 | 0 | 0 | 0 |

| | Pre-Emergence (62.5 g ai/ha) | | | | | |
|---|---|---|---|---|---|---|
| Cmpd | Barnyard grass | Corn | Foxtail, Giant | Morning-glory, Ivy-leaved | Pigweed, Redroot | Velvetleaf |
| 1707 | 80 | 80 | 90 | 10 | 20 | 10 |
| 1708 | 30 | 0 | 80 | 0 | 0 | 0 |
| 1709 | 70 | 70 | 80 | 10 | 20 | 20 |
| 1710 | — | — | — | — | — | — |
| 1711 | 10 | 0 | 70 | 10 | 0 | 0 |
| 1712 | 80 | 10 | 90 | 0 | 0 | 0 |
| 1713 | 70 | 20 | 70 | 0 | 0 | 0 |
| 1714 | 50 | 0 | 70 | 0 | 0 | 0 |
| 1716 | 80 | 0 | 90 | 0 | 10 | 10 |
| 1717 | 40 | 0 | 90 | 0 | 10 | 10 |
| 1718 | 70 | 50 | 80 | 0 | 0 | 0 |
| 1719 | 70 | 10 | 90 | 0 | 0 | 0 |
| 1720 | — | — | — | — | — | — |
| 1721 | 50 | 0 | 60 | 0 | 0 | 0 |
| 1722 | 60 | 30 | 70 | 0 | 10 | 0 |
| 1723 | 40 | 0 | 70 | 0 | 0 | 0 |
| 1724 | 70 | 40 | 70 | 0 | 0 | 0 |
| 1725 | 50 | 0 | 50 | 0 | 0 | 0 |
| 1726 | 50 | 0 | 50 | 0 | 0 | 0 |
| 1727 | 40 | 0 | 60 | 0 | 0 | 0 |
| 1728 | 90 | 80 | 90 | 30 | 80 | 60 |
| 1729 | 0 | 0 | 0 | 0 | 0 | 0 |
| 1730 | 10 | 0 | 50 | 0 | 0 | 0 |
| 1731 | 0 | 0 | 0 | 0 | 0 | 0 |
| 1732 | 0 | 0 | 20 | 0 | 0 | 0 |
| 1733 | 20 | 20 | 80 | 20 | 70 | 50 |
| 1734 | 0 | 0 | 0 | 0 | 0 | 0 |
| 1735 | 0 | 0 | 0 | 0 | 0 | 0 |
| 1736 | 60 | 0 | 90 | 0 | 20 | 10 |
| 1737 | 0 | 0 | 0 | 0 | 0 | 0 |
| 1738 | 0 | 0 | 0 | 0 | 0 | 0 |
| 1739 | 0 | 0 | 0 | 0 | 0 | 0 |
| 1740 | 30 | 0 | 60 | 0 | 0 | 0 |
| 1741 | 40 | 10 | 90 | 0 | 20 | 30 |
| 1742 | 0 | 0 | 80 | 0 | 10 | 0 |
| 1743 | 40 | 20 | 90 | 60 | 60 | 50 |
| 1744 | 0 | 0 | 10 | 0 | 10 | 0 |
| 1745 | 0 | 0 | 10 | 0 | 0 | 0 |
| 1746 | 0 | 0 | 20 | 0 | 0 | 0 |
| 1747 | 0 | 0 | 10 | 0 | 10 | 0 |
| 1748 | 0 | 0 | 0 | 0 | 0 | 0 |
| 1749 | 0 | 0 | 0 | 0 | 0 | 0 |
| 1750 | 10 | 0 | 20 | 0 | 0 | 0 |
| 1751 | 0 | 0 | 0 | 0 | 0 | 0 |
| 1752 | 0 | 0 | 0 | 0 | 0 | 0 |
| 1753 | 70 | 0 | 80 | 0 | 0 | 0 |
| 1754 | 80 | 0 | 90 | 0 | 20 | 0 |
| 1755 | 80 | 60 | 90 | 20 | 40 | 20 |
| 1757 | 10 | 0 | 30 | 0 | 0 | 0 |
| 1760 | 0 | 0 | 0 | 0 | 0 | 0 |
| 1761 | 30 | 0 | 40 | 0 | 0 | 0 |
| 1762 | 80 | 30 | 80 | 10 | 10 | 0 |
| 1763 | 60 | 50 | 90 | 0 | 0 | 0 |
| 1764 | 70 | 20 | 70 | 0 | 10 | 10 |
| 1765 | 50 | 0 | 70 | 0 | 0 | 0 |
| 1766 | 60 | 10 | 70 | 0 | 0 | 0 |
| 1767 | 60 | 30 | 80 | 0 | 0 | 0 |
| 1768 | 0 | 0 | 0 | 0 | 0 | 0 |
| 1769 | 20 | 0 | 40 | 0 | 0 | 0 |
| 1770 | 20 | 0 | 50 | 0 | 0 | 0 |
| 1771 | 0 | 0 | 0 | 0 | 0 | 0 |
| 1772 | 10 | 0 | 80 | 0 | 0 | 0 |
| 1773 | 90 | 80 | 90 | 60 | 20 | 30 |
| 1783 | 90 | 80 | 90 | 10 | 0 | 10 |
| 1784 | 10 | 0 | 0 | 0 | 0 | 0 |
| 1785 | 0 | 0 | 0 | 0 | 0 | 0 |
| 1786 | 0 | 0 | 0 | 0 | 0 | 0 |
| 1787 | 60 | 20 | 70 | 0 | 0 | 10 |
| 1788 | 0 | 0 | 0 | 0 | 0 | 0 |
| 1789 | 0 | 0 | 0 | 0 | 0 | 0 |
| 1790 | 70 | 70 | 70 | 20 | 0 | 0 |
| 1791 | 80 | 70 | 90 | 20 | 0 | 10 |
| 1792 | 70 | 20 | 80 | 0 | 0 | 0 |
| 1793 | 70 | 20 | 90 | 0 | 0 | 0 |
| 1794 | 40 | 50 | 60 | 0 | 0 | 0 |
| 1795 | 70 | 40 | 80 | 10 | 20 | 0 |
| 1796 | 0 | 0 | 0 | 0 | 0 | 0 |
| 1797 | 60 | 50 | 80 | 10 | 0 | 20 |
| 1798 | 0 | 0 | 10 | 0 | 0 | 0 |
| 1799 | 70 | 70 | 90 | 0 | 10 | 0 |
| 1800 | 40 | 0 | 70 | 0 | 20 | 10 |
| 1801 | 80 | 40 | 90 | 0 | 20 | 10 |
| 1802 | 70 | 0 | 90 | 0 | 10 | 20 |
| 1803 | 70 | 0 | 90 | 0 | 0 | 0 |
| 1804 | 80 | 0 | 90 | 0 | 20 | 10 |
| 1805 | 0 | 0 | 0 | 0 | 10 | 20 |
| 1806 | 10 | 0 | 20 | 0 | 0 | 0 |
| 1807 | 0 | 0 | 0 | 0 | 0 | 0 |
| 1808 | 0 | 0 | 20 | 0 | 0 | 0 |
| 1809 | 80 | 80 | 90 | 70 | 0 | 0 |
| 1810 | 90 | 30 | 90 | 30 | 40 | 40 |
| 1811 | 90 | 70 | 90 | 20 | 70 | 50 |
| 1812 | 0 | 0 | 90 | 0 | 20 | 40 |
| 1813 | 0 | 0 | 10 | 0 | 0 | 0 |
| 1814 | 0 | 0 | 0 | 0 | 0 | 0 |
| 1815 | 0 | 0 | 0 | 0 | 0 | 0 |
| 1816 | 90 | 80 | 90 | 60 | 40 | 20 |
| 1817 | 0 | 0 | 0 | 0 | 0 | 0 |
| 1818 | 30 | 0 | 90 | 10 | 0 | 30 |
| 1819 | 60 | 0 | 80 | 0 | 0 | 0 |
| 1820 | 0 | 0 | 0 | 0 | 0 | 0 |
| 1821 | 0 | 10 | 10 | 0 | 0 | 0 |
| 1822 | 90 | 20 | 90 | 20 | 60 | 60 |
| 1823 | 0 | 0 | 0 | 0 | 0 | 0 |
| 1824 | 0 | 0 | 10 | 0 | 0 | 0 |
| 1825 | 0 | 0 | 20 | 0 | 0 | 0 |
| 1826 | 70 | 10 | 80 | 0 | 0 | 0 |
| 1827 | 80 | 0 | 90 | 0 | 0 | 0 |
| 1828 | 80 | 10 | 90 | 0 | 0 | 0 |
| 1829 | 70 | 10 | 80 | 0 | 0 | 0 |
| 1833 | 0 | 0 | 0 | 0 | 0 | 0 |
| 1836 | 70 | 10 | 80 | 20 | 50 | 0 |

| | Pre-Emergence (15.625 g ai/ha) | | | | | |
|---|---|---|---|---|---|---|
| Cmpd | Barnyard grass | Corn | Foxtail, Giant | Morning-glory, Ivy-leaved | Pigweed, Redroot | Velvetleaf |
| 1396 | 80 | 70 | 90 | 0 | 80 | 40 |
| 1397 | 90 | 80 | 90 | 60 | 0 | 0 |
| 1398 | 80 | 20 | 90 | 0 | 20 | 0 |
| 1399 | 0 | 0 | 90 | 0 | 0 | 0 |
| 1400 | 30 | 20 | 60 | 0 | 20 | 10 |
| 1401 | 20 | 0 | 40 | — | 0 | 0 |
| 1402 | 80 | 60 | 90 | 40 | 0 | 0 |
| 1403 | 0 | 0 | 0 | 0 | 0 | 0 |
| 1404 | 0 | 0 | 0 | 0 | 0 | 0 |
| 1405 | 0 | 0 | 0 | 0 | 0 | 0 |
| 1406 | 0 | 0 | 0 | 0 | 0 | 0 |
| 1407 | 10 | 0 | 50 | 0 | 0 | 0 |
| 1408 | 0 | 0 | 0 | 0 | 0 | 0 |
| 1409 | 0 | 0 | 0 | 0 | 0 | 0 |
| 1410 | 0 | 0 | 0 | 0 | 0 | 0 |
| 1411 | 0 | 0 | 0 | 0 | 0 | 0 |
| 1412 | 0 | 0 | 10 | 0 | 20 | 0 |
| 1413 | 0 | 0 | 0 | 0 | 0 | 0 |
| 1414 | 20 | 0 | 60 | 0 | 0 | 0 |
| 1415 | 10 | 0 | 10 | 0 | 10 | 0 |
| 1416 | 0 | 0 | 0 | 0 | 0 | 0 |
| 1417 | 0 | 0 | 0 | 0 | 0 | 0 |
| 1418 | 0 | 0 | 0 | 0 | 0 | 0 |
| 1419 | 10 | 0 | 10 | 0 | 0 | 0 |

| Pre-Emergence (15.625 g ai/ha) | | | | | | | Pre-Emergence (15.625 g ai/ha) | | | | | |
| --- | --- | --- | --- | --- | --- | --- | --- | --- | --- | --- | --- | --- |
| Cmpd | Barnyard grass | Corn | Foxtail, Giant | Morning-glory, Ivy-leaved | Pigweed, Redroot | Velvetleaf | Cmpd | Barnyard grass | Corn | Foxtail, Giant | Morning-glory, Ivy-leaved | Pigweed, Redroot | Velvetleaf |
| 1420 | 60 | 0 | 70 | 0 | 0 | 0 | 1497 | 0 | 0 | 0 | 0 | 0 | 0 |
| 1421 | 10 | 0 | 70 | 0 | 0 | 0 | 1498 | 0 | 0 | 0 | 0 | 0 | 0 |
| 1422 | 0 | 0 | 0 | 0 | 0 | 0 | 1499 | 0 | 0 | 0 | 0 | — | 0 |
| 1423 | 10 | 10 | 10 | 0 | 0 | 0 | 1500 | 30 | 0 | 60 | 0 | 0 | 0 |
| 1424 | 0 | 0 | 0 | 0 | 0 | 0 | 1501 | 0 | 0 | 0 | — | 0 | 0 |
| 1425 | 0 | 0 | 10 | 0 | 0 | 0 | 1502 | 20 | 0 | 60 | 0 | 0 | 0 |
| 1426 | 0 | 0 | 0 | 0 | 0 | 0 | 1503 | 0 | 0 | 0 | — | 0 | 0 |
| 1427 | 0 | 0 | 0 | 0 | 0 | 0 | 1504 | 0 | 0 | 0 | 0 | 0 | 0 |
| 1428 | 50 | 50 | 70 | 10 | 0 | 0 | 1505 | 0 | 0 | 0 | 0 | 0 | 0 |
| 1429 | 0 | 0 | 0 | 0 | 0 | 0 | 1506 | 0 | 0 | 0 | 0 | 0 | 0 |
| 1430 | 0 | 0 | 10 | 0 | 0 | 0 | 1507 | 0 | 0 | 0 | 0 | 0 | 0 |
| 1431 | 0 | 0 | 0 | 0 | 0 | 0 | 1508 | 0 | 0 | 0 | 0 | 0 | 0 |
| 1432 | 0 | 0 | 0 | 0 | 0 | 0 | 1509 | 0 | 0 | 0 | 0 | 0 | 0 |
| 1433 | 0 | 0 | 0 | 0 | 0 | 0 | 1510 | 0 | 0 | 0 | 0 | — | 0 |
| 1434 | 0 | 0 | 0 | 0 | 0 | 0 | 1511 | 0 | 0 | 0 | 0 | 0 | 0 |
| 1435 | 0 | 0 | 0 | 0 | 0 | 0 | 1512 | 0 | 0 | 0 | 0 | 0 | 0 |
| 1436 | 0 | 0 | 0 | 0 | 0 | 0 | 1513 | 0 | 0 | 0 | 0 | 0 | 0 |
| 1437 | 0 | 0 | 0 | 0 | 0 | 0 | 1514 | 0 | 0 | 0 | 0 | 0 | 0 |
| 1438 | 0 | 0 | 0 | 0 | 0 | 0 | 1515 | 0 | 0 | 0 | 0 | 0 | 0 |
| 1439 | 0 | 0 | 0 | 0 | 0 | 0 | 1516 | 0 | 0 | 0 | 0 | 0 | 0 |
| 1440 | 0 | 0 | 0 | 0 | 0 | 0 | 1517 | 0 | 0 | 30 | 0 | 0 | 0 |
| 1441 | 0 | 0 | 0 | 0 | 0 | 0 | 1518 | 0 | 0 | 0 | 0 | 0 | 0 |
| 1442 | 0 | 0 | 0 | 0 | 0 | 0 | 1519 | 0 | 0 | 0 | 0 | 0 | 0 |
| 1443 | 0 | 0 | 0 | 0 | 0 | 0 | 1520 | 20 | 0 | 20 | 0 | 0 | 0 |
| 1444 | 10 | 0 | 50 | 10 | 0 | 0 | 1522 | 0 | 0 | 0 | 0 | 0 | 0 |
| 1445 | 0 | 0 | 0 | 0 | 0 | 0 | 1525 | 0 | 0 | 0 | 0 | 0 | 0 |
| 1446 | 0 | 0 | 0 | 0 | 0 | 0 | 1526 | 20 | 0 | 30 | 10 | 0 | 0 |
| 1447 | 0 | 0 | 50 | 0 | 0 | 0 | 1527 | 0 | 0 | 0 | 0 | 0 | 0 |
| 1448 | 0 | 0 | 0 | 0 | 0 | 0 | 1528 | 0 | 0 | 0 | 0 | 0 | 0 |
| 1449 | 0 | 0 | 10 | 0 | 0 | 0 | 1529 | 0 | 0 | 0 | 0 | 0 | 0 |
| 1450 | 10 | 0 | 40 | 0 | 0 | 0 | 1530 | 0 | 0 | 0 | 0 | 0 | 0 |
| 1451 | 0 | 0 | 0 | 0 | 0 | 0 | 1531 | 0 | 0 | 0 | 0 | 0 | 0 |
| 1452 | 0 | 0 | 0 | 0 | 0 | 0 | 1532 | 0 | 0 | 100 | 0 | 0 | 0 |
| 1453 | 20 | 0 | 40 | 0 | 0 | — | 1533 | 0 | 0 | — | 0 | 0 | 0 |
| 1454 | 20 | 0 | 50 | 20 | 0 | 0 | 1534 | 0 | 0 | 0 | 0 | 0 | 0 |
| 1455 | 30 | 0 | 30 | 0 | — | 0 | 1535 | 0 | 0 | 0 | 0 | 0 | 0 |
| 1456 | 20 | 0 | 60 | 0 | 0 | 0 | 1536 | 0 | 0 | 0 | 0 | 0 | 0 |
| 1457 | 0 | 0 | 0 | 0 | 0 | 0 | 1537 | 0 | 0 | 0 | 0 | 0 | 0 |
| 1458 | 20 | 0 | 20 | 0 | 0 | 0 | 1538 | 0 | 0 | 0 | 0 | 0 | 0 |
| 1459 | 20 | 0 | 40 | 0 | 0 | 0 | 1539 | 0 | 0 | 0 | 0 | 0 | 0 |
| 1460 | 0 | 0 | 10 | 0 | 0 | 0 | 1540 | 0 | 0 | 0 | 0 | 0 | 0 |
| 1461 | 0 | 0 | 30 | 0 | 0 | 0 | 1541 | 0 | 0 | 0 | 0 | 0 | 0 |
| 1462 | 20 | 0 | 0 | 0 | 0 | 0 | 1542 | 0 | 0 | 0 | — | 0 | 0 |
| 1463 | 10 | 0 | 0 | 0 | 0 | 0 | 1543 | 0 | 0 | 0 | 0 | 0 | 0 |
| 1464 | 80 | 0 | 80 | 0 | 0 | 0 | 1544 | 0 | 0 | 0 | 0 | 0 | 0 |
| 1465 | 0 | 0 | 30 | 0 | 0 | 0 | 1545 | 0 | 0 | 0 | — | 0 | 0 |
| 1466 | 0 | 0 | 0 | 0 | 0 | 0 | 1546 | 0 | 0 | 60 | 0 | 0 | 0 |
| 1468 | 10 | 0 | 80 | 0 | 0 | 0 | 1547 | 0 | 0 | 0 | 0 | 0 | 0 |
| 1471 | 10 | 0 | 40 | 0 | 0 | 0 | 1548 | 0 | 0 | 0 | 0 | 0 | 0 |
| 1472 | 10 | 0 | 10 | 0 | 0 | 0 | 1549 | 0 | 0 | 0 | 0 | 0 | 0 |
| 1473 | 20 | 0 | 50 | 10 | 0 | 0 | 1550 | 0 | 0 | 0 | 0 | 0 | 0 |
| 1474 | 10 | 0 | 50 | 10 | 0 | 0 | 1551 | 0 | 0 | 0 | 0 | 0 | 0 |
| 1475 | 10 | 0 | 70 | 0 | 0 | 0 | 1552 | 0 | 0 | 0 | 0 | 0 | 0 |
| 1476 | 60 | 0 | 70 | 0 | 0 | 0 | 1553 | 0 | 0 | 0 | — | 0 | 0 |
| 1477 | 50 | 20 | 60 | 0 | 0 | 0 | 1554 | 0 | 0 | 0 | 0 | 0 | 0 |
| 1478 | 0 | 0 | 0 | 0 | 0 | 0 | 1555 | 0 | 0 | 0 | — | 40 | 0 |
| 1479 | 0 | 0 | 0 | 0 | 0 | 0 | 1556 | 0 | 0 | 0 | 0 | 0 | 0 |
| 1480 | 30 | 20 | 40 | 0 | 0 | 0 | 1557 | 0 | 0 | 0 | 0 | 0 | 0 |
| 1481 | 20 | 30 | 40 | 0 | 0 | 0 | 1558 | 0 | 0 | 0 | 0 | 0 | 0 |
| 1482 | 10 | 30 | 20 | 0 | 0 | 0 | 1559 | 0 | 0 | 0 | 0 | 0 | 0 |
| 1483 | 40 | 30 | 30 | 0 | 20 | 0 | 1560 | 0 | 0 | 0 | 0 | 0 | 0 |
| 1484 | 0 | 20 | 10 | 0 | 0 | 0 | 1561 | 30 | 10 | 30 | — | 0 | 0 |
| 1485 | 60 | 40 | 60 | 0 | 0 | 0 | 1562 | 0 | 0 | — | — | 0 | 0 |
| 1486 | 30 | 10 | 40 | 0 | 0 | 0 | 1563 | 0 | 0 | 0 | 0 | 0 | 0 |
| 1487 | 30 | 10 | 80 | 0 | 0 | 0 | 1564 | 0 | 0 | 0 | 0 | 0 | 0 |
| 1488 | 0 | 0 | 0 | 0 | 0 | 0 | 1565 | 0 | 0 | 0 | 0 | 0 | 0 |
| 1489 | 0 | 0 | 0 | 0 | 0 | 0 | 1566 | 0 | 0 | 0 | 0 | 0 | 0 |
| 1490 | 0 | 0 | 0 | 0 | 0 | 0 | 1567 | 0 | 0 | 0 | 0 | 0 | 0 |
| 1491 | 0 | 0 | 0 | 0 | 0 | 0 | 1568 | 0 | 0 | 0 | 0 | 0 | 0 |
| 1492 | 0 | 0 | 0 | 0 | 0 | 0 | 1569 | 0 | 0 | 0 | 0 | 0 | 0 |
| 1493 | 40 | 0 | 60 | 0 | 0 | 0 | 1570 | 0 | 0 | 0 | 0 | 0 | 0 |
| 1494 | 80 | 0 | 70 | 0 | 0 | 0 | 1571 | 0 | 0 | 0 | 0 | 0 | 0 |
| 1496 | 0 | 0 | 0 | 0 | 0 | 0 | 1572 | 0 | 0 | 0 | 0 | 0 | 0 |

| | Pre-Emergence (15.625 g ai/ha) | | | | | |
|---|---|---|---|---|---|---|
| Cmpd | Barnyard grass | Corn | Foxtail, Giant | Morning-glory, Ivy-leaved | Pigweed, Redroot | Velvetleaf |
| 1573 | 0 | 0 | 0 | 0 | 0 | 0 |
| 1574 | 0 | 0 | 0 | 0 | 0 | 0 |
| 1575 | 0 | 0 | 0 | 0 | 0 | 0 |
| 1576 | 30 | 0 | 30 | 0 | 0 | 0 |
| 1577 | 0 | 0 | 0 | 0 | 0 | 0 |
| 1578 | 0 | 0 | 0 | 0 | 0 | 0 |
| 1579 | 0 | 0 | 0 | 0 | 0 | 0 |
| 1580 | 0 | 0 | 0 | 0 | 0 | 0 |
| 1581 | 0 | 0 | 0 | 0 | 0 | 0 |
| 1582 | 0 | 0 | 0 | 0 | 0 | 0 |
| 1583 | 0 | 0 | 0 | 0 | 0 | 0 |
| 1584 | 0 | 0 | 0 | 0 | 0 | 0 |
| 1585 | 70 | 0 | 70 | 0 | 0 | 0 |
| 1586 | 0 | 0 | 0 | 0 | 0 | 0 |
| 1587 | 0 | 0 | 0 | 0 | 0 | 0 |
| 1588 | 80 | 40 | 70 | 20 | 0 | 0 |
| 1589 | 0 | 0 | 0 | 0 | 0 | 0 |
| 1590 | 0 | 0 | 0 | 0 | 0 | 0 |
| 1591 | 0 | 0 | 0 | 0 | 0 | 0 |
| 1592 | 0 | 0 | 0 | 10 | 0 | 0 |
| 1593 | 0 | 0 | 0 | 0 | 0 | 0 |
| 1594 | 0 | 0 | 0 | 0 | 0 | 0 |
| 1595 | 0 | 0 | 0 | 0 | 0 | 0 |
| 1596 | 0 | 0 | 0 | 0 | 0 | 0 |
| 1597 | 0 | 0 | 0 | 0 | 0 | 0 |
| 1598 | 0 | 0 | 60 | 10 | 10 | 0 |
| 1599 | 0 | 0 | 20 | 10 | 0 | 0 |
| 1600 | 0 | 0 | 0 | 0 | 0 | 0 |
| 1601 | 0 | 0 | 0 | 0 | 0 | 0 |
| 1602 | 0 | 0 | 0 | 0 | 0 | 0 |
| 1603 | 0 | 0 | 0 | 0 | 0 | 0 |
| 1604 | 0 | 0 | 0 | 0 | 0 | 0 |
| 1605 | 0 | 0 | 0 | 0 | 0 | 0 |
| 1606 | 0 | 0 | 0 | 0 | 0 | 0 |
| 1607 | 0 | 0 | 50 | 0 | 0 | 0 |
| 1608 | 0 | 0 | 0 | 0 | 0 | 0 |
| 1609 | 20 | 0 | 70 | 10 | 20 | 10 |
| 1610 | 0 | 0 | 0 | 0 | 0 | 0 |
| 1611 | 0 | 0 | 0 | 0 | 0 | 0 |
| 1612 | 0 | 0 | 0 | 0 | 0 | 0 |
| 1613 | 0 | 0 | 0 | 0 | 0 | 0 |
| 1614 | 0 | 0 | 0 | 0 | 0 | 0 |
| 1615 | 0 | 0 | 0 | 0 | 0 | 0 |
| 1616 | 0 | 0 | 0 | 0 | 0 | 0 |
| 1617 | 10 | 0 | 20 | 0 | 0 | 0 |
| 1618 | 0 | 0 | 0 | 0 | 0 | 0 |
| 1619 | 0 | 0 | 0 | 0 | 0 | 0 |
| 1620 | 0 | 0 | 0 | 0 | 0 | 0 |
| 1621 | 0 | 0 | 0 | 0 | 0 | 0 |
| 1622 | 0 | 0 | 0 | 0 | 0 | 0 |
| 1623 | 10 | 10 | 20 | 10 | 10 | 10 |
| 1624 | 0 | 0 | 20 | 0 | 0 | 0 |
| 1625 | 0 | 0 | 0 | 0 | 0 | 0 |
| 1626 | 0 | 0 | 0 | 0 | 0 | 0 |
| 1627 | 0 | 0 | 70 | 0 | 0 | 0 |
| 1628 | 10 | 0 | 50 | 20 | 0 | 0 |
| 1629 | 10 | 0 | 30 | 10 | 0 | 0 |
| 1630 | 0 | 0 | 0 | 0 | 0 | 0 |
| 1631 | 0 | 0 | 0 | 0 | 0 | 0 |
| 1632 | 0 | 0 | 0 | 0 | 0 | 0 |
| 1633 | 0 | 0 | 0 | 0 | 0 | 0 |
| 1634 | 0 | 0 | 0 | 0 | 0 | 0 |
| 1635 | 0 | 0 | 0 | 0 | 0 | 0 |
| 1636 | 0 | 0 | 0 | 0 | 0 | 0 |
| 1637 | 20 | 0 | 60 | 0 | 20 | 0 |
| 1638 | 0 | 0 | 0 | 0 | 0 | 0 |
| 1639 | 0 | 0 | 30 | 0 | 0 | 0 |
| 1640 | 0 | 0 | 0 | 0 | 0 | 0 |
| 1641 | 0 | 0 | 0 | 0 | 0 | 0 |
| 1642 | 0 | 0 | 0 | 0 | 0 | 0 |
| 1643 | 0 | 0 | 0 | 0 | 0 | 0 |
| 1644 | 0 | 0 | 0 | 0 | 0 | 0 |
| 1645 | 0 | 0 | 0 | 0 | 0 | 0 |
| 1646 | 0 | 0 | 0 | 0 | 0 | 0 |
| 1647 | 0 | 0 | 0 | 0 | 0 | 0 |
| 1648 | 0 | 0 | 0 | 0 | 0 | 0 |
| 1649 | 0 | 0 | 0 | 0 | 0 | 0 |
| 1650 | 10 | 0 | 40 | 0 | 0 | 0 |
| 1651 | 0 | 0 | 0 | 0 | 0 | 0 |
| 1652 | 0 | 0 | 0 | 0 | 0 | 0 |
| 1653 | 0 | 0 | 60 | 0 | 0 | 0 |
| 1654 | 0 | 0 | 20 | 0 | 0 | 0 |
| 1655 | 0 | 0 | 0 | 0 | 0 | 0 |
| 1656 | 0 | 0 | 0 | 0 | 0 | 0 |
| 1657 | 0 | 0 | 0 | 0 | 0 | 0 |
| 1658 | 0 | 0 | 0 | 0 | 0 | 0 |
| 1659 | 0 | 0 | 0 | 0 | 0 | 0 |
| 1660 | 0 | 0 | 0 | 0 | 0 | 0 |
| 1661 | 0 | 0 | 0 | 0 | 0 | 0 |
| 1662 | 0 | 0 | 0 | 0 | 0 | 0 |
| 1663 | 0 | 0 | 0 | 0 | 0 | 0 |
| 1664 | 0 | 0 | 30 | 0 | 0 | 0 |
| 1665 | 0 | 0 | 0 | 0 | 0 | 0 |
| 1667 | 0 | 0 | 0 | 0 | 0 | 0 |
| 1668 | 0 | 0 | 0 | 0 | 0 | 0 |
| 1669 | 0 | 0 | 0 | 0 | 0 | 0 |
| 1670 | 0 | 0 | 0 | 0 | 0 | 0 |
| 1671 | 70 | 30 | 80 | 10 | 0 | 20 |
| 1672 | 0 | 0 | 0 | 0 | 0 | 0 |
| 1673 | 0 | 0 | 0 | 0 | 0 | 0 |
| 1674 | 0 | 0 | 0 | 0 | 0 | 0 |
| 1675 | 0 | 0 | 0 | 0 | 0 | 0 |
| 1676 | 0 | 0 | 0 | 0 | 0 | 0 |
| 1677 | 0 | 0 | 10 | 0 | 0 | 0 |
| 1678 | 0 | 0 | 0 | 0 | 0 | 0 |
| 1679 | 50 | 0 | 90 | 0 | 10 | 10 |
| 1680 | 0 | 0 | 20 | 0 | 20 | 10 |
| 1682 | 0 | 0 | 0 | 0 | 0 | 0 |
| 1683 | 60 | 30 | 70 | 0 | 20 | 0 |
| 1684 | 0 | 0 | 0 | 0 | 0 | 0 |
| 1685 | 30 | 0 | 40 | 10 | 0 | 10 |
| 1686 | 40 | 10 | 60 | 0 | 0 | 0 |
| 1687 | 40 | 0 | 60 | 0 | 0 | 0 |
| 1688 | 50 | 0 | 70 | 0 | 30 | 10 |
| 1690 | 50 | 0 | 70 | 0 | 0 | 0 |
| 1691 | 20 | 0 | 60 | 0 | 0 | 0 |
| 1692 | 20 | 0 | 60 | 0 | 0 | 0 |
| 1693 | 0 | 0 | 0 | 0 | 0 | 0 |
| 1694 | 0 | 0 | 0 | 0 | 0 | 0 |
| 1695 | 50 | 10 | 70 | 0 | 0 | 0 |
| 1696 | 10 | 0 | 60 | 10 | 20 | 10 |
| 1697 | 40 | 0 | 70 | 0 | 0 | 0 |
| 1698 | 60 | 0 | 70 | 10 | 0 | 0 |
| 1699 | 60 | 0 | 80 | 0 | 0 | 0 |
| 1700 | 20 | 0 | 40 | — | 0 | 0 |
| 1701 | 0 | 0 | 40 | 0 | 0 | 0 |
| 1702 | 50 | 20 | 70 | 0 | 0 | 0 |
| 1703 | 50 | 0 | 80 | 0 | 0 | 0 |
| 1704 | 40 | 0 | 50 | 0 | 0 | 0 |
| 1705 | 20 | 0 | 50 | 0 | 0 | 0 |
| 1706 | 40 | 0 | 50 | 0 | 0 | 0 |
| 1707 | 70 | 20 | 80 | 0 | 20 | 10 |
| 1708 | 20 | 0 | 60 | 0 | 0 | 0 |
| 1709 | 60 | 0 | 70 | 0 | 0 | 0 |
| 1710 | — | — | — | — | — | — |
| 1711 | 30 | 0 | 70 | 0 | 0 | — |
| 1712 | 60 | 0 | 80 | 0 | 10 | 0 |
| 1713 | 30 | 10 | 50 | 0 | 0 | 0 |
| 1714 | 0 | 0 | 30 | 0 | 0 | 0 |
| 1716 | 0 | 0 | 30 | 0 | 0 | 0 |
| 1717 | 0 | 0 | 60 | 0 | 0 | 0 |
| 1718 | 60 | 0 | 60 | 0 | 0 | 0 |
| 1719 | 30 | 0 | 70 | — | 0 | 0 |
| 1720 | — | — | — | — | — | — |
| 1721 | 0 | 10 | 30 | 0 | 0 | 0 |
| 1722 | 0 | 10 | 60 | 0 | 0 | 0 |

Pre-Emergence (15.625 g ai/ha)

| Cmpd | Barnyard grass | Corn | Foxtail, Giant | Morning-glory, Ivy-leaved | Pigweed, Redroot | Velvetleaf |
|---|---|---|---|---|---|---|
| 1723 | 10 | 0 | 60 | 0 | 0 | 0 |
| 1724 | 50 | 0 | 70 | 0 | 0 | 0 |
| 1725 | 20 | 0 | 20 | 0 | 0 | 0 |
| 1726 | 0 | 0 | 10 | 0 | 0 | 0 |
| 1727 | 30 | 0 | 50 | 0 | 0 | 0 |
| 1728 | 70 | 30 | 80 | 0 | 30 | 40 |
| 1729 | 0 | 0 | 0 | 0 | 0 | 0 |
| 1730 | 0 | 0 | 20 | 0 | 0 | 0 |
| 1731 | 0 | 0 | 0 | 0 | 0 | 0 |
| 1732 | 0 | 0 | 0 | 0 | 0 | 0 |
| 1733 | 0 | 0 | 10 | 0 | 0 | 0 |
| 1734 | 0 | 0 | 0 | 0 | 0 | 0 |
| 1735 | 0 | 0 | 0 | 0 | 0 | 0 |
| 1736 | 0 | 0 | 80 | 0 | 0 | 0 |
| 1737 | 0 | 0 | 0 | 0 | 0 | 0 |
| 1738 | 0 | 0 | 0 | 0 | 0 | 0 |
| 1739 | 0 | 0 | 0 | 0 | 0 | 0 |
| 1740 | 0 | 0 | 0 | 0 | 0 | 0 |
| 1741 | 0 | 0 | 0 | 0 | 10 | 0 |
| 1742 | 0 | 0 | 50 | 0 | 0 | 0 |
| 1743 | 30 | 30 | 30 | 0 | 20 | 10 |
| 1744 | 0 | 0 | 0 | 0 | 0 | 0 |
| 1745 | 0 | 0 | 0 | 0 | 0 | 0 |
| 1746 | 0 | 0 | 0 | 0 | 0 | 0 |
| 1747 | 0 | 0 | 0 | 0 | 0 | 0 |
| 1748 | 0 | 0 | 0 | 0 | 0 | 0 |
| 1749 | 0 | 0 | 0 | 0 | 0 | 0 |
| 1750 | 0 | 0 | 0 | 0 | 0 | 0 |
| 1751 | 0 | 0 | 0 | 0 | 0 | 0 |
| 1752 | 0 | 0 | 0 | 0 | 0 | 0 |
| 1753 | 30 | 0 | 70 | 0 | 0 | 0 |
| 1754 | 60 | 0 | 80 | 0 | 10 | 10 |
| 1755 | 70 | 20 | 80 | 0 | 0 | 0 |
| 1757 | 0 | 0 | 0 | 0 | 0 | 0 |
| 1760 | 0 | 0 | 0 | 0 | 0 | 0 |
| 1761 | 0 | 0 | 0 | 0 | 0 | 0 |
| 1762 | 70 | 0 | 70 | 0 | 0 | 0 |
| 1763 | 20 | 0 | 80 | 0 | 0 | 0 |
| 1764 | 40 | 0 | 60 | 0 | 0 | 0 |
| 1765 | 20 | 0 | 50 | 0 | 0 | 0 |
| 1766 | 10 | 20 | 30 | 0 | 0 | 0 |
| 1767 | 20 | 0 | 60 | 0 | 0 | 0 |
| 1768 | 0 | 0 | 0 | 0 | 0 | 0 |
| 1769 | 0 | 0 | 20 | 0 | 0 | 0 |
| 1770 | 0 | 0 | 0 | 0 | 0 | 0 |
| 1771 | 0 | 0 | 0 | 0 | 0 | 0 |
| 1772 | 0 | 0 | 30 | 0 | 0 | 0 |
| 1773 | 90 | 70 | 90 | 0 | 20 | 10 |
| 1783 | 50 | 50 | 80 | 10 | 0 | 0 |
| 1784 | 0 | 0 | 10 | 0 | 0 | 0 |
| 1785 | 0 | 0 | 0 | 0 | 0 | 0 |
| 1786 | 0 | 0 | 0 | 0 | 0 | 0 |
| 1787 | 50 | 20 | 60 | 0 | 0 | 0 |
| 1788 | 0 | 0 | 0 | 0 | 0 | 0 |
| 1789 | 0 | 0 | 0 | 0 | 0 | 0 |
| 1790 | 40 | 20 | 70 | 0 | 0 | 0 |
| 1791 | 70 | 20 | 80 | 10 | 0 | 0 |
| 1792 | 30 | 0 | 80 | 0 | 0 | 0 |
| 1793 | 20 | 0 | 30 | 0 | 0 | 0 |
| 1794 | 0 | 30 | 30 | 0 | 0 | 0 |
| 1795 | 30 | 0 | 60 | 0 | 0 | 0 |
| 1796 | 0 | 0 | 0 | 0 | 0 | 0 |
| 1797 | 40 | 10 | 60 | 0 | 0 | 0 |
| 1798 | 0 | 0 | 0 | 0 | 0 | 0 |
| 1799 | 10 | 0 | 50 | 0 | 0 | 0 |
| 1800 | 10 | 0 | 20 | 0 | 10 | 0 |
| 1801 | 40 | 10 | 80 | 0 | 0 | 0 |
| 1802 | 10 | 0 | 70 | 0 | 0 | 0 |
| 1803 | 20 | 0 | 70 | 0 | 30 | 10 |
| 1804 | 0 | 0 | 50 | 0 | 0 | 0 |
| 1805 | 0 | 0 | 0 | 0 | 20 | 0 |
| 1806 | 0 | 0 | 20 | 0 | 0 | 0 |
| 1807 | 0 | 0 | 0 | 0 | 0 | 0 |
| 1808 | 0 | 0 | 0 | 0 | 0 | 0 |
| 1809 | 90 | 60 | 90 | 10 | 0 | 0 |
| 1810 | 60 | 20 | 80 | 0 | 0 | 0 |
| 1811 | 80 | 0 | 90 | 0 | 30 | 10 |
| 1812 | 0 | 0 | 90 | 0 | 0 | 0 |
| 1813 | 0 | 0 | 0 | 0 | 0 | 0 |
| 1814 | 0 | 0 | 0 | 0 | 0 | 0 |
| 1815 | 0 | 0 | 0 | 0 | 0 | 0 |
| 1816 | 90 | 70 | 90 | 20 | 0 | 0 |
| 1817 | 0 | 0 | 0 | 0 | 0 | 0 |
| 1818 | 30 | 0 | 70 | 0 | 0 | 0 |
| 1819 | 0 | 0 | 20 | 0 | 0 | 0 |
| 1820 | 0 | 0 | 0 | 0 | 0 | 0 |
| 1821 | 0 | 0 | 0 | 0 | 0 | 0 |
| 1822 | 70 | 0 | 90 | 0 | 0 | 0 |
| 1823 | 0 | 0 | 0 | 0 | 0 | 0 |
| 1824 | 0 | 0 | 0 | 0 | 0 | 0 |
| 1825 | 0 | 0 | 0 | 0 | 0 | 0 |
| 1826 | 0 | 10 | 20 | 0 | 0 | 0 |
| 1827 | 0 | 0 | 40 | 0 | 0 | 0 |
| 1828 | 70 | 0 | 80 | 0 | 0 | 0 |
| 1829 | 60 | 0 | 70 | 0 | 0 | 0 |
| 1833 | 0 | 0 | 0 | 0 | 0 | 0 |
| 1836 | 10 | 10 | 50 | 10 | 0 | 0 |

Post-Emergence (250 g ai/ha)

| Cmpd | Barnyard grass | Corn | Foxtail, Giant | Morningglory, Ivy-leaved | Pigweed, Redroot | Velvetleaf |
|---|---|---|---|---|---|---|
| 1396 | 80 | 70 | 80 | 60 | 80 | 60 |
| 1397 | 80 | 80 | 80 | 70 | 60 | 40 |
| 1398 | 80 | 80 | 80 | 60 | 60 | 40 |
| 1399 | 80 | 30 | 80 | 70 | 60 | 40 |
| 1400 | 70 | 60 | 70 | 0 | 60 | 30 |
| 1401 | 50 | 50 | 70 | 30 | 30 | 30 |
| 1402 | 80 | 80 | 80 | 60 | 60 | 50 |
| 1403 | 10 | 20 | 0 | 0 | 10 | 0 |
| 1404 | 40 | 40 | 70 | 30 | 30 | 20 |
| 1405 | 0 | 0 | 0 | 0 | 0 | 0 |
| 1406 | 20 | 10 | 0 | 0 | 20 | 20 |
| 1407 | 60 | 20 | 70 | 30 | 30 | 20 |
| 1408 | 40 | 20 | 60 | 20 | 0 | 10 |
| 1409 | 30 | 10 | 40 | 0 | 10 | 10 |
| 1410 | 20 | 10 | 50 | 20 | 10 | 0 |
| 1411 | 0 | 0 | 0 | 0 | 0 | 0 |
| 1412 | 60 | 10 | 70 | 20 | 40 | 40 |
| 1413 | 60 | 0 | 70 | 0 | 20 | 10 |
| 1414 | 60 | 80 | 80 | 30 | 30 | 0 |
| 1415 | 60 | 20 | 70 | 20 | 30 | 20 |
| 1416 | 0 | 0 | 0 | 0 | 0 | 0 |
| 1417 | 60 | 20 | 70 | 30 | 30 | 20 |
| 1418 | 40 | 10 | 70 | 0 | 0 | 0 |
| 1419 | 60 | 20 | 70 | 10 | 30 | 0 |
| 1420 | 40 | 60 | 60 | 0 | 20 | 10 |
| 1421 | 20 | 10 | 50 | 0 | 0 | 0 |
| 1422 | 0 | 0 | 20 | 0 | 0 | 0 |
| 1423 | 10 | 10 | 60 | 0 | 50 | 0 |
| 1424 | 10 | 10 | 20 | 0 | 20 | 0 |
| 1425 | 20 | 10 | 50 | 0 | 40 | 0 |
| 1426 | 20 | 10 | 40 | 0 | 10 | 0 |
| 1427 | 0 | 0 | 0 | 0 | 0 | 0 |
| 1428 | 40 | 20 | 60 | 20 | 40 | 0 |
| 1429 | 20 | 10 | 40 | 20 | 80 | 30 |
| 1430 | 30 | 0 | 50 | 0 | 20 | 0 |
| 1431 | 0 | 0 | 0 | 0 | 40 | 10 |
| 1432 | 0 | 0 | 0 | 0 | 0 | 0 |
| 1433 | 0 | 0 | 0 | 0 | 0 | 0 |
| 1434 | 20 | 10 | 30 | 0 | 20 | 10 |

| | Post-Emergence (250 g ai/ha) | | | | | |
|---|---|---|---|---|---|---|
| Cmpd | Barnyard grass | Corn | Foxtail, Giant | Morningglory, Ivy-leaved | Pigweed, Redroot | Velvetleaf |
| 1435 | 0 | 10 | 0 | 0 | 30 | 0 |
| 1436 | 0 | 0 | 0 | 0 | 0 | 0 |
| 1437 | 0 | 0 | 0 | 0 | 0 | 0 |
| 1438 | 0 | 0 | 0 | 0 | 10 | 0 |
| 1439 | 10 | 10 | 60 | 0 | 40 | 0 |
| 1440 | 10 | 20 | 60 | 10 | 20 | 0 |
| 1441 | 0 | 20 | 20 | 0 | 0 | 0 |
| 1442 | 0 | 0 | 0 | 0 | 0 | 0 |
| 1443 | 0 | 0 | 0 | 0 | 0 | 0 |
| 1444 | 20 | 10 | 60 | 10 | 20 | 0 |
| 1445 | 0 | 0 | 0 | 0 | 0 | 0 |
| 1446 | 0 | 0 | 0 | 0 | 0 | 0 |
| 1447 | 0 | 10 | 50 | 0 | 0 | 0 |
| 1448 | 0 | 10 | 0 | 0 | 30 | 0 |
| 1449 | 30 | 10 | 60 | 10 | 30 | 0 |
| 1450 | 20 | 10 | 60 | 20 | 30 | 0 |
| 1451 | 0 | 0 | 0 | 0 | 0 | 0 |
| 1452 | 0 | 0 | 10 | 10 | 10 | 10 |
| 1453 | 10 | 10 | 50 | 10 | 0 | 0 |
| 1454 | 20 | 30 | 60 | 10 | 20 | 10 |
| 1455 | 20 | 20 | 50 | 20 | 40 | 10 |
| 1456 | 20 | 60 | 70 | 20 | 40 | 20 |
| 1457 | 10 | 10 | 50 | 20 | 0 | 0 |
| 1458 | 20 | 10 | 60 | 30 | 30 | 0 |
| 1459 | 20 | 10 | 60 | 20 | 40 | 0 |
| 1460 | 60 | 40 | 70 | 10 | 20 | 10 |
| 1461 | 50 | 0 | 70 | 0 | 0 | 0 |
| 1462 | 30 | 10 | 70 | 10 | 0 | 0 |
| 1463 | 30 | 10 | 70 | 20 | 10 | 20 |
| 1464 | 50 | 80 | 70 | 50 | 30 | 10 |
| 1465 | 20 | 10 | 70 | 20 | 0 | 10 |
| 1466 | 20 | 20 | 30 | 10 | 80 | 0 |
| 1468 | 40 | 10 | 70 | 10 | 30 | 10 |
| 1471 | 50 | 0 | 70 | 20 | 20 | 10 |
| 1472 | 50 | 40 | 70 | 20 | 10 | 10 |
| 1473 | 50 | 10 | 70 | 20 | 10 | 10 |
| 1474 | 60 | 40 | 70 | 50 | 30 | 20 |
| 1475 | 50 | 70 | 70 | 70 | 50 | 10 |
| 1476 | 60 | 70 | 70 | 60 | 10 | 10 |
| 1477 | 60 | 50 | 70 | 0 | 30 | 20 |
| 1478 | 60 | 20 | 60 | 10 | 10 | 0 |
| 1479 | 20 | 10 | 0 | 0 | 20 | 0 |
| 1480 | 80 | 60 | 70 | 20 | 10 | 20 |
| 1481 | 70 | 60 | 70 | 80 | 20 | 10 |
| 1482 | 60 | 30 | 60 | 0 | 0 | 10 |
| 1483 | 70 | 50 | 70 | 0 | 60 | 30 |
| 1484 | 40 | 30 | 30 | 0 | 20 | 10 |
| 1485 | 70 | 80 | 70 | 20 | 40 | 20 |
| 1486 | 70 | 60 | 70 | 0 | 30 | 10 |
| 1487 | 70 | 70 | 70 | 20 | 30 | 20 |
| 1488 | 20 | 0 | 30 | 0 | 0 | 0 |
| 1489 | 30 | 40 | 40 | 0 | 10 | 0 |
| 1490 | 60 | 40 | 60 | 30 | 0 | 20 |
| 1491 | 60 | 0 | 60 | 10 | 0 | 0 |
| 1492 | 60 | 0 | 60 | 0 | 0 | 20 |
| 1493 | 80 | 80 | 60 | 0 | 0 | 0 |
| 1494 | 50 | 80 | 60 | 50 | 0 | 30 |
| 1496 | 60 | 50 | 60 | 0 | 0 | 20 |
| 1497 | 60 | 50 | 60 | 10 | 0 | 20 |
| 1498 | 30 | 0 | 30 | 0 | 0 | 0 |
| 1499 | 60 | 80 | 70 | 40 | 0 | 20 |
| 1500 | 60 | 60 | 60 | 10 | 0 | 20 |
| 1501 | 60 | 30 | 60 | 0 | 0 | 0 |
| 1502 | 70 | 60 | 80 | 20 | 80 | 40 |
| 1503 | 10 | 10 | 40 | 0 | 0 | 0 |
| 1504 | 0 | 0 | 0 | 0 | 0 | 0 |
| 1505 | 20 | 10 | 30 | 10 | 0 | 0 |
| 1506 | 0 | 0 | 0 | 0 | 0 | 0 |
| 1507 | 0 | 0 | 0 | 0 | 0 | 0 |
| 1508 | 0 | 0 | 0 | 0 | 0 | 0 |
| 1509 | 0 | 0 | 0 | 0 | 0 | 0 |
| 1510 | 0 | 10 | 0 | 0 | 20 | 0 |
| 1511 | 0 | 0 | 0 | 0 | 0 | 0 |
| 1512 | 0 | 0 | 0 | 0 | 0 | 0 |
| 1513 | 0 | 0 | 0 | 0 | 0 | 0 |
| 1514 | 0 | 10 | 0 | 0 | 0 | 0 |
| 1515 | 0 | 0 | 0 | 0 | 0 | 0 |
| 1516 | 0 | 0 | 0 | 0 | 0 | 0 |
| 1517 | 70 | 80 | 60 | 70 | 20 | 20 |
| 1518 | 0 | 0 | 0 | 0 | 0 | 0 |
| 1519 | 0 | 0 | 0 | 0 | 0 | 0 |
| 1520 | 60 | 20 | 70 | 40 | 10 | 10 |
| 1522 | 0 | 10 | 0 | 0 | 0 | 0 |
| 1525 | 0 | 10 | 10 | 20 | 0 | 0 |
| 1526 | 60 | 10 | 60 | 20 | 0 | 10 |
| 1527 | 0 | 10 | 0 | 0 | 0 | 0 |
| 1528 | 0 | 0 | 0 | 0 | 0 | 0 |
| 1529 | 0 | 0 | 0 | 0 | 0 | 0 |
| 1530 | 0 | 0 | 0 | 0 | 0 | 0 |
| 1531 | 0 | 10 | 0 | 0 | 0 | 0 |
| 1532 | 0 | 0 | 0 | 0 | 0 | 0 |
| 1533 | 0 | 0 | 0 | 0 | 0 | 0 |
| 1534 | 0 | 0 | 0 | 10 | 0 | 10 |
| 1535 | 0 | 10 | 0 | 0 | 30 | 0 |
| 1536 | 0 | 0 | 0 | 0 | 0 | 0 |
| 1537 | 0 | 0 | 0 | 0 | 0 | 0 |
| 1538 | 10 | 10 | 50 | 0 | 0 | 0 |
| 1539 | 0 | 0 | 0 | 0 | 0 | 0 |
| 1540 | 0 | 10 | 0 | 10 | 20 | 0 |
| 1541 | 20 | 10 | 50 | 10 | 20 | 0 |
| 1542 | 0 | 0 | 0 | 0 | 0 | 0 |
| 1543 | 0 | 10 | 20 | 30 | 40 | 30 |
| 1544 | 0 | 10 | 0 | 0 | 0 | 0 |
| 1545 | 0 | 0 | 0 | 0 | 0 | 0 |
| 1546 | 80 | 50 | 80 | 30 | 60 | 10 |
| 1547 | 0 | 0 | 0 | 0 | 0 | 0 |
| 1548 | 0 | 0 | 0 | 0 | 0 | 0 |
| 1549 | 0 | 0 | 0 | 0 | 0 | 0 |
| 1550 | 0 | 30 | 0 | 0 | 40 | 0 |
| 1551 | 0 | 10 | 0 | 0 | 0 | 0 |
| 1552 | 0 | 10 | 0 | 0 | 0 | 0 |
| 1553 | 0 | 0 | 0 | 0 | 0 | 0 |
| 1554 | 0 | 0 | 0 | 0 | 0 | 0 |
| 1555 | 40 | 0 | 50 | 50 | 20 | 10 |
| 1556 | 20 | 0 | 0 | 0 | 0 | 0 |
| 1557 | 20 | 20 | 10 | 0 | 0 | 10 |
| 1558 | 20 | 0 | 0 | 0 | 0 | 0 |
| 1559 | 0 | 0 | 0 | 0 | 0 | 0 |
| 1560 | 20 | 0 | 20 | 0 | 20 | 10 |
| 1561 | 50 | 50 | 60 | 60 | 30 | 20 |
| 1562 | 20 | 0 | 20 | 0 | 20 | 0 |
| 1563 | 0 | 0 | 0 | 0 | 0 | 0 |
| 1564 | 20 | 10 | 10 | 0 | 10 | 0 |
| 1565 | 10 | 10 | 50 | 0 | 0 | 30 |
| 1566 | 20 | 0 | 0 | 0 | 0 | 0 |
| 1567 | 10 | 0 | 0 | 0 | 0 | 0 |
| 1568 | 20 | 10 | 0 | 0 | 0 | 0 |
| 1569 | 20 | 0 | 0 | 0 | 0 | 0 |
| 1570 | 10 | 0 | 20 | 10 | 0 | 0 |
| 1571 | 0 | 0 | 0 | 0 | 0 | 0 |
| 1572 | 0 | 0 | 40 | 30 | 20 | 0 |
| 1573 | 0 | 0 | 0 | 0 | 0 | 0 |
| 1574 | 40 | 0 | 60 | 40 | 0 | 0 |
| 1575 | 0 | 0 | 0 | 0 | 0 | 0 |
| 1576 | 70 | 10 | 70 | 20 | 0 | 10 |
| 1577 | 0 | 0 | 0 | 0 | 0 | 0 |
| 1578 | 20 | 10 | 60 | 30 | 30 | 20 |
| 1579 | 10 | 0 | 0 | 0 | 0 | 0 |
| 1580 | 0 | 0 | 0 | 0 | 0 | 0 |
| 1581 | 10 | 0 | 0 | 0 | 0 | 0 |
| 1582 | 0 | 0 | 0 | — | 0 | 0 |
| 1583 | 20 | 0 | 10 | 30 | 20 | 20 |
| 1584 | 70 | 0 | 80 | 10 | 40 | 20 |
| 1585 | 70 | 80 | 70 | 70 | 30 | 30 |
| 1586 | 50 | 30 | 70 | 40 | 40 | 10 |
| 1587 | 40 | 0 | 60 | 40 | 70 | 0 |

Post-Emergence (250 g ai/ha)

| Cmpd | Barn-yard grass | Corn | Foxtail, Giant | Morningglory, Ivy-leaved | Pigweed, Redroot | Velvetleaf |
|---|---|---|---|---|---|---|
| 1588 | 80 | 80 | 70 | 50 | 20 | 40 |
| 1589 | 0 | 0 | 0 | 0 | 0 | 0 |
| 1590 | 30 | 0 | 80 | 30 | 0 | 0 |
| 1591 | 50 | 10 | 80 | 10 | 10 | 10 |
| 1592 | 30 | 10 | 70 | 60 | 10 | 10 |
| 1593 | 20 | 10 | 70 | 0 | 0 | 0 |
| 1594 | 20 | 0 | 20 | 0 | 0 | 0 |
| 1595 | 10 | 0 | 10 | 20 | 20 | 10 |
| 1596 | 70 | 10 | 80 | 20 | 40 | 10 |
| 1597 | 0 | 0 | 0 | 0 | 0 | 0 |
| 1598 | 70 | 60 | 80 | 70 | 70 | 50 |
| 1599 | 70 | 40 | 80 | 50 | 50 | 40 |
| 1600 | 0 | 0 | 0 | 0 | 0 | 0 |
| 1601 | 70 | 30 | 70 | 30 | 30 | 50 |
| 1602 | 40 | 20 | 80 | 50 | 70 | 40 |
| 1603 | 0 | 0 | 0 | 0 | 0 | 0 |
| 1604 | 0 | 0 | 0 | 0 | 0 | 0 |
| 1605 | 30 | 10 | 10 | 0 | 30 | 10 |
| 1606 | 50 | 0 | 80 | 30 | 100 | 60 |
| 1607 | 60 | 60 | 80 | 60 | 70 | 40 |
| 1608 | 10 | 20 | 60 | 40 | 20 | 0 |
| 1609 | 70 | 60 | 80 | 70 | 70 | 50 |
| 1610 | 0 | 0 | 0 | 0 | 0 | 0 |
| 1611 | 0 | 0 | 0 | 0 | 0 | 0 |
| 1612 | 0 | 0 | 0 | 0 | 0 | 0 |
| 1613 | 60 | 0 | 80 | 0 | 60 | 30 |
| 1614 | 0 | 0 | 0 | 0 | 80 | 20 |
| 1615 | 0 | 0 | 0 | 0 | 0 | 0 |
| 1616 | 60 | 0 | 80 | 20 | 60 | 30 |
| 1617 | 60 | 0 | 70 | 0 | 0 | 0 |
| 1618 | 0 | 0 | 0 | 0 | 0 | 0 |
| 1619 | 70 | 10 | 70 | 30 | 50 | 0 |
| 1620 | 0 | 0 | 0 | 0 | 0 | 0 |
| 1621 | 30 | 0 | 40 | 0 | 10 | 0 |
| 1622 | 0 | 0 | 0 | 0 | 0 | 0 |
| 1623 | 80 | 30 | 80 | 60 | 60 | 20 |
| 1624 | 70 | 10 | 80 | 20 | 20 | 10 |
| 1625 | 40 | 10 | 80 | 20 | 50 | 40 |
| 1626 | 0 | 0 | 0 | 0 | 0 | 0 |
| 1627 | 80 | 70 | 80 | 70 | 70 | 40 |
| 1628 | 70 | 50 | 80 | 50 | 60 | 20 |
| 1629 | 70 | 10 | 80 | 30 | 30 | 0 |
| 1630 | 0 | 0 | 0 | 0 | 0 | 0 |
| 1631 | 10 | 10 | 70 | 20 | 20 | 0 |
| 1632 | 10 | 0 | 20 | 0 | 20 | 0 |
| 1633 | 0 | 0 | 0 | 0 | 0 | 0 |
| 1634 | 0 | 0 | 20 | 0 | 0 | 0 |
| 1635 | 30 | 0 | 40 | 0 | 10 | 0 |
| 1636 | 50 | 0 | 70 | 0 | 0 | 0 |
| 1637 | 70 | 10 | 80 | 30 | 70 | 30 |
| 1638 | 0 | 0 | 0 | 0 | 0 | 0 |
| 1639 | 60 | 10 | 80 | 20 | 60 | 20 |
| 1640 | 0 | 0 | 0 | 0 | 0 | 0 |
| 1641 | 0 | 0 | 0 | 0 | 0 | 0 |
| 1642 | 10 | 0 | 70 | 0 | 20 | 0 |
| 1643 | 0 | 0 | 0 | 0 | 0 | 0 |
| 1644 | 20 | 0 | 30 | 40 | 0 | 0 |
| 1645 | 70 | 0 | 80 | 0 | 40 | 0 |
| 1646 | 0 | 0 | 20 | 0 | 0 | 0 |
| 1647 | 50 | 10 | 70 | 20 | 30 | 40 |
| 1648 | 0 | 0 | 0 | 0 | 0 | 0 |
| 1649 | 20 | 0 | 60 | 0 | 40 | 0 |
| 1650 | 80 | 70 | 80 | 20 | 80 | 40 |
| 1651 | 10 | 0 | 90 | 10 | 0 | 10 |
| 1652 | 30 | 0 | 40 | 0 | 0 | 0 |
| 1653 | 80 | 70 | 80 | 40 | 80 | 50 |
| 1654 | 60 | 20 | 80 | 30 | 30 | 40 |
| 1655 | 20 | 0 | 30 | 0 | 40 | 0 |
| 1656 | 30 | 0 | 80 | 0 | 30 | 20 |
| 1657 | 40 | 20 | 70 | 30 | 60 | 20 |
| 1658 | 20 | 10 | 20 | 20 | 40 | 10 |
| 1659 | 20 | 10 | 40 | 0 | 20 | 0 |
| 1660 | 0 | 0 | 0 | 0 | 0 | 0 |
| 1661 | 10 | 0 | 60 | 0 | 40 | 10 |
| 1662 | 0 | 0 | 0 | 0 | 0 | 0 |
| 1663 | 0 | 0 | 0 | 0 | 0 | 0 |
| 1664 | 70 | 80 | 80 | 30 | 80 | 20 |
| 1665 | 40 | 0 | 60 | 0 | 40 | 0 |
| 1667 | 10 | 0 | 20 | 0 | 0 | 0 |
| 1668 | 0 | 0 | 10 | 0 | 0 | 0 |
| 1669 | 70 | 0 | 80 | 60 | 30 | 0 |
| 1670 | 60 | 10 | 80 | 0 | 90 | 0 |
| 1671 | 80 | 80 | 80 | 50 | 50 | 40 |
| 1672 | 0 | 10 | 0 | 0 | 40 | 0 |
| 1673 | 0 | 0 | 10 | 0 | 0 | 0 |
| 1674 | 0 | 0 | 20 | 0 | 0 | 0 |
| 1675 | 0 | 0 | 20 | 0 | 0 | 10 |
| 1676 | 0 | 0 | 0 | 0 | 0 | 0 |
| 1677 | 10 | 0 | 50 | 0 | 0 | 0 |
| 1678 | 30 | 0 | 20 | 0 | 30 | 0 |
| 1679 | 90 | 60 | 80 | 40 | 50 | 40 |
| 1680 | 50 | 0 | 80 | 20 | 60 | 0 |
| 1682 | 0 | 0 | — | 0 | 0 | 0 |
| 1683 | 80 | 80 | 80 | 50 | 40 | 50 |
| 1684 | 0 | 0 | — | 0 | 0 | 0 |
| 1685 | 80 | 70 | 80 | 70 | 70 | 60 |
| 1686 | 80 | 60 | 80 | 70 | 40 | 40 |
| 1687 | 80 | 90 | 80 | 70 | 50 | 50 |
| 1688 | 90 | 60 | — | 60 | 10 | 10 |
| 1690 | 90 | 80 | 90 | 60 | 40 | 40 |
| 1691 | 70 | 70 | — | 30 | 0 | 20 |
| 1692 | 80 | 80 | 80 | 70 | 40 | 30 |
| 1693 | 80 | 70 | 80 | 60 | 60 | 20 |
| 1694 | 0 | 0 | 0 | 0 | 0 | 0 |
| 1696 | 80 | 70 | 80 | 60 | 60 | 10 |
| 1697 | 90 | 80 | 80 | 60 | 70 | 30 |
| 1698 | 80 | 70 | 80 | 70 | 60 | 50 |
| 1699 | 90 | 70 | 80 | 70 | 30 | 30 |
| 1700 | 70 | 40 | 70 | 60 | 0 | 0 |
| 1701 | 70 | 50 | 60 | 30 | 30 | 0 |
| 1702 | 80 | 80 | 80 | 70 | 40 | 70 |
| 1703 | 80 | 80 | 80 | 60 | 80 | 70 |
| 1704 | 80 | 80 | 80 | 70 | 10 | 20 |
| 1705 | 80 | 70 | 80 | 50 | 30 | 10 |
| 1706 | 80 | 70 | 80 | 60 | 20 | 20 |
| 1707 | 80 | 80 | — | 70 | 0 | 30 |
| 1708 | 80 | 70 | 60 | 20 | 0 | 0 |
| 1709 | 80 | 80 | 80 | 70 | 30 | 50 |
| 1710 | — | — | — | — | — | — |
| 1711 | 80 | 40 | 80 | 70 | 0 | 0 |
| 1712 | 90 | 70 | 80 | 70 | 20 | 40 |
| 1713 | 80 | 80 | 80 | 70 | 0 | 20 |
| 1714 | 80 | 50 | 80 | 60 | 90 | 40 |
| 1716 | 80 | 60 | 80 | 10 | 0 | 0 |
| 1717 | 70 | 10 | 80 | 0 | 0 | 0 |
| 1718 | 80 | 80 | 80 | 70 | 70 | 60 |
| 1719 | 80 | 60 | 80 | 20 | 0 | 0 |
| 1720 | — | — | — | — | — | — |
| 1721 | 80 | 10 | 80 | 70 | 0 | 0 |
| 1722 | 80 | 80 | 80 | 70 | 30 | 10 |
| 1723 | 80 | 70 | 80 | 40 | 30 | 20 |
| 1724 | 90 | 90 | 90 | 70 | 60 | 70 |
| 1725 | 70 | 70 | 80 | 70 | 60 | 10 |
| 1726 | 70 | 70 | 70 | 70 | 40 | 20 |
| 1727 | 70 | 10 | 80 | 50 | 0 | 10 |
| 1728 | 80 | 80 | 80 | 70 | 80 | 60 |
| 1729 | 0 | 0 | 0 | 0 | 0 | 0 |
| 1730 | 80 | 0 | 80 | 0 | 0 | 0 |
| 1731 | 0 | 0 | 0 | 0 | 10 | 0 |
| 1732 | 20 | 0 | 50 | 0 | 20 | 0 |
| 1733 | 80 | 70 | 80 | 70 | 80 | 80 |
| 1734 | 0 | 0 | 0 | 0 | 0 | 0 |
| 1735 | 0 | 0 | 0 | 0 | 0 | 0 |
| 1736 | 70 | 70 | 80 | 40 | 0 | 0 |
| 1737 | 0 | 0 | 0 | 0 | 0 | 0 |
| 1738 | 80 | 0 | 70 | 0 | 10 | 10 |

| Post-Emergence (250 g ai/ha) | | | | | | |
|---|---|---|---|---|---|---|
| Cmpd | Barn-yard grass | Corn | Foxtail, Giant | Morningglory, Ivy-leaved | Pigweed, Redroot | Velvetleaf |
| 1739 | 0 | 0 | 0 | 0 | 0 | 0 |
| 1740 | 20 | 0 | — | 20 | 0 | 10 |
| 1741 | 70 | 0 | — | 10 | 0 | 10 |
| 1742 | 80 | 70 | 80 | 40 | 30 | 20 |
| 1743 | 80 | 60 | — | 30 | 50 | 50 |
| 1744 | 70 | 10 | 60 | 40 | 30 | 10 |
| 1745 | 80 | 0 | 70 | 40 | 20 | 0 |
| 1746 | 40 | 10 | 70 | 60 | 20 | 10 |
| 1747 | 80 | 30 | 80 | 50 | 20 | 10 |
| 1748 | 0 | 0 | 0 | 0 | 0 | 0 |
| 1749 | 0 | 0 | 0 | 0 | 0 | 0 |
| 1750 | 20 | 10 | 50 | 10 | 20 | 0 |
| 1751 | 0 | 0 | 10 | 0 | 10 | 10 |
| 1752 | 0 | 0 | 0 | 0 | 0 | 0 |
| 1753 | 70 | 80 | 70 | 60 | 30 | 30 |
| 1754 | 80 | 70 | — | 70 | 70 | 60 |
| 1755 | 80 | 80 | — | 70 | 30 | 60 |
| 1757 | 30 | 0 | 60 | 10 | 0 | 0 |
| 1760 | 10 | 10 | 20 | 20 | 0 | 10 |
| 1761 | 70 | 0 | 70 | 50 | 10 | 10 |
| 1762 | 80 | 80 | 80 | 70 | 10 | 70 |
| 1763 | 70 | 70 | 70 | 50 | 20 | 20 |
| 1764 | 80 | 70 | 80 | 70 | 30 | 60 |
| 1765 | 70 | 10 | 70 | 20 | 0 | 0 |
| 1766 | 80 | 60 | 80 | 40 | 20 | 10 |
| 1767 | 80 | 60 | 80 | 60 | 20 | 60 |
| 1768 | 0 | 0 | 0 | 0 | 0 | 0 |
| 1769 | 50 | 10 | 60 | 20 | 0 | 0 |
| 1770 | 70 | 0 | 70 | 20 | 40 | 30 |
| 1771 | 0 | 0 | — | 0 | 0 | 0 |
| 1772 | 30 | 60 | 80 | 50 | 10 | 30 |
| 1773 | 80 | 80 | 80 | 60 | 40 | 40 |
| 1783 | 80 | 80 | 80 | 70 | 20 | 50 |
| 1784 | 0 | 0 | 0 | 0 | 0 | 0 |
| 1785 | 0 | 0 | — | 0 | 0 | 0 |
| 1786 | 0 | 0 | — | 0 | 20 | 30 |
| 1787 | 60 | 60 | — | 70 | 70 | 40 |
| 1788 | 0 | 10 | 0 | 40 | 20 | 20 |
| 1789 | 0 | 10 | — | 0 | 20 | 20 |
| 1790 | 70 | 80 | 80 | 40 | 0 | 30 |
| 1791 | 80 | 80 | 80 | 70 | 0 | 20 |
| 1792 | 70 | 60 | 80 | 40 | 0 | 40 |
| 1793 | 80 | 50 | 80 | 70 | 0 | 30 |
| 1794 | 70 | 70 | 80 | 70 | 70 | 10 |
| 1795 | 70 | 70 | 80 | 70 | 30 | 20 |
| 1796 | 0 | 0 | 0 | 10 | 20 | 0 |
| 1797 | 80 | 70 | 80 | 80 | 80 | 90 |
| 1798 | 0 | 0 | 10 | 0 | 20 | 0 |
| 1799 | 70 | 70 | 70 | 30 | 70 | 10 |
| 1800 | 80 | 0 | 70 | 20 | 10 | 0 |
| 1801 | 70 | 80 | 80 | 50 | 40 | 0 |
| 1802 | 70 | 60 | 80 | 0 | 40 | 70 |
| 1803 | 70 | 0 | 80 | 10 | 20 | 0 |
| 1804 | 60 | 70 | 80 | 60 | 10 | 10 |
| 1805 | 0 | 0 | 40 | 30 | 40 | 30 |
| 1806 | 50 | 40 | 60 | 0 | 0 | 0 |
| 1807 | 0 | 0 | 0 | 0 | 0 | 0 |
| 1808 | 60 | 0 | 60 | 0 | 0 | 0 |
| 1809 | 80 | 80 | 80 | 70 | 50 | 40 |
| 1810 | 80 | 50 | 80 | 20 | 60 | 40 |
| 1811 | 80 | 80 | 80 | 70 | 80 | 50 |
| 1812 | 70 | 50 | 80 | 70 | 50 | 60 |
| 1813 | 0 | 0 | 20 | 40 | 20 | 10 |
| 1814 | 0 | 0 | 10 | 0 | 0 | 0 |
| 1815 | 0 | 0 | 10 | 0 | 0 | 0 |
| 1816 | 80 | 80 | 80 | 70 | 70 | 30 |
| 1817 | 0 | 0 | 0 | 0 | 0 | 0 |
| 1818 | 80 | 60 | 80 | 40 | 0 | 30 |
| 1819 | 80 | 20 | 80 | 50 | 10 | 0 |
| 1820 | 0 | 0 | 0 | 0 | 0 | 0 |
| 1821 | 0 | 30 | 30 | 10 | 70 | 0 |
| 1822 | 80 | 60 | 80 | 30 | 30 | 40 |
| 1823 | 0 | 0 | 0 | 0 | 0 | 0 |
| 1824 | 10 | 20 | 10 | 10 | 20 | 70 |
| 1825 | 0 | 10 | 50 | 20 | 10 | 20 |
| 1826 | 70 | 50 | 80 | 10 | 50 | 10 |
| 1827 | 80 | 60 | 80 | 10 | 0 | 40 |
| 1828 | 80 | 70 | 80 | 70 | 20 | 10 |
| 1829 | 70 | 60 | 80 | 30 | 60 | 20 |
| 1833 | 0 | 0 | 0 | 0 | 0 | 0 |
| 1836 | 80 | 70 | 70 | 40 | 70 | 50 |

| Post-Emergence (62.5 g ai/ha) | | | | | | |
|---|---|---|---|---|---|---|
| Cmpd | Barn-yard grass | Corn | Foxtail, Giant | Morningglory, Ivy-leaved | Pigweed, Redroot | Velvetleaf |
| 1396 | 80 | 80 | 80 | 60 | 70 | 30 |
| 1397 | 80 | 80 | 80 | 60 | 30 | 10 |
| 1398 | 80 | 70 | 80 | 40 | 50 | 40 |
| 1399 | 70 | 0 | 80 | 30 | 20 | 40 |
| 1400 | 70 | 20 | 70 | 0 | 50 | 10 |
| 1401 | 20 | 0 | 60 | 0 | 0 | 20 |
| 1402 | 80 | 80 | 80 | 40 | 60 | 30 |
| 1403 | 0 | 10 | 0 | 0 | 10 | 0 |
| 1404 | 20 | 20 | 50 | 10 | 40 | 20 |
| 1405 | 0 | 0 | 0 | 0 | 0 | 0 |
| 1406 | 0 | 0 | 0 | 10 | 40 | 20 |
| 1407 | 40 | 10 | 70 | 20 | 10 | 20 |
| 1408 | 0 | 0 | 0 | 0 | 0 | 0 |
| 1409 | 10 | 0 | 0 | 0 | 0 | 0 |
| 1410 | 0 | 0 | 0 | 0 | 0 | 0 |
| 1411 | 0 | 0 | 0 | 0 | 0 | 0 |
| 1412 | 50 | 10 | 60 | 0 | 40 | 40 |
| 1413 | 50 | 0 | 70 | 0 | 10 | 0 |
| 1414 | 50 | 50 | 70 | 30 | 0 | 0 |
| 1415 | 30 | 10 | 60 | 10 | 10 | 0 |
| 1416 | 0 | 0 | 0 | 0 | 0 | 0 |
| 1417 | 40 | 10 | 70 | 20 | 10 | 20 |
| 1418 | 30 | 0 | 50 | 0 | 0 | 0 |
| 1419 | 50 | 10 | 60 | 20 | 20 | 10 |
| 1420 | 40 | 40 | 60 | 10 | 0 | 0 |
| 1421 | 20 | 10 | 40 | 0 | 0 | 0 |
| 1422 | 0 | 10 | 0 | 0 | 0 | 0 |
| 1423 | 10 | 0 | 20 | 0 | 0 | 0 |
| 1424 | 0 | 0 | 0 | 0 | 20 | 0 |
| 1425 | 20 | 10 | 40 | 0 | 30 | 0 |
| 1426 | 0 | 0 | 0 | 0 | 10 | 0 |
| 1427 | 0 | 0 | 0 | 0 | 0 | 0 |
| 1428 | 20 | 10 | 50 | 10 | 10 | 0 |
| 1429 | 10 | 0 | 30 | 10 | 0 | 0 |
| 1430 | 0 | 0 | 10 | 0 | 0 | 0 |
| 1431 | 0 | 0 | 0 | 0 | 0 | 0 |
| 1432 | 0 | 0 | 0 | 0 | 0 | 0 |
| 1433 | 0 | 0 | 0 | 0 | 0 | 0 |
| 1434 | 0 | 0 | 0 | 0 | 0 | 0 |
| 1435 | 0 | 0 | 0 | 0 | 30 | 0 |
| 1436 | 0 | 0 | 0 | 0 | 0 | 0 |
| 1437 | 0 | 0 | 0 | 0 | 0 | 0 |
| 1438 | 0 | 0 | 0 | 0 | 0 | 0 |
| 1439 | 0 | 10 | 20 | 0 | 0 | 0 |
| 1440 | 0 | 10 | 20 | 0 | 10 | 0 |
| 1441 | 0 | 0 | 0 | 0 | 0 | 0 |
| 1442 | 0 | 0 | 0 | 0 | 0 | 0 |
| 1443 | 0 | 0 | 0 | 0 | 0 | 0 |
| 1444 | 10 | 10 | 60 | 10 | 10 | 0 |
| 1445 | 0 | 0 | 0 | 0 | 0 | 0 |
| 1446 | 0 | 0 | 0 | 0 | 0 | 0 |
| 1447 | 0 | 10 | 20 | 0 | 0 | 0 |
| 1448 | 0 | 0 | 0 | 0 | 0 | 0 |
| 1449 | 10 | 0 | 20 | 0 | 0 | 0 |
| 1450 | 10 | 10 | 30 | 10 | 0 | 0 |

| | Post-Emergence (62.5 g ai/ha) | | | | | |
|---|---|---|---|---|---|---|
| Cmpd | Barnyard grass | Corn | Foxtail, Giant | Morningglory, Ivy-leaved | Pigweed, Redroot | Velvetleaf |
| 1451 | 0 | 0 | 0 | 0 | 0 | 0 |
| 1452 | 0 | 0 | 0 | 10 | 0 | 0 |
| 1453 | 10 | 10 | 50 | 0 | 0 | 0 |
| 1454 | 20 | 20 | 60 | 10 | 20 | 0 |
| 1455 | 0 | 10 | 10 | 0 | 0 | 0 |
| 1456 | 10 | 20 | 60 | 30 | 30 | 20 |
| 1457 | 10 | 0 | 20 | 0 | 0 | 0 |
| 1458 | 20 | 10 | 50 | 20 | 30 | 0 |
| 1459 | 10 | 10 | 60 | 0 | 40 | 0 |
| 1460 | 30 | 0 | 70 | 0 | 10 | 0 |
| 1461 | 30 | 0 | 70 | 0 | 0 | 0 |
| 1462 | 20 | 0 | 50 | 20 | 0 | 0 |
| 1463 | 0 | 10 | 0 | 0 | 10 | 10 |
| 1464 | 20 | 10 | 70 | 20 | 10 | 0 |
| 1465 | 10 | 10 | 60 | 0 | 0 | 0 |
| 1466 | 0 | 10 | 10 | 10 | 30 | 0 |
| 1468 | 50 | 10 | 70 | 0 | 0 | 0 |
| 1471 | 30 | 0 | 60 | 0 | 0 | 0 |
| 1472 | 30 | 20 | 50 | 20 | 10 | 10 |
| 1473 | 40 | 10 | 70 | 10 | 0 | 0 |
| 1474 | 50 | 30 | 70 | 50 | 0 | 0 |
| 1475 | 60 | 40 | 70 | 0 | 30 | 10 |
| 1476 | 50 | 20 | 70 | 20 | 0 | 0 |
| 1477 | 60 | 60 | 60 | 0 | 0 | 20 |
| 1478 | 40 | 10 | 30 | 0 | 0 | 0 |
| 1479 | 20 | 10 | 20 | 0 | 0 | 0 |
| 1480 | 70 | 20 | 70 | 0 | 0 | 0 |
| 1481 | 60 | 20 | 60 | 10 | 0 | 0 |
| 1482 | 30 | 30 | 30 | 0 | 0 | 0 |
| 1483 | 40 | 30 | 60 | 0 | 30 | 10 |
| 1484 | 20 | 0 | 10 | 0 | 0 | 0 |
| 1485 | 70 | 70 | 70 | 0 | 20 | 10 |
| 1486 | 60 | 10 | 60 | 0 | 0 | 0 |
| 1487 | 60 | 60 | 70 | 0 | 0 | 0 |
| 1488 | 20 | 10 | 0 | 0 | 0 | 0 |
| 1489 | 0 | 10 | 0 | 0 | 0 | 0 |
| 1490 | 60 | 30 | 60 | 0 | 0 | 0 |
| 1491 | 20 | 0 | 20 | 0 | 0 | 0 |
| 1492 | 30 | 0 | 40 | 0 | 0 | 0 |
| 1493 | 70 | 40 | 60 | 0 | 0 | 0 |
| 1494 | 60 | 30 | 60 | 40 | 0 | 0 |
| 1496 | 50 | 20 | 60 | 0 | 0 | 0 |
| 1497 | 60 | 0 | 60 | 0 | 0 | 0 |
| 1498 | 0 | 0 | 0 | 0 | 0 | 0 |
| 1499 | 60 | 0 | 60 | 0 | 0 | 0 |
| 1500 | 60 | 10 | 60 | 0 | 0 | 0 |
| 1501 | 50 | 20 | 60 | 0 | 0 | 0 |
| 1502 | 60 | 30 | 80 | 0 | 30 | 10 |
| 1503 | 10 | 10 | 20 | 0 | 0 | 0 |
| 1504 | 0 | 0 | 0 | 0 | 0 | 0 |
| 1505 | 0 | 10 | 0 | 0 | 0 | 0 |
| 1506 | 0 | 0 | 0 | 0 | 0 | 0 |
| 1507 | 0 | 0 | 0 | 0 | 0 | 0 |
| 1508 | 0 | 0 | 0 | 0 | 0 | 0 |
| 1509 | 0 | 0 | 0 | 0 | 0 | 0 |
| 1510 | 0 | 0 | 0 | 0 | 0 | 0 |
| 1511 | 0 | 0 | 0 | 0 | 0 | 0 |
| 1512 | 0 | 0 | 0 | 0 | 0 | 0 |
| 1513 | 0 | 0 | 0 | 0 | 0 | 0 |
| 1514 | 0 | 10 | 0 | 0 | 0 | 0 |
| 1515 | 0 | 0 | 0 | 0 | 0 | 0 |
| 1516 | 0 | 0 | 0 | 0 | 0 | 0 |
| 1517 | 50 | 10 | 60 | 30 | 0 | 10 |
| 1518 | 0 | 0 | 0 | 0 | 0 | 0 |
| 1519 | 0 | 10 | 0 | 0 | 0 | 0 |
| 1520 | 30 | 0 | 30 | 30 | 0 | 0 |
| 1522 | 0 | 10 | 0 | 0 | 0 | 0 |
| 1525 | 0 | 0 | 0 | 0 | 0 | 0 |
| 1526 | 0 | 10 | 20 | 10 | 0 | 0 |
| 1527 | 0 | 10 | 0 | 0 | 0 | 0 |
| 1528 | 0 | 0 | 0 | 0 | 0 | 0 |
| 1529 | 0 | 0 | 0 | 0 | 0 | 0 |
| 1530 | 0 | 0 | 0 | 0 | 0 | 0 |
| 1531 | 0 | 0 | 0 | 0 | 0 | 0 |
| 1532 | 0 | 0 | 0 | 0 | 0 | 0 |
| 1533 | 0 | 0 | 0 | 0 | 0 | 0 |
| 1534 | 0 | 0 | 0 | 0 | 0 | 0 |
| 1535 | 0 | 0 | 0 | 0 | 10 | 0 |
| 1536 | 0 | 0 | 0 | 0 | 0 | 0 |
| 1537 | 0 | 0 | 0 | 0 | 0 | 0 |
| 1538 | 0 | 0 | 30 | 0 | 0 | 0 |
| 1539 | 0 | 0 | 0 | 0 | 0 | 0 |
| 1540 | 0 | 10 | 0 | 10 | 0 | 0 |
| 1541 | 0 | 0 | 0 | 0 | 0 | 0 |
| 1542 | 0 | 0 | 0 | 0 | 0 | 0 |
| 1543 | 0 | 0 | 0 | 0 | 0 | 0 |
| 1544 | 0 | 10 | 0 | 0 | 0 | 0 |
| 1545 | 0 | 0 | 0 | 0 | 0 | 0 |
| 1546 | 70 | 20 | 80 | 20 | 60 | 0 |
| 1547 | 0 | 0 | 0 | 0 | 0 | 0 |
| 1548 | 0 | 0 | 0 | 0 | 0 | 0 |
| 1549 | 0 | 0 | 0 | 0 | 0 | 0 |
| 1550 | 0 | 10 | 0 | 0 | 30 | 0 |
| 1551 | 0 | 0 | 0 | 0 | 0 | 0 |
| 1552 | 0 | 10 | 0 | 0 | 0 | 0 |
| 1553 | 0 | 0 | 0 | 0 | 0 | 0 |
| 1554 | 0 | 0 | 0 | 0 | 0 | 0 |
| 1555 | 0 | 10 | 0 | 10 | 0 | 0 |
| 1556 | 0 | 0 | 0 | 0 | 0 | 0 |
| 1557 | 20 | 0 | 0 | 0 | 0 | 0 |
| 1558 | 10 | 0 | 0 | 0 | 0 | 0 |
| 1559 | 0 | 0 | 0 | 0 | 0 | 0 |
| 1560 | 0 | 0 | 0 | 0 | 0 | 0 |
| 1561 | 20 | 0 | 10 | 10 | 20 | 40 |
| 1562 | 0 | 10 | 0 | 0 | 10 | 0 |
| 1563 | 0 | 0 | 0 | 0 | 0 | 0 |
| 1564 | 0 | 0 | 0 | 0 | 0 | 0 |
| 1565 | 0 | 0 | 0 | 0 | 0 | 0 |
| 1566 | 10 | 0 | 0 | 0 | 0 | 0 |
| 1567 | 0 | 0 | 0 | 0 | 0 | 0 |
| 1568 | 10 | 0 | 0 | 0 | 0 | 0 |
| 1569 | 10 | 0 | 0 | 0 | 0 | 0 |
| 1570 | 0 | 0 | 0 | 0 | 0 | 0 |
| 1571 | 0 | 0 | 0 | 0 | 0 | 0 |
| 1572 | 0 | 0 | 0 | 10 | 0 | 0 |
| 1573 | 0 | 0 | 0 | 0 | 0 | 0 |
| 1574 | 0 | 0 | 0 | 0 | 0 | 0 |
| 1575 | 0 | 0 | 0 | 0 | 0 | 0 |
| 1576 | 60 | 20 | 40 | 20 | 0 | 0 |
| 1577 | 0 | 0 | 0 | 0 | 0 | 0 |
| 1578 | 20 | 0 | 10 | 10 | 20 | 10 |
| 1579 | 10 | 0 | 0 | 0 | 0 | 0 |
| 1580 | 0 | 0 | 0 | 0 | 0 | 0 |
| 1581 | 0 | 0 | 0 | 0 | 0 | 0 |
| 1582 | 0 | 0 | 0 | — | 0 | 0 |
| 1583 | 0 | 0 | 20 | 10 | 0 | 0 |
| 1584 | 0 | 10 | 40 | 20 | 0 | 0 |
| 1585 | 80 | 60 | 60 | 30 | 20 | 20 |
| 1586 | 0 | 0 | 0 | 0 | 0 | 10 |
| 1587 | 20 | 0 | 20 | 0 | 10 | 0 |
| 1588 | 80 | 80 | 70 | 20 | 0 | 0 |
| 1589 | 0 | 0 | 0 | 0 | 0 | 0 |
| 1590 | 0 | 0 | 70 | 20 | 0 | 0 |
| 1591 | 30 | 0 | 70 | 10 | 10 | 0 |
| 1592 | 10 | 0 | 60 | 40 | 0 | 10 |
| 1593 | 0 | 10 | 10 | 0 | 0 | 0 |
| 1594 | 20 | 0 | 20 | 0 | 0 | 0 |
| 1595 | 10 | 60 | 0 | 60 | 10 | 10 |
| 1596 | 30 | 0 | 60 | 10 | 10 | 0 |
| 1597 | 0 | 0 | 0 | 0 | 0 | 0 |
| 1598 | 80 | 40 | 80 | 60 | 50 | 20 |
| 1599 | 70 | 0 | 80 | 60 | 50 | 30 |
| 1600 | 0 | 0 | 0 | 0 | 0 | 0 |
| 1601 | 40 | 10 | 80 | 10 | 10 | 20 |
| 1602 | 20 | 0 | 60 | 50 | 50 | 20 |
| 1603 | 0 | 0 | 0 | 0 | 0 | 0 |

| Cmpd | Barnyard grass | Corn | Foxtail, Giant | Morningglory, Ivy-leaved | Pigweed, Redroot | Velvetleaf |
|---|---|---|---|---|---|---|
| 1604 | 0 | 0 | 0 | 0 | 0 | 0 |
| 1605 | 0 | 0 | 0 | 0 | 20 | 0 |
| 1606 | 40 | 0 | 70 | 0 | 40 | 0 |
| 1607 | 50 | 0 | 80 | 30 | 40 | 30 |
| 1608 | 10 | 10 | 10 | 30 | 10 | 0 |
| 1609 | 70 | 10 | 80 | 20 | 70 | 20 |
| 1610 | 0 | 0 | 0 | 0 | 0 | 0 |
| 1611 | 0 | 0 | 0 | 0 | 0 | 0 |
| 1612 | 0 | 0 | 0 | 0 | 0 | 0 |
| 1613 | 20 | 0 | 70 | 0 | 50 | 20 |
| 1614 | 0 | 0 | 0 | 0 | 0 | 0 |
| 1615 | 0 | 0 | 0 | 0 | 0 | 0 |
| 1616 | 10 | 0 | 20 | 10 | 50 | 0 |
| 1617 | 0 | 0 | 40 | 0 | 0 | 0 |
| 1618 | 0 | 0 | 0 | 0 | 0 | 0 |
| 1619 | 10 | 0 | 60 | 10 | 20 | 0 |
| 1620 | 0 | 0 | 0 | 0 | 0 | 0 |
| 1621 | 30 | 0 | 40 | 0 | 20 | 0 |
| 1622 | 0 | 0 | 0 | 0 | 0 | 0 |
| 1623 | 70 | 0 | 70 | 30 | 20 | 0 |
| 1624 | 20 | 10 | 80 | 20 | 30 | 10 |
| 1625 | 30 | 0 | 50 | 0 | 30 | 10 |
| 1626 | 0 | 0 | 0 | 0 | 0 | 0 |
| 1627 | 70 | 30 | 80 | 70 | 60 | 20 |
| 1628 | 70 | 0 | 80 | 20 | 50 | 20 |
| 1629 | 30 | 10 | 80 | 20 | 10 | 10 |
| 1630 | 0 | 0 | 0 | 0 | 0 | 0 |
| 1631 | 10 | 0 | 60 | 20 | 20 | 10 |
| 1632 | 0 | 0 | 0 | 0 | 0 | 0 |
| 1633 | 0 | 0 | 0 | 0 | 0 | 0 |
| 1634 | 0 | 0 | 0 | 0 | 0 | 0 |
| 1635 | 0 | 0 | 10 | 0 | 0 | 0 |
| 1636 | 50 | 0 | 70 | 0 | 0 | 0 |
| 1637 | 70 | 0 | 80 | 20 | 70 | 10 |
| 1638 | 0 | 0 | 0 | 0 | 0 | 0 |
| 1639 | 30 | 0 | 70 | 10 | 20 | 0 |
| 1640 | 0 | 0 | 0 | 0 | 0 | 0 |
| 1641 | 0 | 0 | 0 | 0 | 0 | 0 |
| 1642 | 0 | 0 | 30 | 0 | 0 | 0 |
| 1643 | 0 | 0 | 0 | 0 | 0 | 0 |
| 1644 | 0 | 0 | 20 | 10 | 0 | 0 |
| 1645 | 20 | 0 | 70 | 0 | 40 | 0 |
| 1646 | 0 | 0 | 10 | 0 | 0 | 0 |
| 1647 | 0 | 0 | 30 | 0 | 0 | 0 |
| 1648 | 0 | 0 | 0 | 0 | 0 | 0 |
| 1649 | 0 | 0 | 0 | 0 | 0 | 0 |
| 1650 | 80 | 50 | 80 | 10 | 70 | 20 |
| 1651 | 30 | 0 | 70 | 10 | 0 | 0 |
| 1652 | 20 | 0 | 20 | 0 | 0 | 0 |
| 1653 | 60 | 30 | 80 | 30 | 70 | 40 |
| 1654 | 20 | 0 | 40 | 20 | 20 | 20 |
| 1655 | 20 | 0 | 30 | 0 | 0 | 0 |
| 1656 | 10 | 0 | 30 | 0 | 20 | 0 |
| 1657 | 10 | 10 | 40 | 10 | 40 | 20 |
| 1658 | 0 | 0 | 0 | 0 | 10 | 0 |
| 1659 | 0 | 0 | 0 | 0 | 0 | 0 |
| 1660 | 0 | 0 | 0 | 0 | 0 | 0 |
| 1661 | 20 | 0 | 60 | 0 | 20 | 0 |
| 1662 | 0 | 0 | 0 | 0 | 0 | 0 |
| 1663 | 0 | 0 | 0 | 0 | 0 | 0 |
| 1664 | 60 | 40 | 80 | 20 | 80 | 10 |
| 1665 | 0 | 0 | 0 | 0 | 0 | 0 |
| 1667 | 0 | 0 | 0 | 0 | 0 | 0 |
| 1668 | 0 | 0 | 0 | 0 | 0 | 0 |
| 1669 | 30 | 0 | 50 | 20 | 0 | 0 |
| 1670 | 20 | 0 | 70 | 0 | 20 | 0 |
| 1671 | 70 | 70 | 80 | 70 | 30 | 10 |
| 1672 | 0 | 0 | 0 | 0 | 30 | 0 |
| 1673 | 0 | 0 | 0 | 0 | 0 | 0 |
| 1674 | 0 | 0 | 0 | 0 | 0 | 0 |
| 1675 | 0 | 0 | 0 | 0 | 0 | 0 |
| 1676 | 0 | 0 | 0 | 0 | 0 | 0 |
| 1677 | 10 | 0 | 30 | 0 | 0 | 0 |
| 1678 | 10 | 0 | 10 | 0 | 10 | 0 |
| 1679 | 80 | 0 | 80 | 50 | 30 | 20 |
| 1680 | 20 | 0 | 80 | 10 | 60 | 10 |
| 1682 | 0 | 0 | 0 | 0 | 0 | 0 |
| 1683 | 70 | 40 | 80 | 30 | 10 | 20 |
| 1684 | 0 | 0 | 0 | 0 | 0 | 0 |
| 1685 | 60 | 40 | 70 | 30 | 50 | 30 |
| 1686 | 70 | 10 | 70 | 20 | 20 | 20 |
| 1687 | 50 | 40 | 80 | 60 | 40 | 40 |
| 1688 | 70 | 30 | 80 | 20 | 0 | 0 |
| 1690 | 80 | 70 | 80 | 70 | 20 | 20 |
| 1691 | 70 | 0 | 80 | 60 | 0 | 10 |
| 1692 | 70 | 50 | 80 | 30 | 40 | 20 |
| 1693 | 30 | 10 | 60 | 50 | 50 | 30 |
| 1694 | 0 | 0 | 0 | 0 | 0 | 0 |
| 1695 | 80 | 70 | 80 | 20 | 10 | 10 |
| 1696 | 70 | 70 | 80 | 60 | 50 | 0 |
| 1697 | 70 | 80 | 80 | 60 | 60 | 30 |
| 1698 | 80 | 70 | 80 | 70 | 30 | 10 |
| 1699 | 80 | 30 | 80 | 30 | 0 | 0 |
| 1700 | 50 | 30 | 60 | 20 | 0 | 0 |
| 1701 | 60 | 30 | 60 | 0 | 0 | 0 |
| 1702 | 70 | 20 | 80 | 60 | 10 | 20 |
| 1703 | 70 | 0 | 70 | 60 | 60 | 40 |
| 1704 | 70 | 20 | 80 | 20 | 10 | 0 |
| 1705 | 30 | 0 | 70 | 20 | 0 | 0 |
| 1706 | 60 | 0 | 80 | 0 | 10 | 20 |
| 1707 | 70 | 70 | 80 | 40 | 0 | 20 |
| 1708 | 50 | 30 | 60 | 20 | 0 | 0 |
| 1709 | 70 | 60 | 80 | 50 | 10 | 10 |
| 1710 | — | — | — | — | — | — |
| 1711 | 70 | 10 | 80 | 30 | 0 | 0 |
| 1712 | 80 | 70 | 80 | 30 | 20 | 10 |
| 1713 | 80 | 50 | 80 | 60 | 0 | 0 |
| 1714 | 70 | 30 | 80 | 20 | 80 | 30 |
| 1716 | 60 | 10 | 70 | 0 | 0 | 0 |
| 1717 | 60 | 0 | 70 | 0 | 0 | 0 |
| 1718 | 70 | 50 | 80 | 60 | 40 | 40 |
| 1719 | 60 | 0 | 80 | 10 | 0 | 0 |
| 1720 | — | — | — | — | — | — |
| 1721 | 30 | 10 | 50 | 40 | 0 | 0 |
| 1722 | 60 | 0 | 70 | 30 | 10 | 10 |
| 1723 | 80 | 60 | 80 | 70 | 20 | 10 |
| 1724 | 70 | 30 | 70 | 30 | 10 | 10 |
| 1725 | 30 | 0 | 70 | 70 | 10 | 0 |
| 1726 | 30 | 30 | 70 | 10 | 0 | 0 |
| 1727 | 70 | 0 | 80 | 30 | 0 | 0 |
| 1728 | 80 | 60 | 80 | 20 | 0 | 30 |
| 1729 | 0 | 0 | 0 | 0 | 0 | 0 |
| 1730 | 40 | 0 | 20 | 0 | 0 | 0 |
| 1731 | 0 | 0 | 0 | 0 | 0 | 0 |
| 1732 | 0 | 0 | 10 | 0 | 10 | 10 |
| 1733 | 0 | 50 | 80 | 60 | 20 | 40 |
| 1734 | 0 | 0 | 0 | 0 | 0 | 0 |
| 1735 | 0 | 0 | 0 | 0 | 0 | 0 |
| 1736 | 30 | 0 | 80 | 0 | 0 | 0 |
| 1737 | 0 | 0 | 0 | 0 | 0 | 0 |
| 1738 | 40 | 0 | 40 | 0 | 10 | 10 |
| 1739 | 0 | 0 | 0 | 0 | 0 | 0 |
| 1740 | 0 | 0 | 40 | 0 | 0 | 0 |
| 1741 | 0 | 0 | 80 | 30 | 0 | 0 |
| 1742 | 70 | 0 | 80 | 0 | 20 | 10 |
| 1743 | 0 | 0 | 70 | 0 | 0 | 0 |
| 1744 | 10 | 0 | 20 | 0 | 10 | 0 |
| 1745 | 70 | 0 | 60 | 30 | 0 | 0 |
| 1746 | 0 | 0 | 10 | 10 | 20 | 0 |
| 1747 | 60 | 0 | 60 | 20 | 20 | 0 |
| 1748 | 0 | 0 | 0 | 0 | 0 | 0 |
| 1749 | 0 | 0 | 0 | 0 | 0 | 0 |
| 1750 | 0 | 10 | 0 | 10 | 10 | 0 |
| 1751 | 0 | 0 | 0 | 0 | 0 | 0 |
| 1752 | 0 | 0 | 0 | 0 | 0 | 0 |
| 1753 | 70 | 60 | 60 | 50 | 20 | 20 |

-continued

Post-Emergence (62.5 g ai/ha)

| Cmpd | Barn-yard grass | Corn | Foxtail, Giant | Morningglory, Ivy-leaved | Pigweed, Redroot | Velvetleaf |
|---|---|---|---|---|---|---|
| 1754 | 70 | 60 | 80 | 70 | 40 | 30 |
| 1755 | 70 | 80 | 80 | 70 | 20 | 30 |
| 1757 | 10 | 0 | 20 | 0 | 0 | 0 |
| 1760 | 0 | 0 | 0 | 0 | 0 | 0 |
| 1761 | 0 | 0 | 0 | 40 | 0 | 0 |
| 1762 | 50 | 30 | 70 | 60 | 0 | 0 |
| 1763 | 60 | 20 | 60 | 40 | 0 | 10 |
| 1764 | 50 | 10 | 80 | 30 | 10 | 40 |
| 1765 | 30 | 10 | 60 | 0 | 0 | 0 |
| 1766 | 30 | 20 | 50 | 20 | 0 | 0 |
| 1767 | 50 | 10 | 70 | 30 | 0 | 0 |
| 1768 | 0 | 0 | 0 | 0 | 0 | 0 |
| 1769 | 0 | 0 | 10 | 0 | 0 | 0 |
| 1770 | 0 | 0 | 20 | 10 | 20 | 10 |
| 1771 | 0 | 0 | 0 | 0 | 0 | 0 |
| 1772 | 0 | 0 | 60 | 30 | 0 | 0 |
| 1773 | 80 | 80 | 80 | 10 | 20 | 20 |
| 1783 | 80 | 80 | 80 | 60 | 0 | 20 |
| 1784 | 0 | 0 | 0 | 0 | 0 | 0 |
| 1785 | 0 | 0 | 0 | 0 | 0 | 0 |
| 1786 | 0 | 0 | 10 | 0 | 0 | 0 |
| 1787 | 60 | 50 | 70 | 70 | 20 | 20 |
| 1788 | 0 | 10 | 0 | 0 | 10 | 10 |
| 1789 | 0 | 0 | 0 | 0 | 0 | 0 |
| 1790 | 70 | 70 | 80 | 20 | 0 | 20 |
| 1791 | 80 | 70 | 80 | 70 | 0 | 30 |
| 1792 | 70 | 40 | 80 | 30 | 0 | 20 |
| 1793 | 70 | 30 | 80 | 10 | 0 | 10 |
| 1794 | 40 | 50 | 60 | 50 | 40 | 0 |
| 1795 | 70 | 40 | 80 | 20 | 20 | 0 |
| 1796 | 0 | 0 | 0 | 10 | 10 | 0 |
| 1797 | 70 | 60 | 80 | 40 | 70 | 80 |
| 1798 | 0 | 0 | 20 | 0 | 0 | 0 |
| 1799 | 60 | 60 | 70 | 60 | 60 | 20 |
| 1800 | 10 | 0 | 20 | 10 | 10 | 0 |
| 1801 | 60 | 70 | 80 | 10 | 0 | 0 |
| 1802 | 60 | 0 | 70 | 0 | 0 | 40 |
| 1803 | 0 | 0 | 70 | 10 | 0 | 0 |
| 1804 | 50 | 0 | 70 | 50 | 0 | 10 |
| 1805 | 0 | 0 | 30 | 30 | 60 | 20 |
| 1806 | 20 | 0 | 60 | 0 | 0 | 0 |
| 1807 | 0 | 0 | 0 | 0 | 0 | 0 |
| 1808 | 20 | 0 | 30 | 0 | 0 | 0 |
| 1809 | 80 | 80 | 80 | 70 | 20 | 0 |
| 1810 | 60 | 0 | 80 | 60 | 10 | 30 |
| 1811 | 80 | 60 | 80 | 20 | 60 | 30 |
| 1812 | 0 | 0 | 80 | 50 | 20 | 10 |
| 1813 | 0 | 0 | 0 | 10 | 0 | 0 |
| 1814 | 0 | 0 | 0 | 0 | 0 | 0 |
| 1815 | 0 | 0 | 0 | 0 | 0 | 0 |
| 1816 | 80 | 80 | 80 | 60 | 40 | 30 |
| 1817 | 0 | 0 | 0 | 0 | 0 | 0 |
| 1818 | 30 | 30 | 80 | 10 | 0 | 0 |
| 1819 | 20 | 0 | 40 | 0 | 0 | 0 |
| 1820 | 0 | 0 | 0 | 0 | 0 | 0 |
| 1821 | 0 | 10 | 10 | 0 | 30 | 10 |
| 1822 | 80 | 40 | 80 | 10 | 10 | 30 |
| 1823 | 0 | 0 | 0 | 0 | 0 | 0 |
| 1824 | 0 | 0 | 0 | 0 | 0 | 0 |
| 1825 | 0 | 0 | 0 | 0 | 0 | 0 |
| 1826 | 10 | 20 | 40 | 20 | 0 | 0 |
| 1827 | 70 | 10 | 80 | 10 | 0 | 0 |
| 1828 | 80 | 10 | 80 | 60 | 0 | 20 |
| 1829 | 60 | 0 | 80 | 20 | 20 | 0 |
| 1833 | 0 | 0 | 0 | 0 | 0 | 0 |
| 1836 | 70 | 10 | 70 | 20 | 60 | 20 |

Post-Emergence (15.625 g ai/ha)

| Cmpd | Barn-yard grass | Corn | Foxtail, Giant | Morningglory, Ivy-leaved | Pigweed, Redroot | Velvetleaf |
|---|---|---|---|---|---|---|
| 1396 | 80 | 70 | 80 | 40 | 70 | 40 |
| 1397 | 80 | 80 | 80 | 60 | 0 | 0 |
| 1398 | 80 | 30 | 80 | 0 | 0 | 0 |
| 1399 | 40 | 0 | 60 | 10 | 0 | 0 |
| 1400 | 50 | 10 | 60 | 0 | 20 | 10 |
| 1401 | 0 | 0 | 0 | 0 | 0 | 0 |
| 1402 | 80 | 70 | 80 | 10 | 10 | 0 |
| 1403 | 0 | 10 | 0 | 0 | 10 | 0 |
| 1404 | 10 | 20 | 0 | 0 | 20 | 10 |
| 1405 | 0 | 0 | 0 | 0 | 0 | 0 |
| 1406 | 0 | 20 | 0 | 0 | 0 | 0 |
| 1407 | 10 | 0 | 0 | 0 | 20 | 10 |
| 1408 | 0 | 0 | 0 | 0 | 0 | 0 |
| 1409 | 0 | 0 | 0 | 0 | 0 | 0 |
| 1410 | 0 | 0 | 0 | 0 | 0 | 0 |
| 1411 | 0 | 0 | 0 | 0 | 0 | 0 |
| 1412 | 0 | 20 | 0 | 0 | 30 | 0 |
| 1413 | 20 | 0 | 40 | 0 | 0 | 0 |
| 1414 | 50 | 20 | 70 | 0 | 10 | 0 |
| 1415 | 20 | 20 | 20 | 10 | 10 | 10 |
| 1416 | 0 | 0 | 0 | 0 | 0 | 0 |
| 1417 | 10 | 0 | 0 | 0 | 20 | 10 |
| 1418 | 20 | 10 | 0 | 0 | 0 | 0 |
| 1419 | 30 | 10 | 10 | 0 | 10 | 10 |
| 1420 | 10 | 10 | 50 | 0 | 0 | 0 |
| 1421 | 0 | 10 | 20 | 10 | 0 | 10 |
| 1422 | 0 | 10 | 0 | 0 | 0 | 0 |
| 1423 | 0 | 10 | 0 | 0 | 0 | 0 |
| 1424 | 0 | 0 | 0 | 0 | 10 | 0 |
| 1425 | 0 | 10 | 10 | 0 | 20 | 0 |
| 1426 | 0 | 10 | 0 | 0 | 0 | 0 |
| 1427 | 0 | 0 | 0 | 0 | 0 | 0 |
| 1428 | 20 | 10 | 30 | 10 | 10 | 0 |
| 1429 | 0 | 10 | 0 | 0 | 0 | 0 |
| 1430 | 0 | 0 | 0 | 0 | 0 | 0 |
| 1431 | 0 | 0 | 0 | 0 | 0 | 0 |
| 1432 | 0 | 0 | 0 | 0 | 0 | 0 |
| 1433 | 0 | 0 | 0 | 0 | 0 | 0 |
| 1434 | 0 | 10 | 0 | 0 | 0 | 0 |
| 1435 | 0 | 0 | 0 | 0 | 0 | 0 |
| 1436 | 0 | 0 | 0 | 0 | 0 | 0 |
| 1437 | 0 | 0 | 0 | 0 | 0 | 0 |
| 1438 | 0 | 0 | 0 | 0 | 0 | 0 |
| 1439 | 0 | 10 | 0 | 0 | 0 | 0 |
| 1440 | 0 | 0 | 0 | 0 | 0 | 0 |
| 1441 | 0 | 0 | 0 | 0 | 0 | 0 |
| 1442 | 0 | 0 | 0 | 0 | 0 | 0 |
| 1443 | 0 | 0 | 0 | 0 | 0 | 0 |
| 1444 | 0 | 10 | 0 | 0 | 10 | 0 |
| 1445 | 0 | 0 | 0 | 0 | 0 | 0 |
| 1446 | 0 | 0 | 0 | 0 | 0 | 0 |
| 1447 | 0 | 0 | 10 | 0 | 0 | 0 |
| 1448 | 0 | 0 | 0 | 0 | 0 | 0 |
| 1449 | 0 | 0 | 0 | 0 | 0 | 0 |
| 1450 | 0 | 0 | 0 | 0 | 0 | 0 |
| 1451 | 0 | 0 | 0 | 0 | 0 | 0 |
| 1452 | 0 | 0 | 0 | 0 | 0 | 0 |
| 1453 | 0 | 10 | 10 | 0 | 0 | 0 |
| 1454 | 0 | 10 | 30 | 10 | 0 | 0 |
| 1455 | 0 | 10 | 10 | 0 | 0 | 0 |
| 1456 | 10 | 10 | 50 | 30 | 0 | 0 |
| 1457 | 0 | 0 | 0 | 0 | 0 | 0 |
| 1458 | 10 | 10 | 30 | 10 | 10 | 0 |
| 1459 | 0 | 10 | 10 | 0 | 30 | 0 |
| 1460 | 20 | 10 | 40 | 0 | 0 | 0 |
| 1461 | 0 | 10 | 20 | 0 | 0 | 0 |
| 1462 | 0 | 0 | 0 | 0 | 0 | 0 |
| 1463 | 0 | 0 | 0 | 0 | 0 | 0 |
| 1464 | 20 | 20 | 70 | 10 | 10 | 10 |
| 1465 | 0 | 10 | 0 | 0 | 10 | 10 |
| 1466 | 0 | 0 | 0 | 0 | 10 | 0 |
| 1468 | 10 | 10 | 30 | 10 | 10 | 0 |
| 1471 | 30 | 10 | 10 | 10 | 10 | 10 |
| 1472 | 10 | 10 | 10 | 20 | 0 | 0 |
| 1473 | 40 | 20 | 60 | 0 | 0 | 0 |

Post-Emergence (15.625 g ai/ha)

| Cmpd | Barn-yard grass | Corn | Foxtail, Giant | Morningglory, Ivy-leaved | Pigweed, Redroot | Velvetleaf |
|---|---|---|---|---|---|---|
| 1474 | 20 | 10 | 60 | 40 | 30 | 10 |
| 1475 | 30 | 30 | 70 | 20 | 10 | 10 |
| 1476 | 40 | 10 | 60 | 20 | 10 | 10 |
| 1477 | 50 | 30 | 50 | 0 | 0 | 0 |
| 1478 | 10 | 0 | 10 | 0 | 0 | 0 |
| 1479 | 0 | 10 | 0 | 0 | 0 | 0 |
| 1480 | 50 | 20 | 60 | 0 | 0 | 0 |
| 1481 | 30 | 20 | 40 | 0 | 0 | 0 |
| 1482 | 30 | 20 | 30 | 0 | 0 | 0 |
| 1483 | 30 | 20 | 30 | 0 | 40 | 10 |
| 1484 | 20 | 20 | 10 | 0 | 10 | 0 |
| 1485 | 50 | 40 | 60 | 0 | 0 | 0 |
| 1486 | 40 | 10 | 60 | 0 | 0 | 0 |
| 1487 | 50 | 20 | 60 | 0 | 20 | 0 |
| 1488 | 0 | 0 | 0 | 0 | 0 | 0 |
| 1489 | 0 | 10 | 0 | 0 | 0 | 0 |
| 1490 | 50 | 0 | 50 | 0 | 0 | 0 |
| 1491 | 0 | 0 | 0 | 0 | 0 | 0 |
| 1492 | 0 | 0 | 0 | 0 | 0 | 0 |
| 1493 | 40 | 10 | 40 | 0 | 0 | 0 |
| 1494 | 30 | 10 | 60 | 10 | 0 | 0 |
| 1496 | 20 | 10 | 20 | 0 | 0 | 0 |
| 1497 | 20 | 10 | 30 | 0 | 0 | 0 |
| 1498 | 0 | 0 | 0 | 0 | 0 | 0 |
| 1499 | 50 | 10 | 60 | 20 | 0 | 0 |
| 1500 | 10 | 10 | 40 | 0 | 0 | 0 |
| 1501 | 10 | 10 | 40 | 0 | 0 | 0 |
| 1502 | 20 | 0 | 60 | 0 | 20 | 0 |
| 1503 | 0 | 0 | 0 | 0 | 0 | 0 |
| 1504 | 0 | 0 | 0 | 0 | 0 | 0 |
| 1505 | 0 | 0 | 0 | 0 | 0 | 0 |
| 1506 | 0 | 0 | 0 | 0 | 0 | 0 |
| 1507 | 0 | 0 | 0 | 0 | 0 | 0 |
| 1508 | 0 | 0 | 0 | 0 | 0 | 0 |
| 1509 | 0 | 0 | 0 | 0 | 0 | 0 |
| 1510 | 0 | 0 | 0 | 0 | 0 | 0 |
| 1511 | 0 | 0 | 0 | 0 | 0 | 0 |
| 1512 | 0 | 0 | 0 | 0 | 0 | 0 |
| 1513 | 0 | 0 | 0 | 0 | 0 | 0 |
| 1514 | 0 | 0 | 0 | 0 | 0 | 0 |
| 1515 | 0 | 0 | 0 | 0 | 0 | 0 |
| 1516 | 0 | 0 | 0 | 0 | 0 | 0 |
| 1517 | 0 | 0 | 20 | 20 | 0 | 0 |
| 1518 | 0 | 0 | 0 | 0 | 0 | 0 |
| 1519 | 0 | 10 | 0 | 0 | 0 | 0 |
| 1520 | 0 | 0 | 0 | 10 | 0 | 0 |
| 1522 | 0 | 0 | 0 | 0 | 0 | 0 |
| 1525 | 0 | 0 | 0 | 0 | 0 | 0 |
| 1526 | 0 | 0 | 0 | 0 | 0 | 0 |
| 1527 | 0 | 10 | 0 | 0 | 0 | 0 |
| 1528 | 0 | 0 | 0 | 0 | 0 | 0 |
| 1529 | 0 | 0 | 0 | 0 | 0 | 0 |
| 1530 | 0 | 0 | 0 | 0 | 0 | 0 |
| 1531 | 0 | 0 | 0 | 0 | 0 | 0 |
| 1532 | 0 | 0 | 0 | 0 | 0 | 0 |
| 1533 | 0 | 0 | 0 | 0 | 0 | 0 |
| 1534 | 0 | 0 | 0 | 0 | 0 | 0 |
| 1535 | 0 | 0 | 0 | 0 | 0 | 0 |
| 1536 | 0 | 0 | 0 | 0 | 0 | 0 |
| 1537 | 0 | 0 | 0 | 0 | 0 | 0 |
| 1538 | 0 | 0 | 10 | 0 | 0 | 0 |
| 1539 | 0 | 0 | 0 | 0 | 0 | 0 |
| 1540 | 0 | 0 | 0 | 0 | 0 | 0 |
| 1541 | 0 | 0 | 0 | 0 | 0 | 0 |
| 1542 | 0 | 0 | 0 | 0 | 0 | 0 |
| 1543 | 0 | 0 | 0 | 0 | 0 | 0 |
| 1544 | 0 | 10 | 0 | 0 | 0 | 0 |
| 1545 | 0 | 0 | 0 | 0 | 0 | 0 |
| 1546 | 40 | 0 | 60 | 0 | 30 | 0 |
| 1547 | 0 | 0 | 0 | 0 | 0 | 0 |
| 1548 | 0 | 0 | 0 | 0 | 0 | 0 |
| 1549 | 0 | 0 | 0 | 0 | 0 | 0 |
| 1550 | 0 | 0 | 0 | 0 | 0 | 0 |
| 1551 | 0 | 0 | 0 | 0 | 0 | 0 |
| 1552 | 0 | 10 | 0 | 0 | 0 | 0 |
| 1553 | 0 | 0 | 0 | 0 | 0 | 0 |
| 1554 | 0 | 0 | 0 | 0 | 0 | 0 |
| 1555 | 0 | 0 | 0 | 0 | 0 | 0 |
| 1556 | 0 | 0 | 0 | 0 | 0 | 0 |
| 1557 | 0 | 0 | 0 | 0 | 0 | 0 |
| 1558 | 0 | 0 | 0 | 0 | 0 | 0 |
| 1559 | 0 | 0 | 0 | 0 | 0 | 0 |
| 1560 | 0 | 0 | 0 | 0 | 0 | 0 |
| 1561 | 0 | 0 | 0 | 0 | 0 | 0 |
| 1562 | 0 | 0 | 0 | 0 | 0 | 0 |
| 1563 | 0 | 0 | 0 | 0 | 0 | 0 |
| 1564 | 0 | 0 | 0 | 0 | 0 | 0 |
| 1565 | 0 | 0 | 0 | 0 | 0 | 0 |
| 1566 | 0 | 0 | 0 | 0 | 0 | 0 |
| 1567 | 0 | 0 | 0 | 0 | 0 | 0 |
| 1568 | 0 | 0 | 0 | 0 | 0 | 0 |
| 1569 | 0 | 0 | 0 | 0 | 0 | 0 |
| 1570 | 0 | 0 | 0 | 0 | 0 | 0 |
| 1571 | 0 | 0 | 0 | 0 | 0 | 0 |
| 1572 | 0 | 0 | 0 | 0 | 0 | 0 |
| 1573 | 0 | 0 | 0 | 0 | 0 | 0 |
| 1574 | 0 | 0 | 0 | 0 | 0 | 0 |
| 1575 | 0 | 0 | 0 | 0 | 0 | 0 |
| 1576 | 10 | 0 | 30 | 0 | 0 | 0 |
| 1577 | 0 | 0 | 0 | 0 | 0 | 0 |
| 1578 | 0 | 0 | 0 | 0 | 0 | 20 |
| 1579 | 0 | 0 | 0 | 0 | 0 | 0 |
| 1580 | 0 | 0 | 0 | 0 | 0 | 0 |
| 1581 | 0 | 0 | 0 | 0 | 0 | 0 |
| 1582 | 0 | 0 | 0 | 0 | 0 | 0 |
| 1583 | 0 | 0 | 0 | 0 | 0 | 0 |
| 1584 | 0 | 0 | 0 | 0 | 0 | 0 |
| 1585 | 70 | 30 | 60 | 20 | 0 | 0 |
| 1586 | 0 | 0 | 0 | 0 | 0 | 0 |
| 1587 | 0 | 0 | 0 | 0 | 0 | 0 |
| 1588 | 80 | 60 | 60 | 70 | 0 | 0 |
| 1589 | 0 | 0 | 0 | 0 | 0 | 0 |
| 1590 | 0 | 0 | 0 | 0 | 0 | 0 |
| 1591 | 0 | 0 | 0 | 0 | 0 | 0 |
| 1592 | 0 | 0 | 0 | 0 | 0 | 0 |
| 1593 | 0 | 0 | 0 | 0 | 0 | 0 |
| 1594 | 0 | 0 | 0 | 0 | 0 | 0 |
| 1595 | 10 | 0 | 0 | 0 | 0 | 0 |
| 1596 | 0 | 0 | 0 | 0 | 0 | 0 |
| 1597 | 0 | 0 | 0 | 0 | 0 | 0 |
| 1598 | 30 | 0 | 80 | 30 | 30 | 0 |
| 1599 | 10 | 0 | 60 | 50 | 0 | 0 |
| 1600 | 0 | 0 | 0 | 0 | 0 | 0 |
| 1601 | 0 | 0 | 0 | 0 | 0 | 0 |
| 1602 | 0 | 0 | 0 | 10 | 0 | 0 |
| 1603 | 0 | 0 | 0 | 0 | 0 | 0 |
| 1604 | 0 | 0 | 0 | 0 | 0 | 0 |
| 1605 | 0 | 0 | 0 | 0 | 0 | 0 |
| 1606 | 20 | 0 | 40 | 0 | 40 | 0 |
| 1607 | 0 | 0 | 50 | 20 | 0 | 10 |
| 1608 | 0 | 0 | 0 | 40 | 0 | 0 |
| 1609 | 20 | 10 | 70 | 20 | 30 | 0 |
| 1610 | 0 | 0 | 0 | 0 | 0 | 0 |
| 1611 | 0 | 0 | 0 | 0 | 0 | 0 |
| 1612 | 0 | 0 | 0 | 0 | 0 | 0 |
| 1613 | 0 | 0 | 20 | 0 | 0 | 0 |
| 1614 | 0 | 0 | 0 | 0 | 0 | 0 |
| 1615 | 0 | 0 | 0 | 0 | 0 | 0 |
| 1616 | 10 | 0 | 40 | 0 | 20 | 10 |
| 1617 | 0 | 0 | 20 | 0 | 0 | 0 |
| 1618 | 0 | 0 | 0 | 0 | 0 | 0 |
| 1619 | 0 | 0 | 0 | 0 | 0 | 0 |
| 1620 | 0 | 0 | 0 | 0 | 0 | 0 |
| 1621 | 10 | 0 | 10 | 0 | 0 | 0 |
| 1622 | 0 | 0 | 0 | 0 | 0 | 0 |
| 1623 | 10 | 0 | 30 | 30 | 10 | 0 |

| | Post-Emergence (15.625 g ai/ha) | | | | | |
|---|---|---|---|---|---|---|
| Cmpd | Barnyard grass | Corn | Foxtail, Giant | Morningglory, Ivy-leaved | Pigweed, Redroot | Velvetleaf |
| 1624 | 0 | 0 | 10 | 10 | 0 | 0 |
| 1625 | 0 | 0 | 0 | 0 | 0 | 0 |
| 1626 | 0 | 0 | 0 | 0 | 0 | 0 |
| 1627 | 20 | 0 | 70 | 60 | 20 | 0 |
| 1628 | 30 | 0 | 70 | 20 | 10 | 30 |
| 1629 | 0 | 0 | 0 | 20 | 10 | 20 |
| 1630 | 0 | 0 | 0 | 0 | 0 | 0 |
| 1631 | 0 | 0 | 0 | 0 | 0 | 0 |
| 1632 | 0 | 0 | 0 | 0 | 0 | 0 |
| 1633 | 0 | 0 | 0 | 0 | 0 | 0 |
| 1634 | 0 | 0 | 0 | 0 | 0 | 0 |
| 1635 | 0 | 0 | 0 | 0 | 0 | 0 |
| 1636 | 10 | 0 | 50 | 0 | 0 | 0 |
| 1637 | 20 | 0 | 60 | 0 | 40 | 0 |
| 1638 | 0 | 0 | 0 | 0 | 0 | 0 |
| 1639 | 10 | 0 | 30 | 0 | 0 | 0 |
| 1640 | 0 | 0 | 0 | 0 | 0 | 0 |
| 1641 | 0 | 0 | 0 | 0 | 0 | 0 |
| 1642 | 0 | 0 | 0 | 0 | 0 | 0 |
| 1643 | 0 | 0 | 0 | 0 | 0 | 0 |
| 1644 | 0 | 0 | 0 | 0 | 0 | 0 |
| 1645 | 0 | 0 | 0 | 0 | 0 | 0 |
| 1646 | 0 | 0 | 0 | 0 | 0 | 0 |
| 1647 | 0 | 0 | 0 | 0 | 0 | 0 |
| 1648 | 0 | 0 | 0 | 0 | 0 | 0 |
| 1649 | 0 | 0 | 0 | 0 | 0 | 0 |
| 1650 | 40 | 10 | 70 | 20 | 10 | 0 |
| 1651 | 0 | 0 | 0 | 0 | 0 | 0 |
| 1652 | 0 | 0 | 0 | 0 | 0 | 0 |
| 1653 | 30 | 0 | 60 | 10 | 0 | 0 |
| 1654 | 0 | 0 | 20 | 10 | 10 | 0 |
| 1655 | 0 | 0 | 0 | 0 | 0 | 0 |
| 1656 | 10 | 0 | 20 | 0 | 0 | 0 |
| 1657 | 0 | 0 | 0 | 0 | 0 | 0 |
| 1658 | 0 | 0 | 0 | 0 | 0 | 0 |
| 1659 | 0 | 0 | 0 | 0 | 0 | 0 |
| 1660 | 0 | 0 | 0 | 0 | 0 | 0 |
| 1661 | 0 | 0 | 0 | 0 | 0 | 0 |
| 1662 | 0 | 0 | 0 | 0 | 0 | 0 |
| 1663 | 0 | 0 | 0 | 0 | 0 | 0 |
| 1664 | 0 | 0 | 60 | 0 | 20 | 0 |
| 1665 | 0 | 0 | 0 | 0 | 0 | 0 |
| 1667 | 0 | 0 | 0 | 0 | 0 | 0 |
| 1668 | 0 | 0 | 0 | 0 | 0 | 0 |
| 1669 | 0 | 10 | 30 | 0 | 0 | 0 |
| 1670 | 0 | 0 | 0 | 0 | 0 | 0 |
| 1671 | 70 | 60 | 70 | 0 | 10 | 0 |
| 1672 | 0 | 0 | 0 | 0 | 0 | 0 |
| 1673 | 0 | 0 | 0 | 0 | 0 | 0 |
| 1674 | 0 | 0 | 0 | 0 | 0 | 0 |
| 1675 | 0 | 0 | 0 | 0 | 0 | 0 |
| 1676 | 0 | 0 | 0 | 0 | 0 | 0 |
| 1677 | 0 | 0 | 10 | 0 | 0 | 0 |
| 1678 | 0 | 0 | 0 | 0 | 10 | 0 |
| 1679 | 40 | 0 | 80 | 0 | 0 | 0 |
| 1680 | 20 | 0 | 30 | 10 | 50 | 0 |
| 1682 | 0 | 0 | 0 | 0 | 0 | 0 |
| 1683 | 70 | 20 | 70 | 30 | 30 | 0 |
| 1684 | 0 | 0 | 0 | 0 | 0 | 0 |
| 1685 | 30 | 10 | 70 | 40 | 40 | 10 |
| 1686 | 30 | 0 | 60 | 20 | 30 | 30 |
| 1687 | 0 | 10 | 60 | 20 | 40 | 40 |
| 1688 | 30 | 0 | 60 | 0 | 0 | 0 |
| 1690 | 70 | 10 | 80 | 20 | 0 | 0 |
| 1691 | 30 | 0 | 60 | 0 | 0 | 0 |
| 1692 | 40 | 20 | 60 | 40 | 0 | 0 |
| 1693 | 0 | 0 | 0 | 0 | 20 | 0 |
| 1694 | 0 | 0 | 0 | 0 | 0 | 0 |
| 1695 | 80 | 30 | 80 | 10 | 10 | 0 |
| 1696 | 40 | 50 | 70 | 20 | 70 | 0 |
| 1697 | 60 | 10 | 80 | 30 | 20 | 0 |
| 1698 | 60 | 20 | 80 | 10 | 20 | 0 |
| 1699 | 60 | 0 | 80 | 10 | 0 | 0 |
| 1700 | 20 | 30 | 40 | 20 | 0 | 0 |
| 1701 | 10 | 10 | 40 | 0 | 0 | 0 |
| 1702 | 60 | 20 | 70 | 10 | 10 | 10 |
| 1703 | 50 | 0 | 70 | 60 | 20 | 10 |
| 1704 | 40 | 0 | 70 | 30 | 0 | 0 |
| 1705 | 20 | 10 | 70 | 0 | 0 | 0 |
| 1706 | 40 | 0 | 70 | 20 | 0 | 0 |
| 1707 | 70 | 60 | 80 | 40 | 0 | 0 |
| 1708 | 40 | 10 | 40 | 20 | 0 | 0 |
| 1709 | 30 | 30 | 70 | 10 | 20 | 20 |
| 1710 | — | — | — | — | — | — |
| 1711 | 30 | 0 | 70 | 10 | 0 | 0 |
| 1712 | 50 | 40 | 80 | 10 | 0 | 10 |
| 1713 | 10 | 0 | 60 | 20 | 0 | 0 |
| 1714 | 40 | 20 | 70 | 10 | 70 | 0 |
| 1716 | 0 | 0 | 40 | 0 | 0 | 0 |
| 1717 | 0 | 0 | 30 | 0 | 0 | 0 |
| 1718 | 50 | 30 | 70 | 10 | 30 | 20 |
| 1719 | 0 | 0 | 60 | 0 | 0 | 0 |
| 1720 | — | — | — | — | — | — |
| 1721 | 0 | 0 | 0 | 0 | 0 | 0 |
| 1722 | 10 | 10 | 60 | 20 | 0 | 0 |
| 1723 | 30 | 30 | 70 | 30 | 20 | 10 |
| 1724 | 40 | 0 | 70 | 40 | 0 | 0 |
| 1725 | 0 | 10 | 0 | 30 | 0 | 0 |
| 1726 | 0 | 10 | 0 | 10 | 20 | 0 |
| 1727 | 20 | 0 | 30 | 0 | 0 | 0 |
| 1728 | 70 | 60 | 80 | 0 | 20 | 30 |
| 1729 | 0 | 0 | 0 | 0 | 0 | 0 |
| 1730 | 0 | 0 | 0 | 0 | 0 | 0 |
| 1731 | 0 | 0 | 0 | 0 | 0 | 0 |
| 1732 | 0 | 0 | 0 | 0 | 0 | 0 |
| 1733 | 0 | 0 | 10 | 20 | 10 | 0 |
| 1734 | 0 | 0 | 0 | 0 | 0 | 0 |
| 1735 | 0 | 0 | 0 | 0 | 0 | 0 |
| 1736 | 0 | 0 | 30 | 0 | 0 | 0 |
| 1737 | 0 | 0 | 0 | 0 | 0 | 0 |
| 1738 | 0 | 0 | 20 | 0 | 20 | 0 |
| 1739 | 0 | 0 | 0 | 0 | 0 | 0 |
| 1740 | 0 | 0 | 0 | 0 | 0 | 0 |
| 1741 | 0 | 0 | 50 | 0 | 0 | 0 |
| 1742 | 0 | 0 | 70 | 0 | 0 | 0 |
| 1743 | 0 | 0 | 20 | 0 | 0 | 0 |
| 1744 | 0 | 0 | 0 | 0 | 0 | 0 |
| 1745 | 10 | 0 | 10 | 0 | 0 | 0 |
| 1746 | 0 | 0 | 0 | 0 | 0 | 0 |
| 1747 | 0 | 0 | 10 | 0 | 10 | 0 |
| 1748 | 0 | 0 | 0 | 0 | 0 | 0 |
| 1749 | 0 | 0 | 0 | 0 | 0 | 0 |
| 1750 | 0 | 0 | 0 | 0 | 0 | 0 |
| 1751 | 0 | 0 | 0 | 0 | 0 | 0 |
| 1752 | 0 | 0 | 0 | 0 | 0 | 0 |
| 1753 | 40 | 60 | 60 | 20 | 0 | 10 |
| 1754 | 30 | 10 | 60 | 30 | 0 | 10 |
| 1755 | 60 | 10 | 70 | 60 | 10 | 10 |
| 1757 | 0 | 0 | 0 | 0 | 0 | 0 |
| 1760 | 0 | 0 | 0 | 0 | 0 | 0 |
| 1761 | 0 | 0 | 0 | 0 | 0 | 0 |
| 1762 | 10 | 20 | 60 | 30 | 20 | 10 |
| 1763 | 40 | 20 | 60 | 30 | 0 | 0 |
| 1764 | 40 | 10 | 70 | 10 | 0 | 20 |
| 1765 | 0 | 0 | 10 | 0 | 0 | 0 |
| 1766 | 60 | 30 | 20 | 0 | 0 | 0 |
| 1767 | 40 | 10 | 70 | 30 | 0 | 0 |
| 1768 | 0 | 0 | 0 | 0 | 0 | 0 |
| 1769 | 0 | 0 | 0 | 0 | 0 | 0 |
| 1770 | 0 | 0 | 0 | 0 | 0 | 0 |
| 1771 | 0 | 0 | 0 | 0 | 0 | 0 |
| 1772 | 0 | 0 | 10 | 0 | 0 | 0 |
| 1773 | 80 | 70 | 80 | 20 | 20 | 0 |
| 1783 | 70 | 70 | 80 | 10 | 0 | 0 |
| 1784 | 0 | 0 | 0 | 0 | 0 | 0 |
| 1785 | 0 | 0 | 0 | 0 | 0 | 0 |

-continued

Post-Emergence (15.625 g ai/ha)

| Cmpd | Barn-yard grass | Corn | Foxtail, Giant | Morningglory, Ivy-leaved | Pigweed, Redroot | Velvetleaf |
|---|---|---|---|---|---|---|
| 1786 | 0 | 0 | 0 | 0 | 0 | 0 |
| 1787 | 20 | 30 | 40 | 50 | 20 | 20 |
| 1788 | 0 | 0 | 0 | 0 | 0 | 0 |
| 1789 | 0 | 0 | 0 | 0 | 0 | 0 |
| 1790 | 50 | 50 | 70 | 20 | 0 | 0 |
| 1791 | 70 | 30 | 80 | 20 | 0 | 10 |
| 1792 | 30 | 20 | 70 | 10 | 0 | 0 |
| 1793 | 30 | 10 | 70 | 0 | 0 | 0 |
| 1794 | 0 | 20 | 0 | 20 | 0 | 0 |
| 1795 | 20 | 0 | 60 | 10 | 0 | 0 |
| 1796 | 0 | 0 | 0 | 0 | 0 | 0 |
| 1797 | 30 | 10 | 50 | 0 | 30 | 60 |
| 1798 | 0 | 0 | 0 | 0 | 0 | 0 |
| 1799 | 0 | 10 | 20 | 10 | 0 | 0 |
| 1800 | 0 | 0 | 0 | 0 | 0 | 0 |
| 1801 | 20 | 10 | 70 | 0 | 0 | 0 |
| 1802 | 0 | 0 | 40 | 0 | 0 | 0 |
| 1803 | 0 | 0 | 20 | 0 | 0 | 0 |
| 1804 | 0 | 0 | 0 | 0 | 0 | 0 |
| 1805 | 0 | 0 | 0 | 0 | 10 | 0 |
| 1806 | 0 | 0 | 0 | 0 | 0 | 0 |
| 1807 | 0 | 0 | 0 | 0 | 0 | 0 |
| 1808 | 0 | 0 | 0 | 0 | 0 | 0 |
| 1809 | 80 | 80 | 80 | 20 | 20 | 0 |
| 1810 | 0 | 0 | 20 | 20 | 0 | 20 |
| 1811 | 80 | 40 | 80 | 40 | 20 | 10 |
| 1812 | 0 | 0 | 0 | 0 | 0 | 0 |
| 1813 | 0 | 0 | 0 | 0 | 0 | 0 |
| 1814 | 0 | 0 | 0 | 0 | 0 | 0 |
| 1815 | 0 | 0 | 0 | 0 | 0 | 0 |
| 1816 | 80 | 70 | 80 | 10 | 10 | 0 |
| 1817 | 0 | 0 | 0 | 0 | 0 | 0 |
| 1818 | 0 | 0 | 40 | 0 | 0 | 0 |
| 1819 | 0 | 0 | 0 | 0 | 0 | 0 |
| 1820 | 0 | 0 | 0 | 0 | 0 | 0 |
| 1821 | 0 | 10 | 0 | 0 | 0 | 0 |
| 1822 | 70 | 0 | 70 | 20 | 0 | 0 |
| 1823 | 0 | 0 | 0 | 0 | 0 | 0 |
| 1824 | 0 | 0 | 0 | 0 | 0 | 0 |
| 1825 | 0 | 0 | 0 | 0 | 0 | 0 |
| 1826 | 0 | 0 | 0 | 0 | 0 | 0 |
| 1827 | 0 | 0 | 50 | 0 | 0 | 0 |
| 1828 | 30 | 0 | 70 | 20 | 0 | 0 |
| 1829 | 0 | 20 | 70 | 20 | 0 | 0 |
| 1833 | 0 | 0 | 0 | 0 | 0 | 0 |
| 1836 | 0 | 0 | 50 | 20 | 20 | 10 |

We claim:

1. A compound of Formula 1, N-oxides and salts thereof:

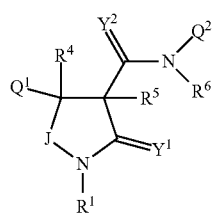

wherein $Q^1$ is a phenyl ring or a naphthalenyl ring system, each ring or ring system optionally substituted with up to 5 substituents independently selected from $R^7$; or a 4- to 7-membered heterocyclic ring or an 8- to 10-membered bicyclic ring system, each ring or ring system containing ring members selected from carbon atoms and 1 to 5 heteroatoms independently selected from up to 2 O, up to 2 S and up to 5 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^7$ on carbon atom ring members and selected from $R^9$ on nitrogen atom ring members; or $Q^1$ is $C_2$-$C_{10}$ alkenyl, $C_2$-$C_{10}$ alkynyl, $C_2$-$C_{10}$ haloalkenyl, $C_2$-$C_{10}$ haloalkynyl, $C_4$-$C_{10}$ cycloalkenyl, $C_4$-$C_{10}$ halocycloalkenyl, $C_2$-$C_8$ alkylcarbonyl or $C_2$-$C_8$ alkoxyalkyl;

$Q^2$ is a phenyl ring or a naphthalenyl ring system, each ring or ring system optionally substituted with up to 5 substituents independently selected from $R^{10}$; or a 4- to 7-membered heterocyclic ring or an 8- to 10-membered bicyclic ring system, each ring or ring system containing ring members selected from carbon atoms and 1 to 4 heteroatoms independently selected from up to 2 O, up to 2 S and up to 5 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^{10}$ on carbon atom ring members and selected from $R^{11}$ on nitrogen atom ring members; or $Q^2$ is $C_2$-$C_{10}$ alkenyl, $C_2$-$C_{10}$ alkynyl, $C_2$-$C_{10}$ haloalkenyl, $C_2$-$C_{10}$ haloalkynyl, $C_4$-$C_{10}$ cycloalkenyl, $C_4$-$C_{10}$ halocycloalkenyl, $C_2$-$C_8$ alkylcarbonyl or $C_2$-$C_8$ alkoxyalkyl;

J is —$CR^2R^3$—, —$NR^{2a}$— or —O—;

$Y^1$ and $Y^2$ are each independently O, S or $NR^{12}$;

$R^1$ is cyano, formyl, $C_3$-$C_8$ alkylcarbonylalkyl, —C($C_1$-$C_4$ alkyl)=N—O($C_1$-$C_4$ alkyl), —C(O)NH$_2$, $C_2$-$C_6$ cyanoalkyl, $C_3$-$C_6$ cycloalkyl, $C_4$-$C_8$ cycloalkenyl; or arylcarbonyl, arylalkenylalkyl, arylcarbonylalkyl or —CPh=N—O($C_1$-$C_4$ alkyl), each optionally substituted on ring members with up to 5 substituents independently selected from $R^{13}$; or $G^1$; or $W^1G^1$;

each $G^1$ is independently phenyl, or a 5- or 6-membered heterocyclic ring, each optionally substituted on ring members with up to 5 substituents independently selected from $R^{13}$;

$W^1$ is $C_1$-$C_3$ alkylene, $C_2$-$C_4$ alkenylene, $C_2$-$C_4$ alkynylene, —($C_1$-$C_2$ alkylene)C(=O)—, —C(=O)($C_1$-$C_2$ alkylene)-, —CH$_2$O—, —CH$_2$NH—, —OCH$_2$—, —NCH$_2$—, —N—, —O—, —S—, —SO— or —SO$_2$— wherein the free bond projecting to the left indicates the connecting point of $W^1$ to N and the free bond projecting to the right indicates the connecting point of $W^1$ to $G^1$;

$R^2$ and $R^3$ are each independently H, halogen, hydroxy, $C_1$-$C_4$ alkyl, $C_1$-$C_4$ haloalkyl or $C_1$-$C_4$ alkoxy; or $R^2$ and $R^3$ are taken together with the carbon atom to which they are bonded to form a $C_3$-$C_7$ cycloalkyl ring;

$R^{2a}$ is $C_1$-$C_6$ alkyl, $C_2$-$C_6$ alkenyl, $C_3$-$C_6$ alkynyl or $C_1$-$C_6$ alkoxy; or $R^1$ and $R^{2a}$ are taken together as $C_3$-$C_6$ alkylene or —CH$_2$OCH$_2$—;

$R^4$ and $R^5$ are each independently H, halogen, hydroxy, $C_1$-$C_4$ alkoxy, $C_1$-$C_4$ haloalkyl or $C_1$-$C_4$ alkyl;

$R^6$ is H, hydroxy, amino, $C_1$-$C_6$ alkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl or $C_3$-$C_{10}$ trialkylsilyl or $G^1$; or $R^6$ and $Q^2$ are taken together with the nitrogen atom to which they are both bonded to form an 8- to 10-membered bicyclic ring system, each ring or ring system containing ring members selected from carbon atoms and 1 to 4 heteroatoms independently selected from up to 2 O, up to 2 S and up to 4 N atoms, wherein up to 3 carbon ring members are independently selected from C(=O) and C(=S), and the sulfur atom ring members are independently selected from $S(=O)_u(=NR^8)_v$, each ring or ring system optionally substituted with up to 5 substituents independently selected from $R^7$ on carbon atom ring members and selected from $R^9$ on nitrogen atom ring members;

each $R^7$ and $R^{10}$ is independently halogen, hydroxy, cyano, nitro, amino, $C_1$-$C_8$ alkyl, $C_1$-$C_8$ cyanoalkyl, $C_1$-$C_8$ cyanoalkoxy, $C_1$-$C_8$ haloalkyl, $C_1$-$C_8$ nitroalkyl, $C_2$-$C_8$ alkenyl, $C_2$-$C_8$ haloalkenyl, $C_2$-$C_8$ nitroalkenyl, $C_2$-$C_8$ alkynyl, $C_2$-$C_8$ haloalkynyl, $C_2$-$C_8$ alkoxyalkyl, $C_3$-$C_8$ alkoxyalkoxyalkyl, $C_2$-$C_8$ haloalkoxyalkyl, $C_2$-$C_8$ haloalkoxyhaloalkoxy, $C_3$-$C_6$ cycloalkyl, cyclopropylmethyl, 1-methylcyclopropyl, 2-methylcyclopropyl, $C_4$-$C_{10}$ cycloalkylalkyl, $C_4$-$C_{10}$ halocycloalkylalkyl, $C_5$-$C_{12}$ alkylcycloalkylalkyl, $C_5$-$C_{12}$ cycloalkylalkenyl, $C_5$-$C_{12}$ cycloalkylalkynyl, $C_3$-$C_8$ cycloalkyl, $C_3$-$C_8$ halocycloalkyl, $C_4$-$C_{10}$ alkylcycloalkyl, $C_6$-$C_{12}$ cycloalkylcycloalkyl, $C_3$-$C_8$ cycloalkenyl, $C_3$-$C_8$ halocycloalkenyl, $C_2$-$C_8$ haloalkoxyalkoxy, $C_2$-$C_8$ alkoxyalkoxy, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylamino, $C_2$-$C_8$ dialkylamino, $C_2$-$C_8$ halodialkylamino, $C_2$-$C_8$ alkylaminoalkyl, $C_2$-$C_8$ haloalkylaminoalkyl, $C_4$-$C_{10}$ cycloalkylaminoalkyl, $C_3$-$C_{10}$ dialkylaminoalkyl, —CHO, $C_2$-$C_8$ alkylcarbonyl, $C_2$-$C_8$ haloalkylcarbonyl, $C_4$-$C_{10}$ cycloalkylcarbonyl, —C(=O)OH, $C_2$-$C_8$ alkoxycarbonyl, $C_2$-$C_8$ haloalkoxycarbonyl, $C_4$-$C_{10}$ cycloalkoxycarbonyl, $C_5$-$C_{12}$ cycloalkylalkoxycarbonyl, —C(=O)NH$_2$, $C_2$-$C_8$ alkylaminocarbonyl, $C_4$-$C_{10}$ cycloalkylaminocarbonyl, $C_3$-$C_{10}$ dialkylaminocarbonyl, $C_1$-$C_8$ alkoxy, $C_1$-$C_8$ haloalkoxy, $C_2$-$C_8$ alkoxyalkoxy, $C_2$-$C_8$ alkenyloxy, $C_2$-$C_8$ haloalkenyloxy, $C_3$-$C_8$ alkynyloxy, $C_3$-$C_8$ haloalkynyloxy, $C_3$-$C_8$ cycloalkoxy, $C_3$-$C_8$ halocycloalkoxy, $C_4$-$C_{10}$ cycloalkylalkoxy, $C_3$-$C_{10}$ alkylcarbonylalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_8$ alkylsulfonyloxy, $C_1$-$C_8$ haloalkylsulfonyloxy, $C_1$-$C_8$ alkylthio, $C_1$-$C_8$ haloalkylthio, $C_3$-$C_8$ cycloalkylthio, $C_1$-$C_8$ alkylsulfinyl, $C_1$-$C_8$ haloalkylsulfinyl, $C_1$-$C_8$ alkylsulfonyl, $C_1$-$C_8$ haloalkylsulfonyl, $C_3$-$C_8$ cycloalkylsulfonyl, formylamino, $C_2$-$C_8$ alkylcarbonylamino, $C_2$-$C_8$ haloalkylcarbonylamino, $C_3$-$C_8$ cycloalkylamino, $C_2$-$C_8$ alkoxycarbonylamino, $C_1$-$C_6$ alkylsulfonylamino, $C_1$-$C_6$ haloalkylsulfonylamino, —SF$_5$, —SCN, SO$_2$NH$_2$, $C_3$-$C_{12}$ trialkylsilyl, $C_4$-$C_{12}$ trialkylsilylalkyl or $C_4$-$C_{12}$ trialkylsilylalkoxy; or $G^2$; or each $R^7$ is independently $R^{26}S(=O)=N—$, $R^{26}S(=O)_2NR^{25}—C(=O)—$, $R^{26}(R^{25}N=)_qS(=O)_p—$, wherein the free bond projecting to the right indicates the connecting point to $Q^1$; or each $R^{10}$ is independently $R^{17}ON=CR^{17a}—$, $(R^{18})_2C=NO—$, $(R^{19})_2NN=CR^{17a}$, $(R^{18})_2C=NNR^{20a}—$, $R^{20}N=CR^{17a}—$, $(R^{18})_2C=N—$, $R^{17}ON=CR^{17a}C(R^{23b})_2—$, $(R^{18})_2C=NOC(R^{24a})_2—$, $R^{26}S(=O)=N—$, $R^{26}S(=O)_2NR^{25}—C(=O)—$ or $R^{26}(R^{25}N=)_qS(=O)_p—$, wherein the free bond projecting to the right indicates the connecting point to $Q^2$;

each $R^8$ is independently H, cyano, $C_2$-$C_3$ alkylcarbonyl or $C_2$-$C_3$ haloalkylcarbonyl;

each $R^9$ and $R^{11}$ is independently cyano, $C_1$-$C_3$ alkyl, $C_2$-$C_3$ alkenyl, $C_2$-$C_3$ alkynyl, $C_3$-$C_6$ cycloalkyl, $C_2$-$C_3$ alkoxyalkyl, $C_1$-$C_3$ alkoxy, $C_2$-$C_3$ alkylcarbonyl, $C_2$-$C_3$ alkoxycarbonyl, $C_2$-$C_3$ alkylaminoalkyl or $C_3$-$C_4$ dialkylaminoalkyl;

each $R^{12}$ is independently H, cyano, hydroxy, CHO, $C_1$-$C_4$ alkyl, $C_1$-$C_4$ haloalkyl, $C_1$-$C_4$ alkoxy, $C_2$-$C_6$ alkylcarbonyl, $C_2$-$C_6$ haloalkylcarbonyl, —(C=O)CH$_3$ or —(C=O)CF$_3$;

each $G^1$ is independently phenyl, or a 5- or 6-membered heterocyclic ring, each optionally substituted on ring members with up to 5 substituents independently selected from $R^{13}$;

each $G^2$ is independently phenyl, phenylmethyl (i.e. benzyl), pyridinylmethyl, phenylcarbonyl (i.e. benzoyl), phenoxy, phenylethynyl, phenylsulfonyl or a 5- or 6-membered heterocyclic ring, each optionally substituted on ring members with up to 5 substituents independently selected from $R^{14}$;

$W^1$ is $C_1$-$C_3$ alkylene, $C_2$-$C_4$ alkenylene, $C_2$-$C_4$ alkynylene, —(C$_1$-$C_2$ alkylene)C(=O)—, —C(=O)(C$_1$-$C_2$ alkylene)-, —CH$_2$O—, —CH$_2$NH—, —OCH$_2$—, —NCH$_2$—, —N—, —O—, —S—, —SO— or —SO$_2$— wherein the free bond projecting to the left indicates the connecting point of $W^1$ to N and the free bond projecting to the right indicates the connecting point of $W^1$ to $G^1$;

each $R^{13}$ and $R^{14}$ is independently halogen, cyano, hydroxy, amino, nitro, —CHO, —C(=O)OH, —C(=O)NH$_2$, —SO$_2$NH$_2$, $C_1$-$C_6$ alkyl, $C_1$-$C_6$ haloalkyl, $C_2$-$C_6$ alkenyl, $C_2$-$C_6$ alkynyl, $C_2$-$C_8$ alkylcarbonyl, $C_2$-$C_8$ haloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylaminosulfonyl, $C_2$-$C_8$ dialkylaminosulfonyl, $C_3$-$C_{10}$ trialkylsilyl, $C_1$-$C_6$ alkylamino, $C_2$-$C_8$ dialkylamino, $C_2$-$C_8$ alkylcarbonylamino, $C_1$-$C_6$ alkylsulfonylamino, phenyl, pyridinyl or thienyl;

each $R^{17}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{17a}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy, $C_1$-$C_6$ alkylthio, $C_1$-$C_6$ haloalkylthio, $C_3$-$C_8$ cycloalkylthio, $C_3$-$C_{10}$ trialkylsilyl or $G^1$;

each $R^{18}$ is independently H, hydroxy, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{19}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{20}$ is independently H, hydroxy, amino, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_2$-$C_8$ haloalkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ alkylsulfinyl, $C_1$-$C_6$ haloalkylsulfinyl, $C_3$-$C_8$ cycloalkylsulfinyl, $C_1$-$C_6$ alkylsulfonyl, $C_1$-$C_6$ haloalkylsulfonyl, $C_3$-$C_8$ cycloalkylsulfonyl, $C_1$-$C_6$ alkylaminosulfonyl, $C_2$-$C_8$ dialkylaminosulfonyl, $C_3$-$C_{10}$ trialkylsilyl or $G^1$;

each $R^{20a}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy, $C_3$-$C_{10}$ trialkylsilyl or $G^1$;

each $R^{23b}$ is independently H, halogen, cyano, hydroxy, $C_1$-$C_4$ alkyl, $C_3$-$C_8$ cycloalkyl, $C_4$-$C_8$ cycloalkylalkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl or $C_3$-$C_6$ cycloalkyl;

each $R^{24a}$ is independently H, $C_1$-$C_4$ alkyl, $C_3$-$C_8$ cycloalkyl, $C_4$-$C_8$ cycloalkylalkyl, $C_1$-$C_4$ haloalkyl, $C_1$-$C_4$ alkoxy, $C_1$-$C_4$ haloalkoxy, $C_2$-$C_4$ alkoxyalkyl, $C_2$-$C_4$ alkylcarbonyl, $C_2$-$C_4$ alkoxycarbonyl or $C_3$-$C_6$ cycloalkyl;

each $R^{25}$ is independently H, cyano, $C_2$-$C_3$ alkylcarbonyl or $C_2$-$C_3$ haloalkylcarbonyl;

each $R^{26}$ is independently H, $C_1$-$C_6$ alkyl, $C_3$-$C_8$ cycloalkyl, $C_4$-$C_8$ cycloalkylalkyl, $C_1$-$C_6$ haloalkyl, $C_2$-$C_6$ alkenyl, $C_3$-$C_6$ alkynyl, $C_2$-$C_8$ alkoxyalkyl, $C_2$-$C_8$ haloalkoxyalkyl, $C_2$-$C_8$ alkylthioalkyl, $C_2$-$C_8$ alkylsulfinylalkyl, $C_2$-$C_8$ alkylsulfonylalkyl, $C_1$-$C_6$ alkoxy, $C_3$-$C_{10}$ trialkylsilyl or $G^1$; and each u and v are independently 0, 1 or 2 in each instance of $S(=O)_u(=NR^8)_v$, provided that the sum of u and v is 0, 1 or 2;

each p and q are independently 0, 1 or 2 in each instance of $R^{26}(R^{25}N=)_qS(=O)_p-$, provided that the sum of u and v is 0, 1 or 2 and when p is 0, q is other than 1 or 2.

2. A herbicidal composition comprising:
a compound, N-oxide or salt of claim 1; and
a surfactant, solid diluent or liquid diluent.

3. The herbicidal composition of claim 2, wherein the composition further comprises an additional active ingredient selected from the group consisting of other herbicides and herbicide safeners.

4. A herbicidal mixture comprising:
a compound, N-oxide or salt of claim 1, and
an additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, metam, methyldymron, oleic acid, oxaziclomefone, pelargonic acid and pyributicarb, and (b16) herbicide safeners; and salts of compounds of (b1) through (b16).

5. A herbicidal mixture comprising:
a compound, N-oxide or salt of claim 1, and
an additional active ingredient selected from (b2) acetohydroxy acid synthase (AHAS) inhibitors, (b9) very long chain fatty acid (VLCFA) elongase inhibitors and (b12) 4-hydroxyphenyl-pyruvate dioxygenase (HPPD) inhibitors; and salts of compounds of (b1), (b9) and (b12).

6. A method for controlling the growth of undesired vegetation comprising contacting the vegetation or its environment with a herbicidally effective amount of a compound, N-oxide or salt of claim 1.

7. A compound of Formula 1 that is

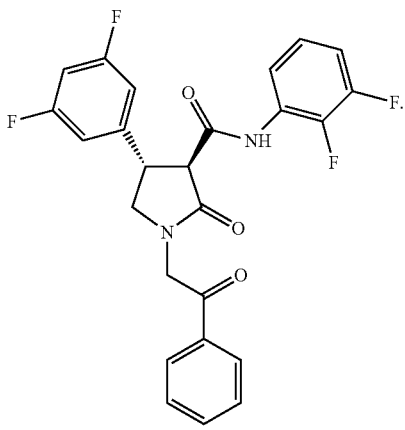 [SMILES: O=C(CN1C[C@H](c2cc(F)cc(F)c2)[C@@H](C(=O)Nc2cccc(F)c2F)C1=O)c1ccccc1]

* * * * *